(12) United States Patent
Ebdrup et al.

(10) Patent No.: US 7,067,517 B2
(45) Date of Patent: Jun. 27, 2006

(54) USE OF COMPOUNDS FOR DECREASING ACTIVITY OF HORMONE-SENSITIVE LIPASE

(75) Inventors: Soren Ebdrup, Roskilde (DK); Johannes Cornelis de Jong, Bagsvaerd (DK); Poul Jacobsen, Slangerup (DK); Holger Claus Hansen, Vaerlose (DK); Per Vedso, Frederiksberg (DK)

(73) Assignee: Nero Nordisk A/S, Bagsvaerd (DK)

( * ) Notice: Subject to any disclaimer, the term of this patent is extended or adjusted under 35 U.S.C. 154(b) by 145 days.

(21) Appl. No.: 10/319,212

(22) Filed: Dec. 13, 2002

(65) Prior Publication Data

US 2003/0166690 A1     Sep. 4, 2003

Related U.S. Application Data

(60) Provisional application No. 60/346,909, filed on Jan. 3, 2002, provisional application No. 60/384,253, filed on May 10, 2002, provisional application No. 60/393,068, filed on Jun. 28, 2002, provisional application No. 60/418,481, filed on Oct. 15, 2002.

(30) Foreign Application Priority Data

| Dec. 14, 2001 | (DK) | 2001 01879 |
|---|---|---|
| Apr. 30, 2002 | (DK) | 2002 00645 |
| Jun. 27, 2002 | (DK) | 2002 01000 |
| Oct. 11, 2002 | (DK) | 2002 01562 |

(51) Int. Cl.
*A61K 31/44*     (2006.01)
*C07D 401/04*    (2006.01)

(52) U.S. Cl. ............... 514/253.01; 548/252; 548/255; 548/257; 548/300.1; 548/356.1; 548/469; 548/484; 546/139; 544/180; 544/224; 544/242; 544/336; 544/358; 544/360; 514/252.12; 514/252.13; 514/253.11

(58) Field of Classification Search ............... 544/336, 544/358, 360; 514/253.11, 252.12, 252.13, 514/253.01; 548/252, 255, 257, 300.1, 356.1, 548/484; 546/139
See application file for complete search history.

(56) References Cited

U.S. PATENT DOCUMENTS

| 4,643,991 A | 2/1987 | Digenis et al. | 514/18 |
|---|---|---|---|
| 5,463,062 A | 10/1995 | Hemmerle et al. | 546/168 |
| 5,837,727 A | 11/1998 | Bauer et al. | 514/483 |
| 5,869,484 A | 2/1999 | Terni et al. | 514/231.2 |

FOREIGN PATENT DOCUMENTS

| BE | 665273 | 6/1965 |
|---|---|---|
| EP | 0587311 A1 | 8/1993 |
| EP | 1201649 A1 | 10/2001 |
| JP | WO 97/01533 A | 1/1997 |
| JP | 10087485 A | 4/1998 |
| WO | 92/07838 | 5/1992 |
| WO | 95/29155 | 11/1995 |
| WO | WO 96/02524 A1 | 2/1996 |
| WO | WO 98/53814 | 12/1998 |
| WO | WO 99/62870 | 12/1999 |
| WO | WO 00/54759 A2 | 9/2000 |
| WO | WO 00/54759 A3 | 9/2000 |
| WO | WO 00/63208 | 10/2000 |
| WO | WO 00/69810 | 11/2000 |
| WO | WO 01/21584 A1 | 3/2001 |
| WO | WO 01/47923 A1 | 7/2001 |
| WO | WO 01/87843 A1 | 11/2001 |
| WO | WO 02/006189 A2 | 1/2002 |
| WO | WO 02/006189 A3 | 1/2002 |
| WO | 02/12210 | 2/2002 |
| WO | WO 02/20483 A1 | 3/2002 |
| WO | 02/42257 | 5/2002 |
| WO | WO 02/38153 A1 | 5/2002 |
| WO | 03/040114 | 5/2003 |

OTHER PUBLICATIONS

Hansen et al., International Journal of Pharmaceutics, vol. 79, pp. 205-212 (1992).
Schmidt et al., Bioorganic & Medicinal Chemistry Letters, vol. 7, No. 8, pp. 1071-1076 (1997).

*Primary Examiner*—Golam M. M. Shameem
(74) *Attorney, Agent, or Firm*—Rosemarie R. Wilk-Orescan; Reza Green; Richard W. Bork

(57) ABSTRACT

Use of compounds to inhibit hormone-sensitive lipase, pharmaceutical compositions comprising the compounds, methods of treatment employing these compounds and compositions, and novel compounds. The present compounds are inhibitors of hormone-sensitive lipase and may be useful in the treatment and/or prevention of medical disorders where a decreased activity of hormone-sensitive lipase is desirable.

23 Claims, No Drawings

USE OF COMPOUNDS FOR DECREASING ACTIVITY OF HORMONE-SENSITIVE LIPASE

Priority of Danish Application No. PA 2001 01879 filed on Dec. 14, 2001; Danish Application No. PA 2002 00645 filed on Apr. 30, 2002; Danish Application No. PA 2002 01000 filed on Jun. 27, 2002; and Danish Application No. PA 2002 01562 filed on Oct. 11, 2002 is claimed under 35 U.S.C. 119. The contents of which are herein incorporated by reference.

Priority of U.S. Provisional Application No. 60/346,909 filed on Jan. 3, 2002; U.S. Provisional Application No. 60/384,253 filed on May 10, 2002; U.S. Provisional Application No. 60/393,068 filed on Jun. 28, 2002 and U.S. Provisional Application No. 60/418,481 filed on Oct. 15, 2002 is claimed under 35 U.S.C. 119. The contents of which are herein incorporated by reference.

FIELD OF THE INVENTION

The present invention relates to compounds, compositions containing them, and their use for treating medical disorders where it is desirable to modulate the activity of hormone-sensitive lipase.

BACKGROUND OF THE INVENTION

The overall energy homeostasis of a mammalian system requires a high degree of regulation to ensure the availability of the appropriate substrate at the appropriate time. Plasma glucose levels rise during the post-prandial state, to return to pre-prandial levels within 2–3 hours. During these 2–3 hours, insulin promotes glucose uptake by skeletal muscle and adipose tissue and decreases the release of free fatty acids (FFA) from adipocytes, to ensure that the two substrates do not compete with each other. When plasma glucose levels fall, an elevation in plasma FFA is necessary to switch from glucose to fat utilization by the various tissues.

In individuals with insulin resistance, FFA levels do not fall in response to insulin, as they do in normal individuals, preventing the normal utilization of glucose by skeletal muscle, adipose and liver. Furthermore, there is a negative correlation between insulin sensitivity and plasma FFA levels.

Hormone-sensitive lipase (HSL) is an enzyme, expressed primarily in adipocytes, that catalyses the conversion of triglycerides to glycerol and fatty acids. It is through the regulation of this enzyme that the levels of circulating FFA are modulated. Insulin leads to the inactivation of HSL with a subsequent fall in plasma FFA levels during the post-prandial state, followed by the activation of the enzyme when the insulin concentration falls and catecholamines rise during the post-absorptive period. The activation of HSL leads to an increase in plasma FFA, as they become the main source of energy during fasting.

The activation-inactivation of HSL is primarily mediated through the cAMP-protein kinase A and AMP-dependent kinase pathways. There are compounds like nicotinic acid and its derivatives, that decrease the activation of HSL via these pathways and cause a decrease in lipolysis that leads to a reduction in the FFA levels. These drugs have a beneficial effect in the utilization of glucose and in the normalization of the excess triglyceride synthesis seen in patients with elevated FFA. However, since these pathways are used by other processes in the body, these drugs have severe side effects.

We have found compounds that specifically inhibit the lipolytic activity of HSL and lead to a decrease in plasma FFA levels. These compounds can be used to treat disorders where a decreased level of plasma FFA is desired, such as insulin resistance, syndrome X, dyslipidemia, abnormalities of lipoprotein metabolism.

One object of the present invention is to provide compounds and pharmaceutical compositions that inhibit the lipolytic activity of HSL. A further object is to provide compounds which have good pharmaceutical properties such as solubility, bioavailability etc.

DEFINITIONS

The following is a detailed definition of the terms used to describe the compounds of the invention.

"Halogen" designates an atom selected from the group consisting of F, Cl, Br and I.

The term "$C_{1-6}$alkyl" in the present context designates a saturated, branched or straight hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl and the like.

The term "$C_{2-6}$-alkyl" in the present context designates a saturated, branched or straight hydrocarbon group having from 2 to 6 carbon atoms. Representative examples include, but are not limited to, ethyl, n-propyl, isopropyl, butyl, isobutyl, sec-butyl, tert-butyl, n-pentyl, isopentyl, neopentyl, tert-pentyl, n-hexyl, isohexyl and the like.

The term "$C_{1-6}$alkoxy" in the present context designates a group —O—$C_{1-6}$-alkyl wherein $C_{1-6}$-alkyl is as defined above. Representative examples include, but are not limited to, methoxy, ethoxy, n-propoxy, isopropoxy, butoxy, isobutoxy, sec-butoxy, tert-butoxy, n-pentoxy, isopentoxy, neopentoxy, tert-pentoxy, n-hexoxy, isohexoxy and the like.

The term "$C_{3-6}$-alkoxy" in the present context designates a group —O—$C_{1-6}$-alkyl wherein $C_{3-6}$-alkyl is a saturated, branched or straight hydrocarbon group having from 3–6 carbon atoms. Representative examples of $C_{3-6}$-alkoxy include, but are not limited to, n-propoxy, isopropoxy, butoxy, isobutoxy, sec-butoxy, tert-butoxy, n-pentoxy, isopentoxy, neopentoxy, tert-pentoxy, n-hexoxy, isohexoxy and the like.

The term "$C_{2-6}$-alkenyl" as used herein, represent an olefinically unsaturated branched or straight hydrocarbon group having from 2 to 6 carbon atoms and at least one double bond. Examples of such groups include, but are not limited to, vinyl, 1-propenyl, 2-propenyl, allyl, iso-propenyl, 1,3-butadienyl, 1-butenyl, hexenyl, pentenyl and the like.

The term "$C_{3-10}$-cycloalkyl" as used herein represents a saturated mono-, bi-, tri- or spirocarbocyclic group having from 3 to 10 carbon atoms. Representative examples are cyclopropyl, cyclobutyl, cyclopentyl, cyclohexyl, cycloheptyl, cyclooctyl, cyclononyl, cyclodecyl, bicyclo[3.2.1]octyl, spiro[4.5]decyl, norpinyl, norbonyl, norcaryl, adamantyl and the like.

The term "$C_{3-8}$-heterocyclyl" as used herein represents a saturated 3 to 8 membered ring containing one or more heteroatoms selected from nitrogen, oxygen and sulfur. Representative examples are pyrrolidyl, piperidyl, piperazinyl, morpholinyl, thiomorpholinyl, aziridinyl, tetrahydrofuranyl and the like.

The term "aryl" as used herein represents a carbocyclic aromatic ring system being either monocyclic, bicyclic, or polycyclic, such as phenyl, biphenyl, naphthyl, anthracenyl, phenanthrenyl, fluorenyl, indenyl, pentalenyl, azulenyl, biphenylenyl and the like. Aryl is also intended to include the partially hydrogenated derivatives of the carbocyclic aromatic systems enumerated above. Non-limiting examples of such partially hydrogenated derivatives are 1,2,3,4-tetrahydronaphthyl, 1,4-dihydronaphthyl and the like.

The term "aryloxy" as used herein represents an aryl which is linked via an oxygen atom, e.g. phenoxy, 1-naphthyloxy, 2-naphthyloxy and the like.

The term "heteroaryl" as used herein represents a heterocyclic aromatic ring system containing one or more heteroatoms selected from nitrogen, oxygen and sulfur such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl (thianaphthenyl), indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, 3,4-dihydroisoquinolinyl, pyrrolinyl, pyrazolinyl, indolinyl, oxazolidinyl, oxazolinyl, oxazepinyl and the like.

The term "perhalomethyl" as used herein designates a methyl moiety substituted with three halogen atoms. Non-limiting examples of perhalomethyl are $CF_3$, $CCl_3$, and $CF_2Cl$.

The term "perhalomethoxy" as used herein designates a perhalomethyl linked via an oxygen atom, e.g. —O—$CF_3$, —O—$CCl_3$, and —O—$CF_2Cl$ The term "ring system" as used herein includes aromatic as well as non-aromatic ring moieties, which may be monocyclic, bicyclic or polycyclic, and they encompass moieties with zero, one or more hetereatoms selected from nitrogen, oxygen and sulphur. Non-limiting examples of such ring systems are aryl, $C_{3-8}$-heterocyclyl and heteroaryl.

The term "heterocyclic system" as used herein includes aromatic as well as non-aromatic ring moieties, which may be monocyclic, bicyclic or polycyclic, and containing in their ring structure one or more heteroatoms selected from nitrogen, oxygen and sulfur. Non-limiting examples of such heterocyclic systems are $C_{3-8}$-heterocyclyl and heteroaryl.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

The term "optionally covalently bound" as used herein means that the substituents in question are either not covalently bound to each other or the substituents are directly connected to each other by a covalent bond. A non-limiting example of such optionally covalently bound substituents is —$NR^1R^2$ wherein $R^1$ is ethyl and $R^2$ is propyl which provided that the substituents, ethyl and propyl, are optionally covalently bound may be ethyl-propyl-amino, 1-piperidyl, 3-methyl-1-pyrrolidyl or 2,3-dimethyl-1-azetidyl.

The term "hydrolysable group" as used herein means a group which can be hydrolysed at certain chemical conditions, i.e. an internal covalent bond in the group can be cleaved to give two compounds. A hydrolysable group does not have to be hydrolysed during carrying out the present invention. For instance, the hydrolysable group —C(=X)-L can be hydrolysed to give the products —C(=X)OH and HL, which means that the covalent bond between —C(X) and L is cleaved. Examples of hydrolysable groups are carbamates, esters and amides.

The terms "disease", "condition" and "disorder" as used herein are used interchangeably to specifiy a state of a patient which is not the normal physiological state of man.

The term "treatment" as used herein means the management and care of a patient having developed a disease, condition or disorder, as well as the management and care of an individual at risk of developing the disease, condition or disorder prior to the clinical onset of said disease, condition or disorder. The purpose of treatment is to combat the disease, condition or disorder, as well as to to combat the development of the disease, condition or disorder. Treatment includes the administration of the active compounds to prevent or delay the onset of the symptoms or complications and to eliminate or control the disease, condition or disorder as well as to alleviate the symptoms or complications associated with the disease, condition or disorder.

The term "effective amount" as used herein means a dosage which is sufficient in order for the treatment of the patient to be effective compared with no treatment.

The term "modulate" as used herein means to influence, i.e. to modulate a parameter means to influence that parameter in a desired way. Examples are to modulate insulin secretion from beta cells and to modulate the plasma level of free fatty acids.

The term "medicament" as used herein means a pharmaceutical composition suitable for administration of the pharmaceutically active compound to a patient.

The term "pharmaceutically acceptable" as used herein means suited for normal pharmaceutical applications, i.e. giving rise to no adverse events in patients etc.

DESCRIPTION OF THE INVENTION

The present invention relates to the use of a compound of the general formula I

(I)

wherein $R^1$ is selected from hydrogen, $C_{1-6}$-alkyl, $C_{2-6}$-alkenyl and $C_{3-10}$-cycloalkyl, each of which is optionally substituted with one or more substituents independently selected from hydroxy, sulfanyl, oxo, halogen, amino, cyano and nitro; and $R^2$ is selected from $C_{1-6}$alkyl, $C_{2-6}$-alkenyl, aryl, heteroaryl, $C_{3-8}$-heterocyclyl and $C_{3-10}$-cycloalkyl, each of which is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; and wherein $R^2$ is optionally covalently bound to $R^1$ by an ether, thioether, C—C or C—N bond, to form a ring system with the N-atom to which $R^1$ and $R^2$ are bound; and X is O or S; and L is a group such that —C(=X)-L is a hydrolysable group; or a pharmaceutically acceptable salt thereof, or a pharmaceutically acceptable solvate thereof, or any tautomeric forms, stereoisomers, mixture of stereoisomers including a racemic mixture, or polymorphs for inhibition of the lipolytic activity of hormone-sensitive lipase against triacylglycerols, diacylglycerols, cholesterol acyl esters or steroid acyl esters.

Another aspect of the invention relates to use of a compound of the general formula I

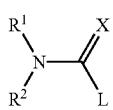

(I)

wherein $R^1$ is selected from hydrogen, $C_{1-6}$-alkyl, $C_{2-6}$-alkenyl and $C_{3-10}$-cycloalkyl, each of which is optionally substituted with one or more substituents independently selected from hydroxy, sulfanyl, oxo, halogen, amino, cyano and nitro; and $R^2$ is selected from $C_{1-6}$-alkyl, $C_{2-6}$-alkenyl, aryl, heteroaryl, $C_{3-8}$-heterocyclyl and $C_{3-10}$-cycloalkyl, each of which is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; and wherein $R^2$ is optionally covalently bound to $R^1$ by an ether, thioether, C—C or C—N bond, to form a ring system with the N-atom to which $R^1$ and $R^2$ are bound; and X is O or S; and L is a group such that —C(=X)-L is a hydrolysable group; or a pharmaceutically acceptable salt thereof, or a pharmaceutically acceptable solvate thereof, or any tautomeric forms, stereoisomers, mixture of stereoisomers including a racemic mixture, or polymorphs for the preparation of a medicament for the treatment of any disorder where it is desirable to modulate the plasma level of free fatty acids, glycerol, LDL-cholesterol, HDL-cholesterol, insulin and/or glucose; and/or modulate intracellular triacylglycerol and cholesterol ester stores, intracellular level of fatty acids, fatty acid esters such as diacylglycerols, phosphatidic acids, long chain acyl-CoA's as well as citrate or malonyl-CoA; and/or increase insulin sensitivity in adipose tissue, skeletal muscle, liver or pancreatic β cells; and/or modulate insulin secretion from pancreatic β cells.

Another aspect of the invention is the use of a compound of the general formula I for the preparation of a pharmaceutical medicament.

In one embodiment the present invention relates to the use of a compound of the general formula (I) for the preparation of a medicament for the treatment of insulin resistance, diabetes type 1, diabetes type 2, metabolic syndrome X, impaired glucose tolerance, hyperglycemia, dyslipidemia, obesity, abnormalities of lipoprotein metabolism and any combination thereof.

Another aspect of the invention is pharmaceutical compositions comprising a compound of formula I

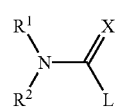

(I)

wherein $R^1$ is selected from hydrogen, $C_{1-6}$-alkyl, $C_{2-6}$-alkenyl and $C_{3-10}$-cycloalkyl, each of which is optionally substituted with one or more substituents independently selected from hydroxy, sulfanyl, oxo, halogen, amino, cyano and nitro; and $R^2$ is selected from $C_{1-6}$-alkyl, $C_{2-6}$-alkenyl, aryl, heteroaryl, $C_{3-8}$-heterocyclyl and $C_{3-10}$-cycloalkyl, each of which is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; and wherein $R^2$ is optionally covalently bound to $R^1$ by an ether, thioether, C—C or C—N bond, to form a ring system with the N-atom to which $R^1$ and $R^2$ are bound; and X is O or S; and L is a group such that —C(=X)-L is a hydrolysable group; or a pharmaceutically acceptable salt thereof, or a pharmaceutically acceptable solvate thereof, or any tautomeric forms, stereoisomers, mixture of stereoisomers including a racemic mixture, or polymorphs.

In another embodiment, the invention is concerned with pharmaceutical compositions containing a compound of formula (I) and uses of the compounds of formula (I), wherein X is O.

In another embodiment, the invention is concerned with pharmaceutical compositions comprising a compound of formula (I) and uses of the compounds of formula (I), wherein X is O.

In another embodiment, the invention is concerned with pharmaceutical compositions containing a compound of formula (I) and uses of the compounds of formula (I), wherein the group L contains an O, via which L is bound to the C in formula (I).

In another embodiment, the invention is concerned with pharmaceutical compositions comprising a compound of formula (I) and uses of the compounds of formula (I), wherein the group L contains an O, via which L is bound to the C in formula (I).

In another embodiment, the invention is concerned with pharmaceutical compositions containing a compound of formula (I) and uses of the compounds of formula (I), wherein the group L contains a N, via which L is bound to the C in formula (I).

In another embodiment, the invention is concerned with pharmaceutical compositions comprising a compound of formula (I) and uses of the compounds of formula (I), wherein the group L contains a N, via which L is bound to the C in formula (I).

In another embodiment, the invention is concerned with pharmaceutical compositions containing a compound of formula (I) and uses of the compounds of formula (I), wherein the group L is selected from the group consisting of

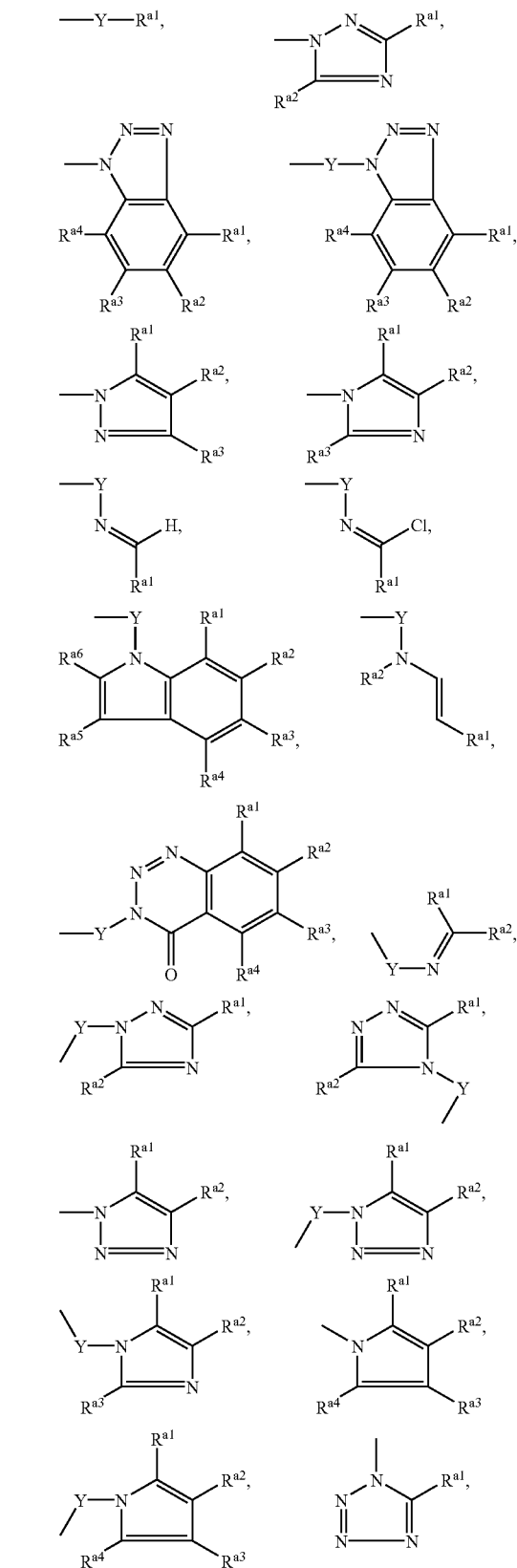

-continued
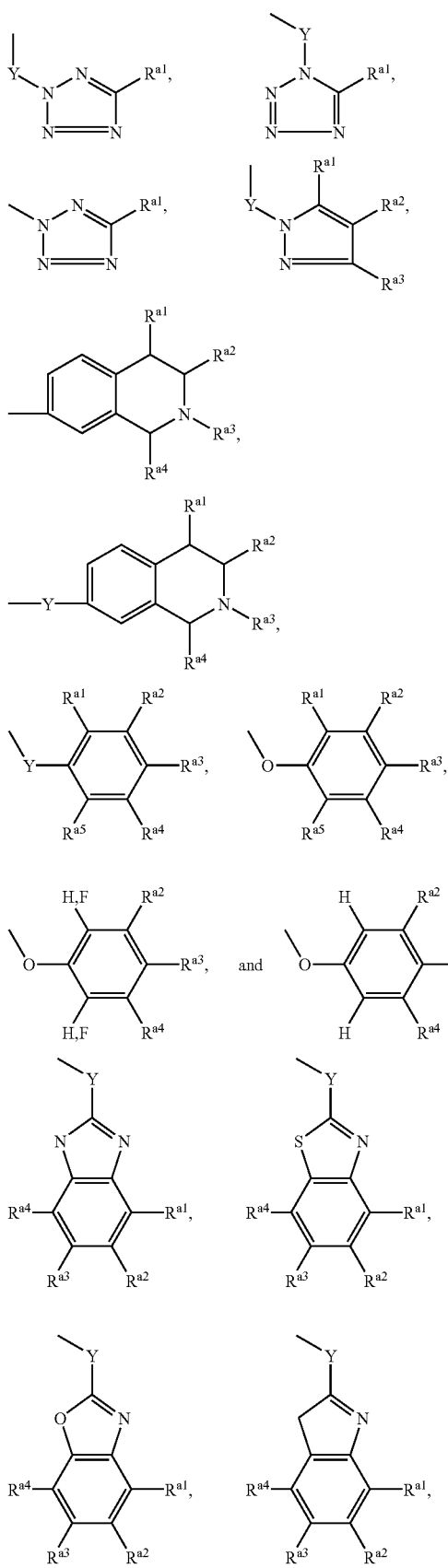
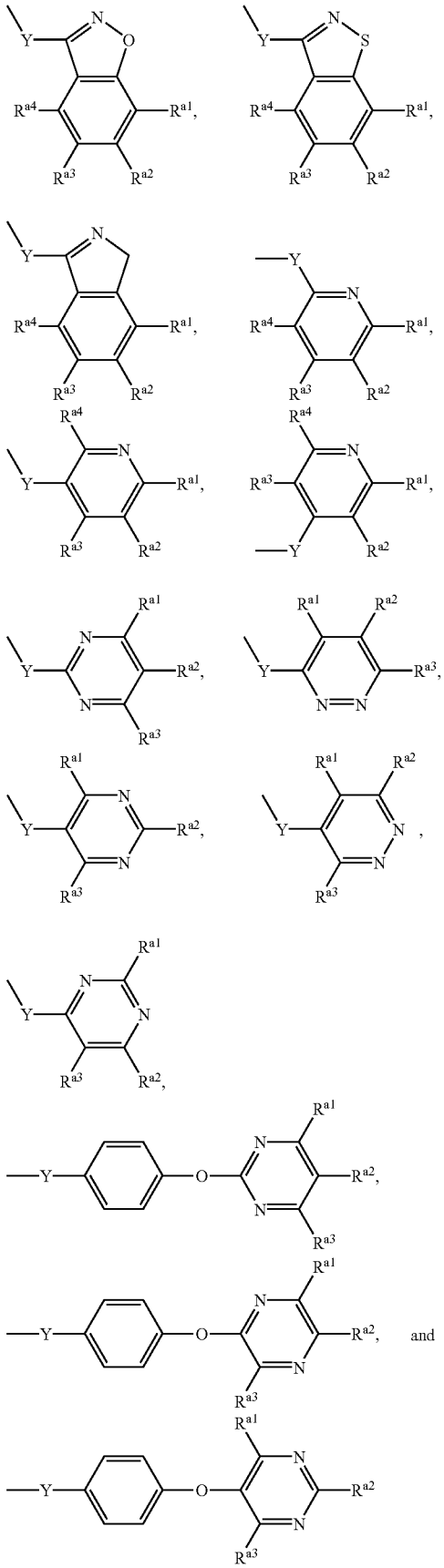

wherein Y is O or S; and $R^{a1}$, $R^{a2}$, $R^{a3}$, $R^{a4}$, $R^{a5}$ and $R^{a6}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl, or $C_{3-10}$-cycloalkyl, wherein each of hydroxy, sulfanyl, sulfo, amino, $C_{1-6}$-alkyl, $C_{2-6}$alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy.

In another embodiment, the invention is concerned with pharmaceutical compositions containing a compound of formula (I) and uses of the compounds of formula (I), wherein at least one of $R^{a1}$, $R^{a2}$, $R^{a3}$, $R^{a4}$, $R^{a5}$ and $R^{a6}$ is F.

In another embodiment, the invention is concerned with pharmaceutical compositions containing a compound of formula (I) and uses of the compounds of formula (I), wherein the group L is an optionally substituted —O-phenyl, via which L is bound to the C in formula (I).

In another embodiment, the invention is concerned with pharmaceutical compositions containing a compound of formula (I) and uses of the compounds of formula (I), wherein $R^1$ and $R^2$ are covalently bound to each other so that the group $R^1$—N—$R^2$ forms a piperazine, said piperazine being bound to the C in formula (I).

In another embodiment, the invention is concerned with pharmaceutical compositions containing a compound of formula (I) and uses of the compounds of formula (I), wherein $R^1$ and $R^2$ are covalently bound to each other so that the group $R^1$—N—$R^2$ forms a piperidine, said piperidine being bound to the C in formula (I).

In another embodiment, the invention is concerned with pharmaceutical compositions containing a compound of formula (I) and uses of the compounds of formula (I), wherein $R^1$ is selected from the group consisting of $C_{1-6}$-alkyl, $C_{2-6}$-alkenyl and $C_{3-10}$-cycloalkyl, each of which is optionally substituted with one or more substituents independently selected from hydroxy, sulfanyl, oxo, halogen, amino, cyano and nitro.

In another embodiment, the invention is concerned with pharmaceutical compositions containing a compound of formula (I) and uses of the compounds of formula (I), wherein $R^1$ is methyl.

In yet another embodiment, the invention is concerned with pharmaceutical compositions containing a compound of formula (I) and uses of the compounds of formula (I), wherein $R^1$ is phenyl.

In another embodiment, the invention is concerned with pharmaceutical compositions containing a compound of formula (I) and uses of the compounds of formula (I), wherein $R^2$ is a heteroaryl.

In another embodiment, the invention is concerned with pharmaceutical compositions containing a compound of formula (I) and uses of the compounds of formula (I), wherein $R^1$ is methyl and $R^2$ is phenyl.

In another embodiment, the invention is concerned with pharmaceutical compositions containing a compound of formula (I) and uses of the compounds of formula (I), wherein the group L is an optionally substituted —O-phenyl via which L is bound to the C in formula (I), and $R^1$ and $R^2$ are covalently bound to each other so that the group $R^1$—N—$R^2$ forms a piperazine, said piperazine being bound to the C in formula (I).

In another embodiment, the invention is concerned with pharmaceutical compositions containing a compound of formula (I) and uses of the compounds of formula (I), wherein the group L is an optionally substituted —O-phenyl via which L is bound to the C in formula (I), and $R^1$ and $R^2$ are covalently bound to each other so that the group $R^1$—N—$R^2$ forms a piperidine, said piperidine being bound to the C in formula (I).

In another embodiment, the invention is concerned with pharmaceutical compositions containing a compound of formula (I) and uses of the compounds of formula (I), wherein the group L is an optionally substituted —O-phenyl via which L is bound to the C in formula (I), and $R^1$ is methyl and $R^2$ is phenyl.

In another embodiment, the invention is concerned with pharmaceutical compositions containing a compound of formula (I) and uses of the compounds of formula (I), wherein $pK_a$ of the group L is between 4 and 12, between 6 and 12, between 7 and 12, between 8 and 12, preferably between 8.5 to 11.5, and most preferable between 9.0 to 11.0.

In another embodiment, the invention is concerned with pharmaceutical compositions containing the compounds of formula (I) and uses of the compounds of formula (I), wherein administration of said compound is by oral administration In another embodiment, the invention is concerned with pharmaceutical compositions containing the compounds of formula (I) and uses of the compounds of formula (I), the nasal, transdermal, pulmonal, or parenteral route.

Another aspect of the invention is a method of treating any disorder where it is desirable to inhibit the lipolytic activity of hormone-sensitive lipase against triacylglycerols, diacylglycerols, cholesterol acyl esters or steroid acyl esters, wherein said method comprises the use as described above.

In another embodiment, the invention is concerned with a method of treating any disorder where it is desirable to modulate the plasma level of free fatty acids or to modulate the handling, storage and oxidation of intracellular fatty acid and cholesterol, wherein said method comprises the use as described above.

In another embodiment, the invention is concerned with said method, wherein said disorder is selected from the group consisting of insulin resistance, diabetes type 1, diabetes type 2, metabolic syndrome X, impaired glucose tolerance,-hyperglycemia, dyslipidemia, obesity, abnormalities of lipoprotein metabolism and any combination thereof.

The present invention also relates to compounds of the general formula II

(II)

wherein R¹ is selected from $C_{1-6}$-alkyl, $C_{2-6}$-alkenyl and $C_{3-10}$-cycloalkyl, each of which is optionally substituted with one or more substituents independently selected from hydroxy, sulfanyl, oxo, halogen, amino, cyano and nitro; and R² is selected from $C_{1-6}$-alkyl, $C_{2-6}$-alkenyl, aryl, heteroaryl, $C_{3-8}$-heterocyclyl and $C_{3-10}$-cycloalkyl, each of which is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$alkyl, $C_{2-6}$-alkenyl, perhalomethyl and perhalomethoxy; and wherein R² is optionally covalently bound to R¹ by an ether, thioether, C—C or C—N bond, to form a ring system with the N-atom to which R¹ and R² are bound; and R³ is selected from hydroxy, sulfanyl, sulfo, amino, $C_{1-6}$alkyl, $C_{2-6}$-alkenyl, aryl, heteroaryl, $C_{3-8}$-heterocyclyl and $C_{3-10}$-cycloalkyl, each of which is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; and X is O or S; or a pharmaceutically acceptable salt thereof, or a pharmaceutically acceptable solvate thereof, or any tautomeric forms, stereoisomers, mixture of stereoisomers including a racemic mixture, or polymorphs.

In an aspect of the invention, compounds are of the general formula III

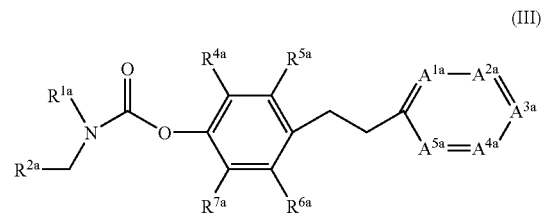

(III)

wherein $R^{1a}$ and $R^{2a}$ are independently selected from $C_{1-6}$-alkyl, $C_{2-6}$-alkenyl, aryl, heteroaryl, $C_{3-8}$-heterocyclyl, and $C_{3-10}$-cycloalkyl, each of which is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano and nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, perhalomethyl and perhalomethoxy; and wherein $R^{1a}$ is optionally covalently bound to $R^{2a}$ by an ether, thioether, C—C or C—N bond, to form a ring system with the N-atom to which $R^{1a}$ and $R^{2a}$ are bound; and $R^{4a}$, $R^{5a}$, $R^{6a}$ and $R^{7a}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, each of which is optionally substituted by one or more substituents selected from hydroxy, sulfanyl, sulfo, oxo, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, perhalomethyl and perhalomethoxy; and $A^{1a}$ is N or C—$R^{8a}$; $A^{2a}$ is N or C—$R^{9a}$; $A^{3a}$ is N or C—$R^{10a}$; $A^{4a}$ is N or C—$R^{11a}$; and $A^{5a}$ is N or C—$R^{12a}$; and wherein $R^{8a}$, $R^{9a}$, $R^{10a}$, $R^{11a}$ and $R^{12a}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, perhalomethyl and perhalomethoxy.

In one embodiment, the invention is concerned with compounds of formula (III), wherein $R^{2a}$ is phenyl, optionally substituted by halogen or methyl.

In another embodiment, the invention in concerned with compounds of formula (III), wherein $R^{1a}$ is selected from methyl and ethyl, optionally substituted by one or more halogen.

In another embodiment, the invention in concerned with compounds of formula (III), wherein $R^{1a}$ and $R^{2a}$ are covalently bound so as to form a ring system with the N-atom to which they are bound, wherein said ring system is a piperidine, piperazine, morpholine, or thiomorpholine.

In another embodiment, the invention in concerned with compounds of formula (III), wherein $R^{4a}$, $R^{5a}$, $R^{6a}$ and $R^{7a}$ are independently selected from hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention in concerned with compounds of formula (III), wherein $A^{1a}$, $A^{2a}$, $A^{3a}$, $A^{4a}$ and $A^{5a}$ are independently selected from N, CH, CF, C—Cl and C—CF$_3$.

In an aspect of the invention, compounds are of the general formula IV

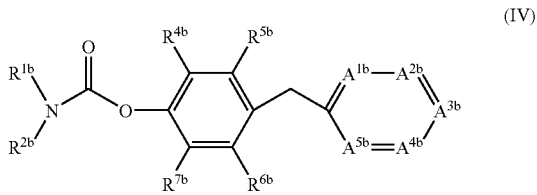

(IV)

wherein $R^{1b}$ and $R^{2b}$ are independently selected from $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, each of which may optionally be substituted with one or more substituents selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy;

wherein $R^{1b}$ is optionally covalently bound to $R^{2b}$ by an ether, thioether, C—C or C—N bond, to form a ring system with the N-atom to which $R^{1b}$ and $R^{2b}$ are bound;

$R^{5b}$ and $R^{6b}$ are independently selected from hydrogen, hydroxy, sulfanyl, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, cyano, nitro, $C_{1-6}$-alkyl, perhalomethyl and perhalomethoxy;

$R^{4b}$ and $R^{7b}$ are independently selected from hydrogen, hydroxy, sulfanyl, halogen, amino, cyano, nitro, sulfo, $C_{1-6}$-alkyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, aryl, heteroaryl, $C_{3-8}$-heterocyclyl and $C_{3-10}$-cycloalkyl is optionally substituted with one or more substituents independently selected from hydroxy, sulfanyl, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, cyano, nitro, $C_{1-6}$-alkyl, perhalomethyl and perhalomethoxy; and $A^{1b}$ is N or C—$R^{8b}$; $A^{2b}$ is N or C—$R^{9b}$; $A^{3b}$ is N or C—$R^{10b}$; $A^{4b}$ is N or C—$R^{11b}$; and $A^{5b}$ is N or C—$R^{12b}$; and wherein $R^{8b}$, $R^{9b}$, $R^{10b}$, $R^{11b}$ and $R^{12b}$ are selected from hydrogen, hydroxy, sulfanyl, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently elected from hydroxy, sulfanyl, oxo, halogen, amino, cyano, nitro, $C_{1-6}$-alkyl, perhalomethyl and perhalomethoxy;

wherein there may optionally be one or more covalent bonds between any of the substituents selected from the group consisting of $R^{4b}$, $R^{5b}$, $R^{6b}$, $R^{7b}$, $R^{8b}$, $R^{9b}$, $R^{10b}$, $R^{11b}$ and $R^{12b}$.

In one embodiment, the invention is concerned with compounds of formula IV, wherein $R^{2b}$ is phenyl, optionally substituted by halogen.

In another embodiment, the invention is concerned with compounds of the general formula IV, wherein $R^{1b}$ is selected from methyl and ethyl, optionally substituted by one or more halogen.

In another embodiment, the invention is concerned with compounds of the general formula IV, wherein $R^{1b}$ and $R^{2b}$ are covalently bound so as to form a ring system with the N-atom to which they are bound, wherein the ring system is a piperidine, piperazine, morpholine, or thiomorpholine.

In another embodiment, the invention is concerned with compounds of the general formula IV, wherein $R^{4b}$, $R^{5b}$, $R^{6b}$ and $R^{7b}$ are independently selected from hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula IV, wherein $A^{1b}$, $A^{2b}$, $A^{3b}$, $A^{4b}$ and $A^{5b}$ are independently selected from N, CH and CF.

In an aspect of the invention, compounds are of the general formula V

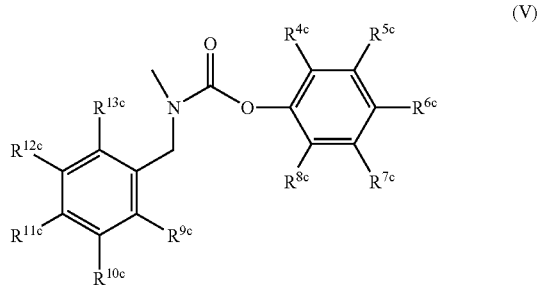

(V)

wherein $R^{4c}$, $R^{5c}$, $R^{6c}$, $R^{7c}$ and $R^{8c}$ are independently selected from hydrogen, hydroxy, sulfanyl, amino, halogen, cyano, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and $R^{9c}$, $R^{10c}$, $R^{11c}$, $R^{12c}$ and $R^{13c}$ are independently selected from hydrogen, sulfanyl, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of sulfanyl, amino, sulfo, $C_{1-6}$-alkyl, $C_{1-6}$-alkoxy, $C_{2-6}$-alkenyl, aryl, heteroaryl, $C_{3-8}$heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and wherein there may optionally be one or more covalent bonds between any of the substituents selected from the group consisting of $R^{4c}$, $R^{5c}$, $R^{6c}$, $R^{7c}$ and $R^{8c}$; and wherein there may optionally be one or more covalent bonds between any of the substituents selected from the group consisting of $R^{9c}$, $R^{10c}$, $R^{11c}$, $R^{12c}$ and $R^{13c}$; and at least one of $R^{4c}$, $R^{5c}$, $R^{6c}$, $R^{7c}$, $R^{8c}$, $R^{9c}$, $R^{10c}$, $R^{11c}$, $R^{12c}$ and $R^{13c}$ different from hydrogen.

In one embodiment, the invention is concerned with compounds of formula V, wherein $R^{9c}$, $R^{10c}$, $R^{11c}$, $R^{12c}$ and $R^{13c}$ are selected from H and F.

In another embodiment, the invention is concerned with compounds of the general formula V, wherein $R^{4c}$, $R^{5c}$, $R^{6c}$, $R^{7c}$ and $R^{8c}$ are independently selected from hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula V, where there are no covalent bonds between any of the substituents $R^{9c}$, $R^{10c}$, $R^{11c}$, $R^{12c}$ and $R^{13c}$.

In another embodiment, the invention is concerned with compounds of the general formula V, where there are no covalent bonds between any of the substituents $R^{4c}$, $R^{5c}$, $R^{6c}$, $R^{7c}$ and $R^{8c}$.

In an aspect of the invention, compounds are of the general formula VI

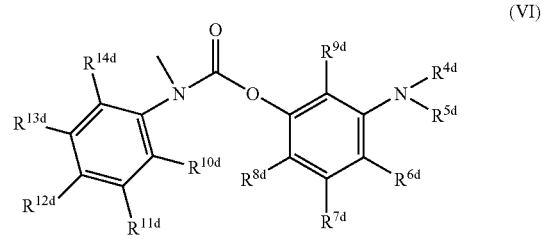

(VI)

wherein $R^{4d}$ and $R^{5d}$ are independently selected from hydrogen, hydroxy, sulfanyl, amino, $C_{2-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, amino, $C_{2-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and $R^{6d}$, $R^{7d}$, $R^{8d}$, $R^{9d}$, $R^{10d}$, $R^{11d}$, $R^{12d}$, $R^{13d}$ and $R^{14d}$ are independently selected from hydrogen, hydroxy, sulfanyl, halogen, amino, cyano, nitro, sulfo, $C_{1-6}$-alkyl, $C_{1-6}$alkoxy, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy:

wherein there may optionally be one or more covalent bonds between any of the substituents selected from the group consisting of $R^{4d}$, $R^{5d}$, $R^{6d}$, $R^{7d}$, $R^{8d}$ and $R^{9d}$; and wherein there may optionally be one or more covalent bonds between any of the substituents selected from the group consisting of $R^{10d}$, $R^{11d}$, $R^{12d}$, $R^{13}$d and $R^{14d}$.

In one embodiment, the invention is concerned with compounds of the general formula VI, wherein $R^{4d}$ and $R^{5d}$ are H.

In another embodiment, the invention is concerned with compounds of the general formula VI, wherein $R^{6d}$, $R^{7d}$, $R^{8d}$ and $R^{9d}$ are selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula VI, wherein $R^{10d}$, $R^{11d}$, $R^{12d}$, $R^{13d}$ and $R^{14d}$ are selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula VI, wherein there are no covalent bonds between any of the substituents $R^{4d}$, $R^{5d}$, $R^{6d}$, $R^{7d}$, $R^{8d}$ and $R^{9d}$.

In another embodiment, the invention is concerned with compounds of the general formula VI, wherein there are no covalent bonds between any of the substituents $R^{10d}$, $R^{11d}$, $R^{12d}$, $R^{13d}$ and $R^{14d}$.

In an aspect of the invention, compounds are of the general formula VII

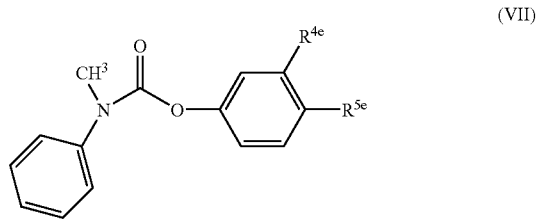

(VII)

wherein $R^{4e}$ is selected from hydrogen, hydroxy, sulfanyl, halogen, amino, cyano, nitro, $C_{2-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of $C_{2-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and $R^{5e}$ is selected from hydrogen, F, cyano, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy;

wherein $R^{4e}$ and $R^{5e}$ may be covalently bound to each other by a C—O bond.

In one embodiment, the invention is concerned with compounds of the general formula VII, wherein $R^{4e}$ or $R^{5e}$ is selected from the group consisting of

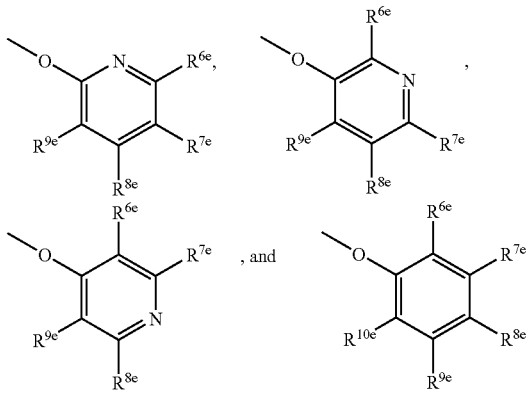

wherein $R^{6e}$, $R^{7e}$, $R^{8e}$, $R^{9e}$ and $R^{10e}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, sulfo, $C_{1-6}$-alkyl, $C_{1-6}$-alkoxy, $C_{2-6}$-alkenyl.

In another embodiment, the invention is concerned with compounds of the general formula VII, wherein $R^{4e}$ or $R^{5e}$ is selected from the group consisting of

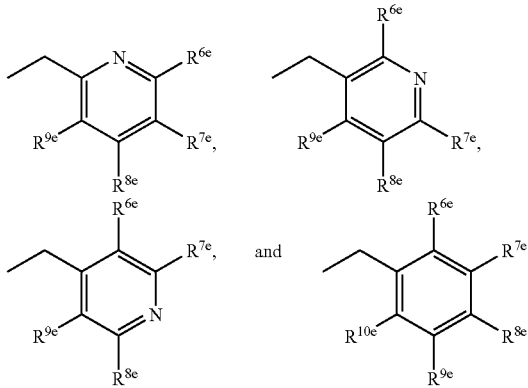

wherein $R^{6e}$, $R^{7e}$, $R^{8e}$, $R^{9e}$ and $R^{10e}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, sulfo, $C_{1-6}$-alkyl, $C_{1-6}$-alkoxy and $C_{2-6}$-alkenyl.

In another embodiment, the invention is concerned with compounds of the general formula VII, wherein at least one of the substituents $R^{6e}$, $R^{7e}$, $R^{8e}$, $R^{9e}$ and $R^{10e}$ are selected from the group consisting of F and perhalomethyl.

In another embodiment, the invention is concerned with compounds of the general formula VII, wherein $R^{4e}$ and $R^{5e}$ are connected by a C—O bond to form the compound

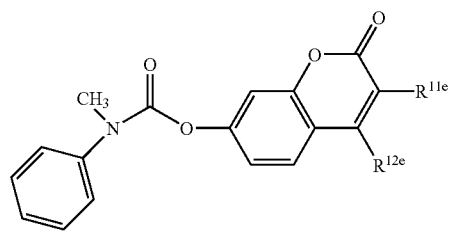

wherein $R^{11e}$ is selected from hydrogen, hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and $R^{12e}$ is selected from hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In an aspect of the invention, compounds are of the general formula VIII

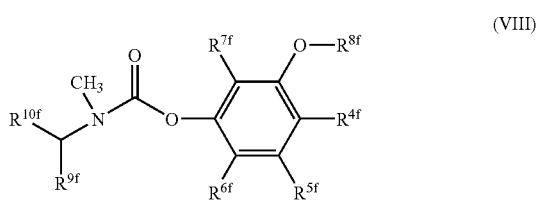

(VIII)

wherein $R^{4f}$, $R^{5f}$, $R^{6f}$, $R^{7f}$, $R^{9f}$ and $R^{10f}$ are independently selected from hydrogen, hydroxy, sulfanyl, halogen, amino, cyano, nitro, sulfo, $C_{1-6}$-alkyl, $C_{1-6}$-alkoxy, $C_{2-6}$-alkenyl, aryl, heteroaryl, $C_{3-8}$heterocyclyl and $C_{3-10}$-cycloalkyl, wherein each of hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: with the proviso that $R^{4f}$ and $R^{5f}$ are not both methoxy; and $R^{8f}$ is selected from hydrogen, sulfo, $C_{1-6}$-alkyl, $C_{1-6}$-alkoxy, $C_{2-6}$-alkenyl, aryl, heteroaryl, $C_{3-8}$-heteroaryl, and $C_{3-10}$-cycloalkyl, wherein each of sulfo, $C_{1-6}$alkyl, $C_{1-6}$alkoxy, $C_{2-6}$-alkenyl, aryl, heteroaryl, $C_{3-8}$-heterocyclyl and $C_{3-10}$-cycloalkyl may optionally be substituted with one or substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{26}$-alkenyl, aryl, heteroaryl, $C_{3-8}$-heterocyclyl and $C_{3-10}$-cycloalkyl, perhalomethyl and perhalomethoxy;

wherein there may optionally be one or more covalent bonds between any of the substituents selected from the group consisting of $R^{4f}$, $R^{5f}$, $R_{6f}$, $R^{7f}$ and $R^{8f}$; and wherein there may optionally be a covalent bond between $R^{9f}$ and $R^{10f}$.

In one embodiment, the invention is concerned with compounds of the general formula VIII, wherein $R^{9f}$ and $R^{10f}$ are covalently bound so as to form a ring system with the C-atom to which they are bound.

In another embodiment, the invention is concerned with compounds of the general formula VIII, wherein said ring system is a cycloalkyl, phenyl, heteroaryl, piperidine, piperazine, morpholine, or thiomorpholine.

In another embodiment, the invention is concerned with compounds of the general formula VIII, wherein $R^{4f}$ and $R^{8f}$ are connected by a C—O bond to form the compound

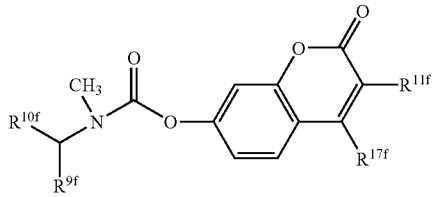

wherein $R^{11f}$ is selected from hydrogen, hydroxy, sulfanyl, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, perhalomethyl and perhalomethoxy; and $R^{17f}$ is selected from hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl; and wherein there may optionally be a covalent bond between $R^{9f}$ and $R^{10f}$.

In an aspect of the invention, compounds are of the general formula IX

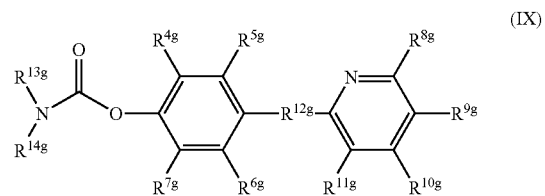

wherein $R^{4g}$, $R^{5g}$, $R^{6g}$, $R^{7g}$, $R^{8g}$, $R^{9g}$, $R^{10g}$ and $R^{11g}$ are independently selected from hydrogen, hydroxy, sulfanyl, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and $R^{12g}$ is selected from the group consisting of —C(=O)—, —C(=O)NH—, —CH$_2$—, —CH$_2$CH$_2$—, —CHR$^{15g}$—, —CH$_2$CHR$^{15g}$—, —CHR$^{15g}$—CH$_2$—, —NH—, —NR$^{15g}$—, —NHC(=O)—, —NR$^{15g}$—C(=O)—, —O—, —S—, —S(=O)—, —S(=O)$_2$—;

wherein $R^{15g}$ is selected from hydrogen, hydroxy, sulfanyl, sulfo, halogen, amino, cyano, nitro, $C_{1-6}$-alkyl, $C_{1-6}$alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, sulfo, $C_{1-6}$-alkyl, $C_{1-6}$-alkoxy, $C_{2-6}$-alkenyl, perhalomethyl and perhalomethoxy; and wherein there may optionally be one or more covalent bonds between any of the substituents selected from the group consisting of $R^{4g}$, $R^{5g}$, $R^{6g}$, $R^{7g}$ and $R^{15g}$; and wherein there may optionally be one or more covalent bonds between any of the substituents selected from the group consisting of $R^{8g}$, $R^{9g}$, $R^{10g}$, $R^{11g}$ and $R^{15g}$; and $R^{13g}$ is selected from hydrogen, hydroxy, sulfanyl, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$alkyl, $C_{1-6}$alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$alkoxy, $C_{2-6}$-alkenyl, aryl, heteroaryl, $C_{3-8}$-heterocyclyl, $C_{3-10}$-cycloalkyl, perhalomethyl and perhalomethoxy: and $R^{14g}$ is selected from hydrogen, hydroxy, sulfanyl, halogen, amino, cyano, nitro, $C_{2-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of $C_{2-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and wherein $R^{13g}$ and $R^{14g}$ may optionally be covalently bound to each other.

In one embodiment, the invention is concerned with compounds of the general formula IX, wherein $R^{13g}$ and $R^{14g}$ are covalently bound so as to form a ring system with the N-atom to which they are bound.

In another embodiment, the invention is concerned with compounds of the general formula IX, wherein said ring system is a piperidine, piperazine, morpholine, or thiomorpholine.

In another embodiment, the invention is concerned with compounds of the general formula IX, wherein there are no covalent bonds between any of the substituents $R^{4g}$, $R^{5g}$, $R^{6g}$, $R^{7g}$ and $R^{15g}$.

In another embodiment, the invention is concerned with compounds of the general formula IX, wherein there are no covalent bonds between any of the substituents $R^{8g}$, $R^{9g}$, $R^{10g}$, $R^{11g}$ and $R^{15g}$.

In another embodiment, the invention is concerned with compounds of the general formula IX, wherein $R^{4g}$, $R^{5g}$, $R^{6g}$, $R^{7g}$, $R^{8g}$, $R^{9g}$, $R^{10g}$, $R^{11g}$ are selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In an aspect of the invention, compounds are of the general formula X

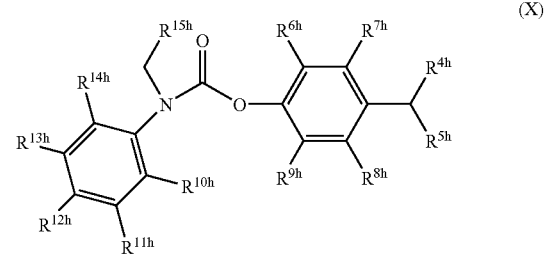

(X)

wherein $R^{4h}$ and $R^{5h}$ are independently selected from cyano, $C_{1-6}$-alkyl, $C_{2-6}$-alkenyl, aryl, heteroaryl, $C_{3-8}$-heterocyclyl and $C_{3-10}$-cycloalkyl, wherein each of $C_{1-6}$-alkyl, $C_{2-6}$-alkenyl, aryl heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and $R^{6h}$, $R^{7h}$, $R^{8h}$, $R^{9h}$, $R^{10h}$, $R^{12h}$, $R^{14h}$ and $R^{15h}$ are independently selected from hydrogen, hydroxy, sulfanyl, halogen, amino, cyano, nitro, $C_{1-6}$alkyl, $C_{1-6}$alkoxy, $C_{2-6}$-alkenyl, aryl, heteroaryl, $C_{3-8}$-heterocyclyl and $C_{3-10}$-cycloalkyl, wherein each of $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy: and $R^{11h}$ and $R^{13h}$ are independently selected from hydrogen, hydroxy, sulfanyl, halogen, amino, cyano, nitro, perhalomethyl, perhalomethoxy, $C_{2-6}$-alkyl, methoxy, $C_{3-6}$-alkoxy, $C_{2-6}$-alkenyl, aryl, heteroaryl, $C_{3-8}$-heterocyclyl and $C_{3-10}$-cycloalkyl, wherein each of sulfanyl, amino, $C_{2-6}$-alkyl, $C_{3-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$alkoxy, $C_{2-6}$-alkenyl, aryl, heteroaryl, $C_{3-8}$-heterocyclyl and $C_{3-10}$-cycloalkyl, perhalomethyl and perhalomethoxy: and wherein there may optionally be one or more covalent bonds between any of the substituents selected from the group consisting of $R^{4h}$, $R^{5h}$, $R^{6h}$, $R^{7h}$, $R^{8h}$, $R^{9h}$; and wherein there may optionally be one or more covalent bonds between any of the substituents selected from the group consisting of $R^{10h}$, $R^{11h}$, $R^{12h}$, $R^{13h}$, $R^{14h}$ and $R^{15h}$.

In one embodiment, the invention is concerned with compounds of the general formula X, wherein $R^{6h}$, $R^{7h}$, $R^{8h}$, $R^{9h}$, $R^{10h}$, $R^{12h}$ and $R^{14h}$ are selected from the group consisting of hydrogen, F, Cl, $C_{1-6}$alkyl, $C_{1-6}$alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula X, wherein there are no covalent bonds between $R^{4h}$, $R^{5h}$, $R^{6h}$, $R^{7h}$, $R^{8h}$ and $R^{9h}$.

In another embodiment, the invention is concerned with compounds of the general formula X, wherein there are no covalent bonds between $R^{10h}$, $R^{11h}$, $R^{12h}$, $R^{13h}$, $R^{14h}$ and $R^{15h}$.

In another embodiment, the invention is concerned with compounds of the general formula X, wherein $R^{15h}$ is hydrogen.

In another embodiment, the invention is concerned with compounds of the general formula X, wherein $R^{11h}$ and $R^{13h}$ are selected from the group consisting of hydrogen, F, Cl, $C_{2-6}$-alkyl, methoxy, $C_{3-6}$-alkoxy, —NHC(=O)—OH, —S(=O)$_2$—NH$_2$, —NH—S(=O)$_2$—OH, hydroxy, amino and perhalomethyl.

In an aspect of the invention, compounds are of the general formula XI $R^{5i}$ s selected from hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$alkyl, $C_{1-6}$alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and $R^{6i}$, $R^{7i}$, $R^{8i}$, $R^{9i}$, $R^{10i}$, $R^{14i}$ and $R^{15i}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy: and $R^{11i}$ and $R^{13i}$ are independently selected from hydrogen, hydroxy, sulfanyl, sulfo, halogen, amino, cyano, nitro, $C_{1-6}$-alkyl, methoxy, $C_{3-6}$-alkoxy, $C_{2-6}$-alkenyl, aryl, heteroaryl, $C_{3-8}$-heterocyclyl and $C_{3-10}$-cycloalkyl, wherein each of sulfanyl, sulfo, $C_{1-6}$-alkyl, $C_{3-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy: and $R^{12i}$ is selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, F, amino, cyano, nitro, sulfo, $C_{1-6}$l-alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy.

In one embodiment, the invention is concerned with compounds of the general formula XI, wherein $R^{6i}$, $R^{7i}$, $R^{8i}$ and $R^{9i}$ are selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XI, wherein $R^{10i}$, $R^{11i}$, $R^{12i}$, $R^{13i}$ and $R^{14i}$ are selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XI, wherein $R^{15i}$ is hydrogen.

In another embodiment, the invention is concerned with compounds of the general formula XI, wherein $R^{10i}$, $R^{11i}$, $R^{12i}$, $R^{13i}$, $R^{14i}$ and $R^{15i}$ are selected from the group consisting of H, F and methyl.

In an aspect of the invention, compounds are of the general formula XII

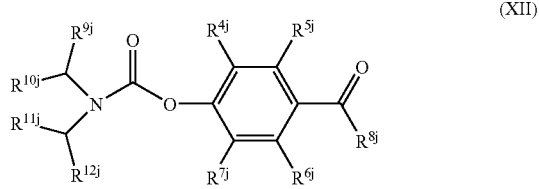

(XII)

wherein $R^{4j}$, $R^{5j}$, $R^{6j}$, $R^{7j}$, $R^{8j}$, $R^{9j}$ and $R^{10j}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_2$-4-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$cycloalkyl, perhalomethyl and perhalomethoxy: and wherein there may optionally be a covalent bond between the substituents $R^{6j}$ and $R^{7j}$; and wherein there may optionally be a covalent bond between $R^{5j}$ and $R^{8j}$; and $R^{11j}$ and $R^{12j}$ are independently selected from cyano, $C_1$-alkyl, $C_{2-6}$-alkenyl, aryl, heteroaryl, $C_{3-8}$-heterocyclyl and $C_{3-10}$-cycloalkyl, wherein each of $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy; and with the proviso that $R^{9j}$ and $R^{10j}$ are both hydrogen, there may optionally be a covalent bond connecting $R^{11j}$ and $R_{12j}$.

In one embodiment, the invention is concerned with compounds of the general formula XII, wherein $R^{4j}$, $R^{5j}$, $R^{6j}$ and $R_{7j}$ are selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XII, wherein at least one of the substituents $R^{4j}$, $R^{5j}$, $R^{6j}$ and $R^{7j}$ are different from hydrogen.

In another embodiment, the invention is concerned with compounds of the general formula XII, wherein $R^{8j}$ is covalently bound to $R^{5j}$.

In an aspect of the invention, compounds are of the general formula XIII

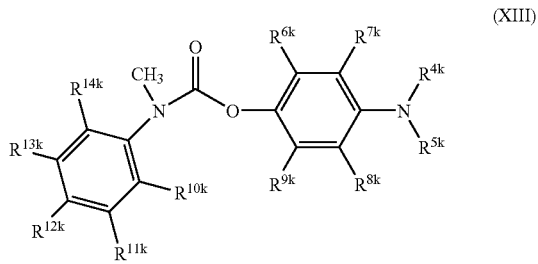

(XIII)

wherein $R^{4k}$ is selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy: and $R^{5k}$ is selected from hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$alkyl, $C_{1-6}$alkoxy, $C_{2-6}$-alkenyl, aryl, heteroaryl, $C_{3-8}$-heterocyclyl and $C_{3-10}$-cycloalkyl, perhalomethyl and perhalomethoxy: with the proviso that when $R^{4k}$ is hydrogen, then $R^{5k}$ is not $C(=O)N(Me)_2$; and $R^{6k}$, $R^{7k}$, $R^{8k}$, $R^{9k}$, $R^{10k}$, $R^{11k}$, $R^{13k}$ and $R^{14k}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy: and $R^{12k}$ is selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl perhalomethyl and perhalomethoxy: and wherein there may optionally be a covalent bond between any of the substituents selected from the group consisting of $R^{4k}$, $R^{5k}$, $R^{7k}$ and $R^{8k}$; and wherein there may optionally be a covalent bond between $R^{5k}$ and any one of the substituents $R^{7k}$ and $R^{8k}$; and wherein there may optionally be one or more covalent bonds between $R^{10k}$, $R^{11k}$, $R^{12k}$, $R^{13k}$ and $R^{14k}$.

In one embodiment, the invention is concerned with compounds of the general formula XIII, wherein the substituents $R^{4k}$ and $R^{5k}$ are connected by a covalent bond.

In another embodiment, the invention is concerned with compounds of the general formula XIII, wherein the substituents $R^{5k}$ and $R^{8k}$ are connected by a covalent bond.

In another embodiment, the invention is concerned with compounds of the general formula XIII, wherein the substituents $R^{10k}$ and $R^{11k}$ are connected by a covalent bond.

In another embodiment, the invention is concerned with compounds of the general formula XIII, wherein the substituents $R^{12k}$ and $R^{13k}$ are connected by a covalent bond.

In another embodiment, the invention is concerned with compounds of the general formula XIII, wherein $R^{6k}$, $R^{7k}$, $R^{8k}$ and $R^{9k}$ are selected from the group consisting of hydrogen, F, Cl, hydroxy, amino, methyl, methoxy, ethoxy and perhalomethyl.

In another embodiment, the invention is concerned with compounds of the general formula XIII, wherein $R^{10k}$, $R^{11k}$, $R^{12k}$, $R^{13k}$ and $R^{14k}$ are selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In an aspect of the invention, compounds are of the general formula XIV

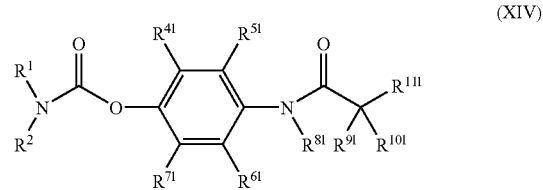

(XIV)

wherein $R^1$ is $C_{1-6}$-alkyl, $C_{2-6}$-alkenyl or $C_{3-10}$-cycloalkyl, each of which is optionally substituted with one or more substituents independently selected from hydroxy, sulfanyl, oxo, halogen, amino, cyano and nitro; and $R^2$ is $C_{1-6}$alkyl, $C_{2-6}$-alkenyl, aryl, heteroaryl, $C_{3-8}$-heterocyclyl, or $C_{3-10}$-cycloalkyl, each which is optionally substituted with one or more substituents independently selected from hydroxy, sulfanyl, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, cyano, nitro, perhalomethyl and perhalomethoxy; with the proviso that when $R^1$ and $R^2$ are identical they are not methyl or benzyl; and $R^2$ is optionally covalently bound to $R^1$ by an ether, thioether or C—C bond, to form a ring system with the N-atom to which $R^1$ and $R^2$ are bound; and $R^{5l}$, $R^{6l}$, $R^{8l}$, $R^{9l}$, $R^{10l}$ and $R^{11l}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$- alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy: and $R^{4l}$ and $R^{7l}$ are independently selected from hydrogen, hydroxy, sulfanyl, sulfo, halogen, amino, cyano, nitro, $C_{1-6}$-alkyl, methoxy, $C_{3-6}$-alkoxy, $C_{2-6}$-alkenyl, aryl, heteroaryl, $C_{3-8}$-heterocyclyl and $C_{3-10}$-cycloalkyl, wherein each of sulfanyl, sulfo, amino, $C_{1-6}$-alkyl, $C_{3-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy: and wherein there may optionally be one or more covalent bonds between any of the substituents selected from the group consisting of $R^{4l}$, $R^{5l}$, $R^{6l}$, $R^{7l}$, $R^{8l}$, $R^{9l}$, $R^{10l}$ and $R^{11l}$.

In one embodiment, the invention is concerned with compounds of the general formula XIV, wherein $R^1$ and $R^2$ are covalently bound so as to form a ring system with the N-atom to which they are bound.

In another embodiment, the invention is concerned with compounds of the general formula XIV, wherein said ring system is a piperidine, piperazine, morpholine, or thiomorpholine.

In another embodiment, the invention is concerned with compounds of the general formula XIV, wherein there are no covalent bonds between $R^1$ and $R^2$.

In another embodiment, the invention is concerned with compounds of the general formula XIV, wherein there are no covalent bonds between $R^{8l}$ and any of the substituents selected from the group consisting of $R^{9l}$, $R^{10l}$, $R^{11l}$.

In another embodiment, the invention is concerned with compounds of the general formula XIV, wherein there are no covalent bonds between $R^{8l}$ and any of the substituents selected from the group consisting of $R^{4l}$, $R^{5l}$, $R^{6l}$ and $R^{7l}$.

In another embodiment, the invention is concerned with compounds of the general formula XIV, wherein there are no covalent bonds between any of the substituents $R^{4l}$, $R^{5l}$, $R^{6l}$, $R^{7l}$, $R^{8l}$, $R^{9l}$, $R^{10l}$ and $R^{11l}$.

In another embodiment, the invention is concerned with compounds of the general formula XIV, wherein $R^{4l}$, $R^{5l}$, $R^{6l}$ and $R^{7l}$ are selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In an aspect of the invention, compounds are of the general formula XV

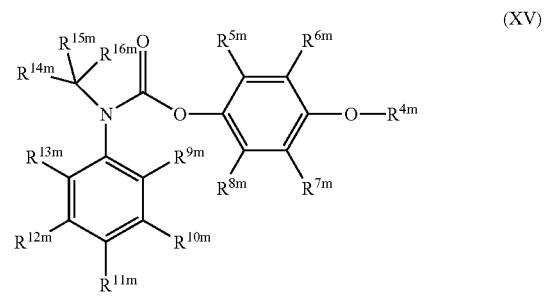

(XV)

wherein $R^{4m}$ is selected from hydrogen, sulfo, $C_{1-6}$-alkyl, $C_{2-6}$-alkenyl, aryl, heteroaryl, $C_{3-8}$-heterocyclyl and $C_{3-10}$-cycloalkyl, wherein each of sulfo, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and $R^{5m}$, $R^{6m}$, $R^{7m}$, $R^{8m}$, $R^{9m}$, $R^{10m}$, $R^{11m}$, $R^{12m}$, $R^{13m}$, $R^{14m}$, $R^{15m}$ and $R^{16m}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy: and wherein there may optionally be one or more covalent bonds between any of the substituents selected from the group consisting of $R^{4m}$, $R^{5m}$, $R^{6m}$, $R^{7m}$ and $R_{8m}$; and wherein there may optionally be one or more covalent bonds between any of the substituents selected from the group consisting of $R^{9m}$, $R^{10m}$, $R^{11m}$, $R^{12m}$, $R^{13m}$, $R^{14m}$, $R^{15m}$ and $R^{16m}$.

In one embodiment, the invention is concerned with compounds of the general formula XV, wherein there are no covalent bonds between any of the substituents selected from the group consisting of $R^{5m}$, $R^{6m}$, $R^{7m}$ and $R^{8m}$.

In another embodiment, the invention is concerned with compounds of the general formula XV, wherein there are no covalent bonds between any of the substituents $R^{9m}$, $R^{10m}$, $R^{11m}$, $R^{12m}$ and $R^{13m}$.

In another embodiment, the invention is concerned with compounds of the general formula XV, wherein there are no covalent bonds between any of the substituents $R^{14m}$, $R^{15m}$ and $R^{16m}$.

In another embodiment, the invention is concerned with compounds of the general formula XV, wherein $R^{4m}$ is covalently bound to $R^{6m}$.

In another embodiment, the invention is concerned with compounds of the general formula XV, wherein $R^{5m}$, $R^{6m}$, $R^{7m}$, $R^{8m}$, $R^{9m}$, $R^{10m}$, $R^{11m}$, $R^{12m}$, $R^{13m}$ and $R^{14m}$ are selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XV, wherein $R^{14m}$, $R^{15m}$ and $R^{16m}$ are selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In an aspect of the invention, compounds are of the general formula XVI

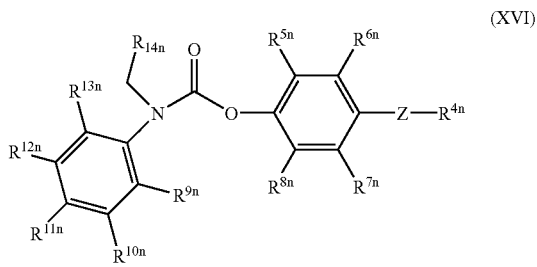

(XVI)

wherein $R^{4n}$ is selected from hydrogen, sulfo, $C_{2-6}$-alkyl, $C_{2-6}$-alkenyl, aryl, heteroaryl, $C_{3-8}$-heterocyclyl and $C_{3-10}$-cycloalkyl, wherein each of sulfo, $C_{2-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy; and Z is selected from S, S(=O) and S(=O)$_2$; and $R^{5n}$, $R^{6n}$, $R^{7n}$, $R^{8n}$, $R^{9n}$, $R^{10n}$, $R^{11n}$, $R^{12n}$, $R^{13n}$ and $R^{14n}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy: and wherein there may optionally be one or more covalent bonds between any of the substituents selected from the group consisting of $R^{4n}$, $R^{5n}$, $R^{6n}$, $R^{7n}$ and $R^{8n}$,; and wherein there may optionally be one or more covalent bonds between any of the substituents selected from the group consisting of $R^{10n}$, $R^{11n}$, $R^{12n}$ and $R^{14n}$; and at least one of the substituents $R^{5n}$, $R^{6n}$, $R^{7n}$, $R^{8n}$, $R^{9n}$, $R^{10n}$, $R^{11n}$, $R^{12n}$, $R^{13n}$ and $R^{14n}$ are different from hydrogen.

In one embodiment, the invention is concerned with compounds of the general formula XVI, wherein there are no covalent bonds between any of the substituents $R^{5n}$, $R^{6n}$, $R^{7n}$ and $R^{8n}$.

In another embodiment, the invention is concerned with compounds of the general formula XVI, wherein there are no covalent bonds between any of the substituents $R^{10n}$, $R^{11n}$, $R^{12n}$.

In another embodiment, the invention is concerned with compounds of the general formula XVI, wherein $R^{14n}$ is not covalently bound to any other substituent selected from the group consisting of $R^{4n}$, $R^{5n}$, $R^{6n}$, $R^{7n}$, $R^{8n}$, $R^{10n}$, $R^{11n}$, $R^{12n}$.

In another embodiment, the invention is concerned with compounds of the general formula XVI, wherein $R^{4n}$ is covalently bound to $R^{6n}$.

In another embodiment, the invention is concerned with compounds of the general formula XVI, wherein $R^{5n}$, $R^{6n}$, $R^{7n}$ and $R^{8n}$ are independently selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XVI, wherein $R^{14n}$ is selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In an aspect of the invention, compounds are of the general formula XVII

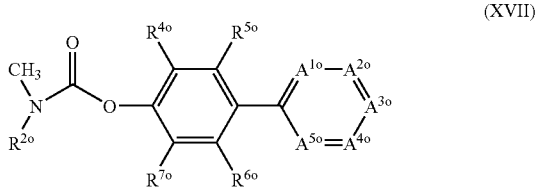

(XVII)

wherein $R^{2o}$ is selected from sulfo, $C_{1-6}$-alkyl, $C_{2-6}$-alkenyl, aryl, heteroaryl, $C_{3-8}$-heterocyclyl and $C_{3-10}$-cycloalkyl, each of which may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; with the proviso that $R^{2o}$, is not methyl; and $R^{4o}$, $R^{5o}$, $R^{6o}$ and $R^{7o}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy: and $A^{1o}$ is N or C—$R^{8o}$; $A^{2o}$ is N or C—$R^{9o}$; $A^{3o}$ is N or C—$R^{10o}$; $A^{4o}$ is N or C—$R^{11o}$; and $A^{5o}$ is N or C—$R^{12o}$; and wherein $R^{8o}$, $R^{9o}$, $R^{10o}$, $R^{11o}$ and $R^{12o}$ are independently selected from hydrogen, hydroxy, sulfanyl, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, cyano, nitro, sulfo, $C^{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, cyano, nitro, $C_{1-6}$alkyl, perhalomethyl and perhalomethoxy; with the proviso that when $A^{1o}$, $A^{2o}$, $A^{3o}$, $A^{4o}$ and $A^{5o}$ are all CH, and $R^{4o}$, $R^{5o}$, $R^{6o}$ and $R^{7o}$ are all hydrogen, then $R^{2o}$ is not phenyl; and wherein there may optionally be one or more covalent bonds between any of the substituents selected from the group consisting of $R^{4o}$, $R^{5o}$, $R^{6o}$, $R^{7o}$, $R^{8o}$, $R^{9o}$, $R^{10o}$, $R^{11o}$ and $R^{12o}$ In one embodiment, the invention is concerned with compounds of the general formula XVII, wherein there are no covalent bonds between any of the substituents $R^{4o}$, $R^{5o}$, $R^{6o}$ and $R^{7o}$.

In another embodiment, the invention is concerned with compounds of the general formula XVII, wherein there are no covalent bonds between any of the substituents $A^{1o}$, $A^{2o}$, $A^{3o}$, $A^{4o}$ and $A^{5o}$.

In another embodiment, the invention is concerned with compounds of the general formula XVII, wherein $R^{2o}$ is selected from the group consisting of cycloalkyl, phenyl, piperidine, piperazine, morpholine, thiomorpholine and heteroaryl.

In another embodiment, the invention is concerned with compounds of the general formula XVII, wherein $R^{4o}$, $R^{5o}$, $R^{6o}$ and $R^{7o}$ are independently selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In an aspect of the invention, compounds are of the general formula XVIII

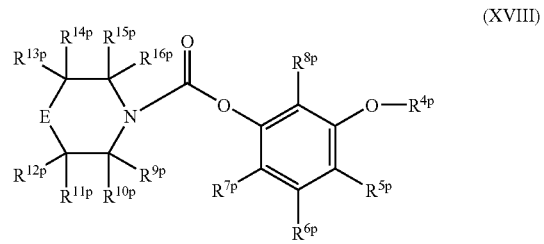

(XVIII)

wherein $R^{4p}$ is selected from hydrogen, sulfo, $C_{2-6}$-alkyl, $C_{2-6}$-alkenyl, aryl, heteroaryl, $C_{3-8}$-heterocyclyl and $C_{3-10}$-cycloalkyl, wherein each of sulfo, $C_{2-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, F, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and $R^{5p}$, $R^{6p}$, $R^{7p}$ and $R^{8p}$ are independently selected from hydrogen, hydroxy, sulfanyl, sulfo, F, amino, cyano, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and $R^{9p}$, $R^{10p}$, $R^{11p}$, $R^{12p}$, $R^{13p}$, $R^{14p}$, $R^{15p}$ and $R^{16p}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and wherein there may optionally be one or more covalent bonds between any of the substituents selected from the group consisting of $R^{5p}$, $R^{6p}$ and $R^{7p}$; and wherein there may optionally be a covalent bond between $R^{4p}$ and $R^{5p}$ so as to form a chromen ring system; and wherein there may optionally be one or more covalent bonds between any of the substituents selected from the group consisting of $R^{9p}$, $R^{10p}$, $R^{11p}$, $R^{12p}$, $R^{13p}$, $R^{14p}$, $R^{15p}$ and $R^{16p}$; and E is selected from the group consisting of —O—, —S—, —S(=O)—, —S(=O)$_2$—, —NR$^{17p}$— and —CR$^{17p}$R$^{18p}$—; and wherein $R^{17p}$ and $R^{18p}$ are independently selected from hydrogen, hydroxy, sulfanyl, sulfo, halogen, amino, cyano, nitro, $C_{1-6}$alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy.

In one embodiment, the invention is concerned with compounds of the general formula XVIII, wherein E is selected from the group consisting of —O— and —CR$^{17p}$R$^{18p}$—.

In another embodiment, the invention is concerned with compounds of the general formula XVIII, wherein $R^{4p}$ and $R^{5p}$ are connected by a covalent bond so as to form said chromen ring system.

In another embodiment, the invention is concerned with compounds of the general formula XVIII, wherein $R^{4p}$ and $R^{5p}$ are connected by a covalent bond so as to form the chromen ring system

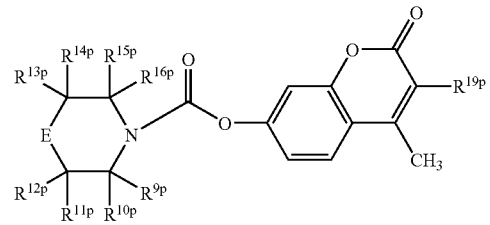

wherein $R^{19p}$ is selected from the group consisting of hydrogen, hydroxy, sulfanyl, sulfo, halogen, amino, cyano, nitro, $C_{1-6}$alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$alkyl, $C_{1-6}$alkoxy, $C_{2-6}$-alkenyl, aryl, heteroaryl, $C_{3-8}$-heterocyclyl, $C_{3-10}$-cycloalkyl, perhalomethyl and perhalomethoxy.

In another embodiment, the invention is concerned with compounds of the general formula XVIII, wherein $R^{4p}$ is selected from the group consisting of

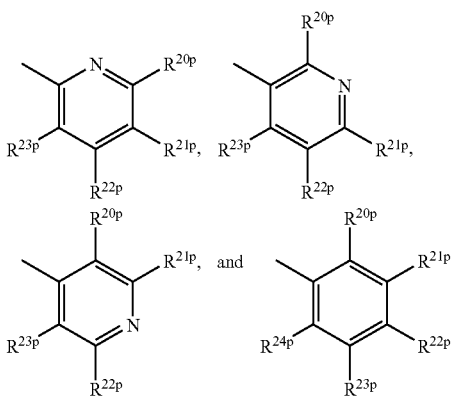

wherein $R^{20p}$, $R^{21p}$, $R^{22p}$, $R^{23p}$ and $R^{24p}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, sulfo, $C_{1-6}$-alkyl, $C_{1-6}$-alkoxy, $C_{2-6}$-alkenyl, perhalomethyl and perhalomethoxy.

In another embodiment, the invention is concerned with compounds of the general formula XVIII, wherein there are no covalent bonds between any of the substituents $R^{4p}$, $R^{5p}$, $R^{6p}$, $R^{7p}$ and $R^{8p}$.

In another embodiment, the invention is concerned with compounds of the general formula XVIII, wherein there are no covalent bonds between any of the substituents $R^{9p}$, $R^{10p}$, $R^{11p}$, $R^{12p}$, $R^{13p}$, $R^{14p}$, $R^{15p}$ and $R^{16p}$.

In another embodiment, the invention is concerned with compounds of the general formula XVIII, wherein $R^{10p}$ and $R^{11p}$ are connected by a covalent bond.

In another embodiment, the invention is concerned with compounds of the general formula XVIII, wherein $R^{9p}$, $R^{10p}$, $R^{11p}$, $R^{12p}$, $R^{13p}$, $R^{14p}$, $R^{15p}$ and $R^{16p}$ are independently selected from hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XVIII, wherein $R^{5p}$, $R^{6p}$, $R^{7p}$ and $R^{8p}$ are independently selected from hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In an aspect of the invention, compounds are of the general formula XIX

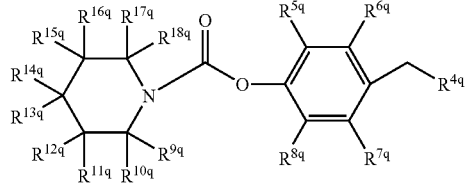

(XIX)

wherein $R^{4q}$, $R^{6q}$, $R^{7q}$, $R^{9q}$, $R^{10q}$, $R^{11q}$, $R^{12q}$, $R^{13q}$, $R^{14a}$, $R^{15q}$, $R^{16q}$, $R^{17q}$, $R^{18q}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and $R^{5q}$ and $R^{8q}$ are independently selected from hydrogen, hydroxy, sulfanyl, sulfo, F, Br, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and wherein there may optionally be one or more covalent bonds between any of the substituents selected from the group consisting of $R^{4q}$, $R^{5q}$, $R^{6q}$, $R^{7q}$ and $R^{8q}$; and wherein there may optionally be one or more covalent bonds between any of the substituents selected from the group consisting of $R^{9q}$, $R^{10q}$, $R^{11q}$, $R^{12q}$, $R^{13q}$, $R^{14q}$, $R^{15q}$, $R^{16q}$, $R^{17q}$ and $R^{18q}$.

In one embodiment, the invention is concerned with compounds of the general formula XIX, wherein $R^{4q}$ and $R^{6q}$ are connected by a covalent bond.

In another embodiment, the invention is concerned with compounds of the general formula XIX, wherein $R^{4q}$ is selected from the group consisting of substituted heteroaryl and substituted $C_{3-8}$-heterocyclyl.

In another embodiment, the invention is concerned with compounds of the general formula XIX, wherein $R^{4q}$ is selected from the group consisting of

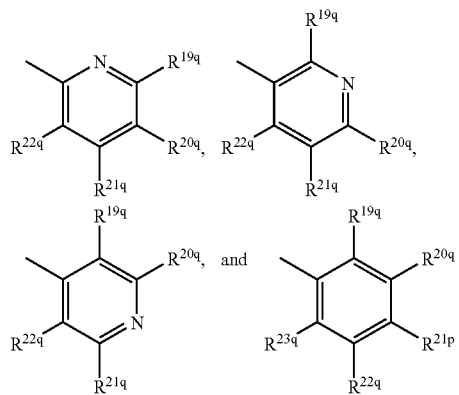

wherein $R^{19q}$, $R^{20q}$, $R^{21q}$, $R^{22q}$ and $R^{23q}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C^{3-10}$-cycloalkyl may optionally be substituted with one or more substituents independently selected from hydroxy, sulfanyl, sulfo, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy.

In another embodiment, the invention is concerned with compounds of the general formula XIX, wherein there are no covalent bonds between any of the substituents $R^{4q}$, $R^{5q}$, $R^{6q}$, $R^{7q}$ and $R^{8q}$.

In another embodiment, the invention is concerned with compounds of the general formula XIX, wherein there are no covalent bonds between any of the substituents $R^{9q}$, $R^{10q}$, $R^{11q}$, $R^{12q}$, $R^{13q}$, $R^{14q}$, $R^{15q}$, $R^{16q}$, $R^{17q}$ and $R^{18q}$.

In another embodiment, the invention is concerned with compounds of the general formula XIX, wherein $R^{10p}$ and $R^{11p}$ are connected by a covalent bond.

In another embodiment, the invention is concerned with compounds of the general formula XIX, wherein $R^{11p}$ and $R^{13p}$ are connected by a covalent bond.

In another embodiment, the invention is concerned with compounds of the general formula XIX, wherein $R^{9q}$, $R^{10q}$, $R^{11q}$, $R^{12q}$, $R^{13q}$, $R^{14q}$, $R^{15q}$, $R^{16q}$, $R^{17q}$ and $R^{18q}$ are independently selected from hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XIX, wherein $R^{9q}$, $R^{10q}$, $R^{11q}$, $R^{12q}$, $R^{14q}$, $R^{15q}$, $R^{16q}$, $R^{17q}$ and $R^{18q}$ are all hydrogen or F.

In another embodiment, the invention is concerned with compounds of the general formula XIX, wherein $R^{5q}$, $R^{6q}$, $R^{7q}$ and $R^{8q}$ are independently selected from hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In an aspect of the invention, compounds are of the general formula XX

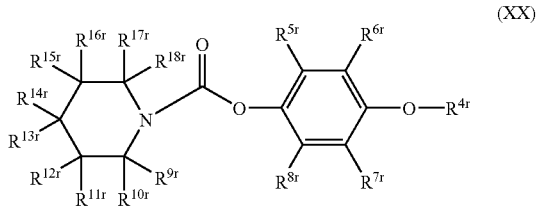

wherein $R^{4r}$ is selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: provided that $R^{4r}$ is not methyl or phenyl; and $R^{5r}$ $R^{6r}$, $R^{7r}$, $R^{8r}$, $R^{9r}$, $R^{10r}$, $R^{11r}$, $R^{12r}$, $R^{13r}$, $R^{14r}$, $R^{15r}$, $R^{16r}$, $R^{17r}$ and $R^{18r}$ are independently selected from hydrogen, hydroxy, sulfanyl, sulfo, F, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and wherein there may optionally be one or more covalent bonds between any of the substituents selected from the group consisting of $R^{5r}$, $R^{6r}$, $R^{7r}$ and $R^{8r}$; and wherein there may optionally be one or more covalent bonds between any of the substituents selected from the group consisting of $R^{9r}$, $R^{10r}$, $R^{11r}$, $R^{12r}$, $R^{13r}$, $R^{14r}$, $R^{15r}$, $R^{16r}$, $R^{17r}$ and $R^{18r}$.

In one embodiment, the invention is concerned with compounds of the general formula XX, wherein $R^{4r}$ and $R^{5r}$ are connected by a covalent bond.

In another embodiment, the invention is concerned with compounds of the general formula XX, wherein $R^{4r}$ is selected from the group consisting of substituted heteroaryl and substituted $C_{3-8}$-heterocyclyl.

In another embodiment, the invention is concerned with compounds of the general formula XX, wherein $R^{4r}$ is selected from the group consisting of

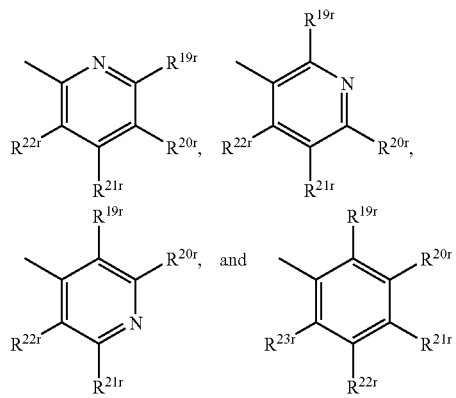

wherein $R^{19r}$, $R^{20r}$, $R^{21r}$, $R^{22r}$ and $R^{23r}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy.

In another embodiment, the invention is concerned with compounds of the general formula XX, wherein there are no covalent bonds between any of the substituents $R^{5r}$, $R^{6r}$, $R^{7r}$ and $R^{8r}$.

In another embodiment, the invention is concerned with compounds of the general formula XX, wherein there are no covalent bonds between any of the substituents $R^{9r}$, $R^{10r}$, $R^{11r}$, $R^{12r}$, $R^{13}r$, $R^{14}r$, $R^{15r}$ and $R^{16r}$.

In another embodiment, the invention is concerned with compounds of the general formula XX, wherein $R^{10r}$ and $R^{11r}$ are connected by a covalent bond.

In another embodiment, the invention is concerned with compounds of the general formula XX, wherein $R^{11r}$ and $R^{13r}$ are connected by a covalent bond.

In another embodiment, the invention is concerned with compounds of the general formula XX, wherein $R^{9r}$, $R^{10r}$, $R^{11r}$, $R^{12r}$, $R^{13r}$, $R^{14r}$, $R^{15r}$, $R^{16r}$, $R^{17r}$ and $R^{18r}$ are independently selected from hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XX, wherein $R^{9r}$, $R^{10r}$, $R^{11r}$, $R^{12r}$, $R^{14r}$, $R^{15r}$, $R^{16r}$, $R^{17r}$ and $R^{18r}$ are all hydrogen or F.

In another embodiment, the invention is concerned with compounds of the general formula XX, wherein $R^{5r}$, $R^{6r}$, $R^{7r}$ and $R^{8r}$ are independently selected from hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In an aspect of the invention, compounds are of the general formula XXI (XXI)

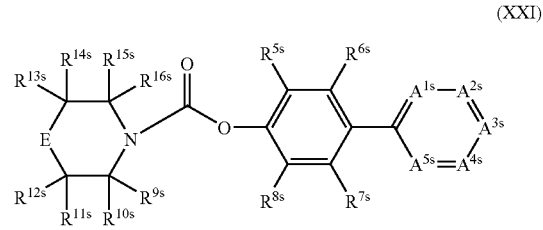

wherein $A^{1s}$ is N or C—$R^{17s}$; $A^{2s}$ is N or C—$R^{18s}$; $A^{3s}$ is N or C—$R^{19s}$; $A^{4s}$ is N or C—$R^{20s}$; and $A^{5s}$ is N or C—$R^{21s}$; and wherein $R^{17s}$, $R^{18s}$, $R^{19s}$, $R^{20s}$ and $R^{21s}$ are independently selected from hydrogen, hydroxy, sulfanyl, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, oxo, halogen, amino, cyano, nitro, $C_{1-6}$-alkyl, $C_{2-6}$-alkenyl, aryl, heteroaryl, $C_{3-8}$-heterocyclyl, $C_{3-10}$-cycloalkyl, perhalomethyl and perhalomethoxy; and $R^{5s}$, $R^{6s}$, $R^{7s}$ and $R^{8s}$ are independently selected from hydrogen, hydroxy, sulfanyl, sulfo, F, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and $R^{9s}$, $R^{10s}$, $R^{11s}$, $R^{12s}$, $R^{13s}$, $R^{14s}$, $R^{15s}$ and $R^{16s}$ are independently selected from hydrogen, hydroxy, sulfanyl, sulfo, F, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: and E is selected from the group consisting of —O—, —S—, —S(═O)—, —S(═O)$_2$—, —NR$^{22s}$— and —CR$^{22s}$R$^{23s}$—; and wherein $R^{22s}$ and $R^{23s}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, $C_{1-6}$-alkyl, $C_{2-6}$-alkenyl, aryl, heteroaryl, $C_{3-8}$-heterocyclyl, $C_{3-10}$-cycloalkyl, perhalomethyl and perhalomethoxy; and wherein there may optionally be one or more covalent bonds between any of the substituents selected from the group consisting of $R^{5s}$, $R^{6s}$, $R^{7s}$ and $R^{8s}$; and wherein there may optionally be one or more covalent bonds between any of the substituents selected from the group consisting of $R^{9s}$, $R^{10s}$, $R^{11s}$, $R^{12s}$, $R^{13s}$, $R^{14s}$, $R^{15s}$, $R^{16s}$, $R^{18s}$, $R^{19s}$, $R^{20s}$, $R^{21s}$, $R^{22s}$ and $R^{23s}$.

In one embodiment, the invention is concerned with compounds of the general formula XXI, wherein E is selected from the group consisting of —O— and —CR$^{22s}$R$^{23s}$—.

In another embodiment, the invention is concerned with compounds of the general formula XXI, wherein there are no covalent bonds between any of the substituents $R^5$s, $R^6$s, $R^{7s}$ and $R^{8s}$.

In another embodiment, the invention is concerned with compounds of the general formula XXI, wherein $R^{5s}$, $R^{6s}$, $R^{7s}$ and $R^{8s}$ are independently selected from the group consisting of hydrogen, F, Cl, $C_{1-6}$-alkyl, $C_{1-6}$-alkoxy, —C(═O)NH$_2$, —NHC(═O)—OH, —S(═O)$_2$—NH$_2$, —NH—S(═O)$_2$—OH, hydroxy, amino and perhalomethyl.

In another embodiment, the invention is concerned with compounds of the general formula XXI, wherein there is a covalent bond between $R^{10s}$ and $R^{11s}$.

In another embodiment, the invention is concerned with compounds of the general formula XXI, wherein there is a covalent bond between $R^{13s}$ and $R^{22s}$.

In another embodiment, the invention is concerned with compounds of the general formula XXI, wherein $R^{9s}$, $R^{10s}$, $R^{11s}$, $R^{12s}$, $R^{13s}$, $R^{14s}$, $R^{15s}$ and $R^{16s}$ are all hydrogen or F.

In an aspect of the invention, compounds are of the general formula XXII

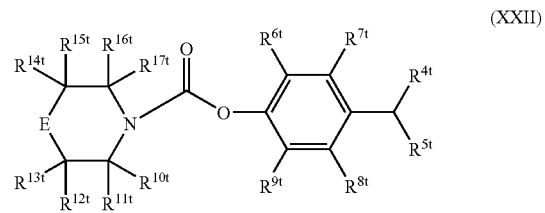

(XXII)

wherein E is selected from the group consisting of —O—, —S—, —S(═O)—, —S(═O)$_2$—, —NR$^{18t}$— and —CR$^{18t}$R$^{19t}$—; and $R^{4t}$, $R^{5t}$, $R^{6t}$, $R^{7t}$, $R^{8t}$, $R^{9t}$, $R^{10t}$, $R^{11t}$, $R^{12t}$, $R^{13t}$, $R^{14t}$, $R^{15t}$, $R^{16t}$, $R^{17t}$, $R^{18t}$ and $R^{19t}$ are independently selected from hydrogen, hydroxy, sulfanyl, sulfo, halogen, amino, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$- heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; with the proviso that $R^{4t}$ and $R^{5t}$ are not both methyl; and wherein there may optionally be one or more covalent bonds between any of the substituents selected from the group consisting of $R^{9t}$, $R^{10t}$, $R^{11t}$, $R^{12t}$, $R^{13t}$, $R^{14t}$, $R^{15t}$, $R^{16t}$, $R^{17t}$, $R^{18t}$ and $R^{19t}$.

In one embodiment, the invention is concerned with compounds of the general formula XXII, wherein E is selected from the group consisting of —O—, —S—, —S(=O)—, —S(=O)$_2$— and —CR$^{18t}$R$^{19t}$—.

In another embodiment, the invention is concerned with compounds of the general formula XXII, wherein $R^{18t}$ is hydrogen or F.

In another embodiment, the invention is concerned with compounds of the general formula XXII, wherein $R^{10t}$, $R^{12t}$, $R^{4t}$ and $R^{6t}$ are all hydrogen.

In another embodiment, the invention is concerned with compounds of the general formula XXII, wherein $R^{6t}$, $R^{7t}$, $R^{8t}$ and $R^{9t}$ are independently selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXII, wherein there is a covalent bond between $R^{11t}$ and $R^{13t}$.

In another embodiment, the invention is concerned with compounds of the general formula XXII, wherein there is a covalent bond between $R^{13t}$ and $R^{19t}$.

In another embodiment, the invention is concerned with compounds of the general formula XXII, wherein $R^{10t}$, $R^{11t}$, $R^{12t}$, $R^{13t}$, $R^{14t}$, $R^{15t}$, $R^{16t}$ and $R^{17t}$ are all hydrogen or F.

In an aspect of the invention, compounds are of the general formula XXIII

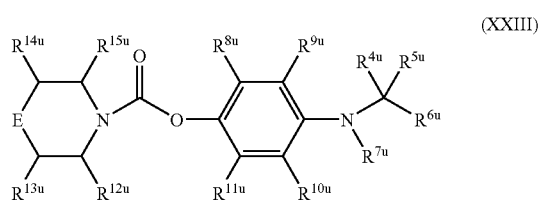

(XXIII)

wherein $R^{4u}$, $R^{5u}$, $R^{6u}$, $R^{7u}$, $R^{8u}$, $R^{9u}$, $R^{10u}$, $R^{11u}$, $R^{12u}$, $R^{13u}$, $R^{14u}$ and $R^{15u}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: with the proviso that $R^{4u}$, $R^{5u}$ and $R^{6u}$ are not all hydrogen; and E is selected from the group consisting of —O—, —S—, —S(=O)—, —S(=O)$_2$—, —NR$^{16u}$— and —CR$^{16u}$R$^{17u}$—;

wherein $R^{16u}$ and $R^{17u}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and wherein there may optionally be one or more covalent bonds between any of the substituents selected from the group consisting of $R^{4u}$, $R^{5u}$ and $R^{6u}$; and wherein there may optionally be one or more covalent bonds between any of the substituents selected from the group consisting of $R^{8u}$, $R^{9u}$, $R^{10u}$ and $R^{11u}$; and wherein there may optionally be one or more covalent bonds between any of the substituents selected from the group consisting of $R^{12u}$, $R^{13u}$, $R^{14u}$, $R^{15u}$, $R^{16u}$ and $R^{17u}$.

In one embodiment, the invention is concerned with compounds of the general formula XXIII, wherein E is selected from the group consisting of —O—, —S—, —S(=O)—, —S(=O)$_2$— and —CR$^{16u}$R$^{17u}$—.

In another embodiment, the invention is concerned with compounds of the general formula XXIII, wherein $R^{17u}$ is hydrogen or F.

In another embodiment, the invention is concerned with compounds of the general formula XXIII, wherein there are no covalent bonds between any of the substituents $R^{8u}$, $R^{9u}$, $R^{10u}$ and $R^{11u}$.

In another embodiment, the invention is concerned with compounds of the general formula XXIII, wherein $R^{8u}$, $R^{9u}$, $R^{10u}$ and $R^{11u}$ are independently selected from the group consisting of hydrogen, F, Cl, $C_{1-6}$-alkyl, $C_{1-6}$-alkoxy, —C(=O)$NH_2$, —NHC(=O)—OH, —S(=O)$_2$—$NH_2$, —NH—S(=O)$_2$—OH, hydroxy, amino and perhalomethyl.

In another embodiment, the invention is concerned with compounds of the general formula XXIII, wherein there is a covalent bond between $R^{12u}$ and $R^{13u}$.

In another embodiment, the invention is concerned with compounds of the general formula XXIII, wherein $R^{12u}$, $R^{13u}$, $R^{14u}$ and $R^{15u}$ are all selected from the group consisting of hydrogen, F, methyl and $C_{1-6}$-alkyl.

In an aspect of the invention, compounds are of the general formula XXIVa-b

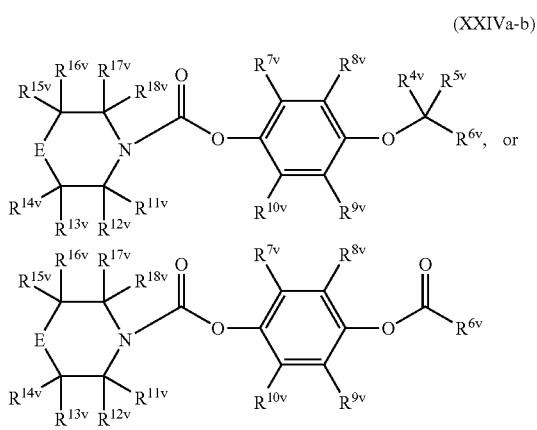

(XXIVa-b)

wherein $R^{4v}$, $R^{5v}$, $R^{6v}$, $R^{7v}$, $R^{8v}$, $R^{9v}$, $R^{10v}$, $R^{11v}$, $R^{12v}$, $R^{13v}$, $R^{14v}$, $R^{15v}$, $R^{16v}$, $R^{17v}$ and $R^{18v}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; with the proviso that none of the substituents $R^{4v}$, $R^{5v}$ and $R^{6v}$ are benzothiazolyl or benzooxazolyl; and E is selected from the group consisting of —O—, —S—, —S(=O)—, —S(=O)$_2$—, —$NR^{19v}$— and —$CR^{19v}R^{20v}$—; and wherein $R^{19v}$ and $R^{20v}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, perhalomethyl and perhalomethoxy; and wherein there may optionally be a covalent bond between the substituents $R^{7v}$ and $R^{8v}$ or between the substituents $R^{9v}$ and $R^{10v}$; and wherein there may optionally be a covalent bond between $R^{6v}$ and a substituent selected from $R^{8v}$ and $R^{9v}$; and wherein there may be a covalent bond between any of the substituents selected from the group consisting of $R^{4v}$, $R^{5v}$ and $R^{6v}$; and wherein there may optionally be one or more covalent bonds between any of the substituents selected from the group consisting of $R^{11v}$, $R^{12v}$, $R^{13v}$, $R^{14v}$, $R^{15v}$, $R^{16v}$, $R^{17v}$, $R^{18v}$, $R^{19v}$ and $R^{20v}$.

In one embodiment, the invention is concerned with compounds of the general formula XXIV, wherein E is selected from the group consisting of —O—, —S—, —S(=O)—, —S(=O)$_2$— and —$CR^{19v}R^{20v}$—.

In another embodiment, the invention is concerned with compounds of the general formula XXIV, wherein $R^{20v}$ is hydrogen or F.

In another embodiment, the invention is concerned with compounds of the general formula XXIV, wherein there are no covalent bonds between any of the substituents $R^{4v}$, $R^{5v}$ and $R^{6v}$.

In another embodiment, the invention is concerned with compounds of the general formula XXIV, wherein there are no covalent bonds between any of the substituents $R^{7v}$, $R^{8v}$, $R^{9v}$ and $R^{10v}$.

In another embodiment, the invention is concerned with compounds of the general formula XXIV, wherein there are no covalent bonds between a substituent selected from the group consisting of $R^{4v}$, $R^{5v}$ and $R^{6v}$ and a substituent selected from the group consisting of $R^{7v}$, $R^{8v}$, $R^{9v}$ and $R^{10v}$.

In another embodiment, the invention is concerned with compounds of the general formula XXIV, wherein $R^{7v}$, $R^{8v}$, $R^{9v}$ and $R^{10v}$ are independently selected from the group consisting of hydrogen, F, Cl, $C_{1-6}$-alkyl, $C_{1-6}$-alkoxy, —C(=O)$NH_2$, —NHC(=O)—OH, —S(=O)$_2$—$NH_2$, —NH—S(=O)$_2$—OH, hydroxy, amino and perhalomethyl.

In another embodiment, the invention is concerned with compounds of the general formula XXIV, wherein there is a covalent bond between $R^{12v}$ and $R^{13v}$.

In another embodiment, the invention is concerned with compounds of the general formula XXIV, wherein $R^{11v}$, $R^{12v}$, $R^{13v}$, $R^{14v}$, $R^{15v}$, $R^{16v}$, $R^{17v}$ and $R^{18v}$ are all hydrogen or F.

In an aspect of the invention, compounds are of the general formula XXV

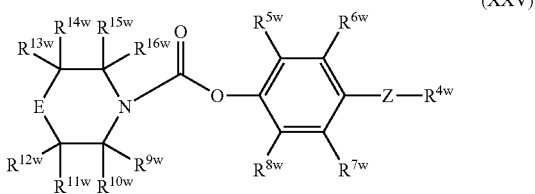

(XXV)

wherein $R^{4w}$ is selected from hydrogen, hydroxy, amino, sulfo, $C_{2-6}$-alkyl, $C_{2-6}$-alkenyl, aryl, heteroaryl, $C_{3-8}$-heterocyclyl and $C_{3-10}$-cycloalkyl, wherein each of hydroxy, amino, sulfo, $C_{2-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl my optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy: with the proviso that $R^{4w}$ is not methyl, morpholine or a 2-chromen derivative; and Z is selected from S, S(=O) and S(=O)$_2$; and $R^{5w}$, $R^{6w}$, $R^{7w}$, $R^{8w}$, $R^{9w}$, $R^{10w}$, $R^{11w}$, $R^{12w}$, $R^{13w}$, $R^{14w}$, $R^{15w}$ and $R^{16w}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, perhalomethyl and perhalomethoxy: and E is selected from the group consisting of —O—, —S—, —S(=O)—, —S(=O)$_2$—, —NR$^{17w}$— and —CR$^{17w}$R$^{18w}$—; and wherein $R^{17w}$ and $R^{18w}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, perhalomethyl and perhalomethoxy; and wherein there may optionally be one or more covalent bonds between any of the substituents selected from the group consisting of $R^{4w}$, $R^{5w}$, $R^{6w}$, $R^{7w}$ and $R^{8w}$; and wherein there may optionally be one or more covalent bonds between any of the substituents selected from the group consisting of $R^{9w}$, $R^{10w}$, $R^{11w}$, $R^{12w}$, $R^{13w}$, $R^{14w}$, $R^{15w}$, $R^{16w}$, $R^{17w}$ and $R^{18w}$.

In one embodiment, the invention is concerned with compounds of the general formula XXV, wherein the only substituents which are covalently bound are $R^{4w}$ and $R^{5w}$.

In another embodiment, the invention is concerned with compounds of the general formula XXV, wherein there are no covalent bonds between any of the substituents $R^{5w}$, $R^{6w}$, $R^{7w}$ and $R^{8w}$.

In another embodiment, the invention is concerned with compounds of the general formula XXV, wherein there are no covalent bonds between any of the substituents $R^{9w}$, $R^{10w}$, $R^{11w}$, $R^{12w}$, $R^{13w}$, $R^{14w}$, $R^{15w}$ and $R^{16w}$.

In another embodiment, the invention is concerned with compounds of the general formula XXV, wherein E is selected from the group consisting of —O—, —S—, —S(=O)—, —S(=O)$_2$— and —CR$^{17w}$R$^{18w}$—.

In another embodiment, the invention is concerned with compounds of the general formula XXV, wherein $R^{18w}$ is hydrogen or F.

In another embodiment, the invention is concerned with compounds of the general formula XXV, wherein $R^{5w}$, $R^{6w}$, $R^{7w}$ and $R^{8w}$ are independently selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXV, wherein there is a covalent bond between $R^{10w}$ and $R^{11w}$.

In another embodiment, the invention is concerned with compounds of the general formula XXV, wherein there is a covalent bond between $R^{13w}$ and $R^{17w}$.

In another embodiment, the invention is concerned with compounds of the general formula XXV, wherein $R^{9w}$, $R^{10w}$, $R^{11w}$, $R^{12w}$, $R^{13w}$, $R^{14w}$, $R^{15w}$ and $R^{16w}$ are all hydrogen or F.

In an aspect of the invention, compounds are of the general formula XXVI

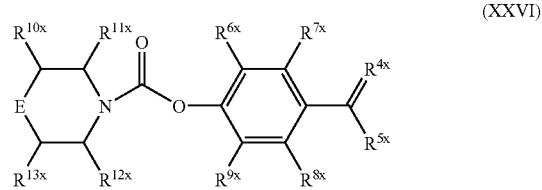

(XXVI)

wherein $R^{4x}$ is selected from imino, $C_{1-6}$-alkyl, $C_{2-6}$-alkenyl, aryl, heteroaryl, $C_{3-8}$-heterocyclyl and $C_{3-10}$-cycloalkyl, wherein each of imino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, perhalomethyl and perhalomethoxy; and $R^{5x}$, $R^{6x}$, $R^{7x}$, $R^{8x}$, $R^{9x}$, $R^{10x}$, $R^{11x}$, $R^{12x}$ and $R^{13x}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and E is selected from the group consisting of —O—, —S—, —S(=O)—, —S(=O)$_2$—, —NR$^{14x}$— and —CR$^{15x}$R$^{16x}$—;

wherein $R^{14x}$ is selected from hydrogen, sulfo, $C_{1-6}$-alkyl, $C_{2-6}$-alkenyl, aryl, heteroaryl, $C_{3-8}$-heterocyclyl and $C_{3-10}$-cycloalkyl, wherein each of sulfo, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, F, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, F, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and $R^{15x}$ and $R^{16x}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and wherein there may optionally be a covalent bond between the substituents $R^{4x}$ and $R^{5x}$; and wherein there may optionally be one or more covalent bonds between any of the substituents selected from the group consisting of $R^{6x}$, $R^{7x}$, $R^{8x}$ and $R^{9x}$; and wherein there may optionally be one or more covalent bonds between any of the substituents selected from the group consisting of $R^{10x}$, $R^{11x}$, $R^{12x}$, $R^{13x}$, $R^{14}x$, $R^{15x}$ and $R^{16x}$.

In one embodiment, the invention is concerned with compounds of the general formula XXVI, wherein $R^{6x}$, $R^{7x}$, $R^{8x}$ and $R^{9x}$ are independently selected from the group consisting of hydrogen, F, Cl, $C_{1-6}$-alkyl, $C_{1-6}$alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXVI, wherein $R^{10x}$, $R^{11x}$, $R^{12x}$ and $R^{13x}$ are independently selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXVI, wherein there is a covalent bond between the substituents $R^{6x}$ and $R^{7x}$.

In another embodiment, the invention is concerned with compounds of the general formula XXVI, wherein there is a covalent bond between the substituents $R^{10x}$ and $R^{11x}$.

In another embodiment, the invention is concerned with compounds of the general formula XXVI, wherein there is a covalent bond between $R^{10x}$ and a substituent selected from $R^{14x}$ and $R^{15x}$.

In an aspect of the invention, compounds are of the general formula XXVII

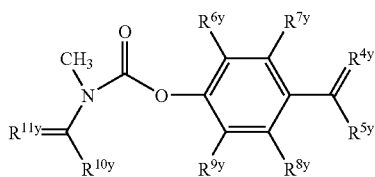

(XXVII)

wherein $R^{4y}$ and $R^{11y}$ are independently selected from imino, $C_{1-6}$-alkyl, $C_{2-6}$-alkenyl, aryl, heteroaryl, $C_{3-8}$-heterocyclyl and $C_{3-10}$-cycloalkyl, wherein each of imino, $C_{1-6}$-alkyl, $C_{2-6}$-alkenyl aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, nitro, sulfo, $C_{1-6}$-alkyl, $C_{1-6}$-alkoxy, $C_{2-6}$-alkenyl, perhalomethyl and perhalomethoxy; and $R^{5y}$, $R^{6y}$, $R^{7y}$, $R^{8y}$, $R^{9y}$ and $R^{10y}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and wherein there may optionally be a covalent bond between the substituents $R^{4y}$ and $R^{5y}$; and wherein there may optionally be one or more covalent bonds between any of the substituents selected from the group consisting of $R^{6y}$, $R^{7y}$, $R^{8y}$ and $R^{9y}$; and wherein there may optionally be a covalent bond between the substituents $R^{10y}$ and $R^{11y}$.

In one embodiment, the invention is concerned with compounds of the general formula XXVII, wherein $R^{6y}$, $R^{7y}$, $R^{8y}$ and $R^{9y}$ are independently selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXVII, wherein there are no covalent bonds between any of the substituents $R^{6y}$, $R^{7y}$, $R^{8y}$ and $R^{9y}$.

In another embodiment, the invention is concerned with compounds of the general formula XXVII, wherein there is a covalent bond between the substituents $R^{4y}$ and $R^{5y}$.

In another embodiment, the invention is concerned with compounds of the general formula XXVII, wherein there is a covalent bond between the substituents $R^{10y}$ and $R^{11y}$.

In an aspect of the invention, compounds are of the general formula XXVIII

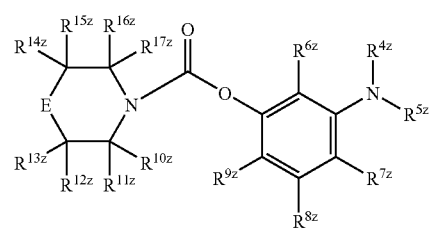

(XXVIII)

wherein $R^{4z}$, $R^{8z}$, $R^{9z}$, $R^{10z}$, $R^{11z}$, $R^{12z}$, $R^{13z}$, $R^{14z}$, $R^{15z}$, $R^{16z}$ and $R^{17z}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and $R^{5z}$ is a carbon bound substituent selected from $C_{1-6}$-alkyl, $C_{2-6}$-alkenyl, aryl, heteroaryl, $C_{3-8}$-heterocyclyl and $C_{3-10}$-cycloalkyl, each of which may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and $R^{6z}$ and $R^{7z}$ are independently selected from hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and E is selected from the group consisting of —O—, —S—, —S(=O)—, —S(=O)$_2$—, —NR$^{18z}$— and —CR$^{19z}$R$^{20z}$—;

wherein $R^{18z}$ is selected from hydrogen, sulfo, $C_{1-6}$-alkyl, $C_{2-6}$-alkenyl, aryl, heteroaryl, $C_{3-8}$-heterocyclyl and $C_{3-10}$-cycloalkyl, wherein each of sulfo, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, F, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, F, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy,
$C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, F, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and $R^{19z}$ and $R^{20z}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and wherein there may optionally be a covalent bond between the substituents $R^{4z}$ and $R^{5z}$; and wherein there may optionally be a covalent bond between any of the substituents $R^{7z}$, $R^{8z}$, and $R^{9z}$; and wherein there may optionally be one or more covalent bonds between any of the substituents selected from the group consisting of $R^{10z}$, $R^{11z}$, $R^{12z}$, $R^{13z}$, $R^{14z}$, $R^{15z}$, $R^{16z}$, $R^{17z}$, $R^{18z}$, $R^{19z}$, and $R^{20z}$.

In one embodiment, the invention is concerned with compounds of the general formula XXVIII, wherein there is a covalent bond between the substituents $R^{4z}$ and $R^{5z}$.

In another embodiment, the invention is concerned with compounds of the general formula XXVIII, wherein $R^{6z}$, $R^{7z}$, $R^{8z}$ and $R^{9z}$ are independently selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXVIII, wherein there is a covalent bond between $R^{13z}$ and a substituent selected from $R^{18z}$ and $R^{19z}$.

In an aspect of the invention, compounds are of the general formula XXIX

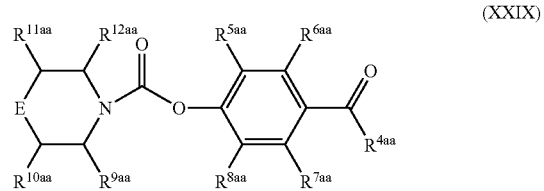

(XXIX)

wherein $R^{4aa}$ is selected from hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl, each of which may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$- alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, F, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, $C_{3-8}$-heterocyclyl, $C_{3-10}$-cycloalkyl, perhalomethyl and perhalomethoxy; and $R^{5aa}$, $R^{6aa}$, $R^{7aa}$, $R^{8aa}$, $R^{9aa}$, $R^{10aa}$, $R^{11aa}$, $R^{12aa}$ and $R^{13aa}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, where each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and wherein there may optionally be a covalent bond between the substituents $R^{5aa}$ and $R^{6aa}$ or between the substituent $R^{7aa}$ and $R^{8aa}$; and wherein there may optionally be one or more covalent bonds between any of the substituents selected from the group consisting of $R^{9aa}$, $R^{10aa}$, $R^{11aa}$ and $R^{12aa}$; and E is selected from the group consisting of —O—, —S—, —S(=O)— and —S(=O)$_2$—.

In one embodiment, the invention is concerned with compounds of the general formula XXIX, wherein there is a covalent bond between the substituents $R^{9aa}$ and $R^{10aa}$.

In another embodiment, the invention is concerned with compounds of the general formula XXIX, wherein $R^{5aa}$, $R^{6aa}$, $R^{7aa}$ and $R^{8aa}$ are independently selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXIX, wherein at least one of the substituents $R^{5aa}$, $R^{6aa}$, $R^{7aa}$ and $R^{8aa}$ are different from hydrogen.

In an aspect of the invention, compounds are of the general formula XXX

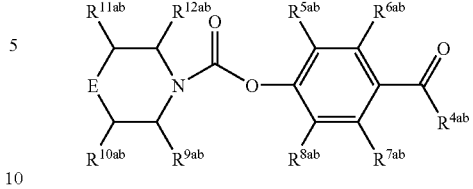

(XXX)

wherein $R^{4ab}$ is selected from sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl, each of which may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, F, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and E is selected from the group consisting of —NR$^{13ab}$— and —CR$^{14ab}$R$^{15ab}$—; and $R^{5ab}$, $R^{6ab}$, $R^{7ab}$, $R^{8ab}$, $R^{9ab}$, $R^{10ab}$, $R^{11ab}$, $R^{12ab}$, $R^{13ab}$, $R^{14ab}$ and $R^{15ab}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and wherein there may optionally be a covalent bond between the substituents $R^{5ab}$ and $R^{6ab}$ or between the substituent $R^{7ab}$ and $R^{8ab}$; and wherein there may optionally be one or more covalent bonds between any of the substituents selected from the group consisting of $R^{9ab}$, $R^{10ab}$, $R^{11ab}$, $R^{12ab}$, $R^{13ab}$, $R^{14ab}$ and $R^{15ab}$.

In one embodiment, the invention is concerned with compounds of the general formula XXX, wherein there is a covalent bond between the substituents $R^{9ab}$ and $R^{10ab}$.

In another embodiment, the invention is concerned with compounds of the general formula XXX, wherein there is a covalent bond between $R^{10ab}$ and a substituent selected from $R^{13ab}$ and $R^{14ab}$.

In another embodiment, the invention is concerned with compounds of the general formula XXX, wherein $R^{5ab}$, $R^{6ab}$, $R^{7ab}$ and $R^{8ab}$ are independently selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXX, wherein at least one of the substituents $R^{5ab}$, $R^{6ab}$, $R^{7ab}$ and $R^{8ab}$ are different from hydrogen.

In another embodiment, the invention is concerned with compounds of the general formula XXX, wherein at least one of the substituents $R^{9ab}$, $R^{10ab}$, $R^{11ab}$, $R^{12ab}$, $R^{13ab}$, $R^{14ab}$ and $R^{15ab}$ are different from hydrogen.

In an aspect of the invention, compounds are of the general formula XXXI

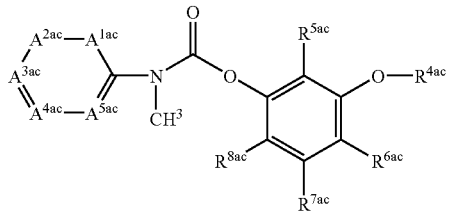

(XXXI)

wherein $R^{4ac}$ is a carbon bound substituent selected from $C_{1-6}$-alkyl, $C_{2-6}$-alkenyl, aryl, heteroaryl, $C_{3-8}$-heterocyclyl and $C_{3-10}$-cycloalkyl, each of which may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and $A^{1ac}$ is N or C—$R^{9ac}$; $A^{3ac}$ is N or C—$R^{10ac}$; and $A^{5ac}$ is N or C—$R^{11ac}$; and $R^{5ac}$, $R^{6ac}$, $R^{7ac}$, $R^{8ac}$, $R^{9ac}$, $R^{10ac}$; and $R^{11ac}$ are independently selected from hydrogen, hydroxy, sulfanyl, sulfo, halogen, amino, cyano, nitro, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{1-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; with the proviso that $A^{3ac}$ is not C—C(OH)(CF$_3$)$_2$; and $A^{2ac}$ is N or C—$R^{12ac}$; and $A^{4ac}$, is N or C—$R^{13ac}$; wherein $R^{12ac}$ and $R^{13ac}$ are independently selected from hydrogen, hydroxy, sulfanyl, sulfo, halogen, amino, cyano, nitro, $C_{1-6}$-alkyl, $C_{2-6}$-alkoxy, $C_{2-6}$-alkenyl, aryl, heteroaryl, $C_{3-8}$-heterocyclyl and $C_{3-10}$-cycloalkyl, wherein each of sulfanyl, sulfo, amino, $C_{1-6}$-alkyl, $C_{2-6}$-alkoxy, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{1-6}$-alkoxy, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{1-6}$-alkoxy, $C_{2-6}$-alkenyl, aryl, heteroaryl, $C_{3-8}$-heterocyclyl, $C_{3-10}$-cycloalkyl, perhalomethyl and perhalomethoxy; and wherein there may optionally be a covalent bond between $R^{4ac}$ and a substituent selected from the group consisting of $R^{5ac}$ and $R^{6ac}$; with the proviso that $A^{1ac}$, $A^{2ac}$, $A^{3ac}$, $A^{4ac}$ and $A^{5ac}$ are not all CH; and wherein there may optionally be a covalent bond between any of the substituents $R^{6ac}$, $R^{7ac}$ and $R^{8ac}$; and wherein there may optionally be one or more covalent bonds between any of the substituents in $A^{1ac}$, $A^{2ac}$, $A^{3ac}$, $A^{4ac}$ and $A^{5ac}$.

In one embodiment, the invention is concerned with compounds of the general formula XXXI, wherein there is a covalent bond between the substituents $R^{4ac}$ and $R^{6ac}$.

In another embodiment, the invention is concerned with compounds of the general formula XXXI, wherein there is a covalent bond between $A^{3ac}$ and $A^{4ac}$.

In another embodiment, the invention is concerned with compounds of the general formula XXXI, wherein there is a covalent bond between $A^{3ac}$ and $A^{2ac}$.

In another embodiment, the invention is concerned with compounds of the general formula XXXI, wherein $R^{5ac}$, $R^{6ac}$, $R^{7ac}$ and $R^{8ac}$ are independently selected from the group consisting of hydrogen, F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXXI, wherein at least one of the substituents A$^{1ac}$, A$^{2ac}$, A$^{3ac}$, A$^{4ac}$ and A$^{5ac}$ are different from CH.

In an aspect of the invention, compounds are of the general formula XXXIIa-b

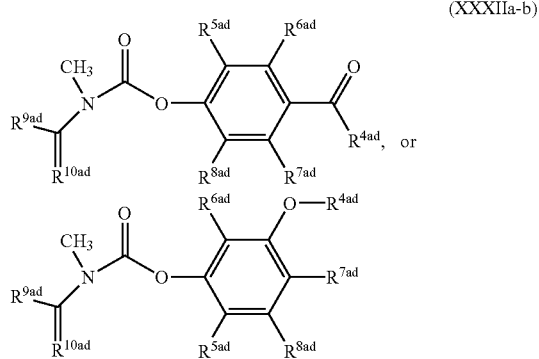

(XXXIIa-b)

wherein R$^{4ad}$ is selected from hydroxy, sulfanyl, sulfo, amino, C$_{1-6}$-alkyl, C$_{2-6}$-alkenyl, aryl, heteroaryl, C$_{3-8}$-heterocyclyl and C$_{3-10}$-cycloalkyl, each of which may optionally be substituted with one or more substituents independently selected from hydroxy, sulfanyl, oxo, halogen, amino, cyano, nitro, sulfo, C$_{1-6}$-alkyl, C$_{1-6}$-alkoxy, C$_{2-6}$-alkenyl, aryl, heteroaryl, C$_{3-8}$-heterocyclyl, and C$_{3-10}$-cycloalkyl, wherein each of the hydroxy, sulfanyl, amino, sulfo, C$_{1-6}$-alkyl, C$_{1-6}$-alkoxy, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, F, amino, cyano, nitro, sulfo, C$_{1-6}$-alkyl, C$_{1-6}$-alkoxy, C$_{2-6}$-alkenyl, aryl, heteroaryl, C$_{3-8}$-heterocyclyl, C$_{3-10}$-cycloalkyl, wherein each of the hydroxy, sulfanyl, amino, sulfo, C$_{1-6}$-alkyl, C$_{1-6}$-alkoxy, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{1-6}$-alkoxy, C$_{2-6}$-alkenyl, aryl, heteroaryl, C$_{3-8}$-heterocyclyl, C$_{3-10}$-cycloalkyl, perhalomethyl and perhalomethoxy; and R$^{5ad}$, R$^{6ad}$, R$^{7ad}$, R$^{8ad}$ and R$^{9ad}$ are independently selected from hydrogen, hydroxy, sulfanyl, sulfo, halogen, amino, cyano, nitro, C$_{1-6}$-alkyl, C$_{1-6}$-alkoxy, C$_{2-6}$-alkenyl, aryl, heteroaryl, C$_{3-8}$-heterocyclyl and C$_{3-10}$-cycloalkyl, wherein each of hydroxy, sulfanyl, sulfo, amino, C$_{1-6}$-alkyl, C$_{1-6}$-alkoxy, C$_{2-6}$-alkenyl, aryl, heteroaryl, C$_{3-8}$-heterocyclyl and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{1-6}$-alkoxy, C$_{2-6}$-alkenyl, aryl, heteroaryl, C$_{3-8}$-heterocyclyl, and C$_{3-10}$-cycloalkyl, wherein each of the hydroxy, sulfanyl, amino, sulfo, C$_{1-6}$-alkyl, C$_{1-6}$-alkoxy, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{1-6}$-alkoxy, C$_{2-6}$-alkenyl, aryl, heteroaryl, C$_{3-8}$-heterocyclyl, C$_{3-10}$-cycloalkyl, perhalomethyl and perhalomethoxy; and R$^{10ad}$ are selected from imino, C$_{1-6}$-alkyl, C$_{2-6}$-alkenyl, aryl, heteroaryl, C$_{3-8}$-heterocyclyl and C$_{3-10}$-cycloalkyl, each of which may optionally be substituted with one or more substituents independently selected from hydroxy, sulfanyl, oxo, halogen, amino, cyano, nitro, sulfo, C$_{1-6}$-alkyl, C$_{1-6}$-alkoxy, C$_{2-6}$-alkenyl, aryl, heteroaryl, C$_{3-8}$-heterocyclyl, and C$_{3-10}$-cycloalkyl, wherein each of the hydroxy, sulfanyl, amino, sulfo, C$_{1-6}$-alkyl, C$_{1-6}$-alkoxy, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{1-6}$-alkoxy, C$_{2-6}$-alkenyl, aryl, heteroaryl, C$_{3-8}$-heterocyclyl, C$_{3-10}$-cycloalkyl, wherein each of the hydroxy, sulfanyl, amino, sulfo, C$_{1-6}$-alkyl, C$_{1-6}$-alkoxy, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{1-6}$-alkoxy, C$_{2-6}$-alkenyl, aryl, heteroaryl, C$_{3-8}$-heterocyclyl, C$_{3-10}$-cycloalkyl, perhalomethyl and perhalomethoxy; and wherein there may optionally be a covalent bond between R$^{4ad}$ and a substituent selected from R$^{6ad}$ and R$^{7ad}$; and wherein there may optionally be a covalent bond between the substituents R$^{9ad}$ and R$^{10ad}$ so as to form a 5-membered ring system.

In one embodiment, the invention is concerned with compounds of the general formula XXXIIa-b, wherein the substituents R$^{9ad}$ and R$^{10ad}$ are covalently bound so as to form a 5-membered ring system.

In another embodiment, the invention is concerned with compounds of the general formula XXXIIa-b, wherein said 5-membered ring system comprises at least one nitrogen atom in the ring.

In another embodiment, the invention is concerned with compounds of the general formula XXXIIa-b, wherein said 5-membered ring system contains 5 carbons in the ring.

In another embodiment, the invention is concerned with compounds of the general formula XXXIIa-b, wherein there is a covalent bond between the substituents R$^{4ad}$ and R$^{7ad}$.

In another embodiment, the invention is concerned with compounds of the general formula XXXIIa-b, wherein R$^{5ad}$, R$^{6ad}$, R$^{7ad}$ and R$^{8ad}$ are independently selected from the group consisting of hydrogen, F, Cl, C$_{1-6}$-alkyl, C$_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another aspect of the invention, compounds are of the general formula XXXIIIa-b

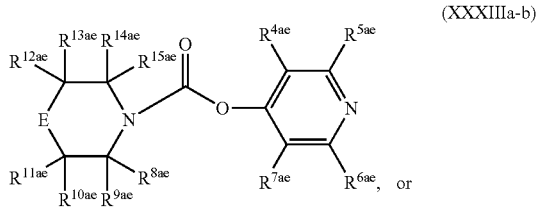

(XXXIIIa-b)

-continued

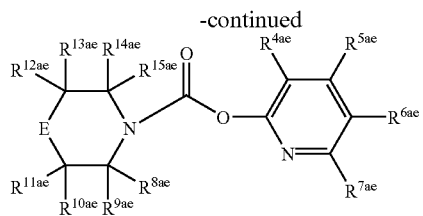

wherein E is selected from the group consisting of —O—, —S—, —S(═O)—, —S(═O)$_2$—, —NR$^{16ae}$— and —CR$^{17ae}$R$^{18ae}$; and R$^{4ae}$, R$^{5ae}$, R$^{6ae}$, R$^{7ae}$, R$^{8ae}$, R$^{9ae}$, R$^{10ae}$, R$^{11ae}$, R$^{12ae}$, R$^{13ae}$, R$^{14ae}$, R$^{15ae}$, R$^{16ae}$, R$^{17ae}$ and R$^{18ae}$ are independently selected from hydrogen, hydroxy, sulfanyl, sulfo, halogen, amino, cyano, nitro, C$_{1-6}$-alkyl, C$_{2-6}$-alkenyl, aryl, heteroaryl, C$_{3-8}$-heterocyclyl and C$_{3-10}$-cycloalkyl, wherein each of hydroxy, sulfanyl, sulfo, amino, C$_{1-6}$-alkyl, C$_{2-6}$-alkenyl, aryl, heteroaryl, C$_{3-8}$-heterocyclyl and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl, and C$_{3-10}$-cycloalkyl, wherein each of the hydroxy, sulfanyl, amino, sulfo, C$_{1-6}$-alkyl, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl, C$_{3-10}$-cycloalkyl, wherein each of the hydroxy, sulfanyl, amino, sulfo, C$_{1-6}$-alkyl, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl and C$_{3-10}$-cycloalkyl, wherein each of the hydroxy, sulfanyl, amino, sulfo, C$_{1-6}$-alkyl, C$_{2-6}$-alkenyl, aryl, heteroaryl, C$_{3-8}$-heterocyclyl and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl, C$_{3-10}$-cycloalkyl, perhalomethyl and perhalomethoxy; and wherein there may optionally be a covalent bond between any of the substituents selected from R$^{4ae}$, R$^{5ae}$, R$^{6ae}$ and R$^{7ae}$; with the proviso that when R$^{5ae}$ and R$^{6ae}$ are covalently bound they do not form a isoquinolin-3-yl or a substituted isoquinolin-3-yl together with the pyridine which they are both bound to; and wherein there may optionally be a covalent bond between any of the substituents selected from R$^{8ae}$, R$^{9ae}$, R$^{10ae}$, R$^{11ae}$, R$^{12ae}$, R$^{13ae}$, R$^{14ae}$, R$^{15ae}$, R$^{16ae}$, R$^{17ae}$ and R$^{18ae}$.

In one embodiment, the invention is concerned with compounds of the general formula XXXIIIa-b, wherein there is a covalent bond between R$^{6ae}$ and R$^{7ae}$.

In another embodiment, the invention is concerned with compounds of the general formula XXXIIIa-b, wherein there is a covalent bond between R$^{5ae}$ and R$^{6ae}$.

In another embodiment, the invention is concerned with compounds of the general formula XXXIIIa-b, wherein at least one of R$^{8ae}$, R$^{9ae}$, R$^{10ae}$, R$^{11ae}$, R$^{12ae}$, R$^{13ae}$, R$^{14ae}$ and R$^{15ae}$ is selected from F, Cl, C$_{1-6}$-alkyl, C$_{1-6}$alkoxy, —C(═O)NH$_2$, —NHC(═O)—OH, —S(═O)$_2$—NH$_2$, —NH—S(═O)$_2$—OH, hydroxy, amino and perhalomethyl.

In another aspect of the invention, compounds are of the general formula XXXIV

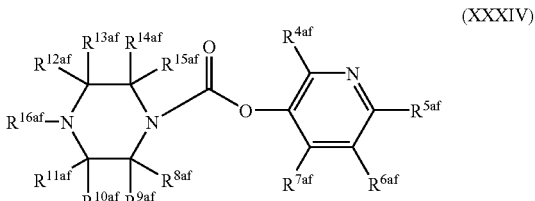

(XXXIV)

wherein R$^{4af}$, R$^{5af}$, R$^{6af}$, R$^{7af}$, R$^{8af}$, R$^{9af}$, R$^{10af}$, R$^{11af}$, R$^{12af}$, R$^{13af}$, R$^{14af}$ and R$^{15af}$ are independently selected from hydrogen, hydroxy, sulfanyl, sulfo, halogen, amino, cyano, nitro, C$_{1-6}$-alkyl, C$_{2-6}$-alkenyl, aryl, heteroaryl, C$_{3-8}$-heterocyclyl and C$_{3-10}$-cycloalkyl, wherein each of hydroxy, sulfanyl, sulfo, amino, C$_{1-6}$-alkyl, C$_{2-6}$-alkenyl, aryl, heteroaryl, C$_{3-8}$-heterocyclyl and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl, and C$_{3-10}$-cycloalkyl, wherein each of the hydroxy, sulfanyl, amino, sulfo, C$_{1-6}$-alkyl, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl, C$_{3-10}$-cycloalkyl, wherein each of the hydroxy, sulfanyl, amino, sulfo, C$_{1-6}$-alkyl, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl and C$_{3-10}$-cycloalkyl, wherein each of the hydroxy, sulfanyl, amino, sulfo, C$_{1-6}$-alkyl, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl, C$_{3-10}$-cycloalkyl, perhalomethyl and perhalomethoxy; and wherein there may optionally be a covalent bond between R$^{6af}$ and any of the substituents selected from R$^{5af}$ and R$^{7af}$; and wherein there may optionally be a covalent bond between the substituents R$^{9af}$ and R$^{10af}$; and R$^{16af}$ is selected from hydrogen, hydroxy, sulfanyl, sulfo, amino, C$_{1-6}$-alkyl, C$_{2-6}$-alkenyl, C$_{3-8}$-heterocyclyl and C$_{3-10}$-cycloalkyl, wherein each of hydroxy, sulfanyl, sulfo, amino, C$_{1-6}$-alkyl, C$_{2-6}$-alkenyl, C$_{3-8}$-heterocyclyl and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl, and C$_{3-10}$-cycloalkyl, wherein each of the hydroxy, sulfanyl, amino, sulfo, C$_{1-6}$-alkyl, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, perhalomethyl and perhalomethoxy; with the proviso that $R^{16af}$ is not methyl; and wherein there may optionally be a covalent bond between the substituents $R^{12af}$ and $R^{16af}$.

In one embodiment, the invention is concerned with compounds of the general formula XXXIV, wherein there is a covalent bond between the substituents $R^{5af}$ and $R^{6af}$.

In another embodiment, the invention is concerned with compounds of the general formula XXXIV, wherein there is a covalent bond between the substituents $R^{9af}$ and $R^{10af}$.

In another embodiment, the invention is concerned with compounds of the general formula XXXIV, wherein at least one of $R^{8af}$, $R^{9af}$, $R^{10af}$, $R^{11af}$, $R^{12af}$, $R^{13af}$, $R^{14af}$ and $R^{15af}$ is selected from F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another aspect of the invention, compounds are of the general formula XXXV

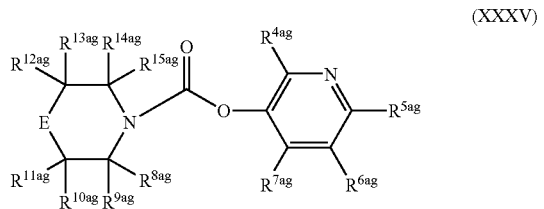

(XXXV)

wherein E is selected from the group consisting of —O—, —S—, —S(=O)—, —S(=O)$_2$— and —CR$^{16ag}$R$^{17ag}$—; and $R^{4ag}$, Rag $R^{5ag}$, $R^{6ag}$, $R^{10ag}$, $R^{11ag}$, $R^{12ag}$, $R^{13ag}$, $R^{16ag}$ and $R^{17ag}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, perhalomethyl and perhalomethoxy; with the proviso that $R^{4ag}$ is not —CH$_2$—N(CH$_3$)$_2$; and wherein there may optionally be a covalent bond between the substituents $R^{5ag}$ and $R^{6ag}$; and $R^{7ag}$ is selected from hydrogen, hydroxy, sulfanyl, sulfo, halogen, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, perhalomethyl and perhalomethoxy;

$R^{8ag}$, $R^{9ag}$, $R^{14ag}$ and $R^{15ag}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, heteroaryl, $C_{3-8}$-heterocyclyl, $C_{3-10}$-cycloalkyl, perhalomethyl and perhalomethoxy; and wherein there may optionally be a covalent bond between the substituents $R^{9ag}$ and $R^{10ag}$; and wherein there may optionally be a covalent bond between the substituents $R^{12ag}$ and $R^{16ag}$.

In one embodiment, the invention is concerned with compounds of the general formula XXXV, wherein there is a covalent bond between the substituents $R^{5ag}$ and $R^{6ag}$.

In another embodiment, the invention is concerned with compounds of the general formula XXXV, wherein there is a covalent bond between the substituents $R^{9ag}$ and $R^{10ag}$.

In another embodiment, the invention is concerned with compounds of the general formula XXXV, wherein at least one of $R^{8ag}$, $R^{9ag}$, $R^{10ag}$, $R^{12ag}$, $R^{13ag}$, $R^{14ag}$ and $R^{15ag}$ are selected from F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another aspect of the invention, compounds are of the general formula XXXVIa-b

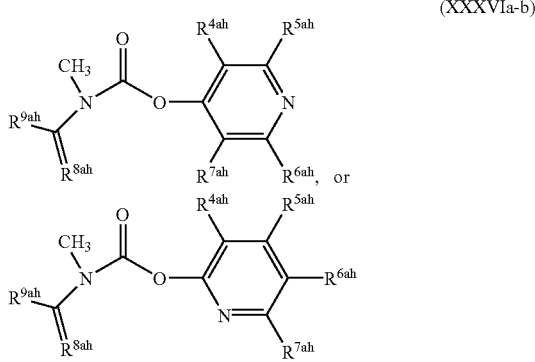

(XXXVIa-b)

wherein $R^{4ah}$, $R^{5ah}$, $R^{6ah}$, $R^{7ah}$, $R^{8ah}$ and $R^{9ah}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, perhalomethyl and perhalomethoxy; with the proviso that $R^{5ah}$ and $R^{6ah}$ are not both CF$_3$; and wherein there may optionally be a covalent bond between any of the substituents selected from $R^{4ah}$, $R^{5ah}$, $R^{6ah}$ and $R^{7ah}$; and wherein there may optionally be a covalent bond between the substituents $R^{8ah}$ and $R^{9ah}$; with the proviso that when $R^{8ah}$ and $R^{9ah}$ together with the carbon to which they are bound forms phenyl then $R^{5ah}$, $R^{6ah}$, $R^{7ah}$ and $R^{8ah}$ are not all hydrogen.

In one embodiment, the invention is concerned with compounds of the general formula XXXVIa-b, wherein there is a covalent bond between $R^{8ah}$ and $R^{9ah}$.

In another embodiment, the invention is concerned with compounds of the general formula XXXVIa-b, wherein there is a covalent bond between $R^{6ah}$ and $R^{7ah}$.

In another embodiment, the invention is concerned with compounds of the general formula XXXVIa-b, wherein there is a covalent bond between $R^{5ah}$ and $R^{6ah}$.

In another embodiment, the invention is concerned with compounds of the general formula XXXVIa-b, wherein at least one of $R^{5ah}$, $R^{6ah}$, $R^{7ah}$ and $R^{8ah}$ are selected from F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another aspect of the invention, compounds are of the general formula XXXVII

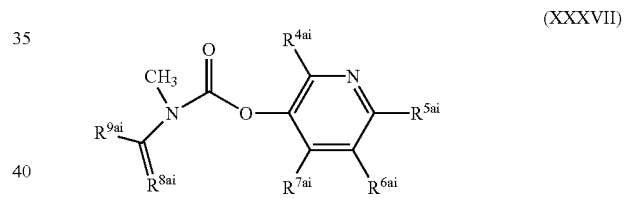

(XXXVII)

$R^{4ai}$, $R^{5ai}$, $R^{6ai}$, $R^{7ai}$, $R^{8ai}$ and $R^{9ai}$ are independently selected from hydrogen, hydroxy, sulfanyl sulfo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, perhalomethyl and perhalomethoxy; with the proviso that $R^{4ai}$ is not $CH_2$—$N(Me)_2$; and wherein there may optionally be a covalent bond between any of the substituents selected from $R^{4ai}$, $R^{5ai}$, $R^{6ai}$ and $R^{7ai}$; and wherein there may optionally be a covalent bond between the substituents $R^{8ai}$ and $R^{9ai}$; with the proviso that $R^{8ai}$ and $R^{9ai}$ together with the carbon to which they are bound do not form 4-methoxy-phenyl, 4-chloro-phenyl or 4-nitro-phenyl.

In one embodiment, the invention is concerned with compounds of the general formula XXXVII, wherein there is a covalent bond between $R^{8ai}$ and $R^{9ai}$.

In another embodiment, the invention is concerned with compounds of the general formula XXXVII, wherein there is a covalent bond between $R^{6ai}$ and $R^{7ai}$.

In another embodiment, the invention is concerned with compounds of the general formula XXXVII, wherein there is a covalent bond between $R^{5ai}$ and $R^{6ai}$.

In another embodiment, the invention is concerned with compounds of the general formula XXXVII, wherein at least one of $R^{5ai}$, $R^{6ai}$, $R^{7ai}$ and $R^{8ai}$ are selected from F, Cl, $C_{1-6}$-alkyl, $C_{1-6}$-alkoxy, —C(=O)$NH_2$, —NHC(=O)—OH, —S(=O)$_2$—$NH_2$, —NH—S(=O)$_2$—OH, hydroxy, amino and perhalomethyl.

In another aspect of the invention, compounds are of the general formula XXXVIII

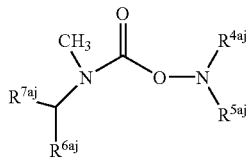

(XXXVIII)

wherein $R^{4aj}$, $R^{5aj}$, $R^{6aj}$ and $R^{7aj}$ are independently selected from amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, perhalomethyl and perhalomethoxy; and wherein there may optionally be a covalent bond between the substituents $R^{4aj}$ and $R^{5aj}$; and wherein there may optionally be a covalent bond between the substituents $R^{6aj}$ and $R^{7aj}$.

In one embodiment, the invention is concerned with compounds of the general formula XXXVIII, wherein there is a covalent bond between $R^{6aj}$ and $R^{7aj}$.

In another embodiment, the invention is concerned with compounds of the general formula XXXVIII, wherein $R^{6aj}$, $R^{7aj}$ and said covalent bond are selected so as to form a ring system selected from an optionally substituted piperidine, piperazine, morpholine and thiomorpholine.

In another embodiment, the invention is concerned with compounds of the general formula XXXVIII, wherein said ring system is selected from piperidine, piperazine, morpholine and thiomorpholine In another embodiment, the invention is concerned with compounds of the general formula XXXVIII, wherein there is a covalent bond between $R^{4aj}$ and $R^{aj}$.

In another aspect of the invention, compounds are of the general formula XXXIX

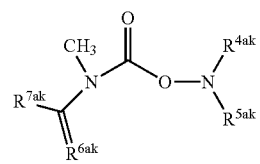

(XXXIX)

wherein $R^{4ak}$, $R^{5ak}$, $R^{6ak}$ and $R^{7ak}$ are independently selected from amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, perhalomethyl and perhalomethoxy; with the proviso that none of $R^{4ak}$ and $R^{5ak}$ are —C(=O)—O— isopropyl; and wherein there may optionally be a covalent bond between the substituents $R^{4ak}$ and $R^{5ak}$; with the proviso that $R^{4ak}$, $R^{5ak}$ and the nitrogen to which they are bound do not form a substituted tetrazolyl moiety; and wherein there may optionally be a covalent bond between the substituents $R^{6ak}$ and $R^{7ak}$;

In one embodiment, the invention is concerned with compounds of the general formula XXXIX, wherein there is a covalent bond between $R^{6ak}$ and $R^{7ak}$.

In another embodiment, the invention is concerned with compounds of the general formula XXXIX, wherein $R^{6ak}$, $R^{7ak}$ and said covalent bond are selected so as to form a ring system selected from an optionally substituted piperidine, piperazine, morpholine and thiomorpholine.

In another embodiment, the invention is concerned with compounds of the general formula XXXIX, wherein said ring system is selected from piperidine, piperazine, morpholine and thiomorpholine In another embodiment, the invention is concerned with compounds of the general formula XXXIX, wherein there is a covalent bond between $R^{4ak}$ and $R^{5ak}$.

In another aspect of the invention, compounds are of the general formula XXXX

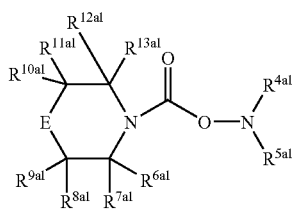

(XXXX)

wherein $R^{4al}$ and $R^{5al}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, $C_{3-10}$-cycloalkyl, perhalomethyl and perhalomethoxy; and wherein there may optionally be a covalent bond between $R^{4al}$ and $R^{5al}$; with the proviso that $R^{4al}$ and $R^{5al}$ together with the nitrogen to which they are bound do not form 2,5-pyrrolidinedione or an annealed ring system comprising 3 or more rings; and wherein E is selected from the group consisting of —O—, —S—, —S(=O)—, —S(=O)$_2$— and —NR$^{14al}$—, —CR$^{15al}$R$^{16al}$—; and $R^{6al}$, $R^{7al}$, $R^{8al}$, $R^{9al}$, $R^{10al}$, $R^{11al}$, $R^{12al}$, $R^{13al}$, $R^{14al}$, $R^{15al}$ and $R^{16al}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, perhalomethyl and perhalomethoxy; and wherein there may optionally be a covalent bond between the substituents $R^{7al}$ and $R^{8al}$; and wherein there may optionally be a covalent bond between the substituents $R^{10al}$ and a substituent selected from $R^{14al}$ and $R^{15al}$.

In one embodiment, the invention is concerned with compounds of the general formula XXXX, wherein there is a covalent bond between the substituents $R^{4al}$ and $R^{5al}$.

In another embodiment, the invention is concerned with compounds of the general formula XXXX, wherein there is a covalent bond between the substituents $R^{7al}$ and $R^{8al}$.

In another embodiment, the invention is concerned with compounds of the general formula XXXX, wherein there is a covalent bond between $R^{10al}$ and a substituent selected from $R^{14al}$ or $R^{15al}$.

In another embodiment, the invention is concerned with compounds of the general formula XXXX, wherein E is —NR$^{14al}$—.

In another embodiment, the invention is concerned with compounds of the general formula XXXX, wherein $R^{14al}$ is selected from F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXXX, wherein E is —CR$^{15al}$R$^{16al}$—.

In another embodiment, the invention is concerned with compounds of the general formula XXXX, wherein R$^{16al}$ is selected from F, Cl, C$_{1-6}$-alkyl, C$_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXXX, wherein R$^{15al}$ is hydrogen.

In another embodiment, the invention is concerned with compounds of the general formula XXXX, wherein at least one of R$^{6al}$, R$^{7al}$, R$^{8al}$, R$^{9al}$, R$^{10al}$, R$^{11al}$, R$^{12al}$ and R$^{13al}$ are selected from F, Cl, C$_{1-6}$-alkyl, C$_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another aspect of the invention, compounds are of the general formula XXXXI

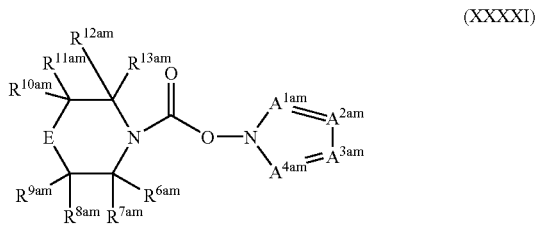

(XXXXI)

wherein E is selected from the group consisting of —O—, —S—, —S(=O)—, —S(=O)$_2$— and —NR$^{14am}$—, —CR$^{15am}$R$^{16am}$—; and wherein A$^{1am}$ is N or C—R$^{17am}$; A$^{2am}$ is N or C—R$^{18am}$; A$^{3am}$ is N or C—R$^{19am}$; A$^{4am}$ is N or C—R$^{20am}$; and R$^{6am}$, R$^{7am}$, R$^{8am}$, R$^{9am}$, R$^{10am}$, R$^{11am}$, R$^{12am}$, R$^{13am}$, R$^{14am}$, R$^{15am}$, R$^{16am}$, R$^{17am}$, R$^{18am}$, R$^{19am}$ and R$^{20am}$ are independently selected from hydrogen, hydroxy, sulfanyl, sulfo, halogen, amino, cyano, nitro, C$_{1-6}$-alkyl, C$_{2-6}$-alkenyl, aryl, heteroaryl, C$_{3-8}$-heterocyclyl and C$_{3-10}$-cycloalkyl, wherein each of hydroxy, sulfanyl, sulfo, amino, C$_{1-6}$-alkyl, C$_{2-6}$-alkenyl, aryl, heteroaryl, C$_{3-8}$-heterocyclyl and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl, and C$_{3-10}$-cycloalkyl, wherein each of the hydroxy, sulfanyl, amino, sulfo, C$_{1-6}$-alkyl, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl, C$_{3-10}$-cycloalkyl, wherein each of the hydroxy, sulfanyl, amino, sulfo, C$_{1-6}$-alkyl, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl and C$_{3-10}$-cycloalkyl, wherein each of the hydroxy, sulfanyl, amino, sulfo, C$_{1-6}$-alkyl, C$_{2-6}$-alkenyl, aryl, heteroaryl, C$_{3-8}$-heterocyclyl, and C$_{3-10}$-cycloalkyl may optionally be substituted with one or more substituents independently selected from hydroxy, sulfanyl, oxo, halogen, amino, cyano, nitro, sulfo, C$_{1-6}$-alkyl, C$_{2-6}$-alkenyl, aryl, heteroaryl, C$_{3-8}$-heterocyclyl, C$_{3-10}$-cycloalkyl, perhalomethyl and perhalomethoxy; with the proviso that R$^{17am}$ and R$^{20am}$ are not both hydroxy; and wherein there may optionally be a covalent bond between R$^{18am}$ and a substituent selected from R$^{17am}$ and R$^{19am}$; and wherein there may optionally be a covalent bond between the substituents R$^{10am}$ and a substituent selected from R$^{14am}$ and R$^{15am}$; and wherein there may optionally be a covalent bond between the substituents R$^{7am}$ and R$^{8am}$.

In one embodiment, the invention is concerned with compounds of the general formula XXXXI, wherein there is a covalent bond between R$^{18am}$ and a substituents selected from R$^{17am}$ and R$^{19am}$.

In another embodiment, the invention is concerned with compounds of the general formula XXXXI, wherein there is a covalent bond between R$^{10am}$ and a substituent selected from R$^{14am}$ or R$^{15am}$.

In another embodiment, the invention is concerned with compounds of the general formula XXXXI, wherein E is —NR$^{14am}$—.

In another embodiment, the invention is concerned with compounds of the general formula XXXXI, wherein R$^{14am}$ is selected from F, Cl, C$_{1-6}$-alkyl, C$_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXXXI, wherein E is —CR$^{15am}$R$^{16am}$—.

In another embodiment, the invention is concerned with compounds of the general formula XXXXI, wherein R$^{16am}$ is selected from F, Cl, C$_{1-6}$-alkyl, C$_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXXXI, wherein R$^{15am}$ is hydrogen.

In another embodiment, the invention is concerned with compounds of the general formula XXXXI, wherein there is a covalent bond between R$^{15am}$ and R$^{16am}$.

In another embodiment, the invention is concerned with compounds of the general formula XXXXI, wherein at least one of R$^{6am}$, R$^{7am}$, R$^{8am}$, R$^{9am}$, R$^{10am}$, R$^{11am}$, R$^{12am}$ and R$^{13am}$ are selected from F, Cl, C$_{1-6}$-alkyl, C$_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another aspect of the invention, compounds are of the general formula XXXXII (XXXXII)

wherein E is selected from the group consisting of —O—, —S—, —S(=O)—, —S(=O)$_2$— and —NR$^{17nm}$—, —CR$^{18an}$R$^{19an}$—; and R$^{4an}$, R$^{5an}$, R$^{6an}$, R$^{7an}$, R$^{8an}$, R$^{9an}$, R$^{10an}$, R$^{11an}$, R$^{12an}$, R$^{13an}$, R$^{14an}$, R$^{15an}$, R$^{16an}$, R$^{17an}$, R$^{18an}$ and R$^{19an}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$heterocyclyl, and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl and $C_{3-10}$-cycloalkyl, wherein each of the hydroxy, sulfanyl, amino, sulfo, $C_{1-6}$-alkyl, $C_{2-6}$-alkenyl, aryl, heteroaryl, $C_{3-8}$-heterocyclyl, and $C_{3-10}$-cycloalkyl may optionally be substituted with one or more substituents independently selected from hydroxy, sulfanyl, oxo, halogen, amino, cyano, nitro, sulfo, $C_{1-6}$-alkyl, $C_{2-6}$-alkenyl, aryl, heteroaryl, $C_{3-8}$-heterocyclyl, $C_{3-10}$-cycloalkyl, perhalomethyl and perhalomethoxy; with the proviso that R$^{4an}$ is not methyl or phenyl; and wherein there may optionally be a covalent bond between R$^{13an}$ and a substituent selected from R$^{17an}$ and R$^{18an}$; and wherein there may optionally be a covalent bond between the substituents R$^{7an}$ and R$^{8an}$.

In one embodiment, the invention is concerned with compounds of the general formula XXXXII, wherein R$^{4an}$ is a substituted heteroaryl.

In another embodiment, the invention is concerned with compounds of the general formula XXXXII, wherein said substituted heteroaryl is a substituted pyridine.

In another embodiment, the invention is concerned with compounds of the general formula XXXXII, wherein there is a covalent bond between the substituents R$^{7an}$ and R$^{8an}$.

In another embodiment, the invention is concerned with compounds of the general formula XXXXII, wherein there is a covalent bond between R$^{13an}$ and a substituents selected from R$^{17an}$ and R$^{18an}$.

In another embodiment, the invention is concerned with compounds of the general formula XXXXII, wherein E is —NR$^{17an}$—.

In another embodiment, the invention is concerned with compounds of the general formula XXXXII, wherein E is —CR$^{18an}$R$^{19an}$—.

In another embodiment, the invention is concerned with compounds of the general formula XXXXII, wherein R$^{19an}$ is selected from F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another embodiment, the invention is concerned with compounds of the general formula XXXXII, wherein R$^{18an}$ is hydrogen.

In another embodiment, the invention is concerned with compounds of the general formula XXXXII, wherein at least one of R$^{5an}$, R$^{6an}$, R$^{7an}$, R$^{8an}$, R$^{10an}$, R$^{11an}$, R$^{12an}$, R$^{13an}$, R$^{14an}$, R$^{15an}$ and R$^{16an}$ are selected from F, Cl, $C_{1-6}$-alkyl, $C_{1-6}$-alkoxy, —C(=O)NH$_2$, —NHC(=O)—OH, —S(=O)$_2$—NH$_2$, —NH—S(=O)$_2$—OH, hydroxy, amino and perhalomethyl.

In another aspect of the invention, compounds are of the general formula XXXXIII

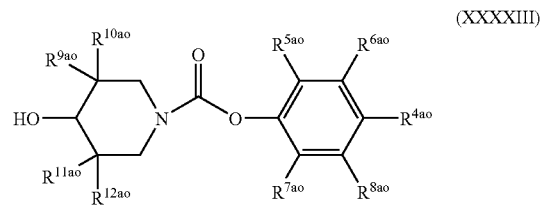

(XXXXIII)

wherein R$^{4ao}$ is selected from hydrogen, hydroxy, sulfo, halogen, amino, cyano, nitro, $C_{1-6}$-alkyl, $C_{2-6}$-alkenyl, aryl, heteroaryl, $C_{3-8}$-heterocyclyl, and $C_{3-10}$-cycloalkyl, wherein each of hydroxy, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; and wherein R$^{5ao}$, R$^{6ao}$, R$^{7ao}$, R$^{8ao}$, R$^{9ao}$, R$^{10ao}$, R$^{11ao}$ and R$^{12ao}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl, and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy;

with the proviso that any one of $R^{6ao}$ and $R^{8ao}$ is not methyl; and with the further proviso that $R^{4ao}$, $R^{5ao}$, $R^{6ao}$, $R^{7ao}$ and $R^{8ao}$ are not all hydrogen; and wherein there may optionally be a covalent bond beween $R^{4ao}$ and $R^{6ao}$; and wherein there may optionally be a covalent bond between $R^{7ao}$ and $R^{8ao}$; and wherein there may optionally be a covalent bond between $R^{9ao}$ and $R^{10ao}$.

In one embodiment the invention is concerned with compounds of the general formula XXXXIII, wherein $R^{5ao}$, $R^{6ao}$, $R^{7ao}$ and $R^{8ao}$ are independently selected from hydrogen and fluor.

In another embodiment the invention is concerned with compounds of the general formula XXXXIII, wherein $R^{9ao}$, $R^{10ao}$, $R^{11ao}$ and $R^{12ao}$ are independently selected from hydrogen and fluor.

In another aspect of the invention, compounds are of the general formulae XXXXIVa-b

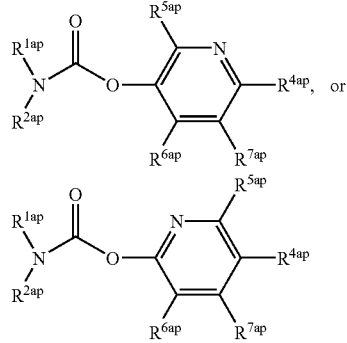

(XXXXIVa-b)

wherein $R^{1ap}$ and $R^{2ap}$ are independently selected from $C_{1-6}$-alkyl, $C_{2-6}$-alkenyl, aryl, heteroaryl, $C_{3-8}$-heterocyclyl, and $C_{3-10}$-cycloalkyl, wherein each of $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; with the proviso that if $R^{1ap}$ and $R^{2ap}$ are identical then they are not methyl or ethyl; and wherein there may optionally be a covalent bond between the substituents $R^{1ap}$ and $R^{2ap}$; and wherein $R^{5ap}$, $R^{6ap}$ and $R^{7ap}$ are independently selected from hydrogen and F; and wherein $R^{4ap}$ is selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl, and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; with the proviso that $R^{4ap}$ is not methyl.

In one embodiment the invention is concerned with compounds of the general formulae XXXXIVa-b, wherein $R^{1ap}$ and $R^{2ap}$ are not identical.

In another aspect of the invention, compounds are of the general formulae XXXXVa-b

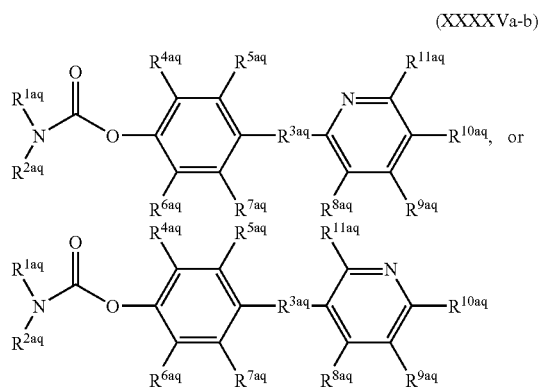

(XXXXVa-b)

wherein $R^{1aq}$ and $R^{2aq}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl, and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; with the proviso that $R^{1aq}$ and $R^{2aq}$ are not both methyl; and wherein there may optionally be a covalent bond between $R^{1aq}$ and $R^{2aq}$; and wherein $R^{3aq}$, $R^{4aq}$, $R^{5aq}$, $R^{6aq}$, $R^{7aq}$, $R^{8aq}$, $R^{9aq}$, $R^{10aq}$ and $R^{11ao}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl, and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; and wherein there may optionally be a covalent bond between $R^{4aq}$ and $R^{5aq}$; and wherein $R^{3aq}$ is selected from the group consisting of —C(=O)—, —C(=O)NH—, —CH$_2$—, —CH$_2$CH$_2$—, —CHF—, —CH$_2$CHF—, —CHFCH$_2$—, —NH—, —S(=O)$_2$—NH—, —NH—S(=O)$_2$—, —NHC(=O)—, —O—, —S—, —S(=O)—, —S(=O)$_2$—; and wherein there may optionally be a covalent bond between two substituents selected from $R^{8aq}$, $R^{9aq}$, $R^{10aq}$ and $R^{11ao}$.

In one embodiment the invention is concerned with compounds of the general formulae XXXXVa-b, wherein there is one covalent bond between the substituents $R^{1aq}$ and $R^{2aq}$.

In another embodiment the invention is concerned with compounds of the general formulae XXXXVa-b, wherein $R^{4aq}$, $R^{5aq}$, $R^{6aq}$ and $R^{7aq}$ are independently selected from hydrogen and fluor.

In another embodiment the invention is concerned with compounds of the general formula XXXXVa-b, wherein $R^{3aq}$ is selected from —O—, —S—, —CH$_2$—, —CH$_2$CH$_2$—, —NH—, —NH—C(=O)—,—C(=O)—NH—, —S(=O)$_2$—NH— and —NH—S(=O)$_2$—.

In another aspect of the invention, compounds are of the general formula XXXXVI

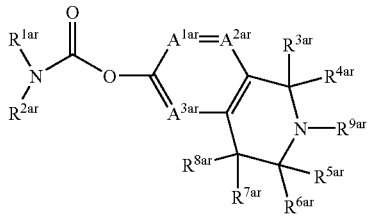

(XXXXVI)

wherein $A^{1ar}$ is N or C—$R^{10ar}$; and $A^{2ar}$ is N or C—$R^{11ar}$; and $A^{3ar}$ is N or C—$R^{12ar}$; and wherein $R^{1ar}$, $R^{2ar}$, $R^{3ar}$, $R^{4ar}$, $R^{5ar}$, $R^{6ar}$, $R^{7ar}$, $R^{8ar}$, $R^{9ar}$, $R^{10ar}$, $R^{11ar}$ and $R^{12ar}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl, and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$alkyl, $C_{2-6}$-alkenyl, perhalomethyl and perhalomethoxy; with the proviso that if $R^{1ar}$ and $R^{2ar}$ are identical then they are not methyl or ethyl; and wherein there may optionally be a covalent bond between $R^{1ar}$ and $R^{2ar}$.

In one embodiment the invention is concerned with compounds of the general formula XXXXVI, wherein $R^{9ar}$ is S(=O)$_2$—$R^{13ar}$ or C(=O)—$R^{13ar}$; and wherein $R^{13ar}$ is selected from hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy In another embodiment the invention is concerned with compounds of the general formula XXXXVI, wherein $R^{1ar}$ and $R^{2ar}$ are not identical.

In another embodiment the invention is concerned with compounds of the general formula XXXXVI, wherein there is a covalent bond between the substituents $R^{1ar}$ and $R^{2ar}$.

In another aspect of the invention, compounds are of the general formula XXXXVII

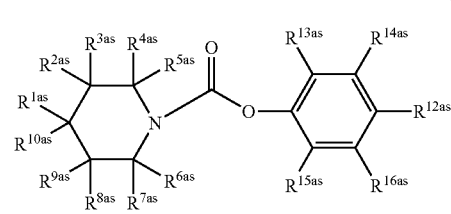

(XXXXVII)

wherein $R^{1as}$, $R^{2as}$, $R^{3as}$, $R^{4as}$, $R^{5as}$, $R^{6as}$, $R^{7as}$, $R^{8as}$ and $R^{9as}$ are independetly selected from hydrogen and fluor; and wherein $R^{10as}$ is selected from aryl and heteroaryl, which is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; and wherein $R^{12as}$ is selected from hydrogen, hydroxy, sulfanyl, sulfo, amino, cyano, $C_{1-6}$-alkyl, $C_{2-6}$-alkenyl, aryl, heteroaryl, $C_{3-8}$-heterocyclyl, and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; and wherein $R^{13as}$, $R^{14as}$, $R^{15as}$ and $R^{16as}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl, and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; with the proviso that $R^{12as}$, $R^{13as}$, $R^{14as}$, $R^{15as}$ and $R^{16as}$ are not all hydrogen; and wherein there may optionally be a covalent bond between the substituents $R^{13as}$ and $R^{14as}$.

In one embodiment the invention is concerned with compounds of the general formula XXXXVII, wherein $R^{13as}$, $R^{14as}$, $R^{15as}$ and $R^{16as}$ are independently selected from hydrogen and fluor.

In another aspect of the invention, compounds are of the general formula XXXXVIII

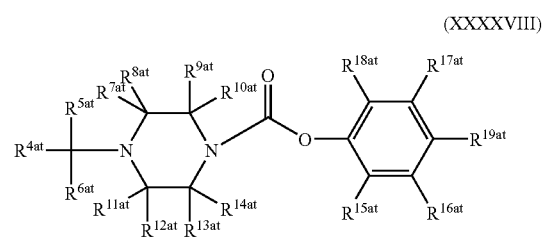

(XXXXVIII)

wherein $R^{5at}$, $R^{6at}$, $R^{7at}$, $R^{8at}$, $R^{9at}$, $R^{10at}$ $R^{11at}$, $R^{12at}$, $R^{13at}$ $R^{14at}$ $R^{15at}$, $R^{16at}$, $R^{17at}$ and $R^{18at}$ are independently selected from hydrogen and fluor; and wherein $R^{4at}$ is selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl, and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$- alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; and wherein $R^{19at}$ is selected from hydrogen, hydroxy, sulfanyl, sulfo, halogen, amino, cyano, $C_{1-6}$-alkyl, $C_{2-6}$-alkenyl, aryl, heteroaryl, $C_{3-8}$-heterocyclyl, and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl may optionally be substituted with one or more substituents independently selected from hydroxy, sulfanyl, sulfo, oxo, fluor, iodine, amino, cyano, nitro, $C_{1-6}$-alkyl, $C_{2-6}$-alkenyl, aryl, heteroaryl, $C_{3-8}$-heterocyclyl and $C_{3-10}$-cycloalkyl; with the proviso that $R^{19at}$ is not methoxy.

In one embodiment the invention is concerned with compounds of the general formula XXXXVIII, wherein $R^{5at}$, $R^{6at}$, $R^{7at}$ $R^{8at}$, $R^{9at}$, $R^{10at}$ $R^{11at}$, $R^{12at}$, $R^{13at}$ $R^{14at}$, $R^{15at}$, $R^{16at}$, $R^{17at}$ and $R^{18at}$ are all hydrogen.

In another embodiment the invention is concerned with compounds of the general formula XXXXVIII, wherein $R^{4at}$ is an optionally substituted aryl or heteroaryl.

In another embodiment, the invention is concerned with compounds of the general formulae I–XXXXVIII, wherein said compound comprises only one F.

In another embodiment, the invention is concerned with compounds of the general formulae I–XXXXVIII, wherein said compound comprises two F and preferably three F.

In another embodiment, the invention is concerned with compounds of the general formulae I–XXXXVIII, wherein said compound comprises a $CF_3$ moiety.

In another embodiment, the invention is concerned with compounds of the general formulae I–XXXXVIII, wherein said compound comprises a hydrophilic substituent selected from the group consisting of hydroxy, amino, $C_{1-6}$-alkoxy, —C(=O)NH$_2$, —NHC(=O)—OH, —S(=O)$_2$—NH$_2$, —NHS(=O)$_2$—OH, —NHC(=O)—R$^{1am}$, —NHS(=O)$_2$—R$^{1am}$, —N(R$^{1am}$)C(=O)—R$^{2am}$, —N(R$^{1am}$)S(=O)$_2$—R$^{2am}$, wherein R$^{1am}$ and R$^{2am}$ are independently selected from $C_{1-6}$-alkyl.

In another embodiment, the invention is concerned with compounds of the general formulae I–XXXXVIII, wherein said compound comprises a moiety selected from the group consisting of

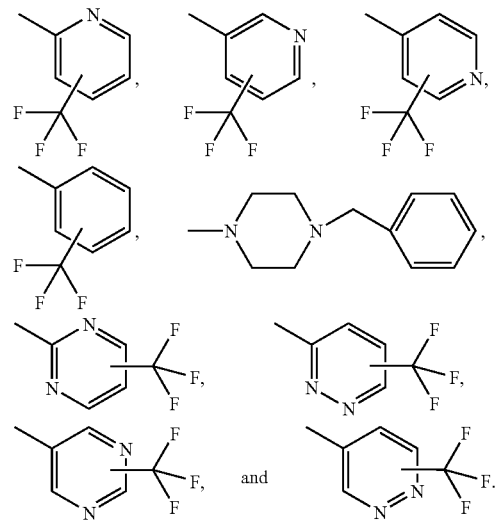

Examples of specific compounds of the invention are:
Methyl-phenyl-carbamic acid 4-(5-trifluoromethyl-pyridin-2-yloxy)-phenyl ester,
Methyl-phenyl-carbamic acid 3-(5-trifluoromethyl-pyridin-2-yloxy)-phenyl ester,
Methyl-phenyl-carbamic acid 4-(3,5-dichloro-pyridin-2-yloxy)-phenyl ester,
Methyl-phenyl-carbamic acid 4-(5-trifluoromethyl-pyridin-2-ylamino)-phenyl ester,
Methyl-phenyl-carbamic acid 4-(3,5-dichloro-pyridin-4-yloxy)-phenyl ester,
Methyl-phenyl-carbamic acid 4-(4-trifluoromethyl-phenoxy)-phenyl ester,
Methyl-phenyl-carbamic acid 4-(2-cyano-5-trifluoromethyl-pyridine-3-yloxy)-phenyl ester,
Methyl-phenyl-carbamic acid 2-benzenesulfonyl-4-(3-chloro-5-trifluoromethyl-pyridine-2-yloxy)-phenyl ester,
Methyl-phenyl-carbamic acid 4-tert-butoxy-phenyl ester,
Methyl-phenyl-carbamic acid 3-(4-fluorobenzyl)-4-methyl-2-oxo-2H-chromen-7-yl ester,
Methyl-phenyl-carbamic acid 4-phenoxy-phenyl ester,
Methyl-phenyl-carbamic acid 4-(4-chlorobenzoyl)-phenyl ester,
Methyl-phenyl-carbamic acid 4-(3-chloro-5-trifluoromethyl)-pyridine-2-yloxy)-phenyl ester,
Methyl-phenyl-carbamic acid 4-[4-(4-chloro-phenyl)-thiazol-2-yl]-phenyl ester,
Methyl-phenyl-carbamic acid 4-pyrrol-1-yl-phenyl ester,
Methyl-phenyl-carbamic acid 4-imidazol-1-yl-phenyl ester,
Methyl-phenyl-carbamic acid 4-(3-chloro-5-trifluoromethyl)-pyridine-2-ylmethyl)-phenyl ester,
Methyl-phenyl-carbamic acid 4-trifluoromethylsulfanyl-phenyl ester,
Methyl-phenyl-carbamic acid 4-pentafluoroethyloxy-phenyl ester,
Methyl-phenyl-carbamic acid 4-benzyloxy-phenyl ester, Methyl-phenyl-carbamic acid 4-benzyl-phenyl ester,
Methyl-phenyl-carbamic acid 4'-cyano-biphenyl-4-yl-ester,
Methyl-phenyl-carbamic acid 4'-bromo-biphenyl-4-yl-ester,
Methyl-phenyl-carbamic acid biphenyl-4-yl-ester,
Methyl-phenyl-carbamic acid 4-[3-(4-chlorophenyl)-ureido]-phenyl ester,
Methyl-phenyl-carbamic acid 4-(4-nitro-phenoxy)-phenyl ester,
Methyl-phenyl-carbamic acid 4-heptylsulfanyl-phenyl ester,
Methyl-phenyl-carbamic acid 4-butoxy-phenyl ester,
Methyl-phenyl-carbamic acid 4-(4-chloro-benzenesulfonyl)-phenyl ester,
Methyl-phenyl-carbamic acid 4-(4-chloromethyl-thiazol-2-yl)-phenyl ester,
Methyl-phenyl-carbamic acid 4-(4,4-dimethyl-2,6-dioxo-piperidin-1-yl)-phenyl ester,
cis-Methyl-phenyl-carbamic acid 4-(1,3-dioxo-octahydro-isoindol-2-yl)-phenyl ester,
Methyl-phenyl-carbamic acid 4-(cyclohexanecarbonyl-amino)-phenyl ester,
Methyl-phenyl-carbamic acid 4-(2-cyclohexyl-acetylamino)-phenyl ester,
cis/trans-Methyl-phenyl-carbamic acid 4-[(4-tert-butyl-cyclohexanecarbonyl)-amino]-phenyl ester,
cis-Methyl-phenyl-carbamic acid 4-[(4-tert-butyl-cyclohexanecarbonyl)-amino]-phenyl ester,
trans-Methyl-phenyl-carbamic acid 4-[(4-tert-butyl-cyclohexanecarbonyl)-amino]-phenyl ester,
Methyl-phenyl-carbamic acid 4-(3,3-dimethyl-butyrylamino)-phenyl ester,
Methyl-phenyl-carbamic acid 3-benzyl-4-methyl-2-oxo-2H-chromen-7-yl ester,
Methyl-phenyl-carbamic acid 3-(3,4-dichloro-benzyl)-4-methyl-2-oxo-2H-chromen-7-yl ester,
Methyl-phenyl-carbamic acid 3-(2-chloro-6-fluoro-benzyl)-4-methyl-2-oxo-2H-chromen-7-yl ester,
Methyl-phenyl-carbamic acid 3-(2,6-dichloro-benzyl)-4-methyl-2-oxo-2H-chromen-7-yl ester,
Methyl-phenyl-carbamic acid 3-(2,6-dichloro-benzyl)-6-chloro-4-methyl-2-oxo-2H-chromen-7-yl ester,
Methyl-phenyl-carbamic acid 6-chloro-3-(2-chloro-6-fluoro-benzyl)-4-n-propy-2-oxo-2H-chromen-7-yl ester,
Methyl-phenyl-carbamic acid 3-(4-methoxy-phenyl)-4-methyl-2-oxo-2H-chromen-7-yl ester,
Methyl-phenyl-carbamic acid 4-methyl-2-oxo-3-phenyl-2H-chromen-7-yl ester,
Methyl-phenyl-carbamic acid 3-(2,5-dimethoxy-phenyl)-4-methyl-2-oxo-2H-chromen-7-yl ester,
Methyl-phenyl-carbamic acid 3-(3,4-dimethoxy-phenyl)-4-methyl-2-oxo-2H-chromen-7-yl ester,
Methyl-phenyl-carbamic acid 4-pyrrolidine-1-yl-phenyl ester,
Methyl-phenyl-carbamic acid 4-piperidine-1-yl-phenyl ester,
Methyl-phenyl-carbamic acid 4-morpholine-1-yl-phenyl ester,
Methyl-phenyl-carbamic acid 4-[(6-chloro-pyridine-3-carbonyl)-amino]-phenyl ester,
Methyl-phenyl-carbamic acid 4-[(6-chloro-pyridine-3-carbonyl)-amino]-phenyl ester,
Methyl-phenyl-carbamic acid 4-[(pyridine-2-carbonyl)-amino]-phenyl ester,
4-Chlor-phenyl-methyl-carbamic acid 4-(5-trifluoromethyl-pyridin-2-yloxy)-phenyl ester,
4-Chlor-phenyl-methyl-carbamic acid 4-(3,5-dichloro-pyridin-2-yloxy)-phenyl ester,
(4-Chloro-phenyl)-methyl-carbamic acid 4-(2-cyano-5-trifluoromethyl-pyridin-3-yloxy)-phenyl ester,
Ethyl-phenyl-carbamic acid 4-(5-trifluoromethyl-pyridin-2-yloxy)-phenyl ester,
Ethyl-phenyl-carbamic acid 4-(4-trifluoromethyl-phenoxy)-phenyl ester,
Methyl-phenyl-carbamic acid pyrazol-1-yl ester,
Methyl-phenyl-carbamic acid 4-bromo-pyrazol-1-yl ester,
Methyl-phenyl-carbamic acid 3,4,5-tribromo-pyrazol-1-yl ester,
Methyl-phenyl-carbamic acid 3-(4-methoxy-phenyl)-pyrazol-1-yl ester,
Methyl-phenyl-carbamic acid imidazol-1-yl ester,
Methyl-phenyl-carbamic acid [1,2,3]triazol-1-yl ester,
Methyl-phenyl-carbamic acid 3-bromo-pyrazol-1-yl ester,
Methyl-phenyl-carbamic acid 5-bromo-pyrazol-1-yl ester,
Methyl-phenyl-carbamic acid 3-chloro-pyrazol-1-yl ester,
Methyl-phenyl-carbamic acid 4-chloro-pyrazol-1-yl ester,
Methyl-phenyl-carbamic acid 5-chloro-pyrazol-1-yl ester,
Methyl-phenyl-carbamic acid 4-iodo-pyrazol-1-yl ester,
Methyl-phenyl-carbamic acid 5-iodo-pyrazol-1-yl ester,
Methyl-phenyl-carbamic acid 3-methyl-pyrazol-1-yl ester,
Methyl-phenyl-carbamic acid 4-methyl-pyrazol-1-yl ester,
Methyl-phenyl-carbamic acid 5-methyl-pyrazol-1-yl ester,
Methyl-phenyl-carbamic acid 4-(4-methoxy-phenyl)-pyrazol-1-yl ester,
Methyl-phenyl-carbamic acid 5-(4-methoxy-phenyl)-pyrazol-1-yl ester,
Methyl-phenyl-carbamic acid 3-(2-methoxy-phenyl)-pyrazol-1-yl ester,
Methyl-phenyl-carbamic acid 3-(4-nitro-phenyl)-pyrazol-1-yl ester,
Methyl-phenyl-carbamic acid 3-(2-nitro-phenyl)-pyrazol-1-yl ester,
Methyl-phenyl-carbamic acid 3-pyridin-2-yl-pyrazol-1-yl ester,
Methyl-phenyl-carbamic acid 4-pyridin-2-yl-pyrazol-1-yl ester,
Methyl-phenyl-carbamic acid 3-(2-fluoro-phenyl)-pyrazol-1-yl ester,
Methyl-phenyl-carbamic acid 4-(2-fluoro-phenyl)-pyrazol-1-yl ester,
Methyl-phenyl-carbamic acid 5-(2-fluoro-phenyl)-pyrazol-1-yl ester,
Methyl-phenyl-carbamic acid 3-phenylsulfanyl-pyrazol-1-yl ester,
Methyl-phenyl-carbamic acid 4-phenylsulfanyl-pyrazol-1-yl ester,
Methyl-phenyl-carbamic acid 5-phenylsulfanyl-pyrazol-1-yl ester,
Methyl-phenyl-carbamic acid 4-thiophen-3-yl-pyrazol-1-yl ester,
Methyl-phenyl-carbamic acid 3-thiophen-2-yl-pyrazol-1-yl ester,
Methyl-phenyl-carbamic acid 4-thiophen-2-yl-pyrazol-1-yl ester,
Methyl-phenyl-carbamic acid 5-thiophen-2-yl-pyrazol-1-yl ester,
Methyl-phenyl-carbamic acid 2-chloro-imidazol-1-yl ester,
Methyl-phenyl-carbamic acid 2-bromo-imidazol-1-yl ester,
Methyl-phenyl-carbamic acid 2-iodo-imidazol-1-yl ester,
Methyl-phenyl-carbamic acid 2-methyl-imidazol-1-yl ester,
Methyl-phenyl-carbamic acid 2-phenylsulfanyl-imidazol-1-yl ester,
Methyl-phenyl-carbamic acid 2-(4-methoxy-phenyl)-imidazol-1-yl ester, Methyl-phenyl-carbamic acid 2-(4-fluoro-phenyl)-imidazol-1-yl ester,
Methyl-phenyl-carbamic acid 2-thiophen-2-yl-imidazol-1-yl ester,
Methyl-phenyl-carbamic acid 2-pyridin-2-yl-imidazol-1-yl ester,
Methyl-phenyl-carbamic acid 2,5-dichloro-imidazol-1-yl ester,
Methyl-phenyl-carbamic acid 4-bromo-2,5-dichloro-imidazol-1-yl ester,
4-(Methyl-phenyl-carbamoyloxy)-benzoic acid 2,5-dioxo-pyrrolidin-1-yl ester,
Methyl-phenyl-carbamic acid 4-(1,3,5-trimethyl-1H-pyrazol-4-ylmethyl)-phenyl ester,
Methyl-phenyl-carbamic acid 4-(2-cyano-ethyl)-phenyl ester,
Methyl-phenyl-carbamic acid 4-([1,2,3,4]thiatriazol-5-ylamino)-phenyl ester,
Methyl-phenyl-carbamic acid 4-pentyl-phenyl ester,
Methyl-phenyl-carbamic acid 4-(2-methoxy-ethyl)-phenyl ester,
Methyl-phenyl-carbamic acid 4-acetyl-phenyl ester,
Methyl-phenyl-carbamic acid pyridin-4-yl ester,
Methyl-phenyl-carbamic acid pyridin-3-yl ester,
Methyl-phenyl-carbamic acid 6-methyl-pyridin-3-yl ester,
Methyl-phenyl-carbamic acid isoquinolin-1-yl ester,
Methyl-phenyl-carbamic acid 3-phenoxy-phenyl ester,
Methyl-phenyl-carbamic acid 3-acetyl-phenyl ester,
Methyl-phenyl-carbamic acid 4-acetyl-2-carbamoyl-phenyl ester,
Methyl-phenyl-carbamic acid 4-acetyl-3-methyl-phenyl ester,
Methyl-phenyl-carbamic acid 1-oxo-indan-4-yl ester,
Methyl-phenyl-carbamic acid benzothiazol-2-yl ester,
Methyl-phenyl-carbamic acid 5-oxo-5,6,7,8-tetrahydro-naphthalen-2-yl ester,
Methyl-phenyl-carbamic acid benzo[d]isoxazol-3-yl ester,
Methyl-phenyl-carbamic acid pyridin-2-yl ester,
Methyl-phenyl-carbamic acid 1-(methyl-phenyl-carbamoyl)-1H-benzimidazol-2-yl ester,
Methyl-phenyl-carbamic acid 4-[(pyridine-3-carbonyl)-amino]-phenyl ester,
Methyl-phenyl-carbamic acid 4-(3-pyridin-3-yl-acryloyl)-phenyl ester,
Methyl-phenyl-carbamic acid 4-[3-(3,4,5-trimethoxy-phenyl)-acryloyl]-phenyl ester,
Methyl-phenyl-carbamic acid 4-diethylcarbamoyl-2-methoxy-phenyl ester,
Methyl-phenyl-carbamic acid 3-phenylcarbamoyl-phenyl ester,
Methyl-phenyl-carbamic acid quinolin-7-yl ester,
Methyl-phenyl-carbamic acid 4-(4-methyl-piperazine-1-carbonyl)-phenyl ester,
Methyl-phenyl-carbamic acid 3-acetylamino-phenyl ester,
Methyl-phenyl-carbamic acid 4-benzoyl-phenyl ester,
Methyl-phenyl-carbamic acid biphenyl-3-yl ester,
Methyl-phenyl-carbamic acid 1H-indol-4-yl ester,
Methyl-phenyl-carbamic acid 5,6,7,8-tetrahydro-naphthalen-1-yl ester,
Methyl-phenyl-carbamic acid 5-oxo-5,6,7,8-tetrahydro-naphthalen-1-yl ester,
Methyl-phenyl-carbamic acid 1,3-dioxo-1,3-dihydro-isobenzofuran-4-yl ester,
Methyl-phenyl-carbamic acid 4-(5-chloro-pyridin-2-yloxy)-phenyl ester,
Methyl-phenyl-carbamic acid 4-morpholin-4-yl-phenyl ester,
Methyl-phenyl-carbamic acid 4-(5,6-dichloro-1,3-dioxo-1,3-dihydro-isoindol-2-yl)-phenyl ester,
Methyl-phenyl-carbamic acid 4-(2-phenoxy-acetylamino)-phenyl ester,
Methyl-phenyl-carbamic acid 4-[2-(4-chloro-phenyl)-ethyl]-phenyl ester,
Methyl-phenyl-carbamic acid 4-[(pyridine-2-carbonyl)-amino]-phenyl ester,
Methyl-phenyl-carbamic acid 4-[methyl-(thiophene-2-carbonyl)-amino]-phenyl ester,
Methyl-phenyl-carbamic acid 4-butyrylamino-phenyl ester,
Methyl-phenyl-carbamic acid 4-(4,6-dimethyl-pyrimidin-2-ylsulfanyl)-phenyl ester,
Methyl-phenyl-carbamic acid 4-methanesulfonyl-phenyl ester,
Methyl-phenyl-carbamic acid 4-[2-(3-oxo-1,2,3,4-tetrahydro-quinoxalin-2-yl)-acetylamino]-phenyl ester,
Methyl-phenyl-carbamic acid 4-phenylacetyl-phenyl ester,
Methyl-phenyl-carbamic acid 4-{[4-(methyl-phenyl-carbamoyloxy)-2-oxo-1,2-dihydro-quinoline-3-carbonyl]-amino}-phenyl ester,
Methyl-phenyl-carbamic acid 4-[(4-hydroxy-2-oxo-1,2-dihydro-quinoline-3-carbonyl)-amino]-phenyl ester,
Methyl-phenyl-carbamic acid 4-(4-hydroxy-benzyl)-phenyl ester
Methyl-phenyl-carbamic acid 4-(4-trifluoromethyl-benzyl-carbamoyl)-phenyl ester,
Methyl-phenyl-carbamic acid 4-(butyl-methyl-carbamoyl)-phenyl ester,
Methyl-phenyl-carbamic acid 4-(methyl-phenethyl-carbamoyl)-phenyl ester,
Methyl-phenyl-carbamic acid 4-[(pyridin-2-ylmethyl)-carbamoyl]-phenyl ester,
Methyl-phenyl-carbamic acid 4-(2-pyridin-2-yl-ethylcarbamoyl)-phenyl ester,
Methyl-phenyl-carbamic acid 4-(2-phenylamino-ethylcarbamoyl)-phenyl ester,
Methyl-phenyl-carbamic acid 4-(3-methyl-butylcarbamoyl)-phenyl ester,
Methyl-phenyl-carbamic acid 4-(3,3-dimethyl-butylcarbamoyl)-phenyl ester,
Methyl-phenyl-carbamic acid 4-[(tetrahydro-furan-2-ylmethyl)-carbamoyl]-phenyl ester,
Methyl-phenyl-carbamic acid 4-cyclohexylcarbamoyl-phenyl ester,
Methyl-phenyl-carbamic acid 4-cyclopropylcarbamoyl-phenyl ester,
Methyl-phenyl-carbamic acid 4-(cyclohexylmethyl-carbamoyl)-phenyl ester,
Methyl-phenyl-carbamic acid 5-nitro-pyridin-2-yl ester,
Methyl-phenyl-carbamic acid pyrimidin-2-yl ester,
Methyl-phenyl-carbamic acid 7-chloro-quinolin-4-yl ester,
Methyl-phenyl-carbamic acid quinolin-4-yl ester,
Methyl-phenyl-carbamic acid 5-methyl-isoxazol-3-yl ester,
Methyl-phenyl-carbamic acid quinoxalin-2-yl ester,
Methyl-phenyl-carbamic acid 4-methyl-quinolin-2-yl ester,
Methyl-phenyl-carbamic acid 3-methyl-quinoxalin-2-yl ester,
Methyl-phenyl-carbamic acid 4,6-dimethyl-pyrimidin-2-yl ester,
Methyl-phenyl-carbamic acid isoquinolin-6-yl ester,
Methyl-phenyl-carbamic acid quinolin-2-yl ester,
Methyl-phenyl-carbamic acid isoquinolin-3-yl ester,
Methyl-phenyl-carbamic acid 4-trifluoromethyl-pyrimidin-2-yl ester,
Methyl-phenyl-carbamic acid 3-nitro-pyridin-2-yl ester,
Methyl-phenyl-carbamic acid 5-chloro-pyridin-2-yl ester, Methyl-phenyl-carbamic acid 5-(2-nitro-phenyl)-pyrimidin-2-yl ester,
Methyl-phenyl-carbamic acid 5-trifluoromethyl-pyridin-2-yl ester,
Methyl-phenyl-carbamic acid 3-chloro-5-trifluoromethyl-pyridin-2-yl ester,
Methyl-phenyl-carbamic acid 5-nitro-3-trifluoromethyl-pyridin-2-yl ester,
Methyl-phenyl-carbamic acid 4,5-dichloro-pyridazin-3-yl ester,
Methyl-phenyl-carbamic acid 5-benzoylamino-pyridin-2-yl ester,
Methyl-phenyl-carbamic acid 5-(cyclohexanecarbonyl-amino)-pyridin-2-yl ester,
Methyl-phenyl-carbamic acid 4,4-dimethyl-2,6-dioxo-3,4,5,6-tetrahydro-2H-[1,3']bipyridinyl-6'-yl ester,
Methyl-phenyl-carbamic acid 5-(2,2-dimethyl-propionylamino)-pyridin-2-yl ester,
Methyl-phenyl-carbamic acid 5-(2-cyclohexyl-acetylamino)-pyridin-2-yl ester,
Methyl-phenyl-carbamic acid 5-(4-methoxy-phenoxy)-pyrimidin-2-yl ester,
Methyl-phenyl-carbamic acid 5-(3,4-dichloro-phenoxy)-pyrimidin-2-yl ester,
Methyl-phenyl-carbamic acid 6-pyridin-2-ylmethyl-pyridazin-3-yl ester,
Methyl-phenyl-carbamic acid 6-(4-methoxy-benzyl)-pyridazin-3-yl ester,
Methyl-phenyl-carbamic acid 6-(2,4-dichloro-benzyl)-pyridazin-3-yl ester,
Methyl-phenyl-carbamic acid 4-iodo-pyrazol-1-yl ester,
Methyl-phenyl-carbamic acid benzotriazol-1-yl ester,
Methyl-phenyl-carbamic acid [1,2,3]triazolo[4,5-b]pyridin-3-yl ester,
Methyl-phenyl-carbamic acid 3-(2-nitro-phenyl)-pyrazol-1-yl ester,
Methyl-phenyl-carbamic acid 3-(4-nitro-phenyl)-pyrazol-1-yl ester,
Methyl-phenyl-carbamic acid 3-pyridin-2-yl-pyrazol-1-yl ester,
Methyl-phenyl-carbamic acid 3-thiophen-2-yl-pyrazol-1-yl ester,
Methyl-phenyl-carbamic acid 3-(2-fluoro-phenyl)-pyrazol-1-yl ester,
Methyl-phenyl-carbamic acid 3-bromo-pyrazol-1-yl ester,
Methyl-phenyl-carbamic acid 5-iodo-pyrazol-1-yl ester,
Methyl-phenyl-carbamic acid 2-chloro-imidazol-1-yl ester,
Methyl-phenyl-carbamic acid 4-(4-methoxy-phenyl)-pyrazol-1-yl ester,
Methyl-phenyl-carbamic acid 5-benzoyl-pyrazol-1-yl ester,
Methyl-phenyl-carbamic acid 5-(4-methoxy-phenyl)-pyrazol-1-yl ester,
Methyl-phenyl-carbamic acid 5-(4-dimethylamino-phenyl)-pyrazol-1-yl ester,
Methyl-phenyl-carbamic acid 4,5-diiodo-pyrazol-1-yl ester,
Methyl-phenyl-carbamic acid 5-thiophen-2-yl-pyrazol-1-yl ester,
Methyl-phenyl-carbamic acid 2-(4-methoxy-phenyl)-imidazol-1-yl ester,
Methyl-phenyl-carbamic acid 2-methylsulfanyl-imidazol-1-yl ester,
Methyl-phenyl-carbamic acid 3,5-bis-(4-methoxy-phenyl)-pyrazol-1-yl ester,
Methyl-phenyl-carbamic acid 4-(4-fluoro-phenyl)-5-(4-methoxy-phenyl)-3-(4-methylphenyl)-pyrazol-1-yl ester,
Methyl-phenyl-carbamic acid 4-benzyl-5-(4-methoxy-phenyl)-3-(methylphenyl)-pyrazol-1-yl ester,
Methyl-phenyl-carbamic acid 4-acetyl-pyrazol-1-yl ester,
Methyl-phenyl-carbamic acid 2-(4-nitro-phenyl)-imidazol-1-yl ester,
Methyl-phenyl-carbamic acid 2-chloro-5-(4-methylphenyl)-imidazol-1-yl ester,
Methyl-phenyl-carbamic acid 4-formyl-pyrazol-1-yl ester,
Methyl-phenyl-carbamic acid 4-hydroxymethyl-pyrazol-1-yl ester,
Methyl-phenyl-carbamic acid 4-phenylethynyl-pyrazol-1-yl ester,
Methyl-phenyl-carbamic acid 2-bromo-imidazol-1-yl ester,
Methyl-phenyl-carbamic acid 2-phenylsulfanyl-imidazol-1-yl ester,
Methyl-o-tolyl-carbamic acid 4-(trifluoromethyl-pyridin-2-yloxy)-phenyl ester,
Methyl-m-tolyl-carbamic acid 4-(5-trifluoromethyl-pyridin-2-yloxy)-phenyl ester,
(3-Chloro-phenyl)-methyl-carbamic acid 4-(5-trifluoromethyl-pyridin-2-yloxy)-phenyl ester,
Methyl-p-tolyl-carbamic acid 4-(5-trifluoromethyl-pyridin-2-yloxy)-phenyl ester,
(3-Fluoro-phenyl)-methyl-carbamic acid 4-(5-trifluoromethyl-pyridin-2-yloxy)-phenyl ester,
(3-Chloro-phenyl)-methyl-carbamic acid 4-trifluoromethyl-pyrimidin-2-yl ester,
Methyl-m-tolyl-carbamic acid 4-trifluoromethyl-pyrimidin-2-yl ester,
Methyl-phenyl-carbamic acid 5-(3,3-dimethyl-butyrylamino)-pyridin-2-yl ester,
Methyl-phenyl-carbamic acid 5-[(pyridine-2-carbonyl)-amino]-pyridin-2-yl ester,
Methyl-phenyl-carbamic acid 2-(4,4-dimethyl-2,6-dioxo-piperidin-1-yl)-pyrimidin-5-yl ester,
Methyl-phenyl-carbamic acid 5-bromo-pyrimidin-2-yl ester,
Methyl-phenyl-carbamic acid 5-[(6-chloro-pyridine-3-carbonyl)-amino]-pyridin-2-yl ester,
Methyl-phenyl-carbamic acid 5-(2,2-dimethyl-propylcarbamoyl)-pyridin-2-yl ester,
Methyl-phenyl-carbamic acid 6-(3,4-dichloro-phenoxy)-pyridazin-3-yl ester,
Methyl-phenyl-carbamic acid 2,6-dioxo-3,4,5,6-tetrahydro-2H-[1,3']bipyridinyl-6'-yl ester,
Methyl-phenyl-carbamic acid 5-(2,5-dioxo-pyrrolidin-1-yl)-pyridin-2-yl ester,
Methyl-phenyl-carbamic acid 5-(4-trifluoromethyl-benzoylamino)-pyridin-2-yl ester,
Methyl-phenyl-carbamic acid quinolin-6-yl ester,
Methyl-phenyl-carbamic acid 5-(4-chloro-benzoylamino)-pyridin-2-yl ester,
4 Methyl-phenyl-carbamic acid 5-(4-methoxy-benzoylamino)-pyridin-2-yl ester,
Methyl-phenyl-carbamic acid 4,4-dimethyl-3,4,5,6-tetrahydro-2H-[1,3']bipyridinyl-6'-yl ester,
Methyl-phenyl-carbamic acid 2-methyl-quinolin-6-yl ester,
{2-[4-(Methyl-phenyl-carbamoyloxy)-phenyl]-ethyl}-carbamic acid tert-butyl ester,
Methyl-phenyl-carbamic acid 4-(2-amino-ethyl)phenyl ester,
Methyl-phenyl-carbamic acid 4-[2-(toluene-4-sulfonylamino)-ethyl]-phenyl ester,
Methyl-phenyl-carbamic acid 4-[2-(5-dimethylamino-naphthalene-1-sulfonylamino)-ethyl]-phenyl ester,
Methyl-phenyl-carbamic acid 4-[2-(3,4-difluoro-benzenesulfonylamino)-ethyl]-phenyl ester,
2-{2-[4-(Methyl-phenyl-carbamoyloxy)-phenyl]-ethylsulfamoyl}-benzoic acid methyl ester, Methyl-phenyl-carbamic acid 4-[2-(2,5-dichloro-thiophene-3-sulfonylamino)-ethyl]-phenyl ester,
Methyl-phenyl-carbamic acid 4-[2-(5-pyridin-2-yl-thiophene-2-sulfonylamino)-ethyl]-phenyl ester,
Methyl-phenyl-carbamic acid 4-[2-(1-methyl-1H-imidazole-4-sulfonylamino)-ethyl]-phenyl ester,
Methyl-phenyl-carbamic acid 4-[2-(5-chloro-1,3-dimethyl-1H-pyrazole-4-sulfonylamino)-ethyl]-phenyl,
Methyl-phenyl-carbamic acid 4-[2-(4-nitro-benzenesulfonylamino)-ethyl]-phenyl ester,
Methyl-phenyl-carbamic acid 4-[2-(6-chloro-imidazo[2,1-b]thiazole-5-sulfonylamino)-ethyl]-phenyl ester,
Methyl-phenyl-carbamic acid 4-[2-(2-trifluoromethoxy-benzenesulfonylamino)-ethyl]-phenyl ester,
Methyl-phenyl-carbamic acid 4-(2-dimethylaminosulfonylamino-ethyl)-phenyl ester,
Methyl-phenyl-carbamic acid 4-(2-methanesulfonylamino-ethyl)-phenyl ester,
Methyl-phenyl-carbamic acid 4-[2-(6-morpholin-4-yl-pyridine-3-sulfonylamino)-ethyl]-phenyl ester,
Methyl-phenyl-carbamic acid 4-[2-(6-phenoxy-pyridine-3-sulfonylamino)-ethyl]-phenyl ester,
Methyl-phenyl-carbamic acid 4-{2-[4-(4-methyl-piperazin-1-yl)-benzenesulfonylamino]-ethyl}-phenyl ester,
Methyl-phenyl-carbamic acid 4-[2-(4-dimethylamino-benzenesulfonylamino)-ethyl]-phenyl ester,
Methyl-phenyl-carbamic acid 4-{2-[4-(2-pyrrolidin-1-yl-ethoxy)-benzenesulfonylamino]-ethyl}-phenyl ester,
Methyl-phenyl-carbamic acid 4-(2-cyclohexyl-ethylsulfamoyl)-phenyl ester,
Methyl-phenyl-carbamic acid 4-(3-methyl-butylsulfamoyl)-phenyl ester,
Methyl-phenyl-carbamic acid 4-(1,1,3,3-tetramethyl-butylcarbamoyl)-phenyl ester,
Methyl-phenyl-carbamic acid 4-[(2-dimethylamino-ethyl)-methyl-carbamoyl]-phenyl ester,
Methyl-phenyl-carbamic acid 4-(cyclopropylmethyl-carbamoyl)-phenyl ester,
Methyl-phenyl-carbamic acid 4-(methyl-pyridin-3-ylmethyl-carbamoyl)-phenyl ester,
Methyl-phenyl-carbamic acid 4-[(1H-benzimidazol-2-ylmethyl)-carbamoyl]-phenyl ester,
Methyl-phenyl-carbamic acid 4-[2-(4-chloro-phenyl)-ethylcarbamoyl]-phenyl ester,
Methyl-phenyl-carbamic acid 5-amino-pyridin-2-yl ester,
Methyl-phenyl-carbamic acid 5-benzenesulfonylamino-pyridin-2-yl ester,
3,3-Dimethyl-4-[6-(methyl-phenyl-carbamoyloxy)-pyridin-3-ylcarbamoyl]-butyric acid,
2,2-Dimethyl-N-[6-(methyl-phenyl-carbamoyloxy)-pyridin-3-yl]-succinamic acid,
Methyl-phenyl-carbamic acid 5-(3,3-dimethyl-2,5-dioxo-pyrrolidin-1-yl)-pyridin-2-yl ester,
Methyl-phenyl-carbamic acid 5-[3,3-dimethyl-5-(4-methylpiperazin-1-yl)-5-oxo-pentanoylamino]-pyridin-2-yl ester,
Methyl-phenyl-carbamic acid 5-[3,3-dimethyl-4-(pyridin-3-ylcarbamoyl)-butyrylamino]-pyridin-2-yl ester,
Methyl-phenyl-carbamic acid 5-(3,3-dimethyl-5-morpholin-4-yl-5-oxo-pentanoylamino)-pyridin-2-yl ester,
Methyl-phenyl-carbamic acid 5-[4-(2-dimethylamino-ethylcarbamoyl)-3,3-dimethyl-butyrylamino]-pyridin-2-yl ester,
Methyl-phenyl-carbamic acid 4-iodo-phenyl ester,
Methyl-phenyl-carbamic acid 4'-trifluoromethyl-biphenyl-4-yl ester,
Methyl-phenyl-carbamic acid 4'-trifluoromethoxy-biphenyl-4-yl ester,
Methyl-phenyl-carbamic acid 4-pyridin-3-yl-phenyl ester,
Methyl-phenyl-carbamic acid 4-(5-chloro-thiophen-2-yl)-phenyl ester,
Methyl-phenyl-carbamic acid 4'-benzylsulfamoyl-biphenyl-4-yl ester,
Methyl-phenyl-carbamic acid 4-styryl-phenyl ester,
Methyl-phenyl-carbamic acid 4-phenylethynyl-phenyl ester,
3-[4-(Methyl-phenyl-carbamoyloxy)-phenyl]-acrylic acid methyl ester,
Methyl-phenyl-carbamic acid 4-(toluene-4-sulfonylamino)-phenyl ester,
Methyl-phenyl-carbamic acid 4-(5-pyridin-2-yl-thiophene-2-sulfonylamino)-phenyl ester,
Methyl-phenyl-carbamic acid 4-(1-methyl-1H-imidazole-4-sulfonylamino)-phenyl ester,
Methyl-phenyl-carbamic acid 4-(2,5-dichloro-thiophene-3-sulfonylamino)-phenyl ester,
Methyl-phenyl-carbamic acid 4-(5-chloro-1,3-dimethyl-1H-pyrazole-4-sulfonylamino)-phenyl ester,
Methyl-phenyl-carbamic acid 4-(5-dimethylamino-naphthalene-1-sulfonylamino)-phenyl ester,
2-[4-(Methyl-phenyl-carbamoyloxy)-phenylsulfamoyl]-benzoic acid methyl ester,
Methyl-phenyl-carbamic acid 4-(3,4-difluoro-benzenesulfonylamino)-phenyl ester,
Methyl-phenyl-carbamic acid 4-pyridin-2-ylmethyl-phenyl ester,
Methyl-phenyl-carbamic acid 4-pyridin-3-ylmethyl-phenyl ester,
Methyl-phenyl-carbamic acid 4-(4-trifluoromethyl-benzyl)-phenyl ester,
Methyl-phenyl-carbamic acid 4-thiophen-3-ylmethyl-phenyl ester,
Methyl-phenyl-carbamic acid 4-thiophen-2-ylmethyl-phenyl ester,
Methyl-phenyl-carbamic acid 4-[2-(4-amino-benzenesulfonylamino)-ethyl]-phenyl ester,
Methyl-phenyl-carbamic acid 4-{2-[(pyridine-3-carbonyl)-amino]-ethyl}-phenyl ester,
Methyl-phenyl-carbamic acid 4-[2-(2-dimethylamino-acetylamino)-ethyl]-phenyl ester,
Methyl-phenyl-carbamic acid 2-(toluene-4-sulfonyl)-1,2,3,4-tetrahydro-isoquinolin-7-yl ester,
Methyl-phenyl-carbamic acid 4-[4-(2-pyrrolidin-1-yl-ethoxy)-benzyl]-phenyl ester,
Methyl-phenyl-carbamic acid 2-[4-(2-pyrrolidin-1-yl-ethoxy)-benzenesulfonyl]-1,2,3,4-tetrahydro-isoquinolin-7-yl ester,
Methyl-phenyl-carbamic acid 4-{2-[(1-methyl-piperidine-4-carbonyl)-amino]-ethyl}-phenyl ester,
Methyl-phenyl-carbamic acid 2-(3,4-difluoro-benzenesulfonyl)-1,2,3,4-tetrahydro-isoquinolin-7-yl ester,
Methyl-phenyl-carbamic acid 1-methyl-2-(toluene-4-sulfonyl)-1,2,3,4-tetrahydro-isoquinolin-7-yl ester,
Methyl-phenyl-carbamic acid 2-[4-(4-methyl-piperazin-1-yl)-benzenesulfonyl]-1,2,3,4-tetrahydro-isoquinolin,
Methyl-phenyl-carbamic acid 1-methyl-2-[4-(4-methyl-piperazin-1-yl)-benzenesulfonyl]-1,2,3,4-tetrahydro-isoquinolin-7-yl ester,
3,3-Dimethyl-4-{2-[4-(methyl-phenyl-carbamoyloxy)-phenyl]-ethylcarbamoyl}-butyric acid,
Methyl-phenyl-carbamic acid 4-{2-[4-(4-methyl-piperazin-1-yl)-benzoylamino]-ethyl}-phenyl ester,
Methyl-phenyl-carbamic acid 4-{2-[4-(4-methyl-piperazin-1-ylmethyl)-benzoylamino]-ethyl}-phenyl ester, Methyl-phenyl-carbamic acid 4-[2-(4,4-dimethyl-2,6-dioxo-piperidin-1-yl)-ethyl]-phenyl ester,
3,3-Dimethyl-4-{2-[4-(methyl-phenyl-carbamoyloxy)-phenyl]-ethylcarbamoyl}-butyric acid ethyl ester,
Methyl-phenyl-carbamic acid 4-hydroxymethyl-phenyl ester,
Methyl-phenyl-carbamic acid 4-(2-hydroxy-ethyl)-phenyl ester,
Methyl-phenyl-carbamic acid 4-(4-dimethylamino-pyridin-2-ylmethyl)-phenyl ester,
Methyl-phenyl-carbamic acid 4-(4-imidazol-1-yl-phenoxymethyl)-phenyl ester,
Methyl-phenyl-carbamic acid 4-[4-(2-dimethylamino-ethyl)-phenoxymethyl]-phenyl ester,
Methyl-phenyl-carbamic acid 4-(pyrazol-1-yloxymethyl)-phenyl ester,
Methyl-phenyl-carbamic acid 4-(imidazol-1-yloxymethyl)-phenyl ester,
Methyl-phenyl-carbamic acid 4-(2-oxo-2H-pyridin-1-ylmethyl)-phenyl ester,
Methyl-phenyl-carbamic acid 4-[2-(pyridin-2-yloxy)-ethyl]-phenyl ester,
Methyl-phenyl-carbamic acid 4-[2-(4-imidazol-1-yl-phenoxy)-ethyl]-phenyl ester,
Methyl-phenyl-carbamic acid 4-{2-[4-(2-dimethylamino-ethyl)-phenoxy]-ethyl}-phenyl ester,
Methyl-phenyl-carbamic acid 4-[2-(pyrazol-1-yloxy)-ethyl]-phenyl ester,
Methyl-phenyl-carbamic acid 4-[2-(imidazol-1-yloxy)-ethyl]-phenyl ester,
Methyl-phenyl-carbamic acid 4-(5-methyl-pyridin-2-ylmethyl)-phenyl ester,
Methyl-phenyl-carbamic acid 4-(4-oxo-4H-pyridin-1-ylmethyl)-phenyl ester,
Methyl-phenyl-carbamic acid 4-[2-(pyridin-3-yloxy)-ethyl]-phenyl ester,
Methyl-phenyl-carbamic acid 4-(2-oxo-2H-pyridin-1-ylmethyl)-phenyl ester,
Methyl-phenyl-carbamic acid 4-(pyridin-3-yloxymethyl)-phenyl ester,
Methyl-phenyl-carbamic acid 4-[2-(2,5-dioxo-pyrrolidin-1-yl)-ethyl]-phenyl ester,
Methyl-phenyl-carbamic acid 4-[2-(1,3-dioxo-1,3-dihydro-pyrrolo[3,4-]pyridin-2-yl)-ethyl]-phenyl ester,
Methyl-phenyl-carbamic acid 4-(1-methyl-1H-imidazol-2-ylsulfanylmethyl)-phenyl ester,
Methyl-phenyl-carbamic acid 4-tetrazol-1-ylmethyl-phenyl ester,
Methyl-phenyl-carbamic acid 4-(2,5-dioxo-pyrrolidin-1-ylmethyl)-phenyl ester,Methyl-phenyl-carbamic acid 4-[2-(2-thioxo-2H-pyridin-1-yl)-ethyl]-phenyl ester,
Methyl-phenyl-carbamic acid 4-(1,3-dioxo-1,3-dihydro-pyrrolo[3,4)pyridin-2-ylmethyl)-phenyl ester,
Methyl-phenyl-carbamic acid 4-[1,2,4]triazol-1-ylmethyl-phenyl ester,
Methyl-phenyl-carbamic acid 4-(2-thioxo-2H-pyridin-1-ylmethyl)-phenyl ester,
Methyl-phenyl-carbamic acid 4-[2-(1-methyl-1H-imidazol-2-ylsulfanyl)-ethyl]-phenyl ester,
Ethyl-phenyl-carbamic acid 4-(2-tetrazol-1-yl-ethyl)-phenyl ester,
Methyl-phenyl-carbamic acid 4-[2-(pyrimidin-2-yloxy)-ethyl]-phenyl ester,
Methyl-phenyl-carbamic acid 4-[2-(pyridin-4-ylsulfanyl)-ethyl]-phenyl ester,
Methyl-phenyl-carbamic acid 4-[2-(1-pyridin-3-yl-1H-imidazol-2-ylsulfanyl)-ethyl]-phenyl ester, and
Methyl-phenyl-carbamic acid 4-[2-(1,3-dioxo-1,3-dihydro-isoindol-2-yl)-ethyl]-phenyl ester.

Further examples of specific compounds of the invention are:
Benzyl-methyl-carbamic acid 4-(5-trifluoromethyl-pyridin-2-yloxy)-phenyl ester, and
Benzyl-methyl-carbamic acid 4-(3,5-dichloro pyridin-2-yloxy)-phenyl ester.

Further examples of specific compounds of the invention are:
Isopropyl-methyl-carbamic acid 4-(5-trifluoromethyl-pyridin-2-yloxy)-phenyl ester,
Cyclohexyl-methyl-carbamic acid 4-(5-trifluoromethyl-pyridin-2-yloxy)-phenyl ester.
Dimethyl-carbamic acid 4-(3,5-dichloro pyridin-2-yloxy)-phenyl ester,
Methyl-pyridin-2-yl-carbamic acid 4-(5-trifluoromethyl-pyridin-2-yloxy)-phenyl ester,
(2-Dimethylamino-ethyl)methylcarbamic acid 4-(5-trifluoromethyl-pyridin-2-yloxy)-phenyl ester,
(6-Methoxy-pyridin-2-yl)-methyl-carbamic acid 4-(5-trifluoromethyl-pyridin-2-yloxy)-phenyl ester,
(4-Methoxy-phenyl)-methyl-carbamic acid 4-(5-trifluoromethyl-pyridin-2-yloxy)-phenyl ester,
(2-Methoxy-phenyl)-methyl-carbamic acid 4-(5-trifluoromethyl-pyridin-2-yloxy)-phenyl ester,
(2-Carbamoyl-4-chloro-phenyl)-methyl-carbamic acid 4-(5-trifluoromethyl-pyridin-2-yloxy)-phenyl ester,
(2-Carbamoyl-phenyl)-methyl-carbamic acid 4-(5-trifluoromethyl-pyridin-2-yloxy)-phenyl ester,
(2-Chloro-phenyl)-methyl-carbamic acid 4-(5-trifluoromethyl-pyridin-2-yloxy)-phenyl ester,
(2,4-Difluoro-phenyl)-methyl-carbamic acid 4-(5-trifluoromethyl-pyridin-2-yloxy)-phenyl ester, and
Methyl-(2-trifluoromethoxy-phenyl)-carbamic acid 4-(5-trifluoromethyl-pyridin-2-yloxy)-phenyl ester.

Further examples of specific compounds of the invention are:
Pyrrolidine1-carboxylic acid 4-(3,5-dichloro-pyridin-2-yloxy)-phenyl ester,
2,3-Dihydro-indole-1-carboxylic acid 4-(5-trifluoromethyl-pyridin-2-yloxy)-phenyl ester, and
1,3-Dihydro-isoindole-2-carboxylic acid 4-(5-trifluoromethyl-pyridin-2-yloxy)-phenyl ester.

Further examples of specific compounds of the invention are:
Piperidine-1-carboxylic acid 4-(5-trifluoromethyl-pyridin-2-yloxy)-phenyl ester,
Piperidine-1-carboxylic acid 3-(5-trifluoromethyl-pyridin-2-yloxy)-phenyl ester,
Piperidine-1-carboxylic acid 4-(3,5-dichloro-pyridin-2-yloxy)-phenyl ester,
Piperidine-1-carboxylic acid 4-(5-trifluoromethyl-pyridin-2-ylamino)-phenyl ester,
Piperidine-1-carboxylic acid 4-(3,5-dichloro-pyridin-4-yloxy)-phenyl ester,
Piperidine-1-carboxylic acid 4-(4-trifluoromethyl-phenoxy)-phenyl ester,
Piperidine-1-carboxylic acid 4-(2-cyano-5-trifluoromethyl-pyridine-3-yloxy)-phenyl ester,
Piperidine-1-carboxylic acid 2-benzenesulfonyl-4-(3-chloro-5-trifluoromethyl-pyridine-2-yloxy)-phenyl ester,
Piperidine-1-carboxylic acid 4-tert-butoxy-phenyl ester,
Piperidine-1-carboxylic acid 3-(4-fluorobenzyl)-4-methyl-2-oxo-2H-chromen-7-yl ester,
Piperidine-1-carboxylic acid 4-phenoxy-phenyl ester, Piperidine-1-carboxylic acid 4-(4-chlorobenzoyl)-phenyl ester,
Piperidine-1-carboxylic acid 4-(3-chloro-5-trifluoromethyl)-pyridine-2-yloxy)-phenyl ester,
Piperidine-1-carboxylic acid 4-[4-(4-chloro-phenyl)-thiazol-2-yl]-phenyl ester,
Piperidine-1-carboxylic acid 4-pyrrol-1-yl-phenyl ester,
Piperidine-1-carboxylic acid 4-imidazol-1-yl-phenyl ester,
Piperidine-1-carboxylic acid 4-(3-chloro-5-trifluoromethyl)-pyridine-2-ylmethyl)-phenyl ester,
Piperidine-1-carboxylic acid 4-trifluoromethylsulfanyl-phenyl ester,
Piperidine-1-carboxylic acid 4-pentafluoromethyloxy-phenyl ester,
Piperidine-1-carboxylic acid 4-benzyloxy-phenyl ester,
Piperidine-1-carboxylic acid 4-benzyl-phenyl ester,
Piperidine-1-carboxylic acid 4'-cyano-biphenyl-4-yl-ester,
Piperidine-1-carboxylic acid 4'-bromo-biphenyl-4-yl-ester,
Piperidine-1-carboxylic acid biphenyl-4-yl-ester,
Piperidine-1-carboxylic acid 4-[3-(4-chlorophenyl)-ureido]-phenyl ester,
Piperidine-1-carboxylic acid 4-(4-nitro-phenoxy)-phenyl ester,
Piperidine-1-carboxylic acid 4-heptylsulfanyl-phenyl ester,
Piperidine-1-carboxylic acid 4-butoxy-phenyl ester,
Piperidine-1-carboxylic acid 4-(4-chloro-benzenesulfonyl)-phenyl ester,
Piperidine-1-carboxylic acid 4-(4-chloromethyl-thiazol-2-yl)-phenyl ester,
Piperidine-1-carboxylic acid 4-(4,4-dimethyl-2,6-dioxo-piperidin-1-yl)-phenyl ester,
cis-Piperidine-1-carboxylic acid 4-(1,3-dioxo-octahydro-isoindol-2-yl)-phenyl ester,
Piperidine-1-carboxylic acid 4-(cyclohexanecarbonyl-amino)-phenyl ester,
Piperidine-1-carboxylic acid 4-(2-cyclohexyl-acetylamino)-phenyl ester,
cis/trans-Piperidine-1-carboxylic acid 4-[(4-tert-butyl-cyclohexanecarbonyl)-amino]-phenyl ester,
cis-Piperidine-1-carboxylic acid 4-[(4-tert-butyl-cyclohexanecarbonyl)-amino]-phenyl ester,
trans-Piperidine-1-carboxylic acid 4-[(4-tert-butyl-cyclohexanecarbonyl)-amino]-phenyl ester,
Piperidine-1-carboxylic acid 4-(3,3-dimethyl-butyrylamino)-phenyl ester,
Piperidine-1-carboxylic acid 3-benzyl-4-methyl-2-oxo-2H-chromen-7-yl ester,
Piperidine-1-carboxylic acid 3-(3,4-dichloro-benzyl)-4-methyl-2-oxo-2H-chromen-7-yl ester,
Piperidine-1-carboxylic acid 3-(2-chloro-6-fluoro-benzyl)-4-methyl-2-oxo-2H-chromen-7-yl ester,
Piperidine-1-carboxylic acid 3-(2,6-dichloro-benzyl)-4-methyl-2-oxo-2H-chromen-7-yl ester,
Piperidine-1-carboxylic acid 3-(2,6-dichloro-benzyl)-6-chloro-4-methyl-2-oxo-2H-chromen-7-yl ester,
Piperidine-1-carboxylic acid 6-chloro-3-(2-chloro-6-fluoro-benzyl)-4-n-propy-2-oxo-2H-chromen-7-yl ester,
Piperidine-1-carboxylic acid 3-(4-methoxy-phenyl)-4-methyl-2-oxo-2H-chromen-7-yl ester,
Piperidine-1-carboxylic acid 4-methyl-2-oxo-3-phenyl-2H-chromen-7-yl ester,
Piperidine-1-carboxylic acid 3-(2,5-dimethoxy-phenyl)-4-methyl-2-oxo-2H-chromen-7-yl ester,
Piperidine-1-carboxylic acid 3-(3,4-dimethoxy-phenyl)-4-methyl-2-oxo-2H-chromen-7-yl ester,
Piperidine-1-carboxylic acid 4-pyrrolidine-1-yl-phenyl ester,
Piperidine-1-carboxylic acid 4-piperidine-1-yl-phenyl ester,
Piperidine-1-carboxylic acid 4-morpholine-1-yl-phenyl ester,
Piperidine-1-carboxylic acid 4-[(6-chloro-pyridine-3-carbonyl)-amino]-phenyl ester,
Piperidine-1-carboxylic acid 4-[(6-chloro-pyridine-3-carbonyl)-amino]-phenyl ester,
Piperidine-1-carboxylic acid 4-[(pyridine-2-carbonyl)-amino]-phenyl ester,
Piperidine-1-carboxylic acid pyrazol-1-yl ester,
Piperidine-1-carboxylic acid 3-bromo-pyrazol-1-yl ester,
Piperidine-1-carboxylic acid 4-bromo-pyrazol-1-yl ester,
Piperidine-1-carboxylic acid 5-bromo-pyrazol-1-yl ester,
Piperidine-1-carboxylic acid 3,4,5-tribromo-pyrazol-1-yl ester,
Piperidine-1-carboxylic acid 4-chloro-pyrazol-1-yl ester,
Piperidine-1-carboxylic acid 4-iodo-pyrazol-1-yl ester,
Piperidine-1-carboxylic acid 3-(4-methoxy-phenyl)-pyrazol-1-yl ester,
Piperidine-1-carboxylic acid 3-(2-methoxy-phenyl)-pyrazol-1-yl ester,
Piperidine-1-carboxylic acid 3-(4-nitro-phenyl)-pyrazol-1-yl ester,
Piperidine-1-carboxylic acid 3-(2-fluoro-phenyl)-pyrazol-1-yl ester,
Piperidine-1-carboxylic acid 3-pyridin-2-yl-pyrazol-1-yl ester,
Piperidine-1-carboxylic acid 4-phenylsulfanyl-pyrazol-1-yl ester,
Piperidine-1-carboxylic acid 3-thiophen-2-yl-pyrazol-1-yl ester,
Piperidine-1-carboxylic acid 5-thiophen-2-yl-pyrazol-1-yl ester,
Piperidine-1-carboxylic acid imidazol-1-yl ester,
Piperidine-1-carboxylic acid 2-chloro-imidazol-1-yl ester,
Piperidine-1-carboxylic acid 2-bromo-imidazol-1-yl ester,
Piperidine-1-carboxylic acid 2-iodo-imidazol-1-yl ester,
Piperidine-1-carboxylic acid 2-methyl-imidazol-1-yl ester,
Piperidine-1-carboxylic acid 2-phenylsulfanyl-imidazol-1-yl ester,
Piperidine-1-carboxylic acid 2-(4-methoxy-phenyl)-imidazol-1-yl ester,
Piperidine-1-carboxylic acid 2-(4-fluoro-phenyl)-imidazol-1-yl ester,
Piperidine-1-carboxylic acid 2-thiophen-2-yl-imidazol-1-yl ester,
Piperidine-1-carboxylic acid 2-pyridin-2-yl-imidazol-1-yl ester,
Piperidine-1-carboxylic acid 2,5-dichloro-imidazol-1-yl ester,
Piperidine-1-carboxylic acid 4-bromo-2,5-dichloro-imidazol-1-yl ester,
2-Methyl-piperidine-1-carboxylic acid 4-(5-trifluoromethyl-pyridin-2-yloxy)-phenyl ester,
3-Methyl-piperidine-1-carboxylic acid 4-(5-trifluoromethyl-pyridin-2-yloxy)-phenyl ester,
4-Methyl-piperidine-1-carboxylic acid 4-(5-trifluoromethyl-pyridin-2-yloxy)-phenyl ester,
4-Benzyl-piperidine-1-carboxylic acid 4-(5-trifluoromethyl-pyridin-2-yloxy)-phenyl ester,
1,4-Dioxa-8-aza-spiro[4.5]decane-8-carboxylic acid 4-(5-trifluoromethyl-pyridin-2-yloxy)-phenyl ester,
3-Hydroxy-piperidine-1-carboxylic acid 4-(5-trifluoromethyl-pyridin-2-yloxy)-phenyl ester,
3,4-Dihydro-1H-isoquinoline-2-carboxylic acid 4-(5-trifluoromethyl-pyridin-2-yloxy)-phenyl ester, 3,4-Dihydro-2H-quinoline-1-carboxylic acid 4-(3,5-dichloro-pyridin-2-yloxy)-phenyl ester,
3,4-Dihydro-2H-quinoline-1-carboxylic acid 4-(2-cyano-5-trifluoromethyl-pyridin-3-yloxy)-phenyl ester,
3,4-Dihydro-2H-quinoline-1-carboxylic acid 3-(3,4-dichloro-benzyl)-4-methyl-2-oxo-2H-chromen-7-yl ester,
3,4-Dihydro-2H-quinoline-1-carboxylic acid 3-benzyl-4-methyl-2-oxo-2H-chromen-7-yl ester,
3,4-Dihydro-2H-quinoline-1-carboxylic acid 3-(2-chloro-6-fluoro-benzyl)-4-methyl-2-oxo-2H-chromen-7-yl ester,
3,4-Dihydro-2H-quinoline-1-carboxylic acid 3-(2,6-dichloro-benzyl)-4-methyl-2-oxo-2H-chromen-7-yl ester,
3,4-Dihydro-2H-quinoline-1-carboxylic acid 3-(2,6-dichloro-benzyl)-6-chloro-4-methyl-2-oxo-2H-chromen-7-yl ester,
3,4-Dihydro-2H-quinoline-1-carboxylic acid 3-(4-fluoro-benzyl)-4-methyl-2-oxo-2H-chromen-7-yl ester,
3,4-Dihydro-2H-quinoline-1-carboxylic acid 6-chloro-3-(2-chloro-6-fluoro-benzyl)-4-n-propy-2-oxo-2H-chromen-7-yl ester,
3,4-Dihydro-2H-quinoline-1-carboxylic acid 3-(4-methoxy-phenyl)-4-methyl-2-oxo-2H-chromen-7-yl ester,
3,4-Dihydro-2H-quinoline-1-carboxylic acid 4-methyl-2-oxo-3-phenyl-2H-chromen-7-yl ester,
3,4-Dihydro-2H-quinoline-1-carboxylic acid 3-(2,5-dimethoxy-phenyl)-4-methyl-2-oxo-2H-chromen-7-yl ester,
3,4-Dihydro-2H-quinoline-1-carboxylic acid 3-(3,4-dimethoxy-phenyl)-4-methyl-2-oxo-2H-chromen-7-yl ester,
7-Trifluoromethyl-3,4-dihydro-2H-quinoline-1-carboxylic acid 4-(5-trifluoromethyl-pyridin-2-yloxy)-phenyl ester,
4-Hydroxymethyl-piperidine-1-carboxylic acid 4-(5-trifluoromethyl-pyridin-2-yloxy)-phenyl ester,
4-Oxo-piperidine-1-carboxylic acid 4-(5-trifluoromethyl-pyridin-2-yloxy)-phenyl ester,
4-[5-(4-Dimethylamino-phenyl)-1H-pyrazol-3-yl]-piperidine-1-carboxylic acid 4-(5-trifluoromethyl-pyridin-2-yloxy)-phenyl ester,
4-(5-Furan-2-yl-1H-pyrazol-3-yl)-piperidine-1-carboxylic acid 4-(5-trifluoromethyl-pyridin-2-yloxy)-phenyl ester,
4-Benzylamino-piperidine-1-carboxylic acid 4-(5-trifluoromethyl-pyridin-2-yloxy)-phenyl ester,
4-(3,4-Dihydro-1H-isoquinolin-2-ylmethyl)-piperidine-1-carboxylic acid 4-(5-trifluoromethyl-pyridin-2-yloxy)-phenyl ester,
3-Hydroxymethyl-piperidine-1-carboxylic acid 4-(5-trifluoromethyl-pyridin-2-yloxy)-phenyl ester,
3-Hydroxy-piperidine-1-carboxylic acid 4-(5-trifluoromethyl-pyridin-2-yloxy)-phenyl ester,
4-Benzyl-4-hydroxy-piperidine-1-carboxylic acid 4-(5-trifluoromethyl-pyridin-2-yloxy)-phenyl ester,
4-Hydroxy-piperidine-1-carboxylic acid 4-(5-trifluoromethyl-pyridin-2-yloxy)-phenyl ester,
4-Pyrrolidin-1-yl-piperidine-1-carboxylic acid 4-(5-trifluoromethyl-pyridin-2-yloxy)-phenyl ester,
4-Hydroxymethyl-piperidine-1-carboxylic acid 4-(5-chloro-pyridin-2-yloxy)-phenyl ester,
1,4-Dioxa-8-aza-spiro[4.5]decane-8-carboxylic acid 4-(5-trifluoromethyl-pyridin-2-yloxy)-phenyl ester,
4-Benzoyl-piperidine-1-carboxylic acid 4-(5-trifluoromethyl-pyridin-2-yloxy)-phenyl ester,
[1,4']Bipiperidinyl-1'-carboxylic acid 4-(5-trifluoromethyl-pyridin-2-yloxy)-phenyl ester,
4-(2-Oxo-2,3-dihydro-benzimidazol-1-yl)-piperidine-1-carboxylic acid 4-(5-trifluoromethyl-pyridin-2-yloxy)-phenyl ester,
3-Diethylcarbamoyl-piperidine-1-carboxylic acid 4-(5-trifluoromethyl-pyridin-2-yloxy)-phenyl ester,
4-Carbamoyl-piperidine-1-carboxylic acid 4-(5-trifluoromethyl-pyridin-2-yloxy)-phenyl ester,
3-Carbamoyl-piperidine-1-carboxylic acid 4-(5-trifluoromethyl-pyridin-2-yloxy)-phenyl ester,
4-(tert-Butyl-dimethyl-silanyloxy)-piperidine-1-carboxylic acid 5-benzoylamino-pyridin-2-yl ester,
4-Hydroxy-piperidine-1-carboxylic acid 5-benzoylamino-pyridin-2-yl ester,
4-Hydroxy-piperidine-1-carboxylic acid 5-trifluoromethyl-pyridin-2-yl ester,
4-Hydroxy-piperidine-1-carboxylic acid 5-(4-chloro-benzoylamino)-pyridin-2-yl ester,
4-Hydroxy-piperidine-1-carboxylic acid 5-(3-methoxy-benzoylamino)-pyridin-2-yl ester,
4-Hydroxy-piperidine-1-carboxylic acid 5-(4-methoxy-benzoylamino)-pyridin-2-yl ester,
4-Hydroxy-piperidine-1-carboxylic acid 5-(2,4-dichloro-benzoylamino)-pyridin-2-yl ester,
4-Hydroxy-piperidine-1-carboxylic acid 5-(4-trifluoromethyl-benzoylamino)-pyridin-2-yl ester,
4-Hydroxy-piperidine-1-carboxylic acid 4,4-dimethyl-2,6-dioxo-3,4,5,6-tetrahydro-2H-[1,3']bipyridinyl-6'-yl ester,
4-Hydroxy-piperidine-1-carboxylic acid 5-(5-trifluoromethyl-pyridin-2-yloxy)-pyridin-2-yl ester,
4-Hydroxy-piperidine-1-carboxylic acid 5-(3,5-dichloro-pyridin-2-yloxy)-pyridin-2-yl ester,
4-Aminomethyl-piperidine-1-carboxylic acid 4-(5-trifluoromethyl-pyridin-2-yloxy)-phenyl ester,
4-Benzimidazol-1-yl-piperidine-1-carboxylic acid 4-(5-trifluoromethyl-pyridin-2-yloxy)-phenyl ester,
4-Hydroxymethyl-piperidine-1-carboxylic acid 4-(2-cyclohexyl-acetylamino)-phenyl ester,
4-(4-Amino-phenyl)-piperidine-1-carboxylic acid 4-(5-trifluoromethyl-pyridin-2-yloxy)-phenyl ester,
4-(Methyl-pyridin-3-ylmethyl-amino)-piperidine-1-carboxylic acid 4-(5-trifluoromethyl-pyridin-2-yloxy)-phenyl ester,
4-(2-Oxo-pyrrolidin-1-yl)-piperidine-1-carboxylic acid 4-(5-trifluoromethyl-pyridin-2-yloxy)-phenyl ester,
4-(Methyl-phenethyl-amino)-piperidine-1-carboxylic acid 4-(5-trifluoromethyl-pyridin-2-yloxy)-phenyl ester,
4-[(Benzyl-ethyl-amino)-methyl]-piperidine-1-carboxylic acid 4-(5-trifluoromethyl-pyridin-2-yloxy)-phenyl ester,
4-[Methyl-phenethyl-amino)-methyl]-piperidine-1-carboxylic acid 4-(5-trifluoromethyl-pyridin-2-yloxy)-phenyl ester,
4-[(Cyclohexyl-methyl-amino)-methyl]-piperidine-1-carboxylic acid 4-(5-trifluoromethyl-pyridin-2-yloxy)-phenyl ester,
4-[(Ethyl-pyridin-4-ylmethyl-amino)-methyl]-piperidine-1-carboxylic acid 4-(5-trifluoromethyl-pyridin-2-yloxy)-phenyl ester,
4-[(Benzyl-methyl-amino)-methyl]-piperidine-1-carboxylic acid 4-(5-trifluoromethyl-pyridin-2-yloxy)-phenyl ester,
4-[(Methyl-pyridin-3-ylmethyl-amino)-methyl]-piperidine-1-carboxylic acid 4-(5-trifluoromethyl-pyridin-2-yloxy)-phenyl ester,
4-(1,3-Dihydro-isoindol-2-ylmethyl)-piperidine-1-carboxylic acid 4-(5-trifluoromethyl-pyridin-2-yloxy)-phenyl ester,
4-Benzotriazol-1-yl-piperidine-1-carboxylic acid 4-(5-trifluoromethyl-pyridin-2-yloxy)-phenyl ester,
4-[(Cyclopropylmethyl-amino)-methyl]-piperidine-1-carboxylic acid 4-(5-trifluoromethyl-pyridin-2-yloxy)-phenyl ester, 4-[Methyl-(2-pyridin-2-yl-ethyl)-amino]-piperidine-1-carboxylic acid 4-(5-trifluoromethyl-pyridin-2-yloxy)-phenyl ester,
4-(Cyclohexyl-methyl-amino)-piperidine-1-carboxylic acid 4-(5-trifluoromethyl-pyridin-2-yloxy)-phenyl ester,
4-(Isopropyl-methyl-amino)-piperidine-1-carboxylic acid 4-(5-trifluoromethyl-pyridin-2-yloxy)-phenyl ester,
4-Hydroxymethyl-piperidine-1-carboxylic acid 4-(3,3-dimethyl-butylcarbamoyl)-phenyl ester ester,
Piperidine-1-carboxylic acid 4,4-dimethyl-2,6-dioxo-3,4,5,6-tetrahydro-2H-[1,3']bipyridinyl-6'-yl,
4-[Methyl-(2-pyridin-4-yl-ethyl)-amino]-piperidine-1-carboxylic acid 4-(5-trifluoromethyl-pyridin-2-yloxy)-phenyl ester,
4-(Cyclopropyl-pyridin-4-ylmethyl-amino)-piperidine-1-carboxylic acid 4-(5-trifluoromethyl-pyridin-2-yloxy)-phenyl ester,
4-[Cyclopropyl-(2-fluoro-benzyl)-amino]-piperidine-1-carboxylic acid 4-(5-trifluoromethyl-pyridin-2-yloxy)-phenyl ester,
4-(Cyclopropyl-pyridin-3-ylmethyl-amino)-piperidine-1-carboxylic acid 4-(5-trifluoromethyl-pyridin-2-yloxy)-phenyl ester,
4-(Cyclopropylmethyl-pyridin-3-ylmethyl-amino)-piperidine-1-carboxylic acid 4-(5-trifluoromethyl-pyridin-2-yloxy)-phenyl ester,
4-(Cyclopropylmethyl-pyridin-3-ylmethyl-amino)-piperidine-1-carboxylic acid 4-(5-trifluoromethyl-pyridin-2-yloxy)-phenyl ester,
4-(4-Hydroxy-piperidin-1-ylmethyl)-piperidine-1-carboxylic acid 4-(5-trifluoromethyl-pyridin-2-yloxy)-phenyl ester,
4-{3-[1-(2-Hydroxy-ethyl)-piperidin-4-yl]-propyl}-piperidine-1-carboxylic acid 4-(5-trifluoromethyl-pyridin-2-yloxy)-phenyl ester,
4-(2-Pyrrolidin-1-yl-ethyl)-piperidine-1-carboxylic acid 4-(5-trifluoromethyl-pyridin-2-yloxy)-phenyl ester,
4-Hydroxy-piperidine-1-carboxylic acid 4-[2-(toluene-4-sulfonylamino)-ethyl]-phenyl ester,
4-Hydroxy-piperidine-1-carboxylic acid 4-[2-(5-pyridin-2-yl-thiophene-2-sulfonylamino)-ethyl]-phenyl,
4-Hydroxy-piperidine-1-carboxylic acid 4-(5-pyridin-2-yl-thiophene-2-sulfonylamino)-phenyl ester,
4-Hydroxy-piperidine-1-carboxylic acid 4-pyridin-2-ylmethyl-phenyl ester,
4-Hydroxy-piperidine-1-carboxylic acid 4-pyridin-3-ylmethyl-phenyl ester,
4-Hydroxy-piperidine-1-carboxylic acid 4-(4-trifluoromethyl-benzyl)-phenyl ester,
4-Hydroxy-piperidine-1-carboxylic acid 4-(5-methyl-pyridin-2-ylmethyl)-phenyl ester,
4-(3-Amino-phenyl)-piperidine-1-carboxylic acid 4-(5-trifluoromethyl-pyridin2-yloxy)-phenyl ester,4-Phenyl-piperidine-1-carboxylic acid 4-(5-methyl-pyridin-2-ylmethyl)-phenyl ester, and
4-(4-Methoxy-phenyl)-3,6-dihydro-2H-pyridine-1-carboxylic acid 4-(5-methyl-pyridin-2-ylmethyl)-phenyl ester.
Further examples of specific compounds of the invention are:
4-Methyl-piperazine-1-carboxylic acid 4-(5-trifluoromethyl-pyridin-2-yloxy)-phenyl ester,
4-Benzyl-piperazine-1-carboxylic acid 4-(5-trifluoromethyl-pyridin-2-yloxy)-phenyl ester,
4-(2-Hydroxyethyl)-piperazine-1-carboxylic acid 4-(5-trifluoromethyl-pyridin-2-yloxy)-phenyl ester,
4-(Pyridin-2-yl)-piperazine-1-carboxylic acid 4-(5-trifluoromethyl-pyridin-2-yloxy)-phenyl ester,
4-(Pyrrolidinocarbonylmethyl)-piperazine-1-carboxylic acid 4-(5-trifluoromethyl-pyridin-2-yloxy)-phenyl ester,
4-Phenyl-piperazine-1-carboxylic acid 4-(5-trifluoromethyl-pyridin-2-yloxy)-phenyl ester,
4-(Isopropylaminocarbonylmethyl)-piperazine-1-carboxylic acid 4-(5-trifluoromethyl-pyridin-2-yloxy)-phenyl ester,
4-Ethyl-piperazine-1-carboxylic acid 4-(5-trifluoromethyl-pyridin-2-yloxy)-phenyl ester,
4-Propyl-piperazine-1-carboxylic acid 4-(5-trifluoromethyl-pyridin-2-yloxy)-phenyl ester,
4-Butyl-piperazine-1-carboxylic acid 4-(5-trifluoromethyl-pyridin-2-yloxy)-phenyl ester,
4-(4-Chlorobenzyl)-piperazine-1-carboxylic acid 4-(5-trifluoromethyl-pyridin-2-yloxy)-phenyl ester,
4-(4-Chlorophenyl)-piperazine-1-carboxylic acid 4-(5-trifluoromethyl-pyridin-2-yloxy)-phenyl ester,
4-(Diphenylmethyl)-piperazine-1-carboxylic acid 4-(5-trifluoromethyl-pyridin-2-yloxy)-phenyl ester,
4-(3-Hydroxypropyl)-piperazine-1-carboxylic acid 4-(5-trifluoromethyl-pyridin-2-yloxy)-phenyl ester,
4-(3-Trifluoromethylphenyl)-piperazine-1-carboxylic acid 4-(5-trifluoromethyl-pyridin-2-yloxy)-phenyl ester,
4-(3-Chlorophenyl)-piperazine-1-carboxylic acid 4-(5-trifluoromethyl-pyridin-2-yloxy)-phenyl ester,
4-(2-Chlorophenyl)-piperazine-1-carboxylic acid 4-(5-trifluoromethyl-pyridin-2-yloxy)-phenyl ester,
4-(3,4-Dichlorophenyl)-piperazine-1-carboxylic acid 4-(5-trifluoromethyl-pyridin-2-yloxy)-phenyl ester,
4-(4-Fluorophenyl)-piperazine-1-carboxylic acid 4-(5-trifluoromethyl-pyridin-2-yloxy)-phenyl ester,
4-(4-Methoxyphenyl)-piperazine-1-carboxylic acid 4-(5-trifluoromethyl-pyridin-2-yloxy)-phenyl ester,
4-(3-Methoxyphenyl)-piperazine-1-carboxylic acid 4-(5-trifluoromethyl-pyridin-2-yloxy)-phenyl ester,
4-(2-Methoxyphenyl)-piperazine-1-carboxylic acid 4-(5-trifluoromethyl-pyridin-2-yloxy)-phenyl ester,
4-(2,4-Dimethoxyphenyl)-piperazine-1-carboxylic acid 4-(5-trifluoromethyl-pyridin-2-yloxy)-phenyl ester,
4-(3,4,5-Trimethoxyphenyl)-piperazine-1-carboxylic acid 4-(5-trifluoromethyl-pyridin-2-yloxy)-phenyl ester,
4-[3-(Trifluoromethyl)pyridin-2-yl]-piperazine-1-carboxylic acid 4-(5-trifluoromethyl-pyridin-2-yloxy)-phenyl ester,
4-(3,4-Methylenedioxy-phenyl)-piperazine-1-carboxylic acid 4-(5-trifluoromethyl-pyridin-2-yloxy)-phenyl ester,
4-(3,4-Methylenedioxy-benzyl)-piperazine-1-carboxylic acid 4-(5-trifluoromethyl-pyridin-2-yloxy)-phenyl ester,
4-(Pyridin-4-yl)-piperazine-1-carboxylic acid 4-(5-trifluoromethyl-pyridin-2-yloxy)-phenyl ester,
4-Cyclopentyl-piperazine-1-carboxylic acid 4-(5-trifluoromethyl-pyridin-2-yloxy)-phenyl ester,
4-(2-Pyrimidinyl)-piperazine-1-carboxylic acid 4-(5-trifluoromethyl-pyridin-2-yloxy)-phenyl ester,
4-(4-Acetylphenyl)-piperazine-1-carboxylic acid 4-(5-trifluoromethyl-pyridin-2-yloxy)-phenyl ester,
4-(2-(2-Hydroxyethoxy)ethyl)-piperazine-1-carboxylic acid 4-(5-trifluoromethyl-pyridin-2-yloxy)-phenyl ester,
4-Benzyl-piperazine-1-carboxylic acid pyrazol-1-yl ester,
4-Benzyl-piperazine-1-carboxylic acid 3-bromo-pyrazol-1-yl ester,
4-Benzyl-piperazine-1-carboxylic acid 4-bromo-pyrazol-1-yl ester,
4-Benzyl-piperazine-1-carboxylic acid 5-bromo-pyrazol-1-yl ester,
4-Benzyl-piperazine-1-carboxylic acid 3,4,5-tribromo-pyrazol-1-yl ester, 4-Benzyl-piperazine-1-carboxylic acid 4-chloro-pyrazol-1-yl ester,
4-Benzyl-piperazine-1-carboxylic acid 4-iodo-pyrazol-1-yl ester,
4-Benzyl-piperazine-1-carboxylic acid 3-(4-methoxy-phenyl)-pyrazol-1-yl ester,
4-Benzyl-piperazine-1-carboxylic acid 3-(2-methoxy-phenyl)-pyrazol-1-yl ester,
4-Benzyl-piperazine-1-carboxylic acid 3-(4-nitro-phenyl)-pyrazol-1-yl ester,
4-Benzyl-piperazine-1-carboxylic acid 3-(2-fluoro-phenyl)-pyrazol-1-yl ester,
4-Benzyl-piperazine-1-carboxylic acid 3-pyridin-2-yl-pyrazol-1-yl ester,
4-Benzyl-piperazine-1-carboxylic acid 4-phenylsulfanyl-pyrazol-1-yl ester,
4-Benzyl-piperazine-1-carboxylic acid 3-thiophen-2-yl-pyrazol-1-yl ester,
4-Benzyl-piperazine-1-carboxylic acid 5-thiophen-2-yl-pyrazol-1-yl ester,
4-Benzyl-piperazine-1-carboxylic acid imidazol-1-yl ester,
4-Benzyl-piperazine-1-carboxylic acid 2-chloro-imidazol-1-yl ester,
4-Benzyl-piperazine-1-carboxylic acid 2-bromo-imidazol-1-yl ester,
4-Benzyl-piperazine-1-carboxylic acid 2-iodo-imidazol-1-yl ester,
4-Benzyl-piperazine-1-carboxylic acid 2-methyl-imidazol-1-yl ester,
4-Benzyl-piperazine-1-carboxylic acid 2-phenylsulfanyl-imidazol-1-yl ester,
4-Benzyl-piperazine-1-carboxylic acid 2-(4-methoxy-phenyl)-imidazol-1-yl ester,
4-Benzyl-piperazine-1-carboxylic acid 2-(4-fluoro-phenyl)-imidazol-1-yl ester,
4-Benzyl-piperazine-1-carboxylic acid 2-thiophen-2-yl-imidazol-1-yl ester,
4-Benzyl-piperazine-1-carboxylic acid 2-pyridin-2-yl-imidazol-1-yl ester,
4-Benzyl-piperazine-1-carboxylic acid 2,5-dichloro-imidazol-1-yl ester,
4-Benzyl-piperazine-1-carboxylic acid 4-bromo-2,5-dichloro-imidazol-1-yl ester,
4-Benzyl-piperazine-1-carboxylic acid 4-bromo-2-chloro-imidazol-1-yl ester,
4-Benzyl-piperazine-1-carboxylic acid 5-(4-methoxy-phenyl)-imidazol-1-yl ester,
4-Benzyl-piperazine-1-carboxylic acid 5-(4-fluoro-phenyl)-imidazol-1-yl ester,
4-Benzyl-piperazine-1-carboxylic acid 5-thiophen-2-yl-imidazol-1-yl ester,
4-Benzyl-piperazine-1-carboxylic acid 5-pyridin-2-yl-imidazol-1-yl ester,
4-Benzyl-piperazine-1-carboxylic acid 4-(5-chloro-pyridin-2-yloxy)-phenyl ester,
4-Pyridin-3-ylmethyl-piperazine-1-carboxylic acid 4-(5-chloro-pyridin-2-yloxy)-phenyl ester,
4-Pyridin-2-yl-piperazine-1-carboxylic acid 4-(5-trifluoromethyl-pyridin-2-yloxy)phenyl ester,
4-(1,3-Benzodioxol-5-yl)-piperazine-1-carboxylic acid 4-(5-trifluoromethyl-pyridin-2-yloxy)-phenyl ester,
4-[2-(2-Hydroxyethoxy)ethyl]-piperazine-1-carboxylic acid 4-(5-trifluoromethyl-pyridin-2-yloxy)-phenyl ester,
4-(Diphenylmethyl)piperazine-1-carboxylic acid 4-(5-trifluoromethyl-pyridin-2-yloxy)-phenyl ester,
4-(4-tert-Butylbenzyl)piperazine-1-carboxylic acid 4-(5-trifluoromethyl-pyridin-2-yloxy)phenyl ester,
4-(4-Fluorobenzyl)-piperazine-1-carboxylic acid 4-(5-trifluoromethyl-pyridin-2-yloxy)-phenyl ester,
4-(2-Thienylethyl)piperazine-1-carboxylic acid 4-(5-trifluoromethyl-pyridin-2-yloxy)phenyl ester,
4-(1-Phenylethyl)piperazine-1-carboxylic acid 4-(5-trifluoromethyl-pyridin-2-yloxy)phenyl ester,
4-Octylpiperazine-1-carboxylic acid 4-(5-trifluoromethyl-pyridin-2-yloxy)phenyl ester,
4-(3-Dimethylamino-propyl)-piperazine-1-carboxylic acid 4-(5-trifluoromethyl-pyridin-2-yloxy)-phenyl ester,
4-Pyrimidin-2-yl-piperazine-1-carboxylic acid 4-(5-trifluoromethyl-pyridin-2-yloxy)-phenyl ester,
4-Cyclopropylmethyl-piperazine-1-carboxylic acid 4-(5-trifluoromethyl-pyridin-2-yloxy)-phenyl ester,
4-Phenethyl-piperazine-1-carboxylic acid 4-(5-trifluoromethyl-pyridin-2-yloxy)-phenyl ester,
4-Pyridin-2-ylmethyl-piperazine-1-carboxylic acid 4-(5-trifluoromethyl-pyridin-2-yloxy)-phenyl ester,
4-Pyridin-3-ylmethyl-piperazine-1-carboxylic acid 4-(5-trifluoromethyl-pyridin-2-yloxy)-phenyl ester,
4-(3-Phenylpropyl)piperazine-1-carboxylic acid 4-(5-trifluoromethyl-pyridin-2-yloxy)-phenyl ester,
4-(4-Phenylbutyl)piperazine-1-carboxylic acid 4-(5-trifluoromethyl-pyridin-2-yloxy)-phenyl ester,
4-(3,4-Dichlorophenyl)piperazine-1-carboxylic acid 4-(5-trifluoromethyl-pyridin-2-yloxy)phenyl ester,
4-(4-Fluorophenyl)piperazine-1-carboxylic acid 4-(5-trifluoromethyl-pyridin-2-yloxy)-phenyl ester,
4-(2-Chlorophenyl)piperazine-1-carboxylic acid 4-(5-trifluoromethyl-pyridin-2-yloxy)-phenyl ester,
4-Methylpiperazine-1-carboxylic acid 4-chlorophenyl ester,
4-(4-Phenylbutyl)piperazine-1-carboxylic acid 4-chlorophenyl ester,
4-[2-(2-Hydroxyethoxy)ethyl]piperazine-1-carboxylic acid 4-(4-trifluoromethylphenoxy)phenyl ester,
4-(1-Ethylpropyl)piperazine-1-carboxylic acid 4-(4-trifluoromethylphenoxy)phenyl ester,
4-Cycloheptylpiperazine-1-carboxylic acid 4-(4-trifluoromethyl-phenoxy)phenyl ester,
4-Cyclohexylpiperazine-1-carboxylic acid 4-(4-trifluoromethyl-phenoxy)phenyl ester,
4-(4-Chlorobenzyl)piperazine-1-carboxylic acid 4-(4-trifluoromethylphenoxy)phenyl ester,
4-(4-Methylbenzyl)piperazine-1-carboxylic acid 4-(4-trifluoromethylphenoxy)phenyl ester,
4-(4-Methoxybenzyl)piperazine-1-carboxylic acid 4-(5-trifluoromethyl-pyridin-2-yloxy)-phenyl ester,
4-(2-Chloro-6-fluoro-benzyl)-piperazine-1-carboxylic acid 4-(5-trifluoromethyl-pyridin-2-yloxy)-phenyl ester,
4-(3-Methoxyphenyl)piperazine-1-carboxylic acid 4-(4-trifluoromethylphenoxy)phenyl ester,
4-Benzyl-piperazine-1-carboxylic acid 4-(3-chloro-5-trifluoromethyl-pyridin-2-yloxy)phenyl ester,
4-Methyl-piperazine-1-carboxylic acid pyrazol-1-yl ester,
4-Cyclopentyl-piperazine-1-carboxylic acid pyrazol-1-yl ester,
4-Phenyl-piperazine-1-carboxylic acid pyrazol-1-yl ester,
4-Pyridin-2-yl-piperazine-1-carboxylic acid pyrazol-1-yl ester,
4-Pyrimidin-2-yl-piperazine-1-carboxylic acid pyrazol-1-yl ester,
4-Benzo[1,3]dioxol-5-yl-piperazine-1-carboxylic acid pyrazol-1-yl ester,
4-Benzyl-piperazine-1-carboxylic acid 4-iodo-pyrazol-1-yl ester,
4-Cyclopentyl-piperazine-1-carboxylic acid 4-iodo-pyrazol-1-yl ester, 4-(4-Fluoro-benzyl)-piperazine-1-carboxylic acid 4-iodo-pyrazol-1-yl ester,
4-Phenyl-piperazine-1-carboxylic acid 4-iodo-pyrazol-1-yl ester,
4-Pyridin-2-yl-piperazine-1-carboxylic acid 4-iodo-pyrazol-1-yl ester,
4-Pyrimidin-2-yl-piperazine-1-carboxylic acid 4-iodo-pyrazol-1-yl ester,
4-Benzo[1,3]dioxol-5-yl-piperazine-1-carboxylic acid 4-iodo-pyrazol-1-yl ester,
4-Methyl-1,4-diazepane-1-carboxylic acid 4-(5-trifluoromethyl-pyridin-2-yloxy)phenyl ester,
4-Benzyl-1,4-diazepane-1-carboxylic acid 4-(5-trifluoromethyl-pyridin-2-yloxy)-phenyl ester,
4-(Tetrahydrofuran-2-ylmethyl)-piperazine-1-carboxylic acid 4-(5-trifluoromethyl-pyridin-2-yloxy)-phenyl ester,
4-Cyclopropylmethyl-piperazine-1-carboxylic acid 4-(3-chloro-5-trifluoromethyl-pyridin-2-yloxy)-phenyl ester,
4-(Tetrahydro-furan-2-ylmethyl)-piperazine-1-carboxylic acid 4-(4-trifluoromethylphenoxy)-phenyl ester,
4-Cyclohexylmethyl-piperazine-1-carboxylic acid 4-(4-trifluoromethyl-phenoxy)-phenyl ester,
4-Cyclohexylmethyl-piperazine-1-carboxylic acid 4-(3-chloro-5-trifluoromethyl-pyridin-2-yloxy)-phenyl ester,
4-Cyclopropylmethyl-piperazine-1-carboxylic acid 4-(4-trifluoromethyl-phenoxy)-phenyl ester,
4-(Tetrahydrofuran-2-ylmethyl)-piperazine-1-carboxylic acid 4-(3-chloro-5-trifluoromethyl-pyridin-2-yloxy)-phenyl ester,
4-Naphthalen-1-ylmethyl-piperazine-1-carboxylic acid 4-(5-trifluoromethyl-pyridin-2-yloxy)-phenyl ester,
4-(2-Cyclohexyl-ethyl)-piperazine-1-carboxylic acid 4-(5-trifluoromethyl-pyridin-2-yloxy)-phenyl ester,
4-(3-Methoxy-phenyl)-piperazine-1-carboxylic acid 4-(5-trifluoromethyl-pyridin-2-yloxy)-phenyl ester,
4-Cyclopropylmethyl-piperazine-1-carboxylic acid 4-[2-(4-chloro-phenyl)-ethylcarbamoyl]-phenyl ester,
4-(Tetrahydro-furan-2-ylmethyl)-piperazine-1-carboxylic acid 4-[2-(4-chloro-phenyl)-ethylcarbamoyl]-phenyl ester,
4-(3,4-Dichloro-benzyl)-piperazine-1-carboxylic acid 4-(5-trifluoromethyl-pyridin-2-yloxy)-phenyl ester,
4-Cyclopropylmethyl-[1,4]diazepane-1-carboxylic acid 4-(5-trifluoromethyl-pyridin-2-yloxy)-phenyl ester,
4-(2-Pyridin-2-yl-ethyl)-piperazine-1-carboxylic acid 4-(5-trifluoromethyl-pyridin-2-yloxy)-phenyl ester,
4-(Pyrazin-2-yl)-piperazine-1-carboxylic acid 4-(5-trifluoromethyl-pyridin-2-yloxy)-phenyl ester,
4-(Benzo-isothiazol-3-yl)-piperazine-1-carboxylic acid 4-(5-trifluoromethyl-pyridin-2-yloxy)-phenyl ester,
4-(5-Chloro-thiophen-2-ylmethyl)-piperazine-1-carboxylic acid 4-(5-trifluoromethyl-pyridin-2-yloxy)-phenyl ester,
4-(3-Trifluoromethyl-phenyl)-piperazine-1-carboxylic acid 4-(5-trifluoromethyl-pyridin-2-yloxy)-phenyl ester,
4-(5-Chloro-2-methyl-phenyl)-piperazine-1-carboxylic acid 4-(5-trifluoromethyl-pyridin-2-yloxy)-phenyl ester,
4-(1-Methyl-piperidin-4-ylmethyl)-piperazine-1-carboxylic acid 4-(5-trifluoromethyl-pyridin-2-yloxy)-phenyl ester,
4-Biphenyl-4-ylmethyl-[1,4]diazepane-1-carboxylic acid 4-(5-trifluoromethyl-pyridin-2-yloxy)-phenyl ester
4-(5-Dimethylamino-naphthalene-1-sulfonyl)-piperazine-1-carboxylic acid 4-(5-trifluoromethyl-pyridin-2-yloxy)-phenyl ester,
4-(3-Methoxy-benzyl)-piperazine-1-carboxylic acid 4-(5-trifluoromethyl-pyridin-2-yloxy)-phenyl ester,
4-(3-Fluoro-benzyl)-piperazine-1-carboxylic acid 4-(5-trifluoromethyl-pyridin-2-yloxy)-phenyl ester,
4-(3-Trifluoromethyl-pyridin-2-yl)-piperazine-1-carboxylic acid 4-(5-trifluoromethyl-pyridin-2-yloxy)-phenyl ester,
4-(3-Fluorobenzyl)-piperazine-1-carboxylic acid 4-(4,6-dimethyl-pyrimidin-2-ylsulfanyl)-phenyl ester,
5-(4-Trifluoromethoxybenzyl)-2,5-diazabicyclo[2.2.1]heptane-2-carboxylic acid 4-(5-trifluoromethylpyridin-2-yloxy)-phenyl ester,
4-(2,4-Dimethoxyphenyl)-piperazine-1-carboxylic acid 4-(5-trifluoromethyl-pyridin-2-yloxy)-phenyl ester,
5-Benzyl-2,5-diazabicyclo[2.2.1]heptane-2-carboxylic acid 4-(5-trifluoromethylpyridin-2-yloxy)-phenyl ester,
4-Pyrimidin-2-yl-piperazine-1-carboxylic acid 4-(5-chloro-pyridin-2-yloxy)-phenyl ester,
4-Cyclopropylmethyl-piperazine-1-carboxylic acid 4-(4,4-dimethyl-2,6-dioxo-piperidin-1-yl)-phenyl ester,
4-(4-Methoxy-benzyl)-piperazine-1-carboxylic acid 4-(4,4-dimethyl-2,6-dioxo-piperidin-1-yl)-phenyl ester,
4-Pyridin-3-ylmethyl-piperazine-1-carboxylic acid 4-(4,4-dimethyl-2,6-dioxo-piperidin-1-yl)-phenyl ester,
4-(4-Methoxy-benzyl)-piperazine-1-carboxylic acid 4-(2-cyclohexyl-acetylamino)-phenyl ester,
4-Cyclopropylmethyl-piperazine-1-carboxylic acid 4-(2-cyclohexyl-acetylamino)-phenyl ester,
4-Pyridin-3-ylmethyl-piperazine-1-carboxylic acid 4-(2-cyclohexyl-acetylamino)-phenyl ester,
4-Cyclopropylmethyl-piperazine-1-carboxylic acid 4-(3,3-dimethyl-butylcarbamoyl)-phenyl ester,
4-Pyridin-3-ylmethyl-piperazine-1-carboxylic acid 4-(3,3-dimethyl-butylcarbamoyl)-phenyl ester,
4-(4-Methoxy-benzyl)-piperazine-1-carboxylic acid 4-(3,3-dimethyl-butylcarbamoyl)-phenyl ester,
4-(2-Pyridin-2-yl-acetyl)-piperazine-1-carboxylic acid 4-(5-trifluoromethyl-pyridin-2-yloxy)-phenyl ester,
Piperazine-1,4-dicarboxylic acid tert-butyl ester 4-(5-trifluoromethyl-pyridin-2-yloxy)-phenyl ester,
Piperazine-1-carboxylic acid 4-(5-trifluoromethyl-pyridin-2-yloxy)-phenyl ester hydrochloride,
4-(2-Pyridin-2-yl-acetyl)-piperazine-1-carboxylic acid 4-(5-trifluoromethyl-pyridin-2-yloxy)-phenyl ester, and
4-(2-Pyridin-4-yl-ethyl)-piperazine-1-carboxylic acid 4-(5-trifluoromethyl-pyridin-2-yloxy)-phenyl ester.

Further examples of specific compounds of the invention are:
Morpholine-4-carboxylic acid 4-(5-trifluoromethyl-pyridin-2-yloxy)-phenyl ester,
Morpholine-4-carboxylic acid 3-(5-trifluoromethyl-pyridin-2-yloxy)-phenyl ester,
Morpholine-4-carboxylic acid 4-(3,5-dichloro-pyridin-2-yloxy)-phenyl ester,
Morpholine-4-carboxylic acid 4-(5-trifluoromethyl-pyridin-2-ylamino)-phenyl ester,
Morpholine-4-carboxylic acid 4-(3,5-dichloro-pyridin-4-yloxy)-phenyl ester,
Morpholine-4-carboxylic acid 4-(4-trifluoromethyl-phenoxy)-phenyl ester,
Morpholine-4-carboxylic acid 4-(2-cyano-5-trifluoromethyl-pyridine-3-yloxy)-phenyl ester,
Morpholine-4-carboxylic acid 2-benzenesulfonyl-4-(3-chloro-5-trifluoromethyl-pyridine-2-yloxy)-phenyl ester,
Morpholine-4-carboxylic acid 4-tert-butoxy-phenyl ester,
Morpholine-4-carboxylic acid 3-(4-fluorobenzyl)-4-methyl-2-oxo-2H-chromen-7-yl ester,
Morpholine-4-carboxylic acid 4-phenoxy-phenyl ester,
Morpholine-4-carboxylic acid 4-(4-chlorobenzoyl)-phenyl ester,
Morpholine-4-carboxylic acid 4-(3-chloro-5-trifluoromethyl)-pyridine-2-yloxy)-phenyl ester, Morpholine-4-carboxylic acid 4-[4-(4-chloro-phenyl)-thiazol-2-yl]-phenyl ester,
Morpholine-4-carboxylic acid 4-pyrrol-1-yl-phenyl ester,
Morpholine-4-carboxylic acid 4-imidazol-1-yl-phenyl ester,
Morpholine-4-carboxylic acid 4-(3-chloro-5-trifluoromethyl)-pyridine-2-ylmethyl)-phenyl ester,
Morpholine-4-carboxylic acid 4-trifluoromethylsulfanyl-phenyl ester,
Morpholine-4-carboxylic acid 4-pentafluoromethyloxy-phenyl ester,
Morpholine-4-carboxylic acid 4-benzyloxy-phenyl ester,
Morpholine-4-carboxylic acid 4-benzyl-phenyl ester,
Morpholine-4-carboxylic acid 4'-cyano-biphenyl-4-yl-ester,
Morpholine-4-carboxylic acid 4'-bromo-biphenyl-4-yl-ester,
Morpholine-4-carboxylic acid biphenyl-4-yl-ester,
Morpholine-4-carboxylic acid 4-[3-(4-chlorophenyl)-ureido]-phenyl ester,
Morpholine-4-carboxylic acid 4-(4-nitro-phenoxy)-phenyl ester,
Morpholine-4-carboxylic acid 4-heptylsulfanyl-phenyl ester,
Morpholine-4-carboxylic acid 4-butoxy-phenyl ester,
Morpholine-4-carboxylic acid 4-(4-chloro-benzenesulfonyl)-phenyl ester,
Morpholine-4-carboxylic acid 4-(4-chloromethyl-thiazol-2-yl)-phenyl ester
Morpholine-4-carboxylic acid 4-(4,4-dimethyl-2,6-dioxo-piperidin-1-yl)-phenyl ester,
cis-Morpholine-4-carboxylic acid 4-(1,3-dioxo-octahydro-isoindol-2-yl)-phenyl ester,
Morpholine-4-carboxylic acid 4-(cyclohexanecarbonyl-amino)-phenyl ester,
Morpholine-4-carboxylic acid 4-(2-cyclohexyl-acetylamino)-phenyl ester,
cis/trans-Morpholine-4-carboxylic acid 4-[(4-tert-butyl-cyclohexanecarbonyl)-amino]-phenyl ester,
cis-Morpholine-4-carboxylic acid 4-[(4-tert-butyl-cyclohexanecarbonyl)-amino]-phenyl ester,
trans-Morpholine-4-carboxylic acid 4-[(4-tert-butyl-cyclohexanecarbonyl)-amino]-phenyl ester,
Morpholine-4-carboxylic acid 4-(3,3-dimethyl-butyrylamino)-phenyl ester,
Morpholine-4-carboxylic acid 3-benzyl-4-methyl-2-oxo-2H-chromen-7-yl ester,
Morpholine-4-carboxylic acid 3-(3,4-dichloro-benzyl)-4-methyl-2-oxo-2H-chromen-7-yl ester,
Morpholine-4-carboxylic acid 3-(2-chloro-6-fluoro-benzyl)-4-methyl-2-oxo-2H-chromen-7-yl ester,
Morpholine-4-carboxylic acid 3-(2,6-dichloro-benzyl)-4-methyl-2-oxo-2H-chromen-7-yl ester,
Morpholine-4-carboxylic acid 3-(2,6-dichloro-benzyl)-6-chloro-4-methyl-2-oxo-2H-chromen-7-yl ester,
Morpholine-4-carboxylic acid 6-chloro-3-(2-chloro-6-fluoro-benzyl)-4-n-propy-2-oxo-2H-chromen-7-yl ester,
Morpholine-4-carboxylic acid 3-(4-methoxy-phenyl)-4-methyl-2-oxo-2H-chromen-7-yl ester,
Morpholine-4-carboxylic acid 4-methyl-2-oxo-3-phenyl-2H-chromen-7-yl ester,
Morpholine-4-carboxylic acid 3-(2,5-dimethoxy-phenyl)-4-methyl-2-oxo-2H-chromen-7-yl ester,
Morpholine-4-carboxylic acid 3-(3,4-dimethoxy-phenyl)-4-methyl-2-oxo-2H-chromen-7-yl ester,
Morpholine-4-carboxylic acid 4-(5,7-bis-trifluoromethyl-[1,8]naphthypyridin-2-yloxy)-phenyl ester,
Morpholine-4-carboxylic acid 4-pyrrolidine-1-yl-phenyl ester,
Morpholine-4-carboxylic acid 4-piperidine-1-yl-phenyl ester,
Morpholine-4-carboxylic acid 4-morpholine-1-yl-phenyl ester,
Morpholine-4-carboxylic acid 4-[(6-chloro-pyridine-3-carbonyl)-amino]-phenyl ester,
Morpholine-4-carboxylic acid 4-[(6-chloro-pyridine-3-carbonyl)-amino]-phenyl ester,
Morpholine-4-carboxylic acid 4-[(pyridine-2-carbonyl)-amino]-phenyl ester,
2.6-dimethyl-morpholine-4-carboxylic acid 4-(5-trifluoromethyl-pyridin-2-yloxy)-phenyl ester,
Morpholine-4-carboxylic acid pyrazol-1-yl ester,
Morpholine-4-carboxylic acid 3-bromo-pyrazol-1-yl ester,
Morpholine-4-carboxylic acid 4-bromo-pyrazol-1-yl ester,
Morpholine-4-carboxylic acid 5-bromo-pyrazol-1-yl ester,
Morpholine-4-carboxylic acid 3,4,5-tribromo-pyrazol-1-yl ester,
Morpholine-4-carboxylic acid 4-chloro-pyrazol-1-yl ester,
Morpholine-4-carboxylic acid 4-iodo-pyrazol-1-yl ester,
Morpholine-4-carboxylic acid 3-(4-methoxy-phenyl)-pyrazol-1-yl ester,
Morpholine-4-carboxylic acid 3-(2-methoxy-phenyl)-pyrazol-1-yl ester,
Morpholine-4-carboxylic acid 3-(4-nitro-phenyl)-pyrazol-1-yl ester,
Morpholine-4-carboxylic acid 3-(2-fluoro-phenyl)-pyrazol-1-yl ester,
Morpholine-4-carboxylic acid 3-pyridin-2-yl-pyrazol-1-yl ester,
Morpholine-4-carboxylic acid 4-phenylsulfanyl-pyrazol-1-yl ester,
Morpholine-4-carboxylic acid 3-thiophen-2-yl-pyrazol-1-yl ester,
Morpholine-4-carboxylic acid 5-thiophen-2-yl-pyrazol-1-yl ester,
Morpholine-4-carboxylic acid imidazol-1-yl ester,
Morpholine-4-carboxylic acid 2-chloro-imidazol-1-yl ester,
Morpholine-4-carboxylic acid 2-bromo-imidazol-1-yl ester,
Morpholine-4-carboxylic acid 2-iodo-imidazol-1-yl ester,
Morpholine-4-carboxylic acid 2-methyl-imidazol-1-yl ester,
Morpholine-4-carboxylic acid 2-phenylsulfanyl-imidazol-1-yl ester,
Morpholine-4-carboxylic acid 2-(4-methoxy-phenyl)-imidazol-1-yl ester,
Morpholine-4-carboxylic acid 2-(4-fluoro-phenyl)-imidazol-1-yl ester,
Morpholine-4-carboxylic acid 2-thiophen-2-yl-imidazol-1-yl ester,
Morpholine-4-carboxylic acid 2-pyridin-2-yl-imidazol-1-yl ester
Morpholine-4-carboxylic acid 2,5-dichloro-imidazol-1-yl ester,
Morpholine-4-carboxylic acid 4-bromo-2,5-dichloro-imidazol-1-yl ester,
Morpholine-4-carboxylic acid 4-bromo-2-chloro-imidazol-1-yl ester,
Morpholine-4-carboxylic acid 5-(4-methoxy-phenyl)-imidazol-1-yl ester,
Morpholine-4-carboxylic acid 5-(4-fluoro-phenyl)-imidazol-1-yl ester,
Morpholine-4-carboxylic acid 5-thiophen-2-yl-imidazol-1-yl ester,
Morpholine-4-carboxylic acid 5-pyridin-2-yl-imidazol-1-yl ester,
Morpholine-4-carboxylic acid 4-trifluoromethyl-pyrimidin-2-yl ester, Morpholine-4-carboxylic acid 4-trifluoromethyl-pyrimidin-2-yl ester,
Morpholine-4-carboxylic acid imidazol-1-yl ester,
Morpholine-4-carboxylic acid 2-bromo-imidazol-1-yl ester,
Morpholine-4-carboxylic acid 2-chloro-imidazol-1-yl ester,
Morpholine-4-carboxylic acid 2-phenylsulfanyl-imidazol-1-yl ester,
Morpholine-4-carboxylic acid 2-(4-methoxy-phenyl)-imidazol-1-yl ester,
Morpholine-4-carboxylic acid 4-bromo-pyrazol-1-yl ester,
Morpholine-4-carboxylic acid 4-iodo-pyrazol-1-yl ester,
Morpholine-4-carboxylic acid 3,4,5-tribromo-pyrazol-1-yl ester,
Morpholine-4-carboxylic acid 3-(4-methoxy-phenyl)-pyrazol-1-yl ester,
Morpholine-4-carboxylic acid 3-thiophen-2-yl-pyrazol-1-yl ester,
Morpholine-4-carboxylic acid pyrazol-1-yl ester, and
1-Oxo-1$\lambda^4$-thiomorpholine-4-carboxylic acid 4-(5-trifluoromethyl-pyridin-2-yloxy)-phenyl ester Further examples of specific compounds of the invention are:
Methyl-o-tolyl-carbamic acid 4-iodo-pyrazol-1-yl ester,
Methyl-m-tolyl-carbamic acid 4-iodo-pyrazol-1-yl ester,
Methyl-p-tolyl-carbamic acid 4-iodo-pyrazol-1-yl ester,
(3-Chloro-phenyl)-methyl-carbamic acid 4-iodo-pyrazol-1-yl ester, (3-Fluoro-phenyl)-methyl-carbamic acid 4-iodo-pyrazol-1-yl ester,4-(3-Trifluoromethyl-pyridin-2-yl)-piperazine-1-carboxylic acid 4-iodo-pyrazol-1-yl ester,
2,6-Dimethyl-morpholine-4-carboxylic acid 4-iodo-pyrazol-1-yl ester,
Thiomorpholine-4-carboxylic acid 4-iodo-pyrazol-1-yl ester,
3,5-Dimethyl-morpholine-4-carboxylic acid 4-iodo-pyrazol-1-yl ester,
Piperidine-1-carboxylic acid 4-iodo-pyrazol-1-yl ester,
Methyl-o-tolyl-carbamic acid 2-chloro-imidazol-1-yl ester,
(3-Fluoro-phenyl)-methyl-carbamic acid 2-chloro-imidazol-1-yl ester, and
Methyl-phenyl-carbamic acid 5-phenylsulfanyl-pyrazol-1-yl ester.

Further examples of compounds of the invention are:
N-Methyl-N-phenyl-5-hexylsulfanyl-3-p-tolyl-[1,2,4]triazole-1-carboxamide,
N-Methyl-N-phenethyl-5-ethyl-3-(4-chlorophenyl)-[1,2,4]triazole-1-carboxamide,
[3-(4-Chlorophenyl)-5-methylsulfanyl-[1,2,4]triazol-1-yl]-morpholin-4-yl-methanone,
N,N-Dimethyl-5-methylsulfanyl-3-naphthalen-2-yl-[1,2,4]triazole-1-carboxamide,
N,N-Dimethyl-3-(4-chloro-phenyl)-5-ethylsulfanyl-[1,2,4]triazole-1-carboxamide, and
N, N-Dimethyl-3-biphenyl-4-yl-5-methylsulfanyl-[1,2,4]triazole-1-carboxamide.

The present invention also encompasses compounds of formulae I–XXXXVIII, which possess a range of pharmaceutically desirable properties.

In one embodiment, the invention is concerned with compounds of formulae I–XXXXVIII, which have a solubility in water of at least 0.5 mg/L, preferably at least 2 mg/L, more preferable at least 10 mg/L, more preferable at least 50 mg/L and most preferable at least 200 mg/L as determined at 25° C. and pH 7.0.

In another embodiment, the invention is concerned with compounds of formulae I–XXXXVI II, which have a solubility in water of at least 0.5 mg/L, preferably at least 2 mg/L, more preferable at least 10 mg/L, more preferable at least 50 mg/L and most preferable at least 200 mg/L as determined at 25° C. and pH 2.0.

In another embodiment, the invention is concerned with compounds of formulae I–XXXXVIII, which have an $IC_{50}$ value of no greater than 5 µM as determined by the assay 3190.2 or 3180.1 disclosed herein.

In another embodiment, the invention is concerned with compounds of formulae I–XXXXVIII, which have an $IC_{50}$ value of less than 1 µM, preferably less than 500 nM, preferably less than 100 nM, preferably less than 50 nM, more preferable less than 25 nM, more preferable less than 10 nM and even more preferable less than 5 nM as determined by the assay 3190.2 or 3180.1 disclosed herein.

In another embodiment, the invention is concerned with compounds of formulae I–XXXXVIII, which are ionized at pH 7.0.

In another embodiment, the invention is concerned with compounds of formulae I–XXXXVIII, which have a $pK_a$ in the range from 8 to 12, preferable from 9 to 12, more preferable from 10 to 12.

In another embodiment, the invention is concerned with compounds of formulae I–XXXXVIII, which have a molar weight of no greater than 1000 D.

In another embodiment, the invention is concerned with compounds of formulae I–XXXXVIII, which have a molar weight of less than 750 D, preferably less than 500 D, more preferable less than 400 D, more preferable less than 300D and even more preferably less than 250 D.

In another aspect the invention is concerned with a process for the preparation of a compound of formulae I–XXXXVIII or their pharmaceutically acceptable salts, which process comprises reacting the appropriate alcohol, Rz-OH, with the appropriate carbamoylating reagent, Lv-C(=O)—NRxRy, in a solvent according to the reaction scheme $P_1$

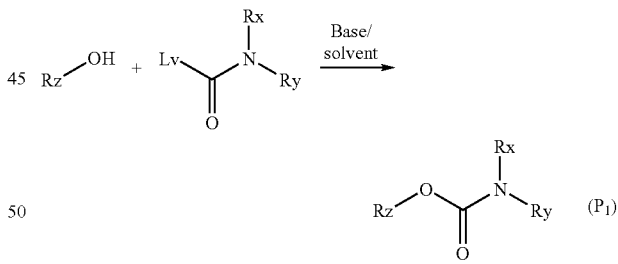

and isolating the disubstituted carbamate product.

In one embodiment, the invention is concerned with process $P_1$, wherein said carbamoylating reagent

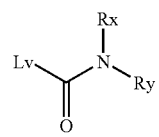

is selected from the group consisting of

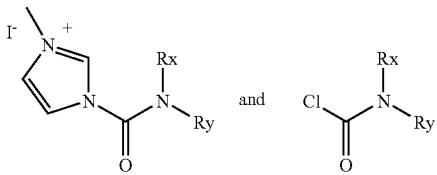

In another embodiment, the invention is concerned with the process of scheme $P_1$, wherein said solvent is selected from the group consisting of tetrahydrofurane, dimethylformamide and N-methylpyrolidone.

In another embodiment, the invention is concerned with the process of scheme $P_1$, wherein said base is selected from the group consisting of triethylamine, N,N-diisopropyl-N-ethylamine and DABCO.

In another aspect the invention is concerned with a process for the preparation of a compound according to the general formula

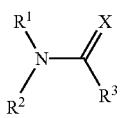

(II)

wherein $R^1$ is selected from $C_{1-6}$-alkyl, $C_{2-6}$-alkenyl and $C_{3-10}$-cycloalkyl, each of which is optionally substituted with one or more substituents independently selected from hydroxy, sulfanyl, oxo, halogen, amino, cyano and nitro; and $R^2$ is selected from $C_{1-6}$-alkyl, $C_{2-6}$-alkenyl, aryl, heteroaryl, $C_{3-8}$-heterocyclyl and $C_{3-10}$-cycloalkyl, each of which is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; and wherein $R^2$ is optionally covalently bound to $R^1$ by an ether, thioether, C—C or C—N bond, to form a ring system with the N-atom to which $R^1$ and $R^2$ are bound; and $R^3$ is selected from hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl, each of which is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; and X is O or S; or a compound according to any one of formulae III–XXXXVIII; or a pharmaceutically acceptable salt thereof;

said process comprising the treatment of the appropriate amine, $R^1$—NH—$R^2$, with the appropriate acylating reagent, Y—C(=X)—$R^3$, in a solvent and in the presence of a base according to the reaction scheme $P_2$

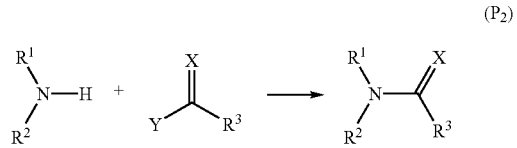

(P2)

In one embodiment, the invention is concerned with the process of scheme $P_2$, wherein Y is Cl.

In another embodiment, the invention is concerned with the process of scheme $P_2$, wherein $R^3$ is an aryloxy group.

In another embodiment, the invention is concerned with the process of scheme $P_2$, wherein said solvent is selected from the group consisting of diethyl ether, tetrahydrofuran and dichloromethane.

In another embodiment, the invention is concerned with the process of scheme $P_2$, wherein said base is selected from the group consisting of trimethylamine, triethylamine, ethyldiisopropyl-amine and 1,4-diazabicyclo[2.2.2]octane.

In another embodiment, the invention is concerned with the process of scheme $P_2$, wherein said base is present as a functionality in one or both of the substituents $R^1$ and $R^2$, thus forming a salt with the acid H—Y.

In another aspect the invention is concerned with a pharmaceutical composition comprising a compound of formulae I–XXXXVIII or a pharmaceutically acceptable salt thereof together with a pharmaceutically acceptable carrier or diluent.

In one embodiment the invention is concerned with a pharmaceutical composition, wherein said composition is in unit dosage form, comprising from about 0.05 to about 2000 mg, preferably from about 0.1 to about 500 mg and even more preferable from about 1.0 to about 100 mg of a compound of formulae I–XXXXVIII or a pharmaceutically acceptable salt thereof.

In another embodiment the invention is concerned with a pharmaceutical composition for use as a medicament for inhibiting the lipolytic activity of hormone-sensitive lipase against triacylglycerols, diacylglycerols, cholesterol acyl esters or steroid acyl esters, said composition comprising a compound of any one of formulae I–XXXXVIII or a pharmaceutically acceptable salt thereof together with a pharmaceutically acceptable carrier or diluent.

In another embodiment the invention is concerned with a pharmaceutical composition for oral, nasal, transdermal, pulmonal, or parenteral administration.

In another aspect the invention is concerned with use of a compound according to any one of formulae I–XXXXVIII for preparation of a medicament for inhibition of the lipolytic activity of hormone-sensitive lipase against triacylglycerols, diacylglycerols, cholesterol acyl esters or steroid acyl esters.

In one embodiment the invention is concerned with said use, wherein a further antidiabetic, antiobesity, antihypertensive or appetite regulating drug is used.

In another aspect the invention is concerned with use of a compound according to any one of formulae I–XXXXVIII for the preparation of a medicament for the treatment of any disorder where it is desirable to modulate the plasma level of free fatty acids, glycerol, LDL-cholesterol, HDL-cholesterol, insulin and/or glucose; and/or modulate intracellular triacylglycerol and cholesterol ester stores, intracellular level of fatty acids, fatty acid esters such as diacylglycerols, phosphatidic acids, long chain acyl-CoA's as well as citrate or malonyl-CoA; and/or increase insulin sensitivity in adipose tissue, skeletal muscle, liver or pancreatic β cells; and/or modulate insulin secretion from pancreatic β cells.

In one embodiment the invention is concerned with said use, wherein said disorder is selected from the group consisting of insulin resistance, diabetes type 1 and 2, metabolic syndrome X, impaired glucose tolerance, hyperglycemia, dyslipidemia, obesity, abnormalities of lipoprotein metabolism and any combination thereof.

In another aspect the invention is concerned with use of a compound according to any one of formulae I–XXXXVIII or a pharmaceutically acceptable salt thereof for the preparation of a medicament.

In another aspect the invention is concerned with a method of treating a disorder of a patient where modulation of the activity of hormone-sensitive lipase is desired, the method comprising administering to said patient an effective amount of a compound according to any one of formulae I–XXXXVIII or a pharmaceutically acceptable salt thereof.

In one embodiment the invention is concerned with said method, wherein said administration is carried out by the oral, nasal, transdermal, pulmonal, or parenteral route.

In another embodiment the invention is concerned with said method, wherein said disorder is selected from the group consisting of insulin resistance, diabetes type 1 and 2, metabolic syndrome X, impaired glucose tolerance, hyperglycemia, dyslipidemia, obesity, abnormalities of lipoprotein metabolism and any combination thereof.

In another embodiment the invention is concerned with said method, wherein a further antidiabetic, antiobesity, antihypertensive or appetite regulating drug is administered to the patient.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, guanidine and the like. Examples of cationic amino acids include lysine, arginine, histidine and the like.

The pharmaceutically acceptable salts are prepared by reacting the compound of formulae I–XXXXVIII with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, aminoacids, aminoalcohols derived from aminoacids; conventional reaction conditions may be employed to convert acid into an amide; the dia-stereomers may be separated either by fractional crystallization or chromatography and the stereoisomers of compound of formulae I–XXXXVIII may be prepared by hydrolysing the pure diastereomeric amide.

Various polymorphs of compound of general formulae I–XXXXVIII forming part of this invention may be prepared by crystallization of compound of formulae I–XXXXVIII under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formulae I–XXXXVIII. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

Furthermore, the invention relates to the use of compounds of the general formulae I–XXXXVIII or their tautomeric forms, their stereoisomers, their polymorphs, their pharmaceutically acceptable salts or pharmaceutically acceptable solvates thereof for the preparation of a pharmaceutical composition for the treatment and/or prevention of disorders where a decreased level of plasma FFA is desirable, such as the conditions mentioned above.

In another aspect, the present invention relates to a method of treating and/or preventing type 2 diabetes, insulin resistance, metabolic syndrome X, impaired glucose tolerance, dyslipidemia and abnormalities of lipoprotein metabolism.

In a still further aspect, the present invention relates to the use of one or more compounds of the general formulae I–XXXXVIII, or pharmaceutically acceptable salts thereof, for the preparation of a pharmaceutical composition for the treatment and/or prevention of type 2 diabetes, insulin resistance, metabolic syndrome X, impaired glucose tolerance, dyslipidemia and abnormalities of lipoprotein metabolism.

In a still further aspect, the present compounds are useful for the delaying or prevention of the progression from impaired glucose tolerance to type 2 diabetes.

In a still further aspect, the present compounds are useful for the delaying or prevention of the progression from non-insulin requiring type 2 diabetes to insulin requiring type 2 diabetes.

In another aspect, the present compounds reduce triglyceride levels and are accordingly useful for the treatment and/or prevention of ailments and disorders such as diabetes and/or obesity.

In still another aspect, the compounds of general formulae I–XXXXVIII are useful for the treatment of hyperglycemia, elevated $HbA_{1c}$ level, hyperinsulinemia, type 1.5 diabetes, latent autoimmune diabetes in adults, maturity onset diabetes, beta-cell apoptosis, hemochromatosis induced diabetes, impaired glucose tolerance, impaired fasting glucose, metabolic syndrome X, insulin resistance, impaired lipid tolerance, cystic fibrosis related diabetes, polycystic ovarian syndrome, and gestational diabetes.

In still another aspect, the compounds of general formulae I–XXXXVIII are useful for the treatment of obesity, dyslipidemia, diabetic dyslipidemia, hyperlipidemia, hypertriglyceridemia, hyperlipoproteinemia, hypercholesterolemia, hypertension, essential hypertension, acute hypertensive emergency, arteriosclerosis, atherosclerosis, restenosis, intermittent claudication (atherosclerosis oblilterens), cardiovascular disease, cardiomyopathy, cardiac hypertrophy, left ventricular hypertrophy, coronary artery disease, early coronary artery disease, heart insufficiency, exercise tolerance, chronic heart failure, mild chronic heart failure, arrhythmia, cardiac dysrythmia, syncopy, heart attack, myocardial infarction, Q-wave myocardial infarction, stroke, acute coronary syndrome, angina pectoris, unstable angina, cardiac bypass reocclusion, diastolic dysfunction, systolic dysfunction, non-Q-wave cardiac necrosis, catabolic changes after surgery, acute pancreatitis, and irritable bowel syndrome In still another aspect, the compounds of general formulae I–XXXXVIII may be useful for the treatment of diabetic retinopathy, background retinopathy, preproliferative retinopathy, proliferative retinopathy, macular edema, cataracts, nephropathy, nephrotic syndrome, diabetic nephropathy, microalbuminuria, macroalbuminuria, neuropathy, diabetic neuropathy, distal symmetrical sensorimotor polyneuropathy, and diabetic autonomic neuropathy.

In still another aspect, the compounds of general formulae I–XXXXVIII are useful for increasing the number of beta-cells in a patient, increasing the size of beta-cells in a patient or stimulating beta-cell proliferation, modulating beta-cell function and insulin secretion in a patient in need thereof, which method comprises administration of an effective amount of a compound of formulae I–XXXXVIII to a patient in need thereof.

The compounds of the invention are also believed to be useful for reducing body weight in a patient in need thereof.

The compounds of the invention are also believed to be useful Use for weight neutral treatment of above mentioned diseases.

The compounds of the invention are also believed to be useful for redistributing fat in a patient in need thereof.

The compounds of the invention are also believed to be useful for redistributing central fat in a patient in need thereof.

The compounds of the invention are also believed to be useful for reducing or preventing central obesity.

The compounds of the invention are also believed to be useful for reducing postprandial serum lipid excursions.

The compounds of the invention are also believed to be useful for the treatment of fatty acid oxidation disorders such as MCAD.

In still another aspect, the compounds of general formulae I–XXXXVIII are believed to be useful for the treatment of a disease, condition or disorder wherein cholesterol is a precursor. Such diseases, conditions or disorders may relate to testosterone, e.g. male contraception, excessive testosterone levels, PCOS and prostate cancer. They may also relate to cortisol or corticotropin, e.g. Cushing disease.

The compounds of the invention are also believed to be useful for the treatment of cancer. Thus, the compounds of the general formulae I–XXXXVIII may be useful for the treatment of insulinoma (pancreatic islet cell tumors), e.g. malignant insulinomas and multiple insulinomas, adipose cell carcinomas, e.g. lipocarconoma.

The compounds of the invention are also believed to be useful for the treatment of phaechromocytoma and other diseases with increased catecholamine incretion.

The compounds of the invention are also believed to be useful for the treatment of prostate cancer, e.g. adenocarcinoma.

In still another aspect, the compounds of general formulae I–XXXXVIII may be useful for the treatment of hepatic steatosis.

In still another aspect, the compounds of general formulae I–XXXXVIII may be useful for the treatment of cirrhosis.

In still another aspect, the compounds of general formulae I–XXXXVIII may be useful for the treatment of AIDS or an AIDS related diseases, condition or disorders In still another aspect, the compounds of general formulae I–XXXXVIII may be useful for the treatment of lipodystrophy In still another aspect, the compounds of general formulae I–XXXXVIII may be useful for the treatment of lactic acidosis.

In yet another aspect, the compounds of the present invention are expected to be useful for the treatment of CNS diseases, conditions or disorders.

Thus, the compound of the present invention may be used for the treatment of Parkinsons disease, Alzheimers disease, ADHD (Attention Deficit Hyperactivity Disorder), feeding disorders such as bulimia and anorexia, depression, anxiety, cognitive memory disorders, age related cognitive decline, mild cognitive impairment and schizophrenia.

In yet another aspect, the compounds of the present invention may be useful for the treatment of inflammatory disorders, e.g. rheumatoid arthritis, psoriasis, systemic inflammatory response syndrome, sepsis and the like.

The present compounds may also be administered in combination with one or more further pharmacologically active substances eg., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, R×R (retinoid×receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, exendin-4, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a biguanide eg. metformin.

In yet another embodiment the present compounds are administered in combination with a meglitinide eg. repaglinide or senaglinide.

In a further embodiment the present compounds are administered in combination with an α-glucosidase inhibitor eg. miglitol or acarbose.

In another embodiment the present compounds are administered in combination with an agent acting on the ATP-dependent potassium channel of the β-cells eg. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds eg. in combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, alatriopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995. It should be understood that any suitable combination of the compounds according to the invention with one or more of the above-mentioned compounds and optionally one or more further pharmacologically active substances are considered to be within the scope of the present invention.

The present invention also relates to processes according to reaction schemes $P_1$ and $P_2$ for the preparation of the above said novel compounds, their derivatives, their analogs, their tautomeric forms, their stereoisomers, their polymorphs, their pharmaceutically acceptable salts or pharmaceutically acceptable solvates.

Pharmaceutical Compositions.

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995. The compositions may appear in conventional forms, for example capsules, tablets, aerosols, solutions, suspensions or topical applications.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferredroute will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well-known in the art.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

The therapeutic dose of the compound will depend upon the frequency and mode of administration, the sex, age, weight and general condition of the subject treated, the nature and severity of the condition treated and any concomitant diseases to be treated and other factors evident to those skilled in the art. The formulations may conveniently be presented in unit dosage form by methods known to those skilled in the art. In one embodiment the composition in unit dosage form, comprises from about 0.05 to about 2000 mg, preferably from about 0.1 to about 500 mg of the compound of formula I pharmaceutically acceptable salt thereof.

In a still further embodiment the pharmaceutical composition is for oral, nasal, transdermal, pulmonal, or parenteral administration.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the invention contains a free base such salts are prepared in a conventional manner by treating a solution or suspension of a free base of the compound with a chemical equivalent of a pharmaceutically acceptable acid, for example, inorganic and organic acids. Representative examples are mentioned above. Physiologically acceptable salts of a compound with a hydroxy group include the anion of said compound in combination with a suitable cation such as sodium or ammonium ion.

For parenteral administration, solutions of the present compounds in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents.

The pharmaceutical compositions formed by combining the compounds of the invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet which may be prepared by conventional tabletting techniques may contain:

Core:

| | |
|---|---|
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | q.s. |
| Coating: | |
| HPMC approx. | 9 mg |
| *Mywacett 9-40 T approx. | 0.9 mg |

*Acylated monoglyceride used as plasticizer for film coating.

The compounds of the invention may be administered to a patient which is a mammal, especially a human in need thereof. Such mammals include also animals, both domestic animals, e.g. household pets, and non-domestic animals such as wildlife.

In a further aspect of the invention the present compounds may be administered in combination with further pharmacologically active substances e.g. an antidiabetic or other pharmacologically active material, including other compounds for the treatment and/or prevention of insulin resistance and diseases, wherein insulin resistance is the pathophysiological mechanism.

Furthermore, the compounds according to the invention may be administered in combination with antiobesity agents or appetite regulating agents.

EXAMPLES

General Methods

All reactions involving air-sensitive reagents were performed under nitrogen using syringe-septum cap techniques. The glassware were dried by heating with a heath-gun. $MgSO_4$ were used to dry solutions. Solvents were removed in vacuo by rotary evaporation. Melting points were recorded on a Büchi 535, Bruker AMX 400 and Bruker DRX 300 instruments were used to record $^1H$ NMR spectra at 400 and 300 MHz respectively with tetramethylsilane (TMS) as internal standard. Coupling constants (J) are given in Hz.

Materials

Test compounds were synthesized or when commercially available they were purchased from Specs, Maybridge, Comgenex, Peakdale or Bionet. For the synthesized compounds the procedure for synthesis and measured characteristics of the compound are stated in the example. All compounds for which no synthesis procedure is stated in the examples are commercially available and have been purchased, or were prepared by standard methods described in the literature.

N-methyl-phenethylcarbamoyl chloride was prepared from N-methyl-phenethylamine and phosgene using triethylamine as a base in dichloromethane. 1-Methyl-3-(morpholine-4-carbonyl)-3H-imidazol-1-ium iodide, 3-(3,4-dihydro-2H-quinoline-1-carbonyl)-1-methyl-3H-imidazol-1-ium iodide and 1-methyl-3-(methyl-phenyl-carbamoyl)-3H-imidazol-1-ium iodide was prepared as described by Batey, R. A., Tetrahedron Lett. 39, 1998, 6267.

1-Hydroxypyrazole was prepared as described in Begtrup, Vedsø, J. Chem. Soc. Perkin Trans 1, 1995, 243. 1-hydroxy-4-bromopyrazole was prepared as described in Balle et al., J. Org. Chem. 64, 1999, 5366. 1-hydroxy-3-(4-methoxyphenyl)pyrazole was prepared as described in Eskildsen et al., J. Org. Chem. 2001 (in press). 1-hydroxyimidazole was prepared as described in Eriksen et al., J. Org. Chem. 63, 1998, 12. 1-hydroxy-1,2,3-triazole was prepared as described in Uhlmann et al., J. Org. Chem. 62, 1997, 9177.

2-Piperidin-4-ylmethyl-1,2,3,4-tetrahydro-isoquinoline, cyclohexyl-methyl-piperidin-4-ylmethyl-amine, methyl-phenethyl-piperidine-4-ylmethyl-amine, ethyl-piperidin-4-ylmethyl-piperidin-4-ylmethylamine, benzyl-methyl-piperidin-4-ylmethyl-amine, benzyl-ethyl-piperidin-4-ylmethyl-amine, methyl-piperidin-4-ylmethyl-piperidin-3-ylmethyl-amine, 1-piperidin-4-ylmethyl-piperidin-4-ol, 2-piperidin-4-ylmethyl-2,3-dihydro-1H-isoindole, cyclopropylmethyl-piperidin-4-ylmethyl-amine was prepared from 4-formylpiperidine-1-carboxylic acid tert.-butyl ester prepared as described by Ting, P. C. (Bioorg, Med. Chem. Lett, 11, 4, 491, 2001) and an appropriate amine by a reductive amination (general procedure 19).

Benzylpiperidine-4-yl-amine, methyl-piperidin-4-yl-(2-pyridin-2-yl-ethyl)-amine, cyclohexyl-methyl-piperidin-4-yl-amine, Isopropyl-methyl-piperidin-4-yl-amine, methyl-phenethyl-piperidin-4-yl-amine, methyl-piperidin-4-yl-pyridin-3-ylmethyl-amine, was prepared from 4-oxopiperidine-1-carboxylic acid tert-butyl ester by a standard reductive amination procedure as described by Mattson R. J. (J. Org. Chem. 55, 2552, 1990).

Cyclopropyl-piperidin-4-yl-pyridin-4-ylmethyl-amine was prepared from 4-(cyclopropyl-pyridin-4-ylmethyl-amino)-piperidine-1-carboxylic acid tert-butyl ester by a classical N-deprotection reaction (HCl (g) in diethyl ether or ethanol). 4-(Cyclopropyl-pyridin-4-ylmethyl-amino)-piperidine-1-carboxylic acid tert-butyl ester was prepared from 4-cyclopropylamino-piperidine-1-carboxylic acid tert-butyl ester and pyridine-4-yl-acetaldehyde by a classical reductive amination procedure as described by Mattson R. J. 4-Cyclopropylamino-piperidine-1-carboxylic acid tert-butyl ester was prepared from cyclopropylamine and 4-oxopiperidine- 1-carboxylic acid tert-butyl ester by a standard reductive amination procedure as described by Mattson R. J. Cyclopropyl-(2-fluoro-benzyl)-piperidin-4-yl-amine, cyclopropyl-piperidin-4-yl-pyridin-3-ylmethyl-amine, cyclopropyl-methyl-piperidin-4-yl-pyridin-3-ylmethyl-amine and cyclopropylmethyl-piperidin-4-yl-pyridin-4-ylmethyl-amine was prepared by a procedure similar to the one described for cyclopropyl-piperidin-4-yl-pyridin-4-ylmethyl-amine.

Chloroformates were synthesized from the appropriate phenols and phosgene or a phosgene substitute like e.g. trichloromethyl chloroformate as described in K onakahara, Ozaki, Sato, Gold, Synthesis 1993 (1) 103–106, except that the crude product was separated from the diisopropylethylamine hydrochloride by extraction with diethyl ether rather than with THF.

Non-commercial N-monosubstitued piperazines were prepared by alkylation (alkylation procedure as described in e.g. Masaguer, Ravina, Tetrahedron Lett. 1996, 37 (29) 5171–5174) of 1-Boc-piperazine, and subsequent removal of the Boc group under acidic conditions, e.g. by heating in a mixture of hydrochloric acid and ethanol. N-Monosubstitued homopiprazines and N-monosubstituted 2,5-diazabicyclo[2.2.1]heptanes were prepared in a similar manner.

Thin layer chromatography was performed on Merck DC-Alufolien, silica gel 60 $F_{254}$ and components were visualized by $UV_{254}$. Flash chromatography was performed using silica gel Merck 60 size 0.04-0-063 mm and a Quad 12/25 flash system.

Preparative HPLC (Method A).

The system consists of two Gilson 322 pumps equipped with 30 ml pump heads. A Gilson 215 combined autoinjector and fraction collector performs injection and fraction collection. Detection is performed with a Gilson Diode array detector.

Separation is performed on Waters Xterra columns 19.8 mm*100 mm, flow rate 25 ml/min. The most widely used gradient starts at 10% acetonitrile in water and ends after 11 min on 100% acetonitrile, the system is buffered by 0.01% TFA. In special cases the gradient is altered to fit the separation need.

Preparative HPLC (Method B)

HPLC Purification:

The following instrumentation is used:
Gilson 306 Pump
Gilson 806 Manometric module
Gilson 811C Dynamic mixer
Gilson UV/VIS-155
Gilson 202 Fraction collector
The instrument is controlled by Gilson Unipoint software.
The HPLC pump is connected to two eluent reservoirs containing:
A: 0.01% TFA in water
B: 0.01% TFA in acetonitrile The purification is performed at room temperature by injecting an appropriate volume of the sample (preferably 2 ml) onto the column, which is eluted with a gradient of acetonitrile.

The HPLC conditions and detector settings used are as follows:

| | |
|---|---|
| Column: | Waters Xterra MS C-18 × 19 × 100 mm |
| Gradient: | 50%–60% acetonitrile linearly during 12 min at 20 ml/min |
| Detection: | 210 and 270 nm |

Preparative HPLC (Method C)

The system consists of two Gilson 322 pumps equipped with 30 ml pump heads. Gilson manometric module 805. A Gilson 215 combined autoinjector and fraction collector performs injection and fraction collection. Detection is performed with a Gilson Diode array detector 170. A sample contain 25–100 mg of material dissolved in 0.5–2.0 ml of solvent (minimum water concentration: 10%).

Separation is performed on Waters Xterra, $RP_{18}$ 7 µm, columns 19 mm×150 mm, flow rate 15 ml/min (sample added with a flow rate of 5 ml/min for about 1 min). The most widely used gradient starts at 5% acetonitrile in water and ends after 14 min on 95% acetonitrile. This concentration is maintained for 6 min. The system is buffered with 0.05% TFA. In special cases the gradient is altered to fit the separation need. The pooled fractions are evaporated to dryness in vacuo.

HPLC-MS.

The following instrumentation was used:
Hewlett Packard series 1100 G1312A Bin Pump
Hewlett Packard series 1100 Column compartment
Hewlett Packard series 1100 G13 15A DAD diode array detector
Hewlett Packard series 1100 MSD
The instrument was controlled by HP Chemstation software.

The HPLC pump was connected to two eluent reservoirs containing:

| | |
|---|---|
| A: | 0.01% TFA in water |
| B: | 0.01% TFA in acetonitrile |

The analysis was performed at 40° C. by injecting an appropriate volume of the sample (preferably 1 µl) onto the column, which is eluted with a gradient of acetonitrile.

The HPLC conditions, detector settings and mass spectrometer settings which were used are as follows:

| | |
|---|---|
| Column | Waters Xterra MS C-18 × 3 mm id |
| Gradient | 10%–100% acetonitrile linear during 7.5 mm at 1.0 ml/min |
| Detection | 210 nm (analogue output from DAD) |
| MS | Ionisation mode API-ES, Scan 100–1000 amu step 0.1 amu |

General Procedure 1

The phenol (1.0 mmol) was dissolved in tetrahydrofuran (15 ml) in a glass screw cap vessel, 1,4-diazabicyclo[2.2.2]octane (DABCO) (2.0 mmol) was added together with the respective carbamoyl chloride (2.0 mmol) at room temperature. The reaction mixture was shaken for 16 hours and poured into ethyl acetate (20 ml) and aqueous citric acid (5%; 20 ml). The organic phase was dried and evaporated to give the crude product.

General Procedure 2

The phenol (1.0 mmol) was dissolved in acetonitrile (15 ml) in a glass screw cap vessel. Triethylamine (1.0 mmol) was added together with the respective 1-methyl-3H-imidazol-1-ium iodide (1.0 mmol) at room temperature. The reaction mixture was shaken for 16–48 hours at 80° C., cooled to room temperature and evaporated. The evaporated reaction mixture was dissolved in dichloromethane (20 ml) and extracted with aqueous hydrogen chloride (0.1 M; 20 ml). The aqueous phase was extracted with dichloromethane (3×20 ml). The combined organic phases were dried and evaporated to give the crude product.

General Procedure 3

The respective phenol (1.0 mmol), 3H-imidazol-1-ium iodide (1.0 mmol) and triethylamine (1.0 mmol) in acetonitrile (3 ml) was heated at 50° C. overnight in a closed vial. The crude product was purified by flash column chromatography (SiO$_2$, ethyl acetate/heptane) yielding the respective carbamate.

General Procedure 4

Carbonyldiimidazole (3.6 mmol) was suspended in THF (10 ml) and the appropriate secondary amine (3.0 mmol) was added. The reaction mixture was refluxed for 24 to 72 hours until no traces of amine could be detected. The reaction mixture was cooled to room temperature and the organic phase evaporated to give the crude product of high purity. The crude product was used without further purification.

General Procedure 5

The crude imidazole carboxamide (3.0 mmol) was dissolved in acetonitrile (10 ml) and methyl iodide (12 mmol.) was added at room temperature. The reaction mixture was stirred for 24 to 48 hours before the organic phase was evaporated to give the crude product, which was used without further purification.

General Procedure 6

The respective 1,2,4-(1H)-triazoles were prepared as described by Blaine (U.S. Pat. No. 3,308,131).
The 1,2,3-(1H)-triazoles were carbamoylated using the following method:
The respective 1,2,4-(1H)-triazole (2.0 mmol) was dissolved in dimethylformamide (10 ml) in a glass screw cap vessel, 1,4-diazabicyclo[2.2.2]octane (DABCO) (5.0 mmol) was added together with the respective carbamoyl chloride (5.0 mmol) at room temperature. The reaction mixture was stirred for 16 hours, evaporated to dryness and ethyl acetate (20 ml) and aqueous citric acid (5%; 20 ml) was added. The phases were separated and the aqueous phase extracted with ethyl acetate (20 ml). The combined organic phases were dried and evaporated to give the crude product.

General Procedure 7

The aryl chloroformate was prepared from the corresponding phenol, trichloromethyl chloroformate and ethyldiisopropylamine in dichloromethane according to the procedure described by T. Konakahara, T. Ozaki, K. Sato and B. Gold, Synthesis, 1993 (1) 103–106, except that the crude reaction mixture was used without removal of ethyldiisopropylamine hydrochloride. To a stirred, freshly prepared solution of the aryl chloroformate in dichloromethane (1 mmol in 3 ml) at −15° C. was added a solution of the substituted piperazine (1 mmol) in dichloromethane (1 mL). The mixture was stirred at 0° C. for 2–6 h. The solvent was removed in vacuo and the solid residue was triturated with diethyl ether (3×5 ml), then with a minute amount of water (½–2 ml) to remove the ethyldiisopropylamine hydrochloride, filtered and dried to give the hydrochloride of the respective piperazine-1-carboxylic acid aryl ester.

General Procedure 8

To a solution of the N-hydroxyazole (1.0 mmol) and ethyldiisopropylamine (1.5 mmol) in CH$_2$Cl$_2$ (3 mL) was added the respective carbamoyl chloride (1.5 mmol) at room temperature. The reaction mixture was stirred for 16 hours, added CH$_2$Cl$_2$ (20 mL) and washed with aqueous citric acid (5%; 3×20 mL). The organic phase was separated, dried (MgSO$_4$) and evaporated to give the crude product.

General Procedure 9

A solution of the substituted piperazine in diethyl ether is added to a stirred solution of an equimolar amount of the aryl chloroformate (prepared from the corresponding phenol by conventional methods) in the same solvent at 0° C. After completion of the addition, the mixture is stirred at 0° C. for 1 hour, then for 1 more hour at room temperature. The mixture is filtered, the filter cake rinsed with diethyl ether and dried to give the hydrochloride of the respective piperazine-1-carboxylic acid aryl ester.

General Procedure 10

A disbstituted amine (1.0 eq) and diisopropylethylamine (1.5 eq) was added to a dried reaction flask under nitrogen. Dichloromethane or tetrahydrofuran was added to give a 0.5 mM concentration of the amine. The appropriate aryl chloroformate (1.0 eq) (prepared from the corresponding phenol by conventional methods) was dissolved in a minimum amount of dichloromethane or tetrahydrofuran and added drop by drop at room temperature. The reaction mixture was stirred overnight, citric acid (5%) was added, and the two phases separated. The aqueous phase was extracted twice with dichloromethane, the combined organic phases were dried with MgSO$_4$, filtered and evaporated to give the crude product.

General Procedure 11

An appropriate amine (1.0 eq.) was dissolved in dichloromethane (0.5 mM concentration of the amine) in a dried reaction flask under nitrogen. The appropriate aryl chloroformate (1.0 eq.) (prepared from the corresponding phenol by conventional methods) was dissolved in a minimum amount of dichloromethane and added drop by drop at room temperature. Heptane was added to give a 20% solution in dichloromethane and the crude product was isolated by filtration. The crude product was washed with a mixture of dichloromethane/heptane (5:1) and dried in vacuum.

General Procedure 12

An appropriate amine (1.0 eq.) and diisopropylethylamine (1.0 eq.) was dissolved in tetrahydrofuran (0.5 mM concentration of the amine) in a dried reaction flask under nitrogen. The appropriate aryl chloroformate (1.0 eq.) (prepared from the corresponding phenol by conventional methods) was dissolved in a minimum amount of tetrahydrofuran and added drop by drop at room temperature. Acetic acid was added to the reaction mixture (pH 3–5) and the reaction mixture filtered. The organic phase was evaporated and the crude product subjected to preparative HPLC.

General Procedure 13

4-(Methyl-phenyl-carbamoyloxy)-benzoic acid 2,5-dioxo-pyrrolidin-1-yl ester (1 eq.), diisopropylethylamine (1.5 eq.) was dissolved in tetrahydrofuran (50 mM of phenol). The reaction mixture was added to a mono or disubstituted amine. The reaction mixture was stirred at 50° C. for 16 hours. Citric acid (5%) and tert-butyl-methylether was added and the two phases separated. The organic phase was evaporated to give the crude product.

General Procedure 14

The phenol (1.0 mmol) was dissolved in tetrahydrofuran (15 ml) in a glass screw cap vessel, 1,4-diazabicyclo[2.2.2]octane (DABCO) (2.0 mmol) was added together with the respective carbamoyl chloride (2.0 mmol) at room temperature. The reaction mixture was shaken for 16 hours. Acetic acid was added to the reaction mixture (pH 3–5) and the reaction mixture filtered. The organic phase was evaporated and the crude product subjected to preparative HPLC.

General Procedure 15

A solution of the substituted piperazine in diethyl ether was added to a stirred solution of an equimolar amount of the aryl chloroformate in the same solvent at 0° C. After completion of the addition, the mixture was stirred at ambient temperature for 1–2 hours. Stirring was discontinued and as much as possible of the solvent was removed by decantation. The residue was rinsed twice with ether by stirring and subsequent decantation and finally dried on a rotary evaporator to give the hydrochloride of the respective piperazine-1-carboxylic acid aryl ester.

If necessary, further purification was achieved by treating the crude product with a mixture of ethyl acetate and a slight excess of sodium bicarbonate (approx. 1.1 eqv.) in water, extracting the aqueous phase twice with ethyl acetate, drying the combined extracts, filtering and evaporating to give the piperazine-1-carboxylic acid aryl ester as a free base.

General Procedure 16

To a solution of the N-hydroxyazole (1.0 mmol) and ethyldiisopropylamine (1.0 mmol) in CHCl$_3$ (1 mL) at –30° C. was added trichloromethyl chloroformiate (1.1 mmol). The solution was stirred at –30° C. for 10 min and at room temperature for 1 h. The solution was evaporated to dryness at room temperature and redissolved in CHCl$_3$ (2 mL) and cooled to –30° C. before addition of the appropriate piperazine (3 mmol). The solution was allowed to warm to room temperature over 30 min and evaporated to give the crude product.

General Procedure 17

To a suspention of N-methyl-N-phenyl-carbamic acid 4-(2-amino-ethyl)phenyl ester as its TFA salt (0.5 mmol) and an aryl sulfonyl chloride(0.75 mmol) in CH$_2$Cl$_2$ (2 mL) was added DIPEA (1.25 mmol). The reaction mixture was stirred at rt for 2–16 h, and evaporated to dryness and redissolved in MeCN and purified by preparative HPLC (Gilson).

General Procedure 18

A solution of the substituted piperazine in diethyl ether was added to a stirred solution of an equimolar amount of the aryl chloroformate in the same solvent at 0° C. Then an equimolar amount of diisopropylethylamine (DIPEA) in diethyl ether solution was added and the mixture was stirred at ambient temperature for 1–2 hours. The solvent was removed on a rotary evaporator and the residue was partitioned between ethyl acetate and water. The aqueous phase was extracted twice with ethyl acetate and the combined organic phases were dried and filtered. Removal of the solvent gave the piperazine-1-carboxylic acid aryl ester.

General Procedure 19

4-Formyl-piperidine-1-carboxylic acid tert-butyl ester (1.5 g, 7.03 mmol) prepared as described by Ting, P. C. was added to a dryed screw cap wessel under nitrogen. The appropriate amine (7.03 mmol) methanol (10 ml) and acetic acid 100 (µl) was added and the reaction mixture was stirred for 2 h. at room temperature. Sodium cyanoborohydride (1.0 M sol. In THF, 4.7 ml) was added during 1 minute and the mixture was stirred for 16 h. at room temperature. The reaction mixture was evaporated to dryness and extracted with dichloromethane (3×75 ml) from a 10% aqueous sodium hydrogene carbonate solution (100 ml). The organic phases were pooled, dried, and evaporated to dryness to give the crude intermediate, which was subjected to flash chromatography (ethyl acetate/heptane/methanole, 1:2:0→4:0:1).

A 3M solution of hydrogen chloride (50 ml) was added to the intermediate and the reaction micture was stirred for 16 h. The reaction mixture was evaporated to dryness to give the crude product, which was dryed in vacoum. The crude product was used without without further purification.

General Procedure 20

The arylboronic acid (1.2 mmol), KF (3.3 mmol), Pd$_2$(dba)$_3$ (0.03 mmol) and Pd(P(t-Bu)$_3$)$_2$ (0.06 mmol) were added to a Schlenk tube under nitrogen. The Schlenk tube was evacuated and refilled with nitrogen five times. Next the aryl halide (1.0 mmol) in THF (2 mL) was added. The reaction mixture was stirred at rt for 16 h.

General Procedure 21

To a suspension of methyl-phenyl-carbamic acid 4-amino-phenyl ester (0.5 mmol), (see preparation below) and an aryl sulfonyl chloride (0.75 mmol) in CH$_2$Cl$_2$ (2 mL) was added DIPEA (1.25 mmol). The reaction mixture was stirred at rt for 2–16 h, and evaporated to dryness and redissolved in MeCN and purified by preparative HPLC (Gilson).

General procedure 22

A solution of 1-benzyloxy-4-iodobenzene (4.1 mmol) in dry THF (20 mL) was cooled to −78° C. n-Butyllithium (1.57 M in hexanes, 4.1 mmol) was added during 2 min. After the mixture was stirred for another 5 min, an aryl aldehyde (4.1 mmol) was added. The mixture was allowed to warm to rt during 20 min and quenched with aqueous NaHCO$_3$. Extraction with CH$_2$Cl$_2$, drying (MgSO$_4$), filtration and evaporation provided the crude diarylmethanols which were recrystallised from EtOAc-heptane. A solution of the diarylmethanol product (2 mmol), NaI (14 mmol) in dry MeCN (20 mL) was added trimethylsilyl chloride (14 mmol) and stirred at 80° C. for 19 h. The purple reaction mixture was evaporated to dryness and treated with an aqueous solution of Na$_2$SO$_3$. The 4-arylmethylphenols were isolated by filtration or after extraction with CH$_2$Cl$_2$ and subsequent purification by flash chromatography (Quad flash 12, EtOAc-heptane).

General Procedure 23

A solution of the sulfonamide (0.2 mmol), 37% aqueous formaldehyde (0.5 mL), anf TFA (2 mL) was heated in a closed vessel in a Smith Creator microwave oven for 300 s at 150° C. The crude product was evaporated to dryness and purified by preparative HPLC (Gilson).

General Procedure 24

A suspention of the phenol (1.0 mmol), 1,4-diazabicyclo[2.2.2]octane (DABCO) (1.5 mmol) and 3-[4-(tert-butyl-dimethyl-silanyloxy)-piperidine-1-carbonyl]-1-methyl-3H-imidazol-1-ium; iodide (1.5 mmol) in CH$_2$Cl$_2$ (1 mL) was stirred at room temperature for 16 hours. The crude product was purified by flash chromatography (Quad flash 12, EtOAc-heptane). The purified tert-butyldimethylsilyl ether was desilylated by stirring with a 3.2 M solution of HCl in Et$_2$O (20 mL) for 3 h at rt.

General Procedure 25

A solution of an alcohol (0.4 mmol), a phenol (0.4 mmol), diisopropylethylamin (0.44 mmol) and tributylphosphine (0.5 mmol) in THF (2 mL) was stirred under nitrogen at rt. ADDP (0.5 mmol) dissolved in THF (2 mL) was added and the reaction mixture was stirred at rt for 16 h, filtered, evaporated to dryness and redissolved in MeCN and purified by preparative HPLC (Gilson).

General Procedure 26

A solution of an alcohol (0.4 mmol), a phenol/thiophenol/N-hydroxyazole/azole or imide (0.4 mmol), diisopropylethylamin (0.44 mmol) and solid supported triphenylphosphine (3 mmol/g, 1.2 mmol) in CH$_2$Cl$_2$ (2 mL) was stirred under nitrogen at rt. Di-tert-butylazodicarboxylate (DBAD, 1.2 mmol) dissolved in CH$_2$Cl$_2$ (1 mL) was added and the reaction mixture was stirred at rt for 16 h. TFA (0.5 mL) was added and the mixture was stirred for further 1 h at rt. Addition of EtOAc, filtration, followed by evaporation to dryness gave a crude which was either purified by flash chromatography (Quad flash 12, EtOAc-heptane) or redissolved in MeCN and purified by preparative HPLC (Gilson).

Preparation of 1-methyl-3H-imidazol-1-ium iodides

1-Methyl-3-(7-trifluoromethyl-3,4-dihydro-2H-quinoline-1-carbonyl)-3H-imidazol-1-ium iodide Step A: Imidazol-1-yl-(7-trifluoromethyl-3,4-dihydro-2H-quinolin-1-yl)-methanone The title product was prepared from 7-(trifluoromethyl)-1,2,3,4-tetrahydroquinoline, as described in the general procedure 4. Light yellow oil. HPLC-MS: m/z=296.1 (M+1); Rt: 2.85 min.

$\delta_H$(300 MHz; CDCl$_3$): 2.11 (qi, 2H), 2.93 (t, 2H), 3.90 (t, 2H), 7.01 (s, 2H), 7.05 (s, 1H), 7.34 (s, 1H), 7.34 (d, 1H), 7.77 (s, 1H).

Step B: 1-Methyl-3-(7-trifluoromethyl-3,4-dihydro-2H-quinoline-1-carbonyl)-3H-imidazol-1-ium iodide The title product was prepared from imidazol-1-yl-(7-trifluoromethyl-3,4-dihydro-2H-quinolin-1-yl)-methanone, as described in the general procedure 5. Light yellow crystals. HPLC-MS: m/z=310.2 (M+1), Rt: 1.84 min.

$\delta_H$(300 MHz; CDCl$_3$): 2.01 (qi, 2H), 2.94 (t, 2H), 3.83 (t, 2H), 3.92 (s, 3H), 7.52 (s, 2H), 7.76 (s, 1H), 7.80 (s, 1H), 7.85 (s, 1H), 9.62 (s, 1H).

3-(cyclohexyl-methyl-carbamoyl)-1-methyl-3H-imidazol-1-ium iodide

Step A: Imidazole-1-carboxylic acid cyclohexyl-methyl-amide

The title product was prepared from cyclohexyl-methyl-amine, as described in the general procedure 4. Off-white crystals. HPLC-MS: m/z=208.1 (M+1), Rt: 1.85 min $\delta_H$(300 MHz; CDCl$_3$): 1.05–1.22 (m, 1H), 1.25–1.45 m, 2H), 1.50–1.61 (dt, 2H), 1.63–1,75 (d, 1H), 1.76.1.95 (m, 4H), 3.80–3.95 (m, 1H), 7.09 (bs, 1H), 7.21 (bs 1H), 7.87 (bs, 1H).

Step B: 3-(cyclohexyl-methyl-carbamoyl)-1-methyl-3H-imidazol-1-ium iodide

The title product was prepared from imidazole-1-carboxylic acid cyclohexyl-methyl-amide, as described in the general procedure 5. Yellow crystals; HPLC-MS: m/z=222.2 (M+1), Rt: 1.15 min.

$\delta_H$(300 MHz; CDCl$_3$): 1.03–1.25, (m, 1H), 1.30–1.60 (m, 4H), 1.62–1.1.78 (m, 1H), 1.82–2.00 (t, 4H), 3.21 (s, 3H), 3.90–4.10 (m, 1H), 4.29 (s, 3H), 7.52 (bs, 1H), 7.66 (bs, 1H), 10.37 (bs, 1H).

3-(2,6-dimethyl-morpholine-4-carbonyl)-1-methyl-3H-imidazol-1-ium iodide

Step A: (2,6-Dimethyl-morpholin-4-yl)-imidazol-1-yl-methanone

The title product was prepared from 2,6-dimethyl-morpholine, as described in the general procedure 4. Colourless oil. PPLC-MS: m/z=210.10 (M+1), Rt: 0.63 min.

$\delta_H$(300 MHz; CDCl$_3$): 1.20 (s, 3H), 1.22 (s, 3H), 2.82 (dd, 2H), 3.60–3.75 (m, 2H), 3.93 (d, 2H), 7.11 (s, 1H), 7.20 (s, 1H), 7.87 (s, 1H).

Step B: 3-(2,6-dimethyl-morpholine-4-carbonyl)-1-methyl-3h-imidazol-1-ium iodide The title product was prepared from, (2,6-Dimethyl-morpholin-4-yl)-imidazol-1-yl-methanone, as described in the general procedure 5. Light yellow oil; HPLC-MS: m/z=224.2 (M+1), Rt: 0.40 min.

δ$_H$(300 MHz; CDCl$_3$): 1.23 (s, 3H), 1.25 (s, 3H), 2.90–3.10 (m, 2H), 3.7–3.9 (m, 2H), 3.95–4.15 (m, 2H), 4.26 (s, 3H), 7.67 (s, 1H), 7.73 (s, 1H) 10.05 (s, 1H).

3-(Benzyl-methyl-carbamoyl)-1-methyl-3H-imidazol-1-ium iodide

Step A: Imidazole-1-carboxylic acid benzyl-methyl-amide

The title product was prepared from benzyl-methyl-amine, as described in the general procedure 4. Light yellow crystals. HPLC-MS: m/z=216.1 (M+1), Rt: 1.53 min.

δ$_H$(300 MHz; CDCl$_3$): 3.04 (s, 3H), 4.65 (s, 3H), 7.08 (bs, 1H), 7.22–7.34 (m, 3H), 7.34–7.50 (m, 3H), 7.93 (bs, bs, 1H).

Step B: 3-(Benzyl-methyl-carbamoyl)-1-methyl-3H-imidazol-1-ium iodide

The title product was prepared from imidazole-1-carboxylic acid benzyl-methyl-amide, as described in the general procedure 5. Light yellow crystals. HPLC-MS m/z=230.1 (M+1), Rt: 1.23 min.

δ$_H$(300MHz; CDCl$_3$): 3.25 (s, 3H), 4.2 (s, 3H), 4.76 (s, 2H), 7.27–7.50 (m, 5H), 7.56 (bs, 1H), 7.70 (bs, 1H), 10.29 (bs, 1H).

3-(Phenyl-ethyl-carbamoyl)-1-methyl-3H-imidazol-1-ium iodide

Step A: Imidazole-1-carboxylic acid phenyl-ethyl-amide

The title product was prepared from phenyl-ethyl-amine, as described in the general procedure 4. Light brown oil. HPLC-MS m/z=216.1 (M+1), Rt: 1.75 min.

δ$_H$(300 MHz; CDCl$_3$): 1.26 (t, 3H), 3.92 (q, 2H), 6.79 (s, 1H), 6.84 (s, 1H), 7.10 (d, 2H), 7.27–7.45 (m, 3H), 7.55 (s, 1H).

Step B: 3-(Phenyl-ethyl-carbamoyl)-1-methyl-3H-imidazol-1-ium iodide

The title product was prepared from imidazole-1-carboxylic acid phenyl-ethyl-amide, as described in the general procedure 5. Light yellow crystals. HPLC-MS m/z=230.2 (M+1), Rt: 1.16 min.

δ$_H$(300 MHz; CDCl$_3$): 1.28 (t, 3H), 3.96 (q, 2H), 4.10 (s, 3H), 7.03 (s, 1H), 7.27 (s, 1H), 7.35–7.60 (m, 6H), 9.70 (s, 1H).

3-(2,3-Dihydro-indole-1-carbonyl)-1-methyl-3H-imidazol-1-ium iodide

Step A: (2,3-Dihydro-indol-1-yl)-imidazol-1-yl-methanone

The title product was prepared from Indoline, as described in the general procedure 4. Pink crystals. HPLC-MS m/z=214.1 (M+1), Rt: 1.62 min.

δ$_H$(300 MHz; CDCl$_3$): 3.21 (t, 2H), 4.21 (t, 2H), 7.21 (dt, 1H, 7.15 (s, 1H), 7.17–7.29 (m, 2H), 7.36 (t, 1H), 7.40 (d, 1H), 8.03 (bs, 1H).

Step B: 3-(2,3-Dihydro-indole-1-carbonyl)-1-methyl-3H-imidazol-1-ium iodide

The title product was prepared from (2,3-dihydro-indol-1-yl)-imidazol-1-yl-methanone, as described in the general procedure 5. Light brown crystals. HPLC-MS m/z=228.1 (M+1), Rt: 0.94 min.

δ$_H$(300 MHz; CDCl$_3$): 3.42 (t, 2H), 4.34 (s, 3H), 4.71 (t, 2H), 7.17–7.36 (m, 4H), 7.78 (bs, 1H), 7.86 (d, 1H), 10.76 (bs, 1H).

3[(4-Chlorophenyl)-methyl-carbamoyl]-1-methyl-3H-imidazol-1-ium iodide

Step A: Imidazole-1-carboxylic acid (4-chloro-phenyl)-methyl-amide

The title product was prepared from 4-chlor-N-methylaniline, as described in the general procedure 4. Light yellow crystals. HPLC-MS m/z=236.1 g/mol (M+1), Rt: 1.91 min.

δ$_H$(300 MHz; CDCl$_3$): 3.47 (s, 3H), 6.85 (s, 1H), 6.87 (s, 1H), 7.06 (d, 2H), 7.36 (d, 2H), 7.60 (s, 1H).

Step B: [(4-Chlorophenyl)-methyl-carbamoyl]-1-methyl-3H-imidazol-1-ium iodide

The title product was prepared from imidazole-1-carboxylic acid (4-chloro-phenyl)-methyl-amide, as described in the general procedure 5. Orange crystals. HPLC-MS m/z=250.1 (M+1), Rt: 1.06 min.

δ$_H$(300 MHz; CDCl$_3$): 3.55 (s, 3H), 4.12 (s, 3H), 7.16 (bs, 1H), 7.35 (t, 1H), 7.41 (d, 1H), 7.45 (t, 1H), 7.51 (t, 1H), 7.53–7.55 (m, 1H), 9.92 (bs, 1H).

3-(isopropyl-methyl-carbamoyl)-1-methyl-3H-imidazol-1-ium iodide

Step A: Imidazole-1-carboxylic acid isopropyl-methyl-amide

The title product was prepared from isopropyl-methylamine, as described in the general procedure 4. Light yellow oil. HPLC-MS m/z=168.1 (M+1), Rt: 0.51 min.

δ$_H$(300 MHz; CDCl$_3$): 1.25 (s, 3H), 1.27 (s, 3H), 2.93 (s, 3H), 4.36 (Qi, 1H), 7.08 (bs, 1H), 7.22 (bs, 1H), 7.88 (bs, 1H).

Step B: 3-(isopropyl-methyl-carbamoyl)-1-methyl-3H-imidazol-1-ium iodide

The title product was prepared from imidazole-1-carboxylic acid isopropyl-methyl-amide, as described in the general procedure 5. Light yellow crystals. HPLC-MS m/z=182.2 (M+1), Rt: 0.41 min.

δ$_H$(300 MHz; CDCl$_3$): 1.31 (s, 3H), 1.35 (s, 3H), 3.17 (s, 3H), 4.29 (s, 3H), 4.30–4.50 (m, 2H), 7.62 bs, 1H), 7.71 (bs, 1H), 10.29 (bs, 1H).

3-(1,3-Dihydroisoindole-2-carbonyl)-1-methyl-3H-imidazol-1-ium iodide

Step A: (1,3-Dihydroisoindole-1-yl)-imidazol-1-yl-methanone

The title product was prepared from isoindole, as described in the general procedure 4. Oil.

Step B: 3-(1,3-Dihydroisoindole-2-carbonyl)-1-methyl-3H-imidazol-1-ium iodide

The title product was prepared from (1,3-dihydroisoindole-1-yl)-imidazol-1-yl-methanone, as described in the general procedure 5. Crystals.

δ$_H$(300 MHz; CDCl$_3$): 3.96 (s, 3H), 4.98 (s, 2H), 5.04 (s, 2H), 7.35 (bs, 3H), 7.44 (bs, 1H), 7.91 (s, 1H), 8.21 (s, 1H), 9.74 (s, 1H).

1-Methyl-3-(piperidine-1-carbonyl)-3H-imidazol-1-ium iodide

Step A: Piperidin-1-yl-imidazol-1-yl-methanone

The title product was prepared from piperidine, as described in the general procedure 4. Oil.

Step B: 1-Methyl-3-(piperidine-1-carbonyl)-3H-imidazol-1-ium iodide

The title product was prepared from piperidin-1-yl-imidazol-1-yl-methanone, as described in the general procedure 5. Oil.

$\delta_H$(300 MHz; CDCl$_3$): 1.74 (s, 6H), 3.66 (bs, 4H), 4.28 (s, 3H), 7.78 (s, 1H), 7.83 (s, 1H), 10.07 (s, 1H).

1-Methyl-3-(2-methyl-piperidine-1-carbonyl)-3H-imidazol-1-ium iodide

Step A: (2-Methyl-piperidin-1-yl)-imidazol-1-yl-methanone

The title product was prepared from 2-methyl-piperidine, as described in the general procedure 4. light yellow oil. HPLC-MS m/z=194.2 (M+1), Rt: 0.92 min.

$\delta_H$(300 MHz; CDCl$_3$): 1.33 (d, 3H) 1.45–1.67 (m, 2H), 1.68–1.85 (m, 4H), 3.17 (dt, 1H), 3.86 (dd, 1H), 4.35–4.50 (m, 1H), 7.09 (s, 1H), 7.18 (s, 1H), 7.84 (s, 1H).

Step B: 1-Methyl-3-(2-methyl-piperidine-1-carbonyl)-3H-imidazol-1-ium iodide

The title product was prepared from (2-methyl-piperidin-1-yl)-imidazol-1-yl-methanone, as described in the general procedure 5. Orange solid. HPLC-MS m/z=208.1 (M+1), Rt: 0.57min.

$\delta_H$(300 MHz; CDCl$_3$): 1.40 (d, H), 1.60–1.98 m, 6H), 3.45 (t, 1H), 3.90 (d, 1H), 4.30 (s, 3H), 4.45–4.60 (m, 1H), 7.59 (s, 1H), 7.62 (s, 1H), 10.06 (s, 1H).

1-Methyl-3-(3-methyl-piperidine-1-carbonyl)-3H-imidazol-1-ium iodide

Step A: (3-Methyl-piperidin-1-yl)-imidazol-1-yl-methanone

The title product was prepared from 3-methyl-piperidine, as described in the general procedure 4. light yellow oil. HPLC-MS m/z=194.2 (M+1), Rt: 1.15 min.

$\delta_H$(300 MHz; CDCl$_3$): 0.94 (d, 3H), 1.05–1.35 (m, 1H), 1.50–2.00 (m, 4H), 2.67 (t, 1H), 3.01 (dt, 1H), 3.98 (t, 2H), 7.09 (s, 1H), 7.19 (s, 1H), 7.85 (s, 1H).

Step B: 1-Methyl-3-(3-methyl-piperidine-1-carbonyl)-3H-imidazol-1-ium iodide

The title product was prepared from (3-methyl-piperidin-1-yl)-imidazol-1-yl-methanone, as described in the general procedure 5. Yellow oil. HPLC-MS m/z=208.1 (M+1), Rt: 0.69 min.

$\delta_H$(300 MHz; CDCl$_3$): 0.97 (d, 3H), 1.15–1.40 (m, 1H), 1.55–2.00 (m, 4H), 2.92 (t, 1H), 3.28 (t, 1H), 3.90–4.15 (m, 2H), 4.28 (s, 3H), 7.60–7.75 (m, 2H), 10.14 (s, 1H).

1-Methyl-3-(4-methyl-piperidine-1-carbonyl)-3H-imidazol-1-ium iodide

Step A: (4-Methyl-piperidin-1-yl)-imidazol-1-yl-methanone

The title product was prepared from 4-methyl-piperidine, as described in the general procedure 4. light yellow oil. HPLC-MS m/z=194.2 (M+1), Rt: 1.32 min.

$\delta_H$(300 MHz; CDCl$_3$): 1.00 (d, 3H), 1.15–1.35 (m, 2H), 1.55–1.85 (m, 3H), 3.02 (dt, 2H), 4.08 (d, 2H), 7.08 (s, 1H), 7.19 (s, 1H), 7.85 (s, 1H).

Step B: 1-Methyl-3-(4-methyl-piperidine-1-carbonyl)-3H-imidazol-1-ium iodide

The title product was prepared from (4-methyl-piperidin-1-yl)-imidazol-1-yl-methanone, as described in the general procedure 5. Yellow oil. HPLC-MS m/z=208.1 (M+1), Rt: 0.65 min.

$\delta_H$(300 MHz; CDCl$_3$): 1.00 (d, 3H), 1.20–1.50 (m, 2H), 1.66–1.90 (m, 3H), 3.32 (t, 2H), 4.13 (d, 2H), 4.28 (s, 3H), 7.58 (s, 1H), 7.64 (s, 1H), 10.15 (s, 1H).

1-Methyl-3-(4-benzyl-piperidine-1-carbonyl)-3H-imidazol-1-ium iodide

Step A: (4-Benzyl-piperidin-1-yl)-imidazol-1-yl-methanone

The title product was prepared from 4-methyl-piperidine, as described in the general procedure 4. light yellow oil. HPLC-MS m/z=270.2 (M+1), Rt: 2.58 min.

$\delta_H$(300 MHz; CDCl$_3$): 1.10–1.50 (m, 2H), 1.65–2.00 (m, 3H), 2.59 (d, 2H), 2.97 (dt, 2H), 4.08 (d, 2H), 7.05–7.40 (m, 7H), 7.84 (s, 1H).

Step B: 1-Methyl-3-(4-benzyl-piperidine-1-carbonyl)-3H-imidazol-1-ium iodide

The title product was prepared from (4-benzyl-piperidin-1-yl)-imidazol-1-yl-methanone, as described in the general procedure 5. Yellow oil. HPLC-MS m/z=208.1 (M+1), Rt: 0.65 min.

$\delta_H$(300 MHz; CDCl$_3$): 1.30–1.50 (m, 2H), 1.75–1.95 (m, 3H), 2.59 (d, 2H), 3.15–3.40 (m, 2H), 4.05–4.20 (m, 2H), 4.25 (s, 3H), 7.10–7.35 (m, 5H), 7.45 (bs, 1H), 7.60 (bs, 1H), 10.22 (s, 1H).

1-Methyl-3-(1,2,3,4-tetrahydroisoquinoline-1-carbonyl)-3H-imidazol-1-ium iodide

Step A: (1,2,3,4-Tetrahydroisoquinoline-1-yl)-imidazol-1-yl-methanone

The title product was prepared from 1,2,3,4-tetrahydroisoquinoline, as described in the general procedure 4. Oil.

Step B: 1-Methyl-3-(1,2,3,4-tetrahydroisoquinoline-1-carbonyl)-3H-imidazol-1-ium iodide The title product was prepared from (1,2,3,4-tetrahydroisoquinoline-1-yl)-imidazol-1-yl-methanone, as described in the general procedure 5. Oil.

$\delta_H$(300 MHz; CDCl$_3$): 2.97 (t, 2H), 3.73 (bs, 2H), 3.94 (s, 3H), 4.75 (s, 2H), 7.15–7.35 (m, 4H), 7.88 (d, 1H), 8.09 (d, 1H), 9.63 (s, 1H).

Preparation of Phenols 1-(4-Hydroxy-phenyl)-4,4-dimethyl-piperidine-2,6-dione

A mixture of 4-aminophenol (3.27 g, 30.0 mmol) and 3,3-dimethylglutaric anhydride (4.26 g, 30.0 mmol) was heated in a round bottom flask at 165° C. for 1 h, followed by heating at 180° C. for 7 h. After cooling to room temperature the solid material was dissolved in hot ethanol, activated charcoal was added and the solution was heated at reflux for 1 h. The solid material was removed by hot filtration. The solvent was evaporated and the residue was crystallised from water/ethanol yielding the title compound (3.51 g, 50% yield, pink solid).

$^1$H NMR (300 MHz, DMSO-d$_6$): δ 1.08 (s, 6H), 2.63 (s, 4H), 6.77+6.86 (AB-system, 4H), 9.56 (s, 1H).

cis-2-(4-Hydroxy-phenyl)-hexahydro-isoindole-1,3-dione

A mixture of 4-aminophenol (5.46 g, 50.0 mmol) and cis-1,2-cyclohexanedicarboxylic anhydride (7.71 g, 50.0 mmol) was heated in a round bottom flask at 170° C. for 2 h. After cooling to room temperature the solid material was dissolved in hot ethanol (200 ml), activated charcoal was added and the solution was heated at reflux for 1 h. The solid material was removed by hot filtration. The solvent was partially evaporated. The solids were collected by filtration, washed quickly with a small amount of ethanol and dried in vacuo at 40° C. yielding the title compound (8.52 g, 69% yield, pink solid).

$^1$H NMR (300 MHz, DMSO-$d_6$): δ 1.38 (m, 4H), 1.73 (m, 4H), 3.02 (m, 2H), 6.82 (d, 2H), 7.02 (d, 2H), 9.66 (s, 1H, OH); HPLC-MS: m/z=246 (M+1); $R_t$=2.53 min.

Cyclohexanecarboxylic acid (4-hydroxy-phenyl)-amide

To a solution of 4-aminophenol (5.00 g, 45.8 mmol) in dichloromethane (50 ml) were added cyclohexanecarbonyl chloride (6.72 g, 45.8 mmol) and pyridine (3.70 ml, 45.8 mmol), while cooling the reaction mixture in an ice bath. After the addition was completed, the cooling bath was removed and stirring was continued overnight at room temperature. Water (100 ml) was added, the organic phase was removed and the resulting solution was extracted with ethyl acetate (3×300 ml). The combined organic phases were washed with water (2×200 ml), dried, filtered and evaporated, yielding an off-white solid. The crude product was purified by flash column chromatography ($SiO_2$, ethyl acetate/heptane (40:60)), yielding a mixture of two compounds, which were dissolved in THF. 6N NaOH (aq, 32 ml) was added and the mixture was stirred at room temperature for 2.5 h. The solution was acidified with concentrated hydrochloric acid and the organic solvent was removed by evaporation. The solid material was collected by filtration, dried and recrystallised from ethyl acetate/heptane, yielding the title compound (4.20 g, 41%, off-white solid).

$^1$H NMR (300 MHz, DMSO-$d_6$): δ 1.12–1.48 (m, 5H), 1.65 (m, 1H), 1.70–1.82 (m, 4H), 2.27 (m, 1H), 6.66 (d, 2H), 7.36 (d, 2H), 9.10 (s, 1H), 9.50 (s, 1H); HPLC-MS: m/z=220 (M+1); $R_t$=2.69 min.

2-Cyclohexyl-N-(4-hydroxy-phenyl)-acetamide

To a solution of 4-aminophenol (3.83 g, 35.1 mmol) in dichloromethane (50 ml) were added cyclohexylacetyl chloride (11.26 g, 70.1 mmol) and pyridine (5.67 ml, 70.1 mmol), while cooling the reaction mixture in an ice bath. After the addition was completed, the cooling bath was removed and stirring was continued overnight at room temperature. The solvent was removed and the residue was dissolved in THF (300 ml). 6N NaOH (aq, 41 ml) was added and the mixture was stirred at room temperature for 4 h. The solution was acidified with 1 N hydrochloric acid. The solvent was removed by evaporation. The solid material was collected by filtration, dried in vacuo at 40° C. and dissolved in methanol (100 ml). A solution of KOH (5.5 g) in methanol (50 ml) was added. After stirring for 1 h at room temperature water (200 ml) was added and the organic solvent was removed by evaporation. The aqueous phase was acidified with 1 N HCl. The solid material was isolated by filtration and dried in vacuo at 40° C. yielding the title compound (6.31 g, 77% yield, pink crystals).

$^1$H NMR (200 MHz, DMSO-$d_6$): δ 0.82–1.32 (m, 5H), 1.54–1.76 (m, 6H), 2.12 (d, 2H), 6.66 (d, 2H), 7.32 (d, 2H), 9.12 (s, 1H), 9.57 (s, 1H); HPLC-MS: m/z=234 (M+1); $R_t$=3.09 min.

cis/trans-4-tert-Butyl-cyclohexanecarboxylic acid (4-hydroxy-phenyl)-amide

To a solution of 4-aminophenol (3.08 g, 28.2 mmol) in dichloromethane (50 ml) were added cis/trans-4-tert-butyl-cyclohexanecarbonyl chloride (11.43 g, 56.4 mmol) and pyridine (4.56 ml, 56.4 mmol), while cooling the reaction mixture in an ice bath. After the addition was completed, the cooling bath was removed and stirring was continued overnight at room temperature. The solvent was removed by evaporation and the residue was dissolved in THF (300 ml). 6N NaOH (aq, 33 ml) was added and the mixture was stirred at room temperature overnight. The organic phase was removed by evaporation. Water (200 ml) was added and the solid material was collected by filtration, washed with water, dried in vacuo at 40° C. and dissolved in methanol (100 ml). A solution of KOH (2.4 g) in methanol (50 ml) was added. After stirring for 2 h at room temperature water (200 ml) was added and the organic phase was removed by evaporation. The aqueous phase was acidified with 1 N HCl and extracted with ethyl acetate (3×300 ml). The combined organic phases were washed with saturated sodium bicarbonate, dried, filtered and evaporated, yielding a pink oil, which was dried in vacuo at 40° C. The solid material was crystallised from ethyl acetate/heptane yielding the title compound (2.03 g, 26%, pink crystals). From the first aqueous extract a second portion of product was isolated by extraction with ethyl acetate (3×250 ml). The combined organic phases were washed with water (400 ml), saturated sodium bicarbonate (2×400 ml), dried, filtered and evaporated, yielding a pink thick oil. Crystallisation from ethyl acetate/heptane yielded a further amount of title compound (2.75 g, 35%).

$^1$H NMR (300 MHz, DMSO-$d_6$): δ 0.80+0.84 (2×s, 9H), 0.98 (m, 2H), 1.23–1.57 (m, 4H), 1.76–1.90 (m, 2H), 2.02–2.14 (m, 1.5H), 2.57 (m, 0.5H), 6.65 (d, 2H), 7.34 (d×d, 2H), 9.09 (s, 1H), 9.36+9.50 (2×s, 1H); HPLC-MS: m/z=276 (M+1); $R_t$=4.19 and 4.27 min.

N-(4-Hydroxy-phenyl)-3,3-dimethyl-butyramide

To a solution of 4-aminophenol (3.27 g, 30.0 mmol) in dichloromethane (50 ml) were added 3,3-dimethyl-butyryl chloride (8.08 g, 60.0 mmol) and pyridine (4.85 ml, 60.0 mmol), while cooling the reaction mixture in an ice bath. After the addition was completed, the cooling bath was removed and stirring was continued overnight at room temperature. The solvent was removed by evaporation and the residue was dissolved in THF (300 ml). 6N NaOH (aq, 35 ml) was added and the mixture was stirred at room temperature overnight. The organic phase was removed by evaporation. Water (200 ml) was added and the solid material was collected by filtration, washed with water, dried in vacuo at 40° C. and dissolved in methanol (100 ml). A solution of KOH (3.37 g) in methanol (50 ml) was added. After stirring for 2 days at room temperature water (300 ml) was added and the organic solvent was removed by evaporation. The aqueous phase was acidified with 1 N HCl. The solids were collected by filtration and dried under vacuum at 40° C. yielding the title compound (1.97 g, 31%, pink solid). The mother liquor was extracted with ethyl acetate (3×250 ml). The combined organic phases were washed with saturated sodium bicarbonate (2×250 ml), dried in vacuo, filtered and evaporated yielding a second amount of the title compound (0.67 g, 10%). From the first aqueous extract another portion of product was isolated by extraction with ethyl acetate (4×250 ml). The combined organic phases were washed with water (400 ml), saturated sodium bicarbonate (2×400 ml), dried, filtered and evaporated yielding a pink thick oil. Crystallisation from ethyl acetate/heptane yielded a third amount of the title compound (2.11 g, 34%).
$^1$H NMR (300 MHz, DMSO-$d_6$): δ 1.00 (s, 9H), 2.12 (s, 2H), 6.67 (d, 2H), 7.33 (d, 2H), 9.12 (s, 1H), 9.50 (s, 1H); HPLC-MS: m/z=208 (M+1); $R_f$=2.50 min.

1-(4-Hydroxy-phenyl)-4,4-dimethyl-piperidine-2,6-dione

A mixture of 4-aminophenol (3.27 g, 30.0 mmol) and 3,3-dimethylglutaric anhydride (4.26 g, 30.0 mmol) was heated in a round bottom flask at 165° C. for 1 h, followed by heating at 180° C. for 7 h. After cooling to room temperature the solid material was dissolved in hot ethanol, activated charcoal was added and the solution was heated at reflux for 1 h. The solid material was removed by hot filtration. The solvent was evaporated and the residue was crystallised (water/ethanol) yielding the title compound (3.51 g, 50%, pink solid).
$^1$H NMR (300 MHz, DMSO-$d_6$): δ 1.08 (s, 6H), 2.63 (s, 4H), 6.77+6.86 (AB-system, 4H), 9.56 (s, 1H).

cis-2-(4-Hydroxy-phenyl)-hexahydro-isoindole-1,3-dione

A mixture of 4-aminophenol (5.46 g, 50.0 mmol) and cis-1,2-cyclohexanedicarboxylic anhydride (7.71 g, 50.0 mmol) was heated in a round bottom flask at 170° C. for 2 h. After cooling to room temperature the solid material was dissolved in hot ethanol (200 ml), activated charcoal was added and the solution was heated at reflux for 1 h. The solid material was removed by hot filtration. The solvent was partially evaporated. The solids were collected by filtration, washed quickly with a small amount of ethanol and dried in vacuo yielding the title compound (8.52 g, 69%, pink solid).
$^1$H NMR (300 MHz, DMSO-$d_6$): δ 1.38 (m, 4H), 1.73 (m, 4H), 3.02 (m, 2H), 6.82 (d, 2H), 7.02 (d, 2H), 9.66 (s, 1H, OH); HPLC-MS: m/z=246 (M+1); $R_f$=2.53 min.

Cyclohexanecarboxylic acid (4-hydroxy-phenyl)-amide

To a solution of 4-aminophenol (5.00 g, 45.8 mmol) in dichloromethane (50 ml) were added cyclohexanecarbonyl chloride (6.72 g, 45.8 mmol) and pyridine (3.70 ml, 45.8 mmol), while cooling the reaction mixture in an ice bath. After the addition was completed, the cooling bath was removed and stirring was continued overnight at room temperature. Water (100 ml) was added, the dichloromethane was removed by evaporation and the resulting solution was extracted with ethyl acetate (3×300 ml). The combined organic phases were washed with water (2×200 ml), dried, filtered and evaporated, yielding an off-white solid. The crude product was purified by flash column chromatography (SiO$_2$, ethyl acetate/heptane (2:3)), yielding a mixture of two compounds, which were dissolved in THF. 6N NaOH (aq, 32 ml) was added and the mixture was stirred at room temperature for 2.5 h. The solution was acidified with concentrated hydrochloric acid. The THF was removed by evaporation. The solid material was collected by filtration, dried in vacuo and recrystallised (ethyl acetate/heptane), yielding the title compound (4.20 g, 41%, off-white solid).
$^1$H NMR (300 MHz, DMSO-$d_6$): δ 1.12–1.48 (m, 5H), 1.65 (m, 1H), 1.70–1.82 (m, 4H), 2.27 (m, 1H), 6.66 (d, 2H), 7.36 (d, 2H), 9.10 (s, 1H), 9.50 (s, 1H); HPLC-MS: m/z=220 (M+1); $R_f$=2.69 min.

2-Cyclohexyl-N-(4-hydroxy-phenyl)-acetamide

To a solution of 4-aminophenol (3.83 g, 35.1 mmol) in dichloromethane (50 ml) were added cyclohexylacetyl chloride (11.26 g, 70.1 mmol) and pyridine (5.67 ml, 70.1 mmol), while cooling the reaction mixture in an ice bath. After the addition was completed, the cooling bath was removed and stirring was continued overnight at room temperature. The solvent was removed by evaporation and the residue was dissolved in THF (300 ml). 6N NaOH (aq, 41 ml) was added and the mixture was stirred at room temperature for 4 h. The solution was acidified with 1 N hydrochloric acid and the organic phase was removed by evaporation. The solid material was collected by filtration, dried and dissolved in methanol (100 ml). A solution of KOH (5.5 g) in methanol (50 ml) was added. After stirring for 1 h at room temperature water (200 ml) was added and the organic solvent was removed by evaporation. The aqueous phase was acidified with 1 N HCl. The title product was isolated by filtration and dried in vacuo (6.31 g, 77%, pink crystals).
$^1$H NMR (200 MHz, DMSO-$d_6$): δ 0.82–1.32 (m, 5H), 1.54–1.76 (m, 6H), 2.12 (d, 2H), 6.66 (d, 2H), 7.32 (d, 2H), 9.12 (s, 1H), 9.57 (s, 1H); HPLC-MS: m/z=234 (M+1); $R_f$=3.09 min.

cis/trans-4-tert-Butyl-cyclohexanecarboxylic acid (4-hydroxy-phenyl)-amide

To a solution of 4-aminophenol (3.08 g, 28.2 mmol) in dichloromethane (50 ml) were added cis/trans-4-tert-butyl-cyclohexanecarbonyl chloride (11.43 g, 56.4 mmol) and pyridine (4.56 ml, 56.4 mmol), while cooling the reaction mixture in an ice bath. After the addition was completed, the cooling bath was removed and stirring was continued overnight at room temperature. The solvent was removed by evaporation and the residue was dissolved in THF (300 ml). 6N NaOH (aq, 33 ml) was added and the mixture was stirred at room temperature overnight. The organic phase was removed by evaporation. Water (200 ml) was added and the solid material collected by filtration, washed with water, dried and dissolved in methanol (100 ml). A solution of KOH (2.4 g) in methanol (50 ml) was added. After stirring for 2 h at room temperature water (200 ml) was added and the organic solvent was removed by evaporation. The aqueous phase was acidified with 1 N HCl and extracted with ethyl acetate (3×300 ml). The combined organic phases were dried and evaporated, yielding a pink oil, which was dried in vacuo. The solid material was crystallised from ethyl acetate/heptane yielding the title compound (2.03 g, 26%) as pink crystals. From the first aqueous extract a second portion of product was isolated by extraction with ethyl acetate (3×250 ml). The combined organic layers were washed with water (400 ml), saturated sodium bicarbonate (2×400 ml), dried, filtered and evaporated, yielding a pink thick oil. Crystallisation from ethyl acetate/heptane yielded a second amount of the title compound (2.75 g, 35%).
$^1$H NMR (300 MHz, DMSO-$d_6$): δ 0.80+0.84 (2×s, 9H), 0.98 (m, 2H), 1.23–1.57 (m, 4H), 1.76–1.90 (m, 2H), 2.02–2.14 (m, 1.5H), 2.57 (m, 0.5H), 6.65 (d, 2H), 7.34 (d×d, 2H), 9.09 (s, 1H), 9.36+9.50 (2×s, 1H); HPLC-MS: m/z=276 (M+1); $R_f$=4.19 and 4.27 min.

N-(4-Hydroxy-phenyl)-3,3-dimethyl-butyramide

To a solution of 4-aminophenol (3.27 g, 30.0 mmol) in dichloromethane (50 ml) were added 3,3-dimethyl-butyryl chloride (8.08 g, 60.0 mmol) and pyridine (4.85 ml, 60.0 mmol), while cooling the reaction mixture in an ice bath. After the addition was completed, the cooling bath was removed and stirring was continued overnight at room temperature. The solvent was removed by evaporation and the residue was dissolved in THF (300 ml). 6N NaOH (aq, 35 ml) was added, the mixture was stirred at room temperature overnight and the solvent was removed by evaporation. Water (200 ml) was added and the solid material is collected by filtration, washed with water, dried in vacuo at 40° C. and dissolved in methanol (100 ml). A solution of KOH (3.37 g) in methanol (50 ml) was added. After stirring for 2 days at room temperature water (300 ml) was added, the organic solvent was removed and the aqueous phase was acidified with 1 N HCl. The solids were collected and dried yielding the title compound (1.97 g, 31% yield, pink solid). The mother liquor was extracted with ethyl acetate (3×250 ml). The combined organic phases were washed with saturated sodium bicarbonate (2×250 ml), dried over sodium sulphate, filtered and evaporated yielding a second amount of the title compound (0.67 g, 10%). From the first aqueous extract another portion of product was isolated by extraction with ethyl acetate (4×250 ml). The combined organic phases were washed with water (400 ml), dried, filtered and evaporated yielding a pink thick oil. Crystallisation from ethyl acetate/heptane yielded a third amount of the title compound (2.11 g, 34%).

$^1$H NMR (300 MHz, DMSO-$d_6$): δ 1.00 (s, 9H), 2.12 (s, 2H), 6.67 (d, 2H), 7.33 (d, 2H), 9.12 (s, 1H), 9.50 (s, 1H); HPLC-MS: m/z=208 (M+1); $R_t$=2.50 min.

4-(3-Trifluoromethyl-phenoxy)-phenol

Hydroquinone monobenzylether (1 g, 5.0 mmol), 3-(trifluoromethyl)-phenyl boronic acid (1.9 g, 10.0 mmol), copper (II) acetate (0.91 g, 5.0 mmol) and triethylamine (2.53 g, 25.0 mmol) were dissolved/suspended in dichloromethane (50 ml). The reaction mixture was stirred for 70 h. at room temperature and evaporated to dryness. The crude intermediate was subjected to flash chromatography (ethyl acetate/heptane (1:4)) (42%) and hydrogenated (10% Pd/C) using ethanol as a solvent. The organic phase was evaporated and aqueous sodium hydroxide (1N, 30 ml) was added together with dichloromethane. The two phases were separated and the aqueous phase extracted with dichloromethane (30 ml×2). The aqueous phase was acidified with aqueous hydrochloric acid (2N) and extracted with dichloromethane (30 ml×5). The organic phase was dried and evaporated to give the crude product (47%). HPLC-MS m/z=254.9 (M+1), Rt: 4.39 min.

$δ_H$(300 MHz; CDCl$_3$): 6.85 (dt, 2H), 6.94 (dt, 2H), 7.10 (dd, 1H), 7.16 (bs, 1H), 7.24–7.30 (m, 1H), 7.39 (t, 1H).

4-Hydroxy-benzoic acid 2,5-dioxo-pyrrolidin-1-yl ester

4-Hydroxybenzoic acid (30 g, 0.217 mmol) and 4-hydroxysuccinamide (25.32 g, 0,220 mmol) were dissolved in 1.4-dioxane (550 ml) at room temperature. After 20 min. the clear solution was cooled to 15° C. and dicyclohexylcarbodiimide (44.82 ml, 0.217 mmol) was added. The reaction mixture was stirred for 18 hours and filtered. The organic phase was evaporated to dryness (86 g). Ethanol (250 ml) was added to the crude product and the mixture heated to reflux. The crude product was crystallized from ethanol/water (5:1) (22 g, 43%), and the mother liquor recrystallized from ethanol/water (25 g, 49%). HPLC-MS: m/z=(M+1); $R_t$: min.

N-(6-Methoxy-pyridin-3-yl)-benzamide

A solution of 5-amino-2-methoxypyridine (2.48 g, 20.0 mmol) and N-ethyldiisopropylamine (2.84 g, 22.0 mmol) in dichloromethane (20 ml) was cooled in an ice-bath. Benzoyl chloride (3.09 g, 22 mmol) was slowly added by means of a syringe. The cooling bath was removed and stirring was continued at room temperature for 18 hours. Dichloromethane was added and the solution was extracted with water. The organic layer was dried over sodium sulphate, filtered and evaporated in vacuo leaving a dark solid. Crystallisation from ethyl acetate:heptane yielded the title compound (3.44 g, 75% yield).

$^1$H NMR (300 MHz, CDCl$_3$): δ 3.93 (s, 3H), 6.77 (d, 1H), 7.44–7.59 (m, 3H), 7.81 (br.s, 1H), 7.87 (d, 2H), 8.01 (dd, 1H), 8.16 (d, 1H); HPLC-MS (Method A): m/z=229 (M+H); $R_t$=2.52 min.

Cyclohexanecarboxylic acid (6-methoxy-pyridin-3-yl)-amide hydrochloride

5-Amino-2-methoxypyride (3.72 g, 30.0 mmol), dissolved in a small amount of tetrahydrofuran, was added slowly to a solution of cyclohexanecarbonyl chloride (4.40 g, 30.0 mmol) in tetrahydrofuran (25 ml). After standing for 0.5 hours diethyl ether (250 ml) was added and the solids were collected by suction yielding the title compound (8.12 g, 100% yield) as a purple solid.

$^1$H NMR (300 MHz, CDCl$_3$): δ 1.11–1.48 (m, 5H), 1.63 (m, 1H), 1.68–1.83 (m, 4H), 2.32 (m, 1H), 3.81 (s, 3H), 6.80 (d, 1H), 7.92 (dd, 1H), 8.00 (br.s, 1H), 8.38 (d, 1H), 9.92 (s, 1H); HPLC-MS (Method A): m/z=235 (M+H); $R_t$=2.89 min.

6'-Methoxy-4,4-dimethyl 4,5-dihydro-3H-[1,3']bipyridinyl-2,6-dione

A mixture of 5-amino-2-methoxypyride (3.72 g, 30.0 mmol) and 3,3-dimethylglutaric anhydride (4.26 g, 30.0 mmol) was heated at 175° C. for 7 hours. After cooling down to room temperature the solid material was dissolved in a small amount of dichloromethane and purified by flash column chromatography (SiO$_2$, ethyl acetate:heptane (40:60)) yielding the title compound (2.56 g, 34% yield) as a white solid.

$^1$H NMR (300 MHz, CDCl$_3$): δ 1.20 (s, 6H), 2.69 (s, 4H), 3.95 (s, 3H), 3.81 (d, 1H), 7.28 (dd, 1H), 7.89 (d, 1H); HPLC-MS (Method A): m/z=249 (M+H); $R_t$=2.43 min.

N-(6-Methoxy-pyridin-3-yl)-2,2-dimethyl-propionamide hydrochloride

5-Amino-2-methoxypyride (3.72 g, 30.0 mmol), dissolved in a small amount of tetrahydrofuran, was added slowly to a solution of 2,2-dimethylpropionyl chloride (3.62 g, 30.0 mmol) in tetrahydrofuran (25 ml). After standing for 0.5 hours diethyl ether (250 ml) was added and a thick oil precipitated. The solvent was decanted and the residue was dried under reduced pressure yielding the title compound (5.50 g, 75% yield) as a purple foam.

$^1$H NMR (300 MHz, CDCl$_3$): δ 1.22 (s, 9H), 3.83 (s, 3H), 6.86 (d, 1H), 8.00 (dd, 1H), 8.42 (d, 1H), 9.41 (s, 1H), 9.54 (br.s, 1H); HPLC-MS (Method A): m/z=209 (M+H); $R_t$=2.28 min.

2-Cyclohexyl-N-(6-methoxy-pyridin-3-yl)-acetamide hydrochloride

5-Amino-2-methoxypyride (3.72 g, 30.0 mmol), dissolved in a small amount of tetrahydrofuran, was added slowly to a solution of cyclohexylacetyl chloride (4.82 g, 30.0 mmol) in tetrahydrofuran (25 ml). After standing for 0.5 hours diethyl ether (250 ml) was added and the solids were collected by suction yielding the title compound (8.54 g, 100% yield) as a purple solid.

$^1$H NMR (300 MHz, DMSO-$d_6$): δ 0.88–1.04 (m, H), 1.09–1.32 (m, 3H), 1.54–1.82 (m, 6H), 2.18 (d, 2H), 3.84 (s, 3H), 6.85 (d, 1H), 7.98 (dd, 1H), 8.41 (d, 1H), 9.81 (br.s, 1H), 10.10 (s, 1H); HPLC-MS (Method A): m/z=249 (M+H); $R_t$=3.32 min.

N-(6-Hydroxy-pyridin-3-yl)-benzamide

N-(6-Methoxy-pyridin-3-yl)-benzamide (2.38 g, 10.4 mmol) was dissolved in a mixture of tetrahydrofuran and diethyl ether. HCl-gas was bubbled into the solution for 5 minutes. More diethyl ether was added and the white precipitate was collected by suction, washed twice with diethyl ether and heated in a kugelrohr apparatus at 180° C. for 0.5 hours. The solid material was crystallised from methanol:water, washed twice with water and dried overnight in a vacuum oven, yielding the title compound (1.19 g, 53% yield) as a grey solid.

$^1$H NMR (300 MHz, CDCl$_3$): δ 6.39 (d, 1H), 7.47–7.61 (m, 3H), 7.18 (dd, 1H), 7.91 (d, 2H), 7.96 (d, 1H); HPLC-MS (Method A): m/z=215 (M+H); $R_t$=1.52 min.

Cyclohexanecarboxylic acid (6-hydroxy-pyridin-3-yl)-amide

Cyclohexanecarboxylic acid (6-methoxy-pyridin-3-yl)-amide hydrochloride (8.12 g, 30.0 mmol) was heated in a kugelrohr apparatus at 190° C. for 25 minutes. After cooling to room temperature the solid material was crystallised from methanol:water, washed twice with water and dried overnight in a vacuum oven, yielding the title compound (3.09 g, 47% yield) as a purple solid.

$^1$H NMR (300 MHz, CDCl$_3$): δ 1.09–1.46 (m, 5H), 1.63 (m,1H), 1.68–1.80 (m, 4H), 2.23 (m, 1H), 6.33 (d, 1H), 7.44 (dd, 1H), 7.87 (d, 1H), 9.54 (s, 1H), 11.29 (br.s, 1H); HPLC-MS (Method A): m/z=221 (M+H); $R_t$=1.84 min.

6'-Hydroxy-4,4-dimethyl-4,5-dihydro-3H-[1,3']bipyridinyl-2,6-dione

6'-Methoxy-4,4-dimethyl-4,5-dihydro-3H-[1,3']bipyridinyl-2,6-dione (2.56 g, 10.3 mmol) was dissolved in a mixture of tetrahydrofuran and diethyl ether. HCl-gas was bubbled into the solution for 5 minutes. More diethyl ether was added and the white precipitate was collected by suction, washed twice with diethyl ether and heated in a kugelrohr apparatus at 190° C. for 15 minutes yielding the title compound (2.16 g, 89% yield) as a white solid.

$^1$H NMR (300 MHz, CDCl$_3$): δ 1.08 (s, 6H), 2.52 (s, 4H), 6.34 (d, 1H), 7.19 (dd, 1H), 7.31 (d, 1H), 11.42 (br.s, 1H); HPLC-MS (Method A): m/z=235 (M+H); $R_t$=1.32 min.

N-(6-Hydroxy-pyridin-3-yl)-2,2-dimethyl-propionamide

Under a stream of nitrogen gas N-(6-methoxy-pyridin-3-yl)-2,2-dimethyl-propionamide hydrochloride (5.50 g, 22.5 mmol) was heated in a round bottom flask at 180° C. for 15 minutes. After cooling to room temperature the solid material was crystallised from a methanol-water mixture, yielding the title compound (1.13 g, 26% yield) as a dark grey solid.

$^1$H NMR (300 MHz, CDCl$_3$): δ 1.18 (s, 9H), 6.32 (d, 1H), 7.53 (dd, 1H), 7.76 (d, 1H), 8.97 (br.s, 1H), 11.30 (br.s, 1H); HPLC-MS (Method A): m/z=195 (M+H); $R_t$=1.15 min.

2-Cyclohexyl-N-(6-hydroxy-pyridin-3-yl)-acetamide

2-Cyclohexyl-N-(6-methoxy-pyridin-3-yl)-acetamide hydrochloride (8.54 g, 30.0 mmol) was heated in a kugelrohr apparatus at 160° C. for 0.5 hours. After cooling to room temperature the solid material was crystallised from a methanol-water mixture, washed twice with water and dried overnight in a vacuum oven, yielding the title compound (4.53 g, 64% yield) as a grey solid.

$^1$H NMR (300 MHz, CDCl$_3$): δ 0.90–1.38 (m, 5H), 1.60–1.92 (m, 6H), 2.17 (d, 2H), 6.50 (d, 1H), 7.50 (dd, 1H), 7.97 (d, 1H), 8.80 (br.s, 1H), 11.81 (br.s, 1H); HPLC-MS (Method A): m/z=235 (M+H); $R_t$=2.29 min.

3-Dimethylamino-2-(4-methoxy-phenoxy)-propenal

Phosphorus oxychloride (18.4 g, 120 mmol) was added to dimethylformamide (8.8 g, 120 mmol), maintaining the temperature below 25° C. by an external ice-bath. Upon completion of the addition the reaction mixture was heated to 50° C. for 45 minutes and then cooled to room temperature. Chloroform (35 ml) was added and the resulting solution was brought to reflux. 4-Methoxyphenoxyacetaldehyde diethylacetal (9.61 g, 40.0 mmol) was added in portions. After heating for 3 hours at reflux the solution was cooled to room temperature and poured carefully onto a solution of potassium carbonate (115 g) in water (100 ml). The mixture was cooled in an ice-bath to around room temperature and extracted twice with dichloromethane. The combined organic layers were dried over sodium sulphate, filtered and evaporated in vacuo yielding a brown oil. The residue was heated with ethyl acetate:heptane and decanted, leaving a brown oil. The solvent was removed in vacuo to give a brown oil, which was purified by flash column chromatography (SiO$_2$, ethyl acetate) yielding the title compound (3.87 g, 44% yield) as a white solid.

$^1$H NMR (300 MHz, CDCl$_3$): δ 3.00 (s, 6H), 3.75 (s, 3H), 6.54 (s, 1H), 7.80+7.87 (AB-system, 4H), 8.80 (s, 1H); HPLC-MS (Method A): m/z=222 (M+H); $R_t$=1.73 min.

2-(3,4-Dichloro-phenoxy)-3-dimethylamino-propenal

Phosphorus oxychloride (18.4 g, 120 mmol) was added to dimethylformamide (8.8 g, 120 mmol), maintaining the temperature below 25° C. by an external ice-bath. Upon completion of the addition the reaction mixture was heated to 50° C. for 45 minutes and then cooled to room temperature. Chloroform (35 ml) was added and the resulting solution was brought to reflux. 3,4-Dichlorophenoxyacetaldehyde diethylacetal (9.61 g, 40.0 mmol) was added in portions. After heating for 3 hours at reflux the solution was cooled to room temperature and poured carefully onto a solution of potassium carbonate (115 g) in water (100 ml). The mixture was cooled in an ice-bath to around room temperature and extracted twice with dichloromethane. The combined organic layers were dried over sodium sulphate, filtered and evaporated in vacuo yielding a brown oil, which was purified by flash column chromatography (SiO$_2$, ethyl acetate) yielding the title compound (5.38 g, 52% yield) as a brown solid.

$^1$H NMR (300 MHz, CDCl$_3$): δ 3.10 (s, 6H), 6.58 (s, 1H), 6.82 (dd, 1H), 7.03 (d, 1H), 7.30 (d, 1H), 8.80 (s, 1H); HPLC-MS (Method A): m/z=260 (M+H); R$_t$=3.14 min.

5-(4-Methoxy-phenoxy)-pyrimidin-2-ol

A solution of sodium ethoxide, prepared from sodium (0.80 g, 35.0 mmol), 3-dimethylamino-2-(4-methoxy-phenoxy)-propenal (3.87 g, 17.5 mmol) and urea (2.10 g, 35.0 mmol) in ethanol (25 ml) was heated at reflux for 4 hours. Water (1 ml) was added and heating was continued for an additional 2 hours. The solution was cooled to room temperature and neutralised with glacial acetic acid. Most of the solvent was removed by evaporation in vacuo. Water was added and the precipitate was isolated by suction, followed by drying in a vacuum oven, yielding the title compound (0.80 g, 21% yield) as a yellow solid.

$^1$H NMR (300 MHz, CDCl$_3$): δ 3.80 (s, 3H), 6.85–7.95 (AB-system, 4H), 8.12 (s, 2H); HPLC-MS (Method A): m/z=219 (M+H); R$_t$=1.77 min.

5-(3,4-Dichloro-phenoxy)-pyrimidin-2-ol

A solution of sodium ethoxide, prepared from sodium (0.95 g, 41.4 mmol), 2-(3,4-dichloro-phenoxy)-3-dimethylamino-propenal (5.38 g, 20.7 mmol) and urea (2.48 g, 41.4 mmol) in ethanol (25 ml) was heated at 60° C. for 4 hours. Water (1 ml) was added and heating was continued for an additional 2 hours. The solution was cooled to room temperature and neutralised with glacial acetic acid. Most of the solvent was removed by evaporation in vacuo. Water was added and the precipitate was isolated by suction, followed by drying in a vacuum oven, yielding the title compound (0.92 g, 17% yield) as a brown solid.

$^1$H NMR (300 MHz, DMSO-d$_6$): δ 7.08 (dd, 1H), 7.38 (d, 1H), 7.59 (d, 1H), 8.35 (s, 2H), 12.06 (br.s, 1H); HPLC-MS (Method A): m/z=257 (M+H); R$_t$=2.75 min.

5-(2-Nitro-phenyl)-pyrimidin-2-ol

A solution of 3-(dimethylamino)-2-(2-nitrophenyl)acrylaldehyde (2.00 g, 9.08 mmol), urea (0.60 g, 9.99 mmol) and concentrated hydrochloric acid (0.50 ml) in ethanol (25 ml) was heated at 60° C. for 18 hours under a nitrogen atmosphere. An additional aliquot of concentrated hydrochloric acid (0.50 ml) was added followed by heating at 70° C. for 24 hours. The solvent was removed by evaporation under reduced pressure. The residue was crystallised from methanol yielding the title compound (0.35 g, 18% yield) as a yellow solid.

$^1$H NMR (300 MHz, DMSO-d$_6$): δ 7.54 (dd, 1H), 7.62 (dt, 1H), 7.76 (dt, 1H), 8.06 (dd, 1H), 8.29 (s, 2H); HPLC-MS (Method A): m/z=218 (M+H); R$_t$=1.26 min.

N-(6-Hydroxy-pyridin-3-yl)-3,3-dimethyl-butyramide 3,3-Dimethylbutyroyl chloride (4.04 g, 30.0 mmol) was added dropwise to a stirred solution of 5-amino-2-methoxypyridine (3.72 g, 30.0 mmol) in tetrahydrofuran (25 mL). After stirring for 1 hour at room temperature, diethyl ether was added and the solid material was isolated by suction. The N-(6-methoxy-pyridin-3-yl)-3,3-dimethyl-butyramide hydrochloride (4.13 g, 15.96 mmol) was heated at 180° C. for 15 minutes. After cooling to room temperature the product was dissolved in methanol. Partial evaporation of the solvent yielded the title compound (1.15 g, 35% yield) as a solid.

$^1$H NMR (300 MHz, DMSO-d$_6$): δ=1.00 (s, 9H), 2.12 (s, 2H), 6.38 (d, 1H), 7.44 (dd, 1H), 7.89 (d, 1H), 9.59 (s, 1H), 11.42 (br.s, 1H); HPLC-MS (Method A): m/z=209 (M+H)$^+$; Rt=1.71 min.

Pyridine-2-carboxylic acid (6-methoxy-pyridin-3-yl)-amide dihydrochloride

5-Amino-2-methoxypyridine (4.40 g, 35.4 mmol), dissolved in a small amount of tetrahydrofuran, was added slowly to a stirred solution of pyridine-2-carbonyl chloride hydrochloride (7.12 g, 40.0 mmol) in tetrahydrofuran (75 mL). After stirring overnight at room temperature diethyl ether was added. The solids were isolated by suction, washed with diethyl ether and dried in a vacuum oven at 45° C., yielding the title compound (7.89 g, 75%).

$^1$H NMR (300 MHz, CDCl$_3$): δ=3.87 (s, 3H), 6.90 (d, 1H), 7.03 (br.s, 2 HCl+H$_2$O), 7.70 (m, 1H), 8.09 (dt, 1H), 8.17 (d, 1H), 8.22 (dd, 1H), 8.68 (d, 1H), 8.73 (m, 1H), 10.82 (s, 1H); HPLC-MS (Method A): m/z=230 (M+H)$^+$; Rt=2.45 min and 264+266; Rt=3.15 min.

Pyridine-2-carboxylic acid (6-hydroxy-pyridin-3-yl)-amide hydrochloride

Pyridine-2-carboxylic acid (6-methoxy-pyridin-3-yl)-amide dihydrochloride (0.66 g, 1.99 mmol) was heated at 180° C. for 10 minutes. After cooling to room temperature, the title compound was obtained and used without further purification.

HPLC-MS (Method A): m/z=216 (M+H)$^+$; Rt=2.14 min.

5-Methoxy-pyrimidin-2-ylamine

Under a nitrogen atmosphere phosphorus pentachloride (21 g, 0.10 mol) was added portionwise to 1,1,3-trimethoxyethane (12.0 g, 0.10 mol) with stirring and external cooling (ice-bath). After addition was completed, stirring was continued for an additional 30 minutes at room temperature. Dimethylformamide (22.5 mL) was added by means of a dropping funnel, while the reaction mixture was cooled externally with an ice-bath. After completion of the addition, the reaction mixture was heated at 60° C. for 70 minutes. The reaction mixture was then cooled in an ice-bath and methanol (50 mL) was added dropwise. The resulting solution was added dropwise to a stirred solution of sodium hydroxide (24 g) in methanol (80 mL) while cooling in an ice-bath. Guanidine nitrate (20.0 g, 0.16 mol) and sodium hydroxide (7.0 g, 0.175 mol) were added and the solution was stirred for 18 hours at room temperature. Water (150 mL) was added and the solution was extracted three times with dichloromethane. The combined organic layers were evaporated in vacuo leaving a brown oil. According to $^1$H NMR analysis a mixture of the desired product and the intermediate β-dimethylamine-α-methoxyacroleine was obtained. The mixture was dissolved in methanol (100 mL). Guanidine nitrate (15.0 g, 0.12 mol) and sodium hydroxide (5.25 g, 0.13 mol) were added and the reaction mixture was heated at 60° C. for 3 hours, followed by stirring at room temperature for 3 days. Water was added and the solution was extracted three times with dichloromethane. The combined organic layers were dried over sodium sulphate, filtered and evaporated in vacuo yielding the title compound (5.43 g, 43% yield) as a yellow solid.

¹H NMR (300 MHz, CDCl₃): δ=3.80 (s, 3H), 5.08 (br.s, 2H), 8.04 (s, 2H); HPLC-MS (Method A): m/z=126 (M+H)⁺; Rt=0.39 min.

1-(5-Methoxy-pyrimidin-2-yl)-4,4-dimethyl-piperidine-2,6-dione

A mixture of 5-methoxy-pyrimidin-2-ylamine (1.00 g, 7.99 mmol) and 3,3-dimethylglutaric anhydride (1.14 g, 7.99 mmol) was heated at 180° C. for 9 hours. After cooling to room temperature the reaction mixture was dissolved in a small amount of dichloromethane and purified by flash column chromatography (SiO₂, ethyl acetate:heptane 70:30), yielding the title compound (0.79 g, 40% yield) as a white solid.
¹H NMR (300 MHz, CDCl₃): δ=1.23 (s, 6H), 2.67 (s, 4H), 3.97 (s, 3H), 8.48 (s, 2H); HPLC-MS (Method A): m/z=250 (M+H)⁺; Rt=1.86 min.

1-(5-Hydroxy-pyrimidin-2-yl)-4,4-dimethyl-piperidine-2,6-dione

A mixture of 1-(5-methoxy-pyrimidin-2-yl)-4,4-dimethyl-piperidine-2,6-dione (0.99 g, 3.97 mmol) and pyridine hydrochloride (1.50 g, 7.99 mmol) was heated at 190° C. for 2.5 hours. After cooling to room temperature the reaction mixture was dissolved in a small amount of dichloromethane and filtered over a short pad of silicagel and washed with ethyl acetate. Evaporation of the solvent in vacuo yielded the title compound (0.60 g, 64% yield) as a white solid.
¹H NMR (300 MHz, CDCl₃): δ=1.23 (s, 6H), 2.65 (s, 4H), 8.42 (s, 2H), 9.94 (br.s, 1H); HPLC-MS (Method A): m/z=236 (M+H)⁺; Rt=1.53 min.

6-Chloro-N-(6-hydroxy-pyridin-3-yl)-nicotinamide

A solution of 6-chloro-nicotinoyl chloride (0.40 g, 2.27 mmol) and 5-amino-2-hydroxypyridine hydrochloride (0.33 g, 2.25 mmol) in dry tetrahydrofuran (15 mL) was stirred at room temperature for 1 hour. Saturated sodium bicarbonate (aq) was added and the solution was extracted three times with dichloromethane. The combined organic layers were dried over sodium sulphate, filtered and evaporated in vacuo. The residue was dissolved in a mixture of methanol (10 mL) and aqueous sodium hydroxide (1N, 2 mL). After stirring for 2 hours at room temperature water was added and the solution was extracted with dichloromethane. The organic layer was dried over sodium sulphate, filtered and evaporated in vacuo, yielding the title compound which was used without further purification.
HPLC-MS (Method A): m/z=250 (M+H)⁺; Rt=1.52 min.

N-(2,2-Dimethyl-propyl)-6-hydroxy-nicotinamide

A solution of 6-hydroxynicotinic acid (1.39 g, 10.0 mmol), 1-hydroxy-7-azabenztriazole (1.50 g, 11.0 mmol), and 1-(3-dimethylaminopropyl)-3-ethylcarbodiimide hydrochloride (2.11 g, 11.0 mmol) in dimethylformamide (25 mL) was stirred at room temperature for 20 minutes. A solution of 2,2-dimethylpropylamine (0.96 g, 11.0 mmol) and N,N-diisopropylethylamine (1.42 g, 11.0 mmol) in a small amount of dimethylformamide was added. Stirring was continued for 0.5 hour at room temperature. Ethyl acetate was added and the reaction mixture was extracted twice with water. The solvent was evaporated in vacuo yielding the title compound, which was used without further purification.
HPLC-MS (Method A): m/z=209 (M+H)⁺; Rt=1.86 min.

3-Chloro-6-(3,4-dichloro-phenoxy)-pyridazine

A solution of 3,6-dichloropyridazine (4.47 g, 30.0 mmol), 3,4-dichlorophenol (4.89 g, 30.0 mmol) and potassium hydroxide (1.68 g, 30.0 mmol) in dimethyl sulfoxide (20 mL) was heated at 60° C. overnight. The solvent was removed by evaporation in vacuo. The residue was purified by flash column chromatography (SiO₂, ethyl acetate:heptane 50:50). Small amounts of starting material were removed by kugelrohr distillation. Crystallisation from ethyl acetate:heptane yielded the title compound (1.74 g, 21% yield) as a white solid.
¹H NMR (300 MHz, CDCl₃): δ=7.10 (dd, 1H), 7.20 (d, 1H), 7.37 (d, 1H), 7.49 (d, 1H), 7.54 (d, 1H); HPLC-MS (Method A): m/z=275 and 277 (M+H)⁺; Rt=4.00 min.

6-(3,4-dichloro-phenoxy)-pyridazin-3-ol

A solution of 3-chloro-6-(3,4-dichloro-phenoxy)-pyridazine (1.74 g, 6.32 mmol) in formic acid (25 mL) was heated at 100° C. for 3 hours. The solvent was removed by evaporation in vacuo yielding the title compound, which was used without further purification.
HPLC-MS (Method A): m/z=257 (M+H)⁺; Rt=3.13 min.

(4-Hydroxy-piperidin-1-yl)-imidazol-1-yl-methanone

A solution of 4-hydroxypiperidine (20.0 g, 198 mmol) and N,N'-carbonyldiimidazole (32.06 g, 198 mmol) in tetrahydrofuran (250 mL) was heated overnight at reflux, followed by stirring at room temperature for two days. The solvent was evaporated yielding the title compound, which was used without further purification.
HPLC-MS (Method A): m/z=196 (M+H)⁺; Rt=0.39 min.

[4-(tert-Butyl-dimethyl-silanyloxy)-piperidin-1-yl]-imidazol-1-yl-methanone tert-Butyldimethylsilyl chloride (30.14 g, 0.20 mol) was added to a stirred solution of (4-hydroxy-piperidin-1-yl)-imidazol-1-yl-methanone (39.05 g, 0.20 mol) in dimethylformamide (200 mL). After stirring for 3 days at room temperature, the solvent was removed by evaporation in vacuo. The residue was redissolved in dichloromethane, extracted twice with water, dried over sodium sulphate, filtered and evaporated in vacuo, yielding the title compound, which was used without further purification.
1H NMR (300 MHz, CDCl₃): δ=0.07 (s, 6H), 0.90 (s, 9H), 1.64 (m, 2H), 1.81 (m, 2H), 3.53–3.74 (m, 4H), 4.06 (m, 1H), 7.07 (m, 1H), 7.18 (m, 1H), 7.86 (m, 1H); HPLC-MS (Method A): m/z=310 (M+H)⁺; Rt=3.40 min.

3-[4-(tert-Butyl-dimethyl-silanyloxy)-piperidine-1-carbonyl]-1-methyl-3H-imidazol-1-ium iodide Methyl iodide (113.5 g, 0.80 mol) was added to a stirred solution of [4-(tert-butyl-dimethyl-silanyloxy)-piperidin-1-yl]-imidazol-1-yl-methanone (61.9 g, 0.20 mol) in acetonitrile (400 mL). After stirring overnight at room temperature the solvent was evaporated in vacuo. The residue was washed with ethyl acetate:heptane and dried in a vacuum oven at 45° C., yielding the title compound (60.92 g, 68% yield over three steps) as a white solid
1H NMR (300 MHz, CDCl₃): δ=0.08 (s, 6H), 0.88 (s, 9H), 1.57 (m, 2H), 1.83 (m, 2H), 3.45 (m, 2H), 3.65 (m, 2H), 3.93 (s, 3H), 4.06 (m, 1H), 7.87 (m, 1H), 8.03 (m, 1H), 9.56 (s, 1H); HPLC-MS (Method A): m/z=324 (M−I⁻)+; Rt=2.95 min.

4-Chloro-N-(6-hydroxy-pyridin-3-yl)-benzamide

4-Chlorobenzoyl chloride (1.75 g, 10.0 mmol) was added carefully to a stirred solution of 5-amino-2-methoxypyridine (1.24 g, 10.0 mmol) in dichloromethane (10 mL). After stirring overnight at room temperature, the solvent is evaporated in vacuo and the residue is heated in a pre-heated kugelrohr oven at 200° C. for 5–10 minutes under house-vacuum (around 20 mbar) yielding the title compound, which was used without further purification.

HPLC-MS (Method A): m/z=249 (M+H)⁺; Rt=2.18 min.

4-Fluoro-N-(6-hydroxy-pyridin-3-yl)-benzamide

Starting from 4-fluorobenzoyl chloride (1.59 g, 10.0 mmol) and using the procedure as described for the preparation of 4-Chloro-N-(6-hydroxy-pyridin-3-yl)-benzamide yielded the title compound, which was used without further purification.

HPLC-MS (Method A): m/z=233 (M+H)⁺; Rt=1.76 min.

N-(6-Hydroxy-pyridin-3-yl)-3-methoxy-benzamide

Starting from 3-methoxybenzoyl chloride (1.71 g, 10.0 mmol) and using the procedure as described for the preparation of 4-Chloro-N-(6-hydroxy-pyridin-3-yl)-benzamide yielded the title compound, which was used without further purification.

HPLC-MS (Method A): m/z=245 (M+H)⁺; Rt=1.81 min.

N-(6-Hydroxy-pyridin-3-yl)-4-methoxy-benzamide

Starting from 4-methoxybenzoyl chloride (1.71 g, 10.0 mmol) and using the procedure as described for the preparation of 4-Chloro-N-(6-hydroxy-pyridin-3-yl)-benzamide yielded the title compound, which was used without further purification.

HPLC-MS (Method A): m/z=245 (M+H)⁺; Rt=1.72 min.

N-(6-Hydroxy-pyridin-3-yl)-4-methoxy-benzamide

Starting from 2,4-dichlorobenzoyl chloride (2.10 g, 10.0 mmol) and using the procedure as described for the preparation of 4-Chloro-N-(6-hydroxy-pyridin-3-yl)-benzamide yielded the title compound, which was used without further purification.

HPLC-MS (Method A): m/z=283 (M+H)⁺; Rt=2.28 min.

N-(6-Hydroxy-pyridin-3-yl)-4-trifluoromethyl-benzamide

Starting from 4-trifluoromethylbenzoyl chloride (2.09 g, 10.0 mmol) and using the procedure as described for the preparation of 4-Chloro-N-(6-hydroxy-pyridin-3-yl)-benzamide yielded the title compound, which was used without further purification.

HPLC-MS (Method A): m/z=283 (M+H)⁺; Rt=2.28 min.

6'-Hydroxy-4,5-dihydro-3H-[1,3']bipyridinyl-2,6-dione

Glutaric anhydride (1.14 g, 10.0 mmol) was added to a solution of 5-amino-2-methoxypyridine (1.24 g, 10.0 mmol) in dichloromethane (25 mL). After standing for 1 hour at room temperature, thionyl chloride (5.95 g, 50.0 mmol) was added, followed by heating to reflux for 0.5 hour. The solvent and excess thionyl chloride were evaporated in vacuo, yielding 4-(6-methoxy-pyridin-3-ylcarbamoyl)-butyryl chloride, which was used without further purification.

¹H NMR (300 MHz, CDCl₃): δ=1.81 (quintet, 2H), 2.28 (t, 2H), 2.38 (t, 2H), 3.87 (s, 3H), 6.91 (d, 1H), 8.00 (dd, 1H), 8.43 (d, 1H), 10.24 (s, 1H, NH).; HPLC-MS (Method A): m/z=253 (M+H)⁺; Rt=1.94 min. (analysed as methyl ester).

The crude 4-(6-methoxy-pyridin-3-ylcarbamoyl)-butyryl chloride was redissolved in dichloromethane (25 mL). Thionyl chloride (5.95 g, 50 mmol) was added and the solution was heated to reflux overnight. The solvent and excess thionyl chloride were evaporated in vacuo, yielding 6'-methoxy-4,5-dihydro-3H-[1,3']bipyridinyl-2,6-dione hydrochloride, which was used without further purification.

¹H NMR (300 MHz, CDCl₃): δ=2.00 (quintet, 2H), 2.72 (t, 4H), 3.88 (s, 3H), 6.90 (d, 1H), 7.51 (dd, 1H), 6.92 (d, 1H), 9.71 (br.s, HCl+H₂O); HPLC-MS (Method A): m/z=221 (M+H)⁺; Rt=1.38 min.

The crude 6'-methoxy-4,5-dihydro-3H-[1,3']bipyridinyl-2,6-dione hydrochloride (2.57 g, 10.0 mmol) was heated in a pre-heated kugerohr oven at 180° C. for 5 minutes. After cooling to room temperature the product was purified by flash column chromatography (SiO₂, ethyl acetate:acetone 25:75), yielding the title compound (0.48 g, 23% yield) as a white solid.

¹H NMR (300 MHz, CDCl₃): δ=2.10 (quintet, 2H), 2.81 (t, 4H), 3.53 (br.s, 3H), 7.12 (br.s, 1H), 7.27 (m, 1H), 7.38 (m, 4H), 7.50 (d, 1H), 8.09 (s, 1H); HPLC-MS (Method A): m/z=340 (M+H)⁺; Rt=2.89 min.

1-(6-Methoxy-pyridin-3-yl)-pyrrolidine-2,5-dione

A mixture of 5-amino-2-methoxypyridine (1.24 g, 10.0 mmol) and succinic anhydride (1.00 g, 10.0 mmol) was heated with a heat gun for 10 minutes. After cooling to room temperature the product was purified by flash column chromatography (SiO₂, ethyl acetate:acetone 25:75). Evaporation of the solvent yielded the title compound as a white solid.

¹H NMR (300 MHz, CDCl₃): δ=2.92 (s, 4H), 3.96 (s, 3H), 6.82 (d, 1H), 7.50 (dd, 1H), 8.11 (d, 1H); HPLC-MS (Method A): m/z=207 (M+H)⁺; Rt=1.26 min.

1-(6-Hydroxy-pyridin-3-yl)-pyrrolidine-2,5-dione 1-(6-Methoxy-pyridin-3-yl)-pyrrolidine-2,5-dione was dissolved in tetrahydrofuran and HCl-gas was bubbled into the solution for 5 minutes. The solvent was evaporated in vacuo and the residue was heated for 10 minutes at 180° C. in a pre-heated kugelrohr oven. After cooling to room temperature the residue was purified by flash column chromatography (SiO₂), yielding the title compound (285 mg, 15% yield over two steps).

¹H NMR (400 MHz, DMSO-d₆): δ=2.72 (s, 4H), 6.40 (d, 1H), 7.31 (dd, 1H), 7.39 (d, 1H), 11.76 (br.s, 1H, OH); HPLC-MS (Method A): m/z=193 (M+H)⁺; Rt=0.37 min.

2-Methoxy-5-(5-trifluoromethyl-pyridin-2-yloxy)-pyridine

A solution of 5-hydroxy-2-methoxypyridine (1.25 g, 10.0 mmol), 2-chloro-5-trifluoro-methylpyridine (1.82 g, 10.0 mmol) and potassium hydroxide (85% pure, 1.08 g, 10.0 mmol) in dimethyl sulfoxide (25 mL) was heated at 90° C.

for 2.5 hours. The solution was cooled to room temperature and poured slowly into water (200 mL). After cooling with an external ice-bath, the precipitate was collected by suction, washed thoroughly with water and dried in a vacuum oven at 45° C., yielding the title compound (2.56 g, 95% yield).

$^1$H NMR (300 MHz, CDCl$_3$): δ=3.95 (s, 3H), 6.80 (d, 1H), 7.04 (d, 1H), 7.41 (dd, 1H), 7.91 (dd, 1H), 8.03 (d, 1H), 8.40 (d, 1H); HPLC-MS (Method A): m/z=271 (M+H)$^+$; Rt=3.88 min.

5-(5-Trifluoromethyl-pyridin-2-yloxy)-pyridin-2-ol

A mixture of 2-methoxy-5-(5-trifluoromethyl-pyridin-2-yloxy)-pyridine (0.28 g, 1.04 mmol) and pyridine hydrochloride (1.00 g, 8.65 mmol) was heated in a kugelrohr oven at 200° C. for 10 minutes. After cooling to room temperature, the reaction mixture is dissolved in dichloromethane and extracted with water, dried over sodium sulphate, filtered and evaporated in vacuo, yielding the title compound (180 mg, 68% yield) as a white solid.

$^1$H NMR (300 MHz, CDCl$_3$): δ=6.63 (m, 1H), 7.06 (d, 1H), 7.42 (m, 2H), 7.92 (dd, 1H), 8.42 (d, 1H); HPLC-MS (Method A): m/z=257 (M+H)$^+$; Rt=2.32 min.

5-(3,5-Dichloro-pyridin-2-yloxy)-2-methoxy-pyridine

A solution of 5-hydroxy-2-methoxypyridine (1.25 g, 10.0 mmol), 2,3,5-trichloropyridine (1.82 g, 10.0 mmol) and potassium hydroxide (85% pure, 1.08 g, 10.0 mmol) in dimethyl sulfoxide (25 mL) was heated at 90° C. for 1.5 hours. The solution was poured slowly into water (200 mL). The precipitate was collected by suction, washed thoroughly with water and dried in a vacuum oven at 45° C., yielding the title compound (2.39 g, 88% yield).

$^1$H NMR (300 MHz, CDCl$_3$): =3.95 (s, 3H), 6.80 (d, 1H), 7.41 (dd, 1H), 7.77 (d, 1H), 7.93 (d, 1H), 8.03 (d, 1H); HPLC-MS (Method A): m/z=271 (M+H)$^+$; Rt=4.18 min.

5-(3,5-Dichloro-pyridin-2-yloxy)-pyridin-2-ol

A mixture of 5-(3,5-dichloro-pyridin-2-yloxy)-2-methoxy-pyridine (2.39 g, 8.82 mmol) and pyridine hydrochloride (7.00 g, 60.6 mmol) was heated in a kugelrohr apparatus at 200° C. for 25 minutes. After cooling to room temperature dichloromethane and water were added. The solid material, which was insoluble in dichloromethane and water, was isolated by suction and dried in a vacuum oven at 45° C., yielding the title compound, which was used without further purification.

HPLC-MS (Method A): m/z=257 (M+H)$^+$; Rt=2.53 min.

4,4-Dimethyl-3,4,5,6-tetrahydro-2H-[1,3']bipyridinyl-6'-ol

Under a nitrogen atmosphere lithium aluminium hydride (1.90 g, 50.0 mmol) was added portionwise to a stirred suspension of 6'-methoxy-4,4-dimethyl-4,5-dihydro-3H-[1,3']bipyridinyl-2,6-dione (2.85 g, 10.0 mmol) in dry diethyl ether (100 mL). After stirring for 3 hours at room temperature, water (1.90 mL), 15% aqueous sodium hydroxide (1.90 mL) and water (5.70 mL) were added respectively. After stirring for 1 hour at room temperature the salts were removed by filtration and washed three times with diethyl ether. The solvent was evaporated in vacuo and the residue was purified by flash column chromatography (SiO$_2$, dichloromethane followed by ethyl acetate/heptane 25/75) yielding the title compound (1.28 g, 58% yield) as a yellow oil.

$^1$H NMR (300 MHz, CDCl$_3$): δ=0.98 (s, 6H), 1.53 (m, 4H), 3.03 (m, 4H), 3.89 (s, 3H), 6.67 (d, 1H), 7.30 (dd, 1H), 7.80 (d, 1H); HPLC-MS (Method A): m/z=221 (M+H)$^+$; Rt=2.14 min.

4,4-Dimethyl-3,4,5,6-tetrahydro-2H-[1,3']bipyridinyl-6'-ol

A mixture of 6'-methoxy-4,4-dimethyl-3,4,5,6-tetrahydro-2H-[1,3']bipyridinyl (1.28 g, 5.81 mmol) and pyridine hydrochloride (5.00 g, 43.3 mmol) was heated in a kugelrohr oven at 200° C. for 15 minutes. After cooling to room temperature water was added and the solution was made slightly basic with aqueous 1N sodium hydroxide. The solution was extracted three times with dichloromethane and the combined organic layers were dried over sodium sulphate, filtered and evaporated in vacuo, yielding the title compound (0.86 g, 72% yield).

HPLC-MS (Method A): m/z=207 (M+H)$^+$; Rt=1.31 min.

Methyl-phenyl-carbamic acid 4-amino-phenyl ester

To a solution of N-Boc protected 4-aminophenol (10 mmol) in CH$_2$Cl$_2$ (50 mL) was added N-methyl-N-phenyl-carbamoyl chloride (15 mmol) and DABCO (15 mmol) at room temperature. The reaction mixture was stirred for 16 hours at rt, added CH$_2$Cl$_2$ (20 mL) and washed with aqueous citric acid (5%) and brine. The organic phase was separated, dried (MgSO$_4$) and evaporated to give the crude product which was purified by FC (Quad flash 40 MeOH—CH$_2$Cl$_2$ 5:95). The purified intermediate was dissolved in CH$_2$Cl$_2$ (90 mL). Addition of TFA (6 mL) and stirring for 4 h. The reaction mixture was evaporated to dryness and dried in vacuo at 50° C. overnight producing the title compound in 72% yield as colorless crystals.

HPLC-MS: m/z=243.1 (M+1); R$_t$=2.02 min.

Example 1 (General Procedure 9)

4-[(1,3-Benzodioxol-5-yl)methyl]-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-piperonylpiperazine, yield 67%. Recrystallisation from 96% ethanol gave white crystals, m.p. 239–240° C.; HPLC-MS m/z=502 (M+H), 524 (M+Na), R$_t$=3.3 min.; $^1$H NMR (DMSO-d$_6$): δ 11.64 (br, 1H, NH), 8.62–8.52 (br, 1H, py-H6), 8.31–8.19 (m, 1H, py-H4), 7.40–7.15 (m, 6H, py-H3+C$_6$H$_4$+1 arom.), 7.15–6.93 (m, 2H, arom), 4.53–3.96 (br, 4H, CH2 at 4.26+2 CH), 3.80–2.89 (br, 6H, water at 3.38+4C—H); IR (KBr): ν 1724 (C═O).

Example 2 (General Procedure 1)

Methyl-phenyl-carbamic acid 4-(5-trifluoromethyl-pyridin-2-yloxy)-phenyl ester

The title compound was prepared from 4-(5-trifluoromethyl-pyridin-2-yloxy)-phenol and N-methyl-N-phenylcarbamoyl chloride. The crude product was purified by preparative HPLC (36%, white crystals). HPLC-MS m/z=389.1 (M+1), Rt: 5.13 min.

$\delta_H$(300 MHz; CDCl$_3$): 3.43 (s, 3H), 6.98 (d, 1H, J 8.7), 7.09–7.22 (m, 4H), 7.30–7.34 (m, 1H), 7.35 (d, 2H, J 7.1), 7.40 (t, 2H, J 6.8), 7.88 (dd, 1H, J 8.7 and 2.3), 8.42 (s, 1H).

Example 3 (General Procedure 1)

Methyl-phenyl-carbamic acid 3-(5-trifluoromethyl-pyridin-2-yloxy)-phenyl ester

The title compound was prepared from 3-(5-trifluoromethyl-pyridin-2-yloxy)-phenol and N-methyl-N-phenylcarbamoyl chloride. The crude product was subjected to flash chromatography (Quad flash 25, dichlormethane) (89%, oil). HPLC-MS m/z=389.1 (M+1), Rt: 5.08 min.

$\delta_H$(300 MHz; DMSO-d$_6$): 3.34 (s, 3H), 7.00–7.15 (m, 3H), 7.27 (t, 2H), 7.35–7.55 (m, 5H), 8.24 (dd, 1H), 8.58 (s, 1H).

Example 4 (General Procedure 1)

Methyl-phenyl-carbamic acid 4-(3,5-dichloro-pyridin-2-yloxy)-phenyl ester

The title compound was prepared from 4-(3,5-dichloro-pyridin-2-yloxy)-phenol and N-methyl-N-phenylcarbamoyl chloride. The crude product was purified by preparative HPLC (53%, crystals). HPLC-MS m/z=389.1 (M+1), Rt: 5.1 min.

$\delta_H$(300 MHz; CDCl$_3$): 3.43 (s, 3H), 7.07–7.20 (m, 4H), 7.27–7.48 (m, 5H), 7.75 (d, 1H, J 2.2), 7.93 (d, 1H, J 2.2).

Example 5 (General Procedure 1)

Methyl-phenyl-carbamic acid 4-(5-trifluoromethyl-pyridin-2-ylamino)-phenyl ester The title compound was prepared from 4-(5-trifluoromethyl-pyridin-2-ylamino)-phenol and N-methyl-N-phenylcarbamoyl chloride. The crude product was purified by preparative HPLC to give the title product (32%, white crystals). HPLC-MS m/z=388.2 (M+1), Rt: 4.72 min.

$\delta_H$(300 MHz; CDCl$_3$): 3.44 (s, 3H), 6.76 (d, 1H), 6.81 (bs, 1H), 7.12 (d, 2H), 7.27–7.45 (m, 6H), 7.63 (dd, 1H), 8.42 (bs, 1H).

Example 6 (General Procedure 1)

Methyl-phenyl-carbamic acid 4-(3,5-dichloro-pyridin-4-yloxy)-phenyl ester

The title compound was prepared from 4-(3,5-dichloro-pyridine-4-yloxy)-phenol and N-methyl-N-phenylcarbamoyl chloride. The crude product was purified by preparative HPLC (41%, white crystals). HPLC-MS m/z=389.1 (M+1), Rt: 4.97 min.

$\delta_H$(300 MHz; CDCl$_3$): 3.42 (s, 3H), 6.81 (d, 2H, J 9.0), 7.07 (d, 2H, J 7.9), 7.25–7.43 (M, 5H), 8.55 (s, 2H).

Example 7 (General Procedure 1)

Methyl-phenyl-carbamic acid 4-(4-trifluoromethyl-phenoxy)-phenyl ester

The title compound was prepared from 4-(4-trifluoromethyl-phenoxy)-phenol and N-methyl-N-phenylcarbamoyl chloride. The crude product was purified by preparative HPLC (78%, white crystals). HPLC-MS m/z=388.0 (M+1), Rt: 5.59 min.

$\delta_H$(300 MHz; CDCl$_3$): 3.43 (s, 3H), 7.02 (d, 4H, J 8.7), 7.14 (d, 2H, J 8.7), 7.31 (1H, d, J 6.8), 7.35 (d, 2H, J 7.2), 7.41 (t, 2H, J 7.1), 7.55 (d, 2H, J 8.6).

Example 8 (General Procedure 1)

Methyl-phenyl-carbamic acid 4-(3-trifluoromethyl-phenoxy)-phenyl ester

The title compound was prepared from 4-(3-trifluoromethyl-phenoxy)-phenol and N-methyl-N-phenylcarbamoyl chloride. The crude product was purified by preparative HPLC (73%, white crystals). HPLC-MS m/z=388.2 (M+1), Rt: 5.37 min.

Example 9 (General Procedure 1)

Methyl-phenyl-carbamic acid 4-(2-cyano-5-trifluoromethyl-pyridine-3-yloxy)-phenyl ester The title compound was prepared from 4-(2-cyano-5-trifluoromethyl-pyridin-3-yloxy)-phenol and N-methyl-N-phenylcarbamoyl chloride. The crude product was purified by preparative HPLC (74%, colourless oil). HPLC-MS m/z=414.1 (M+1), Rt: 4.8 min.

$\delta_H$(300 MHz; CDCl$_3$): 3.44 (s, 3H), 7.11 (d, 2H, J 9), 7.32–7.1 (m, 3H), 7.32–7.50 (m, 5H), 8.63 (s, 1H).

Example 10 (General Procedure 1)

Methyl-phenyl-carbamic acid 2-benzenesulfonyl-4-(3-chloro-5-trifluoromethyl-pyridine-2-yloxy)-phenyl ester The title compound was prepared from 2-benzenesulfonyl-4-(3-chloro-5-trifluoromethyl-pyridine-2-yloxy)-phenol and N-methyl-N-phenylcarbamoyl chloride. The crude product was purified by preparative HPLC (68%, white crystals). HPLC-MS m/z=563.1 (M+1), Rt: 5.3 min.

$\delta_H$(300 MHz; CDCl$_3$): 3.44 (s, 3H), 7.20–7.50 (m, 12H), 7.91 (bs, 1H), 8.00 (d, 1H, J 2.3), 8.23 (s, 1H).

Example 11 (General Procedure 1)

Methyl-phenyl-carbamic acid 4-tert-butoxy-phenyl ester

The title compound was prepared from 4-tert-butoxy-phenol and N-methyl-N-phenylcarbamoyl chloride. The crude product was subjected to flash chromatography (Quad 12/25, flash 12, dichloromethane) followed by a recrystallization from ethanol (41%, crystals). HPLC-MS m/z=300.3 (M+1), Rt: 4.7 min.

$\delta_H$(300 MHz; CDCl$_3$): 1.31 (s, 9H), 3.41 (s, 3H), 6.90–7.07 (m, 4H), 7.20–7.28 (m, 1H), 7.32–7.43 (m, 4H).

Example 12 (General Procedure 1)

Methyl-phenyl-carbamic acid 3-(4-fluorobenzyl)-4-methyl-2-oxo-2H-chromen-7-yl ester The title compound was prepared from 3-(4-fluorobenzyl)-7-hydroxy-4-methyl-2H-chromen-2-one and N-methyl-N-phenylcarbamoyl chloride.

The crude product was of high purity and tested without purification (≈100%, crystals); mp: 185–186° C. HPLC-MS m/z=418.2 (M+1), Rt: 5.2 min.

$\delta_H$(300 MHz; CDCl$_3$): 2.43 (s, 3H), 3.43 (s, 3H), 6.95 (dt, 2H, J 8.7 and 2.3), 7.10 (m, 2H), 7.21 (dt, 2H, J 7.2 and 2.3), 7.27–7.45 (m, 5H), 7.58 (d, 1H, J 8.3).

Example 13 (General Procedure 1)

Methyl-phenyl-carbamic acid 4-phenoxy-phenyl ester

The title compound was prepared from 4-phenoxy-phenol and N-methyl-N-phenylcarbamoyl chloride. The crude product was recrystallized (ethanol/water) (86%, white crystals). HPLC-MS m/z=320.1 (M+1), Rt: 5.13 min.

$\delta_H$(300 MHz; CDCl$_3$): 3.43 (s, 3H), 6.94–7.02 (m, 4H), 7.08 (t, 2H, J 6.8), 7.04–7.12 (m, 1H), 7.32 (t, 2H, J 7.5), 7.28–7.35 (m,1 H), 7.35–7.45 (m, 4H).

Example 14 (General Procedure 1)

Methyl-phenyl-carbamic acid 4-(4-chlorobenzoyl)-phenyl ester

The title compound was prepared from 4-(4-chlorobenzoyl)-phenol and N-methyl-N-phenylcarbamoyl chloride. The crude product was recrystallized (ethanol/water) (90%, white crystals). HPLC-MS m/z=366.1 (M+1), Rt: 5.19 min.

$\delta_H$(300 MHz; CDCl$_3$): 3.45 (s, 3H), 7.19–7.37 (m, 4H), 7.40 (t, 2H, J 7.2), 7.37–7.40 (m, 1H), 7.46 (dt, 2H, J 8.7 and 2,3), 7.73 (dt, 2H, J 8.7 and 2.2), 7.79 (d, 2H, J 8.7).

Example 15 (General Procedure 1)

Methyl-phenyl-carbamic acid 4-(3-chloro-5-trifluoromethyl)-pyridine-2-yloxy)-phenyl ester The title compound was prepared from 4-(3-chloro-5-trifluoromethyl)-pyridine-2-yloxy)-phenol and N-methyl-N-phenylcarbamoyl chloride. Prepared as described in general procedure 1. The crude product was recrystallized (ethanol/water (78%, white crystals). HPLC-MS m/z=423.1 (M+1), Rt: 5.31 min.

$\delta_H$(300 MHz; CDCl$_3$): 3.43 (s, 3H), 7.10–7.23 (m, 4H), 7.27 (t, 1H, J 6.8), 7.35 (d, 2H, J 7.5), 7.41 (t, 2H, J 7.4), 7.96 (d, 1H, J 1.9), 8.23 (bs, 1H).

Example 16 (General Procedure 1)

Methyl-phenyl-carbamic acid 4-[4-(4-chloro-phenyl)-thiazol-2-yl]-phenyl ester

The title compound was prepared from 4-[4-(4-chloro-phenyl)-thiazol-2-yl]-phenol and N-methyl-N-phenylcarbamoyl chloride. The crude product was recrystallized (ethanol/water) (59%, white crystals). HPLC-MS m/z=421.1 (M+1), Rt: 5.85 min $\delta_H$(300 MHz; CDCl$_3$): 3.45 (s, 3H), 7.18–7.25 (m, 2H), 7.27–7.33 (m, 1H), 7.34–7.41 (m, 4H), 7.43 (d, 2H, J 6.8), 7.41–7.46 (m,1 H), 7.92 (dt, 2H, J 8.6 and 2.2), 8.00 (d, 2H, J 8.7).

Example 17 (General Procedure 1)

Methyl-phenyl-carbamic acid 4-pyrrol-1-yl-phenyl ester

The title compound was prepared from 4-pyrrol-1-yl-phenol and N-methyl-N-phenylcarbamoyl chloride. The crude product was recrystallized (ethanol/water) (27%, off-white crystals). HPLC-MS m/z=293.2 (M+1), Rt: 4.51 min.

$\delta_H$(300 MHz; CDCl$_3$): 3.44 (s, 3H), 6.33 (t, 2H, J 2.2), 7.03 (t, 2H, J 2.2), 7.17 (bd, 2H, J 8.3), 7.29 (d, 1H, J 6.8), 7.31–7.38 (m, 4H), 7.41 (t, 2H, J 6.8).

Example 17a (General Procedure 1)

Methyl-phenyl-carbamic acid 4-imidazol-1-yl-phenyl ester

The title compound was prepared from 4-imidazol-1-yl-phenol and N-methyl-N-phenylcarbamoyl chloride. The crude product was subjected to preparative HPLC (4%, clear oil). HPLC-MS m/z=294.1 (M+1), Rt: 2.25 min.

$\delta_H$(300 MHz; CDCl$_3$): 3.44 (s, 3H), 7.27–7.39 (m, 4H), 7.39–7.50 (m, 5H), 7.53 (bs, 1H), 8.83 (bs, 1H).

Example 18 (General Procedure 1)

Methyl-phenyl-carbamic acid 4-(3-chloro-5-trifluoromethyl)-pyridine-2-ylmethyl)-phenyl ester The title compound was prepared from 4-(3-chloro-5-trifluoromethyl)-pyridine-2-ylmethyl)-phenol and N-methyl-N-phenylcarbamoyl chloride.

The crude product was recrystallized (ethanol/water) (74%, white crystals). HPLC-MS m/z=421.1 (M+1), Rt: 5.23 min.

$\delta_H$(300 MHz; CDCl$_3$): 3.40 (s, 3H), 4.33 (s, 2H), 7.03 (d, 2H, J 8.3), 7.20–7.30 (m, 3H), 7.3 (d, 2H, J 7.2), 7.38 (t, 2H, J 7.2), 7.87 (d, 1H, J 1.5), 8.69 (bs, 1H,).

Example 19 (General Procedure 1)

Methyl-phenyl-carbamic acid 4-trifluoromethylsulfanyl-phenyl ester

The title compound was prepared from 4-trifluoromethylsulfanyl-phenol and N-methyl-N-phenylcarbamoyl chloride. The crude product was subjected to preparative HPLC (70%, clear oil). HPLC-MS m/z=328.0 (M+1), Rt: 5.16 min.

$\delta_H$(300 MHz; CDCl$_3$): 3.42 (s, 3H), 7.19 (d, 2H, J 6.4), 7.26–7.7.37 (m, 3H), 7.41 (t, 2H, J 7.9), 7.63 (d, 2H, J 8.3).

Example 20 (General Procedure 1)

Methyl-phenyl-carbamic acid 4-pentafluoromethyloxy-phenyl ester

The title compound was prepared from 4-pentafluoromethyloxy-phenol and N-methyl-N-phenylcarbamoyl chloride. The crude product was subjected to preparative HPLC (66%, clear oil). HPLC-MS m/z=362.0 (M+1), Rt: 5.31 min.

$\delta_H$(300 MHz; CDCl$_3$): 3.42 (s, 3H), 7.10–7.22 (m, 4H), 7.29 (d, 1H, J 7.2), 7.34 (d, 2H, J 7.1), 7.41 (t, 2H, J 7.1).

Example 21 (General Procedure 1)

Methyl-phenyl-carbamic acid 4-benzyloxy-phenyl ester

The title compound was prepared from 4-benzyloxy-phenol and N-methyl-N-phenylcarbamoyl chloride. The crude product was recrystallized (ethanol/water) (83%, white crystals). HPLC-MS m/z=334.2 (M+1), Rt: 4.88 min.

$\delta_H$(300 MHz; CDCl$_3$): 3.41 (s, 3H), 5.03 (s, 2H), 6.92 (dt, 2H, J 9.0 and 2.2), 7.02 (d, 2H, J 8.7), 7.26–7.34 (m, 2H), 7.34–7.38 (m, 4H), 7.38–7.44, m, 4H).

Example 22 (General Procedure 1)

Methyl-phenyl-carbamic acid 4-benzyl-phenyl ester

The title compound was prepared from 4-benzyl-phenol and N-methyl-N-phenylcarbamoyl chloride. The crude product was recrystallized (ethanol/water) (56%, white crystals). HPLC-MS m/z=318.1 (M+l), Rt: 5.05 min.

$\delta_H$(300 MHz; CDCl$_3$): 3.41 (s, 3H), 3.95 (s, 2H), 7.02 (d, 2H), 7.12–7.19 (m, 5H), 7.20–7.25 (m, 2H), 7.26–7.28 (m, 1H), 7.28–7.34 (m, 1H), 7.34–7.42 (m, 3H).

Example 23 (General Procedure 1)

Methyl-phenyl-carbamic acid 4'-cyano-biphenyl-4-yl-ester

The title compound was prepared from 4-hydroxy-4-biphenylcarbonitrile and N-methyl-N-phenylcarbamoyl chloride applying procedure 1. The crude product was recrystallized (ethanol/water) (87%, white crystals). HPLC-MS m/z=329.2 (M+1), Rt: 4.63 min.

$\delta_H$(300 MHz; CDCl$_3$): 3.44 (s, 3H), 7.18–7.26 (m, 2H), 7.26–7.32 (m, 2H), 7.34–7.46 (m, 4H), 7.56 (d, 2H), 7.64 (d, 2H), 7.712 (d, 2H).

Example 24 (General Procedure 1)

Methyl-phenyl-carbamic acid 4'-bromo-biphenyl-4-yl-ester

The title compound was prepared from 4-bromo-4'-hydroxybiphenyl and N-methyl-N-phenylcarbamoyl chloride. The crude product was recrystallized (ethanol) (72%, white crystals). HPLC-MS m/z=382.0) (M+1), Rt: 5.41 min.

$\delta_H$(300 MHz; CDCl$_3$): 3.44 (s, 3H), 7.15–7.23 (d, 2H), 7.26–7.31 (m, 1H), 7.34–7.45 (m, 6H), 7.47.7.57 (m, 4H).

Example 25 (General Procedure 1)

Methyl-phenyl-carbamic acid biphenyl-4-yl-ester

The title compound was prepared from 4-hydroxybiphenyl and N-methyl-N-phenylcarbamoyl chloride applying. The crude product was recrystallized (ethanol) (75%, white crystals).

HPLC-MS m/z=304.2 (M+1), Rt: 4.95 min. $\delta_H$(300 MHz; CDCl$_3$): 3.45 (s, 3H), 7.19 (d, 2H), 7.26–7.37 (m, 2H), 7.37–7.46 (m, 6H), 7.55 (d, 4H).

Example 26 (General Procedure 1)

Methyl-phenyl-carbamic acid 4-[3-(4-chlorophenyl)-ureido]-phenyl ester

The title compound was prepared from 4-[3-(4-chlorophenyl)-ureido]-phenol and N-methyl-N-phenylcarbamoyl chloride. The crude product was subjected to preparative HPLC (33%, off-white crystals). HPLC-MS m/z=396.1 (M+1), Rt: 4.40 min.

$\delta_H$(300 MHz; CDCl$_3$): 3.52 (s, 3H), 6.85–7.03 (m, 7H), 7.09 (d, 2H), 7.30–7.50 (m, 6H).

Example 27 (General Procedure 1)

Methyl-phenyl-carbamic acid 4-(4-nitro-phenoxy)-phenyl ester

The title compound was prepared from 4-(4-nitro-phenoxy)-phenol and N-methyl-N-phenylcarbamoyl chloride. The crude product was subjected to preparative HPLC (71%, white crystals). HPLC-MS m/z=365.0 (M+1), Rt: 4.83 min.

$\delta_H$(300 MHz; CDCl$_3$): 3.44 (s, 3H), 7.00 (d, 2H), 7.06 (d, 2H), 7.26–7.32 (m, 1H), 7.33–7.49 (m, 4H), 8.20 (dt, 2H).

Example 28 (General Procedure 1)

Methyl-phenyl-carbamic acid 4-heptylsulfanyl-phenyl ester

The title compound was prepared from 4-heptylsulfanyl-phenol and N-methyl-N-phenylcarbamoyl chloride. The crude product was subjected to preparative HPLC (74%, colourless oil, HPLC-MS m/z=358.2 (M+1), Rt: 6.21 min.

$\delta_H$(200 MHz; CDCl$_3$): 0.87 (t, 3H), 1.15–1.50 (m, 8H), 1.50–1.75 (m, 2H), 2.86 (t, 2H), 3.41 (s, 3H), 7.04 (d, 2H), 7.15–7.50 (m, 7H).

Example 29 (General Procedure 1)

Methyl-phenyl-carbamic acid 4-butoxy-phenyl ester

The title compound was prepared from 4-butoxy-phenol and N-methyl-N-phenylcarbamoyl chloride. The crude product was recrystallized from ethanol (22%, white crystals). HPLC-MS m/z=300.1 (M+1), Rt: 5.20.

$\delta_H$(300 MHz; CDCl$_3$): 0.96 (t, 3H), 1.45 (qi, 2H), 1.74 (qi, 2H), 3.41 (s, 3H), 3.92 (t, 2H), 6.84 (d, 2H), 6.99 (d, 2H), 7.25–7.27 (m,1 H), 7.30–7.45 (m, 4H).

Example 30 (General Procedure 1)

Methyl-phenyl-carbamic acid 4-(4-chloro-benzenesulfonyl)-phenyl ester

The title compound was prepared from 4-(4-chloro-benzenesulfonyl)-phenol and N-methyl-N-phenylcarbamoyl chloride. The crude product was subjected to preparative HPLC (46%, colourless oil). HPLC-MS m/z=402.1(M+1), Rt: 4.65 min.

$\delta_H$(200 MHz; CDCl$_3$): 3.41 (s, 3H), 7.21–7.35 (m, 5H), 7.39 (d, 2H), 7.46 (dt, 2H, 7.84 (dt, 2H) 7.90 (d, 2H).

Example 31 (General Procedure 1)

Methyl-phenyl-carbamic acid 4-(4-chloromethyl-thiazol-2-yl)-phenyl ester

The title compound was prepared from 4-(4-chloromethyl-thiazol-2-yl)-phenol and N-methyl-N-phenylcarbamoyl chloride. The aqueous phase was adjusted to PH 7.0 (phosphate buffer) before extraction with ethyl acetate. The crude product was subjected to preparative HPLC (21%, white crystals). HPLC-MS m/z=359.0 (M+1), Rt: 4.60.

$\delta_H$(200 MHz; CDCl$_3$): 3.44 (s, 3H), 4.73 (s, 2H), 7.20 (bd, 2H), 7.26–7.48 (m, 6H), 7.92 (bd, 2H).

Example 32 (General Procedure 3)

Methyl-phenyl-carbamic acid 4-(4,4-dimethyl-2,6-dioxo-piperidin-1-yl)-phenyl ester The title product was prepared from 1-(4-hydroxyphenyl)-4,4-dimethylpiperidine-2,6-dione (233 mg, 1.00 mmol)) and 1-methyl-3-(methyl-phenyl-carbamoyl)-3H-imidazol-1-ium iodide (343 mg, 1.00 mmol) by applying general procedure 3 (192 mg, 52%, white solid). HPLC-MS m/z=367 (M+1); R$_t$=3.78 min.

$^1$H NMR (300 MHz, CDCl$_3$): δ 1.19 (s, 6H), 2.65 (s, 4H), 3.42 (s, 3H), 7.03 (d, 2H), 7.15–7.43 (m, 7H).

Example 33 (General Procedure 3)

cis-Methyl-phenyl-carbamic acid 4-(1,3-dioxo-octahydro-isoindol-2-yl)-phenyl ester The title compound (293 mg, 77% yield, white crystals) was prepared from cis-2-(4-hydroxy-phenyl)hexahydroisoindole-1,3-dione (245 mg, 1.00 mmol) and 1-methyl-3-(methyl-phenyl-carbamoyl)-3H-imidazol-1-ium iodide (343 mg, 1.00 mmol). HPLC-MS m/z=379 (M+1); R$_t$=4.08 min.

$^1$H NMR (300 MHz, CDCl$_3$): δ 1.50 (m, 4H), 1.90 (m, 4H), 3.00 (m, 1H), 3.42 (s, 3H), 7.13–7.44 (m, 9H).

Example 34 (General Procedure 3)

Methyl-phenyl-carbamic acid 4-(cyclohexanecarbonyl-amino)-phenyl ester

The title compound (283 mg, 80% yield, white crystals) was prepared from cyclohexanecarboxylic acid (4-hydroxyphenyl) amide (219 mg, 1.00 mmol) and 1-methyl-3-(methyl-phenyl-carbamoyl)-3H-imidazol-1-ium iodide (343 mg, 1.00 mmol). HPLC-MS m/z=353 (M+1); R$_t$=4.23 min.

$^1$H NMR (300 MHz, CDCl$_3$): δ 1.27 (m, 3H), 1.52 (m, 2H), 1.70 (m, 1H), 1.76–1.97 (m, 4H), 2.20 (m, 1H), 3.42 (s, 3H), 7.01 (d, 2H), 7.18 (d, 2H), 7.32–7.50 (m, 7H).

Example 35 (General Procedure 3)

Methyl-phenyl-carbamic acid 4-(2-cyclohexyl-acetylamino)-phenyl ester

The title compound (284 mg, 77% yield, white crystals) was prepared from 2-cyclohexyl-N-(4-hydroxy-phenyl)-acetamide (233 mg, 1.00 mmol) and 1-methyl-3-(methyl-phenyl-carbamoyl)-3H-imidazol-1-ium iodide (343 mg, 1.00 mmol). HPLC-MS m/z=367 (M+1); R$_t$=4.51 min $^1$H NMR (300 MHz, CDCl$_3$): δ 0.87–1.03 (m, 2H), 1.07–1.38 (m, 3H), 1.60–1.92 (m, 6H), 2.14 (d, 2H), 3.41 (s, 3H), 6.97 (d, 2H), 7.26 (m,1 H), 7.30–7.44 (m, 6H), 7.55 (br.s, 1H, NH).

Example 36 (General Procedure 3)

cis/trans-Methyl-phenyl-carbamic acid 4-[(4-tert-butyl-cyclohexanecarbonyl)-amino]-phenyl ester The title compound (353 mg, 86% yield, white crystals) was prepared from cis/trans-4-tert-butyl-cyclohexanecarboxylic acid (4-hydroxy-phenyl)-amide (275 mg, 1.00 mmol) and 1-methyl-3-(methyl-phenyl-carbamoyl)-3H-imidazol-1-ium iodide (343 mg, 1.00 mmol). HPLC-MS m/z=409 (M+1); R$_t$=5.28 and 5.42 min.

$^1$H NMR (300 MHz, CDCl$_3$): δ 0.82–0.86 (2×s, 9H), 1.03 (m, 2H), 1.23–1.70 (m, 4H), 1.82–2.22+2.58 (m, 4H), 3.42 (s, 3H), 7.01 (m, 2H), 7.26 (m, 1H), 7.31–7.48 (m, 7H, arom.+NH).

Example 37 (General Procedure 3)

trans-Methyl-phenyl-carbamic acid 4-[(4-tert-butyl-cyclohexanecarbonyl)-amino]-phenyl ester The title compound was obtained from cis/trans-4-tert-butyl-cyclohexanecarboxylic acid (4-hydroxy-phenyl)-amide by preparative HPLC (method B). R$_t$=5.50 min.

$^1$H NMR (300 MHz, CDCl$_3$): δ 0.85 (s, 9H), 1.03 (m, 3H), 1.52 (m, 2H), 1.88 (m, 2H), 2.01 (m, 2H), 2.12 (tt, J=12.1, 3.3 Hz, 1H), 3.41 (s, 3H), 7.01 (br.d, 2H), 7.26 (m, 1H), 7.31–7.48 (m, 7H, arom.+NH).

Example 38 (General Procedure 3)

cis-Methyl-phenyl-carbamic acid 4-[(4-tert-butyl-cyclohexanecarbonyl)-amino]-phenyl ester The title compound was obtained from cis/trans-4-tert-butyl-cyclohexanecarboxylic acid (4-hydroxy-phenyl)-amide by preparative HPLC (method B). R$_t$=6.34 min.

Example 39 (General Procedure 3)

Methyl-phenyl-carbamic acid 4-(3,3-dimethyl-butyrylamino)-phenyl ester

The title compound (262 mg, 77% yield) was prepared from N-(4-hydroxyphenyl)-3,3-dimethyl-butyramide (275 mg, 1.00 mmol) and 1-methyl-3-(methyl-phenyl-carbamoyl)-3H-imidazol-1-ium iodide (343 mg, 1.00 mmol). HPLC-MS m/z=341 (M+1); R$_t$=4.15 min.

$^1$H NMR (300 MHz, CDCl$_3$): δ 1.07 (s, 9H), 2.16 (s, 2H), 3.43 (s, 3H), 6.98 (d, 2H), 7.26 (m, 1H), 7.32–7.43 (m, 6H), 7.51 (br.s, 1H, NH).

Example 40 (General Procedure 3)

Methyl-phenyl-carbamic acid 3-(benzyl)-4-methyl-2-oxo-2H-chromen-7-yl ester

The title compound was prepared from 3-benzyl-7-hydroxy-4-methyl-2H-chromen-2-one and 3-(methyl-phenyl-carbamoyl)-1-methyl-3H-imidazol-1-ium iodide. HPLC-MS m/z=400 (M+1), Rt: 4.90 min.

Example 41 (General Procedure 3)

Methyl-phenyl-carbamic acid 3-(3,4-dichloro-benzyl)-4-methyl-2-oxo-2H-chromen-7-yl ester The title compound was prepared from 3-(3,4-dichloro-benzyl)-7-hydroxy-4-methyl-2H-chromen-2-one and 3-(methyl-phenyl-carbamoyl)-1-methyl-3H-imidazol-1-ium iodide (white solid). HPLC-MS m/z=468 (M+1), Rt: 5.47 min.

Example 42 (General Procedure 3)

Methyl-phenyl-carbamic acid 3-(2-chloro-6-fluoro-benzyl)-4-methyl-2-oxo-2H-chromen-7-yl ester The title compound was prepared from 3-(2-chloro-6-fluoro-benzyl)-7-hydroxy-4-methyl-2H-chromen-2-one and 3-(methyl-phenyl-carbamoyl)-1-methyl-3H-imidazol-1-ium iodide by applying procedure 3. HPLC-MS m/z=452 (M+1), Rt: 5.15 min.

Example 43 (General Procedure 3)

Methyl-phenyl-carbamic acid 3-(2,6-dichloro-benzyl)-4-methyl-2-oxo-2H-chromen-7-yl ester The title compound was prepared from 3-(2,6-dichloro-benzyl)-7-hydroxy-4-methyl-2H-chromen-2-one and 3-(methyl-phenyl-carbamoyl)-1-methyl-3H-imidazol-1-ium iodide. HPLC-MS m/z=468 (M+1), Rt: 5.37 min.

Example 44 (General Procedure 3)

Methyl-phenyl-carbamic acid 3-(2,6-dichloro-benzyl)-6-chloro-4-methyl-2-oxo-2H-chromen-7-yl ester The title compound was prepared from 3-(2,6-dichloro-benzyl)-6-chloro-7-hydroxy-4-methyl-2H-chromen-2-one and 3-(methyl-phenyl-carbamoyl)-1-methyl-3H-imidazol-1-ium iodide.
HPLC-MS m/z=502 (M+1), Rt: 5.68 min.

Example 45 (General Procedure 3)

Methyl-phenyl-carbamic acid 6-chloro-3-(2-chloro-6-fluoro-benzyl)-4-n-propy-2-oxo-2H-chromen-7-yl ester The title compound was prepared from 3-(4-fluoro-benzyl)-6-chloro-7-hydroxy-4-n-propyl-2H-chromen-2-one and 3-(methyl-phenyl-carbamoyl)-1-methyl-3H-imidazol-1-ium iodide. HPLC-MS m/z=480 (M+1), Rt: 5.61 min.

Example 46 (General Procedure 3)

Methyl-phenyl-carbamic acid 3-(4-methoxy-phenyl)-4-methyl-2-oxo-2H-chromen-7-yl ester The title compound (90 mg, 43% yield, white solid) was prepared from 7-hydroxy-3-(4-methoxy-phenyl)-4-methyl-chromen-2-one (141 mg, 0.50 mmol) and 1-methyl-3-(methyl-phenyl-carbamoyl)-3H-imidazol-1-ium iodide (175 mg, 0.51 mmol).
$^1$H NMR (300 MHz, DMSO-d$_6$): δ 2.28 (s, 3H), 3.38 (s, 3H), 3.80 (s, 3H), 7.00 (d, 2H), 7.18–7.33 (m, 5H), 7.40–7.53 (m, 4H), 7.83 (d, 1H); HPLC-MS: m/z=416 (M+1); R$_t$=4.67 min.

Example 47 (General Procedure 3)

Methyl-phenyl-carbamic acid 4-methyl-2-oxo-3-phenyl-2H-chromen-7-yl ester

The title compound (120 mg, 52% yield, white solid) was prepared from 7-hydroxy-4-methyl-3-phenyl-chromen-2-one (126 mg, 0.50 mmol) and 1-methyl-3-(methyl-phenyl-carbamoyl)-3H-imidazol-1-ium iodide (175 mg, 0.51 mmol).
$^1$H NMR (300 MHz, DMSO-d$_6$): δ 2.26 (s, 3H), 3.37 (s, 3H), 7.16–7.54 (m, 12H), 7.86 (d, 1H); HPLC-MS: m/z=386 (M+1); R$_t$=4.69 min.

Example 48 (General Procedure 3)

Methyl-phenyl-carbamic acid 3-(2,5-dimethoxy-phenyl)-4-methyl-2-oxo-2H-chromen-7-yl ester The title compound (30 mg, 13% yield, white solid) was prepared from 3-(2,5-dimethoxy-phenyl)-7-hydroxy-4-methyl-chromen-2-one (156 mg, 0.50 mmol) and 1-methyl-3-(methyl-phenyl-carbamoyl)-3H-imidazol-1-ium iodide (175 mg, 0.51 mmol).
$^1$H NMR (300 MHz, CDCl$_3$): δ 2.21 (s, 3H), 3.45 (br.s, 3H), 3.72 (s, 3H), 3.79 (s, 3H), 6.74 (m, 1H), 6.92 (m, 2H), 7.12 (br.s, 2H), 7.26–7.46 (m, 5H), 7.63 (d, 1H); HPLC-MS: m/z=446 (M+1); R$_t$=4.60 min.

Example 49 (General Procedure 3)

Methyl-phenyl-carbamic acid 3-(3,4-dimethoxy-phenyl)-4-methyl-2-oxo-2H-chromen-7-yl ester The title compound (30 mg, 13% yield, oil) was prepared from 3-(3,4-dimethoxy-phenyl)-7-hydroxy-4-methyl-chromen-2-one (156 mg, 0.50 mmol) and 1-methyl-3-(methyl-phenyl-carbamoyl)-3H-imidazol-1-ium iodide (175 mg, 0.51 mmol).
$^1$H NMR (300 MHz, CDCl$_3$): δ 2.31 (s, 3H), 3.45 (br.s, 3H), 3.89 (s, 3H), 4.02 (s, 3H), 6.83 (m, 2H), 6.94 (d, 1H), 7.12 (br.s, 2H), 7.27–7.48 (m, 5H), 7.62 (d, 1H); HPLC-MS: m/z=446 (M+1); R$_t$=4.61 min.

Example 50 (General Procedure 2)

4-Chlor-phenyl-methyl-carbamic acid 4-(5-trifluoromethyl-pyridin-2-yloxy)-phenyl ester The title compound was prepared from 4-(5-trifluoromethyl-pyridin-2-yloxy)-phenol and 3[(4-chlorophenyl)-methyl-carbamoyl]-1-methyl-3H-imidazol-1-ium iodide. The crude product was subjected to flash chromatography (ethyl acetate/heptan, 1:5) (77%, white crystals). HPLC-MS m/z=423.1 (M+1), Rt: 5.3 min.
δ$_H$(300 MHz; CDCl$_3$): 3.42 (s, 3H), 6.99 (d, 1H, J 8.7), 7.10–7.20 (m, 4H), 7.30 (d, 2H, J 8.3 ), 7.37 (d, 2H, J 8.6), 7.88 (dd, 1 H, J 8.7 and 2.2), 8.42 bs, 1 H).

Example 51 (General Procedure 2)

4-Chlor-phenyl-methyl-carbamic acid 4-(3,5-dichloro-pyridin-2-yloxy)-phenyl ester The title compound was prepared from 4-(3,5-dichloro-pyridin-2-yloxy)-phenol and 3-[(4-chlorophenyl)-methyl-carbamoyl]-1-methyl-3H-imidazol-1-ium iodide. The crude product was subjected to flash chromatography (Quad flash 12, dichlormethane (67%). HPLC-MS m/z=422.9 (M+1), Rt: 5.5 min.

$\delta_H$(300 MHz; CDCl$_3$): 3.41 (s, 3H), 7.20–7.08 (m, 4H), 7.29 (d, 2H, J 9), 7.37 (dd, 2H, J 6.4 and 2.2), 7.76 (d, 1H, J 2.3), 7.93 (d, 1H, J 2.3).

Example 52 (General Procedure 2)

(4-Chloro-phenyl)-methyl-carbamic acid 4-(2-cyano-5-trifluoromethyl-pyridin-3-yloxy)-phenyl ester The title compound was prepared from 4-(2-cyano-5-trifluoromethyl-pyridin-3-yloxy)-phenol and 3-[(4-chlorophenyl)-methyl-carbamoyl]-1-methyl-3H-imidazol-1-ium iodide. The crude product was purified by preparative HPLC (25%). HPLC-MS m/z=448.2 (M+1), Rt: 5.1 min.

$\delta_H$(300 MHz; CDCl$_3$): 3.43 (s, 3H), 7.12 (d, 2H, J 9.0), 7.19–7.35 (m, 4H), 7.39 (dd, 2H, J 6.6 and 1.8), 7.36–7.41 (m, 1H), 8.63 (d, 1H, J 0.7).

Example 53 (General Procedure 1)

Ethyl-phenyl-carbamic acid 4-(5-trifluoromethyl-pyridin-2-yloxy)-phenyl ester

The title compound was prepared from 4-(4-trifluoromethyl-pyridin-2-yloxy)-phenol and N-ethyl-N-phenylcarbamoyl chloride. The crude product was subjected to flash chromatography (ethyl acetate/heptane, 1:5) (78%, white crystals). HPLC-MS m/z=403.2 (M+1), Rt: 5.17 min.

$\delta_H$(300 MHz; CDCl$_3$): 1.25 (t, 3H, J 6.8), 3.83 (q, 2H, J 6.8), 6.98 (d, 1H, J 8.6), 7.12 (m, 4H), 7.32 (d, 2H, J 7.1), 7.32 (m, 1H), 7.41 (t, 2H, J 7.5), 7.87 (dt, 1H, J 8.7 and 2.7), 8.42 (bs, 1H).

Example 54 (General Procedure 1)

Ethyl-phenyl-carbamic acid 4-(4-trifluoromethyl-phenoxy)-phenyl ester

The title compound was prepared from 4-(4-trifluoromethyl-phenoxy)-phenol and N-ethyl-N-phenylcarbamoyl chloride. The crude product was subjected to flash chromatography (ethyl $\delta_H$(300 MHz; CDCl$_3$): 1.25 (t, 3H, J 7.2), 3.83 (q, 2H, J 7.2), 7.01 (d, 4H, J 8.6), 7.12 (d, 2H, J 8.3), 7.30 (t, 2H, J 6.8), 7.30 (m, 1H), 7.42 (dt, 2H, J 8.6)

Example 55 (General Procedure 2)

Benzyl-methyl-carbamic acid 4-(5-trifluoromethyl-pyridin-2-yloxy)-phenyl ester

The title compound was prepared from 4-(5-trifluoromethyl-pyridin-2-yloxy)-phenol and 3-(benzyl-methyl-carbamoyl)-1-methyl-3H-imidazol-1-ium iodide. The crude product was subjected to flash chromatography (ethyl acetate/heptane, (1:5) (69%, colourless oil) HPLC-MS m/z=403.2 (M+1), Rt: 5.11 min $\delta_H$(300 MHz; CDCl$_3$): 3.03 (d, 3H, J 8.0), 4.64 (d, 2H, J 24.9), 7.00 (d, 1H), 7.10–7.26 (m, 4H), 7.30–7.50 (m, 5H), 7.88 (dd, 1H), 8.43 (s, 1H).

Example 56 (General Procedure 2)

Benzyl-methyl-carbamic acid 4-(3,5-dichloro pyridin-2-yloxy)-phenyl ester

The title compound was prepared from 4-(3,5-dichloro pyridin-2-yloxy)-phenol and 3-(benzyl-methyl-carbamoyl)-1-methyl-3H-imidazol-1-ium iodide.

The crude product was subjected to flash chromatography (Quad flash 12, dichloromethane) (92%, oil). HPLC-MS m/z=403.2 (M+1), Rt: 5.4 min.

$\delta_H$(300 MHz; CDCl$_3$): 3.02 (d, 3H, J 7.2), 4.60 (d, 2H, J 24.1), 7.05–7.25 (m, 4H), 7.28–7.45 (m, 5H), 7.76 (d, 1H, J 2.3) 7.95 (d, 1H, J J 2.2).

Example 57 (General Procedure 2)

tert-Butyl-methyl-carbamic acid 4-(5trifluoromethyl-pyridin-2-yloxy)-phenyl ester The title compound was prepared from 4-(5-trifluoromethyl-pyridin-2-yloxy)-phenol and 3-(tert-Butyl-methyl-carbamoyl)-1-methyl-3H-imidazol-1-ium iodide. The crude product was subjected to preparative HPLC (34%, white crystals). HPLC-MS m/z=369.1 (M+1), Rt: 5.17 min.

$\delta_H$(300 MHz; CDCl$_3$): 1.47 (s, 9H), 3.08 (s, 3H), 6.99 (d, 1H), 7.09–7.20 (m, 4H), 7.87 (dd, 1H), 8.43 (bs, 1H).

Example 58 (General Procedure 2)

Isopropyl-methyl-carbamic acid 4-(5-trifluoromethyl-pyridin-2-yloxy)-phenyl ester The title compound was prepared from 4-(5-trifluoromethyl-pyridin-2-yloxy)-phenol and 3-(isopropyl-methyl-carbamoyl)-1-methyl-3H-imidazol-1-ium iodide. The crude product was subjected to flash chromatography (ethyl acetate/heptane 1:5) (77%, white crystals). HPLC-MS m/z=355.1 (M+1), Rt: 4.80 min.

$\delta_H$(300 MHz; CDCl$_3$): 1.21 (m, 6H), 2.91 (d, 3H), 4.49 (qi, 1H), 6.99 (d, 1H), 7.10–7.25 (m, 4H) 7.88 (dd, 1H), 8.44 (s, 1H).

Example 59 (General Procedure 2)

Cyclohexyl-methyl-carbamic acid 4-(5-trifluoromethyl-pyridin-2-yloxy)-phenyl ester The title compound was prepared from 4-(5-trifluoromethyl-pyridin-2-yloxy)-phenol and 3-(cyclohexyl-methyl-carbamoyl)-1-methyl-3H-imidazol-1-ium iodide. The crude product was subjected to flash chromatography (ethyl acetate/heptane, 1:5) (80%, white crystals). HPLC-MS m/z=395.2 (M+1), Rt: 5.7 min.

$\delta_H$(300 MHz; CDCl$_3$): 1.13 (m, 1H), 1.50–1.30 (m, 4H), 1.68 (d, 1H, J 13.2), 1.75–1.95 (m, 4H), 2.93 (d, 2H, J 12.1), 2.90–3.00 (m, 1H), 4.02 (t, 1H, J 12.1), 6.99 (d, 1H, J 8.7), 7.10–7.17 (, 4H), 7.88 (dd, 1H, J 8.7 and 2.3), 8.44 (s, 1H).

Example 60 (General Procedure 1)

Dimethyl-carbamic acid 4-(3,5-dichloro pyridin-2-yloxy)-phenyl ester

The title compound was prepared from 4-(3,5-dichloro pyridin-2-yloxy)-phenol and dimethyl-carbamoyl chloride.

The crude product was purified by preparative HPLC (38%). HPLC-MS m/z=327.0 (M+1), Rt: 4.7 min.

$\delta_H$(300 MHz; CDCl$_3$): 2.92 (s, 3H), 3.05 (s, 3H), 7.10–7.25 (m, 4H), 8.17 (d, 1H), 8.34 (d, 1H).

Example 61 (General Procedure 1)

Pyrrolidine1-carboxylic acid 4-(3,5-dichloro-pyridin-2-yloxy)-phenyl ester

The title compound was prepared from 4-(3,5-dichloro-pyridine-2-yloxy)-phenol and 1-pyrrolidinecarbamoyl chloride. The crude product was purified by preparative HPLC (64%, white crystals). HPLC-MS m/z=353.0 (M+1), Rt: 5.00 min.

$\delta_H$(300 MHz; CDCl$_3$): 1.95 (qi, 4H, J 6.4), 3.48 (t, 2H, J 6.4), 3.56 (t, 2H, 6.4), 7.10 (t, 1H, J 2.7), 7.13 (t, 1H, J 2.7), 7.17 (t, 1H, J 2.0), 7.20 (t, 1H, J 2.3), 7.76 (d, 1H, J 2.6), 7.95 (d, 1H J, 2.6).

Example 62 (General Procedure 2)

2,3-Dihydro-indole-1-carboxylic acid 4-(5-trifluoromethyl-pyridin-2-yloxy)-phenyl ester The title compound was prepared from 4-(5-trifluoromethyl-pyridin-2-yloxy)-phenol and 3-(2,3-dihydro-indole-1-carbonyl)-1-methyl-3H-imidazol-1-ium iodide. The crude product was subjected to column chromatography(ethyl acetate/heptane, 1:5) (73%, crystals. HPLC-MS m/z=401.1) (M+1), Rt: 5.5 min.

$\delta_H$(300 MHz; CDCl$_3$): 3.24 (t, 2H, J 8.4), 4.25 (t, 2H, J 8.4), 7.10 (m, 2H), 7.15–7.35 (m, 6H), 7.90 (dd, 2H, J 8.7 and 2.6), 8.44 (bs, 1H).

Example 63 (General Procedure 2)

1,3-Dihydro-isoindole-2-carboxylic acid 4-(5-trifluoromethyl-pyridin-2-yloxy)-phenyl ester The title compound was prepared from 4-(5-trifluoromethyl-pyridin-2-yloxy)-phenol and 3-(1,3-dihydro-isoindole-2-carbonyl)-1-methyl-3H-imidazol-1-ium iodide. The crude product was recrystallized (ethanol) (≈100). HPLC-MS m/z=401.1 (M+1), Rt: 5.1 min.

$\delta_H$(300 MHz; CDCl$_3$): 4.85 (s, 2H), 4.95 (s, 2H), 7.01(d, 1H, J 8.69), 7.16 (dt, 2H, J 9.4 and 2.7), 7.22–7.29 (m, 2H), 7.30–7.35 (m, 4H), 7.89 (dd, 1H, J 8.6 and 3.0), 8.45 (m, 1H).

Example 64 (General Procedure 2)

Piperidine-1-carboxylic acid 4-(5-trifluoromethyl-pyridin-2-yloxy)-phenyl ester

The title compound was prepared from 4-(5-trifluoromethyl-pyridin-2-yloxy)-phenol and 1-methyl-3-(piperidine-1-carbonyl)-3H-imidazol-1-ium iodide. The crude product was recrystallized (ethanol) (45%). HPLC-MS m/z=367.02 (M+1), Rt: 4.9 min.

$\delta_H$(300 MHz; CDCl$_3$): 1.65 (bs, 6H), 3.58 (d, 4H, J 21.4), 6.99 (d, 1H, J 8.7), 7.10–7.24 (m, 4H), 7.88 (dd, 1H, J 8.7 and 2.2), 8.44 (bs, 1H).

Example 65 (General Procedure 2)

2-Methyl-piperidine-1-carboxylic acid 4-(5-trifluoromethyl-pyridin-2-yloxy)-phenyl ester The title compound was prepared from 4-(5-trifluoromethyl-pyridin-2-yloxy)-phenol and 1-methyl-3-(2-methyl-piperidine-1-carbonyl)-3H-imidazol-1-ium iodide. The crude product was purified by flash chromatography using a Quad flash 25 (ethyl acetate/heptane (1:6), (71%, white crystals). HPLC-MS m/z=381.1 (M+1), Rt: 5.2 min.

$\delta_H$(300 MHz; CDCl$_3$): 1.26 (d, 3H), 1.40–1.85 (m, 6H), 3.03 (t, 1H), 4.11 (dd, 1H), 4.50–4.65 (m, 1H), 6.95–7.02 (d, 1H), 7.10–7.20 m, 4H), 7.88 (dd, 1H), 8.43 (bs, 1H).

Example 66 (General Procedure 2)

3-Methyl-piperidine-1-carboxylic acid 4-(5-trifluoromethyl-pyridin-2-yloxy)-phenyl ester The title compound was prepared from 4-(5-trifluoromethyl-pyridin-2-yloxy)-phenol and 1-methyl-3-(3-methyl-piperidine-1-carbonyl)-3H-imidazol-1-ium iodide. The crude product was purified by flash chromatography using a Quad flash 25 (ethyl acetate/heptane (1:6), (75%, white crystals). HPLC-MS m/z=381.1 (M+1), Rt: 5.4 min.

$\delta_H$(300 MHz; CDCl$_3$): 0.94 (d, 3H), 1.05–1.20 (m, 1H), 1.50–1.80 (m, 3H), 1.80–1.95 (m, 1H), 2.45–2.75 (dt, 1H), 2.80–3.00 (m, 1H), 4.00–4.25 (m, 2H), 6.95–7.05 (d, 1H), 7.10–7.25 (m, 4H), 7.88 (dd, 1H), 8.43 (bs, 1H).

Example 67 (General Procedure 2)

4-Methyl-piperidine-1-carboxylic acid 4-(5-trifluoromethyl-pyridin-2-yloxy)-phenyl ester The title compound was prepared from 4-(5-trifluoromethyl-pyridin-2-yloxy)-phenol and 1-methyl-3-(4-methyl-piperidine-1-carbonyl)-3H-imidazol-1-ium iodide. The crude product was purified by flash chromatography using a Quad flash 25 (ethyl acetate/heptane (1:6), (73%, white crystals). HPLC-MS m/z=381.1 (M+1), Rt: 5.4 min.

$\delta_H$(300 MHz; CDCl$_3$): 1.00 (d, 3H), 1.23 (dq, 2H), 1.52–1.65 (m, 1H), 1.70 (d, 2H), 2.75–3.05 (m, 2H), 4.15–4.35 (m, 2H), 6.99 (d, 1H), 7.05–7.20 (m, 4H), 7.88 (dd, 1H), 8.43 (s, 1H).

Example 68 (General Procedure 2)

4-Benzyl-piperidine-1-carboxylic acid 4-(5-trifluoromethyl-pyridin-2-yloxy)-phenyl ester The title compound was prepared from 4-(5-trifluoromethyl-pyridin-2-yloxy)-phenol and 1-methyl-3-(4-benzyl-piperidine-1-carbonyl)-3H-imidazol-1-ium iodide. The crude product was purified by flash chromatography using a Quad flash 25 (ethyl acetate/heptane (1:6), (72%, white crystals). HPLC-MS m/z=457.2 (M+1), Rt: 6.0 min.

$\delta_H$(300 MHz; CDCl$_3$): 1.20–1.40 (m, 2H), 1.65–1.85 (m, 3H), 2.59 (d, 2H), 2.70–3.00 (m, 2H), 4.15–4.35 (m, 2H), 6.99 (d, 1H), 7.05–7.22 (m, 6H), 7.22–7.35 (m, 3H), 7.88 (dd, 1H), 8.43 (bs, 1H).

Example 69 (General Procedure 2)

3,4-Dihydro-1H-isoquinoline-2-carboxylic acid 4-(5-trifluoromethyl-pyridin-2-yloxy)-phenyl ester The title compound was prepared from 4-(5-trifluoromethyl-pyridin-2-yloxy)-phenol and 3-(3,4-dihydro-1H-isoquinoline-2-carbonyl)-1-methyl-3H-imidazol-1-ium iodide. The crude product was recrystallized (ethanol) (53%). HPLC-MS m/z=415.2 (M+1), Rt: 5.3 min.

$\delta_H$(300 MHz; CDCl$_3$): 2.96 (d, 2H, J 4.9), 3.86 (dt, 2H, J 23.3 and 6.0), 4.79 (d, 2H, J 35.4), 7.00 (d, 1H, J 8.7), 7.10–7.23 (m, 8H), 7.88 (dt, 1H, J 8.7 and 2.1), 8.44 (s, 1H).

Example 70 (General Procedure 2)

3,4-Dihydro-2H-quinoline-1-carboxylic acid 4-(3,5-dichloro-pyridin-2-yloxy)-phenyl ester The title compound was prepared from 4-(3,5-dichloro-pyridin-2-yloxy)-phenol and 3-(3,4-dihydro-2H-quinoline-1-carbonyl)-1-methyl-3H-imidazol-1-ium iodide. The crude product was recrystallized (ethanol) (68%). HPLC-MS m/z=415.2 (M+1), Rt: 5.6 min.

$\delta_H$(300 MHz; CDCl$_3$): 2.05 (Qi, 2H, J 6.8), 2.85 (t, 2H, J 6.8), 3.92 (t, 2H, J 6.8), 7.06 (dt, (1H, J 7.4 and 1.1), 7.11–7.19 (m, 4H), 7.21 (t, 1H, J 2.8), 7.24 (t, 1H, J 2.7), 7.77 (d, 1H, J 2.3), 7.75–7.80 (m, 1H), 7.95 (d, 1H, J 2.39).

Example 71 (General Procedure 2)

3,4-Dihydro-2H-quinoline-1-carboxylic acid 4-(2-cyano-5-trifluoromethyl-pyridin-3-yloxy)-phenyl ester The title compound was prepared from 4-(2-cyano-5-trifluoromethyl-pyridin-3-yloxy)-phenol and 3-(3,4-dihydro-2H-quinoline-1-carbonyl)-1-methyl-3H-imidazol-1-ium iodide. The crude product was subjected to flash chromatography (Quad flash 12, dichlormethane) (43%, oil).

HPLC-MS m/z=440.2 (M+1), Rt: 5.2 min. $\delta_H$(300 MHz; CDCl$_3$): 2.07 (Qi, 2H, J 6.4), 2.87 (t, 2H, J 6.4), 3.94 (t, 2H, J 6.4), 7.25–7.04 m, 5H), 7.26–7.7.36 (m, 2H), 7.44 (d, 1H, J 1.5), 7.76 (bd, 1H, J 7.2), 8.64 (s, 1H).

Example 72 (General Procedure 3)

3,4-Dihydro-2H-quinoline-1-carboxylic acid 3-(3,4-dichloro-benzyl)-4-methyl-2-oxo-2H-chromen-7-yl ester The title compound was prepared from 3-(3,4-dichloro-benzyl)-7-hydroxy-4-methyl-2H-chromen-2-one and 3-(3,4-dihydro-2H-quinoline-1-carbonyl)-1-methyl-3H-imidazol-1-ium iodide. HPLC-MS m/z=494 (M+1), Rt: 5.86 min.

Example 73 (General Procedure 3)

3,4-Dihydro-2H-quinoline-1-carboxylic acid 3-benzyl-4-methyl-2-oxo-2H-chromen-7-yl ester The title compound was prepared from 3-benzyl-7-hydroxy-4-methyl-2H-chromen-2-one and 3-(3,4-dihydro-2H-quinoline-1-carbonyl)-1-methyl-3H-imidazol-1-ium iodide. HPLC-MS m/z=426 (M+1), Rt: 5.34 min.

Example 74 (General Procedure 3)

3,4-Dihydro-2H-quinoline-1-carboxylic acid 3-(2-chloro-6-fluoro-benzyl)-4-methyl-2-oxo-2H-chromen-7-yl ester The title compound was prepared from 3-(2-chloro-6-fluoro-benzyl)-7-hydroxy-4-methyl-2H-chromen-2-one and 3-(3,4-dihydro-2H-quinoline-1-carbonyl)-1-methyl-3H-imidazol-1-ium iodide. HPLC-MS m/z=478 (M+1), Rt: 5.58 min.

Example 75 (General Procedure 3)

3,4-Dihydro-2H-quinoline-1-carboxylic acid 3-(2,6-dichloro-benzyl)-4-methyl-2-oxo-2H-chromen-7-yl ester The title compound was prepared from 3-(2,6-dichloro-benzyl)-7-hydroxy-4-methyl-2H-chromen-2-one and 3-(3,4-dihydro-2H-quinoline-1-carbonyl)-1-methyl-3H-imidazol-1-ium iodide. HPLC-MS m/z=494 (M+1), Rt: 5.79 min.

Example 76 (General Procedure 3)

3,4-Dihydro-2H-quinoline-1-carboxylic acid 3-(2,6-dichloro-benzyl)-6-chloro-4-methyl-2-oxo-2H-chromen-7-yl ester The title compound was prepared from 3-(2,6-dichloro-benzyl)-6-chloro-7-hydroxy-4-methyl-2H-chromen-2-one and 3-(3,4-dihydro-2H-quinoline-1-carbonyl)-1-methyl-3H-imidazol-1-ium iodide. HPLC-MS m/z=530 (M+1), Rt: 6.09 min.

Example 77 (General Procedure 3)

3,4-Dihydro-2H-quinoline-1-carboxylic acid 3-(4-fluoro-benzyl)-4-methyl-2-oxo-2H-chromen-7-yl ester The title compound was prepared from 3-(4-fluoro-benzyl)-7-hydroxy-4-methyl-2H-chromen-2-one and 3-(3,4-dihydro-2H-quinoline-1-carbonyl)-1-methyl-3H-imidazol-1-ium iodide.
HPLC-MS m/z=444 (M+1), Rt: 5.36 min.

Example 78 (General Procedure 3)

3,4-Dihydro-2H-quinoline-1-carboxylic acid 6-chloro-3-(2-chloro-6-fluoro-benzyl)-4-n-propy-2-oxo-2H-chromen-7-yl ester The title compound was prepared from 3-(4-fluoro-benzyl)-6-chloro-7-hydroxy-4-n-propyl-2H-chromen-2-one and 3-(3,4-dihydro-2H-quinoline-1-carbonyl)-1-methyl-3H-imidazol-1-ium iodide. HPLC-MS m/z=506 (M+1), Rt: 6.01 min.

Example 79 (General Procedure 3)

3,4-Dihydro-2H-quinoline-1-carboxylic acid 3-(4-methoxy-phenyl)-4-methyl-2-oxo-2H-chromen-7-yl ester The title compound (130 mg, 59% yield, white solid) was prepared from 7-hydroxy-3-(4-methoxy-phenyl)-4-methylchromen-2-one (141 mg, 0.50 mmol) and 3-(3,4-dihydro-2H-quinoline-1-carbonyl)-1-methyl-3H-imidazol-1-ium iodide (188 mg, 0.51 mmol).

$^1$H NMR (300 MHz, DMSO-d$_6$): δ 2.00 (quintet, 2H), 2.30 (s, 3H), 2.82 (t, 2H), 3.81 (s, 3H), 3.88 (t, 2H), 7.02 (d, 2H), 7.08 (m, 1H), 7.19 (m, 2H), 7.27 (d, 2H), 7.31 (dd, 1H), 7.41 (d, 1H), 7.72 (d, 1H), 7.88 (d, 1H); HPLC-MS: m/z=442 (M+1); R$_t$=5.13 min.

Example 80 (General Procedure 3)

3,4-Dihydro-2H-quinoline-1-carboxylic acid 4-methyl-2-oxo-3-phenyl-2H-chromen-7-yl ester The title compound (150 mg, 73% yield, white solid) was prepared from 7-hydroxy-4-methyl-3-phenyl-chromen-2-one (126 mg, 0.50 mmol) and 3-(3,4-dihydro-2H-quinoline-1-carbonyl)-1-methyl-3H-imidazol-1-ium iodide (188 mg, 0.51 mmol).

$^1$H NMR (300 MHz, DMSO-d$_6$): δ 1.99 (quintet, 2H), 2.28 (s, 3H), 2.82 (t, 2H), 3.88 (t, 2H), 7.08 (m, 1H), 9.19 (m, 2H), 7.33 (m, 3H), 7.46 (m, 4H), 7.74 (d, 1H), 7.90 (d, 1H); HPLC-MS: m/z=412 (M+1); R$_t$=5.14 min.

Example 81 (General Procedure 3)

3,4-Dihydro-2H-quinoline-1-carboxylic acid 3-(2,5-dimethoxy-phenyl)-4-methyl-2-oxo-2H-chromen-7-yl ester The title compound (50 mg, 21% yield, white solid) was prepared from 3-(2,5-dimethoxy-phenyl)-7-hydroxy-4-methyl-chromen-2-one (156 mg, 0.50 mmol) and 3-(3,4-dihydro-2H-quinoline-1-carbonyl)-1-methyl-3H-imidazol-1-ium iodide (188 mg, 0.51 mmol).

$^1$H NMR (300 MHz, CDCl$_3$): δ 2.08 (quintet, 2H), 2.34 (s, 3H), 2.87 (t, 2H), 3.73 (s, 3H), 3.80 (s, 3H), 3.94 (t, 2H), 6.74 (m, 1H), 6.93 (m, 2H), 7.07–7.26 (m, 5H), 7.68 (d, 1H), 7.77 (br.d, 1H); HPLC-MS: m/z=472 (M+1); R$_t$=5.04 min.

Example 82 (General Procedure 3)

3,4-Dihydro-2H-quinoline-1-carboxylic acid 3-(3,4-dimethoxy-phenyl)-4-methyl-2-oxo-2H-chromen-7-yl ester The title compound (50 mg, 21% yield, oil) was prepared from 3-(3,4-dimethoxy-phenyl)-7-hydroxy-4-methyl-chromen-2-one (156 mg, 0.50 mmol) and 3-(3,4-dihydro-2H-quinoline-1-carbonyl)-1-methyl-3H-imidazol-1-ium iodide (188 mg, 0.51 mmol).

$^1$H NMR (300 MHz, CDCl$_3$): δ 2.08 (quintet, 2H), 2.33 (s, 3H), 2.88 (t, 2H), 3.89 (s, 3H), 4.03 (s, 3H), 4.06 (t, 2H), 6.65 (m, 2H), 6.96 (d, 1H), 7.05–7.25 (m, 5H), 7.68 (d, 1H), 7.77 (br.d, 1H); HPLC-MS: m/z=472 (M+1); R$_t$=5.14 min.

Example 83 (General Procedure 2)

7-Trifluoromethyl-3,4-dihydro-2H-quinoline-1-carboxylic acid 4-(5-trifluoromethyl-pyridin-2-yloxy)-phenyl ester The title compound was prepared from 4-(5-trifluoromethyl-pyridin-2-yloxy)-phenol and 1-methyl-3-(7-trifluoromethyl-3,4-dihydro-2H-quinoline-1-carbonyl)-3H-imidazol-1-ium iodide. The crude product was subjected to preparative HPLC (66%). HPLC-MS m/z: 483.1 (M+1), Rt: 5.87 min.

δ$_H$(200 MHz; CDCl$_3$): 2.08 (Qi, 2H), 2.90 (t, 2H), 3.98 (t, 2H), 7.03 (d, 1H), 7.1–7.40 (m, 6H), 7.90 (dd, 1H), 8.18 (s, 1H), 8.44 (d, 1H).

Example 84 (General Procedure 1)

Morpholine-4-carboxylic acid 4-(5-trifluoromethyl-pyridin-2-yloxy)-phenyl ester

The title compound was prepared from 4-(5-trifluoromethyl-pyridin-2-yloxy)-phenol and morpholine-4-carbonyl chloride. The crude product was purified by preparative HPLC (37%, white crystals). HPLC-MS m/z=369.1 (M+1), Rt: 4.3 min.

δ$_H$(300 MHz; CDCl$_3$): 3.59 (bs, 2H), 3.67 (bs, 2H), 3.76 (m, 4H), 7.01 (d, 1H, J 8.7), 7.12–7.18 (m, 2H), 7.16 (d, 2H, J 3.7), 7.90 (dd, 1H, J 8.7 and 2.6), 8.43 (s, 1H).

Example 85 (General Procedure 1)

Morpholine-4-carboxylic acid 4-(3,5-dichloro-pyridin-4-yloxy)-phenyl ester

The title compound was prepared from 4-(3,5-dichloro-pyridin-4-yloxy)-phenol and morpholine-4-carbonyl chloride. The crude product was purified by preparative HPLC (66%, white crystals. HPLC-MS m/z=368.9 (M+1), Rt: 4.0 min.

δ$_H$(300 MHz; CDCl$_3$): 3.57 (bs, 2H), 3.65 (bs, 2H) 3.74 (m, 4H), 6.83 (d, 1H, J 9), 6.83 (m, 1H) 7.08 (d, 1H, J 9), 7.08 (m, 1H), 8.56 (s, 2H).

Example 86 (General Procedure 1)

Morpholine-4-carboxylic acid 4-(4-trifluoromethyl-phenoxy)-phenyl ester

The title compound was prepared from 4-(4-trifluoromethyl-phenoxy)-phenol and morpholine-4-carbonyl chloride. The crude product was purified by preparative HPLC (74%, white crystals). HPLC-MS m/z=368.1 (M+1), Rt: 4.85 min.

δ$_H$(300 MHz; CDCl$_3$): 3.59 (bs, 2H), 3.68 (bs, 2H), 3.75 (m, 4H), 7.04 (d, 2H, J 6.4), 7.04 (m, 2H), 7.14 (d, 1H, J 9), 7.13 (m, 1H), 7.57 (d, 2H, J 8.3).

Example 87 (General Procedure 1)

Morpholine-4-carboxylic acid 4-tert-butoxy-phenyl ester

The title compound was prepared from 4-(tert-butoxy)-phenol and 4-morpholine-carbamoyl chloride. The crude product was recrystallized (ethanol) (69%, crystals); mp: 128.8–129.5° C. HPLC-MS m/z=280.1 (M+1), Rt: 3.6 min.

δ$_H$(300 MHz; CDCl$_3$): 1.33 (s, 9H, ), 3.58 (bs, 2H), 3.66 (bs, 2H), 6.8–7.1 (m, 4H)

Example 88 (General Procedure 1)

Morpholine-4-carboxylic acid 4-(3,5-dichloro-pyridin-2-yloxy)-phenyl ester

The title compound was prepared from 4-(3,5-dichloro-pyridin-2-yloxy)-phenol and morpholine-4-carbonyl chloride. The crude product was purified by preparative HPLC (45%, crystals. HPLC-MS m/z=369.1 (M+1), Rt: 4.3 min.

Example 89 (General Procedure 1)

Morpholine-4-carboxylic acid 3-(4-fluoro-benzyl)-4-methyl-2-oxo-2H-chromen-7-yl ester The title compound was prepared from 4-(5,7-bis-trifluoromethyl-[1,8]naphthypyridin-2-yloxy)-phenol and morpholine-4-carbonyl chloride. The crude product was tested without purification (≈100%). HPLC-MS m/z=488.0 (M+1), Rt: 5.0 min.

Example 90 (General Procedure 1)

Morpholine-4-carboxylic acid 4-(5,7-bis-trifluoromethyl-[1,8]naphthypyridin-2-yloxy)-phenyl ester The title compound was prepared from 4-(5,7-bis-trifluoromethyl-[1,8]naphthypyridin-2-yloxy)-phenol and morpholine-4-carbonyl chloride. The crude product was tested without purification (≈100%). HPLC-MS m/z=488.0 (M+1), Rt: 5.0 min.

Example 91 (General Procedure 3)

Morpholine-4-carboxylic acid 3-(3,4-dichloro-benzyl)-4-methyl-2-oxo-2H-chromen-7-yl ester The title compound was prepared from 3-(3,4-dichloro-benzyl)-7-hydroxy-4-methyl-2H-chromen-2-one and 3-(morpholine-4-carbonyl)-1-methyl-3H-imidazol-1-ium iodide. HPLC-MS m/z=448 (M+1), Rt: 4.73 min.

Example 92 (General Procedure 3)

Morpholine-4-carbamic acid 3-(benzyl)-4-methyl-2-oxo-2H-chromen-7-yl ester

The title compound was prepared from 3-(benzyl)-7-hydroxy-4-methyl-2H-chromen-2-one and 1-methyl-3-(morpholine-4-carbonyl)-3H-imidazol-1-ium iodide. HPLC-MS m/z=380 (M+1), Rt: 4.05 min.

Example 93 (General Procedure 3)

Morpholine-4-carbamic acid 3-(2-chloro-6-fluoro-benzyl)-4-methyl-2-oxo-2H-chromen-7-yl ester The title compound was prepared from 3-(2-chloro-6-fluoro-benzyl)-7-hydroxy-4-methyl-2H-chromen-2-one and 1-methyl-3-(morpholine-4-carbonyl)-3H-imidazol-1-ium iodide. HPLC-MS m/z=432 (M+1), Rt: 4.36 min.

Example 94 (General Procedure 3)

Morpholine-4-carbamic acid 3-(2,6-dichloro-benzyl)-4-methyl-2-oxo-2H-chromen-7-yl ester The title compound was prepared from 3-(2,6-dichloro-benzyl)-7-hydroxy-4-methyl-2H-chromen-2-one and 1-methyl-3-(morpholine-4-carbonyl)-3H-imidazol-1-ium iodide. HPLC-MS m/z=448 (M+1), Rt: 4.59 min.

Example 95 (General Procedure 3)

Morpholine-4-carbamic acid 3-(2,6-dichloro-benzyl)-4-methyl-2-oxo-2H-chromen-7-yl ester The title compound was prepared from 3-(2,6-dichloro-benzyl)-6-chloro-7-hydroxy-4-methyl-2H-chromen-2-one and 1-methyl-3-(morpholine-4-carbonyl)-3H-imidazol-1-ium iodide. HPLC-MS m/z=484 (M+1), Rt: 4.99 min.

Example 96 (General Procedure 3)

Morpholine-4-carbamic acid 3-(4-fluoro-benzyl)-4-methyl-2-oxo-2H-chromen-7-yl ester The title compound was prepared from 3-(4-fluoro-benzyl)-7-hydroxy-4-methyl-2H-chromen-2-one and 1-methyl-3-(morpholine-4-carbonyl)-3H-imidazol-1-ium iodide. HPLC-MS m/z=398 (M+1), Rt: 4.12 min.

Example 97 (General Procedure 3)

Morpholine-4-carbamic acid 6-chloro-3-(2,6-dichloro-benzyl)-4-n-propy-2-oxo-2H-chromen-7-yl ester The title compound was prepared from 3-(4-fluoro-benzyl)-6-chloro-7-hydroxy-4-n-propyl-2H-chromen-2-one and 1-methyl-3-(morpholine-4-carbonyl)-3H-imidazol-1-ium iodide. HPLC-MS m/z=460 (M+1), Rt: 4.90 min.

Example 98 (General Procedure 3)

Morpholine-4-carboxylic acid 4-methyl-2-oxo-3-phenyl-2H-chromen-7-yl ester

The title compound (75 mg, 41% yield, crystals) was prepared from 7-hydroxy-4-methyl-3-phenyl-chromen-2-one (126 mg, 0.50 mmol) and 1-methyl-3-(morpholine-4-carbonyl)-3H-imidazol-1-ium iodide (165 mg, 0.51 mmol).
$^1$H NMR (300 MHz, CDCl$_3$): δ 2.27 (s, 3H), 3.45 (br.s, 2H), 3.62 (br.s, 2H), 3.68 (m, 4H), 7.23 (dd, 1H), 7.32 (m, 3H), 7.43 (m, 3H), 7.87 (d, 1H); HPLC-MS: m/z=366 (M+1); R$_t$=3.79 min.

Example 99 (General Procedure 3)

Morpholine-4-carboxylic acid 3-(4-methoxy-phenyl)-4-methyl-2-oxo-2H-chromen-7-yl ester The title compound (120 mg, 61% yield, crystals) was prepared from 7-hydroxy-3-(4-methoxy-phenyl)-4-methyl-chromen-2-one (141 mg, 0.50 mmol) and 1-methyl-3-(morpholine-4-carbonyl)-3H-imidazol-1-ium iodide (165 mg, 0.51 mmol).
$^1$H NMR (300 MHz, DMSO-d$_6$): δ 2.29 (s, 3H), 3.43 (br.s, 2H), 3.61 (br.s, 2H), 3.66 (m, 4H), 3.81 (s, 3H), 7.01

(d, 2H), 7.20–7.30 (m, 4H), 7.84 (d, 1H); HPLC-MS: m/z=396 (M+1); $R_t$=3.80 min.

Example 100 (General Procedure 3)

Morpholine-4-carboxylic acid 3-(3,4-dimethoxy-phenyl)-4-methyl-2-oxo-2H-chromen-7-yl ester The title compound (120 mg, 56% yield) was prepared from 3-(3,4-dimethoxy-phenyl)-7-hydroxy-4-methyl-chromen-2-one (156 mg, 0.50 mmol) and 1-methyl-3-(morpholine-4-carbonyl)-3H-imidazol-1-ium iodide (165 mg, 0.51 mmol).
$^1$H NMR (300 MHz, DMSO-$d_6$): δ 2.29 (s, 3H), 3.46 (br.s, 2H), 3.62 (br.s, 2H), 3.67 (m, 4H), 3.74 (s, 3H), 3.81 (s, 3H), 6.83 (dd, 1H), 6.92 (d, 1H), 7.02 (d, 1H), 7.22 (dd, 1H), 7.30 (d, 1H), 7.85 (d, 1H); HPLC-MS: m/z=426 (M+1); $R_t$=3.80 min.

Example 101 (General Procedure 3)

Morpholine-4-carboxylic acid 3-(2,5-dimethoxy-phenyl)-4-methyl-2-oxo-2H-chromen-7-yl ester The title compound (120 mg, 56% yield) was prepared from 3-(2,5-dimethoxy-phenyl)-7-hydroxy-4-methyl-chromen-2-one (156 mg, 0.50 mmol) and 1-methyl-3-(morpholine-4-carbonyl)-3H-imidazol-1-ium iodide (165 mg, 0.51 mmol).
$^1$H NMR (300 MHz, CDCl$_3$): δ 2.23 (s, 3H), 3.60 (br.s, 2H), 3.74 (br.s, 2H+s, 3H), 3.80 (m, 4H+s, 3H), 6.73 (m, 1H), 6.92 (m, 2H), 7.13 (m, 2H), 7.64 (d, 1H); HPLC-MSA): m/z=426 (M+1); $R_t$=3.69 min.

Example 102 (General Procedure 2)

2.6-dimethyl-morpholine-4-carboxylic acid 4-(5-trifluoromethyl-pyridin-2-yloxy)-phenyl ester The title compound was prepared from 4-(5-trifluoromethyl-pyridin-2-yloxy)-phenol and 3-(2,6-dimethyl-morpholine-4-carbonyl)-1-methyl-3H-imidazol-1-ium iodide. The crude product was purified by preparative HPLC (39%, colorless oil). HPLC-MS m/z=397.1 (M+1), Rt: 4.64 min.
$δ_H$(200 MHz; CDCl$_3$): 1.22 (s, 3H), 1.25 (s, 3H), 2.50–3.00 (m, 2H), 3.55–3.9 (m, 2H), 4.00–3.30 bd, 2H), 6.90–7.50 (m, 5H), 7.91 (dd, 1H), 8.44 (bs, 1H).

Example 103

Dimethylcarbamic acid benzotriazol-1-yl ester

Example 104

2-Oxo-N-p-tolylacetamide O-(cyclohexylcarbamoyl)-oxime

Example 105

10,11-Dihydro-dibenzo[a,d]cyclohepten-5-one O-cyclohexylcarbamoyl-oxime

Example 106

1-(4-Chlorophenyl)-non-1-en-3-one O-cyclohexyl-carbamoyl-oxime

Example 107

1,7,7-Trimethyl-bicyclo[2.2.1]heptan-2-one O-cyclohexylcarbamoyl-oxime

Example 108

1-(4-Bromophenyl)-6-methyl-hept-1-en-3-one O-isopropylcarbamoyl-oxime

Example 109

1-(4-Chloro-phenyl)-non-1-en-3-one O-isopropyl-carbamoyl-oxime

Example 110

4-Bromo-2-(4-chlorobenzyl)-2H-pyrazole-3-carbaldehyde O-methylcarbamoyl-oxime

Example 111

1-(4-Bromophenyl)-6-methyl-hept-1-en-3-one O-propylcarbamoyl-oxime

Example 112

N-(4-Fluorobenzylcarbamoyloxy)-isobutyrimidoyl chloride

Example 113

N-(2-Hydroxy-2-phenylethylcarbamoyloxy)-isobutyrimidoyl chloride

Example 114

Dimethylcarbamic acid 6-methanesulfonyl-indol-1-yl ester

Example 115

1-Biphenyl-4-yl-3-methylamino-propenone-cyclohexyl-carbamic acid

Example 116

Dimethylcarbamic acid 4-oxo-1,2,3-benzotriazin-3-yl ester

Example 117

[1-(3-Chloro-5-trifluoromethyl-pyridin-2-yl)-1H-pyrrol-2-yl]-carbamic acid 4-chloro-phenyl ester

Example 118 (General Procedure 6)

N-Methyl-N-phenyl-5-hexylsulfanyl-3-p-tolyl-[1,2,4]triazole-1-carboxamide

The title compound was prepared from p-toluoyl chloride, 1-bromo-hexane and N-methyl-pheny-lcarbamoyl chloride. The crude product was recrystallized (ethanol/water); HPLC-MS m/z=409.2 (M+1), $R_t$: 6.66 min.

δ$_H$(300 MHz; [$^2$H$_6$]DMSO): 0.87 (t, 3H), 1.20–1.35 (m, 4H), 1.35–1.48 (m, 2H), 1.72 (Qi, 2H), 2.99 (s, 3H), 3.25 (t, 2H), 3.46 (s, 3H), 7.13–7.30 (m, 5H), 7.36 (t, 2H), 7.52 (d, 2H).

Example 119 (General Procedure 6)

N-Methyl-N-phenethyl-5-ethyl-3-(4-chlorophenyl)-[1,2,4]triazole-1-carboxamide

The title compound was prepared from 4-chlorobenzoyl chloride, 1-bromo-ethane and N-methyl-phenethyl-carbamoyl chloride. The crude product was subjected to preparative HPLC; HPLC-MS m/z=401.1 (M+1), R$_t$: 6.17 min.

δ$_H$(300 MHz; [$^2$H$_6$]DMSO): 1.37 (t, 3H), 2.98 (t, 2H), 3.11 (bs, 3H), 3.23 (Q, 2H), 3.80 (m, 2H), 7.10–7.40 (m, 5H), 7.58 (d, 2H), 8.03 (d, 2H).

Example 120 (General Procedure 6)

[3-(4-Chlorophenyl)-5-methylsulfanyl-[1,2,4]triazol-1-yl]-morpholin-4-yl-methanone The title compound was prepared from 4-chlorobenzoyl chloride, methyl iodide and morpholine-4-carbonyl chloride. The crude product was used without further purification; HPLC-MS m/z=339.1 (M+1), R$_t$: 4.68 min.

δ$_H$(300 MHz; [$^2$H$_6$]DMSO): 2.68 (s, 3H), 3.25–3.65 (m, 4H), 3.65–3.85 (m, 4H), 7.58 (d, 2H), 8.03 (d, 2H).

Example 121 (General Procedure 6)

N,N-Dimethyl-5-methylsulfanyl-3-naphthalen-2-yl-[1,2,4]triazole-1-carboxamide

The title compound was prepared from 2-naphthoyl chloride, methyl iodide and dimethyl carbamoyl chloride. The crude product was recrystallized from ethanol; HPLC-MS m/z=313.2 (M+1), R$_t$: 4.91 min.

δ$_H$(300 MHz; [$^2$H$_6$]DMSO): 2.74 (s, 3H), 3.18 (s, 6H), 7.53–7.65 (m, 2H), 7.92–8.00 (m, 1H), 8.00–8.17 (m, 3H), 8.62 (s, 1H).

Example 122 (General Procedure 6)

N,N-Dimethyl-3-(4-chloro-phenyl)-5-ethylsulfanyl-[1,2,4]triazole-1-carboxamide

The title compound was prepared from 2-naphthoyl chloride, methyl iodide and dimethyl carbamoyl chloride. The crude product was recrystallized from ethanol; HPLC-MS m/z=311.0 (M+1), R$_t$: 5.13 min.

δ$_H$(300 MHz; [$^2$H$_6$]DMSO): 1.39 (t, 3H), 3.13 (bs, 6H), 3.26 (q, 2H), 7.58 (d, 2H), 8.03 (d, 2H).

Example 123 (General Procedure 6)

N,N-Dimethyl-3-biphenyl-4-yl-5-methylsulfanyl-[1,2,4]triazole-1-carboxamide

The title compound was prepared from 3-biphenylcarbonyl chloride, methyl iodide and dimethyl carbamoyl chloride. The crude product was without further purification; HPLC-MS m/z=339.1 (M+1), R$_t$: 5.27 in.

δ$_H$(300 MHz; [$^2$H$_6$]DMSO): 2.70 (s, 3H), 3.16 (bs, 6H), 7.40 (t, 1H), 7.50 (t, 2H), 7.73 (d, 2H), 7.82 (d, 2H), 8.12 (d, 2H).

Example 124

N,N-Dimethyl-3-(4-chloro-phenyl)-5-methylsulfanyl-[1,2,4]triazole-1-carboxamide

Example 126

N-(4-Chlorophenyl)-3-(4-chlorophenyl)-5-(3-hydroxypropyl)-pyrazole-1-carboxamide

Example 127

5-Morpholin-4-yl-3-(4-phenoxyphenyl)-pyrazole-1-carboxylic acid phenethylamide

Example 128

N-Phenyl-4-(4-chlorobenzenesulfonyl)-5-(4-chlorophenyl)-pyrazole-1-carboxamide

Example 129

N-(3,4-Dichlorophenyl)-2-phenyl-benzimidazole-1-carboxamide

Example 130

Dimethyl-carbamic acid 5-isopropylsulfanyl-4-(3-trifluoromethyl-phenyl)-4H-[1,2,4]triazol-3-yl ester

Example 131

Dimethyl carbamic acid 1-benzyl-2-oxo-3,5-diphenyl-1,2-dihydro-pyridin-4-yl ester

Example 132

Dimethyl-carbamic acid 7-methoxy-1-methyl-2-oxo-1,2-dihydro-quinolin-4-yl ester

Example 133

Dimethyl carbamic acid 4-(3-chloro-phenyl)-5-(4-methyl-benzylsulfanyl)-4H-[1,2,4]triazol-3-yl ester

Example 134 (General Procedure 7)

4-Methyl-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenol and 1-methylpiperazine. White solid, m.p. 249–250° C. (decomp.); HPLC-MS m/z=458 (M+H), R$_t$: 3.15 min.; $^1$H NMR (DMSO-d$_6$): δ 11.56 (br, 1H, NH), 8.61–8.54 (br, 1H, py-H6), 8.30–8.20 (m, 1H, py-H4), 7.32–7.19 (d+br s, 5H, py-H3+C$_6$H$_4$), 4.5–3.0 (br, 10H, 8 CH+H$_2$O), 2.79 (s, 3H, CH$_3$); IR (KBr): ν 1713 (C=O).

Example 135 (General Procedure 7)

4-Benzyl-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenol and 1-benzylpiperazine. White solid, m.p. 229–231° C.; HPLC- MS m/z=458 (M+H), R$_t$: 3.15 min.; $^1$H NMR (DMSO-d$_6$): δ 11.17 (br, 1H, NH), 8.61–8.54 (br, 1H, py-H6), 8.30–8.20 (m, 1H, py-H4), 7.74–7.59 (m, 2H, arom.), 7.52–7.41 (m, 3H, arom.), 7.31–7.17 (d+br s, 5H, py-H3+C$_6$H$_4$), 4.5–4.0 (br, 4H, CH$_2$+2CH), 3.8–3.0 (br, 8H, 6CH+H$_2$O); IR (KBr): ν 1720 (C=O).

Example 136 (General Procedure 7)

4-(2-Hydroxyethyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenol and 1-(2-hydroxyethyl)-piperazine. White solid, m.p. 255° C.; HPLC-MS m/z=412 (M+H), R$_t$: 2.12 min.; $^1$H NMR (DMSO-d$_6$): δ 10.66 (br, 1H, NH), 8.61–8.54 (br, 1H, py-H6), 8.30–8.20 (m, 1H, py-H4), 7.32–7.20 (d+br s, 5H, py-H3+C$_6$H$_4$), 5.39 (br, 1H, OH), 4.18 (br, 2H), 3.87–3.70 (br t, 2H), 3.70–3.02 (br, 8H+water); IR (KBr): ν 1714 (C=O).

Example 137 (General Procedure 7)

4-(2-Oxo-2-pyrrolidin-1-yl-ethyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenol and 1-(pyrrolidinocarbonylmethyl)-piperazine. White solid, m.p. 224° C.; HPLC-MS m/z=479 (M+H), R$_t$: 2.73 min.; $^1$H NMR (DMSO-d$_6$): δ 10.43 (br, 1H, NH), 8.62–8.52 (br, 1H, py-H6), 8.31–8.20 (m, 1H, py-H4), 7.34–7.18 (d+br s, 5H, py-H3+C$_6$H$_4$), 4.40–3.05 (br, CH2 at 4.26+water at 3.37+ N—C—H), 2.03–1.72 (m, 4H, CH$_2$).

Example 138 (General Procedure 7)

4-Phenyl-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenol and 1-phenyl-piperazine (0.5 mmol). The crude product (0.15 g) was partitioned between ethyl acetate (4 ml) and ethyldiisopropylamine (0.04 ml) dissolved in water (4 ml). The organic layer was washed with water (2×5 ml), dried over sodium sulfate. The drying agent was filtered off, and the solvent was removed from the filtrate in vacuo to give the title compound (0.095 g). White crystals, m.p. 117° C.; HPLC-MS m/z=444 (M+H), R$_t$: 5.12 min.; $^1$H NMR (DMSO-d$_6$): δ 8.61–8.55 (br, 1H, py-H6), 8.29–8.20 (m, 1H, py-H4) 7.32–7.14 (m, 7H, py-H3+C$_6$H$_4$+2 arom.), 7.05–6.71 (m, 3H, arom.), 3.83–3.51 (br, 4H, 2CH$_2$), 3.28–2.99 (m, 4H, 2 CH$_2$).

Example 139 (General Procedure 8)

Methyl-phenyl-carbamic acid pyrazol-1-yl ester

The title compound was prepared from 1-hydroxypyrazole and N-methyl-N-phenylcarbamoyl chloride. The crude product was subjected to flash chromatography (Quad flash 25, EtOAc-heptane) (79%, oil which slowly crystallizes). HPLC-MS m/z=218.1 (M+1), Rt: 2.82 min. Mp 63–67° C.

δ$_H$(300 MHz; CDCl$_3$): 3.45 (bs, 3H), 6.28 (s, 3H), 7.30–7.47 (m, 7H).

Example 140 (General Procedure 8)

Methyl-phenyl-carbamic acid 4-bromo-pyrazol-1-yl ester

The title compound was prepared from 1-hydroxy-4-bromopyrazole and N-methyl-N-phenylcarbamoyl chloride. The crude product was subjected to flash chromatography (Quad flash 25, EtOAc-heptane) (89%, oil). HPLC-MS m/z=298.0 (M+1), Rt: 3.77 min.

δ$_H$(300 MHz; CDCl$_3$): 3.44 (bs, 3H), 7.32–7.47 (m, 7H).

Example 141 (General Procedure 8)

Methyl-phenyl-carbamic acid 3,4,5-tribromo-pyrazol-1-yl ester

The title compound was prepared from 1-hydroxy-3,4,5-bromopyrazole and N-methyl-N-phenylcarbamoyl chloride. The crude product was subjected to flash chromatography (Quad flash 25, EtOAc-heptane) (93%, colorless crystals). HPLC-MS m/z=455.8 (M+1), Rt: 4.88 min. Mp 115–119° C.

δ$_H$(300 MHz; CDCl$_3$): 3.44 (bs, 3H), 7.36–7.48 (m, 5H).

Example 142 (General Procedure 8)

Methyl-phenyl-carbamic acid 3-(4-methoxy-phenyl)-pyrazol-1-yl ester

The title compound was prepared from 1-hydroxy-3-(4-methoxyphenyl)pyrazole and N-methyl-N-phenylcarbamoyl chloride. The crude product was subjected to flash chromatography (Quad flash 25, EtOAc-heptane) (93%, oil). HPLC-MS m/z=346.1 (M+Na), Rt: 4.21 min.

δ$_H$(300 MHz; CDCl$_3$): 3.45 (bs, 3H), 3.84 (s, 3H), 6.50 (d, 1H), 6.91 (d, 2H), 7.30–7.48 (m, 6H), 7.70 (d, 2H).

Example 143 (General Procedure 8)

Methyl-phenyl-carbamic acid imidazol-1-yl ester

The title compound was prepared from 1-hydroxyimidazole and N-methyl-N-phenylcarbamoyl chloride. The crude product was subjected to flash chromatography (Quad flash 25, EtOAc-heptane) (68%, oil). HPLC-MS m/z=218.1 (M+1), Rt: 1.53 min.

δ$_H$(300 MHz; CDCl$_3$): 3.45 (bs, 3H), 7.00 (bs, 1H), 7.05 (bs, 1H), 7.32–7.49 (m, 5H), 7.55 (bs, 1H).

Example 144 (General Procedure 8)

Methyl-phenyl-carbamic acid [1,2,3]triazol-1-yl ester

The title compound was prepared from 1-hydroxy-1,2,3-triazole and N-methyl-N-phenylcarbamoyl chloride. The crude product was subjected to flash chromatography (Quad flash 25, EtOAc-heptane) (80%, oil). HPLC-MS m/z=219.1 (M+1), Rt: 2.50 min. Mp 105–106° C.

δ$_H$(300 MHz; CDCl$_3$): 3.46 (bs, 3H), 7.00 (bs, 1H), 7.05 (bs, 1H), 7.31–7.48 (m, 5H), 7.62 (bs, 1H), 7.74 (s, 1H).

Example 145 (General Procedure 7)

4-(Isopropylcarbamoyl-methyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenol and 1-methyl-piperazine. White solid, m.p. 234–235° C.; HPLC-MS m/z=466 (M+H), $R_t$: 2.75 min.; $^1$H NMR (DMSO-$d_6$): δ 10.50 (br, 1H, NH), 8.66–8.54 (br, 2H, NH+py-H6), 8.30–8.20 (dd, 1H, py-H4), 7.31–7.20 (d+br s, 5H, py-H3+$C_6H_4$), 4.00–3.82 (br m, 5H, methin+4 CH), 3.70–3.09 (br, 9H, 6H+water), 1.11 (d, 6H, $CH_3$).

Example 146 (General Procedure 9)

4-Cyclopentyl-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-cyclopentyl-piperazine. White solid, m.p. 294–295° C.; HPLC-MS m/z=436 (M+H), $R_t$: 2.92 min.; $^1$H NMR (DMSO-$d_6$): δ 11.15 (br, 1H, NH), 8.60–8.55 (br, 1H, py-H6), 8.29–8.20 (m, 1H, py-H4), 7.32–7.21 (d+br s, 5H, py-H3+$C_6H_4$), 4.35–3.98 (br, 2H), 3.72–3.37 (br m, 5H), 3.29–2.97 (br, 2H), 2.12–1.45 (br m, 8H).

Example 147 (General Procedure 9)

4-Butyl-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-butyl-piperazine. White solid, m.p. 221–222° C.; HPLC-MS m/z=424 (M+H), $R_t$: 2.94 min.; $^1$H NMR (DMSO-$d_6$): δ 10.86 (br, 1H, NH), 8.60–8.55 (br, 1H, py-H6), 8.29–8.21 (m, 1H, py-H4), 7.31–7.22 (d+br s, 5H, py-H3+$C_6H_4$), 4.32–4.03 (br, 2H), 3.65–3.44 (br m, 4H), 3.28–2.97 (br, 4H), 1.81–1.60 (br m, 2H), 1.45–1.22 (br, 4H), 0.92 (t, 3H, $CH_3$).

Example 148 (General Procedure 1)

4-(Methyl-phenyl-carbamoyloxy)-benzoic acid 2,5-dioxo-pyrrolidin-1-yl ester

The title product was prepared from 4-Hydroxy-benzoic acid 2,5-dioxo-pyrrolidin-1-yl ester and N-methyl-N-phenylcarbamoyl chloride. The crude product was recrystallized from methanol (74%, white crystals).

$^1$H NMR (CDCl$_3$): 8.13 (d, 2H), 7.38–7.55 (m, 6H), 7.30 (t, 1H), 3.37 (s, 3H), 2.89 (s, 4H).

Example 149 (General Procedure 10)

4-Hydroxymethyl-piperidine-1-carboxylic acid 4-(5-trifluoromethyl-pyridin-2-yloxy)-phenyl ester The title product was prepared from 4-(5-trifluoromethyl-pyridin)-2-yloxy)-phenol and 4-hydroxymethylpiperidine. The crude product was subjected to flash chromatography (ethyl acetate/heptane, 1:2→2:1) (78%, light yellow oil). The purified product was crystallized from ethyl acetate/heptane (51%, white solid). HPLC-MS: m/z=397.1 (M+1); $R_t$: 4.08 min.

$^1$H NMR (CDCl$_3$): δ 8.44 (s, 1H), 7.88 (dd, 1H), 7.17 (d, 2H), 7.13 (d, 2H), 7.00 (d, 2H), 4.45–4.20 (bs, 2H), 3.55 (t, 2H), 3.10–2.75 (m, 2H), 1.95–1.65 (m, 3H), 1.47 (t, 1H), 1.29 (dq, 2H).

Example 150 (General Procedure 10)

4-Oxo-piperidine-1-carboxylic acid 4-(5-trifluoromethyl-pyridin-2-yloxy)-phenyl ester The title product was prepared from 4-(5-trifluoromethyl-pyridin)-2-yloxy)-phenol and 4-piperidone monohydrate. The solvent used was a mixture of dichloromethane and dimethyl-formamide (1:1). The crude product was subjected to preparative HPLC (7%, oil). HPLC-MS: m/z=381.1 (M+1); $R_t$: 4.17 min.

Example 151 (General Procedure 10)

4-[5-(4-Dimethylamino-phenyl)-1H-pyrazol-3-yl]-piperidine-1-carboxylic acid 4-(5-trifluoromethyl-pyridin-2-yloxy)-phenyl ester The title product was prepared from 4-(5-trifluoromethyl-pyridin)-2-yloxy)-phenol and N,N-dimethyl-4-[3-(4-piperidinyl)-1H-pyrazol-5-yl]aniline. The solvent used was a mixture of dichloromethane and dimethylformamide (1:2). The crude product was subjected to preparative HPLC (4%, oil). HPLC-MS: m/z=552.2 (M+1); $R_t$: 4.17 min.

$^1$H NMR (CDCl$_3$): 8.44 (d, 1H), 7.89 (dd, 1H), 7.53 (d, 2H), 7.22–7.10 (m, 4H), 7.00 (d, 1H), 6.73 (d, 2H), 6.27 (s, 1H), 4.45–4.20 (ds, 2H), 3.25–2.95 (m, 3H), 2.88 (s, 6H), 2.15–2.00 (m, 2H), 1.90–1.70 (dq, 2H).

Example 152 (General Procedure 10)

4-(5-Furan-2-yl-1H-pyrazol-3-yl)-piperidine-1-carboxylic acid 4-(5-trifluoromethyl-pyridin-2-yloxy)-phenyl ester The title product was prepared from 4-(5-trifluoromethyl-pyridin)-2-yloxy)-phenol and 4-[3-(2-furyl)-1H-pyrazol-5-yl]piperidine. The solvent used was a mixture of dichloromethane and dimethylformamide (1:2). The crude product was subjected to preparative HPLC (4%, oil).

HPLC-MS: m/z=499.1 (M+1); $R_t$: 4.60 min. $^1$H NMR (CDCl$_3$): 8.44 (d, 1H), 7.89 (dd, 1H), 7.45 ((dd, 1H), 7.24–7.10 (m, 4H), 6.99 (d, 1H), 6.62 (d, 1H), 6.48 (dd, 1H), 6.34 (s, 1H), 4.40–4.25 (bs, 2H), 3.25–2.85 (m, 3H), 2.08 (d, 2H), 1.79 (dq, 2H).

Example 153 (General Procedure 10)

4-Benzylamino-piperidine-1-carboxylic acid 4-(5-trifluoromethyl-pyridin-2-yloxy)-phenyl ester The title product was prepared from 4-(5-trifluoromethyl-pyridin)-2-yloxy)-phenol and benzyl-piperidin-4-yl-amine. The crude product was subjected to preparative HPLC (20%, oil).

HPLC-MS: m/z=472.2 (M+1); $R_t$: 3.34 min.

Example 154 (General Procedure 10)

4-(3,4-Dihydro-1H-isoquinolin-2-ylmethyl)-piperidine-1-carboxylic acid 4-(5-trifluoromethyl-pyridin-2-yloxy)-phenyl ester The title product was prepared from 4-(5-trifluoromethyl-pyridin)-2-yloxy)-phenol and 2-Piperidin-4-ylmethyl-1,2,3,4-tetrahydro-isoquinoline. The crude product was subjected to preparative HPLC (12%, oil). HPLC-MS: m/z=512.2 (M+1); $R_t$: 3.21 min.

Example 155 (General Procedure 1)

Methyl-phenyl-carbamic acid 4-(1,3,5-trimethyl-1H-pyrazol-4-ylmethyl)-phenyl ester The title product was prepared from 4-[(1,3,5-trimethyl-1H-pyrazol-4-yl)methyl]phenol and N-methyl-N-phenylcarbamoyl chloride. The crude product was subjected to preparative HPLC (88%, oil). HPLC-MS: m/z=350.0 (M+1); $R_t$: 3.52 min. (66% purity).

Example 156 (General Procedure 10)

3-Hydroxymethyl-piperidine-1-carboxylic acid 4-(5-trifluoromethyl-pyridin-2-yloxy)-phenyl ester The title product was prepared from 4-(5-trifluoromethyl-pyridin)-2-yloxy)-phenol and 3-hydroxymethyl-piperidine. The crude product was subjected to flash chromatography (Quad Flash 12, ethyl acetate/heptane 1:2). (56%, colourless oil). HPLC-MS: m/z=397.1 (M+1); $R_t$: 4.19 min.
$^1$H NMR (DMSO-$d_6$, 90° C.): 8.37 (s, 1H), 8.00 (dd, 1H), 6.95–7.10 (m, 5H), 4.09 (bs, 1H), 3.91 (dd, 1H), 3.78 (d, 1H), 3.21 (m, 1H), 3.15 (t, 1H), 2.80–2.90 (m, 1H), 2.65 (t, 1H), 1.45–1.70 (m, 3H), 1.25–1.45 (m, 1H), 1.08 (q, 1H).

Example 157 (General Procedure 10)

3-Hydroxy-piperidine-1-carboxylic acid 4-(5-trifluoromethyl-pyridin-2-yloxy)-phenyl ester The title product was prepared from 4-(5-trifluoromethyl-pyridin)-2-yloxy)-phenol and 3-hydroxy-piperidine. The crude product was subjected to flash chromatography (Quad Flash 12, ethyl acetate/heptane (1:2) (56%, colourless oil). HPLC-MS: m/z=383.0 (M+1); $R_t$: 3.98 min.
$^1$H NMR (CDCl$_3$): 8.43 (s, 1H), 7.89 (dd, 1H), 7.23–7.10 (m, 4H), 7.00 (d, 1H), 3.80–4.00 (m, 2H), 3.60–3.80 (m, 1H), 3.25–3.50 (m, 2H), 1.80–2.05 (m, 2H), 1.50–1.70 (m, 3H).

Example 158 (General Procedure 10)

4-Benzyl-4-hydroxy-piperidine-1-carboxylic acid 4-(5-trifluoromethyl-pyridin-2-yloxy)-phenyl ester The title product was prepared from 4-(5-trifluoromethyl-pyridin)-2-yloxy)-phenol and 4-benzyl-4-hydroxypiperidine. The crude product was subjected to flash chromatography (Quad Flash 12, ethyl acetate/heptane (1:2) (48%, colourless oil). HPLC-MS: m/z=473.0 (M+1); $R_t$: 5.04 min.
$^1$H NMR (CDCl$_3$): 8.44 (s, 1H), 7.89 (dd, 1H), 7.28–7.45 (m, 3H), 7.10–7.24 (m, 6H), 7.00 (d, 1H), 4.00–4.14 (bs, 2H), 3.15–3.45 (dt, 2H), 2.81 (s, 2H), 1.66–1.85 (dt, 2H), 1.55–1.65 (m, 2H), 1.27 (s, 1H).

Example 159 (General Procedure 1)

Methyl-phenyl-carbamic acid 4-(2-cyano-ethyl)-phenyl ester

The title product was prepared from 3-(4-hydroxyphenyl) proprionitrile and N-methyl-N-phenylcarbamoyl chloride. The crude product was subjected to preparative HPLC (11%, colourless oil). HPLC-MS: m/z=281.2 (M+1); $R_t$: 3.75 min, purity 80%.
$^1$H NMR (CDCl$_3$): 7.26–7.50 (m, 7H), 7.00–7.15 (m, 2H), 3.42 (s, 3H), 2.94 (t, 2H), 2.59 8t, 2H).

Example 160 (General Procedure 1)

Methyl-phenyl-carbamic acid 4-([1,2,3,4]thiatriazol-5-ylamino)-phenyl ester

The title product was prepared from 4-(1,2,3,4-thiatriazol-5-ylamino)phenol and N-methyl-N-phenylcarbamoyl chloride. The crude product was subjected to preparative HPLC. (10%, light brown solid material). HPLC-MS: m/z=328.0 (M+1); $R_t$: 3.69 min, purity 81%.
$^1$H NMR (CDCl$_3$): 7.61 (d, 2H), 7.38–7.52 (m, 4H), 7.19–7.35 (m, 2H), 6.86–6.95 (m, 1H), 3.35 (s, 3H), 3.33 (s, 1H).

Example 161 (General Procedure 1)

Methyl-phenyl-carbamic acid 4-pentyl-phenyl ester

The title product was prepared from 4-pentylphenol and N-methyl-N-phenylcarbamoyl chloride. The crude product was subjected to preparative HPLC. (4%, light brown oil). HPLC-MS: m/z=298.2 (M+1); $R_t$: 5.61 min.
$^1$H NMR (CDCl$_3$): 7.31–7.50 (m, 4H), 7.18–7.30 (m, 1H), 7.13 (d, 2H), 7.00 d, 2H), 3.42 (s, 3H), 2.57 (t, 2H), 1.58 (qi, 2H), 1.20–1.40 (m, 4H), 0.87 (t, 3H).

Example 162 (General Procedure 1)

Methyl-phenyl-carbamic acid 4-(2-methoxy-ethyl)-phenyl ester

The title product was prepared from 4-(2-methoxyethyl) phenol and N-methyl-N-phenylcarbamoyl chloride. The crude product was subjected to preparative HPLC. (4%, light yellow oil). HPLC-MS: m/z=286.1 (M+1); $R_t$: 4.01 min.
$^1$H NMR (CDCl$_3$): 7.30–7.48 (m, 4H), 7.12–7.30 (m, 3H), 7.03 (d, 2H), 3.56 (t, 2H), 3.42 (s, 3H), 3.33 (s, 3H), 2.85 (t, 2H).

Example 163 (General Procedure 10)

4-Hydroxy-piperidine-1-carboxylic acid 4-(5-trifluoromethyl-pyridin-2-yloxy)-phenyl ester The title product was prepared from 4-(5-trifluoromethyl-pyridin)-2-yloxy)-phenol and 4-hydroxypiperidine. The crude product was subjected to flash chromatography (ethyl acetate/heptane (1:1) (48%, light yellow oil). HPLC-MS: m/z=383.0 (M+1); $R_t$: 3.88 min. purity 93%.
$^1$H NMR (CDCl$_3$): 8.44 (s, 1H), 7.89 (dd, 1H), 7.08–7.20 (m, 4H), 6.99 (d, 1H), 3.85–4.10 (m, 3H), 3.20–3.45 (m, 2H), 1.85–2.02 (m, 2H), 1.50–1.70 (m, 3H).

Example 164 (General Procedure 1)

Methyl-phenyl-carbamic acid 4-acetyl-phenyl ester

The title product was prepared from 4'-hydroxyacetophenone and N-methyl-N-phenylcarbamoyl chloride. The crude product was subjected to preparative HPLC. (78%, colourless oil). HPLC-MS: m/z=270.1 (M+1); $R_t$: 3.62 min.
$^1$H NMR (CDCl$_3$): 7.96 (d, 2H), 7.15–7.7.48 (m, 7 H), 3.43 (s, 3H), 2.58 (s, 3H).

Example 165 (General Procedure 1)

Methyl-phenyl-carbamic acid pyridin-4-yl ester

The title product was prepared from 4-hydroxypyridine and N-methyl-N-phenylcarbamoyl chloride. The crude product was subjected to preparative HPLC. (11%, yellow solid). HPLC-MS: m/z=229.2 (M+1); $R_t$: 1.66 min, purity: 67%.

Example 166 (General Procedure 1)

Methyl-phenyl-carbamic acid pyridin-3-yl ester

The title product was prepared from 3-hydroxypyridine and N-methyl-N-phenylcarbamoyl chloride. The crude product was subjected to preparative HPLC. (94%, colourless oil).
HPLC-MS: m/z=229.2 (M+1); $R_t$: 2.54 min. $^1$H NMR (CDCl$_3$): 10.70 (bs, 1H), 8.50 (d, 1H), 8.45–8.65 (m, 1H), 7.70–7.90 (m, 1H), 7.51 (dd, 1H), 7.42 (d, 2H), 7.34 (d, 2H), 7.28–7.37 (m, 1H), 3.43 (s, 3H).

Example 167 (General Procedure 1)

Methyl-phenyl-carbamic acid 6-methyl-pyridin-3-yl ester

The title product was prepared from 3-hydroxy-6-methylpyridine and N-methyl-N-phenylcarbamoyl chloride. The crude product was subjected to preparative HPLC. (79%, colourless oil). HPLC-MS: m/z=243.1 (M+1); $R_t$: 2.24 min.
$^1$H NMR (CDCl$_3$): 10.8 (bs, 1H), 8.54 (m, 1H), 7.76 (m, 1H), 7.26–7.50 (m, 6H), 3.42 (s, 3H), 2.69 (s, 3H).

Example 168 (General Procedure 1)

Methyl-phenyl-carbamic acid isoquinolin-1-yl ester

The title product was prepared from and N-methyl-N-phenylcarbamoyl chloride. The crude product was subjected to preparative HPLC. (15%, colourless oil). HPLC-MS: m/z=279.1 (M+1); $R_t$: 3.67 min.

Example 169 (General Procedure 1)

Methyl-phenyl-carbamic acid 3-phenoxy-phenyl ester

The title product was prepared from 3-phenoxyphenol and N-methyl-N-phenylcarbamoyl chloride. The crude product was subjected to preparative HPLC. (79%, colourless oil).
HPLC-MS: m/z=320.1 (M+1); $R_{t: 5.16}$ min. $^1$H NMR (CDCl$_3$): 7.20–7.50 (m, 8 H), 7.11 (t, 1H), 6.95–7.06 (m, 2H), 6.70–6.93 (m, 3H), 3.40 (s, 3H).

Example 170 (General Procedure 1)

Methyl-phenyl-carbamic acid 3-acetyl-phenyl ester

The title product was prepared from m-hydroxyacetophenone and N-methyl-N-phenylcarbamoyl chloride. The crude product was subjected to preparative HPLC. (62%, colorless oil). HPLC-MS: m/z=270.1 (M+1); $R_t$: 3.56 min.
$^1$H NMR (CDCl$_3$): 7.78 (d, 1H), 7.68 (s, 1H), 7.22–7.50 (m, 7H), 3.43 (s, 3H), 2.58 (s, 3H).

Example 171 (General Procedure 1)

Methyl-phenyl-carbamic acid 4-acetyl-2-carbamoyl-phenyl ester

The title product was prepared from 5-acetylsalicylamide and N-methyl-N-phenylcarbamoyl chloride. The crude product was subjected to preparative HPLC. (87%, white solid). HPLC-MS: m/z=313.1 (M+1); $R_t$: 2.51 min.
$^1$H NMR (CDCl$_3$): 8.47 (bs, 1H), 8.08 (dd, 1H), 7.30–7.52 (m, 6H), 6.05 (bs, 1H), 5.38 (bs, 1H), 3.43 (s, 3H), 2.61 (s, 3H).

Example 172 (General Procedure 1)

Methyl-phenyl-carbamic acid 4-acetyl-3-methyl-phenyl ester

The title product was prepared from 4'-hydroxy-2'-methylacetophenone and N-methyl-N-phenylcarbamoyl chloride. The crude product was subjected to preparative HPLC. (76%, white crystals). HPLC-MS: m/z=284.2 (M+1); $R_t$: 3.95 min.
$^1$H NMR (CDCl$_3$): 7.72 (d, 1H), 7.22–7.47 (m, 5H), 6.90–7.12 (m, 2H), 3.43 (s, 3H), 2.55 (s, 3H), 2.52 (s, 3H).

Example 173 (General Procedure 1)

Methyl-phenyl-carbamic acid 1-oxo-indan-4-yl ester

The title product was prepared from 4-hydroxyindanone and N-methyl-N-phenylcarbamoyl chloride. The crude product was subjected to preparative HPLC. (77%, light yellow oil).
HPLC-MS: m/z=282.1 (M+1); $R_t$: 3.54 min. $^1$H NMR (CDCl$_3$): 7.61 (d, 1H), 7.27–7.50 (m, 7H), 3.45 (s, 3H), 3.00 (ds, 2H), 2.67 (t, 2H).

Example 174 (General Procedure 1)

Methyl-phenyl-carbamic acid benzothiazol-2-yl ester

The title product was prepared from 2-benzothiazolol and N-methyl-N-phenylcarbamoyl chloride. The crude product was subjected to preparative HPLC. (70%, white crystals). HPLC-MS: m/z=307.1 (M+1); $R_t$: 4.24 min, purity 85%.
$^1$H NMR (CDCl$_3$): 7.78 (m, 2H), 7.28–7.50 (m, 7H), 3.40–3.70 (d, 3H).

Example 175 (General Procedure 1)

Methyl-phenyl-carbamic acid 5-oxo-5,6,7,8-tetrahydro-naphthalen-2-yl ester

The title product was prepared from 6-hydroxy-1-tetralone and N-methyl-N-phenylcarbamoyl chloride. The crude product was subjected to preparative HPLC. (49%, colorless oil). HPLC-MS: m/z=296.2 (M+1); $R_t$: 3.90 min.
$^1$H NMR (CDCl$_3$): 8.04 (d, 2H), 7.27–7.50 (m, 5H), 7.00–7.10 (m, 2H), 3.42 (s, 3H), 2.94 (t, 2H), 2.63 (t, 2H), 2.12 (qu, 2H).

Example 176 (General Procedure 1)

Methyl-phenyl-carbamic acid benzo[d]isoxazol-3-yl ester

The title product was prepared from benzo[d]isoxazol-3-ol and N-methyl-N-phenylcarbamoyl chloride. The crude product was subjected to preparative HPLC. (53%, colorless oil). HPLC-MS: m/z=291.1 (M+23); $R_t$: 4.05 min.
$^1$H NMR (CDCl$_3$): 7.60–7.75 (m, 1H), 7.49–7.60 (m, 2H), 7.38–7.48 (m, 4H), 7.28–7.36 (m, 2H), 3.46 (s, 3H).

Example 177 (General Procedure 1)

Methyl-phenyl-carbamic acid pyridin-2-yl ester

The title product was prepared from 2-hydroxypyridine and N-methyl-N-phenylcarbamoyl chloride. The crude product was subjected to preparative HPLC. (57%, colorless oil). HPLC-MS: m/z=229.1 (M+23); $R_t$: 2.80 min.
$^1$H NMR (CDCl$_3$): 8.38 (d, 1H), 7.75 (t, 1H), 7.35–7.45 (m, 4H), 7.22–7.34 (m, 1H), 7.14–7.21 (t, 1H), 6.99–7.15 (bs, 1H), 3.44 (s, 3H).

Example 178 (General Procedure 1)

Methyl-phenyl-carbamic acid 1-(methyl-phenyl-carbamoyl)-1H-benzimidazol-2-yl ester The title product was prepared from 2-hydroxybenzimidazole and N-methyl-N-phenylcarbamoyl chloride. The crude product was subjected to preparative HPLC. (14%, white crystals). HPLC-MS: m/z=401.2 (M+1); $R_t$: 3.88 min, purity: 83%.
$^1$H NMR (CDCl$_3$): 7.32 (dd, 2H), 7.24–7.28 (m, 2H), 7.21–7.24 (m, 2H), 7.29 (t, 1H), 7.12–7.19 (m, 5H), 7.09–7.15 m, 2H), 3.28 (s, 6H).

Example 179 (General Procedure 1)

Methyl-phenyl-carbamic acid 4-[(pyridine-3-carbonyl)-amino]-phenyl ester

The title product was prepared from N-(4-Hydroxy-phenyl)-nicotinamide and N-methyl-N-phenylcarbamoyl chloride. The crude product was subjected to preparative HPLC. (1%, light yellow crystals). HPLC-MS: m/z=348.1 (M+1); $R_t$: 2.96 min.

Example 180 (General Procedure 11)

4-Pyrrolidin-1-yl-piperidine-1-carboxylic acid 4-(5-trifluoromethyl-pyridin-2-yloxy)-phenyl ester The title product was prepared from 4-(5-trifluoromethyl-pyridin)-2-yloxy)-phenol and 4-(1-pyrrolidinyl)piperidine. The crude product was used without further purification (68%, white solid). HPLC-MS: m/z=436.2 (M+1); $R_t$: 2.98 min.
$^1$H NMR (DMSO-d6): 10.90 (bs, 1H), 8.57 (s, 1H), 8.24 (dd, 1H), 7.15–7.30 (m, 5H), 4.00–4.40 (m, 2H), 3.45–3.60 (m, 2H), 2.75–3.25 (m, 4H), 2.05–2.25 (d, 2H), 1.80–2.05 (m, 5H), 1.60–1.80 (m, 2H).

Example 181 (General Procedure 12)

Methyl-o-tolyl-carbamic acid 4-(trifluoromethyl-pyridin-2-yloxy)-phenyl ester

The title product was prepared from 4-(5-trifluoromethyl-pyridin)-2-yloxy)-phenol and N-methyl-o-toluidine. The crude product was subjected to preparative HPLC (51%, colorless oil). HPLC-MS: m/z=403.2 (M+1); $R_t$: 4.89 min.
$^1$H NMR (CDCl$_3$): 8.40 (s, 1H), 7.87 (dd, 1H), 7.05–7.18 (m, 4H), 6.96 (d, 1H), 3.30 (s, 3H), 2.36 (s, 3H).

Example 182 (General Procedure 12)

Methyl-pyridin-2-yl-carbamic acid 4-(5-trifluoromethyl-pyridin-2-yloxy)-phenyl ester The title product was prepared from 4-(5-trifluoromethyl-pyridin)-2-yloxy)-phenol and 2-(methylamino)pyridine. The crude product was subjected to preparative HPLC (55%, white solid). HPLC-MS: m/z=390.1 (M+1); $R_t$: 4.31 min.

Example 183 (General Procedure 12)

Methyl-m-tolyl-carbamic acid 4-(5-trifluoromethyl-pyridin-2-yloxy)-phenyl ester

The title product was prepared from 4-(5-trifluoromethyl-pyridin)-2-yloxy)-phenol and N-methyl-m-toluidine. The crude product was subjected to preparative HPLC (51%, colorless oil). HPLC-MS: m/z=403.2 (M+1); $R_t$: 4.98 min.
$^1$H NMR (CDCl$_3$): 8.42 (s, 1H), 7.88 (dd, 1H), 7.28 (d, 1H), 7.05–7.25 (m, 7H), 6.97 (d, 1H), 3.41 (s, 3H), 2.38 (s, 3H).

Example 184 (General Procedure 12)

(3-Chloro-phenyl)-methyl-carbamic acid 4-(5-trifluoromethyl-pyridin-2-yloxy)-phenyl ester The title product was prepared from 4-(5-trifluoromethyl-pyridin)-2-yloxy)-phenol and 3-chloro-N-methylaniline. The crude product was subjected to preparative HPLC (54%, colorless oil). HPLC-MS: m/z=423.1 (M+1); $R_t$: 5.07 min.
$^1$H NMR (CDCl$_3$): 8.42 (m, 1H), 7.88 (dd, 1H), 7.39 (m, 1H), 7.33 (t, 1H), 7.22–7.30 (m, 2H), 7.10–7.7.22 (m, 4H), 6.99 (d, 1H), 3.43 (s, 3H).

Example 185 (General Procedure 12)

Methyl-p-tolyl-carbamic acid 4-(5-trifluoromethyl-pyridin-2-yloxy)-phenyl ester

The title product was prepared from 4-(5-trifluoromethyl-pyridin)-2-yloxy)-phenol and N-methyl-p-toluidine. The crude product was subjected to preparative HPLC (54%, white solid).

HPLC-MS: m/z=403.2 (M+1); $R_t$: 4.99 min. $^1$H NMR (CDCl$_3$): 8.42 (s, 1H), 7.87 (dd, 1H), 7.05–7.30 (m, 8H), 6.98 (d, 1H), 3.40 (s, 3H), 2.36 (s, 3H).

Example 186 (General Procedure 14)

Methyl-phenyl-carbamic acid 4-(3-pyridin-3-yl-acryloyl)-phenyl ester

The title product was prepared from 1-(4-hydroxy-phenyl)-3-pyridin-3-yl-prop-2-en-1-one and N-methyl-N-phenylcarbamoyl chloride. The crude product was subjected to preparative HPLC (56%, off-white solid). HPLC-MS: m/z=359.0 (M+1); $R_t$: 3.27 min.

$^1$H NMR (CDCl$_3$): 8.87 (d, 1H), 8.65 (dd, 1H), 8.03 (d, 2H), 7.97 (dt, 1H), 7.79 (d, 1H), 7.57 (d, 1H), 7.33–7.47 (m, 5H), 7.27–7.33 (m, 3H), 3.44 (s, 3H), 3.49 (t, 1H), 1.21 (t, 1H).

Example 187 (General Procedure 14)

Methyl-phenyl-carbamic acid 4-[3-(3,4,5-trimethoxy-phenyl)-acryloyl]-phenyl ester The title product was prepared from 1-(4-hydroxyphenyl)-3-(3,4,5-trimethoxyphenyl)prop-2-en-1-one and N-methyl-N-phenylcarbamoyl chloride. The crude product was subjected to preparative HPLC (82%, yellow solid). HPLC-MS: m/z=448.2 (M+1); $R_t$: 4.61 min.

$^1$H NMR (CDCl$_3$): 8.01 (d, 2H), 7.70 (d, 1H), 7.33–7.47 (m, 4H), 7.28–7.33 (m, 2H), 6.86 (s, 1H), 3.92 (s, 6H), 3.90 (s, 3H), 3.45 (s, 3H).

Example 188 (General Procedure 14)

Methyl-phenyl-carbamic acid 4-diethylcarbamoyl-2-methoxy-phenyl ester

The title product was prepared from N,N-diethyl-4-hydroxy-3-methoxy-benzamide and N-methyl-N-phenylcarbamoyl chloride. The crude product was subjected to preparative HPLC (58%, colorless oil). HPLC-MS: m/z=357.1 (M+1); $R_t$: 3.64 min.

$^1$H NMR (CDCl$_3$): 7.34–7.44 (m, 4H), 7.21–7.28 (m, 1H), 7.03–7.09 (d, 1H), 6.99 (d, 1H), 6.90 (dd, 1H), 3.87 (s, 3H), 3.15–3.65 (bs, 4H), 3.43 (s, 3H), 1.05–1.35 (m, 6H).

Example 189 (General Procedure 14)

Methyl-phenyl-carbamic acid 3-phenylcarbamoyl-phenyl ester

The title product was prepared from 3-hydroxy-N-phenyl-benzamide and N-methyl-N-phenylcarbamoyl chloride. The crude product was subjected to preparative HPLC (54%, white solid). HPLC-MS: m/z=347.2 (M+1); $R_t$: 4.01 min.

$^1$H NMR (CDCl$_3$): 7.76 (s, 1H), 7.68 (d, 1H), 7.58–7.65 (m, 3H), 7.27–7.51 (m, 8H), 7.15 (t, 1H), 3.44 (s, 3H).

Example 190 (General Procedure 14)

Methyl-phenyl-carbamic acid quinolin-7-yl ester

The title product was prepared from 7-hydroxyquinoline and N-methyl-N-phenylcarbamoyl chloride. The crude product was subjected to preparative HPLC (28%, white solid). HPLC-MS: m/z=279.1 (M+1); $R_t$: 2.55 min.

$^1$H NMR (CDCl$_3$): 8.93 (dd, 1H), 8.18 (d, 1H), 7.83–7.86 (m, 1H), 7,82 (d, 1H), 7.35–7.50 (m, 6H), 7.27–7.32 (m, 1H), 3.47 (s, 1H).

Example 191 (General Procedure 14)

Methyl-phenyl-carbamic acid 4-(4-methyl-piperazine-1-carbonyl)-phenyl ester

The title product was prepared from 1-(4-hydroxybenzoyl)-4-methyl-piperazine and N-methyl-N-phenylcarbamoyl chloride. The crude product was subjected to preparative HPLC (22%, colorless oil). HPLC-MS: m/z=354.1 (M+1); $R_t$: 2.07 min.

$^1$H NMR (CDCl$_3$): 7.37–7.49 (m, 4H), 7.28–7.37 (m, 3H), 7.16–7.25 (m, 2H), 4.60–4.00 (bs, 2H), 3.43 (s, 3H), 3.35–3.90 (bs, 4H), 2.82 (s, 3H), 2.55–2.90 (bs, 2H).

Example 192 (General Procedure 14)

Methyl-phenyl-carbamic acid 3-acetylamino-phenyl ester

The title product was prepared from 3-acetamidophenol and N-methyl-N-phenylcarbamoyl chloride. The crude product was subjected to preparative HPLC (66%, white solid). HPLC-MS: m/z=285.1 (M+1); $R_t$: 3.09 min.

$^1$H NMR (CDCl$_3$): 7.40–7.49 (m, 1H), 7.31–7.40 (m, 5H), 7.25–7.30 (m, 1H), 7.22 (d, 1H), 7.14 (d, 1H), 6–84 (bd, 1H), 3.42 (s, 3H), 2.10 (s, 3H).

Example 193 (General Procedure 14)

Methyl-phenyl-carbamic acid 4-benzoyl-phenyl ester

The title product was prepared from (4-hydroxy-phenyl)-phenyl-methanone and N-methyl-N-phenylcarbamoyl chloride. The crude product was subjected to preparative HPLC (36%, colorless oil). HPLC-MS: m/z=332.2 (M+1); $R_t$: 4.42 min.

$^1$H NMR (CDCl$_3$): 7.75–7.85 (m, 4H), 7.58 (tt, 1H), 7.33–7.52 (m, 6H), 7.27–7.32 (m, 1H), 7.18–7.25 (m, 2H), 3.44 (s, 3H).

Example 194 (General Procedure 14)

Methyl-phenyl-carbamic acid biphenyl-3-yl ester

The title product was prepared from 3-phenylphenol and N-methyl-N-phenylcarbamoyl chloride. The crude product was subjected to preparative HPLC (52%, colorless oil). HPLC-MS: m/z=304.2 (M+1); $R_t$: 4.75 min.

$^1$H NMR (CDCl$_3$): 7.52–7.67 (m, 2H), 7.22–7.52 (m, 11H), 7.03–7.22 (m, 1H), 3.45 (s, 3H).

Example 195 (General Procedure 14)

Methyl-phenyl-carbamic acid 1H-indol-4-yl ester

The title product was prepared from 4-hydroxyindole and N-methyl-N-phenylcarbamoyl chloride. The crude product was subjected to preparative HPLC (48%, off-white solid). HPLC-MS: m/z=267.1 (M+1); $R_t$: 3.57 min.

$^1$H NMR (CDCl$_3$): 8.20 (ds, 1H), 7.36–7.50 (m, 4H), 7.17–7.35 (m, 2H), 7.08–7.17 (m, 2H), 6.94 (d, 1H), 6.44 (s, 1H), 3.48 (s, 3H).

Example 196 (General Procedure 14)

Methyl-phenyl-carbamic acid 5,6,7,8-tetrahydro-naphthalen-1-yl ester

The title product was prepared from 5,6,7,8-tetrahydro-1-naphthol and N-methyl-N-phenylcarbamoyl chloride. The crude product was subjected to preparative HPLC (42%, colorless oil). HPLC-MS: m/z=282.1 (M+1); $R_t$: 4.77 min.

$^1$H NMR (CDCl$_3$): 7.33–7.45 (m, 4H), 7.22–7.32 (m, 1H), 7.02–7.13 (t, 1H), 6.82–7.96 (m, 2H), 3.42 (s, 3H), 2.70–2.82 (m, 2H), 2.50–2.65 (m, 2H), 1.62–1.83 (m, 4H).

Example 197 (General Procedure 14)

Methyl-phenyl-carbamic acid 5-oxo-5,6,7,8-tetrahydro-naphthalen-1-yl ester

The title product was prepared from 5,6,7,8-tetrahydro-1-naphthol and N-methyl-N-phenylcarbamoyl chloride. The crude product was subjected to preparative HPLC (60%, colorless oil). HPLC-MS: m/z=296.1 (M+1); $R_t$: 3.81 min.

$^1$H NMR (CDCl$_3$): 7.91 (dd, 1H), 7.21–7.50 (m, 7H), 3.44 (s, 3H), 2.60–2.93 (bs, 2H), 2.62 (t, 2H), 2.02–2.20 (m, 2H).

Example 198 (General Procedure 14)

Methyl-phenyl-carbamic acid 1,3-dioxo-1,3-dihydro-isobenzofuran-4-yl ester

The title product was prepared from 4-hydroxy-isobenzofuran-1,3-dione and N-methyl-N-phenylcarbamoyl chloride. The crude product was subjected to preparative HPLC (50%, white solid). HPLC-MS: m/z=298.1 (M+1); $R_t$: 2.58 min, purity: 85%.

$^1$H NMR (CDCl$_3$): 7.90 (d, 1H), 7.48–7.62 (m, 2H), 7.28–7.45 (m, 5H), 3.38 (s, 3H).

Example 199 (General Procedure 1)

Methyl-phenyl-carbamic acid 4-(5-chloro-pyridin-2-yloxy)-phenyl ester

The title product was prepared from 4-(5-chloro-pyridin-2-yloxy)-phenol and N-methyl-N-phenylcarbamoyl chloride. The crude product was subjected to column chromatography (ethyl acetate/heptane (1:5) (85%, white solid). HPLC-MS: m/z=355.1 (M+1); $R_t$: 4.56 min.

$^1$H NMR (CDCl$_3$): 8.10 (d, 1H), 7.62 (dd, 1H), 7.31–7.44 (m, 4H), 7.25–7.30 (m, 1H), 7.05–7.20 (m, 4H), 6.84 (d, 1H), 3.43 (s, 3H).

Example 200 (General Procedure 14)

(3-Fluoro-phenyl)-methyl-carbamic acid 4-(5-trifluoromethyl-pyridin-2-yloxy)-phenyl ester The title product was prepared from 4-(5-Trifluoromethyl-pyridin-2-yloxy)-phenol and 3-fluoro-N-methylaniline. The crude product was subjected to preparative HPLC (31%, white solid).

HPLC-MS: m/z=407.0 (M+1); $R_t$: 4.93 min. $^1$H NMR (CDCl$_3$): 8.42 (s, 1H), 7.88 (dd, 1H), 7.36 (q, 1H), 7.07–7.24 (m, 6H), 7.00 (d, 1H), 7.92–7.05 (m, 1H), 3.44 (s, 3H).

Example 201 (General Procedure 11)

4-Benzyl-piperazine-1-carboxylic acid 4-(5-chloro-pyridin-2-yloxy)-phenyl ester

The title product was prepared from 4-(5-chloro-pyridin-2-yloxy)-phenol and 1-benzylpiperazine. The title product precipitated from the reaction mixture and was collected by filtration (88%, off-white solid). HPLC-MS: m/z=424.1 (M+1); $R_t$: 2.91 min.

$^1$H NMR (CDCl$_3$): 13.86 (bs, 1H), 8.11 (d, 1H), 7.60–7.70 (m, 3H), 7.45–7.55 (m, 3H), 7.05–7.20 (m, 4H), 6.98 (d, 1H), 4.26–4.40 (m, 2H, 4.15–4.25 (m, 2H), 3.38–3.53 (m, 2H), 3.60–4.15 (m, 2H), 2.72–2.92 (m, 2H).

Example 202 (General Procedure 11)

4-Pyridin-3-ylmethyl-piperazine-1-carboxylic acid 4-(5-chloro-pyridin-2-yloxy)-phenyl ester The title product was prepared from 4-(5-chloro-pyridin-2-yloxy)-phenol and (3-pyridylmethyl)piperazine. The title product precipitated from the reaction mixture and was collected by filtration and recrystallized from ethanol (35%, off-white solid). HPLC-MS: m/z=425.2 (M+1); $R_t$: 2.39 min.

$^1$H NMR (CDCl$_3$): 13.00–14.50 (bs, 1H), 8.72 (d, 2H), 8.50 (bs, 1H), 8.11 (d, 1H), 7.64 (dd, 1H), 7.56 (bs, 1H), 7.06–7.14 (m, 4H), 6.88 (d, 1H), 3.6–4.4 (m, 6H), 2.70–3.50 (m, 4H).

Example 203 (General Procedure 14)

4-Hydroxymethyl-piperidine-1-carboxylic acid 4-(5-chloro-pyridin-2-yloxy)-phenyl ester The title product was prepared from 4-(5-chloro-pyridin-2-yloxy)-phenol and 4-hydroxymethyl-piperidine. The crude product was subjected to column chromatography (ethyl acetate/heptane, 1:1) (75%, colorless oil). HPLC-MS: m/z=363.1 (M+1); $R_t$: 3.58 min.

$^1$H NMR (CDCl$_3$): 8.12 (d, 1H), 7.64 (dd, 1H), 7.05–7.24 (m, 4H), 6.85 (d, 1H), 4.33 (ds, 2H), 3.56 (t, 2H), 2.75–3.10 (m, 2H), 1.69–1.95 (m, 3H), 1.56 (s, 1H), 1.19–1.45 (m, 2H).

Example 204 (General Procedure 1)

Methyl-phenyl-carbamic acid 4-morpholin-4-yl-phenyl ester

The title product was prepared from and 4-morpholin-4-yl-phenol and N-methyl-N-phenylcarbamoyl chloride. The crude product was extracted with dichloromethane from citric acid (5%). The combined organic phases were evaporated and the product crystallized from ethanol (22%, crystals). HPLC-MS: m/z=313.2 (M+1); $R_t$: 3.75 min.

$^1$H NMR (DMSO-d6): 7.35–7.50 (m, 4H), 7.22–7.32 (m, 1H), 7.00 (d, 2H), 6.92 (d, 2H), 3.72 (t, 4H), 3.32 (s, 3H), 3.05 (t, 4H).

Example 205 (General Procedure 1)

1,4-Dioxa-8-aza-spiro[4.5]decane-8-carboxylic acid 4-(5-trifluoromethyl-pyridin-2-yloxy)-phenyl ester The title product was prepared from 4-(5-trifluoromethyl-pyridin)-2-yloxy)-phenol and 4-piperidone ethylene ketal. The crude product was extracted with dichloromethane from citric acid (5%). The combined organic phases were evaporated and the product crystallized from ethanol (61%, crystals). HPLC-MS: m/z=425.2 (M+1); $R_t$: 4.45 min.

Example 206 (General Procedure 14)

The title product was prepared from 2-(4-hydroxy-phenyl)-indan-1,3-dione and N-methyl-N-phenylcarbamoyl chloride. The crude product was subjected to preparative HPLC (1%, oil). HPLC-MS: m/z=372.1 (M+1); $R_t$: 4.80 min.

Example 207 (General Procedure 14)

Methyl-phenyl-carbamic acid 4-(5,6-dichloro-1,3-dioxo-1,3-dihydro-isoindol-2-yl)-phenyl ester The title product was prepared from 5,6-dichloro-2-(4-hydroxy-phenyl)-isoindole-1,3-dione and N-methyl-N-phenylcarbamoyl chloride. The crude product was subjected to preparative HPLC (2%,). HPLC-MS: m/z=441.1 (M+1); $R_t$: 5.00 min.

Example 208 (General Procedure 14)

Methyl-phenyl-carbamic acid 4-(2-phenoxy-acetylamino)-phenyl ester

The title product was prepared from N-(4-hydroxy-phenyl)-2-phenoxy-acetamide and N-methyl-N-phenylcarbamoyl chloride. The crude product was purified by preparative HPLC (54%, oil). HPLC-MS: m/z=277.2 (M+1); $R_t$: 4.19 min.

Example 209 (General Procedure 14)

Methyl-phenyl-carbamic acid 4-[2-(4-chloro-phenyl)-ethyl]-phenyl ester

The title product was prepared from 4-(4-chlorophenethyl)-phenol and N-methyl-N-phenylcarbamoyl chloride. The crude product was subjected to preparative HPLC (57%, white crystals). HPLC-MS: m/z=366.1 (M+1); $R_t$: 5.58 min.

$^1$H NMR (CDCl$_3$): 7.31–7.45 (m, 4H), 7.17–7.30 (m, 3H), 6.96–7.12 (m, 6H), 3.41 (s, 3H), 2.85 (s, 4H).

Example 210 (General Procedure 14)

Methyl-phenyl-carbamic acid 4-[(pyridine-2-carbonyl)-amino]-phenyl ester

The title product was prepared from pyridine-2-carboxylic acid (4-hydroxy-phenyl)-amide and N-methyl-N-phenylcarbamoyl chloride. The crude product was subjected to preparative HPLC (41%,). HPLC-MS: m/z=348.1 (M+1); $R_t$: 4.00 min.

$^1$H NMR (CDCl$_3$): 7.32–7.47 (m, 4H), 7.24–7.31 (m, 3H), 7.10–7.23 (m, 4H), 7.79 (d, 2H), 3.41 (m, 6H).

Example 211 (General Procedure 14)

Methyl-phenyl-carbamic acid 4-[methyl-(thiophene-2-carbonyl)-amino]-phenyl ester The title product was prepared from thiophene-2-carboxylic acid (4-hydroxy-phenyl)-methyl-amide and N-methyl-N-phenylcarbamoyl chloride. The crude product was subjected to preparative HPLC (16%, oil). HPLC-MS: m/z=367.2 (M+1); $R_t$: 3.97 min.

Example 212 (General Procedure 14)

Methyl-phenyl-carbamic acid 4-butyrylamino-phenyl ester

The title product was prepared from 4'-hydroxybutyranilide and N-methyl-N-phenylcarbamoyl chloride. The crude product was subjected to preparative HPLC (60%, white solid). HPLC-MS: m/z=313.2 (M+1); $R_t$: 3.58 min.

Example 213 (General Procedure 14)

Methyl-phenyl-carbamic acid 4-(4,6-dimethyl-pyrimidin-2-ylsulfanyl)-phenyl ester The title product was prepared from 4-(4,6-dimethylpyrimidin-2-ylsulfanyl)-phenol and N-methyl-N-phenylcarbamoyl chloride. The crude product was subjected to preparative HPLC (59%, white solid). HPLC-MS: m/z=366.1 (M+1); $R_t$: 4.50 min.

$^1$H NMR (CDCl$_3$): 7.59 (d, 2H), 7.32–7.45 (m, 4H), 7.23–7.31 (m, 1H), 7.16 (d, 2H), 6.68 (s, 1H), 3.43 (s, 1H), 2.32.

Example 214 (General Procedure 14)

Methyl-phenyl-carbamic acid 4-methanesulfonyl-phenyl ester

The title product was prepared from 4-methylsulfonylphenol and N-methyl-N-phenylcarbamoyl chloride. The crude product was subjected to preparative HPLC (50%, white solid). HPLC-MS: m/z=306.1 (M+1); $R_t$: 3.22 min.

Example 215 (General Procedure 14)

Methyl-phenyl-carbamic acid 4-[2-(3-oxo-1,2,3,4-tetrahydro-quinoxalin-2-yl)-acetylamino]-phenyl ester The title product was prepared from N-(4-hydroxyphenyl)-2-(3-oxo-1,2,3,4-tetrahydro-2-quinoxalinyl)acetamide and N-methyl-N-phenylcarbamoyl chloride. The crude product was subjected to preparative HPLC (20%, yellow solid). HPLC-MS: m/z=431.2 (M+1); $R_t$: 3.55 min.

Example 216 (General Procedure 14)

Methyl-phenyl-carbamic acid 4-phenylacetyl-phenyl ester

The title product was prepared from benzyl 4-hydroxyphenyl ketone and N-methyl-N-phenylcarbamoyl chloride. The crude product was subjected to preparative HPLC (68%, light yellow oil). HPLC-MS: m/z=431.2 (M+1); $R_t$: 3.55 min.

Example 217 (General Procedure 12)

4-Benzoyl-piperidine-1-carboxylic acid 4-(5-trifluoromethyl-pyridin-2-yloxy)-phenyl ester The title product was prepared from 4-(5-trifluoromethyl-pyridin)-2-yloxy)-phenol and 4-benzoylpiperidine (29%, white solid). HPLC-MS: m/z=471.3 (M+1); $R_t$: 5.12 min.

Example 218 (General Procedure 11)

[1,4']Bipiperidinyl-1'-carboxylic acid 4-(5-trifluoromethyl-pyridin-2-yloxy)-phenyl ester The title product was prepared from 4-(5-trifluoromethyl-pyridin)-2-yloxy)-phenol and 4-piperidinopiperidine. The crude product was filtered from the reaction mixture and washed with diethyl ether to give the title product (50%, off-white solid). HPLC-MS: m/z=450.1 (M+1); $R_t$: 3.12 min.

Example 219 (General Procedure 12)

4-(2-Oxo-2,3-dihydro-benzimidazol-1-yl)-piperidine-1-carboxylic acid 4-(5-trifluoromethyl-pyridin-2-yloxy)-phenyl ester The title product was prepared from 4-(5-Trifluoromethyl-pyridin-2-yloxy)-phenol and 1-piperidin-4-yl-1,3-dihydro-benzoimidazol-2-one (44%, oil). HPLC-MS: m/z=499.1 (M+1); $R_t$: 4.35 min.
$^1$H NMR (CDCl$_3$): 10.15 (s, 1H), 8.44 (s, 1H), 7.90 (dd, 1H), 7.23 (t, 1H), 7.13–7.20 (m, 4H), 7.06–7.13 (m, 2H), 7.02 (d, 1H), 4.40–4.70 (m, 3H), 2.95–3.30 (m, 2H), 2.40–2.63 (m, 2H), 1.86 (d, 2H).

Example 220 (General Procedure 12)

3-Diethylcarbamoyl-piperidine-1-carboxylic acid 4-(5-trifluoromethyl-pyridin-2-yloxy)-phenyl ester The title product was prepared from 4-(5-Trifluoromethyl-pyridin-2-yloxy)-phenol and N,N-diethylnipecotamide (56%, oil). HPLC-MS: m/z=466.1 (M+1); $R_t$: 4.51 min.

Example 221 (General Procedure 12)

4-Carbamoyl-piperidine-1-carboxylic acid 4-(5-trifluoromethyl-pyridin-2-yloxy)-phenyl ester The title product was prepared from 4-(5-Trifluoromethyl-pyridin-2-yloxy)-phenol and piperidine-4-carboxylic acid amide. The crude product was subjected to preparative HPLC (47%, white solid). HPLC-MS: m/z=410.2 (M+1); $R_t$: 3.45 min.

Example 222 (General Procedure 12)

3-Carbamoyl-piperidine-1-carboxylic acid 4-(5-trifluoromethyl-pyridin-2-yloxy)-phenyl ester The title product was prepared from 4-(5-Trifluoromethyl-pyridin-2-yloxy)-phenol and nipecotamide. The crude product was purified by preparative HPLC (60%, white solid). HPLC-MS: m/z=410.2 (M+l); $R_t$: 3.45 min.

Example 223 (General Procedure 14)

Methyl-phenyl-carbamic acid 4-{[4-(methyl-phenyl-carbamoyloxy)-2-oxo-1,2-dihydro-quinoline-3-carbonyl]-amino}-phenyl ester The title product was prepared from 4-hydroxy-2-oxo-1,2-dihydro-quinoline-3-carboxylic acid (4-hydroxyphenyl)-amide and N-methyl-N-phenylcarbamoyl chloride. The crude product was subjected to preparative HPLC (6.6%, oil). HPLC-MS: m/z=563.2 (M+1); $R_t$: 4.46 min.
$^1$H NMR (CDCl$_3$): 8.38 (d, 1H), 7.75 (t, 1H), 7.35–7.45 (m, 4H), 7.22–7.34 (m, 1H), 7.14–7.21 (t, 1H), 6.99–7.15 (bs, 1H), 3.44 (s, 3H).

Example 224 (General Procedure 14)

Methyl-phenyl-carbamic acid 4-[(4-hydroxy-2-oxo-1,2-dihydro-quinoline-3-carbonyl)-amino]-phenyl ester The title product was prepared from 4-hydroxy-2-oxo-1,2-dihydro-quinoline-3-carboxylic acid (4-hydroxy-phenyl)-amide and N-methyl-N-phenylcarbamoyl chloride (5%,). HPLC-MS: m/z=430.1 (M+1); $R_t$: 4.80 min, purity: 70%.

Example 225 (General Procedure 14)

Methyl-phenyl-carbamic acid 4-(4-hydroxy-benzyl)-phenyl ester

The title compound was prepared from 4,4'-dihydroxy-diphenylmethane and N-methyl-N-phenylcarbamoyl chloride. The crude product was subjected to preparative HPLC (21%, white crystals which turn red after standing). HPLC-MS: m/z=324.2 (M+1); $R_t$: 4.21 min.

Example 226 (General Procedure 13)

Methyl-phenyl-carbamic acid 4-(4-trifluoromethyl-benzylcarbamoyl)-phenyl ester

The title product was prepared from 4-(methyl-phenyl-carbamoyloxy)-benzoic acid 2,5-dioxo-pyrrolidin-1-yl ester and 4-trifluoromethyl-benzylamine (94%, white crystals). HPLC-MS: m/z=429.2 (M+1); $R_t$: 4.35 min.

Example 227 (General Procedure 13)

Methyl-phenyl-carbamic acid 4-(butyl-methyl-carbamoyl)-phenyl ester

The title product was prepared from 4-(methyl-phenyl-carbamoyloxy)-benzoic acid 2,5-dioxo-pyrrolidin-1-yl ester and n-butyl-methyl-amine. The crude product was subjected to preparative HPLC (20%, oil). HPLC-MS: m/z=341.2 (M+1); $R_t$: 3.96 min.

Example 228 (General Procedure 13)

Methyl-phenyl-carbamic acid 4-(methyl-phenethyl-carbamoyl)-phenyl ester

The title product was prepared from 4-(methyl-phenyl-carbamoyloxy)-benzoic acid 2,5-dioxo-pyrrolidin-1-yl ester and methyl-phenethyl-amine. The crude product was subjected to preparative HPLC (29%, oil). HPLC-MS: m/z=389.2 (M+1); $R_t$: 4.15 min.

Example 229 (General Procedure 13)

Methyl-phenyl-carbamic acid 4-[(pyridin-2-ylmethyl)-carbamoyl]-phenyl ester

The title product was prepared from 4-(methyl-phenyl-carbamoyloxy)-benzoic acid 2,5-dioxo-pyrrolidin-1-yl ester and 2-aminomethylpyridine. The crude product was used without further purification (57%, oil). HPLC-MS: m/z=362.2 (M+1); $R_t$: 2.43 min.
$^1$H NMR (MeOH-d$_4$): 8.50 (d, 1H), 7.92 (d, 2H), 7.83 (dt, 1H), 7.38–7.50 (m, 5H), 7.26–7.37 (m, 2H), 7.15–7.26 (m, 2H), 4.69 (s, 2H), 3.41 (s, 3H).

Example 230 (General Procedure 13)

Methyl-phenyl-carbamic acid 4-(2-pyridin-2-yl-ethylcarbamoyl)-phenyl ester

The title product was prepared from 4-(methyl-phenyl-carbamoyloxy)-benzoic acid 2,5-dioxo-pyrrolidin-1-yl ester and 2-aminoethylpyridine. The crude product was used without further purification (26%, oil). HPLC-MS: m/z=376.2 (M+1); $R_t$: 2.25 min.
$^1$H NMR (MeOH-d$_4$): 8.51 (d, 1H), 7.87 (dt, 1H), 7.78 (d, 2H), 7.33–7.50 m, 6H), 7.25–7.33 (m, 1H), 7.18 (d, 2H), 3.74 (t, 2H), 3.41 (bs, 3H), 3.13 (t, 2H).

Example 231 (General Procedure 13)

Methyl-phenyl-carbamic acid 4-(2-phenylamino-ethylcarbamoyl)-phenyl ester

The title product was prepared from 4-(methyl-phenyl-carbamoyloxy)-benzoic acid 2,5-dioxo-pyrrolidin-1-yl ester and N-phenylethylenediamine. The crude product was used without further purification (80%, off-white foam). HPLC-MS: m/z=390.2 (M+1); $R_t$: 3.51 min.
$^1$H NMR (MeOH-d$_4$): 7.82 (d, 2H), 7.36–7.48 (m, 4H), 7.22–7.34 (m, 1H), 7.15–7.22 (d, 2H), 7.10 (t, 2H), 6.69 (d, 2H), 6.62 (t, 1H), 3.72 (t, 2H), 3.57 (t, 2H), 3.40 (s, 3H), 3.20 (s, 1H).

Example 232 (General Procedure 13)

Methyl-phenyl-carbamic acid 4-(3-methyl-butylcarbamoyl)-phenyl ester

The title product was prepared from 4-(methyl-phenyl-carbamoyloxy)-benzoic acid 2,5-dioxo-pyrrolidin-1-yl ester and iso-amylamine. The crude product was used without further purification (95%, oil). HPLC-MS: m/z=341.2 (M+1); $R_t$: 3.99 min.
$^1$H NMR (MeOH-d$_4$): 7.82 (d, 2H), 7.36–7.50 (m, 4H), 7.26–7.35 (m, 1H), 7.15–7.24 (d, 2H), 3.34–3.46 (m, 5H), 1.67 (sept, 1H), 1.50 (q, 2H), 0.96 (d, 6H).

Example 233 (General Procedure 13)

Methyl-phenyl-carbamic acid 4-(3,3-dimethyl-butylcarbamoyl)-phenyl ester

The title product was prepared from 4-(methyl-phenyl-carbamoyloxy)-benzoic acid 2,5-dioxo-pyrrolidin-1-yl ester and 3,3-dimethylbutylamine. The crude product was used without further purification (88%, oil). HPLC-MS: m/z=355.1 (M+1); $R_t$: 3.10 min.
$^1$H NMR (MeOH-d$_4$): 7.82 (d, 2H), 7.36–7.50 (m, 4H), 7.25–7.35 (m, 1H), 7.15–7.25 (d, 2H), 3.33–3.47 (m, 5H), 1.49–1.57 (m, 2H), 0.97 (s, 9H).

Example 234 (General Procedure 13)

Methyl-phenyl-carbamic acid 4-[(tetrahydro-furan-2-ylmethyl)-carbamoyl]-phenyl ester The title product was prepared from 4-(methyl-phenyl-carbamoyloxy)-benzoic acid 2,5-dioxo-pyrrolidin-1-yl ester and C-(tetrahydro-furan-2-yl)methylamine. The crude product was used without further purification (86%, oil). HPLC-MS: m/z=(M+1); $R_t$: min.
$^1$H NMR (MeOH-d$_4$): 7.84 (d, 2H), 7.35–7.50 (m, 4H), 7.25–7.35 (m, 1H), 7.12–7.25 (d, 2H), 4.10 (qui, 1H), 3.87 (q, 1H), 3.68–3.82 (m, 1H), 3.41 (s, 3H), 3.35–3.54 (m, 2H), 1.82–2.10 (m, 3H), 1.58–1.72 (m, 1H).

Example 235 (General Procedure 13)

Methyl-phenyl-carbamic acid 4-cyclohexylcarbamoyl-phenyl ester

The title product was prepared from 4-(methyl-phenyl-carbamoyloxy)-benzoic acid 2,5-dioxo-pyrrolidin-1-yl ester and cyclohexylamine. The crude product was used without further purification (79%, off-white crystals). HPLC-MS: m/z=353.2 (M+1); $R_t$: 3.98 min.
$^1$H NMR (MeOH-d$_4$): 8.18 (d, 1H), 7.85 (d, 2H), 7.36–7.52 (m, 4H), 7.25–7.33 (m, 1H), 7.20 (d, 2H), 3.74 (m, 1H), 1.77–1.88 (m, 2H), 1.65–1.77 (m, 2H), 1.60 (d, 1H), 1.24–1.40 (m, 4H), 1.07–1.23 (m, 1H).

Example 236 (General Procedure 13)

Methyl-phenyl-carbamic acid 4-cyclopropylcarbamoyl-phenyl ester

The title product was prepared from 4-(methyl-phenyl-carbamoyloxy)-benzoic acid 2,5-dioxo-pyrrolidin-1-yl ester and cyclopropylamine. The crude product was used without further purification (97%, oil). HPLC-MS: m/z=311.2 (M+1); $R_t$: 3.21 min.

¹H NMR (MeOH-d₄): 7.81 (d, 2H), 7.36–7.50 (m, 4H), 7.25–7.36 (m, 1H), 7.18 (d, 2H), 3.40 (bs, 3H), 2.78–2.87 (m,1H), 0.75–0.85 (m, 2H), 0.57–0.65 (m, 2H).

Example 237 (General Procedure 13)

Methyl-phenyl-carbamic acid 4-(cyclohexylmethyl-carbamoyl)-phenyl ester

The title product was prepared from 4-(methyl-phenyl-carbamoyloxy)-benzoic acid 2,5-dioxo-pyrrolidin-1-yl ester and C-cyclohexyl-methylamine. The crude product was used without further purification (84%, oil). HPLC-MS: m/z=367.3 (M+1); $R_t$: 4.28 min.

¹H NMR (MeOH-d₄): 7.81 (d, 2H), 7.36–7.49 (m, 4H), 7.25–7.32 (m, 1H), 7.19 (d, 2H), 3.40 (bs, 3H), 3.20 (d, 2H), 1.55–1.82 (m, 5H), 1.13–1.35 (m, 4H), 0.90–1.10 (m, 2H).

Example 238

Methyl-phenyl-carbamic acid 5-nitro-pyridin-2-yl ester

A solution of 2-hydroxy-5-nitropyridine (1.40 g, 10.0 mmol), 1-methyl-3-(methyl-phenyl-carbamoyl)-3H-imidazol-1-ium iodide (3.43 g, 10.0 mmol) and triethylamine (0.42 ml, 10.0 mmol) in acetonitrile (25 ml) was heated at 50° C. for 5 h. The solvent was evaporated in vacuo and the residue was purified by flash column chromatography (SiO₂, ethyl acetate:heptane (25:75)) followed by crystallisation from ethyl acetate:heptane yielding the title compound (1.13 g, 41% yield) as a white solid.

¹H NMR (300 MHz, CDCl₃): δ 3.44 (br.s, 3H), 7.17 (br.d, 1H), 7.27–7.45 (m, 5H), 8.49 (br.d, 1H), 9.19 (br.s 1H); HPLC-MS (Method A): m/z=296 (M+Na); $R_t$: 3.45 min.

Example 239

Methyl-phenyl-carbamic acid pyrimidin-2-yl ester

A solution of 2-hydroxypyrimidine hydrochloride (0.40 g, 3.00 mmol), 1-methyl-3-(methyl-phenyl-carbamoyl)-3H-imidazol-1-ium iodide (1.03 g, 3.00 mmol) and triethylamine (0.83 ml, 6.00 mmol) in acetonitrile (15 ml) was stirred at room temperature overnight. The solvent was evaporated in vacuo and the residue was purified by flash column chromatography (SiO₂, ethyl acetate) followed by crystallisation from ethyl acetate:heptane yielding the title compound (0.08 g, 12% yield) as a white solid.

¹H NMR (300 MHz, CDCl₃): δ 3.43 (br.s, 3H), 7.14–7.31 (m, 2H), 7.39 (m, 4H), 8.68 (d, 2H); HPLC-MS (Method A): m/z=252 (M+Na); $R_t$=2.32 min.

Example 240

Methyl-phenyl-carbamic acid 7-chloro-quinolin-4-yl ester

A solution of 7-chloro-4-hydroxyquinoline (0.54 g, 3.00 mmol), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 18 hours. The solvent was evaporated in vacuo and the residue was purified by flash column chromatography (SiO₂, ethyl acetate:heptane (40:60)) yielding the title compound (0.87 g, 93% yield) as a colourless oil which solidified upon standing.

¹H NMR (300 MHz, CDCl₃): δ 3.47 (br.s, 3H), 7.28–7.58 (m, 8H), 8.05 (br.s, 1H), 8.85 (d, 1H); HPLC-MS (Method A): m/z=313 (M+H); $R_t$=3.79 min.

Example 241

Methyl-phenyl-carbamic acid quinolin-4-yl ester

A mixture of 4-hydroxyquinoline (0.44 g, 3.00 mmol) ), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 18 hours. The solvent was evaporated in vacuo and the residue was purified by flash column chromatography (SiO₂, ethyl acetate:heptane (50:50)) yielding the title compound (0.75 g, 90% yield) as a white solid.

¹H NMR (300 MHz, CDCl₃): δ 3.49 (br.s, 3H), 7.37 (br.t, 1H), 7.41–7.62 (m, 7H), 7.69 (br.t, 1H), 8.08 (br.d, 1H), 8.87 (d, 1H); HPLC-MS (Method A): m/z=279 (M+H); $R_t$=2.56 min.

Example 242

Methyl-phenyl-carbamic acid 5-methyl-isoxazol-3-yl ester

A mixture of 3-hydroxy-5-methylisoxazole (0.30 g, 3.00 mmol) ), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 18 hours. The solvent was evaporated in vacuo and the residue was purified by flash column chromatography (SiO₂, ethyl acetate:heptane (25:75)) yielding the title compound (0.67 g, 96% yield) as a colourless oil.

¹H NMR (300 MHz, CDCl₃): δ 2.40 (s, 3H), 3.40 (br.s, 3H), 6.14 (br.s, 1H), 7.28–7.44 (m, 5H); HPLC-MS (Method A): m/z=255 (M+Na); $R_t$=3.31 min.

Example 243

Methyl-phenyl-carbamic acid quinoxalin-2-yl ester

A mixture of 2-hydroxyquinoxaline (0.44 g, 3.00 mmol) ), 1-methyl-3-(methyl-phenyl-carbamoyl)-3H-imidazol-1-ium iodide (1.03 9, 3.00 mmol) and triethylamine (0.42 ml, 3.00 mmol) in acetonitrile (15 ml) was stirred at room temperature for 18 hours followed by heating at 40° C. for 24 hours. The solvent was evaporated in vacuo and the residue was purified by flash column chromatography (SiO₂, ethyl acetate:heptane (30:70)) yielding the title compound (0.65 g, 77% yield) as a white solid.

¹H NMR (300 MHz, CDCl₃): δ 3.48 (br.s, 3H), 7.29 (m, 1H), 7.41 (m, 4H), 7.72 (m, 2H), 8.00 (m, 1H), 8.10 (m, 1H), 8.67 (br.s, 1H); HPLC-MS (Method A): m/z=280 (M+H); $R_t$=3.66 min.

Example 244

Methyl-phenyl-carbamic acid 4-methyl-quinolin-2-yl ester

A mixture of 2-hydroxy-4-methylquinoline (0.48 g, 3.00 mmol) ), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 18 hours followed by heating at 50° C.

for 4 days. The solvent was evaporated in vacuo and the residue was purified by flash column chromatography (SiO$_2$, ethyl acetate:heptane (30:70)) yielding the title compound (0.24 g, 27% yield) as a white solid.

$^1$H NMR (300 MHz, CDCl$_3$): δ 2.70 (s, 3H), 3.49 (br.s, 3H), 7.08 (m, 1H), 7.27 (m, 1H), 7.40 (m, 4H), 7.53 (t, 1H), 7.69 (t, 1H), 7.96 (d, 1H), 8.00 (d, 1H); HPLC-MS (Method A): m/z=293 (M+H); R$_t$=3.88 min.

Example 245

Methyl-phenyl-carbamic acid 3-methyl-quinoxalin-2-yl ester

A mixture of 2-hydroxy-3-methylquinoxaline (0.48 g, 3.00 mmol) ), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 18 hours followed by heating at 50° C. for 3 days. The solvent was evaporated in vacuo and the residue was purified by flash column chromatography (SiO$_2$, ethyl acetate:heptane (50:50)) yielding the title compound (0.59 g, 67% yield) as a white solid.

$^1$H NMR (300 MHz, CDCl$_3$): δ 2.61 (br.s, 3H), 3.48 (br.s, 3H), 7.30 (m, 1H), 7.42 (m, 4H), 7.69 (m, 2H), 7.99 (m, 2H); HPLC-MS (Method A): m/z=294 (M+H); R$_t$=3.92 min.

Example 246

Methyl-phenyl-carbamic acid 4,6-dimethyl-pyrimidin-2-yl ester

A solution of 4,6-dimethyl-2-hydroxypyrimidine (0.37 g, 3.00 mmol) ), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 18 hours. The solvent was evaporated in vacuo and the residue was purified by flash column chromatography (SiO$_2$, ethyl acetate:heptane (50:50)) yielding the title compound (0.46 g, 60% yield) as a white solid.

$^1$H NMR (300 MHz, CDCl$_3$): δ 2.48 (s, 6H), 3.43 (br.s, 3H), 6.92 (br.s, 1H), 7.22 (m, 1H), 7.37 (m, 4H); HPLC-MS (Method A): m/z=258 (M+H); R$_t$=2.77 min.

Example 247

Methyl-phenyl-carbamic acid isoquinolin-6-yl ester

A solution of 6-hydroxyquinoline (0.44 g, 3.00 mmol), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 18 hours. The solvent was evaporated in vacuo and the residue was purified by flash column chromatography (SiO$_2$, ethyl acetate:heptane (50:50)) yielding the title compound (0.80 g, 96% yield) as a white solid.

$^1$H NMR (300 MHz, CDCl$_3$): δ 3.47 (s, 3H), 7.28 (m, 1H), 7.33–7.54 (m, 6H), 7.59 (s, 1H), 8.08 (d, 2H), 8.86 (m, 1H); HPLC-MS (Method A): m/z=279 (M+H); R$_t$=2.63 min.

Example 248

Methyl-phenyl-carbamic acid quinolin-2-yl ester

A solution of 2-hydroxyquinoline (0.44 g, 3.00 mmol), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 18 hours. More acetonitrile (60 ml) was added and the solution was heated at 50° C. for 3 days. The solvent was evaporated in vacuo and the residue was purified by flash column chromatography (SiO$_2$, ethyl acetate:heptane (40:60)) yielding the title compound (0.33 g, 40% yield) as a white solid.

$^1$H NMR (300 MHz, CDCl$_3$): δ 3.50 (br.s, 3H), 7.14–7.30 (m, 2H), 7.42 (m, 4H), 7.52 (t, 1H), 7.71 (t, 1H), 7.82 (d, 1H), 8.00 (d, 1H), 8.19 (d, 1H); HPLC-MS (Method A): m/z=279 (M+H); R$_t$=3.91 min.

Example 249

Methyl-phenyl-carbamic acid isoquinolin-3-yl ester

A solution of 3-hydroxyisoquinoline (0.44 g, 3.00 mmol), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 18 hours. The solvent was evaporated in vacuo and the residue was purified by flash column chromatography (SiO$_2$, ethyl acetate:heptane (50:50)) yielding the title compound (0.82 g, 99% yield) as a white solid.

$^1$H NMR (300 MHz, CDCl$_3$): δ 3.49 (br.s, 3H), 7.24 (m, 1H), 7.33–7.47 (m, 5H), 7.51 (t, 1H), 7.63 (t, 1H), 7.77 (d, 1H), 7.94 (d, 1H), 9.06 (s, 1H); HPLC-MS (Method A): m/z=279 (M+H); R$_t$=3.68 min.

Example 250

Methyl-phenyl-carbamic acid 4-trifluoromethyl-pyrimidin-2-yl ester

A solution of 4-(trifluoromethyl)-2-pyrimidol (0.49 g, 3.00 mmol), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 3 days. The solvent was evaporated in vacuo and the residue was purified by flash column chromatography (SiO$_2$, ethyl acetate:heptane (30:70)) yielding the title compound (0.35 g, 39% yield) as a colourless oil.

$^1$H NMR (300 MHz, CDCl$_3$): δ 3.45 (br.s, 3H), 7.28 (m, 1H), 7.38 (m, 4H), 7.52 (br.s, 1H), 8.93 (br.s, 1H); HPLC-MS (Method A): m/z=320 (M+Na); R$_t$=3.58 min.

Example 251

Morpholine-4-carboxylic acid 4-trifluoromethyl-pyrimidin-2-yl ester

A solution of 4-(trifluoromethyl)-2-pyrimidol (0.49 g, 3.00 mmol), 4-morpholinecarbonyl chloride (0.45 g, 3.00 mmol) and 1,4-diazabicyclo[2.2.2]octane (0.51 g, 3.00 mmol) in N,N-dimethylformamide (15 ml) was stirred at room temperature for 2 hours. Water was added and the solution was extracted twice with dichloromethane. The combined organic layers were dried over sodium sulphate, filtered and evaporated in vacuo. The residue was purified by flash column chromatography (SiO$_2$, ethyl acetate:heptane (30:70→50:50)) yielding the title compound (0.66 g, 80% yield) as a white solid.

$^1$H NMR (300 MHz, CDCl$_3$): δ 3.57–3.81 (m, 8H), 7.57 (d, 1H), 8.97 (d, 1H).; HPLC-MS (Method A): m/z=300 (M+Na); R$_t$=2.36 min.

Example 252

Methyl-phenyl-carbamic acid 3-nitro-pyridin-2-yl ester

A solution of 2-hydroxy-3-nitropyridine (0.42 g, 3.00 mmol), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 3 days. The solvent was evaporated in vacuo and the residue was purified by flash column chromatography ($SiO_2$, ethyl acetate:heptane (40:60)) yielding the title compound (0.41 g, 50% yield) as a yellow solid.

$^1$H NMR (300 MHz, $CDCl_3$): δ 3.41+3.58 (2 x br.s, 3H), 7.30 (m, 1H), 7.42 (m, 5H), 8.45 (br.d, 1H), 8.49 (br.s, 1H); HPLC-MS (Method A): m/z=296 (M+Na); $R_t$=3.22 min.

Example 253

Methyl-phenyl-carbamic acid 5-chloro-pyridin-2-yl ester

A solution of 5-chloro-2-pyridol (0.39 g, 3.00 mmol), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 3 days. The solvent was evaporated in vacuo and the residue was purified by flash column chromatography ($SiO_2$, ethyl acetate:heptane (30:70)) yielding the title compound (0.78 g, 99% yield) as a white solid.

$^1$H NMR (300 MHz, $CDCl_3$): δ 3.44 (br.s, 3H), 7.00 (br.s, 1H), 7.27 (m, 1H), 7.39 (m, 4H), 7.69 (d, 1H), 8.30 (d, 1H); HPLC-MS (Method A): m/z=285 (M+Na); $R_t$=3.47 min.

Example 254

Methyl-phenyl-carbamic acid 5-(2-nitro-phenyl)-pyrimidin-2-yl ester

A solution of 5-(2-nitrophenyl)-pyrimidin-2-ol (0.35 g, 1.61 mmol), 1-methyl-3-(methyl-phenyl-carbamoyl)-3H-imidazol-1-ium iodide (0.55 g, 1.61 mmol) and triethylamine (0.22 ml, 1.61 mmol) in acetonitrile (15 ml) was heated at 50° C. for 18 hours. The solvent was evaporated in vacuo and the residue was purified by flash column chromatography ($SiO_2$, ethyl acetate:heptane (50:50)) yielding the title compound (0.18 g, 32% yield) as a yellow oil.

$^1$H NMR (300 MHz, $CDCl_3$): δ 3.47 (br.s, 3H), 7.29 (m, 1H), 7.40 (m, 5H), 7.63 (dt, 1H), 7.72 (dt, 1H), 8.10 (d, 1H), 8.61 (br.s, 2H); HPLC-MS (Method A): m/z=351 (M+H), 373 (M+Na), 723 (2M+Na).; $R_t$=3.65 min.

Example 255

Methyl-phenyl-carbamic acid 5-trifluoromethyl-pyridin-2-yl ester

A solution of 2-hydroxy-5-(trifluoromethyl)pyridine (0.49 g, 3.00 mmol), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 18 hours. The solvent was evaporated in vacuo and the residue was purified by flash column chromatography ($SiO_2$, ethyl acetate:heptane (15:85)) yielding the title compound (0.59 g, 66% yield) as a white solid.

$^1$H NMR (300 MHz, $CDCl_3$): δ 3.43 (br.s, 3H), 7.23 (br.s, 1H), 7.28 (m, 1H), 7.37 (m, 4H), 7.94 (br.d, 1H), 8.62 (br.s, 1H); HPLC-MS (Method A): m/z=319 (M+Na); $R_t$=3.85 min.

Example 256

Methyl-phenyl-carbamic acid 3-chloro-5-trifluoromethyl-pyridin-2-yl ester

A solution of 3-chloro-5-(trifluoromethyl)-2-pyridinol (0.59 g, 3.00 mmol), 1-methyl-3-(methyl-phenyl-carbamoyl)-3H-imidazol-1-ium iodide (1.03 g, 3.00 mmol) and triethylamine (0.42 ml, 3.00 mmol) in acetonitrile (15 ml) was stirred at room temperature for 18 hours. The solvent was evaporated in vacuo and the residue was purified by flash column chromatography ($SiO_2$, ethyl acetate:heptane (15:85)) yielding the title compound (146 mg, 15% yield) as a white solid.

$^1$H NMR (300 MHz, $CDCl_3$): δ 3.43 (br.s, 3H), 7.30 (m, 1H), 7.40 (d, 4H), 8.00 (br.s, 1H), 8.52 (br.s, 1H).; HPLC-MS (Method A): m/z=353 (M+Na); $R_t$=4.29 min.

Example 257

Methyl-phenyl-carbamic acid 5-nitro-3-trifluoromethyl-pyridin-2-yl ester

A solution of 2-hydroxy-5-nitro-3-(trifluoromethyl)pyridine (0.36 g, 1.73 mmol), N-methyl-N-phenylcarbamoyl chloride (0.44 g, 2.59 mmol) and 1,4-diazabicyclo[2.2.2]octane (0.29 g, 2.59 mmol) in tetrahydrofuran (15 ml) was stirred at room temperature for 18 hours. The solvent was evaporated in vacuo and the residue was purified by flash column chromatography ($SiO_2$, ethyl acetate:heptane (15:85)) yielding the title compound (0.55 g, 92% yield) as an orange solid.

$^1$H NMR (300 MHz, $CDCl_3$): δ 3.46 (br.s, 3H), 7.23–7.46 (m, 5H), 8.70 (br.s, 1H), 9.37 (br.s, 1H); HPLC-MS (Method A): m/z=364 (M+H); $R_t$=4.08 min.

Example 258

(3-Chloro-phenyl)-methyl-carbamic acid 4-trifluoromethyl-pyrimidin-2-yl ester At 0° C. diphosgene (0.99 g, 5.00 mmol) was added to a stirred solution of 4-trifluoromethyl-2-hydroxypyrimidine (1.64 g, 10.0 mmol) in tetrahydrofuran (25 ml). The cooling bath was removed and stirring was continued at room temperature for 1 hour. (3-Chlorophenyl)-methylamine (0.35 g, 2.50 mmol) was added to one-fourth of the solution. After stirring overnight at room temperature the solvent was evaporated in vacuo and the residue was purified by flash column chromatography ($SiO_2$, ethyl acetate:heptane (20:80)) followed by preparative HPLC, yielding the title compound (332 mg, 40%) as a colourless oil.

$^1$H NMR (300 MHz, $CDCl_3$): δ 3.45 (br.s, 3H), 7.23–7.44 (m, 4H), 7.56 (d, 1H), 8.94 (d, 1H);

HPLC-MS (Method A): m/z=354 (M+H); $R_t$=4.03 min.

Example 259

Methyl-m-tolyl-carbamic acid 4-trifluoromethyl-pyrimidin-2-yl ester

At 0° C. diphosgene (0.99 g, 5.00 mmol) was added to a stirred solution of 4-trifluoromethyl-2-hydroxypyrimidine (1.64 g, 10.0 mmol) in tetrahydrofuran (25 ml). The cooling bath was removed and stirring was continued at room temperature for 1 hour. Methyl-m-tolyl-amine (0.30 g, 2.50 mmol) was added to one-fourth of the solution. After stirring overnight at room temperature the solvent was evaporated in vacuo and the residue was purified by flash column chromatography (SiO$_2$, ethyl acetate:heptane (20:80)) followed by preparative HPLC, yielding the title compound (51 mg, 7%) as a colourless oil.

$^1$H NMR (300 MHz, CDCl$_3$): δ 2.37 (s, 3H), 3.42 (br.s, 3H), 7.07–7.31 (m, 4H), 7.52 (br.s, 1H), 8.92 (br.s, 1H); HPLC-MS (Method A): m/z=334 (M+Na); R$_f$=3.92 min.

Example 260

Morpholine-4-carboxylic acid 4-trifluoromethyl-pyrimidin-2-yl ester

A solution of 4-trifluoromethyl-2-hydroxypyrimidine (0.49 g, 3.00 mmol), 4-morpholinecarbonyl chloride (0.45 g, 3.00 mmol) and 1,4-diazabicyclo[2.2.2]octane (0.34 g, 3.00 mmol) in dimethylformamide (15 ml) was stirred at room temperature for 1 hour. Water and brine were added and the solution was extracted twice with dichloromethane. The combined organic layers were dried over sodium sulphate, filtered and evaporated in vacuo. The residue was purified by flash column chromatography (SiO$_2$, ethyl acetate:heptane (30:70→50:50)) yielding the title compound (0.66 g, 80% yield) as a white solid.

$^1$H NMR (300 MHz, CDCl$_3$): δ 3.45 (br.s, 3H), 7.23–7.44 (m, 4H), 7.56 (d, 1H), 8.94 (d, 1H);
HPLC-MS (Method A): m/z=354 (M+H); R$_f$=4.03 min.

Example 261

Methyl-phenyl-carbamic acid 4,5-dichloro-pyridazin-3-yl ester

A solution of 4,5-dichloro-3-hydroxypyridazine (0.49 g, 3.00 mmol), N-methyl-N-phenylcarbamoyl chloride (0.51 g, 3.00 mmol) and triethylamine (0.42 ml, 3.00 mmol) in tetrahydrofuran (15 ml) was stirred at room temperature for 3 days. The solvent was evaporated in vacuo and the residue was purified by flash column chromatography (SiO$_2$, ethyl acetate:heptane (20:80)) yielding the title compound (0.12 g, 14% yield) as a white solid.

$^1$H NMR (300 MHz, CDCl$_3$): δ 3.50 (s, 3H), 7.18–7.32 (m, 5H), 7.63 (s, 1H); HPLC-MS (Method A): m/z=320 (M+Na); R$_f$=2.91 min.

Example 262

Methyl-phenyl-carbamic acid 5-benzoylamino-pyridin-2-yl ester

A solution of N-(6-hydroxy-pyridin-3-yl)-benzamide (0.64 g, 3.00 mmol), N-methyl-N-phenylcarbamoyl chloride (0.51 g, 3.00 mmol) and 1,4-diazabicyclo[2.2.2]octane (0.34 g, 3.00 mmol) in dimethylformamide (15 ml) was stirred at room temperature for 1 hour. Water was added and the precipitates were collected by suction. The solids were dissolved in dichloromethane and the solution was dried over sodium sulphate, filtered and evaporated in vacuo. The residue was dissolved in ethyl acetate and filtered over a short pad of silica. Evaporation of the solvent in vacuo yielded the title compound (0.70 g, 68% yield) as a thick oil.

$^1$H NMR (300 MHz, CDCl$_3$): δ 3.40 (br.s, 3H), 6.90 (br.s, 1H), 7.26 (m, 1H), 7.31–7.44 (m, 6H), 7.50 (m, 1H), 7.88 (d, 2H), 8.08 (dd, 1H), 8.37 (d, 1H), 8.79 (br.s, 1H); HPLC-MS (Method A): m/z=348 (M+H); R$_f$=3.49 min.

Example 263

Methyl-phenyl-carbamic acid 5-(cyclohexanecarbonyl-amino)-pyridin-2-yl ester

A solution of cyclohexanecarboxylic acid (6-hydroxy-pyridin-3-yl)-amide (0.66 g, 3.00 mmol), N-methyl-N-phenylcarbamoyl chloride (0.51 g, 3.00 mmol) and 1,4-diazabicyclo[2.2.2]octane (0.34 g, 3.00 mmol) in dimethylformamide (20 ml) was stirred at room temperature for 18 hours. Water was added and the precipitates were collected by suction. The solids were dissolved in dichloromethane and the solution was dried over sodium sulphate, filtered and evaporated in vacuo. The residue was crystallised from ethyl acetate:heptane yielding the title compound (0.75 g, 71% yield) as a slightly coloured solid.

$^1$H NMR (300 MHz, CDCl$_3$): δ 1.18–1.33 (m, 3H), 1.42–1.59 (m, 2H), 1.60 (m, 1H), 1.77–194 (m, 4H), 2.20 (m,1H), 3.45 (br.s, 3H), 6.91 (br.s, 1H), 7.28 (m, 1H), 7.39 (m, 4H), 7.94 (br.s, 1H), 8.00 (dd, 1H), 8.20 (d, 1H); HPLC-MS (Method A): m/z=354 (M+H); R$_f$=3.74 min.

Example 264

Methyl-phenyl-carbamic acid 4,4-dimethyl-2,6-dioxo-3,4,5,6-tetrahydro-2H-[1,3']bipyridinyl-6'-yl ester A solution of 6'-hydroxy-4;4-dimethyl-4,5-dihydro-3H-[1,3']bipyridinyl2,6-dione (0.70 g, 3.00 mmol), N-methyl-N-phenylcarbamoyl chloride (0.51 g, 3.00 mmol) and 1,4-diazabicyclo[2.2.2]octane (0.34 g, 3.00 mmol) in dimethylformamide (20 ml) was stirred at room temperature for 18 hours. Water was added and the precipitates were collected by suction and subsequently dried in a vacuum oven yielding the title compound (0.75 g, 71% yield) as a white solid.

$^1$H NMR (300 MHz, CDCl$_3$): δ 1.20 (s, 6H), 2.68 (s, 4H), 3.44 (br.s, 3H), 7.14 (br.s, 1H), 7.25 (m, 1H), 7.37 (m, 4H), 7.48 (br.d, 1H), 8.08 (d, 1H); HPLC-MS (Method A): m/z=368 (M+H); R$_f$=3.41 min.

Example 265

Methyl-phenyl-carbamic acid 5-(2,2-dimethyl-propionylamino)-pyridin-2-yl ester

A solution of N-(6-hydroxy-pyridin-3-yl)-2,2-dimethyl-propionamide (0.58 g, 3.00 mmol), N-methyl-N-phenylcarbamoyl chloride (0.51 g, 3.00 mmol) and 1,4-diazabicyclo[2.2.2]octane (0.34 g, 3.00 mmol) in dimethylformamide (20 ml) was stirred at room temperature for 1 hour. Water was added and a thick oil was being formed. The water was decanted and the residue was dissolved in dichloromethane. The solution was dried over sodium sulphate, filtered and evaporated in vacuo yielding the title compound (0.55 g, 56% yield) as a brown oil that solidified upon standing.

$^1$H NMR (300 MHz, CDCl$_3$): δ 1.29 (s, 9H), 3.43 (br.s, 3H), 6.97 (br.s, 1H), 7.26 (m, 1H), 7.38 (m, 4H), 7.64 (br.s, 1H), 8.10 (dd, 1H), 8.28 (br.s, 1H); HPLC-MS (Method A): m/z=348 (M+H); R$_t$=3.49 min.

Example 266

Methyl-phenyl-carbamic acid 5-(2-cyclohexyl-acetylamino)-pyridin-2-yl ester

A solution of 2-cyclohexyl-N-(6-hydroxy-pyridin-3-yl)-acetamide (0.70 g, 3.00 mmol), N-methyl-N-phenylcarbamoyl chloride (0.51 g, 3.00 mmol) and 1,4-diazabicyclo[2.2.2]octane (0.34 g, 3.00 mmol) in dimethylformamide (15 ml) was stirred at room temperature for 1 hour. Water was added and the precipitates were collected by suction. The solids were dissolved in dichloromethane and the solution was dried over sodium sulphate, filtered and evaporated in vacuo. The residue was crystallised from ethyl acetate:heptane yielding the title compound (0.79 g, 72% yield) as a brown solid.

$^1$H NMR (300 MHz, CDCl$_3$): δ 0.86–1.01 (m, 2H), 1.05–1.37 (m, 3H), 1.60–1.78 (m, 5H), 1.83 (m, 1H), 2.13 (d, 2H), 3.46 (br.s, 3H), 6.90 (br.s, 1H), 7.27 (m, 1H), 7.39 (m, 4H), 7.98 (d, 1H), 8.12 (s+br.s, 2H, CH+NH); HPLC-MS (Method A): m/z=368 (M+H); R$_t$=4.04 min.

Example 267

Methyl-phenyl-carbamic acid 5-(4-methoxy-phenoxy)-pyrimidin-2-yl ester

A solution of 5-(4-methoxy-phenoxy)-pyrimidin-2-ol (0.44 g, 2.00 mmol), N-methyl-N-phenylcarbamoyl chloride (0.34 g, 2.00 mmol) and 1,4-diazabicyclo[2.2.2]octane (0.22 g, 2.00 mmol) in dimethylformamide (15 ml) was stirred at room temperature for 1 hour. Water was added and the precipitates were collected by suction. The solids were dissolved in dichloromethane and the solution was dried over sodium sulphate, filtered and evaporated in vacuo. The residue was crystallised from ethyl acetate:heptane yielding the title compound (0.55 g, 79% yield) as an off-white solid.

$^1$H NMR (300 MHz, CDCl$_3$): δ 3.43 (br.s, 3H), 3.82 (s, 3H), 6.91+7.00 (AB-system, 2×2H), 7.26 (m, 1H), 6.39 (m, 4H), 8.33 (s, 2H); HPLC-MS (Method A): m/z=352 (M+H); R$_t$=4.02 min.

Example 268

Methyl-phenyl-carbamic acid 5-(3,4-dichloro-phenoxy)-pyrimidin-2-yl ester

A solution of 5-(3,4-dichloro-phenoxy)-pyrimidin-2-ol (0.51 g, 2.00 mmol), N-methyl-N-phenylcarbamoyl chloride (0.34 g, 2.00 mmol) and 1,4-diazabicyclo[2.2.2]octane (0.22 g, 2.00 mmol) in dimethylformamide (15 ml) was stirred at room temperature for 1 hour. Water was added and the precipitates were collected by suction. The solids were dissolved in dichloromethane and the solution was dried over sodium sulphate, filtered and evaporated in vacuo. The residue was crystallised from ethyl acetate:heptane yielding the title compound (0.51 g, 65% yield) as an off-white solid.

$^1$H NMR (300 MHz, CDCl$_3$): δ 3.44 (br.s, 3H), 6.89 (dd, 1H), 7.14 (d, 1H), 7.27 (m, 1H), 7.39 (m, 4H), 7.44 (d, 1H), 8.42 (s, 2H); HPLC-MS (Method A): m/z=390 (M+H); R$_t$=4.66 min.

Example 269

Methyl-phenyl-carbamic acid 6-pyridin-2-ylmethyl-pyridazin-3-yl ester

A solution of 6-(2-pyridinylmethyl)-3-pyridazinol (100 mg, 0.53 mmol), N-methyl-N-phenylcarbamoyl chloride (91 mg, 0.53 mmol) and 1,4-diazabicyclo[2.2.2]octane (60 mg, 0.53 mmol) in dimethylformamide (10 ml) was stirred at room temperature for 2 hours. Water was added and the solution was extracted twice with dichloromethane. The combined organic layers were dried over sodium sulphate, filtered and evaporated in vacuo. The residue was purified by flash column chromatography (SiO$_2$, ethyl acetate) yielding the title compound (70 mg, 41% yield) as a yellow oil.

$^1$H NMR (300 MHz, CDCl$_3$): δ 3.42 (br.s, 3H), 4.50 (s, 2H), 7.11–7.33 (m, 4H), 7.39 (d, 4H), 7.60 (m, 2H), 8.52 (d, 1H); HPLC-MS (Method A): m/z=321 (M+H); R$_t$=1.98 min.

Example 270

Methyl-phenyl-carbamic acid 6-(4-methoxy-benzyl)-pyridazin-3-yl ester

A solution of 6-(2-pyridinylmethyl)-3-pyridazinol (97 mg, 0.45 mmol), N-methyl-N-phenylcarbamoyl chloride (76 mg, 0.45 mmol) and 1,4-diazabicyclo[2.2.2]octane (50 mg, 0.45 mmol) in dimethylformamide (10 ml) was stirred at room temperature for 2 hours. Water was added and the solution was extracted twice with dichloromethane. The combined organic layers were dried over sodium sulphate, filtered and evaporated in vacuo. The residue was purified by flash column chromatography (SiO$_2$, ethyl acetate:heptane (50:50)) yielding the title compound (117 mg, 41% yield) as a white solid.

$^1$H NMR (300 MHz, CDCl$_3$): δ 3.43 (br.s, 3H), 3.79 (s, 3H), 4.28 (s, 2H), 6.83 (d, 2H), 7.17 (d, 2H), 7.27 (m, 3H), 7.40 (d, 4H); HPLC-MS (Method A): m/z=350 (M+H); R$_t$=3.60 min.

Example 271

Methyl-phenyl-carbamic acid 6-(2,4-dichloro-benzyl)-pyridazin-3-yl ester

A solution of 6-(2,4-dichlorobenzyl)-3-pyridazinol (98 mg, 0.38 mmol), N-methyl-N-phenylcarbamoyl chloride (65 mg, 0.38 mmol) and 1,4-diazabicyclo[2.2.2]octane (43 mg, 0.38 mmol) in dimethylformamide (10 ml) was stirred at room temperature for 2 hours. Water was added and the solution was extracted twice with dichloromethane. The combined organic layers were dried over sodium sulphate, filtered and evaporated in vacuo. The residue was purified by flash column chromatography (SiO$_2$, ethyl acetate:heptane (40:60)) yielding the title compound (119 mg, 80% yield) as a yellow oil.

$^1$H NMR (300 MHz, CDCl$_3$): δ 3.43 (br.s, 3H), 4.42 (s, 2H), 7.17–7.44 (m, 10H); HPLC-MS (Method A): m/z=388 (M+H); R$_t$=4.44 min.

Example 272 (General Procedure 15)

4-Pyridin-2-yl-piperazine-1-carboxylic acid 4-(5-trifluoromethyl-pyridin-2-yloxy)phenyl ester The hydrochloride of the title compound was prepared from 4-(5-trifluoromethyl-pyridin-2-yloxy)phenyl chloroformate and 1-pyridin-2-yl-piperazine. White crystals, yield 87%; m.p. 247–248° C.; HPLC-MS: m/z=445 (M+H); IR (KBr): ν 1713 (C=O) cm$^{-1}$.

Example 273 (General Procedure 15)

4-(1,3-Benzodioxol-5-yl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(1,3-benzodioxol-5-yl)-piperazine. The crude product was partitioned between dichlorormethane and 1 M aqueous sodium carbonate. The organic layer was washed with water, dried and evaporated. The residue was triturated with ethyl acetate-heptane (1:4) and the precipitate was collected by filtration and dried to give the title compound. Yield 39%; m.p. 146–147° C.; $^1$H NMR (DMSO-d$_6$): δ 8.60–8.56 (br, 1H), 8.29–8.20 (dd-like, 1H), 7.31–7.20 (m, 5H), 6.84–6.72 (d-like, 1H), 6.76–6.72 (d-like, 1H), 6.45–6.36 (dd-like, 1H), 3.81–3.47 (br m, 4H), 3.16–3.00 (br,m, 4H); HPLC-MS: m/z=488 (M+H); IR (KBr): ν 1719 (C=O) cm$^{-1}$.

Example 274 (General Procedure 15)

4-[2-(2-Hydroxyethoxy)ethyl]-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 2-(2-hydroxyethoxy)ethyl-piperazine. Yield 13%; $^1$H NMR (DMSO-d$_6$): δ 10.8 (br), 8.61–8.54 (br, 1H), 8.30–8.21 (dd-like, 1H), 7.32–7.19 (m, 5H), 4.3–3.9 (br, 2H), 3.9–3.0 (br m, alicyclics and aliphatics+water); HPLC-MS: m/z=456(M+H); IR (KBr): ν 1724 (C=O) cm$^{-1}$.

Example 275 (General Procedure 15)

4-(Diphenylmethyl)piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(diphenylmethyl)piperazine, white crystals, yield 74%;

m.p. 168–169° C.;

$^1$H NMR (DMSO-d$_6$): δ 12.4 (br, 1H), 8.60–8.54 (d-like m, 1H), 8.28–8.20 (dd-like m, 1H), 7.98–7.82 (br, 2H), 7.55–7.15 (br m, 13 H), 5.6 (br, 1H), 4.35–3.48 (br, 3.35–3.0 (br, 5H); IR (KBr): ν 1723 (C=O) cm$^{-1}$.

Example 276 (General Procedure 15)

4-(4-tert-Butylbenzyl)piperazine-1-carboxylic acid 4-(5-trifluoromethyl-pyridin-2-yloxy)phenyl ester The hydrochloride of the title compound was prepared from 4-(5-trifluoromethyl-pyridin-2-yloxy)-phenyl chloroformate and 1-(4-tert-butylbenzyl)diphenylmethyl)piperazine, white crystals, yield 56%; m.p. 274–275° C.; HPLC-MS: m/z=514 (M+H); IR (KBr): ν 1721 (C=O) cm$^{-1}$.

Example 277 (General Procedure 15)

4-(4-Fluorobenzyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(4-fluorobenzyl)piperazine, white crystals, yield 69%;

m.p. 240–243° C.; HPLC-MS: m/z=476 (M+H), 498 (M+Na); IR (KBr): ν 1720 (C=O) cm$^{-1}$.

Example 278 (General Procedure 15)

4-(2-Thienylethyl)piperazine-1-carboxylic acid 4-(5-trifluoromethyl-pyridin-2-yloxy)phenyl ester The hydrochloride of the title compound was prepared from 4-(5-trifluoromethyl-pyridin-2-yloxy)-phenyl chloroformate and 1-(2-thienylethyl)piperazine, white crystals, yield 62%; m.p. 236–237° C.; $^1$H NMR (DMSO-d$_6$): δ 11.51 (br s, 1H), 8.61–8.54 (br m, 1H), 7.48–7.17 (m, 6H), 7.06–6.89 (m, 2H), 4.4–3.9 (br, 2H), 3.9–2.6 (br m, 16.5 H~12H+water); HPLC-MS: m/z=478 (M+H); IR (KBr): ν 1714 (C=O) cm$^{-1}$.

Example 279 (General Procedure 15)

4-(1-Phenylethyl)piperazine-1-carboxylic acid 4-(5-trifluoromethyl-pyridin-2-yloxy)phenyl ester The crude hydrochloride of the title compound was prepared from 4-(5-trifluoromethyl-pyridin-2-yloxy)-phenyl chloroformate and 1-(1-phenylethyl)piperazine. Trituration with water, filtering and drying of the residue gave white crystals, yield 31%; m.p. 242° C.; $^1$H NMR (DMSO-d$_6$): δ 11.56 (br s, 1H), 8.61–8.52 (br m, 1H), 8.30–8.19 (dd-like m, 1H), 7.77–7.31 (br m, 5H), 7.31–7.13 (m, 5H), 4.60–3.27 (br m, 6H+water), 3.27–2.57 (br, 3H), 1.73 (br d, 3H); IR (KBr): ν 1712 (C=O) cm$^{-1}$.

Example 280 (General Procedure 15)

4-Octylpiperazine-1-carboxylic acid 4-(5-trifluoromethyl-pyridin-2-yloxy)phenyl ester The crude hydrochloride of the title compound was prepared from 4-(5-trifluoromethyl-pyridin-2-yloxy)-phenyl chloroformate and 1-(1-phenylethyl)piperazine. Trituration with water, filtering and drying of the residue gave white crystals, yield 31%; m.p. 244–245° C.; $^1$H NMR (DMSO-d$_6$): δ 11.16 (br s, 1H), 8.61–8.57 (br m, 1H), 8.30–8.20 (dd-like m, 1H), 7.32–7.18 (m, 5H), 4.39–3.96 (br, 2H), 3.77–3.38 (br, 4H), 3.25–2.88 (br, 4H), 1.84–1.58 (br, 2H), 1.42–1.12 (br s, 10H), 0.87 (br t, 3H); IR (KBr): ν 1731, 1713 (C=O) cm$^{-1}$.

Example 281 (General Procedure 15)

4-(3-Dimethylamino-propyl)-piperazine-1-carboxylic acid 4-(5-trifluoromethyl-pyridin-2-yloxy)-phenyl ester The crude hydrochloride of the title compound was prepared from 4-(5-trifluoromethyl-pyridin-2-yloxy)-phenyl chloroformate and 1-(3-dimethylaminopropyl)piperazine. A suspension of the product in ether was stirred with an excess of HCl in ether and the precipitate was washed with ether and dried to give the dihydrochloride of the title compound as white crystals, m.p. 292–293° C.; ¹H NMR (DMSO-d6):, 11.35 (br s, 1H), 10.46 (br s, 1H), 8.61–8.52 (br m, 1H), 8.31–8.17 (m, 1H), 7.35–7.16 (m, 5H), 4.45–4.00 (br, 2H), 3.80–3.45 (br, 4H), 3.30–3.01 (br, 6H), 2.78 (br s, 6H), 2.31–2.07 (br, 2H); IR (KBr): ν 1731, 1713 (C=O) cm⁻¹.

Example 282 (General Procedure 15)

4-Pyrimidin-2-yl-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(pyrimidin-2-yl)piperazine. The crude product was dried in vacuo at 50° C. for 80 min and extracted with ether. The ether phase was evaporated and the residue was purified by flash chromatography on silica eluted with ethyl acetate-heptane 1:1 to give the title compound as white needles. Yield 14%; m.p. 120–121° C.; ¹H NMR (DMSO-$d_6$): δ 8.61–8.56 (br, 1H), 8.41 (d, J=4.8 Hz, 2H), 8.29–8.20 (dd-like, 1H), 7.31–7.20 (m, 5H), 6,69 (t-like m, J~4.8 Hz, 1H), 3.94–3.78 (br s, 4H), 3.78–3.45 (br d, 4H); HPLC-MS: m/z=446 (M+H); IR (KBr): ν 1719 (C=O) cm⁻¹.

Example 283 (General Procedure 15)

4-Cyclopropylmethyl-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-cyclopropylpiperazine, yield 62%. Recrystallisation from 0.2 M HCl gave white crystals, m.p. 238–239° C.; ¹H NMR (DMSO-$d_6$): δ 11.51 (br s, 1H), 8.61–8.55 (m, 1H), 8.30–8.20 (m, dd, 1H), 7.32–7.19 (m, d+s, 5H), 4.44–4.00 (br, 2H), 3.80–3.40 (br m, 4H), 3.29–2.93 (br m, 4H), 1.28–1.05 (br m, 1H), 0.75–0.58 (m, 2H), 0.50–0.35 (m, 2H). IR (KBr): ν 1730,1713 (C=O) cm⁻¹.

Example 284 (General Procedure 15)

4-Methyl-1,4-diazepane-1-carboxylic acid 4-(5-trifluoromethyl-pyridin-2-yloxy)phenyl ester The hydrochloride of the title compound was prepared from 4-(5-trifluoromethyl-pyridin-2-yloxy)-phenyl chloroformate and 1-methylhomopiperazine; white crystals, m.p. 210–211° C.; ¹H NMR (DMSO-$d_6$): δ 11.27 (br s, 1H), 8.61–8.54 (m, 1H), 8.30–8.20 (dd-like m, 1H), 7.34–7.18 (m, 5H), 4.13–3.08 (br, 11H, 8H+water), 2.80 (br s, 3H), 2.47–1.98 (br m, 2H);
IR (KBr): ν 1723, 1711 (C=O) cm⁻¹.

Example 285 (General Procedure 15)

4-Phenethyl-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-phenethylpiperazine, yield 54%. Recrystallisation from 99% EtOH gave white crystals, m.p. 245–247° C.; ¹H NMR (DMSO-$d_6$): δ 11.72 (br, 1H), 8.63–8.53 (br, 1H), 8.31–8.19 (dd-like m, 1H), 7.44–7.16 (m, 10H), 4.44–4.01 (br, 2H), 3.83–3.45 (br, 4H), 3.45–2.95 (br, ~8H, 6H+water); IR (KBr): ν 1713 (C=O) cm⁻¹.

Example 286 (General Procedure 15)

4-Pyridin-2-ylmethyl-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-pyridin-2-ylmethyl-piperazine. White crystals, yield 64%;
m.p. 189–190° C.; ¹H NMR (DMSO-$d_6$): δ 8.72–8.63 (m, 1H), 8.60–8.55 (br, 1H), 8.29–8.20 (dd-like,1H), 8.02–7.90 (m, 1H), 7.80–7.65 (m, 1H), 7.56–7.45 (m,1H), 7.31–7.22 (m, 5H), 4.52 (br s, 2H), 4.08–3.68 (br, 4H+NH+water); HPLC-MS: m/z=459 (M+H); IR (KBr): ν 1717 (C=O) cm⁻¹.

Example 287 (General Procedure 15)

4-Pyridin-3-ylmethyl-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-pyridin-3-ylmethyl-piperazine. Trituration with water, filtering and drying of the residue gave white crystals. ¹H NMR (DMSO-$d_6$): δ 8.78–8.51 (m, 3H), 8.30–8.18 (dd-like, 1H), 8.12–8.00 (br d, 1H), 7.57–7.46 (m,1H), 7.32–7.17 (m, 5H), 4.65–4.11 (br, 2H), 4.11–2.78 (br m, 6H+water); HPLC-MS: m/z=459 (M+H); IR (KBr): ν 1723 (C=O) cm⁻¹.

Example 288 (General Procedure 15)

4-(3-Phenylpropyl)piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(3-phenylpropyl)piperazine, yield 68%. m.p. 235–238° C.; ¹H NMR (DMSO-$d_6$): δ 11.51 (br, 1H), 8.61–8.55 (br, 1H), 8.29–8.20 (dd-like m, 1H), 7.38–7.16 (m, 10H), 4.38–3.96 (br, 2H), 3.83–3.40 (br, 4H), 3.30–2.91 (br, 4H), 2.75–2.57 (t-like m, 2H), 2.20–1.94 (m, 2H); IR (KBr): ν 1715 (C=O) cm⁻¹.

Example 289 (General Procedure 15)

4-(4-Phenylbutyl)piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(4-phenylbutyl)piperazine, yield 71%. m.p. 232–234° C.;
¹H NMR (DMSO-$d_6$): δ 11.32 (br s, 1H), 8.61–8.55 (br, 1H), 8.29–8.20 (dd-like m, 1H), 7.36–7.13 (m, 10H), 4.40–3.97 (br, 2H), 3.81–3.39 (br m, 4H), 3.26–2.91 (br, 4H), 2.71–2.55 (t-like m, 2H), 1.88–1.51 (br m, 4H); IR (KBr): ν 1728, 1713 (C=O) cm⁻¹.

Example 290 (General Procedure 15)

4-Benzyl-1,4-diazepane-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-benzylhomopiperazine, crude yield 70%. 0.20 g Of the crude product was heated with 3 ml of water, cooled at 0° C., the precipitate filtered off and dried; m.p. 231–233° C.; $^1$H NMR (DMSO-$d_6$): δ 11.38 (brs, 1H), 8.62–8.55 (br, 1H), 8.30–8.20 (dd-like m, 1H), 7.76–7.60 (br, 2H), 7.52–7.41 (br m, 3H), 7.32–7.19 (m, 5H), 4.38 (br s, 2H), 4.18–3.01 (br m, 8H+water), 2.6–2.0 (br, 2H+DMSO); IR (KBr): ν 1726, 1710 (C=O) cm$^{-1}$.

Example 291 (General Procedure 15)

4-(3,4-Dichlorophenyl)piperazine-1-carboxylic acid 4-(5-trifluoromethyl-pyridin-2-yloxy)phenyl ester The hydrochloride of the title compound was prepared from 4-(5-trifluoromethyl-pyridin-2-yloxy)-phenyl chloroformate and 1-(3,4-dichlorophenyl)piperazine. The crude product was partitioned between dichlorormethane and 2 M aqueous sodium carbonate. The organic layer was washed with water, dried and evaporated. The residue was triturated with ethyl acetate-heptane (1:4) and the precipitate was collected by filtration and dried to give the title compound as white crystals. Yield 28%; m.p. 115–116° C.; $^1$H NMR (DMSO-$d_6$): δ 8.61–8.55 (br, 1H), 8.30–8.20 (dd-like, 1H), 7.48–7.40 (d-like,1H), 7.31–7.16 (m, 6H), 7.04–6.94 (dd-like, 1H), 3.83–3.47 (br m, 4H), 3.36–3.24 (br s, 4H+water); HPLC-MS: m/z=512 (M+H); IR (KBr): ν 1724, 1706 cm$^{-1}$.

Example 292 (General Procedure 15)

4-(4-Fluorophenyl)piperazine-1-carboxylic acid 4-(5-trifluoromethyl-pyridin-2-yloxy)phenyl ester The hydrochloride of the title compound was prepared from 4-(5-trifluoromethyl-pyridin-2-yloxy)-phenyl chloroformate and 1-(4-fluorophenyl)piperazine. White crystals, yield 20%; m.p. 131–132° C.; $^1$H NMR (DMSO-$d_6$): δ 8.61–8.53 (br, 1H), 8.30–8.19 (dd-like, 1H), 7.33–7.17 (m, 5H), 7.17–6.95 (m, 4H), 3.85–3.47 (br d, 4H), 3.25–3.07 (br m, 4H); HPLC-MS: m/z=462 (M+H); IR (KBr): ν 1739, 1714 cm$^{-1}$.

Example 293 (General Procedure 15)

4-(2-Chlorophenyl)piperazine-1-carboxylic acid 4-(5-trifluoromethyl-pyridin-2-yloxy)phenyl ester The the hydrochloride of title compound was prepared from 4-(5-trifluoromethyl-pyridin-2-yloxy)-phenyl chloroformate and 1-(2-chlorophenyl)piperazine. Drying in vacuo at 50° C. for 3½ h gave the title compound; $^1$H NMR (DMSO-$d_6$): δ 8.61–8.55 (br, 1H), 8.29–8.20 (dd-like, 1H), 7.53–7.41 (m, 1H), 7.39–7.17 (m, 7H), 7.14–7.03 (m, 1H), 4.58 (br s, NH+water), 3.85–3.55 (br m, 4H), 3.12–2.99 (br m, 4H); HPLC-MS: m/z=478 (M+H); IR (KBr): ν 1733 (C=O) cm$^{-1}$.

Example 294 (General Procedure 15)

(2-Dimethylamino-ethyl)methylcarbamic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and N,N,N'-trimethylethylenediamine; m.p. 139–140° C.; $^1$H NMR (MeOH-$d_6$): δ 8.45–8.38 (br, 1H), 8.15–8.05 (dd-like m, 1H), 7.31–7.11 (m, 5H), 3.84–3.73 (br m, 2H), 3.54–3.38 (br m, 3H), 3.19 (br s, 2H), 2.99 (br s, 6H); traces of impurities at 3.9 (br) and 3.1 (br); IR (KBr): ν 2695, 1705 cm$^1$ (C=O) cm$^{-1}$.

Example 295 (General Procedure 15)

4-Methylpiperazine-1-carboxylic acid 4-chlorophenyl ester

The hydrochloride of the title compound was prepared from 4-chlorophenyl chloroformate and 1-methylpiperazine, yield 81%. White crystals, m.p. 237–240° C.; $^1$H NMR (DMSO-$d_6$): δ 11.67 (br s, 1H), 7.50, 7.45, 7.24, 7.20 (AB-system, d=7.47 and 7.22; J=8.84 Hz, 4H), 4.40–3.91 (br, 2H, 3.77–2.92 (br m, 6H+water), 2.77 (s, 3H); IR (KBr): ν 1717 (C=O) cm$^{-1}$.

Example 296 (General Procedure 15)

4-(4-Phenylbutyl)piperazine-1-carboxylic acid 4-chlorophenyl ester

The hydrochloride of the title compound was prepared from 4-chlorophenyl chloroformate and 1-(4-phenylbutyl) piperazine, yield 86%. White crystals, m.p. 230–232° C.; $^1$H NMR (DMSO-$d_6$): δ 11.43 (br,1H), 7.51–7.43 (d-like m, 2H), 7.33–7.15 (m, 7H), 4.33–3.95 (br, max at 4.21 and 4.10 ppm; 2H), 3.72–3.36 (br m, 4H), 3.22–2.96 (br, max at 3.10 ppm, 4H), 2.62 (t, J=7.54 Hz, 2H), 1.84–1.69 (m, 2H), 1.69–1.54 (m, 2H) ppm; IR (KBr): ν 1736, 1720 (C=O) cm$^{-1}$.

Example 297 (General Procedure 15)

4-[2-(2-Hydroxyethoxy)ethyl]piperazine-1-carboxylic acid 4-(4-trifluoromethylphenoxy)phenyl ester The hydrochloride of the title compound was prepared from 4-(4-trifluoromethylphenoxy)phenyl chloroformate and 2-(2-hydroxyethoxy)ethyl-piperazine. Pale powder, m.p. 176–178° C.; $^1$H NMR (MeOH-$d_4$): δ Two AB-systems: 7.68–7.58 (d-like, 2H) and 7.29–7.04 (m, 6H); 4.74–3.18 (complex, 16 H, partly overlapping with MeOH-$d_4$); HPLC-MS m/z=455 (M+H), 477 (M+Na), $R_t$=3.08 min.; IR (KBr): ν 1718 (C=O) cm$^{-1}$.

Example 298 (General Procedure 15)

4-(1-Ethylpropyl)piperazine-1-carboxylic acid 4-(4-trifluoromethylphenoxy)phenyl ester The hydrochloride of the title compound was prepared from 4-(4-trifluoromethylphenoxy)phenyl chloroformate and 1-(1-ethylpropyl)piperazine, yield 74%. White crystals, $^1$H NMR (DMSO-$d_6$): δ 10.59 (br s, 1H), 2 AB-systems: 7.81–7.70 (d-like, 2H) and 7.31–7.09 (m, 6H); 4.38–3.99 (br s, 2H), 3.90–3.38 (br, 4H), 3.33–2.99 (br, 3H), 2.01–1.77 (m, 2H), 1.77–1.49 (m, 2H), 0.98 (t, 6H); HPLC-MS m/z=437 (M+H).

Example 299 (General Procedure 15)

4-Cycloheptylpiperazine-1-carboxylic acid 4-(4-trifluoromethyl-phenoxy)phenyl ester The hydrochloride of the title compound was prepared from 4-(4-trifluoromethylphenoxy)phenyl chloroformate and 1-cycloheptylpiperazine. The crude product was partitioned between dichlorormethane and aqueous sodium carbonate. The organic layer was washed with water, dried and evaporated. The residue was triturated with ethyl acetate-heptane (1:4) and the precipitate was collected by filtration and dried to give the title compound. White crystals, $^1$H NMR (MeOH-d$_4$): δ Two AB-systems: 7.68–7.58 (d-like, 2H) and 7.23–7.04 (m, 6H); 3.86–3.50 (br d, 4H), 2.98–2.66 (br, 5H), 2.04–1.37 (m, 12H); HPLC-MS m/z=463 (M+H); IR (KBr): ν 1730, 1707 cm$^{-1}$.

Example 300 (General Procedure 15)

4-Cyclohexylpiperazine-1-carboxylic acid 4-(4-trifluoromethyl-phenoxy)phenyl ester The hydrochloride of the title compound was prepared from 4-(4-trifluoromethylphenoxy)phenyl chloroformate and 1-cyclohexylpiperazine, yield 80%. White crystals, m.p. 290–291° C., $^1$H NMR (DMSO-d$_6$): δ 10.82 (br s, 1H), 2 AB-systems: 7.83–7.69 (d-like, 2H) and 7.32–7.10 (m, 6H); 4.40–4.02 (br, 2H), 3.75–3.39 (br, 4H), 3.31–2.98 (br, 3H), 2.23–2.02 (m, 2H), 1.92–1.74 (m, 2H), 1.70–0.97 (m, 6H); HPLC-MS m/z=449 (M+H); IR (KBr): ν 1717 (C=O) cm$^{-1}$.

Example 301 (General Procedure 15)

4-(4-Chlorobenzyl)piperazine-1-carboxylic acid 4-(4-trifluoromethylphenoxy)phenyl ester The hydrochloride of the title compound was prepared from 4-(4-trifluoromethylphenoxy)phenyl chloroformate and 1-(4-chlorobenzyl)piperazine, yield 86%. White crystals, m.p. 232–234° C.; $^1$H NMR (DMSO-d$_6$): δ 11.92 (br s, 1H), 3 AB-systems: 7.83–7.62 (t-like, 4H) and 7.62–7.48 (d-like, 2H), and 7.32–7.07 (m, 6H); 4.51–3.95 (br s at 4.37 ppm overlapping with br signal at 4.2 ppm, 4H), 3.95–2.95 (br m, 9H: 6H+water); IR (KBr): ν 1717 (C=O) cm$^{-1}$.

Example 302 (General Procedure 15)

4-(4-Methylbenzyl)piperazine-1-carboxylic acid 4-(4-trifluoromethylphenoxy)phenyl ester The hydrochloride of the title compound was prepared from 4-(4-trifluoromethylphenoxy)phenyl chloroformate and 1-(4-methylbenzyl)piperazine, yield 96%. White crystals, m.p. 250–252° C.; HPLC-MS m/z=472 (M+H); IR (KBr): ν 1720 (C=O) cm$^{-1}$.

Example 303 (General Procedure 15)

4-(4-Methoxybenzyl)piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(4-methoxybenzyl)piperazine, yield 78%. White crystals, m.p. 237–238° C.; HPLC-MS m/z=488 (M+H); IR (KBr): ν 1719 (C=O) cm$^{-1}$.

Example 304 (General Procedure 15)

4-(2-Chloro-6-fluoro-benzyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(2-chloro-6-fluorobenzyl)piperazine. White crystals, m.p. 204–205° C. (from ethanol); HPLC-MS m/z=510 (M+H); IR (KBr): ν 1726 (C=O) cm$^{-1}$;

Example 305 (General Procedure 15)

4-(3-Methoxyphenyl)piperazine-1-carboxylic acid 4-(4-trifluoromethylphenoxy)phenyl ester The hydrochloride of the title compound was prepared from 4-(4-trifluoromethylphenoxy)phenyl chloroformate and 1-(3-methoxyphenyl)piperazine. White crystals, m.p. 168–171° C. (sinters at 160° C.); HPLC-MS m/z=473(M+1); IR (KBr): ν 1739, 1716 (C=O) cm$^{-1}$.

Example 306 (General Procedure 15)

4-Benzyl-piperazine-1-carboxylic acid 4-(3-chloro-5-trifluoromethyl-pyridin-2-yloxy)phenyl ester The hydrochloride of the title compound was prepared from 4-(3-chloro-5-trifluoromethyl-pyridin-2-yloxy)-phenyl chloroformate and 1-benzyl-piperazine, yield 94%. White crystals; m.p. 111–113° C. (resolidifies) and 114–115° C.; HPLC-MS m/z=492 (M+H).

Example 307 (General Procedure 8)

Methyl-phenyl-carbamic acid 4-iodo-pyrazol-1-yl ester

The title compound was prepared from 1-hydroxy-4-iodopyrazole and N-methyl-N-phenylcarbamoyl chloride applying the general procedure 8. The crude product was purified by flash chromatography (Quad flash 12, EtOAc-heptane) (98%, oil).

$^1$H NMR (300 MHz; CDCG$_3$): δ 3.44 (bs, 3H), 7.30–7.48 (m, 7H).; HPLC-MS: m/z=343.9 (M+1); R$_t$=4.12 min.

Example 308 (General Procedure 8)

Methyl-phenyl-carbamic acid benzotriazol-1-yl ester

The title compound was prepared from 1-hydroxybenzotriazole and N-methyl-N-phenylcarbamoyl chloride applying the general procedure 8. The crude product was purified by flash chromatography (Quad flash 12, EtOAc-heptane) (98%, crystallizes slowly).

$^1$H NMR (300 MHz; CDCl$_3$): δ 3.50 (bs, 3H), 7.37–7.57 (m, 8H), 8.04 (d, 1H).; HPLC-MS: m/z=269.0 (M+1); R$_t$=3.69 min.

Example 309 (General Procedure 8)

Methyl-phenyl-carbamic acid [1,2,3]triazolo[4,5-b]pyridin-3-yl ester

The title compound was prepared from [1,2,3]Triazolo[4,5-b]pyridin-3-ol and N-methyl-N-phenylcarbamoyl chloride applying the general procedure 8. The crude product was purified by flash chromatography (Quad flash 12, EtOAc-heptane) (99%, oil).
$^1$H NMR (300 MHz; CDCl$_3$): δ 3.50 (bs, 3H), 7.30–7.60 (m, 6H), 8.40 (d, 1H), 8.75 (d, 1H); HPLC-MS: m/z=270.0 (M+1); R$_f$=3.18 min.

Example 310 (General Procedure 8)

Methyl-phenyl-carbamic acid 3-(2-nitro-phenyl)-pyrazol-1-yl ester

The title compound was prepared from 1-hydroxy-3-(2-nitrophenyl)pyrazole and N-methyl-N-phenylcarbamoyl chloride applying the general procedure 8. The crude product was purified by flash chromatography (Quad flash 12, EtOAc-heptane) (94%, oil).
$^1$H NMR (300 MHz; CDCl$_3$): δ 3.45 (bs, 3H), 6.44 (bs, 1H), 7.30–7.50 (m, 7H), 7.58 (dt, 1H), 7.72–7.78 (m, 2H); HPLC-MS: m/z=339.1 (M+1); R$_f$=4.15 min.

Example 311 (General Procedure 8)

Methyl-phenyl-carbamic acid 3-(4-nitro-phenyl)-pyrazol-1-yl ester

The title compound was prepared from 1-hydroxy-3-(4-nitrophenyl)pyrazole and N-methyl-N-phenylcarbamoyl chloride applying the general procedure 8. The crude product was purified by flash chromatography (Quad flash 12, EtOAc-heptane) (99%, yellow crystals).
$^1$H NMR (300 MHz; CDCl$_3$): δ 3.47 (bs, 3H), 6.70 (bd, 1H), 7.32–7.50 (m, 6H), 7.94 (d, 2H), 8.26 (d, 2H); HPLC-MS: m/z=339.1 (M+1); R$_f$=4.41 min.

Example 312 (General Procedure 8)

Methyl-phenyl-carbamic acid 3-pyridin-2-yl-pyrazol-1-yl ester

The title compound was prepared from 1-hydroxy-3-(2-pyridyl)pyrazole and N-methyl-N-phenylcarbamoyl chloride applying the general procedure 8. The crude product was purified by flash chromatography (Quad flash 12, EtOAc-heptane) (90%, oil).
$^1$H NMR (300 MHz; CDCl$_3$): δ 3.48 (bs, 3H), 6.95 (d, 1H), 7.20 (dd, 1H), 7.30–7.48 (m, 6H), 7.70 (dt, 1H), 7.93 (d,1H), 8.61 (d, 1H); HPLC-MS: m/z=295.1 (M+1); R$_f$=2.75 min.

Example 313 (General Procedure 8)

Methyl-phenyl-carbamic acid 3-thiophen-2-yl-pyrazol-1-yl ester

The title compound was prepared from 1-hydroxy-3-(2-thienyl)pyrazole and N-methyl-N-phenylcarbamoyl chloride applying the general procedure 8. The crude product was purified by flash chromatography (Quad flash 12, EtOAc-heptane) (66%, oil).
$^1$H NMR (300 MHz; CDCl$_3$): δ 3.46 (bs, 3H), 6.48 (bd, 1H), 7.03 (dd, 1H), 7.25 (dd, 1H), 7.30–7.48 (m, 7H); HPLC-MS: m/z=300.1 (M+1); R$_f$=4.16 min.

Example 314 (General Procedure 8)

Methyl-phenyl-carbamic acid 3-(2-fluoro-phenyl)-pyrazol-1-yl ester

The title compound was prepared from 1-hydroxy-3-(2-fluorophenyl)pyrazole and N-methyl-N-phenylcarbamoyl chloride applying the general procedure 8. The crude product was purified by flash chromatography (Quad flash 12, EtOAc-heptane) (97%, oil).
$^1$H NMR (300 MHz; CDCl$_3$): δ 3.48 (bs, 3H), 6.75 (bt, 1H), 7.07–7.47 (m, 9H), 7.97 (dt, 1H); HPLC-MS: m/z=312.1 (M+1); R$_f$=4.45 min.

Example 315 (General Procedure 8)

Methyl-phenyl-carbamic acid 3-bromo-pyrazol-1-yl ester

The title compound was prepared from 1-hydroxy-3-bromopyrazole and N-methyl-N-phenylcarbamoyl chloride applying the general procedure 8. The crude product was purified by flash chromatography (Quad flash 12, EtOAc-heptane) (63%, oil).
$^1$H NMR (300 MHz; CDCl$_3$): δ 3.43 (bs, 3H), 6.31 (d, 1H), 7.26–7.48 (m, 6H).; HPLC-MS: m/z=298.0 (M+1); R$_f$=3.97 min.

Example 316 (General Procedure 8)

Methyl-phenyl-carbamic acid 5-iodo-pyrazol-1-yl ester

The title compound was prepared from 1-hydroxy-5-iodopyrazole and N-methyl-N-phenylcarbamoyl chloride applying the general procedure 8. The crude product was purified by flash chromatography (Quad flash 12, EtOAc-heptane) (64%, oil).
$^1$H NMR (300 MHz; CDCl$_3$): δ 3.48 (bs, 3H), 6.42 (d, 1H), 7.28–7.47 (m, 6H).; HPLC-MS: m/z=343.9 (M+1); R$_f$=3.81 min.

Example 317 (General Procedure 8)

Methyl-phenyl-carbamic acid 2-chloro-imidazol-1-yl ester

The title compound was prepared from 1-hydroxy-2-chloroimidazole, hydrochloride and N-methyl-N-phenylcarbamoyl chloride applying the general procedure 8. The crude product was purified by flash chromatography (Quad flash 12, EtOAc-heptane) (77%, oil).
$^1$H NMR (300 MHz; CDCl$_3$): δ 3.45 (bs, 3H), 6.90 (bs, 1H), 7.07 (bs, 1H), 7.35–7.40 (m, 3H), 7.46 (bt, 2H); HPLC-MS: m/z=251.9 (M+1); R$_f$=3.29 min.

Example 318 (General Procedure 8)

Methyl-phenyl-carbamic acid 4-(4-methoxy-phenyl)-pyrazol-1-yl ester

The title compound was prepared from 1-hydroxy-4-(4-methoxyphenyl)pyrazole and N-methyl-N-phenylcarbamoyl chloride applying the general procedure 8. The crude product was purified by flash chromatography (Quad flash 12, EtOAc-heptane) (6%, oil).

$^1$H NMR (300 MHz; CDCl$_3$): δ 3.45 (bs, 3H), 3.82 (s, 3H), 6.90 (d, 2H), 7.30–7.48 (m, 7H), 7.54 (bs, 2H); HPLC-MS: m/z=346.1 (M+23); R$_f$=4.16 min.

Example 319 (General Procedure 8)

Methyl-phenyl-carbamic acid 5-benzoyl-pyrazol-1-yl ester

The title compound was prepared from 1-hydroxy-5-benzoylpyrazole and N-methyl-N-phenylcarbamoyl chloride applying the general procedure 8. The crude product was purified by flash chromatography (Quad flash 12, EtOAc-heptane) (30%, crystals).

$^1$H NMR (300 MHz; CDCl$_3$): δ 3.48 (bs, 3H), 6.69 (bs, 1H), 7.27–7.52 (m, 8H), 7.63 (t, 1H), 7.79 (d, 2H); HPLC-MS: m/z=344.0 (M+23); R$_f$=4.41 min.

Example 320 (General Procedure 8)

Methyl-phenyl-carbamic acid 5-(4-methoxy-phenyl)-pyrazol-1-yl ester

The title compound was prepared from 1-hydroxy-5-(4-methoxyphenyl)pyrazole and N-methyl-N-phenylcarbamoyl chloride applying the general procedure 8. The crude product was purified by flash chromatography (Quad flash 12, EtOAc-heptane) (38%, yellow crystals).

$^1$H NMR (300 MHz; CDCl$_3$): δ 3.33 (bs, 3H), 3.86 (s, 3H), 6.34 (d, 1H), 6.95 (d, 2H), 7.25–7.45 (m, 8H); HPLC-MS: m/z=324.1 (M+1); R$_f$=4.27 min.

Example 321 (General Procedure 8)

Methyl-phenyl-carbamic acid 5-(4-dimethylamino-phenyl)-pyrazol-1-yl ester

The title compound was prepared from 1-hydroxy-5-(4-dimethylaminophenyl)-pyrazole and N-methyl-N-phenyl-carbamoyl chloride applying the general procedure 8. The crude product was purified by flash chromatography (Quad flash 12, EtOAc-heptane) (27%, crystals).

$^1$H NMR (300 MHz; CDCl$_3$): δ 3.02 (s, 6H), 3.35 (bs, 3H), 6.30 (d, 1H), 6.72 (d, 2H), 7.30–7.46 (m, 8H); HPLC-MS: m/z=337.1 (M+1); R$_f$=4.11 min.

Example 322 (General Procedure 8)

Methyl-phenyl-carbamic acid 4,5-diiodo-pyrazol-1-yl ester

The title compound was prepared from 1-hydroxy-4,5-diiodopyrazole and N-methyl-N-phenylcarbamoyl chloride applying the general procedure 8. The crude product was purified by flash chromatography (Quad flash 12, EtOAc-heptane) (76%, crystals).

$^1$H NMR (300 MHz; CDCl$_3$): δ 3.45 (bs, 3H), 7.30–7.50 (m, 6H).; HPLC-MS: m/z=369.9 (M+1); R$_f$=4.56 min.

Example 323 (General Procedure 8)

Methyl-phenyl-carbamic acid 5-thiophen-2-yl-pyrazol-1-yl ester

The title compound was prepared from 1-hydroxy-5-(2-thienyl)pyrazole and N-methyl-N-phenylcarbamoyl chloride applying the general procedure 8. The crude product was purified by flash chromatography (Quad flash 12, EtOAc-heptane) (51%, crystals).

$^1$H NMR (300 MHz; CDCl$_3$): δ 3.44 (bs, 3H), 6.45 (bs, 1H), 7.09 (dd, 1H), 7.26 (bs, 1H), 7.28–7.49 (m, 7H); HPLC-MS: m/z=300.1 (M+1); R$_f$=4.18 min.

Example 324 (General Procedure 8)

Methyl-phenyl-carbamic acid 2-(4-methoxy-phenyl)-imidazol-1-yl ester

The title compound was prepared from 1-hydroxy-2-(4-methoxyphenyl)imidazole, hydrochloride and N-methyl-N-phenylcarbamoyl chloride applying the general procedure 8. The crude product was purified by flash chromatography (Quad flash 12, EtOAc-heptane) (89%, crystals).

$^1$H NMR (300 MHz; CDCl$_3$): δ 3.33 (bs, 3H), 3.86 (s, 3H), 6.92 (d, 2H), 7.04 (d, 1H), 7.10 (bs, 1H), 7.28 (d, 2H), 7.34–7.50 (m, 3H), 7.60 (bd, 2H); HPLC-MS: m/z=324.1 (M+1); R$_f$=2.87 min.

Example 325 (General Procedure 8)

Methyl-phenyl-carbamic acid 2-methylsulfanyl-imidazol-1-yl ester

The title compound was prepared from 1-hydroxy-2-methylsulfanyl-imidazole hydrochloride and N-methyl-N-phenylcarbamoyl chloride applying the general procedure 8. The crude product was purified by flash chromatography (Quad flash 12, EtOAc-heptane) (97%, oil).

$^1$H NMR (300 MHz; CDCl$_3$): δ 2.56 (s, 3H), 3.44 (bs, 3H), 7.00 (bs, 1H), 7.08 (bs, 1H), 7.32–7.49 (m, 5H); HPLC-MS: m/z=264.1 (M+1); R$_f$=2.99 min.

Example 326 (General Procedure 8)

Methyl-phenyl-carbamic acid 3,5-bis-(4-methoxy-phenyl)-pyrazol-1-yl ester

The title compound was prepared from 1-hydroxy-3,5-bis-(4-methoxyphenyl)pyrazole and N-methyl-N-phenylcarbamoyl chloride applying the general procedure 8. The crude product was purified by flash chromatography (Quad flash 12,.EtOAc-heptane) (29%, beige crystals).

$^1$H NMR (300 MHz; CDCl$_3$): δ 3.35 (bs, 3H), 3.84 (s, 3H), 3.88 (s, 3H), 6.57 (s, 1H), 6.92 (d, 2H), 6.97 (d, 2H), 7.25–7.48 (m, 7H), 7.74 (d, 2H); HPLC-MS: m/z=881.2 (2M+23); R$_f$=5.26 min.

Example 327 (General Procedure 8)

Methyl-phenyl-carbamic acid 4-(4-fluoro-phenyl)-5-(4-methoxy-phenyl)-3-(4-methylphenyl)-pyrazol-1-yl ester The title compound was prepared from 1-hydroxy-4-(4-fluorophenyl)-5-(4-methoxyphenyl)-3-(4-methylphenyl)pyrazole and N-methyl-N-phenylcarbamoyl chloride applying the general procedure 8. The crude product was purified by flash chromatography (Quad flash 12, EtOAc-heptane) (11%, crystals).
$^1$H NMR (300 MHz; CDCl$_3$): δ 2.32 (s, 3H), 3.32 (bs, 3H), 3.83 (s, 3H), 6.87 (d, 2H), 6.93 (d, 2H), 7.12–7.48 (m, 13H); HPLC-MS: m/z=530.2 (M+23); R$_t$=6.04 min.

Example 328 (General Procedure 8)

Methyl-phenyl-carbamic acid 4-benzyl-5-(4-methoxy-phenyl)-3-(methylphenyl)-pyrazol-1-yl ester The title compound was prepared from 1-hydroxy-4-benzyl-5-(4-methoxyphenyl)-3-(4-methylphenyl)pyrazole and N-methyl-N-phenylcarbamoyl chloride applying the general procedure 8. The crude product was purified by flash chromatography (Quad flash 12, EtOAc-heptane) (14%, oil).
$^1$H NMR (300 MHz; CDCl$_3$): δ 2.31 (s, 3H), 3.31 (bs, 3H), 3.83 (s, 3H), 3.95 (s, 2H), 6.89 (d, 2H), 7.08–7.39 (m, 13H), 7.43 (d, 2H); HPLC-MS: m/z=504.2 (M+1); R$_t$=6.11 min.

Example 329 (General Procedure 8)

Methyl-phenyl-carbamic acid 4-acetyl-pyrazol-1-yl ester

The title compound was prepared from 1-hydroxy-4-acetylpyrazole and N-methyl-N-phenylcarbamoyl chloride applying the general procedure 8. The crude product was purified by flash chromatography (Quad flash 12, EtOAc-heptane) (89%, oil).
$^1$H NMR (300 MHz; CDCl$_3$): δ 2.44 (s, 3H), 3.44 (bs, 3H), 7.32–7.48 (m, 5H), 7.78 (bs, 1H), 7.85 (bs, 1H).

Example 330 (General Procedure 8)

Methyl-phenyl-carbamic acid 2-(4-nitro-phenyl)-imidazol-1-yl ester

The title compound was prepared from 1-hydroxy-2-(4-nitrophenyl)imidazole, hydrochloride and N-methyl-N-phenylcarbamoyl chloride applying the general procedure 8. The crude product was purified by flash chromatography (Quad flash 12, EtOAc-heptane) (90%, yellow crystals).
$^1$H NMR (300 MHz; CDCl$_3$): δ 3.38 (bs, 3H), 7.16 (s, 1H), 7.20 (s, 1H), 7.31 (d, 2H), 7.38–7.61 (m, 3H), 7.86 (bs, 2H), 8.25 (d, 2H).

Example 331 (General procedure 8)

Methyl-phenyl-carbamic acid 2-chloro-5-(4-methylphenyl)-imidazol-1-yl ester

The title compound was prepared from 1-hydroxy-2-chloro-5-(4-methylphenyl)imidazole, hydrochloride and N-methyl-N-phenylcarbamoyl chloride applying the general procedure 8. The crude product was purified by flash chromatography (Quad flash 12, EtOAc-heptane) (80%, oil).
$^1$H NMR (300 MHz; CDCl$_3$): δ 2.40 (s, 3H), 3.33 (bs, 3H), 7.00 (s, 1H), 7.19–7.29 (m, 6H), 7.35–7.50 (m, 3H).

Example 332 (General Procedure 8)

Methyl-phenyl-carbamic acid 4-formyl-pyrazol-1-yl ester

The title compound was prepared from 1-hydroxy-4-formylpyrazole and N-methyl-N-phenylcarbamoyl chloride applying the general procedure 8. The crude product was purified by flash chromatography (Quad flash 12, EtOAc-heptane) (73%, oil).
$^1$H NMR (300 MHz; CDCl$_3$): δ 3.45 (bs, 3H), 7.29–7.50 (m, 5H), 7.84 (bs, 1H), 7.90 (bs, 1H), 9.83 (s, 1H).

Example 333 (General Procedure 8)

Methyl-phenyl-carbamic acid 4-hydroxymethyl-pyrazol-1-yl ester

The title compound was prepared from 1-hydroxy-4-hydroxymethylpyrazole and N-methyl-N-phenylcarbamoyl chloride applying the general procedure 8. The crude product was purified by flash chromatography (Quad flash 12, EtOAc-heptane) (62%, oil).
$^1$H NMR (300 MHz; CDCl$_3$): δ 2.33 (bs, 1H), 3.40 (bs, 3H), 4.50 (s, 2H), 7.28–7.46 (m, 7H).

Example 334 (General Procedure 8)

Methyl-phenyl-carbamic acid 4-phenylethynyl-pyrazol-1-yl ester

The title compound was prepared from 1-hydroxy-4-phenylethynylpyrazole and N-methyl-N-phenylcarbamoyl chloride applying the general procedure 8. The crude product was purified by flash chromatography (Quad flash 12, EtOAc-heptane) (40%, yellow crystals).
$^1$H NMR (300 MHz; CDCl$_3$): δ 3.42 (bs, 3H), 7.30–7.58 (m, 12H).

Example 335 (General Procedure 8)

Methyl-phenyl-carbamic acid 2-bromo-imidazol-1-yl ester

The title compound was prepared from 1-hydroxy-2-bromoimidazole, hydrochloride and N-methyl-N-phenylcarbamoyl chloride applying the general procedure 8. The crude product was purified by flash chromatography (Quad flash 12, EtOAc-heptane) (63%, oil).
$^1$H NMR (300 MHz; CDCl$_3$): δ 3.45 (bs, 3H), 6.98 (bd, 1H), 7.11 (bs, 1H), 7.33–7.50 (m, 5H); HPLC-MS: m/z=296.0 (M+1); R$_t$=2.90 min.

Example 336 (General Procedure 8)

Methyl-phenyl-carbamic acid 2-phenylsulfanyl-imidazol-1-yl ester

The title compound was prepared from 1-hydroxy-2-phenylsulfanylimidazole hydrochloride and N-methyl-N-phenylcarbamoyl chloride applying the general procedure 8.

The crude product was purified by flash chromatography (Quad flash 12, EtOAc-heptane) (61%, oil).

$^1$H NMR (300 MHz; CDCl$_3$): δ 3.35 (s, 3H), 7.12 (bd, 1H), 7.17–7.39 (m, 11H); HPLC-MS: m/z=326.0 (M+1); R$_t$=3.65 min.

Example 337 (General Procedure 8)

Morpholine-4-carboxylic acid imidazol-1-yl ester

The title compound was prepared from 1-hydroxyimidazole and 4-morpholine carbonyl chloride applying the general procedure 8. The crude product was purified by preparative HPLC (water-acetonitrile-0. 1% TFA) (36%, crystals).

$^1$H NMR (300 MHz; CDCl$_3$): δ 3.57 (bs, 2H), 3.66 (bs, 2H), 3.78 (t, 4H), 7.12 (bs, 1H), 7.15 (bt, 1H), 7.90 (s, 1H); HPLC-MS: m/z=198.1 (M+1); R$_t$=0.36 min.

Example 338 (General Procedure 8)

Morpholine-4-carboxylic acid 2-bromo-imidazol-1-yl ester

The title compound was prepared from 1-hydroxy-2-bromoimidazole, hydrochloride and 4-morpholine carbonyl chloride applying the general procedure 8. The crude product was purified by flash chromatography (Quad flash 12, EtOAc) (98%, crystals).

$^1$H NMR (300 MHz; CDCl$_3$): δ 3.60 (bs, 2H), 3.71 (bs, 2H), 3.80 (t, 4H), 7.02 (d, 1H), 7.18 (d, 1H); HPLC-MS: m/z=276.0 (M+1); R$_t$=1.73 min.

Example 339 (General Procedure 8)

Morpholine-4-carboxylic acid 2-chloro-imidazol-1-yl ester

The title compound was prepared from 1-hydroxy-2-chloroimidazole, hydrochloride and 4-morpholine carbonyl chloride applying the general procedure 8. The crude product was purified by flash chromatography (Quad flash 12, EtOAc) (54%, oil).

$^1$H NMR (300 MHz; CDCl$_3$): δ 3.58 (bs, 2H), 3.68 (bs, 2H), 3.69 (t, 4H), 6.94 (d, 1H), 7.10 (d, 1H); HPLC-MS: m/z=232.0(M+1); R$_t$=1.69 min.

Example 340 (General Procedure 8)

Morpholine-4-carboxylic acid 2-phenylsulfanyl-imidazol-1-yl ester

The title compound was prepared from 1-hydroxy-2-phenylsulfanylimidazole, hydrochloride and 4-morpholine carbonyl chloride applying the general procedure 8. The crude product was purified by flash chromatography (Quad flash 12, EtOAc) (98%, oil).

$^1$H NMR (300 MHz; CDCl$_3$): δ 3.46 (bs, 4H), 3.66 (bs, 4H), 7.15 (d, 1H), 7.18–7.31 (m, 6H); HPLC-MS: m/z=306.1 (M+1); R$_t$=2.75 min.

Example 341 (General Procedure 8)

Morpholine-4-carboxylic acid 2-(4-methoxy-phenyl)-imidazol-1-yl ester

The title compound was prepared from 1-hydroxy-2-(4-methoxyphenyl)imidazole, hydrochloride and 4-morpholine carbonyl chloride applying the general procedure 8. The crude product was purified by flash chromatography (Quad flash 12, EtOAc) (49%, crystals).

$^1$H NMR (300 MHz; CDCl$_3$): δ 3.51 (bs, 2H), 3.62–3.76 (m, 6H), 3.86 (s, 3H), 6.96 (d, 2H), 7.08 (d, 1H), 7.11 (d,1H), 7.70 (d, 2H); HPLC-MS: m/z=304.1 (M+1); R$_t$=1.81 min.

Example 342 (General Procedure 8)

Morpholine-4-carboxylic acid 4-bromo-pyrazol-1-yl ester

The title compound was prepared from 1-hydroxy-4-bromopyrazole and 4-morpholine carbonyl chloride applying the general procedure 8. The crude product was purified by flash chromatography (Quad flash 12, EtOAc-heptane) (85%, crystals).

$^1$H NMR (300 MHz; CDCl$_3$): δ 3.57 (bs, 2H), 3.68 (bs, 2H), 3.79 (t, 4H), 7.35 (d, 1H), 7.43 (d, 1H); HPLC-MS: m/z=298.0 (M+23); R$_t$=2.46 min.

Example 343 (General Procedure 8)

Morpholine-4-carboxylic acid 4-iodo-pyrazol-1-yl ester

The title compound was prepared from 1-hydroxy-4-iodopyrazole and 4-morpholine carbonyl chloride applying the general procedure 8. The crude product was purified by flash chromatography (Quad flash 12, EtOAc-heptane) (99%, crystals).

$^1$H NMR (300 MHz; CDCl$_3$): δ 3.56 (bs, 2H), 3.66 (bs, 2H), 3.77 (t, 4H), 7.41 (d, 1H), 7.44 (d, 1H); HPLC-MS: m/z=324.0 (M+1); R$_t$=2.65 min.

Example 344 (General Procedure 8)

Morpholine-4-carboxylic acid 3,4,5-tribromo-pyrazol-1-yl ester

The title compound was prepared from 1-hydroxy-3,4,5-tribromopyrazole and 4-morpholine carbonyl chloride applying the general procedure 8. The crude product was purified by flash chromatography (Quad flash 12, EtOAc-heptane) (90%, crystals).

$^1$H NMR (300 MHz; CDCl$_3$): δ 3.59 (bs, 2H), 3.69 (bs, 2H), 3.79 (t, 4H); HPLC-MS: m/z=455.6 (M+23); R$_t$=3.91 min.

Example 345 (General Procedure 8)

Morpholine-4-carboxylic acid 3-(4-methoxy-phenyl)-pyrazol-1-yl ester

The title compound was prepared from 1-hydroxy-3-(4-methoxyphenyl)pyrazole and 4-morpholine carbonyl chloride applying the general procedure 8. The crude product was purified by flash chromatography (Quad flash 12, EtOAc-heptane) (62%, crystals).

¹H NMR (300 MHz; CDCl₃): δ 3.58 (bs, 2H), 3.71 (bs, 2H), 3.79 (t, 4H), 3.84 (s, 3H), 6.53 (d, 1H), 6.92 (d, 2H), 7.40 (d, 1H), 7.71 (d, 2H); HPLC-MS: m/z=326.0 (M+23); $R_t$=3.21 min.

Example 346 (General Procedure 8)

Morpholine-4-carboxylic acid 3-thiophen-2-yl-pyrazol-1-yl ester

The title compound was prepared from 1-hydroxy-3-(2-thienyl)pyrazole and 4-morpholine carbonyl chloride applying the general procedure 8. The crude product was purified by flash chromatography (Quad flash 12, EtOAc-heptane) (75%, crystals).

¹H NMR (300 MHz; CDCl₃): δ 3.57 (bs, 2H), 3.69 (bs, 2H), 3.79 (t, 4H), 6.51 (d, 1H), 7.04 (dd, 1H), 7.26 (dd, 1H), 7.34 (dd, 1H), 7.40 (d, 1H); HPLC-MS: m/z=280.0 (M+1); $R_t$=3.12 min.

Example 347 (General Procedure 8)

Morpholine-4-carboxylic acid pyrazol-1-yl ester

The title compound was prepared from 1-hydroxypyrazole and 4-morpholine carbonyl chloride applying the general procedure 8. The crude product was purified by flash chromatography (Quad flash 12, EtOAc-heptane) (94%, crystals).

¹H NMR (300 MHz; CDCl₃): δ 3.57 (bs, 2H), 3.69 (bs, 2H), 3.79 (t, 4H), 6.32 (t, 1H), 7.38 (dd, 1H), 7.41 (dd, 1H); HPLC-MS: m/z=198.0 (M+1); $R_t$=1.18 min.

Example 348 (General Procedure 16)

4-Methyl-piperazine-1-carboxylic acid pyrazol-1-yl ester

The title compound was prepared from 1-hydroxypyrazole and N-methylpiperazine applying the general procedure 16. The crude product was purified by preparative HPLC (water-acetonitrile-0.1% TFA) (17%, salt with TFA).

¹H NMR (300 MHz; CDCl₃): δ 2.36 (s, 3H), 2.50 (bt, 4H), 3.59 (bs, 2H), 3.71 (bs, 2H), 6.31 (t, 1H), 7.38 (dd, 1H), 7.40 (dd, 1H); HPLC-MS: m/z=211.0 (M+1); $R_t$=0.40 min.

Example 349 (General Procedure 16)

4-Cyclopentyl-piperazine-1-carboxylic acid pyrazol-1-yl ester

The title compound was prepared from 1-hydroxypyrazole and N-cyclopentylpiperazine applying the general procedure 16. The crude product was purified by preparative HPLC (water-acetonitrile-0.1% TFA) (34%, salt with TFA).

¹H NMR (300 MHz; CDCl₃): δ 1.45–2.01 (m, 8H), 2.70 (bs, 4H), 2.92 (bs, 1H), 3.55 (bt, 1H), 3.63 (bs, 2H), 3.77 (bs, 2H), 6.31 (t, 1H), 7.38 (dd, 1H), 7.41 (dd, 1H); HPLC-MS: m/z=265.1 (M+1); $R_t$=0.54 min.

Example 350 (General Procedure 16)

4-Phenyl-piperazine-1-carboxylic acid pyrazol-1-yl ester

The title compound was prepared from 1-hydroxypyrazole and N-phenylpiperazine applying the general procedure 16. The crude product was purified by flash chromatography (Quad flash 12, EtOAc-heptane) (48%, crystals).

¹H NMR (300 MHz; CDCl₃): δ 3.25 (bt, 4H), 3.72 (bs, 2H), 3.85 (bs, 2H), 6.33 (t, 1H), 6.92–6.98 (m, 3H), 7.27–7.33 (m, 2H), 7.38 (dd, 1H), 7.41 (dd, 1H); HPLC-MS: m/z=273 (M+1); $R_t$=3.06 min.

Example 351 (General Procedure 16)

4-Pyridin-2-yl-piperazine-1-carboxylic acid pyrazol-1-yl ester

The title compound was prepared from 1-hydroxypyrazole and 1-(2-pyridyl)piperazine applying the general procedure 16. The crude product was purified by flash chromatography (Quad flash 12, EtOAc-heptane) (59%, crystals).

¹H NMR (300 MHz; CDCl₃): δ 3.62–3.85 (m, 8H), 6.32 (t, 1H), 6.66–6.72 (m, 2H), 7.39 (dd, 1H), 7.42 (dd, 1H), 7.53 (dt, 1H), 8.21 (d, 1H); HPLC-MS: m/z=274.1 (M+1); $R_t$=0.63 min.

Example 352 (General Procedure 16)

4-Pyrimidin-2-yl-piperazine-1-carboxylic acid pyrazol-1-yl ester

The title compound was prepared from 1-hydroxypyrazole and 1-(2-pyrimidyl)piperazine applying the general procedure 16. The crude product was purified by flash chromatography (Quad flash 12, EtOAc-heptane) (57%, crystals).

¹H NMR (300 MHz; CDCl₃): δ 3.65 (bs, 2H), 3.78 (bs, 2H), 3.95 (bs, 4H), 6.32 (t, 1H), 6.58 (t, 2H), 7.38 (dd, 1H), 7.42 (dd, 1H), 8.35 (d, 1H); HPLC-MS: m/z=275.2 (M+1); $R_t$=2.14 min.

Example 353 (General Procedure 16)

4-Benzo[1,3]dioxol-5-yl-piperazine-1-carboxylic acid pyrazol-1-yl ester

The title compound was prepared from 1-hydroxypyrazole and 1-Benzo[1,3]dioxol-5-ylpiperazine applying the general procedure 16. The crude product was purified by flash chromatography (Quad flash 12, EtOAc-heptane) (92%, crystals).

¹H NMR (300 MHz; CDCl₃): δ 3.11 (bt, 4H), 3.71 (bs, 2H), 3.83 (bs, 2H), 5.93 (s, 2H), 6.32 (t, 1H), 6.39 (dd, 1H), 6.57 (d, 1H), 6.74 (d, 1H), 7.37 (dd, 1H), 7.41 (dd, 1H); HPLC-MS: m/z=317.2 (M+1); $R_t$=2.96 min.

Example 354 (General Procedure 16)

4-Benzyl-piperazine-1-carboxylic acid 4-iodo-pyrazol-1-yl ester

The title compound was prepared from 1-hydroxy-4-iodopyrazole and 1-benzylpiperazine applying the general procedure 16. The crude product was purified by flash chromatography (Quad flash 12, EtOAc-heptane) (32%, oil).

¹H NMR (300 MHz; CDCl₃): δ 2.53 (bs, 4H), 3.57 (bs, 4H), 3.67 (bs, 2H), 7.28–7.38 (m, 5H), 7.40 (d, 1H), 7.43 (d, 1H); HPLC-MS: m/z=413.0 (M+1); $R_t$=1.75 min.

Example 355 (General Procedure 16)

4-Cyclopentyl-piperazine-1-carboxylic acid 4-iodo-pyrazol-1-yl ester

The title compound was prepared from 1-hydroxy-4-iodopyrazole and N-cyclopentylpiperazine applying the general procedure 16. The crude product was purified by flash chromatography (Quad flash 12, EtOAc-heptane-3% Et$_3$N) (61%, crystals).

$^1$H NMR (300 MHz; CDCl$_3$): δ 1.33–1.94 (m, 8H), 2.46–2.61 (m, 5H), 3.57 (bt, 2H), 3.67 (bt, 2H), 3.63 (bs, 2H), 3.77 (bs, 2H), 7.40 (d, 1H), 7.44 (d, 1H); HPLC-MS: m/z=391. (M+1); R$_f$=1.31 min.

Example 356 (General Procedure 16)

4-(4-Fluoro-benzyl)-piperazine-1-carboxylic acid 4-iodo-pyrazol-1-yl ester

The title compound was prepared from 1-hydroxy-4-iodopyrazole and 1-(4-fluorobenzyl)piperazine applying the general procedure 16. The crude product was purified by flash chromatography (Quad flash 12, EtOAc-heptane) (48%, crystals).

$^1$H NMR (300 MHz; CDCl$_3$): δ 2.50 (t, 4H), 3.51 (s, 2H), 3.57 (bt, 2H), 3.66 (bt, 2H), 7.02 (t, 2H), 7.29 (dd, 2H), 7.40 (d, 1H), 7.43 (d, 1H); HPLC-MS: m/z=431.0 (M+1); R$_f$=1.79 min.

Example 357 (General Procedure 16)

4-Phenyl-piperazine-1-carboxylic acid 4-iodo-pyrazol-1-yl ester

The title compound was prepared from 1-hydroxy-4-iodopyrazole and N-phenylpiperazine applying the general procedure 16. The crude product was purified by flash chromatography (Quad flash 12, EtOAc-heptane) (52%, crystals).

$^1$H NMR (300 MHz; CDCl$_3$): δ 3.25 (t, 4H), 3.72 (bs, 2H), 3.81 (bs, 2H), 6.90–6.97 (m, 3H), 7.30 (t, 2H), 7.41 (d,1H), 7.47 (d, 1H); HPLC-MS: m/z=399.1 (M+1); R$_f$=3.91 min.

Example 358 (General Procedure 16)

4-Pyridin-2-yl-piperazine-1-carboxylic acid 4-iodo-pyrazol-1-yl ester

The title compound was prepared from 1-hydroxy-4-iodopyrazole and 1-(2-pyridyl)piperazine applying the general procedure 16. The crude product was purified by flash chromatography (Quad flash 12, EtOAc-heptane) (45%, crystals).

$^1$H NMR (300 MHz; CDCl$_3$): δ 3.62–3.82 (m, 8H), 6.66–6.72 (m, 2H), 7.42 (d, 1H), 7.47 (d, 1H), 7.54 (dt, 1H), 8.22 (d, 1H); HPLC-MS: m/z=400.0 (M+1); R$_f$=1.47 min.

Example 359 (General Procedure 16)

4-Pyrimidin-2-yl-piperazine-1-carboxylic acid 4-iodo-pyrazol-1-yl ester

The title compound was prepared from 1-hydroxy-4-iodopyrazole and 1-(2-pyrimidyl)piperazine applying the general procedure 16. The crude product was purified by flash chromatography (Quad flash 12, EtOAc-heptane) (10%, crystals).

$^1$H NMR (300 MHz; CDCl$_3$): δ 3.62 (bs, 2H), 3.72 (bs, 2H), 3.95 (bs, 4H), 6.58 (t, 2H), 7.41 (d, 1H), 7.46 (d, 1H), 8.36 (d, 1H); HPLC-MS: m/z=401.0 (M+1); R$_f$=3.09 min.

Example 360 (General Procedure 16)

4-Benzo[1,3]dioxol-5-yl-piperazine-1-carboxylic acid 4-iodo-pyrazol-1-yl ester

The title compound was prepared from 1-hydroxy-4-iodopyrazole and 1-Benzo[1,3]dioxol-5-ylpiperazine applying the general procedure 16. The crude product was purified by flash chromatography (Quad flash 12, EtOAc-heptane) (59%, crystals).

$^1$H NMR (300 MHz; CDCl$_3$): δ 3.11 (t, 4H), 3.69 (bs, 2H), 3.80 (bs, 2H), 5.92 (s, 2H) 6.38 (dd, 1H), 6.56 (d, 1H), 6.73 (d, 1H), 7.41 (d, 1H), 7.45 (d, 1H); HPLC-MS: m/z=443.0 (M+1); R$_f$=3.79 min.

Example 361

4-(1-Ethylpropyl)piperazine-1-carboxylic acid 3-trifluoromethylphenyl ester hydrochloride salt To a stirred mixture of 1-(1-ethylpropyl)piperazine (175 μl, 1.0 mmol) and dry DCM (10 ml) was added 3-trifluoromethylphenyl chloroformate (250 mg, 1.1 mmol). The mixture was stirred overnight at room temperature and then diluted with DCM (50 ml). The reaction mixture was washed with 1 N NaOH (3×25 ml) and water (2×25 ml). The organic solution was concentrated and the residue was dissolved in a 0.5 N HCl solution (15 ml) and a small portion of acetonitrile. The acidic solution was concentrated and stirred with ethyl acetate (15 ml). The solid was isolated and dried to give 330 mg (86%) of the title compound as a solid.

M.p. 260–261° C. $^1$H NMR (400 MHz, DMSO-d$_6$): δ 0.98 (t, 6H), 1.63 (hept, 2H), 1.86–1.98 (m, 2H), 3.03–3.12 (m, 1H), 3.12–3.31 (m, 2H), 3.41–3.49 (m, 2H), 3.52–3.85 (m, 2H), 4.05–4.35 (m, 2H), 7.47–7.70 (m, 4H), 11.0 (brs, 1H).

Example 362

4-(1-Ethylpropyl)piperazine-1-carboxylic acid naphthalen-1-yl ester hydrochloride salt To a stirred mixture of 1-(1-ethylpropyl)piperazine (175 μl, 1.0 mmol) and dry DCM (10 ml) was added 1-napthalenyl chloroformate (225 mg, 1.1 mmol). The mixture was stirred overnight at room temperature and then diluted with DCM (50 ml). The reaction mixture was washed with 1 N NaOH (3×25 ml) and water (2×25 ml). The organic solution was concentrated and the residue was dissolved in a 0.5 N HCl solution (15 ml) and a small portion of acetonitrile. The acidic solution was concentrated and stirred with ethyl acetate (15 ml). The solid was isolated and dried to give 310 mg (85%) of the title compound as a solid.

M.p. 288–290° C. $^1$H NMR (400 MHz, DMSO-d$_6$): δ 1.00 (t, 6H), 1.63 (hept, 2H), 1.86–2.02 (m, 2H), 3.07–3.18 (m, 1H), 3.18–3.42 (m, 2H), 3.42–3.55 (m, 2H), 3.55–3.73 (m, 1H), 3.78–3.95 (m, 1H), 4.05–4.25 (m, 1H), 4.35–4.55 (m, 1H), 7.35 (d, 1H), 7.53 (t, 1H), 7.56–7.7.61 (m, 2H), 7.85 (d, 1H), 7.90–8.05 (m, 2H), 10.75 (brs, 1H).

Example 363

4-(1-Ethylpropyl)piperazine-1-carboxylic acid 4-fluorophenyl ester hydrochloride salt To a stirred mixture of 1-(1-ethylpropyl)piperazine (350 μl, 2.0 mmol) and dry DCM (15 ml) was added 4-fluorophenyl chloroformate (350 mg, 2.0 mmol). The mixture was stirred overnight at room temperature and then diluted with DCM (50 ml). The reaction mixture was washed with 1 N NaOH (3×25 ml) and water (2×25 ml). The organic solution was concentrated and the residue was re-evaporated twice with acetonitrile to give 590 mg of the free base. The hydrochloride salt was prepared from 465 mg free base by addition of a 0.5 N HCl solution (15 ml) and a small portion of acetonitrile. The acidic solution was concentrated and stirred with ethyl acetate (15 ml). The solid was isolated and dried to give 470 mg (90%) of the title compound as a solid.

M.p. 275–277° C. $^1$H NMR (400 MHz, DMSO-$d_6$): δ 0.98 (t, 6H), 1.64 (hept, 2H), 1.85–1.95 (m, 2H), 3.02–3.11 (m, 1H), 3.11–3.28 (m, 2H), 3.38–3.46 (m, 2H), 3.50–3.80 (m, 2H), 4.00–4.30 (m, 2H), 7.18–7.26 (m, 4H), 10.85 (brs, 1H).

Example 364

4-(1-Ethylpropyl)piperazine-1-carboxylic acid 2-nitrophenyl ester hydrochloride salt To a stirred mixture of 1-(1-ethylpropyl)piperazine (175 μl, 1.0 mmol) and dry DCM (10 ml) was added 2-nitrophenyl chloroformate (201 mg, 1.0 mmol). The mixture was stirred overnight at room temperature and then diluted with DCM (50 ml). The reaction mixture was washed with 1 N NaOH (3×25 ml) and water (2×25 ml). The organic solution was concentrated and the residue was dissolved in a 0.5 N HCl solution (15 ml). The acidic solution was concentrated and stirred with ethyl acetate (15 ml). The solid was isolated and dried to give 310 mg (86%) of the title compound as a solid.

M.p. 251–253° C. $^1$H NMR (400 MHz, DMSO-$d_6$): δ 0.96 (t, 6H), 1.65 (hept, 2H), 1.83–1.95 (m, 2H), 3.06–3.25 (m, 3H), 3.42–3.53 (m, 2H), 3.53–3.83 (m, 2H), 4.02–4.13 (m, 1H), 4.20–4.34 (m, 1H), 7.50–7.55 (m, 2H), 7.83 (t, 1H), 8.13 (d, 1H), 10.9 (brs, 1H).

Example 365

4-(1-Ethylpropyl)piperazine-1-carboxylic acid 4-methoxycarbonylphenyl ester hydrochloride salt To a stirred mixture of 1-(1-ethylpropyl)piperazine (350 μl, 2.0 mmol) and dry DCM (15 ml) was added 4-methoxycarbonylphenyl chloroformate (430 mg, 2.0 mmol). The mixture was stirred overnight at room temperature and then diluted with DCM (50 ml). The reaction mixture was washed with 1 N NaOH (3×25 ml) and water (2×25 ml). The organic solution was concentrated and re-evaporated twice with acetonitrile. The residue was dissolved in a 0.5 N HCl solution (15 ml) and a small portion of acetonitrile. The acidic solution was concentrated and stirred with ethyl acetate (15 ml). The solid was isolated and dried to give 670 mg (90%) of the title compound as a solid.

M.p. 248° C. decomp. $^1$H NMR (400 MHz, DMSO-$d_6$): δ 0.97 (t, 6H), 1.63 (hept, 2H), 1.85–1.95 (m, 2H), 3.02–3.11 (m, 1H), 3.11–3.30 (m, 2H), 3.40–3.48 (m, 2H), 3.50–3.80 (m, 2H), 3.85 (s, 3H), 4.05–4.33 (m, 2H), 7.33 (d, 2H), 8.00 (d, 2H)), 10.7 (brs, 1H).

Example 366

Methyl-phenyl-carbamic acid 5-(3,3-dimethyl-butyrylamino)-pyridin-2-yl ester A solution of N-(6-hydroxy-pyridin-3-yl)-3,3-dimethyl-butyramide (0.42 g, 2.00 mmol), N-methyl-N-phenylcarbamoyl chloride (0.37 g, 2.20 mmol) and 1,4-diazabicyclo[2,2,2]octane (0.25 g, 2.20 mmol) in tetrahydrofuran (20 mL) was stirred at room temperature for 2.5 hours. Water was added and the solution was extracted three times with dichloromethane. The combined organic layers were dried over sodium sulphate, filtered and evaporated in vacuo.

The residue was redissolved in ethyl acetate and the solution was filtered over a short pad of silicagel. Evaporation of the solvent and crystallisation of the solid from ethyl acetate:heptane yielded the title compound (0.54 g, 79% yield) as a white solid.

$^1$H NMR (300 MHz, CDCl$_3$): δ=1.03 (s, 9H), 2.15 (s, 2H), 3.47 (br.s, 3H), 6.91 (br.s, 1H) 7.27 (m, 1H), 7.38 (m, 4H), 7.99 (br.s+dd, 2H), 8.13 (d, 1H); HPLC-MS (Method A): m/z=342 (M+H)$^+$; Rt=3.67 min.

Example 367

Methyl-phenyl-carbamic acid 5-[(pyridine-2-carbonyl)-aminol-pyridin-2-yl ester A solution of pyridine-2-carboxylic acid (6-hydroxy-pyridin-3-yl)-amide hydrochloride (0.50 g, 1.99 mmol), N-methyl-N-phenylcarbamoyl chloride (0.44 g, 2.59 mmol) and 1,4-diazabicyclo[2,2,2]octane (0.54 g, 4.81 mmol) in dimethylformamide (15 mL) was stirred at room temperature for 1 hour. Water was added and the solids were isolated by suction, re-dissolved in dichloromethane. The solution was dried over sodium sulphate, filtered and evaporated in vacuo. The residue was purified by flash column chromatography (SiO$_2$, ethyl acetate:heptane 50:50) yielding the title compound (0.38 g, 55% yield) as a white solid.

$^1$H NMR (300 MHz, CDCl$_3$): δ=3.45 (br.s, 3H), 7.11 (br.s, 1H), 7.26 (m, 1H), 7.40 (d, 4H), 7.51 (m, 1H), 7.92 (dt, 1H), 8.28 (d, 1H), 8.45 (dd, 1H), 8.60 (m, 2H), 10.10 (s, 1H); HPLC-MS (Method A): m/z=349 (M+H)$^+$; Rt=3.31 min.

Example 368

Methyl-phenyl-carbamic acid 2-(4,4-dimethyl-2,6-dioxo-piperidin-1-yl)-pyrimidin-5-yl ester A solution of 1-(5-hydroxy-pyrimidin-2-yl)-4,4-dimethyl-piperidine-2,6-dione (0.60 g, 2.55 mmol), N-methyl-N-phenylcarbamoyl chloride (0.48 g, 2.81 mmol) and 1,4-diazabicyclo-[2,2,2]octane (0.31 g, 2.81 mmol) in dichloromethane (25 mL) was stirred at room temperature for 15 minutes. The solvent was evaporated in vacuo and the residue was purified by flash column chromatography (SiO$_2$, ethyl acetate:heptane 50:50), yielding the title compound as a white solid.

$^1$H NMR (300 MHz, CDCl$_3$): δ=1.22 (s, 6H), 2.65 (s, 4H), 3.44 (br.s, 3H), 7.28–7.48 (m, 5H), 8.68 (br.s, 2H); HPLC-MS (Method A): m/z=369 (M+H)$^+$; Rt=3.45 min.

Example 369

Methyl-phenyl-carbamic acid
5-bromo-pyrimidin-2-yl ester

A mixture of 4-bromo-2-hydroxypyrimidine (0.96 g, 5.49 mmol), N-methyl-N-phenylcarbamoyl chloride (1.02 g, 6.04 mmol) and 1,4-diazabicyclo[2,2,2]octane (0.68 g, 6.04 mmol) in dry tetrahydrofuran (15 mL) was stirred at room temperature for 1 hour. Dichloromethane was added and the solution was extracted twice with water. The organic layer was dried over sodium sulphate, filtered and evaporated in vacuo yielding the title compound (1.70 g, 100% yield) as a white solid.

$^1$H NMR (300 MHz, CDCl$_3$): δ=3.43 (br.s, 3H), 7.27 (m, 1H), 7.38 (m, 4H), 8.68 (br.s, 2H); HPLC-MS (Method A): m/z=330 and 332 (M+H)$^+$; Rt=3.33 min.

Example 370

Methyl-phenyl-carbamic acid 5-[(6-chloro-pyridine-3-carbonyl)-amino]-pyridin-2-yl ester A mixture of 4-chloro-N-(6-hydroxy-pyridin-3-yl)-nicotinamide (0.56 g, 2.25 mmol), N-methyl-N-phenylcarbamoyl chloride (0.51 g, 3.00 mmol) and 1,4-diazabicyclo[2,2,2]octane (0.67 g, 6.00 mmol) in dry tetrahydrofuran (15 mL) was stirred at room temperature for 1 hour. Dichloromethane was added and the solution was extracted twice with water. The organic layer was dried over sodium sulphate, filtered and evaporated in vacuo. The residue was purified by flash column chromatography (SiO$_2$, ethyl acetate:heptane 70:30) followed by crystallised from ethyl acetate:heptane, yielding the title compound (44 mg, 5% yield)

HPLC-MS (Method A): m/z=383 (M+H)$^+$; Rt=3.40 min.

Example 371

Methyl-phenyl-carbamic acid
5-(2,2-dimethyl-propylcarbamoyl)-pyridin-2-yl ester

A solution of N-(2,2-dimethyl-propyl)-6-hydroxy-nicotinamide (0.50 g, 2.40 mmol), N-methyl-N-phenylcarbamoyl chloride (0.41 g, 2.40 mmol) and 1,4-diazabicyclo[2,2,2]octane (0.27 g, 2.40 mmol) in tetrahydrofuran (15 mL) was stirred at room temperature for 3 hours. The solvent was evaporated in vacuo and the residue was purified by flash column chromatography (first column: SiO$_2$, dichloromethane:ethyl acetate 95:5, second column: SiO$_2$, ethyl acetate), yielding the title compound (0.43 g, 52% yield).

$^1$H NMR (300 MHz, CDCl$_3$): δ=0.97 (s, 9H), 3.26 (d, 2H), 3.44 (br.s, 3H), 6.26 (br.s, 1H), 7.08 (br.s, 1H), 7.29 (m, 1H), 7.39 (m, 4H), 8.13 (br.d, 1H), 8.70 (br.s, 1H); HPLC-MS (Method A): m/z=383 (M+H)$^+$; Rt=3.40 min.

Example 372

[Methyl-phenyl-carbamic acid
6-(3,4-dichloro-phenoxy)-pyridazin-3-yl ester

A solution of 6-(3,4-dichloro-phenoxy)-pyridazin-3-ol (0.51 g, 2.00 mmol), N-methyl-N-phenylcarbamoyl chloride (0.36 g, 2.10 mmol) and 1,4-diazabicyclo[2,2,2]octane (0.24 g, 2.10 mmol) in tetrahydrofuran (15 mL) was stirred at room temperature for 2 hours. The solvent was evaporated in vacuo and the residue was purified by flash column chromatography (SiO$_2$, ethyl acetate:heptane 30:70), yielding the title compound (0.34 g, 44% yield).

$^1$H NMR (300 MHz, CDCl$_3$): δ=3.43 (br.s, 3H), 7.10 (dd, 1H), 7.20–7.51 (m, 9H); HPLC-MS (Method A): m/z=389 (M+H)$^+$; Rt=4.56 min.

Example 373

4-(tert-Butyl-dimethyl-silanyloxy)-piperidine-1-carboxylic acid 5-benzoylamino-pyridin-2-yl ester A solution of N-(6-hydroxy-pyridin-3-yl)-benzamide (214 mg, 1.00 mmol), 3-[4-(tert-butyl-dimethyl-silanyloxy)-piperidine-1-carbonyl]-1-methyl-3H-imidazol-1-ium iodide (451 mg, 1.00 mmol) and 1,4-diazabicyclo[2,2,2]octane (112 mg, 1.00 mmol) in dimethylformamide (10 mL) was stirred for 18 hours at room temperature followed by heating for 3 days at 40° C. The solvent was evaporated in vacuo and the residue was purified by flash column chromatography (SiO$_2$, ethyl acetate:heptane 40:60), yielding the title compound (364 mg, 77% yield)

$^1$H NMR (300 MHz, CDCl$_3$): δ=0.08 (s, 6H), 0.91 (s, 9H), 1.59 (m, 2H), 1.78 (m, 2H), 3.50 (m, 1H), 3.62 (m, 2H), 3.76 (m, 1H), 4.00 (m, 1H), 6.87 (d, 1H), 7.41 (m, 2H), 7.50 (m, 1H), 7.90 (d, 2H), 8.01 (dd, 1H), 8.36 (d, 1H), 9.03 (s, 1H, NH); HPLC-MS (Method A): m/z=456 (M+H)$^+$; Rt=5.23 min.

Example 374

4-Hydroxy-piperidine-1-carboxylic acid
5-benzoylamino-pyridin-2-yl ester

Hydrofluoric acid (min. 40% in water, 0.50 mL) was added to a stirred solution of 4-(tert-butyl-dimethyl-silanyloxy)-piperidine-1-carboxylic acid 5-benzoylamino-pyridin-2-yl ester (364 mg, 0.77 mmol) in acetonitrile. After stirring overnight at room temperature the solvent was evaporated in vacuo. The residue was redissolved in dichloromethane. After addition of triethylamine (1 mL) the solution was filtered over a short pad of silicagel and washed with ethyl acetate:acetone 50:50. Evaporation of the solvent yielded the title compound (180 mg, 68% yield) as a white solid.

$^1$H NMR (400 MHz, CDCl$_3$+DMSO-d$_6$): δ=1.60 (m, 2H), 1.91 (m, 2H), 3.25 (m, 2H), 4.02 (m, 1H), 4.41 (d, 1H), 7.07 (d, 1H), 7.44–7.61 (m, 3H), 7.99 (m, 2H), 8.35 (dd, 1H), 8.72 (d, 1H), 10.19 (s, 1H, NH); HPLC-MS (Method A): m/z=342 (M+H)$^+$; Rt=2.37 min.

Example 375

4-Hydroxy-piperidine-1-carboxylic acid
5-trifluoromethyl-pyridin-2-yl ester

A solution of 2-hydroxy-5-trifluoromethylpyridine (0.32 g, 2.00 mmol), 4-(tert-butyl-dimethyl-silanyloxy)-piperidine-1-carboxylic acid 5-benzoylamino-pyridin-2-yl ester (0.90 g, 2.00 mmol) and triethylamine (0.20 g, 2.00 mmol) in acetonitrile (10 mL) was stirred at room temperature for three days. Hydrofluoric acid (min. 40% in water, 0.50 mL) was added and stirring was continued for 18 hours. The solvent was evaporated in vacuo and the residue was purified by flash column chromatography (SiO$_2$, ethyl acetate:heptane 75:25), followed by crystallisation from ethyl acetate:heptane, yielding the title compound (0.27 g, 47% yield) as a white solid.

¹H NMR (300 MHz, CDCl₃): δ=1.64 (m, 3H, 2×CH+OH), 1.96 (m, 2H), 3.33 (m, 1H), 3.45 (m, 1H), 4.00 (m, 3H), 7.27 (d, 1H), 8.00 (dd, 1H), 8.64 (d, 1H); HPLC-MS (Method A): m/z=313 (M+Na)⁺; Rt=2.45 min.

Example 376

4-Hydroxy-piperidine-1-carboxylic acid 5-(4-chloro-benzoylamino)-pyridin-2-yl ester A solution of 4-chloro-N-(6-hydroxy-pyridin-3-yl)-benzamide (0.50 g, 2.00 mmol), 4-(tert-butyl-dimethyl-silanyloxy)-piperidine-1-carboxylic acid 5-benzoylamino-pyridin-2-yl ester (0.90 g, 2.00 mmol) and triethylamine (0.20 g, 2.00 mmol) in dimethylformamide (10 mL) was stirred overnight at room temperature. The solvent was evaporated in vacuo. The residue was dissolved in dichloromethane, filtered over a short pad of silicagel and washed with ethyl acetate:heptane 50:50. The solvent was evaporated in vacuo and the residue was redissolved in acetonitrile and hydrofluoric acid (min. 40% in water, 0.50 mL) was added. After stirring overnight at room temperature the solvent was evaporated in vacuo. Dichloromethane and triethylamine (1 mL) were added and the solution was extracted twice with water, dried over sodium sulphate, filtered and evaporated in vacuo. Crystallisation from ethyl acetate:heptane yielded the title compound (321 mg, 43% yield).

¹H NMR (300 MHz, DMSO-d₆): δ=1.50 (m, 2H), 1.80 (m, 2H), 3.16 (m, 1H), 3.31 (m, 1H), 3.75 (m, 2H), 3.88 (m, 1H), 4.81 (d, 1H), 7.18 (d, 1H), 7.62 (d, 2H), 8.01 (d, 2H), 8.24 (dd, 1H), 8.66 (d, 1H), 10.58 (s, 1H).; HPLC-MS (Method A): m/z=376 (M+H)⁺; Rt=2.81 min.

Example 377

4-Hydroxy-piperidine-1-carboxylic acid 5-(3-methoxy-benzoylamino)-pyridin-2-yl ester Starting from N-(6-hydroxy-pyridin-3-yl)-3-methoxy-benzamide (0.49 g, 2.00 mmol) and using the procedure as described in Example 376 yielded the title compound (347 mg, 47% yield).

¹H NMR (300 MHz, CDCl₃+DMSO-d₆): δ=1.51 (m, 2H), 1.82 (m, 2H), 3.16 (m, 1H), 3.30 (m, 1H), 3.79 (s, 3H+m, 2H), 3.92 (m, 1H), 4.28 (br.s, 1H), 6.98 (m, 2H), 7.30 (t, 1H), 7.47 (m, 2H), 8.24 (dd, 1H), 8.64 (d, 1H), 10.04 (s, 1H); HPLC-MS (Method A): m/z=372 (M+H)⁺; Rt=2.58 min.

Example 378

4-Hydroxy-piperidine-1-carboxylic acid 5-(4-methoxy-benzoylamino)-pyridin-2-yl ester Starting from N-(6-hydroxy-pyridin-3-yl)-4-methoxy-benzamide (0.49 g, 2.00 mmol) and using the procedure as described in Example 376 yielded the title compound (297 mg, 40% yield).

¹H NMR (300 MHz, CDCl₃): δ=1.61 (m, 2H), 1.92 (m, 2H), 3.25 (m, 1H), 3.39 (m, 1H), 3.89 (s, 3H+m, 3H), 4.03 (m, 1H), 6.96 (d, 2H), 7.06 (d, 1H), 7.98 (d, 2H), 8.34 (dd, 1H), 8.67 (d, 1H), 9.72 (s, 1H); HPLC-MS (Method A): m/z=372 (M+H)⁺; Rt=2.53 min.

Example 379

4-Hydroxy-piperidine-1-carboxylic acid 5-(2,4-dichloro-benzoylamino)-pyridin-2-yl ester Starting from 2,4-dichloro-N-(6-hydroxy-pyridin-3-yl)-benzamide (0.49 g, 2.00 mmol) and using the procedure as described in Example 376 yielded the title compound (367 mg, 45% yield).

¹H NMR (300 MHz, CDCl₃): δ=1.62 (m, 2H), 1.90 (m, 2H), 3.24 (m, 1H), 3.39 (m, 1H), 3.88 (m, 3H), 4.01 (m, 1H), 7.03 (d, 1H), 7.32 (d, 1H), 7.47 (s, 1H), 7.53 (d, 1H), 8.28 (dd, 1H), 8.58 (d, 1H), 10.1 (s, 1H); HPLC-MS (Method A): m/z=410 and 412 (M+H)⁺; Rt=2.99 min.

Example 380

4-Hydroxy-piperidine-1-carboxylic acid 5-(4-trifluoromethyl-benzoylamino)-pyridin-2-yl ester Starting from N-(6-hydroxy-pyridin-3-yl)-4-trifluoromethyl-benzamide (0.56 g, 2.00 mmol) and using the procedure as described in Example 376 yielded the title compound (367 mg, 45% yield).

¹H NMR (300 MHz, CDCl₃): δ=1.61 (m, 2H), 1.93 (m, 2H), 3.27 (m, 1H), 3.41 (m, 1H), 3.67 (br.s, 1H), 3.91 (m, 2H), 4.05 (m, 1H), 7.08 (d, 1H), 7.74 (d, 2H), 8.14 (d, 2H), 8.37 (dd, 1H), 8.67 (d, 1H), 10.11 (s, 1H); HPLC-MS (Method A): m/z=410 (M+H)⁺; Rt=3.18 min.

Example 381

4-Hydroxy-piperidine-1-carboxylic acid 4,4-dimethyl-2,6-dioxo-3,4,5,6-tetrahydro-2H-[1,3']bipyridinyl-6'-yl ester A solution of 6'-hydroxy-4,4-dimethyl-4,5-dihydro-3H-[1,3']bipyridinyl-2,6-dione (468 mg, 2.00 mmol), 4-(tert-butyl-dimethyl-silanyloxy)-piperidine-1-carboxylic acid 5-benzoylamino-pyridin-2-yl ester (0.90 g, 2.00 mmol) and triethylamine (0.20 g, 2.00 mmol) in dimethylformamide (10 mL) was stirred at room temperature for 18 hours. The solvent was evaporated in vacuo. The residue was dissolved in ethyl acetate, filtered over a short pad of silicagel and washed with ethyl acetate. The solvent was evaporated in vacuo and the residue was dissolved in 1N HCl in ethyl acetate (10 mL, 10.0 mmol). After stirring for 1.5 hours at room temperature the solvent was evaporated in vacuo. The white solid was washed with a small amount of ethyl acetate and diethyl ether and dissolved in a few millilitres of dichloromethane and triethylamine (1 mL). Purification by flash column chromatography (SiO₂, ethyl acetate:acetone 90:10) yielded the title compound (182 mg, 25% yield) as a white solid.

¹H NMR (300 MHz, CDCl₃): δ=1.22 (s, 6H), 1.61 (m, 2H), 1.92 (m, 2H), 2.70 (s, 4H), 3.28 (m, 1H), 3.40 (m, 1H), 3.63 (d, 1H), 3.84–4.08 (m, 3H), 7.21 (d, 1H), 7.51 (dd, 1H), 8.07 (d, 1H); HPLC-MS (Method A): m/z=362 (M+H)⁺; Rt=2.25 min.

Example 382

Methyl-phenyl-carbamic acid 2,6-dioxo-3,4,5,6-tetrahydro-2H-[1,3']bipyridinyl-6'-yl ester A solution of N-methyl-N-phenyl carbamoyl chloride (170 mg, 1.00 mmol), 6'-hydroxy-4,5-dihydro-3H-[1,3]bipyridinyl-2,6-dione (206 mg, 1.00 mmol) and 1,4-diazabicyclo[2,2,2]octane (112 mg, 1.00 mmol) in tetrahydrofuran (10 mL) was stirred at room temperature for 18 hours. The solvent was evaporated in vacuo and the residue was purified by flash column chromatography ($SiO_2$, first ethyl acetate:heptane 75:25 followed by pure ethyl acetate). Evaporation of the solvent yielded the title compound (260 mg, 77% yield) as a white solid.

$^1$H NMR (300 MHz, $CDCl_3$): δ=2.10 (quintet, 2H), 2.81 (t, 4H), 3.53 (br.s, 3H), 7.12 (br.s, 1H), 7.27 (m, 1H), 7.38 (m, 4H), 7.50 (d, 1H), 8.09 (s, 1H); HPLC-MS (Method A): m/z=340 (M+H)$^+$; Rt=2.89 min.

Example 383

Methyl-phenyl-carbamic acid 5-(2,5-dioxo-pyrrolidin-1-yl)-pyridin-2-yl ester

A solution of N-methyl-N-phenyl carbamoyl chloride (170 mg, 1.00 mmol), 1-(6-hydroxy-pyridin-3-yl)-pyrrolidine-2,5-dione (192 mg, 1.00 mmol) and 1,4-diazabicyclo[2,2,2]octane (112 mg, 1.00 mmol) in tetrahydrofuran (10 mL) was stirred at room temperature for 4 hours. The solvent was evaporated in vacuo and the residue was purified by flash column chromatography ($SiO_2$, ethyl acetate:heptane 80:20) yielding the title compound (275 mg, 85% yield) as a white solid.

$^1$H NMR (300 MHz, $CDCl_3$): δ=2.89 (s, 4H), 3.44 (br.s, 3H), 7.14 (br.s, 1H), 7.27 (m, 1H), 7.39 (m, 4H), 7.74 (br.d, 1H), 8.38 (s, 1H); HPLC-MS (Method A): m/z=326 (M+H)$^+$; Rt=2.78 min.

Example 384

Methyl-phenyl-carbamic acid 5-(4-trifluoromethyl-benzoylamino)-pyridin-2-yl ester A solution of N-(6-hydroxy-pyridin-3-yl)-4-trifluoromethyl-benzamide (1.41 g, 5.00 mmol), N-methyl-N-phenylcarbamoyl chloride (0.85 g, 5.00 mmol) and 1,4-diazabicyclo[2,2,2]octane (0.56 g, 5.00 mmol) in dimethylformamide (10 mL) was stirred at room temperature overnight. The solvent was evaporated in vacuo and the residue was purified by flash column chromatography ($SiO_2$, ethyl acetate: heptane 50:50) yielding the title compound (1.34 g, 64% yield) as a white solid.

$^1$H NMR (300 MHz, $CDCl_3$): δ=3.35+3.51 (2×br.s, 3H), 6.83 (br.s, 1H), 7.24–7.42 (m, 5H), 7.60 (d, 2H), 7.98 (d, 3H), 8.33 (s, 1H), 9.03+9.18 (2×br.s, 1H, NH); HPLC-MS (Method A): m/z=416 (M+H)$^+$; Rt=4.14 min.

Example 385

Methyl-phenyl-carbamic acid quinolin-6-yl ester

A solution of 6-hydroxyquinoline (1.00 g, 6.89 mmol), N-methyl-N-phenylcarbamoyl chloride (1.17 g, 6.89 mmol) and 1,4-diazabicyclo[2,2,2]octane (0.77 g, 6.89 mmol) in dichloromethane (20 mL) was stirred at room temperature for 1.25 hours. More dichloromethane was added and the solution was extracted with water. The organic layer was dried over sodium sulphate, filtered and evaporated in vacuo. The residue was purified by flash column chromatography ($SiO_2$, ethyl acetate:heptane 50:50). Evaporation of the solvent and recrystallised from ethylacetate/heptane yielded the title compound (1.33 g, 69% yield) as a white solid.

$^1$H NMR (300 MHz, $CDCl_3$): δ=3.48 (s, 3H), 7.22–7.64 (m, 8H), 8.09 (d, 2H), 8.87 (m, 1H); HPLC-MS (Method A): m/z=279 (M+H)$^+$; Rt=2.56 min.

Example 386

4-Hydroxy-piperidine-1-carboxylic acid 5-(5-trifluoromethyl-pyridin-2-yloxy)-pyridin-2-yl ester A solution of 5-(5-trifluoromethyl-pyridin-2-yloxy)-pyridin-2-ol (180 mg, 0.70 mmol), 3-[4-(tert-butyl-dimethyl-silanyloxy)-piperidine-1-carbonyl]-1-methyl-3H-imidazol-1-ium iodide (317 mg, 0.70 mmol) and triethylamine (98 μL) in acetonitrile (10 mL) was stirred at room temperature overnight. The solvent was evaporated in vacuo. The residue was redissolved in some dichloromethane, chloromethane, filtered over a short pad of silicagel and washed with ethyl acetate:heptane 50:50. The solvent was evaporated in vacuo and the residue was dissolved in 3.2N HCl in ether (10 mL). After stirring for 1 hour at room temperature the solvent was evaporated in vacuo and the residue was dissolved in dichloromethane. Triethylamine (0.5 mL) was added and the solution was extracted with water. The organic layer was dried over sodium sulphate, filtered and evaporated in vacuo to yield the title compound (174 mg, 65% yield) as a thick oil.

$^1$H NMR (300 MHz, $CDCl_3$): δ 1.63 (m, 2H), 1.79 (br.s, 1H, OH), 1.97 (m, 2H), 3.31 (m, 1H), 3.43 (m, 1H), 3.89–4.12 (m, 3H), 7.09 (d, 1H), 7.18 (d, 1H), 7.62 (dd, 1H), 7.94 (dd, 1H), 8.23 (d, 1H), 8.39 (d, 1H); HPLC-MS (Method A): m/z=384 (M+H)$^+$; Rt=3.00 min.

Example 387

4-Hydroxy-piperidine-1-carboxylic acid 5-(3,5-dichloro-pyridin-2-yloxy)-pyridin-2-yl ester Starting from 5-(3,5-dichloro-pyridin-2-yloxy)-pyridin-2-ol (265 mg, 1.03 mmol) and using the procedure as described in Example 386 yielded the title compound (121 mg, 54% yield) as a thick oil.

$^1$H NMR (300 MHz, $CDCl_3$): δ=1.62 (m, 2H), 1.94 (m, 2H), 3.06 (br.s, 1H), 3.28 (m, 1H), 3.41 (m, 1H), 3.90 (m, 2H), 4.01 (m, 1H), 7.18 (d, 1H), 7.62 (dd, 1H), 7.79 (d, 1H), 7.94 (d, 1H), 8.22 (d, 1H).; HPLC-MS (Method A): m/z=384 (M+H)$^+$; Rt=3.35 min.

Example 388

Methyl-phenyl-carbamic acid 5-(4-chloro-benzoylamino)-pyridin-2-yl ester

A solution of 4-chloro-N-(6-hydroxy-pyridin-3-yl)-benzamide (0.50 g, 2.01 mmol), N-methyl-N-phenylcarbamoyl chloride (0.34 g, 2.01 mmol) and 1,4-diazabicyclo[2,2,2]octane (0.22 g, 0.34 mmol) in dimethylformamide (10 mmol) was stirred at room temperature for 2 hours. Water (100 mL) was added and a thick oil was being formed. The water was decanted and the residue dissolved in dichloromethane, dried over sodium sulphate, filtered and evaporated in vacuo. Ethyl acetate was added and the solution was heated briefly (some of the compound does not dissolve). The solvent was decanted and heptane was added to it. After standing overnight, the crystals were isolated by suction, washed with heptane and dried in a vacuum oven at 45° C. Further purification by flash column chromatography ($SiO_2$, ethyl acetate:heptane 50:50), yielded the title compound (0.41 g, 53% yield) as a white solid.

$^1$H NMR (300 MHz, CDCl$_3$): δ=3.38 (br.s, 3H), 6.84 (br.s, 1H), 7.20–7.42 (m, 7H), 7.80 (d, 2H), 7.97 (dd, 1H), 8.32 (d, 1H), 9.09 (br.s, 1H); HPLC-MS (Method A): m/z=382 (M+H)$^+$; Rt=3.63 min.

Example 389

4 Methyl-phenyl-carbamic acid 5-(4-methoxy-benzoylamino)-pyridin-2-yl ester

A solution of N-(6-hydroxy-pyridin-3-yl)-4-methoxy-benzamide (1.22 g, 5.00 mmol), N-methyl-N-N-phenylcarbamoyl chloride (0.85 g, 5.00 mmol) and 1,4-diazabicyclo[2,2,2]octane (0.56 g, 5.00 mmol) in dimethylformamide (20 mL) was stirred at room temperature for 2 hours. Water (100 mL) was added. The solids were isolated by suction and washed with water. Crystallisation from ethyl acetate:heptane yielded the title compound (1.08 g, 57% yield).

$^1$H NMR (300 MHz, CDCl$_3$): δ=3.42 (br.s, 3H), 3.86 (s, 3H), 6.89 (d, 2H+br.s, 1H), 7.27 (m, 1H), 7.39 (m, 4H), 7.84 (d, 2H), 8.11 (dd, 1H), 8.34 (d, 1H), 8.51 (br.s, 1H); HPLC-MS (Method A): m/z=378 (M+H)$^+$; Rt=3.55 min.

Example 390

Methyl-phenyl-carbamic acid 4,4-dimethyl-3,4,5,6-tetrahydro-2H-[1,3']bipyridinyl-6'-yl ester A solution of 4,4-dimethyl-3,4,5,6-tetrahydro-2H-[1,3']bipyridinyl-6'-ol (0.86 g, 4.17 mmol), N-methyl-N-phenyl-carbamoyl chloride (0.71 g, 4.17 mmol) and 1,4-diazabicyclo[2,2,2]octane (0.47 g, 4.17 mmol) in dichloromethane (10 mL) was stirred at room temperature for 2 hours. Extra dichloromethane was added and the solution was washed with water, dried over sodium sulphate, filtered and evaporated in vacuo. Crystallisation from ethyl acetate:heptane yielded the title compound (0.58 g, 41% yield)

$^1$H NMR (300 MHz, CDCl$_3$): δ=0.99 (s, 6H), 1.52 (m, 4H), 3.16 (m, 4H), 3.43 (br.s, 3H), 6.92 (br.d, 1H), 7.20–7.41 (m, 6H), 7.98 (d, 1H); HPLC-MS (Method A): m/z=340 (M+H)$^+$; Rt=4.21 min.

Example 391

Methyl-phenyl-carbamic acid 2-methyl-quinolin-6-yl ester

A solution of 2-methylquinolin-6-ol (1.00 g, 6.28 mmol), N-methyl-N-phenylcarbamoyl chloride (1.07 g, 6.28 mmol) and 1,4-diazabicyclo[2,2,2]octane (0.70 g, 6.28 mmol) in dichloromethane (10 mL) was stirred at room temperature for 18 hours. Extra dichloromethane was added and the solution was extracted twice with water, dried over sodium sulphate and filtered. Some ethyl acetate and heptane were added and the solution was slowly evaporated in vacuo yielding the title compound (1.64 g, 89% yield) as a white solid.

$^1$H NMR (300 MHz, CDCl$_3$): δ=2.71 (s, 3H), 3.45 (br.s, 3H), 7.25 (m, 2H), 7.40 (m, 5H), 7.54 (s, 1H), 7.98 (t, 2H); HPLC-MS (Method A): m/z=293 (M+H)$^+$; Rt=2.16 min.

Example 392 (General Procedure 17)

{2-[4-(Methyl-phenyl-carbamoyloxy)-phenyl]-ethyl}-carbamic acid tert-butyl ester Tyramin was N-Boc protected as described in J. Org. Chem, 49, 1984, 1016. To a solution of the N-Boc protected tyramin (10 mmol) in CH$_2$Cl$_2$ (50 mL) was added N-methyl-N-phenylcarbamoyl chloride (15 mmol) and DABCO (15 mmol) at room temperature. The reaction mixture was stirred for 16 hours at rt, added CH$_2$Cl$_2$ (20 mL) and washed with aqueous citric acid (5%) and brine. The organic phase was separated, dried (MgSO$_4$) and evaporated to give the crude product which was purified by FC (Quad flash 40 MeOH—CH$_2$Cl$_2$ 5:95) to give 3.45 g (93%) of the title compound as colorless crystals.

HPLC-MS: m/z=393.4 (M+Na); R$_t$=4.44 min.

Example 393 (General Procedure 17)

Methyl-phenyl-carbamic acid 4-(2-amino-ethyl)phenyl ester

{2-[4-(Methyl-phenyl-carbamoyloxy)-phenyl]-ethyl}-carbamic acid tertbutyl ester(3.7 g; 10 mmol) from above was dissolved in CH$_2$Cl$_2$ (90 mL). Addition of TFA (6 mL) and stirring for 4 h. The reaction mixture was evaporated to dryness and dried in vacuo at 50° C. overnight producing the title compound as a TFA salt in quantitative yield as yellow hygroscopic crystals.

HPLC-MS: m/z=271.1 (M+1); R$_t$=2.17 min.

Example 394 (General Procedure 17)

Methyl-phenyl-carbamic acid 4-[2-(toluene-4-sulfonylamino)-ethyl]-phenyl ester

The title compound was prepared in 39% yield as a clear oil using toluenesulfonyl chloride as the aryl sulfonyl chloride.

HPLC-MS: m/z=425.2 (M+1); R$_t$=4.33 min.

Example 395 (General Procedure 17)

Methyl-phenyl-carbamic acid 4-[2-(5-dimethylamino-naphthalene-1-sulfonylamino)-ethyl]-phenyl ester The title compound was prepared in 29% yield as a yellow fluorescent oil using 5-dimethylamino-naphthalene-1-sulfonyl chloride as the aryl sulfonyl chloride.

HPLC-MS: m/z=505.1 (M+1); R$_t$=4.58 min.

Example 396 (General Procedure 17)

Methyl-phenyl-carbamic acid 4-[2-(3,4-difluoro-benzenesulfonylamino)-ethyl]-phenyl ester The title compound was prepared in 40% yield as a clear oil using 3,4-difluoro-benzenesulfonyl chloride as the aryl sulfonyl chloride.

HPLC-MS: m/z=447.1 (M+1); R$_t$=4.47 min.

Example 397 (General Procedure 17)

2-{2-[4-(Methyl-phenyl-carbamoyloxy)-phenyl]-ethylsulfamoyl}-benzoic acid methyl ester The title compound was prepared in 30% yield as an oil using 2-chlorosulfonyl-benzoic acid methyl ester as the aryl sulfonyl chloride.
HPLC-MS: m/z=469.1 (M+1); $R_t$=4.37 min.

Example 398 (General Procedure 17)

Methyl-phenyl-carbamic acid 4-[2-(2,5-dichloro-thiophene-3-sulfonylamino)-ethyl]-phenyl ester The title compound was prepared in 39% yield as an oil using 2,5-dichloro-thiophene-3-sulfonyl chloride as the aryl sulfonyl chloride.
HPLC-MS: m/z=487.0 (M+1); $R_t$=4.80 min.

Example 399 (General Procedure 17)

Methyl-phenyl-carbamic acid 4-[2-(5-pyridin-2-yl-thiophene-2-sulfonylamino)-ethyl]-phenyl ester The title compound was prepared in 12% yield as crystalls using 5-pyridin-2-yl-thiophene-2-sulfonyl chloride as the aryl sulfonyl chloride.
HPLC-MS: m/z=494.0 (M+1); $R_t$=4.42 min.

Example 400 (General Procedure 17)

Methyl-phenyl-carbamic acid 4-[2-(1-methyl-1H-imidazole-4-sulfonylamino)-ethyl]-phenyl ester The title compound was prepared in 42% yield as a yellow oil using 1-methyl-1H-imidazole-4-sulfonyl chloride as the aryl sulfonyl chloride.
HPLC-MS: m/z=415.1 (M+1); $R_t$=3.31 min.

Example 401 (General Procedure 17)

Methyl-phenyl-carbamic acid 4-[2-(5-chloro-1,3-dimethyl-1H-pyrazole-4-sulfonylamino)-ethyl]-phenyl The title compound was prepared in 22% yield as an oil using 5-chloro-1,3-dimethyl-1H-pyrazole-4-sulfonyl chloride as the aryl sulfonyl chloride.
HPLC-MS: m/z=463.1 (M+1); $R_t$=3.91 min.

Example 402 (General Procedure 17)

Methyl-phenyl-carbamic acid 4-[2-(4-nitro-benzenesulfonylamino)-ethyl]-phenyl ester The title compound was prepared in 25% yield as a yellow oil using 4-nitro-benzenesulfonyl chloride as the aryl sulfonyl chloride.
HPLC-MS: m/z=456.0 (M+1); $R_t$=4.19 min.

Example 403 (General Procedure 17)

Methyl-phenyl-carbamic acid 4-[2-(6-chloro-imidazo[2,1-b]thiazole-5-sulfonylamino)-ethyl]-phenyl ester The title compound was prepared in 18% yield as an oil using 6-chloro-imidazo[2,1-b]thiazole-5-sulfonyl chloride as the aryl sulfonyl chloride.
HPLC-MS: m/z=490.9 (M+1); $R_t$=3.90 min.

Example 404 (General Procedure 17)

Methyl-phenyl-carbamic acid 4-[2-(2-trifluoromethoxy-benzenesulfonylamino)-ethyl]-phenyl ester The title compound was prepared in 38% yield as an oil using 2-trifluoromethoxy-benzenesulfonyl chloride as the aryl sulfonyl chloride.
HPLC-MS: m/z=495.1 (M+1); $R_t$=4.49 min.

Example 405 (General Procedure 17)

Methyl-phenyl-carbamic acid 4-(2-dimethylaminosulfonylamino-ethyl)-phenyl ester

The title compound was prepared in 32% yield as an oil using dimethylaminosulfamoyl chloride as the sulfonyl chloride.
HPLC-MS: m/z=378.1 (M+1); $R_t$=3.62 min.

Example 406 (General Procedure 17)

Methyl-phenyl-carbamic acid 4-(2-methanesulfonylamino-ethyl)-phenyl ester

The title compound was prepared in 22% yield as an oil using methanesulfonyl chloride as the sulfonyl chloride.
HPLC-MS: m/z=349.0 (M+1); $R_t$=3.26 min.

Example 407 (General Procedure 17)

Methyl-phenyl-carbamic acid 4-[2-(6-morpholin-4-yl-pyridine-3-sulfonylamino)-ethyl]-phenyl ester The title compound was prepared in 55% yield as crystals using 6-morpholin-4-yl-pyridine-3-sulfonyl chloride as the aryl sulfonyl chloride.
HPLC-MS: m/z=497.0 (M+1); $R_t$=3.90 min.

Example 408 (General Procedure 17)

Methyl-phenyl-carbamic acid 4-[2-(6-phenoxy-pyridine-3-sulfonylamino)-ethyl]-phenyl ester The title compound was prepared in 54% yield as crystals using 6-phenoxy-pyridine-3-sulfonyl chloride as the aryl sulfonyl chloride.
HPLC-MS: m/z=504.4 (M+1); $R_t$=4.45 min.

Example 409

Methyl-phenyl-carbamic acid 4-{2-[4-(4-methyl-piperazin-1-yl)-benzenesulfonylamino]-ethyl}phenyl ester To a stirred solution of 1-(4-bromophenyl)-4-methylpiperazine (2.05 g, 8.0 mmol) in THF (10 mL) was added dropwise 1.57 M solution in hexanes n-BuLi (4.6 mL, 7.2 mmol) over a 5-min period at −78° C. The mixture was stirred at −78° C. for 15 min. Then gaseous sulphur dioxide (ca. 5 g) was added causing an immediate precipitation. The mixture was allowed to warm to room temperature and stirred for 1 h. The precipitated lithium; 4-(4-methyl-piperazin-1-yl)-benzenesulfinate was isolated by filtration under $N_2$ (g), washed with THF (20 mL) and dried in vacuo providing 1.83 g (96%) of the lithium sulfinate as a solid. This lithium sulfinate (83 mg, 0.34 mmol) was suspended in $CH_2Cl_2$ (1 mL) and stirred with NCS (45 mg, 0.34 mmol) for 10 min at rt. A solution of N-methyl-N-phenyl-carbamic acid 4-(2-amino-ethyl)phenyl ester as its TFA salt (0.26 mmol) in $CH_2Cl_2$ (1.5 mL) was added together with DIPEA (0.90 mmol). The mixture was stirred at rt for 16 h and quenched with HOAc (2 mL) and water (2 mL). Extraction with $CH_2Cl_2$ and drying of the combined organic extracts gave the crude product which was purified by preparative HPLC (Gilson). This gave 54 mg (33%) of the title compound as its TFA salt as colorless crystals.

HPLC-MS: m/z=509.0 (M+1); $R_t$=2.88 min.

Example 410

Methyl-phenyl-carbamic acid 4-[2-(4-dimethylamino-benzenesulfonylamino)-ethyl]-phenyl ester To a stirred solution of (4-bromo-phenyl)-dimethylamine (4.02 g, 20 mmol) in THF (25 mL) was added dropwise 1.57 M solution in hexanes n-BuLi (11.5 mL, 18 mmol) over a 5-min period at −78° C. The mixture was stirred at −78° C. for 15 min. Then gaseous sulphur dioxide (ca. 5 g) was added causing an immediate precipitation. The mixture was allowed to warm to room temperature and stirred for 1 h. The precipitated lithium sulfinate was isolated by filtration under $N_2$ (g), washed with THF (20 mL) and dried in vacuo providing 2.99 g (87%) of lithium; 4-dimethylamino-benzenesulfinate as a bluegreen solid. This lithium sulfinate (65 mg, 0.34 mmol) was suspended in $CH_2Cl_2$ (1 mL) and stirred with NCS (45 mg, 0.34 mmol) for 10 min at rt. A solution of N-methyl-N-phenyl-carbamic acid 4-(2-amino-ethyl)phenyl ester as its TFA salt (0.26 mmol) in $CH_2Cl_2$ (1.5 mL) was added together with DIPEA (0.90 mmol). The mixture was stirred at rt for 16 h and quenched with HOAc (2 mL) and water (2 mL). Extraction with $CH_2Cl_2$ and drying of the combined organic extracts gave the crude product which was purified by preparative HPLC (Gilson). This gave 37 mg (31%) of the title compound as an oil.

HPLC-MS: m/z=454.5 (M+1); $R_t$=4.16 min.

Example 411

Methyl-phenyl-carbamic acid 4-{2-[4-(2-pyrrolidin-1-yl-ethoxy)-benzenesulfonylamino]-ethyl}-phenyl ester To a stirred solution of 1-[2-(4-bromo-phenoxy)-ethyl]-pyrrolidine (6.72 g, 25 mmol) in THF (45 mL) was added dropwise 1.6 M solution in hexanes n-BuLi (14 mL, 22.4 mmol) over a 5-min period at −78° C. The mixture was stirred at −78° C. for 15 min. Then gaseous sulphur dioxide (ca. 6 g) was added causing an immediate precipitation. The mixture was allowed to warm to room temperature and stirred for 1 h. The precipitated lithium sulfinate was isolated by filtration under $N_2$ (g), washed with THF (40 mL) and dried in vacuo providing 5.04 g (78%) of lithium; 4-(2-pyrrolidin-1-yl-ethoxy)-benzenesulfinate as a solid. This lithium sulfinate (179 mg, 0.69 mmol) was suspended in $CH_2Cl_2$ (2 mL) and stirred with NCS (80 mg, 0.60 mmol) for 10 min at rt. A solution of N-methyl-N-phenyl-carbamic acid 4-(2-amino-ethyl)phenyl ester as its TFA salt (0.55 mmol) in $CH_2Cl_2$ (3 mL) was added together with DIPEA (2.0 mmol). The mixture was stirred at rt for 16 h and evaporated to dryness. It was then redissolved in MeCN and purified by preparative HPLC (Gilson). This gave 89 mg (25%) of the title compound as its TFA salt as a crystals.

HPLC-MS: m/z=524.5 (M+1); $R_t$=3.04 min.

Example 412 (General Procedure 15)

4-(Tetrahydrofuran-2-ylmethyl)-piperazine-1-carboxylic acid 4-(5-trifluoromethyl-pyridin-2-yloxy)-phenyl ester The hydrochloride of the title compound was prepared from 4-(5trifluoromethyl-pyridin-2-yloxy)-phenyl chloroformate and 1-(tetrahydrofuran-2-ylmethyl)-piperazine, crude yield 0.28 g (89%). The crude product was stirred with a mixture of ethyl acetate (10 ml) and a solution of sodium bicarbonate (0.05 g) in water (5 ml). The aqueous layer was extracted with ethyl acetate (10+5 ml), the combined organic phases were washed with brine (5 ml), dried over sodium sulfate, filtered and evaporated. The residue was triturated with heptane (3 ml), filtered and dried to give the title compound, White crystals, m.p. 98–100° C.; $^1$H NMR (CDCl$_3$) δ 8.52–8.37 (br, 1H), 7.98–7.83 (dd, 1H), 7.25–7.06 (m, 4H), 7.00 (d, J=8.5 Hz), 4.18–3.47 (m, 7H), 2.76–2.36 (m, 6H), 2.13–1.74 (m, 3H), 1.64–1.40 (m, 1H); IR (KBr): ν 1715 (C=O) cm$^{-1}$.

Example 413 (General Procedure 15)

4-Cyclopropylmethyl-piperazine-1-carboxylic acid 4-(3-chloro-5-trifluoromethyl-pyridin-2-yloxy)-phenyl ester The hydrochloride of the title compound was prepared from 4-(3-chloro-5-trifluoromethyl-pyridin-2-yloxy)-phenyl chloroformate and 1-cyclopropylmethyl-piperazine, yield 83%. White crystals, m.p. 254–255° C.; IR (KBr): ν 1728 (C=O) cm$^{-1}$.

Example 414 (General Procedure 15)

4-(Tetrahydro-furan-2-ylmethyl)-piperazine-1-carboxylic acid 4-(4-trifluoromethylphenoxy)-phenyl ester The hydrochloride of the title compound was prepared from 4-(4-trifluoromethyl-phenoxy)-phenyl chloroformate and 1-(tetrahydro-furan-2-ylmethyl)-piperazine, yield 93%. White crystals, m.p. 216–217° C.; IR (KBr): ν 1730 (C=O) cm$^{-1}$.

Example 415 (General Procedure 15)

4-Cyclohexylmethyl-piperazine-1-carboxylic acid 4-(4-trifluoromethyl-phenoxy)-phenyl ester The hydrochloride of the title compound was prepared from 4-(4-trifluoromethyl-phenoxy)-phenyl chloroformate and 1-cyclohexylmethyl-piperazine, yield 93%. White crystals, m.p. 256–258° C.; IR (KBr): ν 1715 (C=O) cm⁻.

Example 416 (General Procedure 15)

4-Cyclohexylmethyl-piperazine-1-carboxylic acid 4-(3-chloro-5-trifluoromethyl-pyridin-2-yloxy)-phenyl ester The hydrochloride of the title compound was prepared from 4-(3-chloro-5-trifluoromethyl-pyridin-2-yloxy)-phenyl chloroformate and 1-cyclohexylmethyl-piperazine, yield 76%. White crystals, m.p. 265–266° C.; IR (KBr): ν 1732 (C=O) cm$^{-1}$.

Example 417 (General Procedure 15)

4-Cyclopropylmethyl-piperazine-1-carboxylic acid 4-(4-trifluoromethyl-phenoxy)-phenyl ester The hydrochloride of the title compound was prepared from 4-(4-trifluoromethyl-phenoxy)-phenyl chloroformate and 1-cyclopropylmethyl-piperazine, yield 43%. White crystals, m.p. 238–239° C.; IR (KBr): ν 1725 (C=O) cm$^{-1}$.

Example 418 (General Procedure 15)

4-(Tetrahydro-furan-2-ylmethyl)-piperazine-1-carboxylic acid 4-(3-chloro-5-trifluoromethyl-pyridin-2-yloxy)-phenyl ester The hydrochloride of the title compound was prepared from 4-(3-chloro-5-trifluoromethyl-pyridin-2-yloxy)-phenyl chloroformate and 1-(tetrahydrofuran-2-ylmethyl)-piperazine, yield 23%. White crystals, m.p. 98–100° C.; IR (KBr): ν 1731 (C=O) cm⁻.

Example 419 (General Procedure 15)

4-Naphthalen-1-ylmethyl-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-naphthalen-1-ylmethyl-piperazine, yield 71%. White crystals, m.p. 218–219° C.; IR (KBr): ν 1713 (C=O) cm$^{-1}$.

Example 420 (General Procedure 15)

4-(2-Cyclohexyl-ethyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(2-cyclohexyl-ethyl)-piperazine, yield 90%. White crystals, m.p. 274–276° C.; IR (KBr): ν 1715 (C=O) cm⁻.

Example 421 (General Procedure 15)

4-(3-Methoxy-phenyl)-piperazine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and 1-(3-methoxy-phenyl)-piperazine, yield 96%. White solid, m.p. 109–111° C.; IR (KBr): ν 1721 (C=O) cm$^{-1}$.

Example 422 (General Procedure 15)

4-Cyclopropylmethyl-piperazine-1-carboxylic acid 4-[2-(4-chloro-phenyl)-ethylcarbamoyl]-phenyl ester The title compound was prepared from 4-[2-(4-chlorophenyl)-ethylcarbamoyl]-phenyl chloroformate and 1-cyclopropylmethyl-piperazine, yield 18%. White crystals, m.p. 225–226° C.; IR (KBr): ν 1710 (ester C=O), 1661 (amide C=O) cm$^{-1}$.

Example 423 (General Procedure 15)

4-(Tetrahydro-furan-2-ylmethyl)-piperazine-1-carboxylic acid 4-[2-(4-chloro-phenyl)-ethylcarbamoyl]-phenyl ester The title compound was prepared from 4-[2-(4-chlorophenyl)-ethylcarbamoyl]-phenyl chloroformate and 1-(tetrahydrofuran-2-ylmethyl)-piperazine, yield 12%. White crystals, m.p. 220–221° C.; IR (KBr): ν 1708 (ester C=O), 1660 (amide C=O) cm$^{-1}$.

Example 424 (General Procedure 15)

4-(3,4-Dichloro-benzyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(3,4-dichloro-benzyl)-piperazine, yield 86%. White crystals, m.p. 229–230° C.; IR (KBr): ν 1717 (C=O) cm$^{-1}$.

Example 425 (General Procedure 15)

4-Cyclopropylmethyl-[1,4]diazepane-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-cyclopropylmethyl-[1,4]diazepane, yield 61%. White crystals, m.p. 208–209° C.; IR (KBr): ν 1711 (C=O) cm$^{-1}$.

Example 426 (General Procedure 15)

4-(2-Pyridin-2-yl-ethyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(2-pyridin-2-yl-ethyl)-piperazine, yield 81%. White crystals, m.p. 281–282° C.; IR (KBr): ν 1713 (C=O) cm$^{-1}$.

Example 427 (General Procedure 18)

4-(Pyrazin-2-yl)-piperazine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and 1-(pyrazin-2-yl)-piperazine- White crystals, m.p. 160–161° C.; HPLC-MS: m/z=446 (M+1) at $R_t$=4.0 min.; $^1$H NMR (DMSO-d$_6$): δ 8.60–8.57 (m, 1H), 8.39–8.36 (m, 1H), 8.27–8.22 (dd-like, 1H), 8.14–8.11 (m, 1H)7.91–7.87 (d-like, 1H), 7.29–7.21 (m, 5H), 3.80–3.64 (br, 6H), 3.64–3.50 (br, 2H); IR (KBr): ν 1737, 1714 (C=O) cm$^{-1}$.

Example 428 (General Procedure 15)

4-(Benzo-isothiazol-3-yl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(benzo-isothiazol-3-yl)-piperazine. Drying on a rotary evaporator of the crude product gave the title compound as the free base. Purification by flash chromatography (silica, ethyl acetate-heptane 1:4) gave white crystals, m.p. 132–133° C.; IR (KBr): ν 1726 (C=O) cm$^{-1}$.

Example 429 (General Procedure 15)

4-(5-Chloro-thiophen-2-ylmethyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(5-chloro-thiophen-2-ylmethyl)-piperazine, yield 48%. White crystals, m.p. 225–226° C. (from EtOH); $^1$H NMR (DMSO-d$_6$): δ 12.00 (br, 1H), 8.60–8.55 (1H), 8.27–8.21 (dd-like, 1H), 7.33–7.20 (m, 6H), 7.20–7.15 (d, 1H), 4.55 (br s, 2H), 4.40–4.00 (br, 2H), 3.74–3.27 (br, 4H+H$_2$O); 3.27–2.97 (br, 2H); IR (KBr): ν 1723 (C=O) cm$^{-1}$.

Example 430 (General Procedure 15)

4-(3-Trifluoromethyl-phenyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(3-trifluoromethyl-phenyl)-piperazine. The crude product was converted to the free base, yield 56%. White crystals, m.p. 87–88° C.; IR (KBr): ν 1719 (C=O) cm$^{-1}$.

Example 431 (General Procedure 15)

4-(5-Chloro-2-methyl-phenyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(5-chloro-2-methyl-phenyl)-piperazine The crude product was converted to the free base, yield 26%. White crystals; HPLC-MS:m/z=492(M+H) at Rt=5.5 min.; IR (KBr): ν 1722 (C=O) cm$^{-1}$.

Example 432 (General Procedure 15)

4-(1-Methyl-piperidin-4-ylmethyl)-piperazine-1-carboxylic acid 4-(5-trifluoromethyl-pyridin-2-yloxy)-phenyl ester The dihydrochloride of the title compound was prepared from 4-(5-trifluoromethyl-pyridin-2-yloxy)-phenyl chloroformate and 1-(1-methyl-piperidin-4-ylmethyl)-piperazine, yield 6%. White crystals, m.p. 305–306° C.; IR (KBr): ν 1713 (C=O) cm$^{-1}$.

Example 433 (General Procedure 15)

4-Biphenyl-4-ylmethyl-[1,4]diazepane-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-biphenyl-4-ylmethyl-[1,4]diazepane. The crude product was converted to the free base, yield 17%. White crystals, m.p. 143° C.; HPLC-MS: m/z=548(M+H) at $R_t$=3.6 min.; IR (KBr): ν 1711 (C=O) cm$^{-1}$.

Example 434 (General Procedure XX)

4-(5-Dimethylamino-naphthalene-1-sulfonyl)-piperazine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and 1-(5-dimethylamino-naphthalene-1-sulfonyl)-piperazine and purified by flash chromatography (ethyl acetate-heptane 1:4), yield 32%. Pale crystals, HPLC-MS: m/z: 601(M+1) at $R_t$=5.2 min.;m.p. ° C.; IR (KBr): ν 1723 (C=O) cm$^{-1}$.

Example 435 (General Procedure 15)

4-(3-Methoxy-benzyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(3-methoxy-benzyl)-piperazine, yield 99%. White crystals, m.p. 214–215° C.; HPLC-MS: m/z: 489(M+1) at $R_t$=2.8 min.; IR (KBr): ν 1712 (C=O) cm$^{-1}$.

Example 436 (General Procedure 15)

4-(3-Fluoro-benzyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy-phenyl chloroformate and 1-(3-fluoro-benzyl)-piperazine, yield 77%. White crystals, m.p. 138–139° C.; HPLC-MS: m/z: 476 (M+1) at $R_t$=3.0 min.; IR (KBr): ν 1714 (C=O) cm$^{-1}$.

Example 437 (General Procedure 18)

4-(3-Trifluoromethyl-pyridin-2-yl)-piperazine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and 1-(3-trifluoromethyl-pyridin-2-yl)-piperazine, yield 25%. White crystals, m.p. 131–132° C.; HPLC-MS: m/z: 513 (M+1) at $R_t$=5.0 min.; IR (KBr): ν 1722 (C=O) cm$^{-1}$.

Example 438 (General Procedure 15)

4-(3-Fluorobenzyl)-piperazine-1-carboxylic acid 4-(4,6-dimethyl-pyrimidin-2-ylsulfanyl)-phenyl ester The hydrochloride of the title compound was prepared from 4-(4,6-dimethyl-pyrimidin-2-ylsulfanyl)-phenyl chloroformate and 1-(3-fluorobenzyl)-piperazine. The crude product was converted to the free base, yield 48%. White crystals, m.p. 117–118° C.; HPLC-MS: m/z: 453 (M+1) at Rt=2.6 min.; IR (KBr): ν 1714 (C=O) cm$^{-1}$.

Example 439 (General Procedure 15)

5-(4-Trifluoromethoxybenzyl)-2,5-diazabicyclo[2.2.1]heptane-2-carboxylic acid 4-(5-trifluoromethylpyridin-2-yloxy)-phenyl ester The hydrochloride of the title compound was prepared from 4-(5-trifluoromethyl-pyridin-2-yloxy)-phenyl chloroformate and 2-(4-trifluoromethoxybenzyl)-2,5-diazabicyclo[2.2.1]heptane. The crude product was converted to the free base, yield 20%. Oil; HPLC-MS: m/z: 554 (M+1) at $R_t$=3.1 min.; IR (KBr): ν 1723 (C=O) cm$^{-1}$.

Example 440 (General Procedure 18)

1-Oxo-1λ$^4$-thiomorpholine-4-carboxylic acid 4-(5-trifluoromethyl-pyridin-2-yloxy)-phenyl ester The title compound was prepared from 4-(5-trifluoromethyl-pyridin-2-yloxy)-phenyl chloroformate and thiomorpholine 1-oxide and purified by flash chromatography (ethyl acetate), yield 37%. White crystals, m.p. 156–157° C.; $^1$H NMR (CDCl$_3$) δ 8.47–8.40 (s-like, 1H), 7.94–7.87 (dd-like, 1H), 7.24–7.13 (m, 4H), 7.06–6.99 (d-like, 4H), 4.31–3.91 (m, 4H), 2.97–2.87–2.75 (m, 2H+2H); IR (KBr): ν 1710 (C=O) cm$^{-1}$.

Example 441 (General Procedure 18)

4-(2,4-Dimethoxyphenyl)-piperazine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and 1-(2,4-dimethoxyphenyl)-piperazine. Purified by flash chromatography (ethyl acetate-heptane 1:4), yield 69%. White crystals, m.p. 98–99° C.; HPLC-MS: m/z=504 (M+1) at Rt=4.0 min.; IR (KBr): ν 1733, 1712 (C=O) cm$^{-1}$.

Example 442 (General Procedure 15)

5-Benzyl-2,5-diazabicyclo[2.2.1]heptane-2-carboxylic acid 4-(5-trifluoromethylpyridin-2-yloxy)-phenyl ester The hydrochloride of the title compound was prepared from 4-(5-trifluoromethyl-pyridin-2-yloxy)-phenyl chloroformate and 2-benzyl-2,5-diazabicyclo[2.2.1]heptane. The crude product was converted to the free base and further purified by flash chromatography (ethyl acetate-heptane 1:4), yield 16%. White crystals, m.p. 114–115° C.; HPLC-MS: m/z: 470 (M+1) at $R_t$=2.6 min.; IR (KBr): ν 1718 (C=O) cm$^{-1}$.

Example 443 (General Procedure 10)

4-Aminomethyl-piperidine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and 4-aminomethylpiperidine. The crude product was purified by preparative HPLC (Method C) (32%, off-white crystals). HPLC-MS m/z=396.1 (M+1), Rt: 2.65 min. purity: 86%.

Example 444 (General Procedure 10)

4-Pyrimidin-2-yl-piperazine-1-carboxylic acid 4-(5-chloro-pyridin-2-yloxy)-phenyl ester The title compound was prepared from 4-(5-trifluoromethyl-pyridin-2-yloxy)-phenyl chloroformate and 1-(2-pyrimidinyl)-piperazine, two equivalent of diisopropylethylamine was added. The crude product was obtained by filtration of the reaction mixture. The crude product was washed with diethyl ether and subjected to column chromatography, ethyl acetate/heptane (1:3) (18%, white crystals). HPLC-MS m/z=412.1 (M+1), Rt: 4.12 min.

Example 445 (General Procedure 12)

4-Cyclopropylmethyl-piperazine-1-carboxylic acid 4-(4,4-dimethyl-2,6-dioxo-piperidin-1-yl)-phenyl ester The title compound was prepared from 4-(4,4-dimethyl-2,6-dioxo-piperidin-1-yl)-phenyl chloroformate and 1-cyclopropylmethyl-piperazine, preparative HPLC (Method C) (45%, off-white crystals). HPLC-MS m/z=400.3 (M+1), Rt: 1.83 min.

Example 446 (General Procedure 12)

4-(4-Methoxy-benzyl)-piperazine-1-carboxylic acid 4-(4,4-dimethyl-2,6-dioxo-piperidin-1-yl)-phenyl ester The title compound was prepared from 4-(4,4-dimethyl-2,6-dioxo-piperidin-1-yl)-phenyl chloroformate and 1-(4-methoxybenzyl)-piperazine, preparative HPLC (Method C) (54%, white crystals). HPLC-MS m/z=466.3 (M+1), Rt: 2.26 min.

Example 447 (General Procedure 12)

4-Pyridin-3-ylmethyl-piperazine-1-carboxylic acid 4-(4,4-dimethyl-2,6-dioxo-piperidin-1-yl)-phenyl ester The title compound was prepared from 4-(4,4-dimethyl-2,6-dioxo-piperidin-1-yl)-phenyl chloroformate and 1-pyridin-3-ylmethyl-piperazine, hydrochloride, preparative HPLC (Method C) (75%, colourless oil). HPLC-MS m/z=437.2 (M+1), Rt: 1.70 min.

Example 448 (General Procedure 12)

4-(4-Methoxy-benzyl)-piperazine-1-carboxylic acid 4-(2-cyclohexyl-acetylamino)-phenyl ester The title compound was prepared from 4-(2-cyclohexyl-acetylamino)-phenyl chloroformate and 1-(4-methoxybenzyl)-piperazine, preparative HPLC (Method C) (49%, white crystals). HPLC-MS m/z=466.3 (M+1), Rt: 2.85 min.

Example 449 (General Procedure 12)

4-Cyclopropylmethyl-piperazine-1-carboxylic acid 4-(2-cyclohexyl-acetylamino)-phenyl ester The title compound was prepared from 4-(2-cyclohexyl-acetylamino)-phenyl chloroformate and 1-cyclopropylmethyl-piperazine, preparative HPLC (methode C (60%, off-white crystals). HPLC-MS m/z=400.3 (M+1), Rt: 2.42 min.

Example 450 (General Procedure 12)

4-Pyridin-3-ylmethyl-piperazine-1-carboxylic acid 4-(2-cyclohexyl-acetylamino)-phenyl ester The title compound was prepared from 4-(2-cyclohexyl-acetylamino)-phenyl chloroformate and 1-pyridin-3-ylmethyl-piperazine, hydrochloride, preparative HPLC (methode C) (64%, white crystals). HPLC-MS m/z=437.4 (M+1), Rt: 2.38 min.

Example 451 (General Procedure 14)

Methyl-phenyl-carbamic acid 4-(2-cyclohexyl-ethylsulfamoyl)-phenyl ester

The title compound was prepared from N-(2-cyclohexylethyl)-4-hydroxy-benzenesulfonamide and N-methyl-N-phenyl carbamoylchloride, preparative HPLC (Method C) (14%, light yellow oil). HPLC-MS m/z=417.3 (M+1), Rt: 4.89 min.

Example 452 (General Procedure 14)

Methyl-phenyl-carbamic acid 4-(3-methyl-butylsulfamoyl)-phenyl ester

The title compound was prepared from 4-hydroxy-N-(3-methyl-butyl)-benzenesulfonamide and N-methyl-N-phenyl carbamoylchloride, preparative HPLC (Method C) (11%, light yellow oil). HPLC-MS m/z=377.2 (M+1), Rt: 4.32 min.

Example 453 (General Procedure 12)

(6-Methoxy-pyridin-2-yl)-methyl-carbamic acid 4-(5-trifluoromethyl-pyridin-2-yloxy)-phenyl ester The crude product was prepared from 4-(5-trifluoromethyl-pyridin-2-yloxy)-phenyl chloroformate and and 2-methoxy-6-methylaminopyridine. The reaction mixture was evaporated to dryness, dissolved in dichloromethane (100 ml) and extracted with a aqueous phosphate buffer, pH 7. The aqueous phase was extracted with dichloromethane (100 ml×2) and the combined organic phases were dryed and evaporated to dryness. The product was subjected to flash chromatography, ethyl acetate/heptane (1:7) to give the titlew product (86%, white crystals). HPLC-MS m/z=420.4 (M+1), Rt: 5.23 min.

Example 454 (General Procedure 12)

4-Benzimidazol-1-yl-piperidine-1-carboxylic acid 4-(5-trifluoromethyl-pyridin-2-yloxy)-phenyl ester The crude product was prepared from 4-(5-trifluoromethyl-pyridin-2-yloxy)-phenyl chloroformate and 1-piperidine-4-yl-1H-benzimidazole, 5 equivalent of diisopropylamine was added, preparative HPLC (method C) (23%, colourless crystals). HPLC-MS m/z=483.3 (M+1), Rt: 3.14 min.

Example 455 (General Procedure 12)

4-Hydroxymethyl-piperidine-1-carboxylic acid 4-(2-cyclohexyl-acetylamino)-phenyl ester The title compound was prepared from 4-(2-cyclohexyl-acetylamino)-phenyl chloroformate and 4-hydroxymethyl-piperidine, praeparative HPLC (Method C) (37%, off-white crystals). HPLC-MS m/z=375.2 (M+1), Rt: 3.41 min.

Example 456 (General Procedure 12)

4-(4-Amino-phenyl)-piperidine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and 4-(4-aminophenyl)piperidine, hydrochloride, praeparative HPLC (Method C) (30%, light yellow crystals). HPLC-MS m/z=458.2 (M+1), Rt: 3.42 min.

Example 457 (General Procedure 12)

4-(Methyl-pyridin-3-ylmethyl-amino)-piperidine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and methyl-piperidin-4-yl-pyridin-3-ylmethyl-amine, hydrochloride, praeparative HPLC (Method C) (31%, orange oil). HPLC-MS m/z=487.1 (M+1), Rt: 2.64 min.

Example 458 (General Procedure 12)

4-(2-Oxo-pyrrolidin-1-yl)-piperidine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and 1-piperidin-4-yl-pyrrolidine-2-one, hydrochloride, praeparative HPLC (Method C) (55%, semi-crystaline oil). HPLC-MS m/z=450.1 (M+1), Rt: 3.81 min.

Example 459 (General Procedure 12)

4-(Methyl-phenethyl-amino)-piperidine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and methyl-phenethyl-piperidin-4-yl-amine, hydrochloride, praeparative HPLC (Method C) (37%, colourless oil). HPLC-MS m/z=500.1 (M+1), Rt: 3.26 min.

Example 460

4-[(Benzyl-ethyl-amino)-methyl]-piperidine-1-carboxylic acid 4-(5-trifluoromethyl-pyridin-2-yloxy)-phenyl ester Benzyl-ethyl-piperidin-4-ylmethyl-amine (1.42 mmol) was dissolved in dichloromethane. 4-(5-Trifluoromethyl-pyridin-2-yloxy)-phenyl chloroformate (1.42 mmol, 0.451 g) (prepared from the corresponding phenol by conventional methods) was added at room temperature. The reaction mixture was stirred overnight and evaporated to dryness. The crude product was subjected to column chromatography, ethyl acetate/heptane (1:3)→Triethylamine/ethyl acetate 1:9). The fractions containing the title product, was evaporated to dryness and HCl (g) in ethyl acetate was added and stirred for 16 hours. The solution was evaporated to dryness and dryed in vacuom for 16 h. to give the title product. (58%, light yellow crystals). HPLC-MS m/z=514.1 (M+1), Rt: 3.27 min.

Example 461 (General Procedure 12)

4-[Methyl-phenethyl-amino)-methyl]-piperidine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and methyl-phenethyl-piperidin-4-ylmethyl-amine, hydrochloride, 5 equivalent of diisopropylamine was added, praeparative HPLC (Method C) (46%, colourless crystals). HPLC-MS m/z=514.1 (M+1), Rt: 3.31 min.

Example 462 (General Procedure 12)

4-[(Cyclohexyl-methyl-amino)-methyl]-piperidine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and cyclohexyl-methyl-piperidine-4-ylmethyl-amine, hydrochloride, 5 equivalent of diisopropylamine was added, praeparative HPLC (Method C) (43%, white crystals). HPLC-MS m/z=492.3 (M+1), Rt: 3.22 min.

Example 463 (General Procedure 12)

4-[(Ethyl-pyridin-4-ylmethyl-amino)-methyl]-piperidine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and ethyl-piperidin-4-ylmethyl-pyridin-4-ylmethyl-amine, hydrochloride, 5 equivalent of diisopropylamine was added, praeparative HPLC (Method C) (25%, off-white crystals). HPLC-MS m/z=515.2 (M+1), Rt: 2.77 min.

Example 464 (General Procedure 12)

4-[(Benzyl-methyl-amino)-methyl]-piperidine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and benzyl-methyl-piperidin-4-ylmethyl-amine, hydrochloride, 5 equivalent of diisopropylamine was added, praeparative HPLC (Method C) (56%, colourless crystals). HPLC-MS m/z=500.2 (M+1), Rt: 3.18 min.

Example 465 (General Procedure 12)

4-[(Methyl-pyridin-3-ylmethyl-amino)-methyl]-piperidine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and methyl-piperidine-4-ylmethyl-pyridine-4-ylmethyl-amine, hydrochloride, 5 equivalent of diisopropylamine was added, praeparative HPLC (Method C) (36%, colourless crystals). HPLC-MS m/z=501.1 (M+1), Rt: 2.74 min.

Example 466 (General Procedure 12)

4-(1,3-Dihydro-isoindol-2-ylmethyl)-piperidine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and 2-piperidin-4-ylmethyl-2,3-dihydro-1H-isoindole, hydrochloride, 5 equivalent of diisopropylamine was added, praeparative HPLC (Method C) (63%, colourless crystals). HPLC-MS m/z=498.1 (M+1), Rt: 3.07 min.

Example 467

4-Benzotriazol-1-yl-piperidine-1-carboxylic acid 4-(5-trifluoromethyl-pyridin-2-yloxy)-phenyl ester The title compound was prepared from 4-(5-trifluoromethyl-pyridin-2-yloxy)-phenyl chloroformate and 1-piperidin-4-yl-1H-benzotriazole, hydrochloride, 5 equivalent of diisopropylamine was added, praeparative HPLC (Method C) (7%, colourless crystals). HPLC-MS m/z=506.2 (M+1), Rt: 4.56 min.

Example 468 (General Procedure 12)

4-[(Cyclopropylmethyl-amino)-methyl]-piperidine-1-carboxylic acid 4-(5-trifluoromethyl-pyridin-2-yloxy)-phenyl ester Cyclopropylmethyl-piperidine-4-ylmethyl-amine (0.65 mmol, 110 mg) was dissolve in dichloromethane. 4-(5-trifluoromethyl-pyridin-2-yloxy)-phenyl chloroformate (0.65 mmol, 0.208 g) (prepared from the corresponding phenol by conventional methods) was added at −15° C. for 15 min and stired at room temperature overnight and evaporated to dryness. The crude product was purified by preparative HPLC (Method C) (16%, colourless crystals). HPLC-MS m/z=450.1 (M+1), Rt: 2.98 min.

Example 469 (General Procedure 12)

4-[Methyl-(2-pyridin-2-yl-ethyl)-amino]-piperidine-1-carboxylic acid 4-(5-trifluoromethyl-pyridin-2-yloxy)-phenyl ester The title product was prepared from methyl-piperidin-4-yl-(2-pyridin-2-yl-ethyl)-amine and 4-(5-trifluoromethyl-pyridin-2-yloxy)-phenyl chloroformate, 5 equivalent of diisopropylamine was added, preparative HPLC (method C) (48%, colourless oil). HPLC-MS m/z=501.1 (M+1), Rt: 2.77 min.

Example 470 (General Procedure 12)

4-(Cyclohexyl-methyl-amino)-piperidine-1-carboxylic acid 4-(5-trifluoromethyl-pyridin-2-yloxy)-phenyl ester The title product was prepared from cyclohexyl-methyl-piperidin-4-yl-amine, dihydrochloride and 4-(5-trifluoromethyl-pyridin-2-yloxy)-phenyl chloroformate, 2 equivalent of diisopropylamine; dimethylformamide/tetrahydrofuran (2:1). The reaction mixture was evaporated to dryness and the crude product extracted with ethyl acetate from an aqueous HCl solution saturated with sodium chloride, pH 1–2. The title product was crystallized from ethyl acetate during evaporation of the solvent, filtered and dryed in vacuum (45%, white crystals). HPLC-MS m/z=478.2 (M+1), Rt: 3.10 min.

Example 471 (General Procedure 12)

4-(Isopropyl-methyl-amino)-piperidine-1-carboxylic acid 4-(5-trifluoromethyl-pyridin-2-yloxy)-phenyl ester The title product was prepared from isopropyl-methyl-piperidin-4-yl-amine, dihydrochloride and 4-(5-trifluoromethyl-pyridin-2-yloxy)-phenyl chloroformate; dimethylformamide as solvent, preparative HPLC (method C) (77%, light yellow oil). HPLC-MS m/z=438.3 (M+1), Rt: 2.77 min.

Example 472 (General Procedure 12)

(4-Methoxy-phenyl)-methyl-carbamic acid 4-(5-trifluoromethyl-pyridin-2-yloxy)-phenyl ester The title product was prepared from N-methyl-p-anisidine and 4-(5-trifluoromethyl-pyridin-2-yloxy)-phenyl chloroformate, preparative HPLC (method C) (61%, off-white crystals). HPLC-MS m/z=419.2 (M+1), Rt: 4.67 min.

Example 473 (General Procedure 12)

(2-Methoxy-phenyl)-methyl-carbamic acid 4-(5-trifluoromethyl-pyridin-2-yloxy)-phenyl ester The title product was prepared from 2-methoxy-N-methylamine and 4-(5-trifluoromethyl-pyridin-2-yloxy)-phenyl chloroformate, preparative HPLC (method C) (63%, colourless oil). HPLC-MS m/z=419.2 (M+1), Rt: 4.75 min.

Example 474 (General Procedure 12)

(2-Carbamoyl-4-chloro-phenyl)-methyl-carbamic acid 4-(5-trifluoromethyl-pyridin-2-yloxy)-phenyl ester.

The title product was prepared from 5-chloro-2-(methylamino)-benzamide and 4-(5-trifluoromethyl-pyridin-2-yloxy)-phenyl chloroformate, preparative HPLC (method C) (31%, light yellow oil). HPLC-MS m/z=466.1 (M+1), Rt: 3.99 min.

Example 475 (General Procedure 12)

(2-Carbamoyl-phenyl)-methyl-carbamic acid 4-(5-trifluoromethyl-pyridin-2-yloxy)-phenyl ester The title product was prepared from 2-(methylamino)benzamide and 4-(5-trifluoromethyl-pyridin-2-yloxy)-phenyl chloroformate, preparative HPLC (method C) (57%, light yellow oil). HPLC-MS m/z=454.2 (M+Na), Rt: 3.66 min.

Example 476 (General Procedure 12)

(2-Chloro-phenyl)-methyl-carbamic acid 4-(5-trifluoromethyl-pyridin-2-yloxy)-phenyl ester The title product was prepared from 2-chlor-N-methylaniline and 4-(5-trifluoromethyl-pyridin-2-yloxy)-phenyl chloroformate, preparative HPLC (method C) (48%, light yellow oil). HPLC-MS m/z=423.1 (M+1), Rt: 4.98 min.

Example 477 (General Procedure 12)

(2,4-Difluoro-phenyl)-methyl-carbamic acid 4-(5-trifluoromethyl-pyridin-2-yloxy)-phenyl ester The title product was prepared from 2,4-difluouro-N-methylaniline and 4-(5-trifluoromethyl-pyridin-2-yloxy)-phenyl chloroformate, preparative HPLC (method C) (37%, white crystals). HPLC-MS m/z=425.1 (M+1), Rt: 4.90 min.

Example 478 (General Procedure 12)

Methyl-(2-trifluoromethoxy-phenyl)-carbamic acid 4-(5-trifluoromethyl-pyridin-2-yloxy)-phenyl ester The title product was prepared from N-methyl-2-(trifluoromethoxy)-aniline and 4-(5-trifluoromethyl-pyridin-2-yloxy)-phenyl chloroformate, preparative HPLC (method C) (49%, colourless oil). HPLC-MS m/z=473.2 (M+1), Rt: 5.18 min.

Example 479 (General Procedure 13)

Methyl-phenyl-carbamic acid 4-(1,1,3,3-tetramethyl-butylcarbamoyl)-phenyl ester

The title product was prepared from tert-octylamine and 4-(methyl-phenyl-carbamoyloxy)-benzoic acid 2,5-dioxo-pyrrolidin-1-yl ester, preparative HPLC (method C) (26%, white crystals). HPLC-MS m/z=383.5 (M+1), Rt: 4.67 min.

Example 480 (General Procedure 13)

Methyl-phenyl-carbamic acid 4-[(2-dimethylamino-ethyl)-methyl-carbamoyl]-phenyl ester The title product was prepared from N,N,N'-trimethylethylendiamine and 4-(methyl-phenyl-carbamoyloxy)-benzoic acid 2,5-dioxo-pyrrolidin-1-yl ester, preparative HPLC (method C) (2%, colourless oill). HPLC-MS m/z=356.2 (M+1), Rt: 2.17 min.

Example 481 (General Procedure 13)

Methyl-phenyl-carbamic acid 4-(cyclopropylmethyl-carbamoyl)-phenyl ester

The title product was prepared from cyclopropylmethylamine and 4-(methyl-phenyl-carbamoyloxy)-benzoic acid 2,5-dioxo-pyrrolidin-1-yl ester. The crude product was used without further purification (100%, semi-crystal oil). HPLC-MS m/z=325.1 (M+1), Rt: 3.40 min.

Example 482 (General Procedure 13)

Methyl-phenyl-carbamic acid 4-(methyl-pyridin-3-ylmethyl-carbamoyl)-phenyl ester The title product was prepared from methyl-pyridin-3-ylmethyl-amine and 4-(methyl-phenyl-carbamoyloxy)-benzoic acid 2,5-dioxo-pyrrolidin-1-yl ester. The crude product was subjected to preparative HPLC (method C) (48%, clear colourless oil). HPLC-MS m/z=376.2 (M+1), Rt: 2.37 min.

Example 483 (General Procedure 13)

Methyl-phenyl-carbamic acid 4-[(1H-benzimidazol-2-ylmethyl)-carbamoyl]-phenyl ester The title product was prepared from C-(1H-benzimidazol-2-yl)-methylamine and 4-(methyl-phenyl-carbamoyloxy)-benzoic acid 2,5-dioxo-pyrrolidin-1-yl ester. The crude product was subjected to preparative HPLC (method C) (8%, off-white crystals). HPLC-MS m/z=401.1 (M+1), Rt: 2.56 min.

Example 484 (General Procedure 13)

Methyl-phenyl-carbamic acid 4-[2-(4-chloro-phenyl)-ethylcarbamoyl]-phenyl ester

The title product was prepared from 2-(4-chloro-phenyl)-ethylamine and 4-(methyl-phenyl-carbamoyloxy)-benzoic acid 2,5-dioxo-pyrrolidin-1-yl ester. The crude product was subjected to preparative HPLC (method C) (39%, off-white crystals). HPLC-MS m/z=409.2 (M+1), Rt: 4.27 min.

Example 485

4-Cyclopropylmethyl-piperazine-1-carboxylic acid 4-(3,3-dimethyl-butylcarbamoyl)-phenyl ester The title product was prepared from 1-cyclopropylmethylpiperazine (0.35 mmol) dissolved in dichloromethane (5 ml). 4-(3,3-dimethyl-butylcarbamoyl)-phenyl chloroformate (0.35 mmol) was added at room temperature. The reaction mixture was stirred for 16 h and evaporated to dryness and subjected to preparative HPLC (metod C) (5%, white crystals). HPLC-MS m/z=388.2 (M+1), Rt: 2.43 min.

Example 486

4-Hydroxymethyl-piperidine-1-carboxylic acid 4-(3,3-dimethyl-butylcarbamoyl)-phenyl ester ester The title product was prepared from 4-hydroxymethylpiperidine (0.35 mmol) was dissolved in dichloromethane (5 ml). Diisopropylethylamine (0.35 mmol was added together with 4-(3,3-dimethyl-butylcarbamoyl)-phenyl chloroformate (0.35 mmol) at room temperature. The reaction mixture was stirred for 16 h and evaporated to dryness and subjected to preparative HPLC (metod C). (25%, white crystals). HPLC-MS m/z=363.3 (M+1), Rt: 3.27 min.

Example 487

4-Pyridin-3-ylmethyl-piperazine-1-carboxylic acid 4-(3,3-dimethyl-butylcarbamoyl)-phenyl ester The title product was prepared from 1-pyridin-3-ylmethyl-piperazine was dissolved in dichloromethane (5 ml). 4-(3,3-Dimethyl-butylcarbamoyl)-phenyl chloroformate (0.35 mmol) was added at room temperature. The reaction mixture was stirred for 16 h and evaporated to dryness and subjected to preparative HPLC (metod C) (88%, light yellow oil). HPLC-MS m/z=425.4 (M+1), Rt: 2.33 min.

Example 488

4-(4-Methoxy-benzyl)-piperazine-1-carboxylic acid 4-(3,3-dimethyl-butylcarbamoyl)-phenyl ester The title product was prepared from 1-(4-methoxy-benzyl)-piperazine (0.35 mmol) was dissolved in dichloromethane (5 ml). 4-(3,3-Dimethyl-butylcarbamoyl)-phenyl chloroformate (0.35 mmol) was added at room temperature. The reaction mixture was stirred for 16 h and evaporated to dryness and subjected to preparative HPLC (metod C). (54%, colourless semi-crystaline oil). HPLC-MS m/z=454.3 (M+1), Rt: 2.78 min.

Example 489

4-(2-Pyridin-2-yl-acetyl)-piperazine-1-carboxylic acid 4-(5-trifluoromethyl-pyridin-2-yloxy)-phenyl ester a) Piperazine-1,4-dicarboxylic acid tert-butyl ester 4-(5-trifluoromethyl-pyridin-2-yloxy)-phenyl ester (General Procedure 18)

The title compound was prepared from 4-(5-trifluoromethyl-pyridin-2-yloxy)-phenyl chloroformate and 1-tert-butoxycarbonyl-piperazin, yield 59% (recrystallized from EtOAc-heptane 1:1). White crystals, m.p. 165–166° C.; $^1$H NMR (CDCl$_3$) □ 8.45–8.42 (m, 1H), 7.92–7.87 (m, dd-like, 1H), 7.21–7.12 (AB-system, 4H), 7.03–6.98 (m, d-like, 1H), 3.72–3.45 (br m, 8H), 1.49 (s, 9H); $^{13}$C-NMR (CDCl$_3$) □ (ref. CDCl$_3$ 77.00 ppm):165.71, 154.56, 153.51, 150.21, 148.34, 145.43 (q, J=4.4 Hz), 136.701 (q, J=3 Hz), 123.65 (q, J=271.5 Hz), 122.86, 122.24, 121.62 (q, J=33 Hz), 11.20, 80.32, 44.38, 43.78, 44.6–42.3 (br), 28.36 ppm; IR (KBr) □ 1722 (C=O), 1691(C=O) cm$^{-1}$.

b) Piperazine-1-carboxylic acid 4-(5-trifluoromethyl-pyridin-2-yloxy)-phenyl ester hydrochloride Piperazine-1,4-dicarboxylic acid tert-butyl ester 4-(5-trifluoromethyl-pyridin-2-yloxy)-phenyl ester (0.12 g, 0.26 mmol) was stirred at 100° C. for 10 min in a mixture of ethanol (3 ml) and concentrated hydrochloric acid (1 ml). The solvent was removed in vacuum. The residue was stirred with toluene (10 ml) and evaporated, then stirred with ethanol and evaporated to dryness to give white crystals (0.10 g). Recrystallization from absolute ethanol gave the title compound. White crystals, 0.068 g (65%); m.p. 279–282° C. (decomp.); $^1$H-NMR (DMSO) □ 9.62 (br, 2H, NH$_2$+), 8.61–8.55 (m, 1H), 8.29–8.21 (m, dd-like, 1H), 7.30–7.20 (m, 5H), 3.86 and 3.70 (br s, 4H), 3.19 (br s, 4H); $^{13}$C-NMR (DMSO) □ (ref DMSO 39.50 ppm): 165.51, 152.71, 149.98, 148.04, 145.20 (J=4.4 Hz), 137.62 (J=3.7 Hz), 123.87 (J=271.5 Hz), 123.11, 123.39, 120.39 (J=32.2 Hz), 111.80, 42.15 and a broad signal partly overlapping with the DMSO signal. IR (KBr) □ 1731, 1709 (C=O) cm$^{-1}$.

c) 4-(2-Pyridin-2-yl-acetyl)-piperazine-1-carboxylic acid 4-(5-trifluoromethyl-pyridin-2-yloxy)-phenyl ester Triethylamine (0.026 ml) was added to a stirred solution of (pyridin-2-yl)acetic acid hydrochloride (0.033 g, 0.19 mmol) in DMF (2.5 ml) at 0° C. 1-Hydroxy-benzotriazole containing 8% of water (0.034 g) and then 1-(3-dimethylaminopropyl)-3-ethylcarbodiimide hydrochloride (0.044 g) was added and the mixture was stirred for 50 min. Piperazine-1-carboxylic acid 4-(5-trifluoromethyl-pyridin-2-yloxy)-phenyl ester hydrochloride (0.070 g) in a mixture of DMF (1 ml) and triethylamine (0.032 ml) was added and stirring was continued over night at room temperature. The solvent was removed in vacuum and the residue was partitioned between dichloromethane (10 ml) and water (10 ml). The organic phase was washed with water (10 ml), dried over sodium sulfate, filtered and evaporated. The residue was triturated with etherpetroleumsether 1:1 and the (2+1 ml). The residue was dried to give the title compound. White solid, m.p. 143–146° C.; HPLC-MS m/z: IR (KBr) □ 1732 (C=O), 1643 (C=O).

Example 490 (General Procedure 15)

4-(2-Pyridin-4-yl-ethyl)-piperazine-1-carboxylic acid 4-(5-trifluoromethyl-pyridin-2-yloxy)-phenyl ester The hydrochloride of the title compound was prepared from 4-(5-trifluoromethyl-pyridin-2-yloxy)-phenyl chloroformate and 1-(4-pyridin-2-yl-ethyl)-piperazine. White crystals, m.p. 268–271° C. (decomp); IR (KBr) □ 2680, 2579, 2456 (N$^+$—H), 1731, 1713 (C=O) cm$^{-1}$; HPLC-MS m/z: 473 (M+H) Rt=2.3 min.

Example 491

Methyl-phenyl-carbamic acid 5-amino-pyridin-2-yl ester

A solution of methyl-phenyl-carbamic acid 5-nitro-pyridin-2-yl ester (10.41 g, 38.1 mmol) in tetrahydrofuran (100 mL) was hydrogenated in a Parr apparatus with wet 5% palladium on carbon and 20 psi hydrogen pressure. After 2 hours the solution was filtered over a short pad of Celite, washed thoroughly with ethyl acetate and evaporated in vacuo, yielding title compound (9.51 g, 103% yield) as a thick oil, which solidified upon standing.
$^1$H NMR (300 MHz, CDCl$_3$): δ=3.40 (br.s, 3H), 3.70 (br.s, 2H), 6.80 (br.d, 1H), 6.97 (dd, 1H), 7.22 (m, 1H), 7.36 (m, 4H), 7.72 (d, 1H); HPLC-MS (Method A): m/z=244 (M+H)$^+$; R$_t$=2.28 min.

Example 492

Methyl-phenyl-carbamic acid 5-benzenesulfonylamino-pyridin-2-yl ester

Benzenesulphonyl chloride (0.18 g, 1.00 mmol), dissolved in a small amount of dichloromethane, was added dropwise to a stirred solution of methyl-phenyl-carbamic acid 5-amino-pyridin-2-yl ester (0.24 g, 1.00 mmol) and triethylamine (0.10 g, 1.00 mmol) in dichloromethane (10 mL). After stirring for 4 hours the solution was extracted with water and evaporated in vacuo. The residue was purified by flash column chromatography (SiO$_2$, ethyl acetate:heptane 40:60 followed by 50:50) yielding the title compound (108 mg, 23% yield) as a white solid.
$^1$H NMR (300 MHz, CDCl$_3$): δ=3.46 (br.s, 3H), 6.82 (br.s, 1H), 7.24–7.52 (m, 9H), 7.63 (m, 3H), 7.84 (br.s, 1H); HPLC-MS (Method A): m/z=384 (M+H)$^+$; R$_t$=3.26 min.

Example 493

3,3-Dimethyl-4-[6-(methyl-phenyl-carbamoyloxy)-pyridin-3-ylcarbamoyl]-butyric acid A solution of methyl-phenyl-carbamic acid 5-amino-pyridin-2-yl ester (243 mg, 1.00 mmol) and 3,3-dimethylglutaric anhydride (142 mg, 1.00 mmol) in dichloromethane (10 mL) was stirred at room temperature for 48 hours. Evaporation of the solvent yielded the title compound as a thick oil.
HPLC-MS (Method A): m/z=386 (M+H)$^+$; R$_t$=2.76 min.

Example 494

Piperidine-1-carboxylic acid 4,4-dimethyl-2,6-dioxo-3,4,5,6-tetrahydro-2H-[1,3']bipyridinyl-6'-yl 1-Piperidinecarbonyl chloride (63 microL, 0.50 mmol) was added to a solution of 6'-hydroxy-4,4-dimethyl-4,5-dihydro-3H-[1,3']bipyridinyl-2,6-dione (117 mg, 0.50 mmol) and DABCO (56 mg, 0.50 mmol) in dimethylformamide (10 mL). After stirring for 1 hour at room temperature water was added and the solution was extracted twice with dichloromethane. The combined organic layers were dried over sodium sulphate, filtered and evaporated in vacuo. The residue was crystallised from ethyl acetate:heptane yielding the title compound (0.12 g, 69% yield) as a white solid.
$^1$H NMR (300 MHz, CDCl$_3$): δ=1.21 (s, 6H), 1.64 (s, 6H), 2.69 (s, 4H), 3.53 (m, 2H), 3.63 (m, 2H), 7.22 (d, 1H), 7.49 (dd, 1H), 8.09 (d, 1H); HPLC-MS (Method A): m/z=346 (M+H)$^+$; R$_t$=3.12 min.

Example 495

2,2-Dimethyl-N-[6-(methyl-phenyl-carbamoyloxy)-pyridin-3-yl]-succinamic acid A solution of methyl-phenyl-carbamic acid 5-amino-pyridin-2-yl ester (0.49 g, 2.00 mmol) and 2,2-dimethylsuccinic anhydride (0.26 g, 2.00 mmol) in dichloromethane (10 mL) was stirred at room temperature overnight. Evaporation of the solvent in vacuo yielded the title compound. HPLC-MS (Method A): m/z=372 (M+H)$^+$; R$_t$=2.84 min.

Example 496

Methyl-phenyl-carbamic acid 5-(3,3-dimethyl-2,5-dioxo-pyrrolidin-1-yl)-pyridin-2-yl ester A mixture of thionyl chloride (0.726 mL, 10.00 mmol) and 2,2-dimethyl-N-[6-(methyl-phenyl-carbamoyloxy)-pyridin-3-yl]-succinamic acid (0.74 g, 2.00 mmol) in dichloromethane (25 mL) was stirred at room temperature for 18 hours. The solvent and excess thionyl chloride were evaporated in vacuo. The crude product was redissolved in dichloromethane (25 mL) and pyridine (316 mg, 4.00 mmol) was added. The solution was extracted with water, dried over sodium sulphate, filtered and evaporated in vacuo. The residue was purified by flash column chromatography (SiO$_2$, ethyl acetate:heptane 50:50), yielding the title compound (490 mg, 69% yield) as a white solid.

$^1$H NMR (300 MHz, CDCl$_3$): δ=1.43 (s, 6H), 2.74 (s, 2H), 3.45 (br.s, 3H), 7.14 (br.s, 1H), 7.26 (m, 1H), 7.38 (m, 4H), 7.76 (br.d, 1H), 8.39 (s, 1H); HPLC-MS (Method A): m/z=354 (M+H)$^{30}$ ; R$_t$=3.35 min.

Example 497

Methyl-phenyl-carbamic acid 5-[3,3-dimethyl-5-(4-methyl-piperazin-1-yl)-5-oxo-pentanoylamino]-pyridin-2-yl ester Thionyl chloride (56 microL, 0.78 mmol) was added to a stirred solution of 3,3-dimethyl-4-[6-(methyl-phenyl-carbamoyloxy)-pyridin-3-ylcarbamoyl]-butyric acid (0.15 g, 0.39 mmol) in dichloromethane (5 mL) and 2 drops of dimethylformamide. After stirring for 10 minutes N-methylpiperazine (1 mL) was added and stirring was continued for 2 hours. The solvent was evaporated in vacuo. The residue was redissolved in dichloromethane and extracted with water, dried over sodium sulphate, filtered and evaporated in vacuo. The crude product was purified by filtration over a short column (SiO$_2$, ethyl acetate followed by acetone) yielding the title compound (93 mg, 51% yield) as a thick oil.

$^1$H NMR (300 MHz, CDCl$_3$): δ=1.11 (s, 6H), 2.32 (s, 3H), 2.43 (m, 8H), 3.42 (br.s, 3H), 3.61 (m, 2H), 3.74 (m, 2H), 7.00 (br.s, 1H), 7.38 (d, 4H), 8.21 (dd, 1H), 8.47 (d, 1H), 10.90 (s, 1H);
HPLC-MS (Method A): m/z=468 (M+H)$^+$; R$_t$=2.20 min.

Example 498

Methyl-phenyl-carbamic acid 5-[3,3-dimethyl-4-(pyridin-3-ylcarbamoyl)-butyrylamino]-pyridin-2-yl ester Thionylchloride (237 microL, 3.27 mmol) was added to a stirred solution of 3,3-dimethyl-4-[6-(methyl-phenyl-carbamoyloxy)-pyridin-3-ylcarbamoyl]-butyric acid (0.63 g, 1.63 mmol) in dichloromethane (10 mL). After stirring for 10 minutes the solution was divided into 4 equal portions of acid chloride. To one portion was added 2-aminopyridine (0.5 mL) and after stirring for 2 hours at room temperature the crude product was purified by flash column chromatography (SiO$_2$, ethyl acetate followed by ethyl acetate:acetone 90:10), yielding the title compound (105 mg, 56% yield).

$^1$H NMR (300 MHz, CDCl$_3$): δ=1.09 (s, 6H), 2.36 (s, 2H), 2.38 (s, 2H), 3.44 (br.s, 3H), 6.95 (br.s, 1H), 7.26 (m, 2H), 7.38 (m, 4H), 8.05 (dd, 1H), 8.10 (dt, 1H), 8.30 (m, 2H), 8.67 (d, 1H), HPLC-MS (Method A): m/z=462 (M+H)$^+$; R$_t$=2.52 min.

Example 499

Methyl-phenyl-carbamic acid 5-(3,3-dimethyl-5-morpholin-4-yl-5-oxo-pentanoylamino)-pyridin-2-yl ester Thionylchloride (237 microL, 3.27 mmol) was added to a stirred solution of 3,3-dimethyl-4-[6-(methyl-phenyl-carbamoyloxy)-pyridin-3-ylcarbamoyl]-butyric acid (0.63 g, 1.63 mmol) in dichloromethane (10 mL). After stirring for 10 minutes the solution was divided into 4 equal portions of acid chloride. To one portion was added morpholine (0.5 mL) and after stirring for 2 hours at room temperature the crude product was purified by flash column chromatography (SiO$_2$), yielding the title compound (117 mg, 63% yield).

$^1$H NMR (300 MHz, CDCl$_3$): δ=1.11 (s, 6H), 2.44 (s, 4H), 3.42 (br.s, 3H), 3.59 (m, 2H), 3.70 (m, 6H), 7.00 (br.s, 1H), 7.24 (m, 1H), 7.38 (d, 4H), 8.21 (dd, 1H), 8.45 (d, 1H), 10.76 (s, 1H); HPLC-MS (Method A): m/z=455 (M+H)$^+$; R$_t$=2.87 min.

Example 500

Methyl-phenyl-carbamic acid 5-[4-(2-dimethylamino-ethylcarbamoyl)-3,3-dimethyl-butyrylamino]-pyridin-2-yl ester Thionylchloride (237 microL, 3.27 mmol) was added to a stirred solution of 3,3-dimethyl-4-[6-(methyl-phenyl-carbamoyloxy)-pyridin-3-ylcarbamoyl]-butyric acid (0.63 g, 1.63 mmol) in dichloromethane (10 mL). After stirring for 10 minutes the solution was divided into 4 equal portions of acid chloride. To one portion was added N,N-dimethylethylenediamine (0.5 mL) and after stirring for 2 hours at room temperature the crude product was purified by flash column chromatography (SiO$_2$), yielding the title compound (74 mg, 39% yield).

$^1$H NMR (300 MHz, CDCl$_3$): δ=1.10 (s, 6H), 2.22 (s, 2H), 2.27 (s, 6H), 2.44 (m, 4H), 3.37 (m, 2H), 3.43 (br.s, 3H), 6.60 (br.t, 1H), 7.00 (br.s, 1H), 7.25 (m, 1H), 7.38 (d, 4H), 8.21 (dd, 1H), 8.46 (d, 1H), 10.70 (s, 1H); HPLC-MS (Method A): m/z=456 (M+H)$^+$; R$_t$=1.93 min.

Example 501 (General Procedure 12)

4-[Methyl-(2-pyridin-4-yl-ethyl)-amino]-piperidine-1-carboxylic acid 4-(5-trifluoromethyl-pyridin-2-yloxy)-phenyl ester The title product was prepared from methyl-piperidine-4-yl-(2-pyridin-4-yl-ethyl)-amine and 4-(5-trifluoromethyl-pyridin-2-yloxy)-phenyl chloroformate, 3 equivalent of diisopropylamine was added, preparative HPLC (method C) (15%, colourless oil). HPLC-MS m/z=501.4 (M+1), Rt: 2.04 min.

Example 502 (General Procedure 12)

4-(Cyclopropyl-pyridin-4-ylmethyl-amino)-piperidine-1-carboxylic acid 4-(5-trifluoromethyl-pyridin-2-yloxy)-phenyl ester The title product was prepared from cyclopropyl-piperidine-4-yl-pyridin-4-ylmethyl-amine and 4-(5-trifluoromethyl-pyridin-2-yloxy)-phenyl chloroformate, 3 equivalent of diisopropylamine was added, solvent: dimethylformamide. The crude reaction mixture was evaporated without addition of acetic acid, preparative HPLC (method C) (19%, yellow oil). HPLC-MS m/z=(M+1), Rt: 2.82 min.

Example 503 (General Procedure 12)

4-[Cyclopropyl-(2-fluoro-benzyl)-amino]-piperidine-1-carboxylic acid 4-(5-trifluoromethyl-pyridin-2-yloxy)-phenyl ester The title product was prepared from cyclopropyl-(2-fluoro-benzyl)-piperidin-4-yl-amine and 4-(5-trifluoromethyl-pyridin-2-yloxy)-phenyl chloroformate, 3 equivalent of diisopropylamine was added, solvent: dimethylformamide. The crude reaction mixture was evaporated without addition of acetic acid, preparative HPLC (method C) (60%, colourless oil). HPLC-MS m/z=(M+1), Rt: 3.02 min.

Example 504 (General Procedure 12)

4-(Cyclopropyl-pyridin-3-ylmethyl-amino)-piperidine-1-carboxylic acid 4-(5-trifluoromethyl-pyridin-2-yloxy)-phenyl ester The title product was prepared from cyclopropyl-piperidin-4-yl-pyridin-3-ylmethyl-amine and 4-(5-trifluoromethyl-pyridin-2-yloxy)-phenyl chloroformate, 3 equivalent of diisopropylamine was added, solvent: dimethylformamide. The crude reaction mixture was evaporated without addition of acetic acid, preparative HPLC (method C) (26%, light brown solid). HPLC-MS m/z=(M+1) 513.3, Rt: 2.64 min.

Example 505 (General Procedure 12)

4-(Cyclopropylmethyl-pyridin-3-ylmethyl-amino)-piperidine-1-carboxylic acid 4-(5-trifluoromethyl-pyridin-2-yloxy)-phenyl ester The title product was prepared from cyclopropylmethyl-piperidin-4-yl-pyridin-3-ylmethyl-amine and 4-(5-trifluoromethyl-pyridin-2-yloxy)-phenyl chloroformate, 3 equivalent of diisopropylamine was added, solvent: dimethylformamide. The crude reaction mixture was evaporated without addition of acetic acid, preparative HPLC (method C) (47%, off-white solid. HPLC-MS m/z=(M+1) 513.3, Rt: 2.70 min.

Example 506 (General Procedure 12)

4-(Cyclopropylmethyl-pyridin-3-ylmethyl-amino)-piperidine-1-carboxylic acid 4-(5-trifluoromethyl-pyridin-2-yloxy)-phenyl ester The title product was prepared from cyclopropylmethyl-piperidin-4-yl-pyridin-4-ylmethyl-amine and 4-(5-trifluoromethyl-pyridin-2-yloxy)-phenyl chloroformate, 3 equivalent of diisopropylamine was added, solvent: dimethylformamide. The crude reaction mixture was evaporated without addition of acetic acid, preparative HPLC (method C) (22%, off-white solid. HPLC-MS m/z=(M+1) 513.3, Rt: 2.70 min.

Example 507 (General Procedure 12)

4-(4-Hydroxy-piperidin-1-ylmethyl)-piperidine-1-carboxylic acid 4-(5-trifluoromethyl-pyridin-2-yloxy)-phenyl ester The title product was prepared from 1-piperidin-4-ylmethyl-piperidine-4-ol (released form the correspondent hydrochloride by a standard procedure) and 4-(5-trifluoromethyl-pyridin-2-yloxy)-phenyl chloroformate, preparative HPLC (method C) (reaction performed in a mixture of dichloromethane and dimethylformamide). 1.7 M HCl in ethyl acetate was added to the pooled fractions containing the title product, and the fractions was evaporated to dryness (92%, white solid. HPLC-MS m/z=(M+1) 480.4, Rt: 2.38 min.

Example 508 (General Procedure 11)

4-{3-[1-(2-Hydroxy-ethyl)-piperidin-4-yl]-propyl}-piperidine-1-carboxylic acid 4-(5-trifluoromethyl-pyridin-2-yloxy)-phenyl ester The title product was prepared from 2-[4-(3-piperidin-4-yl-propyl)-piperidin-1-yl]-ethanol and 4-(5-trifluoromethyl-pyridin-2-yloxy)-phenyl chloroformate. The reaction mixture was evaporated, diethyl ether (30 ml) was added and the title product isolated by filtration, washed with diethyl ether and ried to give (67%, white solid. HPLC-MS m/z=(M+1) 536.2, Rt: 3.39 min.

Example 509 (General Procedure 12)

4-(2-Pyrrolidin-1-yl-ethyl)-piperidine-1-carboxylic acid 4-(5-trifluoromethyl-pyridin-2-yloxy)-phenyl ester The title product was prepared from 2-[4-(3-piperidin-4-yl-propyl)-piperidin-1-yl]-ethanol and 4-(5-trifluoromethyl-pyridin-2-yloxy)-phenyl chloroformate, preparative HPLC (method C). 1.7 M HCl in ethyl acetate was added to the pooled fractions containing the title product, and the fractions was evaporated to dryness (65%, white solid). HPLC-MS m/z=(M+1) 464.1, Rt: 2.99 min.

Example 510 (General Procedure 16)

Methyl-o-tolyl-carbamic acid 4-iodo-pyrazol-1-yl ester

The title compound was prepared from 1-hydroxy-4-iodopyrazole and methyl-o-tolylamine. The crude product was purified by flash chromatography (Quad flash 12, EtOAc-heptane) (40%, oil).

HPLC-MS: m/z=380.1 (M+23); $R_f$=4.05 min.

Example 511 (General Procedure 16)

Methyl-m-tolyl-carbamic acid 4-iodo-pyrazol-1-yl ester

The title compound was prepared from 1-hydroxy-4-iodopyrazole and methyl-m-tolylamine. The crude product was purified by flash chromatography (Quad flash 12, EtOAc-heptane) (44%, oil).

HPLC-MS: m/z=380.1 (M+23); $R_t$=4.13 min.

Example 512 (General Procedure 16)

Methyl-p-tolyl-carbamic acid 4-iodo-pyrazol-1-yl ester

The title compound was prepared from 1-hydroxy-4-iodopyrazole and methyl-p-tolylamine. The crude product was purified by flash chromatography (Quad flash 12, EtOAc-heptane) (55%, oil).

HPLC-MS: m/z=380.1 (M+23); $R_t$=4.13 min.

Example 513 (General Procedure 16)

(3-Chloro-phenyl)-methyl-carbamic acid 4-iodo-pyrazol-1-yl ester

The title compound was prepared from 1-hydroxy-4-iodopyrazole and 3-chlorophenyl-methylamine. The crude product was purified by flash chromatography (Quad flash 12, EtOAc-heptane) (54%, oil).

HPLC-MS: m/z=399.9 (M+23); $R_t$=4.28 min.

Example 514 (General Procedure 16)

(3-Fluoro-phenyl)-methyl-carbamic acid 4-iodo-pyrazol-1-yl ester

The title compound was prepared from 1-hydroxy-4-iodopyrazole and 3-fluorophenyl-methylamine. The crude product was purified by flash chromatography (Quad flash 12, EtOAc-heptane) (51%, oil).

HPLC-MS: m/z=384.0 (M+23); $R_t$=4.00 min.

Example 515 (General Procedure 16)

4-(3-Trifluoromethyl-pyridin-2-yl)-piperazine-1-carboxylic acid 4-iodo-pyrazol-1-yl ester The title compound was prepared from 1-hydroxy-4-iodopyrazole and 1-(3-trifluoromethylpyridin-2-yl)piperazine. The crude product was purified by flash chromatography (Quad flash 12, EtOAc-heptane) (13%, oil).

HPLC-MS: m/z=468.1 (M+1); $R_t$=4.38 min.

Example 516 (General Procedure 16)

2,6-Dimethyl-morpholine-4-carboxylic acid 4-iodo-pyrazol-1-yl ester

The title compound was prepared from 1-hydroxy-4-iodopyrazole and 2,6-dimethylmorpholin. The crude product was purified by flash chromatography (Quad flash 12, EtOAc-heptane) (11%, oil).

HPLC-MS: m/z=374.0 (M+23); $R_t$=3.24 min.

Example 517 (General Procedure 16)

Thiomorpholine-4-carboxylic acid 4-iodo-pyrazol-1-yl ester

The title compound was prepared from 1-hydroxy-4-iodopyrazole and thiomorpholin. The crude product was purified by flash chromatography (Quad flash 12, EtOAc-heptane) (27%, oil).

HPLC-MS: m/z=340.0 (M+1); $R_t$=3.22 min.

Example 518 (General Procedure 16)

3,5-Dimethyl-morpholine-4-carboxylic acid 4-iodo-pyrazol-1-yl ester

The title compound was prepared from 1-hydroxy-4-iodopyrazole and 3,5-dimethylmorpholin. The crude product was purified by flash chromatography (Quad flash 12, EtOAc-heptane) (15%, oil).

HPLC-MS: m/z=352.0 (M+1); $R_t$=3.17 min.

Example 519 (General Procedure 16)

Piperidine-1-carboxylic acid 4-iodo-pyrazol-1-yl ester

The title compound was prepared from 1-hydroxy-4-iodopyrazole and piperidine. The crude product was purified by flash chromatography (Quad flash 12, EtOAc-heptane) (46%, oil).

HPLC-MS: m/z=322.0 (M+1); $R_t$=3.38 min.

Example 520 (General Procedure 16)

Methyl-o-tolyl-carbamic acid 2-chloro-imidazol-1-yl ester

The title compound was prepared from 1-hydroxy-2-chloroimidazole, hydrochloride and methyl-o-tolylamine. The crude product was purified by preparative HPLC (Gilson) (4%, red oil).

HPLC-MS: m/z=266.0 (M); $R_t$=3.28 min.

Example 521 (General Procedure 16)

(3-Fluoro-phenyl)-methyl-carbamic acid 2-chloro-imidazol-1-yl ester

The title compound was prepared from 1-hydroxy-2-chloroimidazole, hydrochloride and 3-fluorophenyl-methylamine. The crude product was purified by preparative HPLC (Gilson) (2%, oil).

HPLC-MS: m/z=270.1 (M); $R_t$=3.08 min.

Example 522

Methyl-phenyl-carbamic acid 4-iodo-phenyl ester

To a solution of 4-iodophenol (30 mmol) in $CH_2Cl_2$ (100 mL) was added N-methyl-N-phenylcarbamoyl chloride (27 mmol) and diisopropylethylamine (60 mmol) at room temperature. The reaction mixture was stirred for 16 hours at rt, added $CH_2Cl_2$ (20 mL) and washed with aqueous citric acid (5%), aqueous $Na_2CO_3$ and brine. The organic phase was dried ($MgSO_4$) and evaporated to give the crude product which was purified by FC (Quad flash 40 EtOAc-Heptane) to give 6.55 g (69%) of the title compound as light brown crystals.
$^1$H NMR (300 MHz; CDCl$_3$): δ 3.38 (br s, 3H), 6.88 (d, 2H), 7.22–7.46 (m, 5H), 7.62 (d, 2H); HPLC-MS: m/z=354.0 (M+1); R$_t$=4.54 min.

Example 523 (General Procedure 20)

Methyl-phenyl-carbamic acid 4'-trifluoromethyl-biphenyl-4-yl ester

The title compound was prepared from methyl-phenyl-carbamic acid 4-iodo-phenyl ester and 4-trifluoromethylphenylboronic acid. The crude product was purified by flash chromatography (Quad flash 12, EtOAc-heptane 1:9) (42%, light brown crystals).
HPLC-MS: m/z=372.1 (M+1); R$_t$=5.19 min.

Example 524 (General Procedure 20)

Methyl-phenyl-carbamic acid 4'-trifluoromethoxy-biphenyl-4-yl ester

The title compound was prepared from methyl-phenyl-carbamic acid 4-iodo-phenyl ester and 4-trifluoromethoxyphenylboronic acid. The crude product was purified by flash chromatography (Quad flash 12, EtOAc-heptane 1:9) (17%, brown oil).
HPLC-MS: m/z=388.1 (M+1); R$_t$=5.27 min.

Example 525 (General Procedure 20)

Methyl-phenyl-carbamic acid 4-pyridin-3-yl-phenyl ester

The title compound was prepared from methyl-phenyl-carbamic acid 4-iodo-phenyl ester and pyridine-3-boronic acid. The crude product was purified by preparative HPLC (Gilson) (5%, brown oil).
$^1$H NMR (300 MHz; CDCl$_3$): δ 3.46 (br s, 3H), 7.29–7.46 (m, 7H), 7.61 (d, 2H), 7.88 (dd, 1H), 8.41 (d, 1H), 8.78 (d, 1H); HPLC-MS: m/z=305.1 (M+1); R$_t$=2.99 min.

Example 526 (General Procedure 20)

Methyl-phenyl-carbamic acid 4-(5-chloro-thiophen-2-yl)-phenyl ester

The title compound was prepared from methyl-phenyl-carbamic acid 4-iodo-phenyl ester and 5-chloro-2-thiopheneboronic acid. The crude product was purified by flash chromatography (Quad flash 12, EtOAc-heptane 1:9) (53%, pink crystals).
$^1$H NMR (300 MHz; CDCl$_3$): δ 3.43 (br s, 3H), 6.87/d, 1H), 7.00 (d, 1H), 7.13 (br d, 2H), 7.26–7.48 (m, 7H); HPLC-MS: m/z=344.0 (M+1); R$_t$=5.16 min.

Example 527 (General Procedure 20)

Methyl-phenyl-carbamic acid 4'-benzylsulfamoyl-biphenyl-4-yl ester

The title compound was prepared from methyl-phenyl-carbamic acid 4-iodo-phenyl ester and 4-benzylsulfamoyl-benzeneboronic acid. The crude product was purified by preparative HPLC (Gilson) (35%, pink crystals).
HPLC-MS: m/z=473.0 (M+1); R$_t$=4.80 min.

Example 528

Methyl-phenyl-carbamic acid 4-styryl-phenyl ester

Styrene (1.2 mmol), N-methyldicyclohexylamine (1.2 mmol), Pd$_2$(dba)$_3$ (0.03 mmol), Pd(P(t-Bu)$_3$)$_2$ (0.06 mmol) and methyl-phenyl-carbamic acid 4-iodo-phenyl ester (1.0 mmol) were added to a Schlenk tube under nitrogen. The Schlenk tube was evacuated and refilled with nitrogen five times. Then dioxane (2 mL) was added and the reaction mixture was stirred at 70° C. for 8 h. The crude product was purified by flash chromatography (Quad flash 12, EtOAc-heptane) giving the title compound in 17% yield as colorless crystals.
HPLC-MS: m/z=330.1 (M+1); R$_t$=5.08 min.

Example 529

Methyl-phenyl-carbamic acid 4-phenylethynyl-phenyl ester

Phenylacetylene (1.2 mmol), diisopropylamine (1.2 mmol), CuI (0.03 mmol), Pd$_2$(dba)$_3$ (0.03 mmol), Pd(P(t-Bu)$_3$)$_2$ (0.06 mmol) and methyl-phenyl-carbamic acid 4-iodo-phenyl ester (1.0 mmol) were added to a Schlenk tube under nitrogen. The Schlenk tube was evacuated and refilled with nitrogen five times. Then dioxane (2 mL) was added and the reaction mixture was stirred at 70° C. for 8 h. The crude product was purified by flash chromatography (Quad flash 12, EtOAc-heptane) giving the title compound in 41% yield as brown oil.
HPLC-MS: m/z=328.1 (M+1); R$_t$=5.07 min.

Example 530

3-[4-(Methyl-phenyl-carbamoyloxy)-phenyl]-acrylic acid methyl ester

Methylacrylate (1.2 mmol), N-methyldicyclohexylamine (1.2 mmol), Pd$_2$(dba)$_3$ (0.03 mmol), Pd(P(t-Bu)$_3$)$_2$ (0.06 mmol) and methyl-phenyl-carbamic acid 4-iodo-phenyl ester (1.0 mmol) were added to a Schlenk tube under nitrogen. The Schlenk tube was evacuated and refilled with nitrogen five times. Then dioxane (2 mL) was added and the reaction mixture was stirred at 70° C. for 8 h. The crude product was purified by flash chromatography (Quad flash 12, EtOAc-heptane) giving the title compound in 70% yield as a yellow solid.
HPLC-MS: m/z=312.1 (M+1); R$_t$=4.19 min.

Example 531 (General Procedure 8)

Methyl-phenyl-carbamic acid 5-phenylsulfanyl-pyrazol-1-yl ester

The title compound was prepared from 1-hydroxy-5-phenylsulfanylpyrazole and N-methyl-N-phenylcarbamoyl chloride. The crude product was purified by flash chromatography (Quad flash 12, EtOAc-heptane) (80%, oil).
$^1$H NMR (300 MHz; CDCl$_3$): δ 3.36 (br s, 3H), 6.47 (d, 1H) 7.16–7.32 (m, (m, 10H), 7.40 (d, 1H); HPLC-MS: m/z=326.0 (M+1); R$_t$=4.42 min.

Example 532 (General Procedure 21)

Methyl-phenyl-carbamic acid 4-(toluene-4-sulfonylamino)-phenyl ester

The title compound was prepared in 8% yield as a clear oil using toluenesulfonyl chloride as the aryl sulfonyl chloride.

HPLC-MS: m/z=397.1 (M+1); $R_t$=4.13 min

Example 533 (General Procedure 21)

Methyl-phenyl-carbamic acid 4-(5-pyridin-2-yl-thiophene-2-sulfonylamino)-phenyl ester The title compound was prepared in 7% yield as an oil using 5-pyridin-2-yl-thiophene-2-sulfonyl chloride as the aryl sulfonyl chloride.

HPLC-MS: m/z=466.1 (M+1); $R_t$=4.23 min.

Example 534 (General Procedure 21)

Methyl-phenyl-carbamic acid 4-(1-methyl-1H-imidazole-4-sulfonylamino)-phenyl ester The title compound was prepared in 21% yield as crystals using 1-methyl-1H-imidazole-4-sulfonyl chloride as the aryl sulfonyl chloride.

HPLC-MS: m/z=387.1 (M+1); $R_t$=3.14 min.

Example 535 (General Procedure 21)

Methyl-phenyl-carbamic acid 4-(2,5-dichloro-thiophene-3-sulfonylamino)-phenyl ester The title compound was prepared in 2% yield as an oil using 2,5-dichloro-thiophene-3-sulfonyl chloride as the aryl sulfonyl chloride.

HPLC-MS: m/z=458.6 (M+1); $R_t$=4.38 min.

Example 536 (General Procedure 21)

Methyl-phenyl-carbamic acid 4-(5-chloro-1,3-dimethyl-1H-pyrazole-4-sulfonylamino)-phenyl ester The title compound was prepared in 3% yield as an oil using 5-chloro-1,3-dimethyl-1H-pyrazole-4-sulfonyl chloride as the aryl sulfonyl chloride.

HPLC-MS: m/z=435.1 (M+1); $R_t$=3.74 min.

Example 537 (General Procedure 21)

Methyl-phenyl-carbamic acid 4-(5-dimethylamino-naphthalene-1-sulfonylamino)-phenyl ester The title compound was prepared in 14% yield as orange crystals using 5-dimethylamino-naphthalene-1-sulfonyl chloride as the aryl sulfonyl chloride.

HPLC-MS: m/z=476.0 (M+1); $R_t$=4.48 min.

Example 538 (General Procedure 21)

2-[4-(Methyl-phenyl-carbamoyloxy)-phenylsulfamoyl]-benzoic acid methyl ester

The title compound was prepared in 48% yield as a yellow oil using 2-chlorosulfonyl-benzoic acid methyl ester as the aryl sulfonyl chloride.

HPLC-MS: m/z=441.1 (M+1); $R_t$=4.19 min.

Example 539 (General Procedure 21)

Methyl-phenyl-carbamic acid 4-(3,4-difluoro-benzenesulfonylamino)-phenyl ester

The title compound was prepared in 1% yield as a clear oil using 3,4-difluoro-benzenesulfonyl chloride as the aryl sulfonyl chloride.

HPLC-MS: m/z=419.1 (M+1); $R_t$=4.23 min.

Example 540 (General Procedure 22 and 1)

Methyl-phenyl-carbamic acid 4-pyridin-2-ylmethyl-phenyl ester

4-Pyridin-2-ylmethyl-phenol was prepared following general procedure PVe3 using pyridine-2-carboxaldehyde. Subsequent carbamoylation using general procedure 1 ($CH_2Cl_2$ was used as solvent) produced the crude product which was purified by flash chromatography (Quad flash 12, EtOAc-heptane) (86%, oil).

$^1$H NMR (400 MHz; $CDCl_3$): δ 3.40 (br s, 3H), 4.14 (s, 2H), 7.04–7.12 (m, 4H), 7.21–7.26 (m, 3H), 7.32–7.40 (m, 4H), 7.55 (t, 1H), 8.52 (d, 1H).

Example 541 (General Procedure 22 and 1)

Methyl-phenyl-carbamic acid 4-pyridin-3-ylmethyl-phenyl ester

4-Pyridin-3-ylmethyl-phenol was prepared following general procedure PVe3 using pyridine-3-carboxaldehyde. Subsequent carbamoylation using general procedure 1 ($CH_2Cl_2$ was used as solvent) produced the crude product which was purified by flash chromatography (Quad flash 12, EtOAc-heptane) (50%, oil).

$^1$H NMR (400 MHz; $CDCl_3$): δ 3.42 (brs, 3H), 3.96 (s, 2H), 7.03–7.42 (m, 11H), 8.46 (d, 1H), 8.49 (d, 1H).

Example 542 (General Procedure 22 and 1)

Methyl-phenyl-carbamic acid 4-(4-trifluoromethyl-benzyl)-phenyl ester 4-(4-Trifluoromethyl-benzyl)-phenol was prepared following general procedure PVe3 using 4-trifluoromethylbenzaldehyde. Subsequent carbamoylation using general procedure 1 ($CH_2Cl_2$ was used as solvent) produced the crude product which was purified by flash chromatography (Quad flash 12, EtOAc-heptane) (92%, oil).

$^1$H NMR (400 MHz; $CDCl_3$): δ 3.42 (br s, 3H), 4.00 (s, 2H), 7.06 (br s, 2H), 7.13 (d, 2H), 7.24–7.40 (m, 7H), 7.52 (d, 2H).

Example 543 (General Procedure 22 and 1)

Methyl-phenyl-carbamic acid 4-thiophen-3-ylmethyl-phenyl ester

4-Thiophen-3-ylmethyl-phenol was prepared following general procedure PVe3 using thiophene-3-carboxaldehyde. Subsequent carbamoylation using general procedure 1 ($CH_2Cl_2$ was used as solvent) produced the crude product which was purified by flash chromatography (Quad flash 12, EtOAc-heptane) (83%, oil).

$^1$H NMR (400 MHz; $CDCl_3$): δ 3.42 (bs, 3H), 3.95 (s, 2H), 6.86–7.39 (m, 12H).

Example 544 (General Procedure 22 and 1)

Methyl-phenyl-carbamic acid 4-thiophen-2-ylmethyl-phenyl ester

4-Thiophen-2-ylmethyl-phenol phenol was prepared following general procedure PVe3 using thiophene-3-carboxaldehyde. Subsequent carbamoylation using general procedure 1 ($CH_2Cl_2$ was used as solvent) produced the crude product which was purified by flash chromatography (Quad flash 12, EtOAc-heptane) (83%, oil).

$^1$H NMR (400 MHz; $CDCl_3$): δ 3.40 (brs, 3H), 4.13 (s, 2H), 6.78 (dd, 1H), 6.90 (dd, 1H), 7.04 (br d, 2H), 7.13 (dd, 1H), 7.20–7.39 (m, 7H). HPLC-MS: m/z=324.1 (M+1); $R_t$32 4.82 min.

Example 545

4-Hydroxy-piperidine-1-carboxylic acid 4-[2-(toluene-4-sulfonylamino)-ethyl]-phenyl ester N-Boc protected tyramin (10 mmol), triethylamine (10 mmol) and 3-[4-(tert-Butyl-dimethyl-silanyloxy)-piperidine-1-carbonyl]-1-methyl-3H-imidazol-1-ium; iodide (10 mmol) in MeCN (25 mL) was stirred at room temperature for 16 hours. Acetonitrile was removed by evaporation and the crude product was purified by flash chromatography (Quad flash 40, EtOAc-heptane 1:2) providing 72% 4-tert-butylsilanyloxy-piperidine-1-carboxylic acid 4-(2-tert-butoxycarbonylamino-ethyl)-phenyl ester. This was deprotected by stirring with a 3.2 M solution of HCl in $Et_2O$ (50 mL) for 3 h at rt and subsequently washed with ether to give 91% of 4-(4-hydroxy-piperidine-1-carbonyloxy)-phenyl-ammonium; chloride as a solid. This compound was N-tosylated as described for methyl-phenyl-carbamic acid 4-[2-(toluene-4-sulfonylamino)-ethyl]-phenyl ester to give the title compound in 26% yield as yellow crystals after purification by flash chromatography (Quad flash 12, $CH_2Cl_2$-MeOH 95:5).

HPLC-MS: m/z=391.0 (M+1); $R_t$=3.04 min.

Example 546

4-Hydroxy-piperidine-1-carboxylic acid 4-[2-(5-pyridin-2-yl-thiophene-2-sulfonylamino)-ethyl]-phenyl 4-(4-Hydroxy-piperidine-1-carbonyloxy)-phenyl-ammonium; chloride (see above) was N-sulfonylated as described for methyl-phenyl-carbamic acid 4-[2-(5-pyridin-2-yl-thiophene-2-sulfonylamino)-ethyl]-phenyl ester to give the title compound in 59% yield as an oil after purification by preparative HPLC (Gilson).

HPLC-MS: m/z=488.0 (M+1); $R_t$=3.10 min.

Example 547

4-Hydroxy-piperidine-1-carboxylic acid 4-(5-pyridin-2-yl-thiophene-2-sulfonylamino)-phenyl ester N-Boc protected 4-aminophenol (10 mmol), triethylamine (10 mmol) and 3-[4-(tert-Butyl-dimethyl-silanyloxy)-piperidine-1-carbonyl]-1-methyl-3H-imidazol-1-ium; iodide (10 mmol) in MeCN (25 mL) was stirred at room temperature for 16 hours. Acetonitrile was removed by evaporation and the crude product was purified by flash chromatography (Quad flash 40, EtOAc-heptane 1:2) providing 64% 4-tert-butylsilanyloxy-piperidine-1-carboxylic acid 4-tert-butoxycarbonylamino-phenyl ester. This was deprotected by stirring with a 3.2 M solution of HCl in $Et_2O$ (50 mL) for 3 h at rt and subsequently washed with ether to give 91% of 4-(4-Hydroxy-piperidine-1-carbonyloxy)-phenyl-ammonium; chloride as a hygroscopic solid. This compound was N-sulfonylated as described for methyl-phenyl-carbamic acid 4-[2-(5-pyridin-2-yl-thiophene-2-sulfonylamino)-ethyl]-phenyl ester to give the title compound in 1% yield as crystals after purification by preparative HPLC (Gilson).

HPLC-MS: m/z=482.8 (M+1); $R_t$=1.01 min.

Example 548

Methyl-phenyl-carbamic acid 4-[2-(4-amino-benzenesulfonylamino)-ethyl]-phenyl ester Methyl-phenyl-carbamic acid 4-[2-(4-nitro-benzenesulfonylamino)-ethyl]-phenyl ester, 5% palladium on carbon, and ethanol were stirred under hydrogen at 1 bar and rt for 16 h. Filtration and removal of ethanol produced the title compound in 94% yield as an oil.

HPLC-MS: m/z=426.1 (M+1); $R_t$=3.61 min.

Example 549

Methyl-phenyl-carbamic acid 4-{2-[(pyridine-3-carbonyl)-amino]-ethyl}-phenyl ester A solution of 3-pyridinecarboxylic acid (0.3 mmol), EDAC (0.36 mmol) and triethylamine (0.36 mmol) in $CH_2Cl_2$ (10 mL) was added N-hydroxybenzoetriazole and N-methyl-N-phenyl-carbamic acid 4-(2-amino-ethyl)phenyl ester as its TFA salt (0.3 mmol). The mixture was stirred 16 h at rt and purified by preparative HPLC (Gilson) to give the title compound in 15% yield as an oil.

HPLC-MS: m/z=376.1 (M+1); $R_t$=3.01 min.

Example 550

Methyl-phenyl-carbamic acid 4-[2-(2-dimethylamino-acetylamino)-ethyl]-phenyl ester A solution of N,N-dimethylglycine, HCl (0.3 mmol), EDAC (0.36 mmol) and triethylamine (1.0 mmol) in $CH_2Cl_2$ (10 mL) was added N-hydroxybenzoetriazole and N-methyl-N-phenyl-carbamic acid 4-(2-amino-ethyl)phenyl ester as its TFA salt (0.3 mmol). The mixture was stirred 16 h at rt and purified by preparative HPLC (Gilson) to give the title compound in 66% yield as an oil.

HPLC-MS: m/z=356.4 (M+1); $R_t$=2.09 min.

Example 551 (General Procedure 23)

Methyl-phenyl-carbamic acid 2-(toluene-4-sulfonyl)-1,2,3,4-tetrahydro-isoquinolin-7-yl ester The title compound was prepared using methyl-phenyl-carbamic acid 4-[2-(toluene-4-sulfonylamino)-ethyl]-phenyl ester as the sulfonamide. The crude product was purified by flash chromatography (Quad flash 12, EtOAc-heptane 2:3) (71%, yellow oil).

HPLC-MS: m/z=437.4 (M+1); $R_t$=4.43 min.

Example 552

Methyl-phenyl-carbamic acid 4-[4-(2-pyrrolidin-1-yl-ethoxy)-benzyl]-phenyl ester To a stirred solution of 1-[2-(4-bromo-phenoxy)-ethyl]-pyrrolidine (2.89 g, 10.7 mmol) in THF (30 mL) was added dropwise 1.6 M solution in hexanes n-BuLi (7 mL, 10.2 mmol) over a 5-min period at −78° C. The mixture was stirred at −78° C. for 15 min before 4-trimethylsilyloxybenzaldehyde (2.08 g, 10.7 mmol) was added. The mixture was allowed to warm to rt during 20 min and quenched with water. Extraction with $CH_2Cl_2$, drying ($MgSO_4$), filtration and evaporation provided the crude diarylmethanol which was dissolved in $CH_2Cl_2$ (30 mL) and stirred with triethylsilane (4 mL) and TFA (5 mL) for 16 h at rt. Evaporation gave 3.0 g (84%) 4-[4-(2-pyrrolidin-1-yl-ethoxy)-benzyl]-phenol. This was carbamoylated using general procedure 1 ($CH_2Cl_2$ was used as solvent) to give the title product after purification by preparative HPLC (Gilson) (35%, oil).

HPLC-MS: m/z=431.5 (M+1); $R_t$=2.93 min.

Example 553 (General Procedure 24)

4-Hydroxy-piperidine-1-carboxylic acid 4-pyridin-2-ylmethyl-phenyl ester

The title compound was prepared as its hydrochloride using 4-pyridin-2-ylmethyl-phenol as the phenol.

$^1$H NMR (300 MHz; $D_2O$): δ 1.50 (br s, 2H), 1.90 (d, 2H), 3.04–3.27 (m, 2H), 3.78–4.08 (m, 3H), 4.41 (s, 2H), 7.07 (d, 2H), 7.30 (d, 2H), 7.79–7.85 (m, 2H), 8.40 (dt, 1H), 8.55 (d, 1H).

Example 554 (General Procedure 24)

4-Hydroxy-piperidine-1-carboxylic acid 4-pyridin-3-ylmethyl-phenyl ester

The title compound was prepared as its hydrochloride using 4-pyridin-3-ylmethyl-phenol as the phenol.

$^1$H NMR (300 MHz; $D_2O$): δ 1.48 (br s, 2H), 1.90 (d, 2H), 3.03–3.26 (m, 2H), 3.80–4.05 (m, 3H), 4.18 (s, 2H), 7.03 (d, 2H), 7.25 (d, 2H), 7.40 (dd, 1H), 8.40 (d, 1H), 8.54–8.57 (m, 2H).

Example 555 (General Procedure 24)

4-Hydroxy-piperidine-1-carboxylic acid 4-(4-trifluoromethyl-benzyl)-phenyl ester The title compound was prepared using 4-(4-trifluoromethyl-benzyl)-phenol as the phenol.

$^1$H NMR (300 MHz; $D_2O$): δ 1.43–1.55 (m, 2H), 1.76–1.88 (m, 2H), 3.10–3.29 (m, 2H), 3.79–3.94 (m, 5H), 6.97 (d, 2H), 7.08 (d, 2H), 7.20 (d, 1H), 7.45 (d, 2H).

Example 556 (General Procedure 23)

Methyl-phenyl-carbamic acid 2-[4-(2-pyrrolidin-1-yl-ethoxy)-benzenesulfonyl]-1,2,3,4-tetrahydro-isoquinolin-7-yl ester The title compound was prepared using methyl-phenyl-carbamic acid 4-{2-[4-(2-pyrrolidin-1-yl-ethoxy)-benzenesulfonylamino]-ethyl}-phenyl ester as the sulfonamide. The crude product was purified by preparative HPLC (Gilson) and isolated as its TFA salt (45%, foam).

HPLC-MS: m/z=536.2 (M+1); $R_t$=3.10 min.

Example 557

Methyl-phenyl-carbamic acid 4-{2-[(1-methyl-piperidine-4-carbonyl)-amino]-ethyl}-phenyl ester A solution of 1-methylpiperidine-4-carboxylic acid (0.3 mmol), EDAC (0.36 mmol) and triethylamine (1.0 mmol) in $CH_2Cl_2$ (10 mL) was added N-hydroxybenzoetriazole and N-methyl-N-phenyl-carbamic acid 4-(2-amino-ethyl)phenyl ester as its TFA salt (0.3 mmol). The mixture was stirred 16 h at rt and purified by preparative HPLC (Gilson) to give the title compound in 5% yield as an oil.

HPLC-MS: m/z=396.4 (M+1); $R_t$=2.03 min.

Example 558 (General Procedure 23)

Methyl-phenyl-carbamic acid 2-(3,4-difluoro-benzenesulfonyl)-1,2,3,4-tetrahydro-isoquinolin-7-yl ester The title compound was prepared using methyl-phenyl-carbamic acid 4-[2-(3,4-difluoro-benzenesulfonylamino)-ethyl]-phenyl ester as the sulfonamide. The crude product was purified by preparative HPLC (Gilson) (24%, oil).

HPLC-MS: m/z=481.0 (M+23); $R_t$=4.73 min.

Example 559 (General Procedure 23)

Methyl-phenyl-carbamic acid 1-methyl-2-(toluene-4-sulfonyl)-1,2,3,4-tetrahydro-isoquinolin-7-yl ester The title compound was prepared using methyl-phenyl-carbamic acid 4-[2-(toluene-4-sulfonylamino)-ethyl]-phenyl ester as the sulfonamide and acetaldehyde in stead of formaldehyde. The crude product was purified by preparative HPLC (Gilson) (22%, brown oil).

HPLC-MS: m/z=451.5 (M+1); $R_t$=4.43 min.

Example 560 (General Procedure 23)

Methyl-phenyl-carbamic acid 2-[4-(4-methyl-piperazin-1-yl)-benzenesulfonyl]-1,2,3,4-tetrahydro-isoquinolin The title compound was prepared using methyl-phenyl-carbamic acid 4-{2-[4-(4-methyl-piperazin-1-yl)-benzenesulfonylamino]-ethyl}-phenyl ester as the sulfonamide. The crude product was purified by preparative HPLC (Gilson) and isolated as its TFA salt (79%, crystals).

HPLC-MS: m/z=521.5 (M+1); $R_t$=2.65 min.

Example 561 (General Procedure 23)

Methyl-phenyl-carbamic acid 1-methyl-2-[4-(4-methyl-piperazin-1-yl)-benzenesulfonyl]-1,2,3,4-tetrahydro-isoquinolin-7-yl ester The title compound was prepared using methyl-phenyl-carbamic acid 4-{2-[4-(4-methyl-piperazin-1-yl)-benzenesulfonylamino]-ethyl}-phenyl ester as the sulfonamide and acetaldehyde in stead of formaldehyde. The crude product was purified by preparative HPLC (Gilson) (12%, brown oil).

HPLC-MS: m/z=535.4 (M+1); $R_t$=2.69 min.

Example 562

3,3-Dimethyl-4-{2-[4-(methyl-phenyl-carbamoyloxy)-phenyl]-ethylcarbamoyl}-butyric acid A solution of 3,3-dimethylglutaric anhydride (0.3 mmol), diisopropylethylamine (0.30 mmol) and N-methyl-N-phenyl-carbamic acid 4-(2-amino-ethyl)phenyl ester as its TFA salt (0.3 mmol) in $CH_2Cl_2$ (3 mL) was stirred 1 h at rt. The mixture was washed with water and brine, dried and evaporated to give the title compound in 95% yield as an oil.

HPLC-MS: m/z=413.2 (M+1); $R_t$=3.20 min.

Example 563

Methyl-phenyl-carbamic acid 4-{2-[4-(4-methyl-piperazin-1-yl)-benzoylamino]-ethyl}-phenyl ester A solution of 4-(4-methylpiperazino)benzoic acid (0.3 mmol), EDAC (0.36 mmol) and triethylamine (1.0 mmol) in $CH_2Cl_2$ (10 mL) was added N-hydroxybenzoetriazole and N-methyl-N-phenyl-carbamic acid 4-(2-amino-ethyl)phenyl ester as its TFA salt (0.3 mmol). The mixture was stirred 16 h at rt and purified by preparative HPLC (Gilson) to give the title compound in 54% yield as its crystalline hydrochloride after treatment with HCl in diethyl ether.

HPLC-MS: m/z=473.2 (M+1); $R_t$=2.22 min.

Example 564

Methyl-phenyl-carbamic acid 4-{2-[4-(4-methyl-piperazin-1-ylmethyl)-benzoylamino]-ethyl}-phenyl ester A solution of 4-(4-methylpiperazinyl)methyl benzoic acid (0.3 mmol), EDAC (0.36 mmol) and triethylamine (1.0 mmol) in $CH_2Cl_2$ (10 mL) was added N-hydroxybenzoetriazole and N-methyl-N-phenyl-carbamic acid 4-(2-amino-ethyl)phenyl ester as its TFA salt (0.3 mmol). The mixture was stirred 16 h at rt and purified by preparative HPLC (Gilson) to give the title compound in 25% yield as its crystalline hydrochloride after treatment with HCl in diethyl ether.

HPLC-MS: m/z=487.3 (M+1); $R_t$=2.13 min.

Example 565

Methyl-phenyl-carbamic acid 4-[2-(4,4-dimethyl-2,6-dioxo-piperidin-1-yl)-ethyl]-phenyl ester A solution of 3,3-dimethylglutaric anhydride (0.3 mmol), diisopropylethylamine (0.30 mmol) and N-methyl-N-phenyl-carbamic acid 4-(2-amino-ethyl)phenyl ester as its TFA salt (0.3 mmol) in $CH_2Cl_2$ (3 mL) was stirred 1 h at rt. Thionylchloride (3 mmol) was added and the mixture was stirred for 2 h at rt. Addition of ethanol (5 mL) followed by evaporation to dryness gave a crude product which was purified by flash chromatography (Quad flash 12, EtOAc-heptane 1:1). This gave the title compound in 23% yield as crystals. Furthermore 3,3-dimethyl-4-{2-[4-(methyl-phenyl-carbamoyloxy)-phenyl]-ethylcarbamoyl}-butyric acid ethyl ester could be isolated in 27% yield as an oil (see characterization below)

$^1$H NMR (400 MHz; CDCl$_3$): δ 1.04 (s, 6H), 2.47 (s, 4H), 2.79 (t, 2H), 3.42 (br s, 3H), 3.97 (t, 2H), 7.03 (br d, 2H), 7.21–7.28 (m, 3H), 7.33–7.41 (m, 4H).

HPLC-MS: m/z=395.2 (M+1); $R_t$=4.23 min.

Example 566

3,3-Dimethyl-4-{2-[4-(methyl-phenyl-carbamoyloxy)-phenyl]-ethylcarbamoyl}-butyric acid ethyl ester For experimental details, see preparation of methyl-phenyl-carbamic acid 4-[2-(4,4-dimethyl-2,6-dioxo-piperidin-1-yl)-ethyl]-phenyl ester.

$^1$H NMR (400 MHz; CDCl$_3$): δ 1.05 (s, 6H), 1.24 (t, 3H), 2.19 (s, 2H), 2.22 (s, 2H), 2.80 (t, 2H), 3.42 (br s, 3H), 3.50 (q, 2H), 4.1 (q, 2H), 6.53 (t, 1H), 7.03 (br d, 2H), 7.18 (d, 2H), 7.26 (t, 1H), 7.33–7.41 (m, 4H). HPLC-MS: m/z=441.2 (M+1); $R_t$=4.11 min.

Example 567

Methyl-phenyl-carbamic acid 4-hydroxymethyl-phenyl ester

To a solution of 4-hydroxymethylphenol (10 mmol) and 4-diazabicyclo[2.2.2]octane (DABCO) (10 mmol) in $CH_2Cl_2$ (30 mL) was added N-methyl-N-phenylcarbamoyl chloride (10 mmol). The reaction mixture was stirred for 16 hours at rt, added $CH_2Cl_2$ (20 mL) and washed with 1M aqueous HCl and brine. The organic phase was dried (MgSO$_4$) and evaporated to give the crude product which was purified by FC (Quad flash 40 EtOAc-Heptane 1:1) to give 2.18 g (85%) of the title compound as an oil.

$^1$H NMR (400 MHz; CDCl$_3$): δ 1.70 (br s, 1H), 3.40 (br s, 3H), 4.66 (s, 2H), 7.08 (br d, 2H), 7.25–7.42 (m, 7H); HPLC-MS: m/z=258.1 (M+1); $R_t$=2.99 min.

Example 568

Methyl-phenyl-carbamic acid 4-(2-hydroxy-ethyl)-phenyl ester

To a solution of 4-(2-Hydroxyethyl)phenol (10 mmol) and 4-diazabicyclo[2.2.2]octane (DABCO) (10 mmol) in $CH_2Cl_2$ (30 mL) was added N-methyl-N-phenylcarbamoyl chloride (10 mmol). The reaction mixture was stirred for 16 hours at rt, added $CH_2Cl_2$ (20 mL), and washed with 1M aqueous HCl and brine. The organic phase was dried (MgSO$_4$) and evaporated to give the 2.69 g (99%) of the title compound as crystals.

$^1$H NMR (400 MHz; CDCl$_3$): δ 1.52 (brs, 1H), 2.84 (t, 2H), 3.41 (br s, 3H), 3.81 (t, 2H), 7.04 (br d, 2H), 7.20 (d, 2H), 7.22–7.42 (m, 5H); HPLC-MS: m/z=272.1 (M+1); $R_t$=3.17 min.

Example 569 (General Procedure 1)

Methyl-phenyl-carbamic acid 4-(4-dimethylamino-pyridin-2-ylmethyl)-phenyl ester

A solution of 2-(dimethylamino)ethanol (32 mmol) in hexane (120 mL) was cooled to −5° C. and n-BuLi (64 mmol) was added. After 30 min 4-(dimethylamine=pyridine (16 mmol) was added and the red-orange mixture was stirred for further 1 h. The solution was cooled to −78° C. and 4-(trimethylsilyloxy)benzaldehyde (40 mmol) dissolved in hexane (80 mL) was added and the suspension was allowed to warm to rt over 20 min. The reaction mixture was quenched with water, and the aqueous phase was washed with $CH_2Cl_2$. The aqueous phase was evaporated to dryness, added NaI (96 mmol) and dissolved in MeCN (160 mL). Addition of trimethylsilylchloride (96 mmol) and stirring at rt for 16 h. The purple reaction mixture was evaporated to dryness and treated with an aqueous solution of $Na_2SO_3$ and pH was adjusted to 8. Extraction with $CH_2Cl_2$ gave after evaporation 560 mg (15%) slightly impure 4-(4-dimethylamino-pyridin-2-ylmethyl)phenol as yellow crystals. This was carbamoylated using general procedure 1 ($CH_2Cl_2$ was used as solvent) to give the title product as its hydrochloride after purification by preparative HPLC (Gilson) and treatment with HCl in $Et_2O$ (48%, ligt yellow crystals).

HPLC-MS: m/z=362.2 (M+1); $R_t$=2.27 min.

Example 570 (General Procedure 25)

Methyl-phenyl-carbamic acid 4-(4-imidazol-1-yl-phenoxymethyl)-phenyl ester

The title compound was prepared in 53% yield as light yellow crystals using and 4-imidazol-1-yl-phenol. $^1$H NMR (400 MHz; $CDCl_3$): δ 3.42 (br s, 3H), 5.08 (s, 2H), 7.03 (d, 2H), 7.12–7.42 (m, 15H), 7.77 (s, 1H); HPLC-MS: m/z=400.1 (M+1); $R_t$=2.62 min.

Example 571 (General Procedure 25)

Methyl-phenyl-carbamic acid 4-[4-(2-dimethylamino-ethyl)-phenoxymethyl]-phenyl ester The title compound was prepared in 52% yield as colorless crystals using methyl-phenyl-carbamic acid 4-hydroxymethyl-phenyl ester and 4-(2-dimethylaminoethyl)-phenol. $^1$H NMR (400 MHz; $CDCl_3$): δ 2.85 (s, 6H), 2.98–3.02 (m, 2H), 3.17–3.21 (m, 2H), 3.42 (br s, 3H), 5.02 (s, 2H), 6.90 (d, 2H), 7.12 (d, 2H), 7.25–7.43 (m, 7H); HPLC-MS: m/z=405.2 (M+1); $R_t$=2.91 min.

Example 572 (General Procedure 25)

Methyl-phenyl-carbamic acid 4-(pyrazol-1-yloxymethyl)-phenyl ester

The title compound was prepared in 79% yield as an oil using and 1-hydroxypyrazole. $^1$H NMR (400 MHz; $CDCl_3$): δ 3.42 (br s, 3H), 5.26 (s, 2H), 6.03 (t, 1H), 6.95 (dd, 1H), 7.11 (br s, 2H), 7.25–7.42 (m, 8H); HPLC-MS: m/z=324.1 (M+1); $R_t$=3.58 min.

Example 573 (General Procedure 25)

Methyl-phenyl-carbamic acid 4-(imidazol-1-yloxymethyl)-phenyl ester

The title compound was prepared as its TFA salt in 87% yield as a solid using methyl-phenyl-carbamic acid 4-hydroxymethyl-phenyl ester and 1-hydroxyimidazole, hydrochloride. $^1$H NMR (400 MHz; $CDCl_3$): δ 3.42 (br s, 3H), 5.21 (s, 2H), 6.95 (s, 1H), 7.16–7.45 (m, 10H) 8.28 (br s, 1H); HPLC-MS: m/z=324.1 (M+1); $R_t$=1.92 min.

Example 574 (General Procedure 25)

Methyl-phenyl-carbamic acid 4-(2-oxo-2H-pyridin-1-ylmethyl)-phenyl ester

The title compound was prepared in 29% yield as an oil using methyl-phenyl-carbamic acid 4-(2-hydroxy-ethyl)-phenyl ester and 2-hydroxypyridine. In addition 50% of the isomeric methyl-phenyl-carbamic acid 4-[2-(pyridin-2-yloxy)-ethyl]-phenyl ester was isolated, see characterization below. $^1$H NMR (400 MHz; $CDCl_3$): δ 3.05 (t, 2H), 3.41 (br s, 3H), 4.14 (s, 2H), 6.08 (t, 1H), 6.66 (d, 1H), 6.90 (dd, 1H), 7.02 (br s, 2H), 7.10 (d, 2H), 7.25–7.42 (m, 6H); HPLC-MS: m/z=349.2 (M+1); $R_t$=3.04 min.

Example 575 (General Procedure 25)

Methyl-phenyl-carbamic acid 4-[2-(pyridin-2-yloxy)-ethyl]-phenyl ester

The title compound was prepared in 50% yield as an oil using methyl-phenyl-carbamic acid 4-(2-hydroxy-ethyl)-phenyl ester and 2-hydroxypyridine. In addition 29% of the isomeric methyl-phenyl-carbamic acid 4-(2-oxo-2H-pyridin-1-ylmethyl)-phenyl ester was isolated, see characterization above. $^1$H NMR (400 MHz; $CDCl_3$): δ 3.08 (t, 2H), 3.41 (br s, 3H), 4.49 (s, 2H), 6.73 (d, 1H), 6.88 (dd, 1H), 7.05 (br d, 2H), 7.22–7.42 (m, 7H), 7.61 (dt, 1H), 8.18 (dd, 1H); HPLC-MS: m/z=349.2 (M+1); $R_t$=3.97 min.

Example 576 (General Procedure 25)

Methyl-phenyl-carbamic acid 4-[2-(4-imidazol-1-yl-phenoxy)-ethyl]-phenyl ester

The title compound was prepared as its TFA salt in 62% yield as an oil using methyl-phenyl-carbamic acid 4-(2-hydroxy-ethyl)-phenyl ester and 4-imidazol-1-yl-phenol.

$^1$H NMR (400 MHz; $CDCl_3$): δ 3.11 (t, 2H), 3.42 (br s, 3H), 4.22 (s, 2H), 7.00–7.10 (m, 5H), 7.25–7.42 (m, 9H), 7.52 (s, 1H), 8.81 (s, 1H); HPLC-MS: m/z=414.2 (M+1); $R_t$=2.73 min.

Example 577 (General Procedure 25)

Methyl-phenyl-carbamic acid 4-{2-[4-(2-dimethylamino-ethyl)-phenoxy]-ethyl}-phenyl ester The title compound was prepared as its TFA salt in 92% yield as an oil using methyl-phenyl-carbamic acid 4-(2-hydroxy-ethyl)-phenyl ester and 4-(2-dimethylaminoethyl)-phenol.

HPLC-MS: m/z=419.2 (M+1); $R_t$=2.77 min.

Example 578 (General Procedure 25)

Methyl-phenyl-carbamic acid 4-[2-(pyrazol-1-yloxy)-ethyl]-phenyl ester

The title compound was prepared in 62% yield as an oil using methyl-phenyl-carbamic acid 4-(2-hydroxy-ethyl)-phenyl ester and 1-hydroxypyrazole.
$^1$H NMR (400 MHz; CDCl$_3$): δ 3.02 (t, 2H), 3.42 (br s, 3H), 4.50 (t, 2H), 6.16 (t, 1H), 7.05 (br d, 2H), 7.20–7.41 (m, 9H); HPLC-MS: m/z=338.2 (M+1); R$_t$=3.74 min.

Example 579 (General Procedure 25)

Methyl-phenyl-carbamic acid 4-[2-(imidazol-1-yloxy)-ethyl]-phenyl ester

The title compound was prepared as its TFA salt in 79% yield as an oil using methyl-phenyl-carbamic acid 4-(2-hydroxy-ethyl)-phenyl ester and 1-hydroxyimidazole hydrochlorid.
$^1$H NMR (400 MHz; CDCl$_3$): δ 3.06 (t, 2H), 3.42 (br s, 3H), 4.52 (t, 2H), 7.08–7.42 (m, 11H), 8.53 (s, 1H); HPLC-MS: m/z=338.2 (M+1); R$_t$=2.18 min.

Example 580 (General Procedure 1)

Methyl-phenyl-carbamic acid 4-(5-methyl-pyridin-2-ylmethyl)-phenyl ester

To a stirred solution of 2-bromo-5-methylpyridine (3.45 g, 20 mmol) in THF (10 mL) was added dropwise 1.6 M solution in hexanes n-BuLi (12 mL, 19.2 mmol) over a 10-min period at −78° C. The mixture was stirred at −78° C. for 2 min before 4-trimethylsilyloxybenzaldehyde (4.2 g, 21.6 mmol) dissolved in THF (10 mL) was added. The mixture was allowed to warm to −40° C. and quenched with water. The pH of the aqueous phase was adjusted to 7 which causes precipitation of 4-[hydroxy-(5-methyl-pyridin-2-yl)-methyl]phenol. This was isolated by filtration to give 1.13 g (27%) of 4-[hydroxy-(5-methyl-pyridin-2-yl)-methyl]phenol as crystals. This intermediate was dissolved in CH$_2$Cl$_2$ (15 mL) and stirred with triethylsilane (4 mL) and TFA (5 mL) for 16 h at 50° C. Evaporation gave 99% of 4-(5-methyl-pyridin-2-ylmethyl)phenol as a hygroscopic solid. This was carbamoylated using general procedure 1 (CH$_2$Cl$_2$ was used as solvent and N-phenyl-N-methyl carbamoyl chloride) to give 99% of the title product as its crystalline hydrochloride after purification by flash chromatography (Quad flash 12, EtOAc-heptane) and treatment with HCl in Et$_2$O.
$^1$H NMR (400 MHz; CDCl$_3$): δ 2.50 (s, 3H), 3.41 (br s, 3H), 4.57 (s, 2H), 7.10 (br s, 2H), 7.25–7.42 (m, 8H), 8.00 (dd, 1H), 8.46 (br s, 1H); HPLC-MS: m/z=333.1 (M+1); R$_t$=2.60 min.

Example 581 (General Procedure 24)

4-Hydroxy-piperidine-1-carboxylic acid 4-(5-methyl-pyridin-2-ylmethyl)-phenyl ester The title compound was prepared as its hydrochloride using of 4-(5-methyl-pyridin-2-ylmethyl)phenol as the phenol.
$^1$H NMR (300 MHz; CDCl$_3$): δ 1.57–1.67 (m, 3H), 1.95 (d, 2H), 2.51 (s, 3H), 3.21–3.40 (m, 2H), 3.90–4.05 (m, 3H), 4.58 (s, 2H), 7.11 (d, 2H), 7.38 (d, 2H), 7.45 (d, 1H), 8.02 (d, 1H), 8.48 (br s, 1H).

Example 582 (General Procedure 25)

Methyl-phenyl-carbamic acid 4-(4-oxo-4H-pyridin-1-ylmethyl)-phenyl ester

The title compound was prepared in 33% yield as colorless crystals using methyl-phenyl-carbamic acid 4-hydroxymethyl-phenyl ester and 4-hydroxypyridine. $^1$H NMR (400 MHz; CDCl$_3$): δ 3.43 (br s, 3H), 4.92 (s, 2H), 6.43 (d, 2H), 7.17 (br s, 4H), 7.22–7.42 (m, 9H), HPLC-MS: m/z=335.0 (M+1); R$_t$=2.55 min.

Example 583 (General Procedure 25)

Methyl-phenyl-carbamic acid 4-[2-(pyridin-3-yloxy)-ethyl]-phenyl ester

The title compound slightly contaminated with tributylphosphine oxide was prepared in 80% yield as an oil using methyl-phenyl-carbamic acid 4-(2-hydroxy-ethyl)-phenyl ester and 3-hydroxypyridine.
$^1$H NMR (400 MHz; CDCl$_3$): δ 3.11 (t, 2H), 3.42 (br s, 3H), 4.23 (t, 2H), 7.07 (br d, 2H), 7.24–7.41 (m, 9H), 8.29 (br s, 1H), 8.40 (br s, 1H); HPLC-MS: m/z=349.2 (M+1); R$_t$=2.87 min.

Example 584 (General Procedure 25)

Methyl-phenyl-carbamic acid 4-(2-oxo-2H-pyridin-1-ylmethyl)-phenyl ester

The title compound was prepared in 66% yield as an oil using methyl-phenyl-carbamic acid 4-hydroxymethyl-phenyl ester and 2-hydroxypyridine. $^1$H NMR (400 MHz; CDCl$_3$): δ 3.42 (br s, 3H), 5.12 (s, 2H), 6.13 (t, 1H), 6.60 (d, 1H), 7.10 (br s, 2H), 7.22–7.41 (m, 9H); HPLC-MS: m/z=335.2 (M+1); R$_t$=2.97 min.

Example 585 (General Procedure 25)

Methyl-phenyl-carbamic acid 4-(pyridin-3-yloxymethyl)-phenyl ester

The title compound was prepared in 43% yield as an oil using methyl-phenyl-carbamic acid 4-hydroxymethyl-phenyl ester and 3-hydroxypyridine. $^1$H NMR (400 MHz; CDCl$_3$): δ 3.44 (br s, 3H), 5.12 (s, 2H), 7.17 (br s, 2H), 7.27–7.46 (m, 9H), 8.29 (br s, 1H), 8.49 (br s, 1H); HPLC-MS: m/z=335.0 (M+1); R$_t$=2.74 min.

Example 586 (General Procedure 26)

Methyl-phenyl-carbamic acid 4-[2-(2,5-dioxo-pyrrolidin-1-yl)-ethyl]-phenyl ester The title compound was prepared in 85% yield as crystals using methyl-phenyl-carbamic acid 4-(2-hydroxy-ethyl)-phenyl ester and succinimide. $^1$H NMR (400 MHz; CDCl$_3$): δ 2.65 (s, 4H), 2.86 (t, 2H), 3.41 (br s, 3H), 3.72 (t, 2H), 7.04 (br d, 2H), 7.19 (d, 2H), 7.26–7.42 (m, 5H); HPLC-MS: m/z=353.2 (M+1); R$_t$=3.17 min.

Example 587 (General Procedure 26)

Methyl-phenyl-carbamic acid 4-[2-(1,3-dioxo-1,3-dihydro-pyrrolo[3,4-]pyridin-2-yl)-ethyl]-phenyl ester The title compound was prepared in 58% yield as crystals using methyl-phenyl-carbamic acid 4-(2-hydroxy-ethyl)-phenyl ester and 3,4-pyridinedicarboximide. $^1$H NMR (400 MHz; CDCl$_3$): δ 2.98 (t, 2H), 3.40 (br s, 3H), 3.93 (t, 2H), 7.05 (br d, 2H), 7.20–7.42 (m, 7H), 7.73 (dd, 1H), 9.06 (d, 1H), 9.12 (d, 1H); HPLC-MS: m/z=402.1 (M+1); R$_t$=3.56 min.

Example 588 (General Procedure 26)

Methyl-phenyl-carbamic acid 4-(1-methyl-1H-imidazol-2-ylsulfanylmethyl)-phenyl ester The title compound was prepared as its TFA salt in 22% yield as an oil using methyl-phenyl-carbamic acid 4-hydroxymethyl-phenyl ester and 2-mercapto-1-methylimidazole. $^1$H NMR (400 MHz; CDCl$_3$): δ 3.34 (s, 3H), 3.40 (br s, 3H), 4.30 (s, 2H), 6.98 (br s, 2H), 7.08–7.11 (m, 3H), 7.27–7.42 (m, 5H), 7.48 (d, 1H); HPLC-MS: m/z=354.1 (M+1); R$_t$=2.12 min.

Example 589 (General Procedure 26)

Methyl-phenyl-carbamic acid 4-tetrazol-1-ylmethyl-phenyl ester

The title compound was prepared in 6% yield as an oil using methyl-phenyl-carbamic acid 4-hydroxymethyl-phenyl ester and tetrazole. $^1$H NMR (400 MHz; CDCl$_3$): δ 3.42 (br s, 3H), 5.57 (s, 2H), 7.17 (br s, 2H), 7.26–7.42 (m, 7H), 8.52 (s, 1H); HPLC-MS: m/z=332.0 (M+23); R$_t$=3.24 min.

Example 590 (General Procedure 26)

Methyl-phenyl-carbamic acid 4-(2,5-dioxo-pyrrolidin-1-ylmethyl)-phenyl ester

The title compound was prepared in 57% yield as beige crystals using methyl-phenyl-carbamic acid 4-hydroxymethyl-phenyl ester and succinimide. $^1$H NMR (400 MHz; CDCl$_3$): δ 2.68 (s, 4H), 3.41 (br s, 3H), 4.60 (s, 2H), 7.04 (br d, 2H), 7.23–7.41 (m, 7H); HPLC-MS: m/z=339.1 (M+1); R$_t$=3.40 min.

Example 590 (General Procedure 26)

Methyl-phenyl-carbamic acid 4-[2-(2-thioxo-2H-pyridin-1-yl)-ethyl]-phenyl ester

The title compound was prepared in 25% yield as an oil using methyl-phenyl-carbamic acid 4-(2-hydroxy-ethyl)-phenyl ester and 2-mercaptopyridine. HPLC-MS: m/z=365.2 (M+1); R$_t$=4.08 min.

Example 591 (General Procedure 26)

Methyl-phenyl-carbamic acid 4-(1,3-dioxo-1,3-dihydro-pyrrolo[3,4)pyridin-2-ylmethyl)-phenyl ester The title compound was prepared in 21% yield as an oil using methyl-phenyl-carbamic acid 4-hydroxymethyl-phenyl ester and 3,4-pyridinedicarboximide. $^1$H NMR (400 MHz; CDCl$_3$): δ 3.40 (br s, 3H), 4.82 (s, 2H), 7.06 (d, 2H), 7.22–7.44 (m, 8H), 7.73 (d, 1H), 9.04 (d, 1H), 9.12 (s, 1H); HPLC-MS: m/z=388.0 (M+1); R$_t$=3.80 min.

Example 592 (General Procedure 26)

Methyl-phenyl-carbamic acid 4-[1,2,4]triazol-1-ylmethyl-phenyl ester

The title compound was prepared as its TFA salt in 27% yield as an oil using methyl-phenyl-carbamic acid 4-hydroxymethyl-phenyl ester and 1,2,4-triazole. $^1$H NMR (400 MHz; CDCl$_3$): δ 3.42 (br s, 3H), 5.34 (s, 2H), 7.15 (br d, 2H), 7.26–7.43 (m, 7H), 8.10 (s, 1H), 8.38 (s, 1H); HPLC-MS: m/z=309.1 (M+1); R$_t$=2.74 min.

Example 593 (General Procedure 26)

Methyl-phenyl-carbamic acid 4-(2-thioxo-2H-pyridin-1-ylmethyl)-phenyl ester

The title compound was prepared in 14% yield as an oil using methyl-phenyl-carbamic acid 4-hydroxymethyl-phenyl ester and 2-mercaptopyridine. HPLC-MS: m/z=351.1 (M+1); R$_t$=3.95 min.

Example 594 (General Procedure 26)

Methyl-phenyl-carbamic acid 4-[2-(1-methyl-1H-imidazol-2-ylsulfanyl)-ethyl]-phenyl ester The title compound was prepared as its TFA salt in 37% yield as an oil using methyl-phenyl-carbamic acid 4-(2-hydroxy-ethyl)-phenyl ester and 2-mercapto-1-methylimidazole. NMR (400 MHz; CDCl$_3$): δ 3.01 (t, 2H), 3.40 (br s, 3H), 3.47 (s, 1H), 3.64 (t, 2H), 6.92 (br d, 2H), 6.98 (s, 1H), 7.08 (d, 2H), 7.26–7.43 (m, 6H); HPLC-MS: m/z=368.2 (M+1); R$_t$=2.30 min.

Example 595 (General Procedure 26)

Methyl-phenyl-carbamic acid 4-(2-tetrazol-1-yl-ethyl)-phenyl ester

The title compound was prepared in 10% yield as an oil using methyl-phenyl-carbamic acid 4-(2-hydroxy-ethyl)-phenyl ester and tetrazole. NMR (400 MHz; CDCl$_3$): δ 3.19 (t, 2H), 3.40 (br s, 3H), 3.47 (s, 1H), 4.61 (t, 2H), 6.98–7.07 (m, 4H), 7.25–7.42 (m, 5H), 8.26 (s, 1H); HPLC-MS: m/z=324.1 (M+1); R$_t$=3.36 min.

Example 596 (General Procedure 26)

Methyl-phenyl-carbamic acid 4-[2-(pyrimidin-2-yloxy)-ethyl]-phenyl ester

The title compound was prepared in 24% yield as light yellow crystals using methyl-phenyl-carbamic acid 4-(2-hydroxy-ethyl)-phenyl ester and 2-hydroxypyrimidine. NMR (400 MHz; CDCl$_3$): δ 3.11 (t, 2H), 3.42 (br s, 3H), 4.54 (t, 2H), 6.93 (t, 1H), 7.05 (d, 2H), 7.25–7.42 (m, 7H), 8.51 (d, 2H); HPLC-MS: m/z=350.2 (M+1); R$_t$=2.86 min.

Example 597 (General Procedure 26)

Methyl-phenyl-carbamic acid 4-[2-(pyridin-4-ylsulfanyl)-ethyl]-phenyl ester

The title compound was prepared as its TFA salt in 5% yield as an oil using methyl-phenyl-carbamic acid 4-(2-hydroxy-ethyl)-phenyl ester and 4-mercaptopyridine. NMR (400 MHz; CDCl$_3$): δ 3.07 (t, 2H), 3.36 (t, 2H), 3.44 (br s, 3H), 7.06 (br d, 2H), 7.20 (d, 2H), 7.25–7.43 (m, 7H), 8.51 (d, 2H); HPLC-MS: m/z=365.2 (M+1); R$_t$=2.53 min.

Example 598 (General Procedure 12)

4-(3-Amino-phenyl)-piperidine-1-carboxylic acid 4-(5-trifluoromethyl-pyridin2-yloxy)-phenyl ester, The title product was prepared from 4-(3-aminophenyl) piperidine (released form the correspondent hydrochloride by a standard procedure) and 4-(5-trifluoromethyl-pyridin-2-yloxy)-phenyl chloroformate, preparative HPLC (method C) (reaction performed in a mixture of dichloromethane and dimethylformamide, 5:3). 1.7 M HCl in ethyl acetate was added to the pooled fractions containing the title product, and the fractions was evaporated to dryness (7%, light yellow solid). HPLC-MS m/z=(M+1) 458.0, Rt: 3.09 min.

Example 599 (General Procedure 26)

Methyl-phenyl-carbamic acid 4-[2-(1-pyridin-3-yl-1H-imidazol-2-ylsulfanyl)-ethyl]-phenyl ester The title compound was prepared as its TFA salt in 5% yield as an oil using methyl-phenyl-carbamic acid 4-(2-hydroxy-ethyl)-phenyl ester and 3-(2thio-1H-imidazol-1-yl) pyridine. NMR (400 MHz; CDCl$_3$): δ 2.95 (t, 2H), 3.42 (br s, 2H), 3.56 (t, 3H), 6.98 (br d, 2H), 7.05 (d, 2H), 7.15 (d, 1H), 7.23–7.43 (m, 5H), 7.48 (d, 1H), 7.53 (dd, 1H), 7.70 (ddd, 1H), 8.65 (d, 1H), 8.77 (dd, 1H); HPLC-MS: m/z=431.2 (M+1); R$_t$ 2.79 min.

Example 600 (General Procedure 26)

Methyl-phenyl-carbamic acid 4-[2-(1,3-dioxo-1,3-dihydro-isoindol-2-yl)-ethyl]-phenyl ester The title compound was prepared in 39% yield as an oil using methyl-phenyl-carbamic acid 4-(2-hydroxy-ethyl)-phenyl ester and isoindole-1,3-dione. NMR (400 MHz; CDCl$_3$): δ 2.98 (t, 2H), 3.41 (br s, 2H), 3.89 (t, 3H), 7.04 (br d, 2H), 7.20–7.40 (m, 7H), 7.68–7.71 (m, 2H), 7.80–7.83 (m, 2H); HPLC-MS: m/z=401.1 (M+1); R$_t$=4.41 min.

Example 601

4-Phenyl-piperidine-1-carboxylic acid 4-(5-methyl-pyridin-2-ylmethyl)-phenyl ester To a solution of 4-(5-methyl-pyridin-2-ylmethyl)phenol (0.8 mmol) prepared as described above and ethyldiisopropylamine (1.5 mmol) in CH$_2$Cl$_2$ (5 mL) at −30° C. was added trichloromethyl chloroformiate (1.0 mmol). The solution was stirred at −30° C. for 10 min and at reflux temperature for 2 h. The solution was evaporated to dryness and redissolved in CH$_2$Cl$_2$ (5 mL) and cooled to 0° C. before addition of 4-phenylpiperidine (1.5 mmol). The solution was stirred at room temperature for 16 h evaporated to give the crude product which was purified by FC (Quad flash 40 CH$_2$Cl$_2$:Et$_2$O:Heptane:Et$_3$N 1:1:2:0.25->1:1:1:0.25) to give the title compound in 28% yield as an oil.

$^1$H NMR (400 MHz; CDCl$_3$): δ 1.70–1.80 (m, 2H), 1.91 (br d, 2H), 2.29 (s, 3H), 2.72 (tt, 1H), 2.94 (br t, 1H), 3.08 (br t, 1H), 4.10 (s, 2H), 4.42 (br s, 1H), 7.00 (d, 1H), 7.06 (d, 2H), 7.21–7.26 (m, 5H), 7.32 (d, 2H), 7.38 (dd, 1H), 8.37 (d, 1H); HPLC-MS: m/z=387.2 (M+1); R$_t$=2.95 min.

Example 602

4-(4-Methoxy-phenyl)-3,6-dihydro-2H-pyridine-1--carboxylic acid 4-(5-methyl-pyridin-2-ylmethyl)-phenyl ester To a solution of 4-(5-methyl-pyridin-2-ylmethyl)phenol (0.8 mmol) prepared as described above and ethyldiisopropylamine (1.5 mmol) in CH$_2$Cl$_2$ (5 mL) at −30° C. was added trichloromethyl chloroformiate (1.0 mmol). The solution was stirred at −30° C. for 10 min and at reflux temperature for 2 h. The solution was evaporated to dryness and redissolved in CH$_2$Cl$_2$ (5 mL) and cooled to 0° C. before addition of 4-(4-methoxyphenyl)-1,2,3,6-tetrahydro-pyridine (1.5 mmol). The solution was stirred at room temperature for 16 h evaporated to give the crude product which was purified by FC (Quad flash 40 CH$_2$Cl$_2$:Et$_2$O:Heptane:Et$_3$N 1:1:2:0.25->1:1:1:0.25) to give the title compound in 10% yield as colorless crystals.

$^1$H NMR (400 MHz; CDCl$_3$): δ 2.30 (s, 3H), 2.60 (br s, 2H), 3.75–3.88 (m, 5H), 4.12 (s, 2H), 4.20 (br s, 1H), 4.30 (br s, 1H), 5.98 (br s, 1H), 6.88 (d, 2H), 7.00 (d, 1H), 7.07 (d, 2H), 7.24 (d, 2H), 7.34 (d, 2H), 7.39 (dd, 1H), 8.38 (d, 1H); HPLC-MS: m/z=415.3 (M+1); R$_t$=2.95 min.

Pharmacological Methods

Compounds of formula I may be evaluated in vitro for their efficacy and potency to inhibit HSL, and such evaluation may be performed as described below.

Assays

Hormone-Sensitive Lipase (HSL)

Materials. The Hormone-sensitive lipase was provided by Dr. Cecilia Holm, from Lund University Sweden or produced and purified by Novo Nordisk (NN) using the reagents and protocols used by Dr. Holm. The substrates used are: $^3$H-labeled triolein (TO) from Amersham, Buckinghamshire, U.K. cat No. TRA191; 5–20 Ci/mmol dissolved in toluene, triolein (Sigma, Cat. No. T-1740), fluorochrome-labeled triacylglyceride (cis-octadec-9-enoic acid 2-[12-(7-nitrobenzo[1,2,5]oxadiazol-4-ylamino)dodecanoyloxy]-1-cis-octadec-9-enoyloxymethyl-ethyl ester) prepared by Novo Nordisk (NN) by conventional methods, and 1,3-(di[$^3$H]-stearin), 2-(PEG-Boitin)glycerol prepared in collaboration with Amersham Pharmacia Biotech, UK and described in WO 01/073442. Phosphatidyl choline (PC) and phosphatidyl inositol (PI) are from Sigma (St Luis Mo. cat. Nos. P-3556 and P-5954 respectively). All other reagents are of commercial grade and obtained from various commercial sources.

Methods.

3180.1: Assay for determination of inhibitor IC$_{50}$ values.

A lipid emulsion with $^3$H-Triolein and phospholipid is used as substrate with a standard concentration of highly purified HSL. BSA is added as product receptor. The substrate is prepared as follows:

30 µl PC:PI (20 mg/ml solution of PC:PI 3:1 prepared in chloroform)+128 µl cold TO+15 µl $^3$H-TO are mixed and then evaporated under a gentle stream of $N_2$ followed by 20–30 minutes in a Speedvac to ensure the absence of residual solvent.

Compound and HSL are incubated for 30 min at 25° C. before addition of substrate. Reaction is stopped after 30 min at 25° C. by adding a mixture of methanol, chloroform and heptane at high pH. Formed product is separated from substrate by phase separation.

Standard concentrations of compound are 100 µM, 20 µM, 4 µM, 0.8 µM, 0.166 µM and 0.032 µM (sample concentrations).

Results are given as $IC_{50}$ values after 4PL fit of obtained activity data.

3180.2: Assay for determination of percent inhibition by compound at 10 µM concentration.

A lipid emulsion with $^3$H-Triolein and phospholipid is used as substrate with a standard cencentration of highly purified HSL. BSA is added as product receptor. The substrate is prepared as follows:

30 µl PC:PI (20 mg/ml solution of PC:PI 3:1 prepared in chloroform)+128 µl cold TO+15 µl $^3$H-TO are mixed and then evaporated under a gentle stream of $N_2$ followed by 20–30 minutes in a Speedvac to ensure the absence of residual solvent.

Compound and HSL are incubated for 30 min at 25° C. before addition of substrate. Reaction is stopped after 30 min at 25° C. by adding a mixture of methanol, chloroform and heptane at high pH. Formed product is separated from substrate by phase separation.

Results are given as percent activity relative to an un-inhibited sample (no compound).

3190.1: Assay for determination of percent inhibition of hormone sensitive lipase by compound at 10 µM sample concentration.

A lipid emulsion with fluorochrome-labeled triacylglyceride and phospholipid is used as substrate with a standard concentration of highly purified HSL (12 µg/mL initial concentration corresponding to 600 ng/mL final concentration). BSA is added as product receptor. The transfer of the fluorochrome from the lipid phase to the water (BSA) phase changes the fluorescent properties of the fluorochrome. The changes can be monitored on a fluorimeter with an excitation wavelength of 450 nm and an emission wavelength of 545 nm.

Compound and HSL (20 µL compound, 10 µL enzyme and 70 µL PED-BSA buffer) is pre-incubated for 30 min at 25° C. before addition of substrate (100 µL). Amount of formed product is measured after 120 min incubation at 37° C.

Results are given as percent activity relative to a non-inhibited sample (no compound).

3190.2: Assay for determination of $IC_{50}$ value for the inhibition of hormone sensitive lipase by compound. Standard concentrations of compound are 100 µM and 5-fold dilutions (initial concentration corresponding to 10 µM final concentration and 5-fold).

A lipid emulsion with fluorochrome-labeled triacylglyceride and phospholipid is used as substrate with a standard concentration of highly purified HSL (12 µg/mL initial concentration corresponding to 600 ng/mL final concentration). BSA is added as product receptor. The transfer of the fluorochrome from the lipid phase to the water (BSA) phase changes the fluorescent properties of the fluorochrome. The changes can be monitored on a fluorimeter with an excitation wavelength of 450 nm and an emission wavelength of 545 nm.

Compound and HSL (20 µL compound, 10 µL enzyme and 70 µL PED-BSA buffer) is pre-incubated for 30 min at 25° C. before addition of substrate (100 µL). Amount of formed product is measured after 120 min incubation at 37° C.

Results are given as $IC_{50}$ values after 4PL fit of obtained activity data.

2848.2: This high-volume screening assay uses para-nitrophenyl butyrate (p-NPB) as substrate for HSL. HSL cleaves p-NPB and the reaction is monitored as an increase in the concentration of para-nitrophenol (p-NP). p-NP can be monitored as an increase in UV-absorbance at 405 nm. The reaction is carried out at room-temp. for 20 min. The action is not stopped, but instead UV-abs is measured at a fixed time (20 min.) Due to autohydrolysis of the substrate the reaction is read at t=0 min. too and t=20 min. and the increase in Abs is calculated as the difference between the two readings. When a compound that inhibits HSL is present, it results in a relative decrease in UV-absorbance.

% $Eff$(% Inhibition)=$(S-S0Eff)/(SmaxEff-S0Eff) \times 100$

Where S=signal in UV-abs., S0Eff=assaybuffer alone, SmaxEff=Assaybuffer with the lipase inhibitor.

2898.2: This method is an enzyme assay based upon SPA (scintillation proximity assay) particles. The substrate, 1,3-(di-[$^3$H]-stearin), 2-(PEG-Biotin)-glycerol, is marked with $^3$H in both fatty acid moieties in the tri-glyceride. The third moiety of the tri-glyceride is a PEG linked Biotin. The substrate binds through Biotin to streptavidin in the SPA particles and the proximity between the radioactive tritium in the stearic acid moiety and the SPA particle results in emission of light from the SPA particles. The assay is an on-bead assay where HSL degrades the substrate, where after $^3$H-stearin acid is released from the bead. The amount of light emitted is proportional to the amount of substrate bound to the receptor. When a compound that inhibits the activity of HSL is present it results in a decrease in degradation of the substrate and thus an increase in the amount of light emitted and a concomitant increase in % Eff.

% $Eff$(% Inhibition)=$(S-S0Eff)/(SmaxEff-S0Eff) \times 100$

Where S=signal in dpm., SOEff=no inhibitor added, SmaxEff=with maximum concentration of inhibitor.

Results

With these methods the following results were obtained for the compounds of the examples.

| Compound according to example # | Test 3190.1 HSL_FL % ACTIVITY All | Test 3180.2 HSL % ACTIVITY All | Test 2898.2 HSL2 % Inhibition All | Test 2848.2 HSL % Inhibition All |
|---|---|---|---|---|
| 120 | | 40 | | |
| 122 | | 14 | | |
| 123 | | 22 | | |
| 121 | | 24 | | |
| 118 | | 24 | | |
| 119 | | 10 | | |
| 47 | 42 | | | |
| 46 | 43 | | | |
| 11 | 17 | | | |
| 87 | 48 | | | |
| 81 | 36 | | | |

-continued

| Compound according to example # | Test 3190.1 HSL_FL % ACTIVITY All | Test 3180.2 HSL % ACTIVITY All | Test 2898.2 HSL2 % Inhibition All | Test 2848.2 HSL % Inhibition All |
|---|---|---|---|---|
| 48 | 15 | | | |
| 61 | 23 | | | |
| 6 | 49 | | | |
| 85 | 88 | | | |
| 90 | 24 | | | |
| 54 | 52 | | | |
| 62 | 88 | | | |
| 59 | 16 | | | |
| 24 | 30 | | | |
| 20 | 51 | | | |
| 92 | | 62 | | |
| 73 | 39 | | | |
| 109 | | | | 15.9 |
| 106 | | | | 23.8 |
| 108 | | | | 37.2 |
| 114 | | | | 42.4 |
| 126 | | | | 33 |
| 110 | | | | 18.8 |
| 111 | | | | 36.2 |
| 107 | | | | 59.9 |
| 105 | | | | 26.8 |
| 104 | | | | 19.8 |
| 127 | | | | 58.7 |
| 128 | | | | 33.8 |
| 103 | | 2 | 101.4 | |
| 115 | | 85 | 73.6 | |
| 113 | | | 18.3 | |
| 129 | | | | 27 |
| 112 | | | 86 | |
| 116 | | | | 23.5 |
| 124 | | | 75.1 | |
| 117 | | 2 | | |
| 130 | | | | 30.1 |
| 131 | | | | 21.6 |
| 132 | | | | 19.6 |
| 133 | | | | 15.8 |
| 144 | 25 | | | |

The invention claimed is:

1. A method of inhibiting the lipolytic activity of hormone-sensitive lipase against triacylglycerols, diacylglycerols, cholesterol acyl esters or steroid acyl esters, comprising: administering to a subject in need of such treatment a compound of formula I

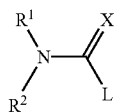

wherein $R^1$ is selected from hydrogen, $C_{1-6}$-alkyl, $C_{2-6}$-alkenyl and $C_{3-10}$-cycloalkyl, each of which is optionally substituted with one or more substituents independently selected from hydroxy, sulfanyl, oxo, halogen, amino, cyano and nitro; and $R^2$ is selected from $C_{1-6}$-alkyl, $C_{2-6}$-alkenyl, aryl, heteroaryl, $C_{3-8}$-heterocyclyl and $C_{3-10}$-cycloalkyl, each of which is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, perhalomethyl and perhalomethoxy; and wherein $R^2$ is optionally covalently bound to $R^1$ by an ether, thioether C—C or C—N bond, to form a ring system with the N-atom to which $R^1$ and $R^2$ are bound; and X is O; and L is a group such that —C(=X)-L is a hydrolysable group; or a pharmaceutically acceptable salt thereof, or a pharmaceutically acceptable solvate thereof, or any tautomeric forms, stereoisomers, mixture of stereoisomers, racemic mixture, or polymorphs thereof.

2. The method according to claim 1, wherein the group L of formula I comprises an O, via which L is bound to the C in formula I.

3. The method according to claim 1, wherein the group L of formula I comprises a N, via which L is bound to the C in formula I.

4. The method according claim 1, wherein the group L of formula I is selected from the group consisting of

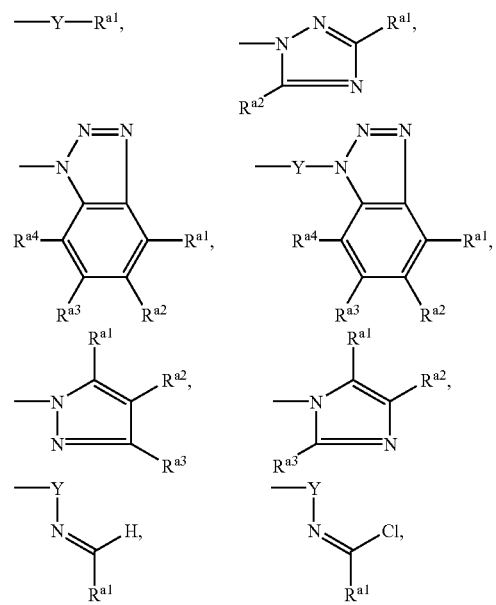

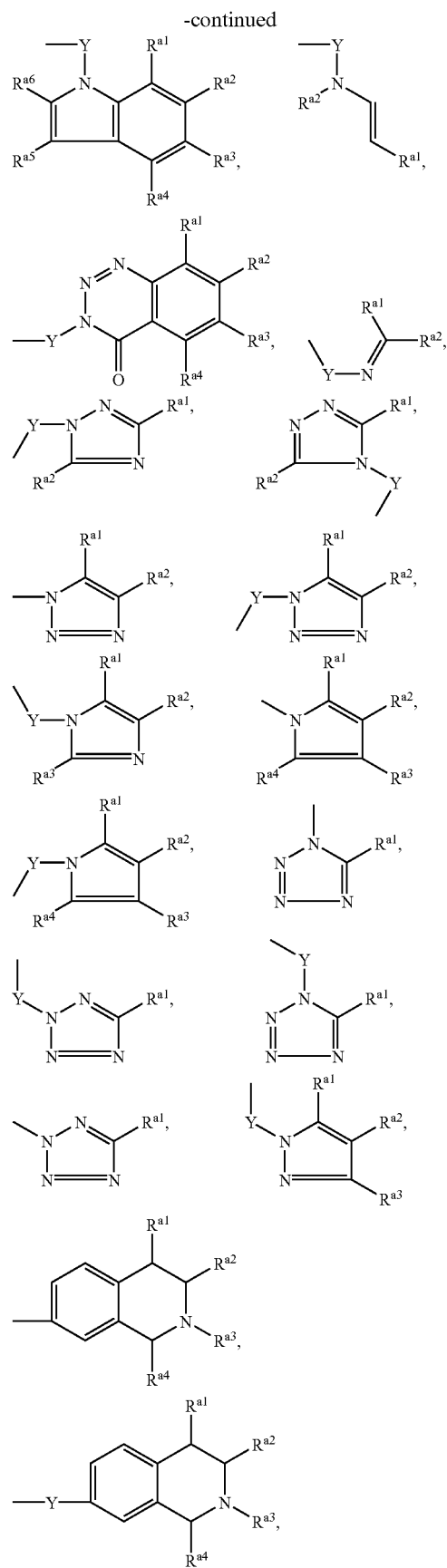
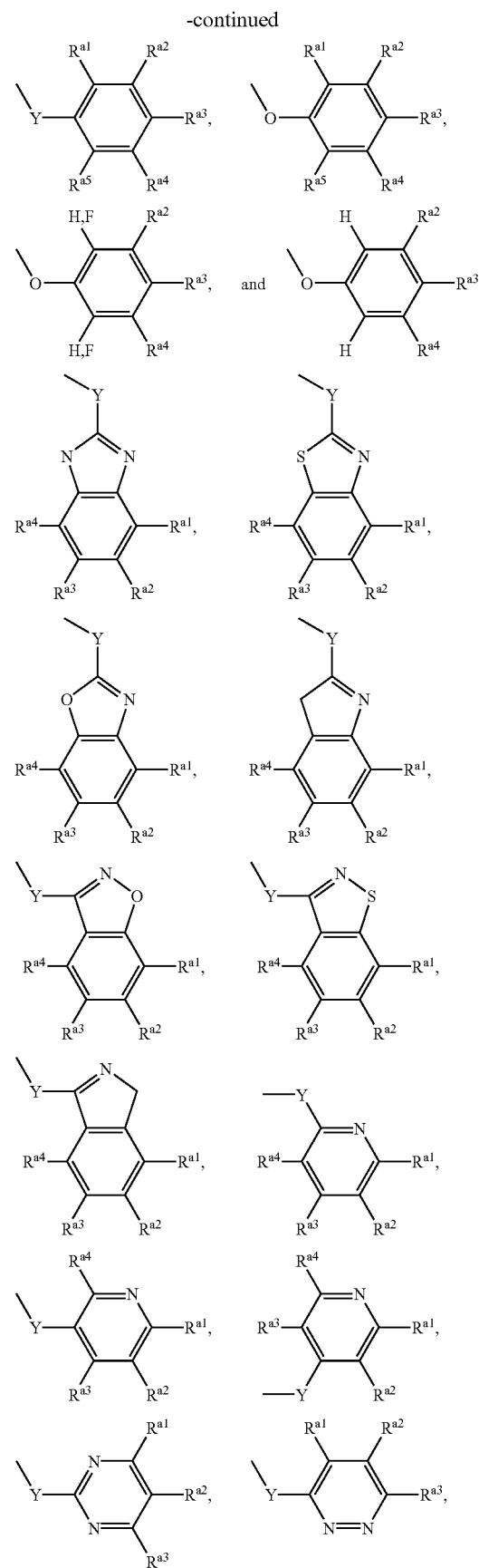

-continued

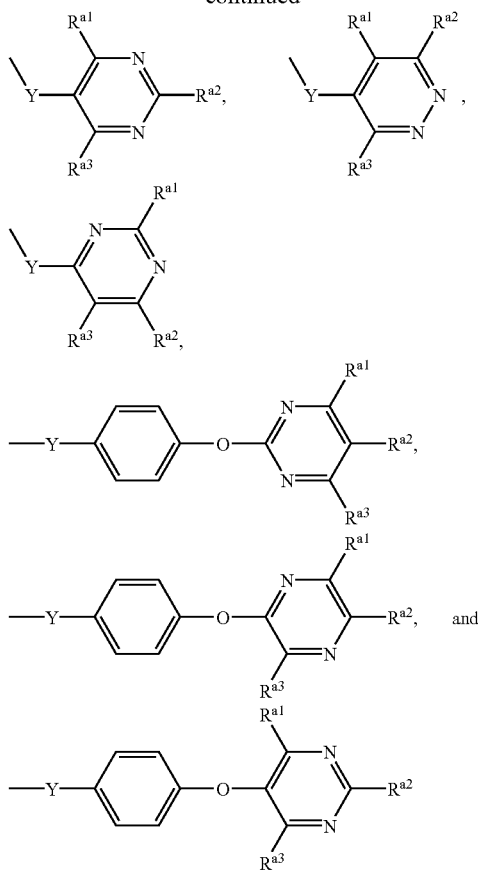

wherein Y is O or S; and $R^{a1}$, $R^{a2}$, $R^{a3}$, $R^{a4}$, $R^{a5}$ and $R^{a6}$ are independently selected from hydrogen, hydroxy, sulfanyl, sulfo, halogen, amino, cyano, nitro, $C_{1-6}$-alkyl, $C_{2-6}$-alkenyl, aryl, heteroaryl, $C_{3-8}$-heterocyclyl, or $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-8}$-heterocyclyl and $C_{3-10}$-cycloalkyl is optionally substituted with one or more substituents independently selected from hydroxy, sulfanyl, suite, oxo, halogen, amino, cyano, nitro, $C_{1-6}$-alkyl, $C_{2-6}$-alkenyl, aryl, heteroaryl, $C_{3-8}$-heterocyclyl and $C_{3-10}$-cycloalkyl, wherein each of hydroxy, sulfanyl, sulfo, amino, $C_{1-6}$-alkyl, $C_{2-6}$-alkenyl, aryl, heteroaryl, $C_{3-4}$-heterocyclyl and $C_{3-10}$-cycloalkyl is optionally substituted with one or more substituents independently selected from hydroxy, sulfanyl, sulfo, oxo, halogen, amino, cyano, nitro, $C_{1-6}$-alkyl, $C_{2-4}$-alkenyl, perhalomethyl and perhalomethoxy.

5. The method according to claim 4, wherein at least one of $R^{a1}$, $R^{a2}$, $R^{a3}$, $R^{a4}$, $R^{a5}$, and $R^{a6}$ is F.

6. The method according to claim 1, wherein the group L of formula I is an optionally substituted —O-phenyl, via which L is hound to the C in formula I.

7. The method according to claim 1, wherein $R^1$ and $R^2$ are covalently bound to each other so that the group $R^1$—N—$R^2$ forms a piperazine, said piperazine being bound to the C in formula I.

8. The method according to claim 1, wherein $R^1$ and $R^2$ are covalently bound to each other so tat the group $R^1$—N—$R^2$ forms a piperidine, said piperidine being bound to the C in formula I.

9. The method according to claim 1, wherein $R^1$ is selected from the group consisting of $C_{1-6}$-alkyl, $C_{2-6}$-alkenyl and $C_{3-10}$-cycloalkyl, each of which is optionally substituted with one or more substituents independently selected from hydroxy, sulfanyl, oxo, halogen, amino, cyano and nitro.

10. The method according to claim 1, wherein $R^1$ is methyl.

11. The method according to claim 1, wherein $R^2$ is phenyl.

12. The method according to claim 1, wherein $R^2$ is a heteroaryl.

13. The method according to claim 1, wherein $R^1$ is methyl and $R^2$ is phenyl.

14. The method according to claim 1, wherein the group L of formula I is an optionally substituted O-phenyl via which L is bound to the C in formula (I), and $R^1$ and $R^2$ are covalently bound to each other so that the group $R^1$—N—$R^2$ forms a piperazine, said piperazine being bound to the C in formula I.

15. The method according to claim 1, wherein the group L of formula I is an optionally substituted O-phenyl via which L is bound to the C in formula (I), and $R^1$ and $R^2$ are covalently bound to each other so that the group $R^1$—N—$R^2$ forms a piperidine, said piperidine being bound to the C in formula I.

16. The method according to claim 1, wherein the group L of formula I is an optionally substituted O-phenyl via which L is bound to the C in formula I, and $R^1$ is methyl and $R^2$ is phenyl.

17. The method according to claim 1, wherein $pK_a$ of the group L of formula I is between 4 and 12.

18. The method according to claim 17, wherein $pK_a$ of the group L of formula I is between 6 and 12.

19. The method according to claim 17, wherein $pK_a$ of the group L of formula I is between 7 and 12.

20. The method according to claim 17, wherein $pK_a$ of the group L of formula I is between 8 and 12.

21. The method according to claim 17, wherein $pK_a$ of the group L of formula I is between 8.5 to 11.5.

22. The method according to claim 17, wherein $pK_a$ of the group L of formula I is between 9.0 to 11.0.

23. The method according to claim 1, wherein the compound is selected from the group:

Methyl-phenyl-carbamic acid 4-(4,4-dimethyl-2,6-dioxo-piperidin-1-yl)-phenyl ester;

Methyl-phenyl-carbamic acid 4-trifluoromethyl-pyrimidin-2-yl ester;

(3-Chloro-phenyl)-methyl-carbamic acid 4-trifluoromethyl-pyrimidin-2-yl ester;

Methyl-phenyl-carbamic acid 4,4-dimethyl-2,6-dioxo-3,4,5,6-tetrahydro-2H-[1,3']bipyridinyl-6'-yl ester;

4-Pyridin-2-yl-piperazine-1-carboxylic acid 4-(5-trifluoromethyl-pyridin-2-yloxy)phenyl ester;

4-(4-Fluorobenzyl)-piperazine-1-carboxylic acid 4-(5-trifluoromethyl-pyridin-2-yloxy)-phenyl ester, 4-Pyrimidin-2-yl-piperazine-1-carboxylic acid 4-(5-trifluoromethyl-pyridin-2-yloxy)-phenyl ester;

4-Cyclopropylmethyl-piperazine-1-carboxylic acid 4-(5-trifluoromethyl-pyridin-2-yloxy)-phenyl ester, 4-Methyl-1,4-diazepane-1-carboxylic acid 4-(5-trifluoromethyl-pyridin-2-yloxy)phenyl ester;

4-Pyridin-2-ylmethyl-piperazine-1-carboxylic acid 4-(5-trifluoromethyl-pyridin-2-yloxy)-phenyl ester;

4-Pyridin-3-ylmethyl-piperazine-1-carboxylic acid 4-(5-trifluoromethyl-pyridin-2-yloxy)-phenyl ester;

4-Benzyl-1,4-diazepane-1-carboxylic acid 4-(5-trifluoromethyl-pyridin-2-yloxy)-phenyl ester, 4-(4-Fluorophenyl)piperazine-1-carboxylic acid 4-(5-trifluoromethyl-pyridin-2-yloxy)phenyl ester;

4-(2-Chlorophenyl)piperazine-1-carboxylic acid 4-(5-trifluoromethyl-pyridin-2-yloxy)phenyl ester;

4-(4-Methoxybenzyl)piperazine-1-carboxylic acid 4-(5-trifluoromethyl-pyridin-2-yloxy)-phenyl ester, 4-(3-Methoxyphenyl)piperazine-1-carboxylic acid 4-(4-trifluoromethylphenoxy)phenyl ester;

Methyl-phenyl-carbamic acid 2-(4,4-dimethyl-2,6-dioxo-piperidin-1-yl)-pyrimidin-5-yl ester;

4-(Tetrahydrofuran-2-ylmethyl)-piperazine-1-carboxylic acid 4-(5-trifluoromethyl-pyridin-2-yloxy)-phenyl ester;

4-Cyclopropylmethyl-piperazine-1-carboxylic acid 4-(3-chloro-5-trifluoromethyl-pyridin-2-yloxy)-phenyl ester; and 4-(Tetrahydro-furan-2-ylmethyl)-piperazine-1-carboxylic acid 4-(4-trifluoromethylphenoxy)-phenyl ester.

* * * * *